(12) United States Patent
Kelly et al.

(10) Patent No.: US 11,820,781 B2
(45) Date of Patent: *Nov. 21, 2023

(54) BIFUNCTIONAL COMPOUNDS FOR DEGRADING BTK VIA UBIQUITIN PROTEOSOME PATHWAY

(71) Applicant: Nurix Therapeutics, Inc., San Francisco, CA (US)

(72) Inventors: Aileen Kelly, San Francisco, CA (US); Arthur T. Sands, San Francisco, CA (US)

(73) Assignee: Nurix Therapeutics, Inc., San Francisco, CA (US)

(*) Notice: Subject to any disclaimer, the term of this patent is extended or adjusted under 35 U.S.C. 154(b) by 248 days.

This patent is subject to a terminal disclaimer.

(21) Appl. No.: 17/111,454

(22) Filed: Dec. 3, 2020

(65) Prior Publication Data

US 2021/0198280 A1 Jul. 1, 2021

Related U.S. Application Data

(60) Provisional application No. 62/943,720, filed on Dec. 4, 2019, provisional application No. 63/010,524, filed on Apr. 15, 2020.

(51) Int. Cl.
| | | |
|---|---|---|
| *A61P 35/00* | (2006.01) | |
| *A61P 19/00* | (2006.01) | |
| *A61P 37/00* | (2006.01) | |
| *C07D 487/10* | (2006.01) | |
| *C07D 498/10* | (2006.01) | |
| *C07D 401/14* | (2006.01) | |
| *C07D 413/14* | (2006.01) | |
| *C07D 417/14* | (2006.01) | |
| *C07D 471/04* | (2006.01) | |
| *C07D 471/10* | (2006.01) | |
| *C07D 487/04* | (2006.01) | |
| *C07D 491/107* | (2006.01) | |

(52) U.S. Cl.
CPC .......... *C07D 498/10* (2013.01); *C07D 401/14* (2013.01); *C07D 413/14* (2013.01); *C07D 417/14* (2013.01); *C07D 471/04* (2013.01); *C07D 471/10* (2013.01); *C07D 487/04* (2013.01); *C07D 487/10* (2013.01); *C07D 491/107* (2013.01)

(58) Field of Classification Search
CPC .......... A61P 35/00; A61P 19/00; A61P 37/00; C07D 487/10
See application file for complete search history.

(56) References Cited

U.S. PATENT DOCUMENTS

| | | | |
|---|---|---|---|
| 10,130,659 B2 | 11/2018 | Wardell et al. | |
| 10,166,257 B2 | 1/2019 | Wardell et al. | |
| 10,272,113 B2 | 4/2019 | Wardell et al. | |
| 10,363,273 B2 | 7/2019 | Wardell et al. | |
| 10,398,734 B2 | 9/2019 | Wardell et al. | |
| 10,415,015 B2 | 9/2019 | Veerapathran et al. | |
| 10,420,799 B2 | 9/2019 | Wardell et al. | |
| 10,463,697 B2 | 11/2019 | Wardell et al. | |
| 10,517,894 B2 | 12/2019 | Frank et al. | |
| 10,537,595 B2 | 1/2020 | Wardell et al. | |
| 10,639,330 B2 | 5/2020 | Wardell et al. | |
| 10,646,517 B2 | 5/2020 | Wardell et al. | |
| 10,653,723 B1 | 5/2020 | Wardell et al. | |
| 10,695,372 B2 | 6/2020 | Wardell et al. | |
| 10,894,063 B2 | 1/2021 | Wardell et al. | |
| 10,918,666 B2 | 2/2021 | Wardell et al. | |
| 10,933,094 B2 | 3/2021 | Wardell et al. | |
| 10,946,044 B2 | 3/2021 | Wardell et al. | |
| 10,946,045 B2 | 3/2021 | Wardell et al. | |
| 10,953,046 B2 | 3/2021 | Wardell et al. | |
| 10,953,047 B2 | 3/2021 | Wardell et al. | |
| 11,007,226 B2 | 5/2021 | Wardell et al. | |
| 11,013,770 B1 | 5/2021 | Wardell et al. | |
| 11,026,974 B2 | 6/2021 | Wardell et al. | |
| 11,040,070 B2 | 6/2021 | Wardell et al. | |
| 11,052,115 B2 | 7/2021 | Wardell et al. | |
| 11,052,116 B2 | 7/2021 | Wardell et al. | |
| 11,058,728 B1 | 7/2021 | Frank et al. | |
| 11,083,752 B2 | 8/2021 | Wardell et al. | |
| 11,123,371 B2 | 9/2021 | Wardell et al. | |
| 11,479,556 B1 | 10/2022 | Robbins et al. | |
| 2007/0054355 A1 | 3/2007 | Reiss et al. | |
| 2017/0015655 A1 | 1/2017 | Kaieda et al. | |
| 2020/0323904 A1 | 10/2020 | Sands et al. | |
| 2021/0053961 A1 | 2/2021 | Sands et al. | |
| 2021/0053986 A1 | 2/2021 | Sands et al. | |
| 2021/0085717 A1 | 3/2021 | Gosling et al. | |
| 2021/0087259 A1 | 3/2021 | Gosling et al. | |
| 2022/0143195 A1 | 5/2022 | Kato et al. | |
| 2023/0024442 A1 | 1/2023 | Robbins et al. | |
| 2023/0029378 A1 | 1/2023 | Robbins et al. | |

FOREIGN PATENT DOCUMENTS

| | | | |
|---|---|---|---|
| WO | WO 2007/072225 A2 | 6/2007 | |
| WO | WO 2008/033403 A2 | 3/2008 | |

(Continued)

OTHER PUBLICATIONS

International Search Report and Written Opinion for International Patent Application PCT/US2019/056112, 8 pages, dated Dec. 6, 2019.

(Continued)

*Primary Examiner* — Bruck Kifle
(74) *Attorney, Agent, or Firm* — Squire Patton Boggs (US) LLP

(57) ABSTRACT

This disclosure relates to compounds useful for degrading BTK via a ubiquitin proteolytic pathway. The description also provides pharmaceutically acceptable compositions comprising said compounds and methods of using the compositions in the treatment of various disease, conditions, or disorders.

34 Claims, 13 Drawing Sheets

(56) References Cited

FOREIGN PATENT DOCUMENTS

| WO | WO 2009/073905 A2 | 6/2009 |
|---|---|---|
| WO | WO 2009/098144 A1 | 8/2009 |
| WO | WO 2011/140488 A1 | 11/2011 |
| WO | WO 2012/020008 A1 | 2/2012 |
| WO | WO 2012/089736 A1 | 7/2012 |
| WO | WO 2013/067264 A1 | 5/2013 |
| WO | WO 2013/067274 A1 | 5/2013 |
| WO | WO 2013/106643 A2 | 7/2013 |
| WO | WO 2013/1066543 A2 | 7/2013 |
| WO | WO 2014/040965 A1 | 3/2014 |
| WO | WO 2015/084998 A1 | 6/2015 |
| WO | WO 2016/196776 A2 | 12/2016 |
| WO | WO 2018/098275 A1 | 5/2018 |
| WO | WO 2019/148005 A1 | 8/2019 |
| WO | WO 2020/081450 A1 | 4/2020 |
| WO | WO 2020/167518 A1 | 8/2020 |
| WO | WO 2020/210508 A1 | 10/2020 |
| WO | WO 2020/236654 A1 | 11/2020 |
| WO | WO 2020/264398 A1 | 12/2020 |
| WO | WO 2021/021761 A1 | 2/2021 |
| WO | WO 2021/061853 A1 | 4/2021 |
| WO | WO 2021/061870 A1 | 4/2021 |
| WO | WO 2021/091575 A1 | 5/2021 |
| WO | WO 2021/113557 A1 | 6/2021 |
| WO | WO 2023/004163 A1 | 1/2023 |
| WO | WO 2023/287928 A1 | 1/2023 |
| WO | WO 2023/076303 A1 | 5/2023 |

OTHER PUBLICATIONS

Marshall et al., "Superior Activity of the Type C Class of ISS In Vitro and In Vivo Across Multiple Species", DNA and Cell Biology, vol. 24, No. 2, 2005, pp. 63-72.

Yang et al., "Exploiting Synthetic Lethality for the Therapy of ABC Diffuse Large B Cell Lymphoma", Cancer Cell, 21, 2012, pp. 723-737, DOI 10.1016/j.ccr.2012.05.024.

Bondeson et al., "Catalytic in vivo protein knockdown by small-molecule PROTACs", Nature Chemical Biology, published online Jun. 10, 2015; DOI: 10.1038/NCHEMBIO.1858.

Ye et al., "Engineered Artificial Antigen Presenting Cells Facilitate Direct and Efficient Expansion of Tumor Infiltrating Lymphocytes", Journal of Translation Medicine 2011, 9:131, 13 pages.

Good et al., Proliferative tracing with single-cell mass cytometry optimizes generation of stem cell memory-like T cells, Nature Biotechnology Mar. 2019; 37(3): 259-266. DOI:10.1038/s41587-019-0033-2.

Howe et al, "Models of Energy in the Human Jurkat T Cell Line", Assay and Drug Development Technologies, vol. 1, No. 4, 2003, pp. 537-544.

Stewart et al., "Efforts toward elucidating Thalidomide's molecular target: an expedient synthesis of the first Thalidomide biotin analogue", Org. Biomol. Chem., 2010, 8:4059-4062.

Tigno-Aranjuez et al., "Inhibition of RIP2's tyrosine kinase activity limits NOD2-driven cytokine responses", Genes & Development, 2010, 24:2666-2677; http://www.genesdev.org/cgi/doi/10.1101/gad.964410.

Hines et al., "Posttranslational protein knockdown coupled to receptor tyrosine kinase activation with phophoPROTACs", 2013, PNAS, 110(22):8942-8947.

International Search Report and Written Opinion for International Patent Application PCT/US2019/015250, 10 pages, dated Jun. 11, 2019.

International Search Report and Written Opinion for International Patent Application PCT/US2020/016489, 8 pages, dated May 27, 2020.

International Search Report and Written Opinion for International Patent Application PCT/US2020/033274, 19 pages, dated Oct. 23, 2020.

International Search Report and Written Opinion for International Patent Application PCT/US2020/027492, 21 pages, dated Aug. 11, 2020.

International Search Report and Written Opinion for International Patent Application PCT/US2020/039957, 16 pages, dated Oct. 5, 2020.

International Search Report and Written Opinion for International Patent Application PCT/US2020/043788, 16 pages, dated Oct. 23, 2020.

International Search Report and Written Opinion for International Patent Application PCT/US2020/063176, 12 pages, dated Mar. 5, 2021.

International Search Report and Written Opinion for International Patent Application PCT/US2020/052317, 12 pages, dated Apr. 1, 2021.

International Search Report and Written Opinion for International Patent Application PCT/US2020/052335, 12 pages, dated Apr. 1, 2021.

Riling et al.: "Abstract A206: Small-molecule Cbl-b inhibitors as novel intracellular checkpoint inhibitors for cancer immunotherapy I Molecular Cancer Therapeutics", Jan. 1, 2018 (Jan. 1, 2018), XP055700949, Retrieved from the Internet:URL:https:// mct.aacrjournals.org/content/17/1_Supplement/A206 [retrieved on Jun. 4, 2020].

Gosling et al.: "Abstract 2696: Genetic and pharmacologic evaluation of the ubiquitin ligase CBL-B as a small-molecule, tumor immunotherapy target I Cancer Research", Apr. 3, 2019 (Apr. 3, 2019), XP055701108, Retrieved from the Internet:U RL:https://cancerres.aacrjournals.org/content/79/13_Supplement/2696 [retrieved on Jun. 4, 2020].

International Search Report and Written Opinion for International Patent Application PCT/US2019/060584, 13 pages, dated Dec. 6, 2019.

International Search Report and Written Opinion for International Patent Application PCT/US2022/037029, 11 pages, dated Oct. 10, 2022.

International Search Report and Written Opinion for International Patent Application PCT/US2022/038084, 10 pages, dated Oct. 11, 2022.

International Search Report and Written Opinion for International Patent Application PCT/US2022/047767, 12 pages, dated Feb. 6, 2023.

Orally dosed BTK CTM confers dose- and time-proportional reduction in BTK in circulating B cells Anti-tumor activity associated with BTK degradation in a xenograft model of acquired resistance to ibrutinib

BIFUNCTIONAL COMPOUNDS FOR DEGRADING BTK VIA UBIQUITIN PROTEOSOME PATHWAY

CROSS-REFERENCE TO RELATED APPLICATIONS

This application claims priority to U.S. Provisional Application No. 62/943,720, filed Dec. 4, 2019, U.S. Provisional Application No. 63/010,524, filed Apr. 15, 2020, and incorporates International Application No. PCT/US2019/56112, filed Oct. 14, 2019, each of which is incorporated by reference in their entireties.

FIELD

This disclosure provides novel bifunctional compounds for proteolytically degrading targeted Bruton's tyrosine kinases (BTK) and methods for treating diseases modulated by BTK.

BACKGROUND

B cell receptor (BCR) signaling controls B cell development, as well as mature B cell activation, signaling, and survival. Mis-regulation of the BCR signaling pathway is associated with numerous disease indications involving B cell function, and targeting B cells and BCR signaling has clear therapeutic potential (Woyach, et al.; *Blood*, 120(6); 1175-1184, 2012). For example, depletion of B cells with monoclonal antibodies targeting CD20 has significant effects in treatment of B cell malignancies and auto-immune and inflammatory diseases (Cang, et al.; *J Hematolo Oncol.* 5; 64, 2012.).

BTK is a member of the TEC family of kinases and is a crucial signaling hub in the BCR pathway. Mutations in BTK result in X-linked agammaglobulinaemia (XLA), in which B cell maturation is impaired, resulting in reduced immunoglobulin production (Hendriks, et al.; *Expert Opin Ther Targets* 15; 1002-1021, 2011). The central role of BTK in B cell signaling and function makes BTK an attractive therapeutic target for B cell malignancies as well as autoimmune and inflammatory diseases. Ibrutinib, a covalent inhibitor of BTK, has been approved to treat chronic lymphocytic leukemia (CLL), mantle cell lymphoma (MCL) and other B cell malignancies, as well as graft-versus-host disease (GvHD) (Miklos, et al.; *Blood*, 120(21); 2243-2250, 2017). Currently, ibrutinib and second-generation BTK inhibitors are being investigated for oncology and immune-related indications such as rheumatoid arthritis (Akinleye, et al.; *J of Hematolo Oncol.* 6: 59, 2013; Liu, et al.; *J Pharm and Exper Ther.* 338(1): 154-163. 2011; Di Paolo, et al.; *Nat Chem Biol.* 7(1): 41-50, 2011).

As an alternative to stoichiometric inhibition, proteolytic degradation of BTK could have dramatic consequences for B cell function by effectively blocking BCR signaling. Removal of BTK protein would eliminate BTK kinase activity as well as any protein interaction or scaffolding function of BTK. Specific degradation of BTK could be accomplished using heterobifunctional small molecules to recruit BTK to a ubiquitin ligase and thus promoting ubiquitylation and proteasomal degradation of BTK. Thalidomide derivatives, such as lenalidomide or pomalidomide, can be used to recruit potential substrates to cereblon (CRBN), a component of a ubiquitin ligase complex. This unique therapeutic approach could present a mechanism of action for interfering with BTK activity and BCR signaling that is distinct from the mechanism of stoichiometric BTK inhibition. Furthermore, this degradative approach could effectively target the C481S mutated form of BTK, which mutation has been clinically observed and confers resistance to inhibition by ibrutinib (Woyach, et al.; *Blood*, 120(6): 1175-1184, 2012.).

Presently, there remains a need for bifunctional molecules that can induce the in vivo proteolytic degradation of BTK via a ubiquitin proteolytic pathway.

SUMMARY

Provided herein are methods of using bifunctional compounds that induce the proteolytic degradation of BTK via a ubiquitin proteolysis pathway.

In one aspect, provided herein are methods of treating or preventing cancer in a subject in need thereof. The methods comprise the step of orally administering to the subject an amount of a bifunctional compound capable of inducing proteolytic degradation of Bruton's tyrosine kinase. In certain embodiments, the amount is effective to treat or prevent the cancer.

In another aspect, provided herein are methods of degrading Bruton's tyrosine kinase in a subject in need thereof. The methods comprise the step of orally administering to the subject an amount of a bifunctional compound capable of inducing proteolytic degradation of Bruton's tyrosine kinase. In certain embodiments, the amount is effective to degrade Bruton's tyrosine kinase in the subject.

In another aspect, provided herein are methods of preventing B cell activation in a subject in need thereof. The methods comprise the step of orally administering to the subject an amount of a bifunctional compound capable of inducing proteolytic degradation of Bruton's tyrosine kinase. In certain embodiments, the amount is effective to prevent B cell activation.

In another aspect, provided herein are methods of degrading a mutant Bruton's tyrosine kinase. The methods comprise the step of contacting a cell expressing the mutant Bruton's tyrosine kinase with an amount of a bifunctional compound capable of inducing proteolytic degradation of Bruton's tyrosine kinase. In certain embodiments, the amount is effective to degrade the mutant Bruton's tyrosine kinase. In certain embodiments, the mutant Bruton's tyrosine kinase is a C481 mutant. In certain embodiments, the mutant Bruton's tyrosine kinase is a C481S mutant.

In the methods, the bifunctional compounds comprise a moiety capable of specifically binding BTK and further comprise a moiety capable of recruiting an ubiquitin ligase to degrade the BTK. Particular compounds are described herein. The compounds can be administered in any form, including pharmaceutically acceptable salts and pharmaceutical compositions.

DETAILED DESCRIPTION

Figure 1:
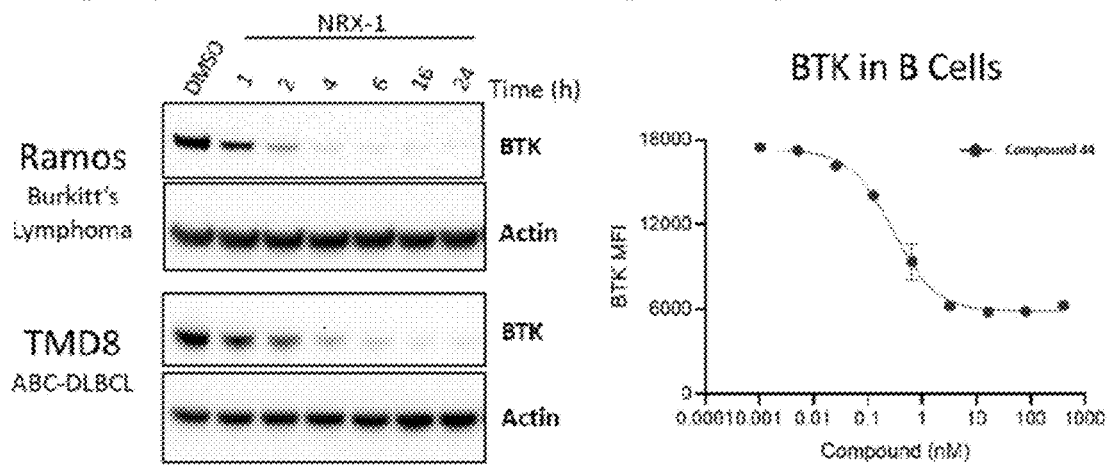
FIG. 1 provides BTK degradation by a compound herein in B lymphoma cell lines and in primary human B cells.

Provided herein are methods of using bifunctional compounds that induce the proteolytic degradation of Bruton's tyrosine kinase (BTK) via a ubiquitin proteolysis pathway.

As used herein, the following definitions shall apply unless otherwise indicated.

Definitions

For purposes herein, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As described herein, "protecting group" refers to a moiety or functionality that is introduced into a molecule by chemical modification of a functional group in order to obtain chemoselectivity in a subsequent chemical reaction. Standard protecting groups are provided in Wuts and Greene: "Greene's Protective Groups in Organic Synthesis," 4th Ed, Wuts, P. G. M. and Greene, T. W., Wiley-Interscience, New York: 2006.

As described herein, compounds herein optionally may be substituted with one or more substituents, such as those illustrated generally herein, or as exemplified by particular classes, subclasses, and species of the description.

As used herein, the term "hydroxyl" or "hydroxy" refers to an —OH moiety.

As used herein, the term "aliphatic" encompasses the terms alkyl, alkenyl, and alkynyl, each of which are optionally substituted as set forth below.

As used herein, an "alkyl" group refers to a saturated aliphatic hydrocarbon group containing 1-12 (e.g., 1-8, 1-6, or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino, alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, or heterocycloaliphaticamino), sulfonyl (e.g., aliphatic-$SO_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-$SO_2$-amino)alkyl), aminoalkyl, amidoalkyl, (cycloaliphatic)alkyl, or haloalkyl.

As used herein, an "alkenyl" group refers to an aliphatic carbon group that contains 2-8 (e.g., 2-12, 2-6, or 2-4) carbon atoms and at least one double bond. Like an alkyl group, an alkenyl group can be straight or branched. Examples of an alkenyl group include, but are not limited to, allyl, 1- or 2-isopropenyl, 2-butenyl, and 2-hexenyl. An alkenyl group can be optionally substituted with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino, alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, heterocycloaliphaticamino, or aliphaticsulfonylamino), sulfonyl (e.g., alkyl-$SO_2$—, cycloaliphatic-$SO_2$—, or aryl-$SO_2$—), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-$SO_2$-amino)alkenyl), aminoalkenyl, amidoalkenyl, (cycloaliphatic)alkenyl, or haloalkenyl.

As used herein, an "alkynyl" group refers to an aliphatic carbon group that contains 2-8 (e.g., 2-12, 2-6, or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl (e.g., aliphaticsulfanyl or cycloaliphaticsulfanyl), sulfinyl (e.g., aliphaticsulfinyl or cycloaliphaticsulfinyl), sulfonyl (e.g., aliphatic-$SO_2$—, aliphaticamino-$SO_2$—, or cycloaliphatic-SO$_2$—), amido (e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl)carbonylamino, heteroaralkylcarbonylamino, heteroarylcarbonylamino, or heteroarylaminocarbonyl), urea, thiourea, sulfamoyl, sulfamide, alkoxycarbonyl, alkylcarbonyloxy, cycloaliphatic, heterocycloaliphatic, aryl, heteroaryl, acyl (e.g., (cycloaliphatic)carbonyl or (heterocycloaliphatic)carbonyl), amino (e.g., aliphaticamino), sulfoxy, oxo, carboxy, carbamoyl, (cycloaliphatic)oxy, (heterocycloaliphatic)oxy, or (heteroaryl)alkoxy.

As used herein, an "amido" encompasses both "aminocarbonyl" and "carbonylamino." These terms when used alone or in connection with another group refer to an amido group such as —N(R$^X$)—C(O)—R$^Y$ or —C(O)—N(R$^X$)$_2$, when used terminally, and —C(O)—N(R$^X$)— or —N(R$^X$)—C(O)— when used internally, wherein R$^X$ and R$^Y$ can be aliphatic, cycloaliphatic, aryl, aralphatic, heterocycloaliphatic, heteroaryl, or heteroaralphatic. Examples of amido groups include alkylamido (such as alkylcarbonylamino or alkylaminocarbonyl), (heterocycloaliphatic)amido, (heteroaralkyl)amido, (heteroaryl)amido, (heterocycloalkyl)alkylamido, arylamido, aralkylamido, (cycloalkyl)alkylamido, or cycloalkylamido.

As used herein, an "amino" group refers to —NR$^X$R$^Y$ wherein each of R$^X$ and R$^Y$ is independently hydrogen (H or —H), aliphatic, cycloaliphatic, (cycloaliphatic)aliphatic, aryl, aralphatic, heterocycloaliphatic, (heterocycloaliphatic) aliphatic, heteroaryl, carboxy, sulfanyl, sulfinyl, sulfonyl, (aliphatic)carbonyl, (cycloaliphatic)carbonyl, ((cycloaliphatic)aliphatic)carbonyl, arylcarbonyl, (aralphatic)carbonyl, (heterocycloaliphatic)carbonyl, ((heterocycloaliphatic)aliphatic)carbonyl, (heteroaryl)carbonyl, or (heteroaralphatic)carbonyl, each of which being defined herein and being optionally substituted. Examples of amino groups include alkylamino, dialkylamino, or arylamino. When the term "amino" is not the terminal group (e.g., alkylcarbonylamino), it is represented by —NR$^X$—, where R$^X$ has the same meaning as defined above.

As used herein, an "aryl" group used alone or as part of a larger moiety as in "aralkyl," "aralkoxy," or "aryloxyalkyl" refers to monocyclic (e.g., phenyl); bicyclic (e.g., indenyl, naphthalenyl, tetrahydronaphthyl, or tetrahydroindenyl); and tricyclic (e.g., fluorenyl tetrahydrofluorenyl, tetrahydroanthracenyl, or anthracenyl) ring systems in which the monocyclic ring system is aromatic or at least one of the rings in a bicyclic or tricyclic ring system is aromatic. The bicyclic and tricyclic groups include benzofused 2-3 membered carbocyclic rings. For example, a benzofused group includes phenyl fused with two or more C$_{4-8}$ carbocyclic moieties. An aryl is optionally substituted with one or more substituents including aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (aralphatic)oxy; (heteroaralphatic) oxy; aroyl; heteroaroyl; amino; oxo (on a non-aromatic carbocyclic ring of a benzofused bicyclic or tricyclic aryl); nitro; carboxy; amido; acyl (e.g., (aliphatic)carbonyl; (cycloaliphatic)carbonyl; ((cycloaliphatic)aliphatic)carbonyl; (aralphatic)carbonyl; (heterocycloaliphatic)carbonyl; ((heterocycloaliphatic)aliphatic)carbonyl; or (heteroaralphatic) carbonyl); sulfonyl (e.g., aliphatic-SO$_2$— or amino-SO$_2$—); sulfinyl (e.g., aliphatic-S(O)— or cycloaliphatic-S(O)—); sulfanyl (e.g., aliphatic-S—); cyano; halo; hydroxy; mercapto; sulfoxy; urea; thiourea; sulfamoyl; sulfamide; or carbamoyl. Alternatively, an aryl can be unsubstituted.

Non-limiting examples of substituted aryls include haloaryl (e.g., mono-, di- (such as p,m-dihaloaryl), and (trihalo)aryl); (carboxy)aryl (e.g., (alkoxycarbonyl)aryl, ((aralkyl)carbonyloxy)aryl, and (alkoxycarbonyl)aryl); (amido)aryl (e.g., (aminocarbonyl)aryl, (((alkylamino)alkyl) aminocarbonyl)aryl, (alkylcarbonyl)aminoaryl, (arylaminocarbonyl)aryl, and (((heteroaryl)amino)carbonyl)aryl); aminoaryl (e.g., ((alkylsulfonyl)amino)aryl or ((dialkyl)amino)aryl); (cyanoalkyl)aryl; (alkoxy)aryl; (sulfamoyl)aryl (e.g., (aminosulfonyl)aryl); (alkylsulfonyl)aryl; (cyano)aryl; (hydroxyalkyl)aryl; ((alkoxy)alkyl)aryl; (hydroxy)aryl, ((carboxy)alkyl)aryl; (((dialkyl)amino)alkyl)aryl; (nitroalkyl)aryl; (((alkylsulfonyl)amino)alkyl)aryl; ((heterocycloaliphatic)carbonyl)aryl; ((alkylsulfonyl)alkyl)aryl; (cyanoalkyl)aryl; (hydroxyalkyl)aryl; (alkylcarbonyl)aryl; alkylaryl; (trihaloalkyl)aryl; p-amino-m-alkoxycarbonylaryl; p-amino-m-cyanoaryl; p-halo-m-aminoaryl; or (m-(heterocycloaliphatic)-o-(alkyl))aryl.

As used herein, an "aralphatic" such as an "aralkyl" group refers to an aliphatic group (e.g., a C$_{1-4}$ alkyl group) that is substituted with an aryl group. "Aliphatic," "alkyl," and "aryl" are defined herein. An example of an aralphatic such as an aralkyl group is benzyl.

As used herein, an "aralkyl" group refers to an alkyl group (e.g., a C$_{1-4}$ alkyl group) that is substituted with an aryl group. Both "alkyl" and "aryl" have been defined above. An example of an aralkyl group is benzyl. An aralkyl is optionally substituted with one or more substituents such as aliphatic (e.g., alkyl, alkenyl, or alkynyl, including carboxyalkyl, hydroxyalkyl, or haloalkyl such as trifluoromethyl), cycloaliphatic (e.g., cycloalkyl or cycloalkenyl), (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, amido (e.g., aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, or heteroaralkylcarbonylamino), cyano, halo, hydroxy, acyl, mercapto, alkylsulfanyl, sulfoxy, urea, thiourea, sulfamoyl, sulfamide, oxo, or carbamoyl.

As used herein, a "bicyclic ring system" includes 6-12 (e.g., 8-12 or 9-, 10-, or 11-) membered structures that form two rings, wherein the two rings have at least one atom in common (e.g., two atoms in common). Bicyclic ring systems include bicycloaliphatics (e.g., bicycloalkyl or bicycloalkenyl), bicycloheteroaliphatics, bicyclic aryls, and bicyclic heteroaryls.

As used herein, a "cycloaliphatic" group encompasses a "cycloalkyl" group and a "cycloalkenyl" group, each of which are optionally substituted as set forth below.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, or ((aminocarbonyl)cycloalkyl)cycloalkyl.

A "cycloalkenyl" group, as used herein, refers to a non-aromatic carbocyclic ring of 3-10 (e.g., 4-8) carbon atoms having one or more double bonds. Examples of cycloalkenyl groups include cyclopentenyl, 1,4-cyclohexa-di-enyl, cycloheptenyl, cyclooctenyl, hexahydro-indenyl, octahydronaphthyl, cyclohexenyl, bicyclo[2.2.2]octenyl, or bicyclo[3.3.1]nonenyl.

A cycloalkyl or cycloalkenyl group can be optionally substituted with one or more substituents such as phospho, aliphatic (e.g., alkyl, alkenyl, or alkynyl), cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino), nitro, carboxy (e.g., HOOC—, alkoxycarbonyl, or alkylcarbonyloxy), acyl (e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl], cyano, halo, hydroxy, mercapto, sulfonyl (e.g., alkyl-$SO_2$— and aryl-$SO_2$—), sulfinyl (e.g., alkyl-S(O)—), sulfanyl (e.g., alkyl-S—), sulfoxy, urea, thiourea, sulfamoyl, sulfamide, oxo, or carbamoyl.

As used herein, the term "heterocycloaliphatic" encompasses heterocycloalkyl groups and heterocycloalkenyl groups, each of which being optionally substituted as set forth below.

As used herein, a "heterocycloalkyl" group refers to a 3-10 membered mono- or bicylic (fused, bridged, or spiro) (e.g., 5- to 10-membered mono- or bicyclic) saturated ring structure, in which one or more of the ring atoms is a heteroatom (e.g., nitrogen (N), oxygen (O), sulfur (S), or combinations thereof). Non-limiting examples of a heterocycloalkyl group include piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholinyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, decahydro-2,7-naphthyridine, 2,8-diazaspiro[4.5]decane, 2,7-diazaspiro[3.5]nonane, octahydropyrrolo[3,4-c]pyrrole, octahydro-1H-pyrrolo[3,4-b]pyridine, and 2,6-dioxa-tricyclo[3.3.1.0$^{3,7}$]nonyl. A monocyclic heterocycloalkyl group can be fused with a phenyl moiety to form structures, such as tetrahydroisoquinoline, that would be categorized as heteroaryls.

A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom (e.g., N, O, or S). Monocyclic and bicyclic heterocycloaliphatics are numbered according to standard chemical nomenclature.

A heterocycloalkyl or heterocycloalkenyl group can be optionally substituted with one or more substituents such as phospho, aliphatic (e.g., alkyl, alkenyl, or alkynyl), cycloaliphatic, (cycloaliphatic)aliphatic, heterocycloaliphatic, (heterocycloaliphatic)aliphatic, aryl, heteroaryl, alkoxy, (cycloaliphatic)oxy, (heterocycloaliphatic)oxy, aryloxy, heteroaryloxy, (araliphatic)oxy, (heteroaraliphatic)oxy, aroyl, heteroaroyl, amino, amido (e.g., (aliphatic)carbonylamino, (cycloaliphatic)carbonylamino, ((cycloaliphatic)aliphatic)carbonylamino, (aryl)carbonylamino, (araliphatic)carbonylamino, (heterocycloaliphatic)carbonylamino, ((heterocycloaliphatic)aliphatic)carbonylamino, (heteroaryl)carbonylamino, or (heteroaraliphatic)carbonylamino], nitro, carboxy (e.g., HOOC—, alkoxycarbonyl, or alkylcarbonyloxy), acyl (e.g., (cycloaliphatic)carbonyl, ((cycloaliphatic)aliphatic)carbonyl, (araliphatic)carbonyl, (heterocycloaliphatic)carbonyl, ((heterocycloaliphatic)aliphatic)carbonyl, or (heteroaraliphatic)carbonyl), nitro, cyano, halo, hydroxy, mercapto, sulfonyl (e.g., alkylsulfonyl or arylsulfonyl), sulfinyl (e.g., alkylsulfinyl), sulfanyl (e.g., alkylsulfanyl), sulfoxy, urea, thiourea, sulfamoyl, sulfamide, oxo, or carbamoyl.

A "heteroaryl" group, as used herein, refers to a monocyclic, bicyclic, or tricyclic ring system having four to fifteen ring atoms wherein one or more of the ring atoms is a heteroatom (e.g., N, O, S, or combinations thereof) and in which the monocyclic ring system is aromatic or at least one of the rings in the bicyclic or tricyclic ring systems is aromatic. A heteroaryl group includes a benzofused ring system having two to three rings. For example, a benzofused group includes benzo fused with one or two 4- to 8-membered heterocycloaliphatic moieties (e.g., indolizyl, indolyl, isoindolyl, 3H-indolyl, indolinyl, benzo[b]furyl, benzo[b]thiophene-yl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, phthalazyl, quinazolyl, quinoxalyl, isoquinolyl, 4H-quinolizyl, benzo-1,2,5-thiadiazolyl, or 1,8-naphthyridyl. Other examples of heteroaryls include 1,2,3,4-tetrahydroisoquinoline and 4,5,6,7-tetrahydropyrazolo[1,5-a]pyrazine.

Without limitation, monocyclic heteroaryls include furyl, thiophene-yl, 2H-pyrrolyl, oxazolyl, thiazolyl, imidazolyl, pyrazolyl, isoxazolyl, isothiazolyl, 1,3,4-thiadiazolyl, 2H-pyranyl, 4H-pranyl, pyridyl, pyridazyl, pyrimidyl, pyrazolyl, pyrazyl, or 1,3,5-triazyl. Monocyclic heteroaryls are numbered according to standard chemical nomenclature.

Without limitation, bicyclic heteroaryls include indolizyl, indolyl, isoindolyl, 3H-indolyl, indolinyl, benzo[b]furyl, benzo[b]thiophenyl, quinolinyl, isoquinolinyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, or pteridyl. Bicyclic heteroaryls are numbered according to standard chemical nomenclature.

A heteroaryl is optionally substituted with one or more substituents such as aliphatic (e.g., alkyl, alkenyl, or alkynyl); cycloaliphatic; (cycloaliphatic)aliphatic; heterocycloaliphatic; (heterocycloaliphatic)aliphatic; aryl; heteroaryl; alkoxy; (cycloaliphatic)oxy; (heterocycloaliphatic)oxy; aryloxy; heteroaryloxy; (araliphatic)oxy; (heteroaraliphatic)oxy; aroyl; heteroaroyl; amino; oxo (on a non-aromatic carbocyclic or heterocyclic ring of a bicyclic or tricyclic heteroaryl); carboxy; amido; acyl (e.g., aliphaticcarbonyl; (cycloaliphatic)carbonyl; ((cycloaliphatic)aliphatic)carbonyl; (araliphatic)carbonyl; (heterocycloaliphatic)carbonyl; ((heterocycloaliphatic)aliphatic)carbonyl; or (heteroaraliphatic)carbonyl); sulfonyl (e.g., aliphaticsulfonyl or aminosulfonyl); sulfinyl (e.g., aliphaticsulfinyl); sulfanyl (e.g., aliphaticsulfanyl); nitro; cyano; halo; hydroxy; mercapto; sulfoxy; urea; thiourea; sulfamoyl; sulfamide; or carbamoyl. Alternatively, a heteroaryl can be unsubstituted.

Non-limiting examples of substituted heteroaryls include (halo)heteroaryl (e.g., mono- and di-(halo)heteroaryl); (carboxy)heteroaryl (e.g., (alkoxycarbonyl)heteroaryl); cyanoheteroaryl; aminoheteroaryl (e.g., ((alkylsulfonyl)amino)

heteroaryl and ((dialkyl)amino)heteroaryl); (amido) heteroaryl (e.g., aminocarbonylheteroaryl, ((alkylcarbonyl) amino)heteroaryl, ((((alkyl)amino)alkyl)aminocarbonyl) heteroaryl, (((heteroaryl)amino)carbonyl)heteroaryl, ((heterocycloaliphatic)carbonyl)heteroaryl, and ((alkylcarbonyl)amino)heteroaryl); (cyanoalkyl)heteroaryl; (alkoxy) heteroaryl; (sulfamoyl)heteroaryl (e.g., (aminosulfonyl)heteroaryl); (sulfonyl)heteroaryl (e.g., (alkylsulfonyl) heteroaryl); (hydroxyalkyl)heteroaryl; (alkoxyalkyl) heteroaryl; (hydroxy)heteroaryl; ((carboxy)alkyl)heteroaryl; (((dialkyl)amino)alkyl)heteroaryl; (heterocycloaliphatic) heteroaryl; (cycloaliphatic)heteroaryl; (nitroalkyl)heteroaryl; (((alkylsulfonyl)amino)alkyl)heteroaryl; ((alkylsulfonyl)alkyl)heteroaryl; (cyanoalkyl)heteroaryl; (acyl) heteroaryl (e.g., (alkylcarbonyl)heteroaryl); (alkyl) heteroaryl; or (haloalkyl)heteroaryl (e.g., trihaloalkylheteroaryl).

As used herein, a "heteroaraliphatic" (such as a heteroaralkyl group) refers to an aliphatic group (e.g., a $C_{1-4}$ alkyl group) that is substituted with a heteroaryl group. "Aliphatic," "alkyl," and "heteroaryl" have been defined above.

As used herein, a "heteroaralkyl" group refers to an alkyl group (e.g., a $C_{1-4}$ alkyl group) that is substituted with a heteroaryl group. Both "alkyl" and "heteroaryl" have been defined above.

A heteroaralkyl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl)carbonylamino, (heterocycloalkylalkyl) carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, "cyclic moiety" and "cyclic group" refer to mono-, bi-, and tri-cyclic ring systems including cycloaliphatic, heterocycloaliphatic, aryl, or heteroaryl, each of which has been previously defined.

As used herein, a "bridged bicyclic ring system" refers to a bicyclic heterocyclicalipahtic ring system or bicyclic cycloaliphatic ring system in which the rings are bridged. Examples of bridged bicyclic ring systems include, but are not limited to, adamantanyl, norbornanyl, bicyclo[3.2.1] octyl, bicyclo[2.2.2]octyl, bicyclo[3.3.1]nonyl, bicyclo [3.3.2]decyl, 2-oxabicyclo[2.2.2]octyl, 1-azabicyclo[2.2.2] octyl, 3-azabicyclo[3.2.1]octyl, and 2,6-dioxa-tricyclo [3.3.1.0$^{3,7}$]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, arylcarbonylamino, aralkylcarbonylamino, (heterocycloalkyl) carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, an "acyl" group refers to a formyl group or $R^X$—C(O)— (such as alkyl-C(O)—, also referred to as "alkylcarbonyl") where $R^X$ and "alkyl" have been defined previously. Acetyl and pivaloyl are examples of acyl groups.

As used herein, an "aroyl" or "heteroaroyl" refers to an aryl-C(O)— or a heteroaryl-C(O)—. The aryl and heteroaryl portion of the aroyl or heteroaroyl is optionally substituted as previously defined herein.

As used herein, an "alkoxy" group refers to an alkyl-O— group where "alkyl" has been defined previously herein.

As used herein, a "carbamoyl" group refers to a group having the structure —O—CO—NR$^X$R$^Y$ or —NR$^X$—CO—O—R$^Z$, wherein R$^X$ and R$^Y$ have been defined above and R$^Z$ can be aliphatic, aryl, araliphatic, heterocycloaliphatic, heteroaryl, or heteroaraliphatic.

As used herein, a "carboxy" group refers to —COOH, when used as a terminal group; or —OC(O)— or —C(O)O— when used as an internal group.

As used herein, an ester refers to —COOR$^X$ when used as a terminal group; or —COOR$^X$-when used as an internal group, wherein R$^X$ has been defined above.

As used herein, a formate refers to —OC(O)H.

As used herein, an acetate refers to —OC(O)R$^X$, wherein R$^X$ has been defined above.

As used herein, a "haloaliphatic" group refers to an aliphatic group substituted with one to three halogen. For instance, the term haloalkyl includes the group —CF$_3$.

As used herein, a "mercapto" or "sulfhydryl" group refers to —SH.

As used herein, a "sulfo" group refers to —SO$_3$H or —SO$_3$R$^X$ when used terminally or —S(O)$_3$— when used internally.

As used herein, a "sulfamide" group refers to the structure —NR$^X$—S(O)$_2$—NR$^Y$R$^Z$ when used terminally and —NR$^X$—S(O)$_2$—NR$^Y$— when used internally, wherein R$^X$, R$^Y$, and R$^Z$ have been defined above.

As used herein, a "sulfamoyl" group refers to the structure —O—S(O)$_2$—NR$^Y$R$^Z$ wherein R and R$^Z$ have been defined above.

As used herein, a "sulfonamide" group refers to the structure —S(O)$_2$—NR$^X$R$^Y$ or —NR$^X$—S(O)$_2$—R$^Z$ when used terminally; or —S(O)$_2$—NR$^X$— or —NR$^X$—S(O)$_2$— when used internally, wherein R$^X$, R$^Y$, and R$^Z$ are defined above.

As used herein a "sulfanyl" group refers to —S—R$^X$ when used terminally and —S— when used internally, wherein R$^X$ has been defined above. Examples of sulfanyls include aliphatic-S—, cycloaliphatic-S—, aryl-S—, or the like.

As used herein a "sulfinyl" group refers to —S(O)—R$^X$ when used terminally and —S(O)— when used internally, wherein R$^X$ has been defined above. Examples of sulfinyl groups include aliphatic-S(O)—, aryl-S(O)—, (cycloaliphatic(aliphatic))-S(O)—, cycloalkyl-S(O)—, heterocycloaliphatic-S(O)—, heteroaryl-S(O)—, and/or the like.

As used herein, a "sulfonyl" group refers to —S(O)$_2$—R$^X$ when used terminally and —S(O)$_2$-when used internally, wherein R$^X$ has been defined above. Examples of sulfonyl groups include aliphatic-S(O)$_2$—, aryl-S(O)$_2$—, (cycloaliphatic(aliphatic))-S(O)$_2$—, cycloaliphatic-S(O)$_2$—, heterocycloaliphatic-S(O)$_2$—, heteroaryl-S(O)$_2$—, (cycloaliphatic (amido(aliphatic)))-S(O)$_2$—, and/or the like.

As used herein, a "sulfoxy" group refers to —O—S(O)—R$^X$ or —S(O)—O—R$^X$, when used terminally and —O—S(O)— or —S(O)—O— when used internally, where R$^X$ has been defined above.

As used herein, a "halogen" or "halo" group refers to fluorine (F), chlorine (Cl), bromine (Br), or iodine (I).

As used herein, an "alkoxycarbonyl," which is encompassed by the term carboxy, used alone or in connection with another group refers to a group such as alkyl-O—C(O)—.

As used herein, an "alkoxyalkyl" refers to an alkyl group such as alkyl-O-alkyl-, wherein alkyl has been defined above.

As used herein, a "carbonyl" refers to —C(O)—.

As used herein, an "oxo" refers to =O.

As used herein, the term "phospho" refers to phosphinates and phosphonates. Examples of phosphinates and phosphonates include —P(O)(R$^P$)$_2$, wherein R$^P$ is aliphatic, alkoxy, aryloxy, heteroaryloxy, (cycloaliphatic)oxy, (heterocycloaliphatic)oxy, aryl, heteroaryl, cycloaliphatic or amino.

As used herein, an "aminoalkyl" refers to the structure (R)$_2$N-alkyl-.

As used herein, a "cyanoalkyl" refers to the structure (NC)-alkyl-.

As used herein, a "urea" group refers to the structure —NR$^X$—CO—NR$^Y$R$^Z$ and a "thiourea" group refers to the structure —NR$^X$—CS—NR$^Y$R$^Z$ each when used terminally and —NR$^X$—CO—NR$^Y$— or —NR$^X$—CS—NR$^Y$— each when used internally, wherein R$^X$, R$^Y$, and R$^Z$ have been defined above.

As used herein, a "guanidine" group refers to the structure —N=C(N(R$^X$R$^Y$))N(R$^X$R$^Y$) or —NR$^X$—C(=NR$^X$)NR$^X$R$^Y$ wherein R$^X$ and R$^Y$ have been defined above.

As used herein, the term "amidino" group refers to the structure —C=(NR$^X$)N(R$^X$R$^Y$) wherein R$^X$ and R$^Y$ have been defined above.

As used herein, the term "vicinal" generally refers to the placement of substituents on a group that includes two or more carbon atoms, wherein the substituents are attached to adjacent carbon atoms.

As used herein, the term "geminal" generally refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl (i.e., R$^X$O(O)C-alkyl) is an example of a carboxy group used terminally. A group is internal when the group is present in the middle of or within the termini of a substituent of the chemical structure. Alkylcarboxy (e.g., alkyl-C(O)O— or alkyl-OC(O)—) and alkylcarboxyaryl (e.g., alkyl-C(O)O-aryl- or alkyl-O(CO)-aryl-) are examples of carboxy groups used internally.

As used herein, an "aliphatic chain" refers to a branched or straight aliphatic group (e.g., alkyl groups, alkenyl groups, or alkynyl groups). A straight aliphatic chain has the structure —[CH$_2$]$_v$—, where v is 1-12. A branched aliphatic chain is a straight aliphatic chain that is substituted with one or more aliphatic groups. A branched aliphatic chain has the structure —[CQQ]$_v$— where each Q is independently a hydrogen (H or —H) or an aliphatic group; however, Q shall be an aliphatic group in at least one instance. The term aliphatic chain includes alkyl chains, alkenyl chains, and alkynyl chains, where alkyl, alkenyl, and alkynyl are defined above.

The phrase "optionally substituted" is used herein interchangeably with the phrase "substituted or unsubstituted." As described herein, compounds herein can optionally be substituted with one or more substituents, such as are illustrated generally above, or as exemplified by particular classes, subclasses, and species of the description. As described herein, the variables R, R$^1$, R$^2$, L, Y, and Z, and other variables contained in Formula (A), (B), (C), (D), (E), (F), (G), (H), (J), (K), (M), (X), (I), (I-A), (I-B), (II), (II-A), (II-B), (III), and (IV) described herein encompass specific groups, such as alkyl and aryl. Unless otherwise noted, each of the specific groups for the variables R, R$^{10}$, R$^4$, R$^1$, R$^2$, L, L, D, W, E, V, G, Y, and Z, and other variables contained therein can be optionally substituted with one or more substituents described herein. Each substituent of a specific group is further optionally substituted with one to three of halo, cyano, oxo, alkoxy, hydroxy, amino, nitro, aryl, cycloaliphatic, heterocycloaliphatic, heteroaryl, haloalkyl, and alkyl. For instance, an alkyl group can be substituted with alkylsulfanyl and the alkylsulfanyl can be optionally substituted with one to three of halo, cyano, oxo, alkoxy, hydroxy, amino, nitro, aryl, haloalkyl, and alkyl. As an additional example, the cycloalkyl portion of a (cycloalkyl) carbonylamino can be optionally substituted with one to three of halo, cyano, alkoxy, hydroxy, nitro, haloalkyl, and alkyl. When two alkoxy groups are bound to the same atom or adjacent atoms, the two alkxoy groups can form a ring together with the atom(s) to which they are bound.

As used herein, the term "substituted," whether preceded by the term "optionally" or not, refers generally to the replacement of hydrogen atoms in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different at every position. A ring substituent, such as a heterocycloalkyl, can be bound to another ring, such as a cycloalkyl, to form a spiro-bicyclic ring system, for example, both rings share one common atom. Non-limiting examples of spiro heterocycloalkyls include

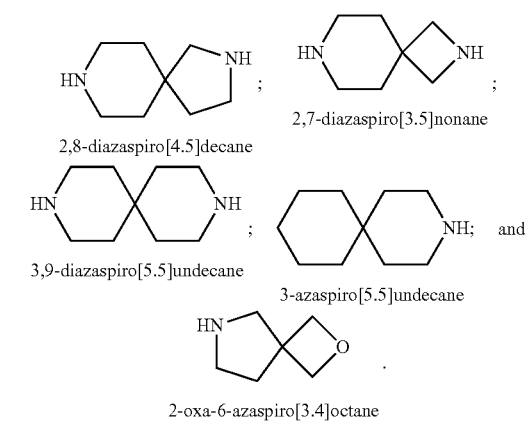

As one of ordinary skill in the art will recognize, combinations of substituents envisioned by this description are those combinations that result in the formation of stable or chemically feasible compounds.

As used herein, the phrase "stable or chemically feasible" refers to compounds that are not substantially altered when subjected to conditions to allow for their production, detection, and their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an "effective amount" is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., Cancer Chemother. Rep., 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

As used herein, the term "about" means within 10% of a value. For example, a dose that is about 100 mg/kg provides that the does can 90 mg/kg to 110 mg/kg. By way of further example, an amount of an additional therapeutic agent ranging from about 50% to about 100% provides that the amount of additional therapeutic agent ranges from 45-55% to 90-110%. A person of skill in the art will appreciate the scope and application of the term "about" when used to describe other values disclosed herein.

Unless otherwise stated, structures depicted herein also are meant to include all isomeric (e.g., enantiomeric, diastereomeric, and geometric (or conformational)) forms of the structure; for example, the (R)- and (S)-configurations for each asymmetric center, (Z)- and (E)-double bond isomers, and (Z)- and (E)-conformational isomers. Therefore, single stereochemical isomers as well as enantiomeric, diastereomeric, and geometric (or conformational) mixtures of the present compounds are within the scope of the description. Alternatively, as used herein, "enantiomeric excess (ee)" refers to a dimensionless mol ratio describing the purity of chiral substances that contain, for example, a single stereogenic center. For instance, an enantiomeric excess of zero would indicate a racemic (e.g., 50:50 mixture of enantiomers, or no excess of one enantiomer over the other). By way of further example, an enantiomeric excess of ninety-nine would indicate a nearly stereopure enantiomeric compound (i.e., large excess of one enantiomer over the other). The percentage enantiomeric excess, % ee=([(R)-compound]−[(S)-compound])/([(R)-compound]+[(S)-compound])×100, where the (R)-compound>(S)-compound; or % ee=([(S)-compound]−[(R)-compound])/([(S)-compound]+[(R)-compound])×100, where the (S)-compound>(R)-compound. Moreover, as used herein, "diastereomeric excess (de)" refers to a dimensionless mol ratio describing the purity of chiral substances that contain more than one stereogenic center. For example, a diastereomeric excess of zero would indicate an equimolar mixture of diastereoisomers. By way of further example, diastereomeric excess of ninety-nine would indicate a nearly stereopure diastereomeric compound (i.e., large excess of one diastereomer over the other). Diastereomeric excess may be calculated via a similar method to ee. As would be appreciated by a person of skill, de is usually reported as percent de (% de). % de may be calculated in a similar manner to % ee.

In certain embodiments, the compounds or inhibitors described herein have an ee, de, % ee, or % de greater than zero. For example, in certain embodiments, the compounds or inhibitors described herein have an ee, de, % ee, or % de of ten. In certain embodiments, the compounds or inhibitors described herein have an ee, de, % ee, or % de of twenty-five. In certain embodiments, the compounds or inhibitors described herein have an ee, de, % ee, or % de of fifty. In certain embodiments, the compounds or inhibitors described herein have an ee, de, % ee, or % de of seventy-five.

In certain embodiments, the compounds or inhibitors described herein have an ee, de, % ee, or % de range from ninety to one hundred. In certain embodiments, the compounds or inhibitors described herein have an ee, de, % ee, or % de range from ninety-five to one hundred. In certain embodiments, the compounds or inhibitors described herein have an ee, de, % ee, or % de range from ninety-seven to one hundred. In certain embodiments, the compounds or inhibitors described herein have an ee, de, % ee, or % de range from ninety-eight to one hundred. In certain embodiments, the compounds or inhibitors described herein have an ee, de, % ee, or % de range from ninety-nine to one hundred.

In one embodiment of a compound or inhibitor described herein, the ee, de, % ee, or % de is one. In one embodiment of a compound or inhibitor described herein, the ee, de, % ee, or % de is two. In one embodiment of a compound or inhibitor described herein, the ee, de, % ee, or % de is three. In one embodiment of a compound or inhibitor described herein, the ee, de, % ee, or % de is four. In one embodiment of a compound or inhibitor described herein, the ee, de, % ee, or % de is five. In one embodiment of a compound or inhibitor described herein, the ee, de, % ee, or % de is six. In one embodiment of a compound or inhibitor described herein, the ee, de, % ee, or % de is seven. In one embodiment of a compound or inhibitor described herein, the ee, de, % ee, or % de is eight. In one embodiment of a compound or inhibitor described herein, the ee, de, % ee, or % de is nine. In one embodiment of a compound or inhibitor described herein, the ee, de, % ee, or % de is ten. In one embodiment of a compound or inhibitor described herein, the ee, de, % ee, or % de is eleven. In one embodiment of a compound or inhibitor described herein, the ee, de, % ee, or % de is twelve. In one embodiment of a compound or inhibitor described herein, the ee, de, % ee, or % de is thirteen. In one embodiment of a compound or inhibitor described herein, the ee, de, % ee, or % de is fourteen. In one embodiment of a compound or inhibitor described herein, the ee, de, % ee, or % de is fifteen. In one embodiment of a compound or inhibitor described herein, the ee, de, % ee, or % de is sixteen. In one embodiment of a compound or inhibitor described herein, the ee, de, % ee, or % de is seventeen. In one embodiment of a compound or inhibitor described herein, the ee, de, % ee, or % de is eighteen. In one embodiment of a compound or inhibitor described herein, the ee, de, % ee, or % de is nineteen. In one embodiment of a compound or inhibitor described herein, the ee, de, % ee, or % de is twenty. In one embodiment of a compound or inhibitor described herein, the ee, de, % ee, or % de is twenty-one. In one embodiment of a compound or inhibitor described herein, the ee, de, % ee, or % de is twenty-two. In one embodiment of a compound or inhibitor described herein, the ee, de, % ee, or % de is twenty-three. In one embodiment of a compound or inhibitor described herein, the ee, de, % ee, or % de is twenty-four. In one embodiment of a compound or inhibitor described herein, the ee, de, % ee, or % de is twenty-five. In one embodiment of a compound or inhibitor described herein, the ee, de, % ee, or % de is twenty-six. In one embodiment of a compound or inhibitor described herein, the ee, de, % ee, or % de is twenty-seven. In one embodiment of a compound or inhibitor described herein, the ee, de, % ee, or % de is twenty-eight. In one embodiment of a compound or inhibitor described herein, the ee, de, % ee, or % de is twenty-nine. In one embodiment of a compound or inhibitor described herein, the ee, de, % ee, or % de is thirty. In one embodiment of a compound or inhibitor described herein, the ee, de, % ee, or % de is thirty-one. In one embodiment of a compound or inhibitor described herein, the ee, de, % ee, or % de is thirty-two. In one embodiment of a compound or inhibitor described herein, the ee, de, % ee, or % de is thirty-three. In one embodiment of a compound or inhibitor described herein, the ee, de, % ee, or % de is thirty-four. In one embodiment of a compound or inhibitor described herein, the ee, de, % ee, or % de is thirty-five. In one embodiment of a compound or inhibitor described herein, the ee, de, % ee, or % de is thirty-six. In one embodiment of a compound or inhibitor described herein, the ee, de, % ee, or % de is thirty-seven. In one embodiment of a compound or inhibitor described herein, the ee, de, % ee, or % de is thirty-eight. In one embodiment of a compound or inhibitor described herein, the ee, de, % ee, or % de is thirty-nine. In one embodiment of a compound or inhibitor described herein, the ee, de, % ee, or % de is forty. In one embodiment of a compound or inhibitor described herein, the ee, de, % ee, or % de is forty-one. In one embodiment of a compound or inhibitor described herein, the ee, de, % ee, or % de is forty-two. In one embodiment of a compound or inhibitor described herein, the ee, de, % ee, or % de is forty-three. In one embodiment of a compound or inhibitor described herein, the ee, de, % ee, or % de is forty-four. In one embodiment of a compound or inhibitor described herein, the ee, de, % ee, or % de is forty-five. In one embodiment of a compound or inhibitor described herein, the ee, de, % ee, or % de is forty-six. In one embodiment of a compound or inhibitor described herein, the ee, de, % ee, or % de is forty-seven. In one embodiment of a compound or inhibitor described herein, the ee, de, % ee, or % de is forty-eight. In one embodiment of a compound or inhibitor described herein, the ee, de, % ee, or % de is forty-nine. In one embodiment of a compound or inhibitor described herein, the ee, de, % ee, or % de is fifty. In one embodiment of a compound or inhibitor described herein, the ee, de, % ee, or % de is fifty-one. In one embodiment of a compound or inhibitor described herein, the ee, de, % ee, or % de is fifty-two. In one embodiment of a compound or inhibitor described herein, the ee, de, % ee, or % de is fifty-three. In one embodiment of a compound or inhibitor described herein, the ee, de, % ee, or % de is fifty-four. In one embodiment of a compound or inhibitor described herein, the ee, de, % ee, or % de is fifty-five. In one embodiment of a compound or inhibitor described herein, the ee, de, % ee, or % de is fifty-six. In one embodiment of a compound or inhibitor described herein, the ee, de, % ee, or % de is fifty-seven. In one embodiment of a compound or inhibitor described herein, the ee, de, % ee, or % de is fifty-eight. In one embodiment of a compound or inhibitor described herein, the ee, de, % ee, or % de is fifty-nine. In one embodiment of a compound or inhibitor described herein, the ee, de, % ee, or % de is sixty. In one embodiment of a compound or inhibitor described herein, the ee, de, % ee, or % de is sixty-one. In one embodiment of a compound or inhibitor described herein, the ee, de, % ee, or % de is sixty-two. In one embodiment of a compound or inhibitor described herein, the ee, de, % ee, or % de is sixty-three. In one embodiment of a compound or inhibitor described herein, the ee, de, % ee, or % de is sixty-four. In one embodiment of a compound or inhibitor described herein, the ee, de, % ee, or % de is sixty-five. In one embodiment of a compound or inhibitor described herein, the ee, de ee, or % de is sixty-six. In one embodiment of a compound or inhibitor described herein, the ee, de, % ee, or % de is sixty-seven. In one embodiment of a compound or inhibitor described herein, the ee, or % de is sixty-eight. In one embodiment of a compound or inhibitor described herein, the ee, or % de is sixty-nine. In one embodiment of a compound or inhibitor described herein, the ee, de, % ee, or % de is seventy. In one embodiment of a compound or inhibitor described herein, the ee, de, % ee, or % de is seventy-one. In one embodiment of a compound or inhibitor described herein, the ee, de, % ee, or % de is seventy-two. In one embodiment of a compound or inhibitor described herein, the ee, de, % ee, or % de is seventy-three. In one embodiment of a compound or inhibitor described herein, the ee, de, % ee, or % de is seventy-four. In one embodiment of a compound or inhibitor described herein, the ee, de, % ee, or % de is seventy-five. In one embodiment of a compound or inhibitor described herein, the ee, de, % ee, or % de is seventy-six. In one embodiment of a compound or inhibitor described herein, the ee, de, % ee, or % de is seventy-seven. In one embodiment of a compound or inhibitor described herein, the ee, de, % ee, or % de is seventy-eight. In one embodiment of a compound or inhibitor described herein, the ee, de, % ee, or % de is seventy-nine. In one embodiment of a compound or inhibitor described herein, the ee, de, % ee, or % de is eighty. In one embodiment of a compound or inhibitor described herein, the ee, de, % ee, or % de is eighty-one. In one embodiment of a compound or inhibitor described herein, the ee, de, % ee, or % de is eighty-two. In one embodiment of a compound or inhibitor described herein, the ee, de, % ee, or % de is eighty-three. In one embodiment of a compound or inhibitor described herein, the ee, de, % ee, or % de is eighty-four. In one embodiment of a compound or inhibitor described herein, the ee, de, % ee, or % de is eighty-five. In one embodiment of a compound or inhibitor described herein, the ee, de, % ee, or % de is eighty-six. In one embodiment of a compound or inhibitor described herein, the ee, de, % ee, or % de is eighty-seven. In one embodiment of a compound or inhibitor described herein, the ee, de, % ee, or % de is eighty-eight. In one embodiment of a compound or inhibitor described herein, the ee, de, % ee, or % de is eighty-nine. In one embodiment of a compound or inhibitor described herein, the ee, de, % ee, or % de is ninety. In one embodiment of a compound or inhibitor described herein, the ee, de, % ee, or % de is ninety-one. In one embodiment of a compound or inhibitor described herein, the ee, de, % ee, or % de is ninety-two. In one embodiment of a compound or inhibitor described herein, the ee, de, % ee, or % de is ninety-three. In one embodiment of a compound or inhibitor described herein, the ee, de, % ee, or % de is ninety-four. In one embodiment of a compound or inhibitor described herein, the ee, de, % ee, or % de is ninety-five. In one embodiment of a compound or inhibitor described herein, the ee, de, % ee, or % de is ninety-six. In one embodiment of a compound or inhibitor described herein, the ee, de, % ee, or % de is ninety-seven. In one embodiment of a compound or inhibitor described herein, the ee, de, % ee, or % de is ninety-eight. In one embodiment of a compound or inhibitor described herein, the ee, de, % ee, or % de is ninety-nine. In one embodiment of a compound or inhibitor described herein, the ee, de, % ee, or % de is one hundred. In certain embodiments, compounds or inhibitors described within Table 1 herein have an ee, de, % ee, or % de as described within this paragraph. In certain embodiments, compound or inhibitor 32, 34, 44, 57, 72, 121, 130, 149, 194, 195, 196, 197, 198, 199, 200, 201, 202, 203, 204, 205, 206, 207, 208, 209, 210, 211, 212, 213, 214, 215, 216, 217, 218, as described in the Examples and/or Biological Examples have an ee, de, % ee, or % de as described within this paragraph. Unless otherwise stated, all tautomeric forms of the compounds of the description are within the scope of the description. Additionally, unless otherwise stated, structures depicted herein also are meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this description. Such compounds are useful, for example, as analytical tools or probes in biological assays, or as therapeutic agents.

As used herein, the term "& 1" means that a compound including the "& 1" notation at a particular chemical element or atom (e.g., carbon) within the compound was prepared as a mixture of two stereoisomers at the noted chemical element or atom (e.g., a diastereomeric mixture having a de or % de as described above).

Chemical structures and nomenclature are derived from ChemDraw, version 11.0.1, Cambridge, Mass.

It is noted that the use of the descriptors "first," "second," "third," or the like is used to differentiate separate elements (e.g., solvents, reaction steps, processes, reagents, or the like) and may or may not refer to the relative order or relative chronology of the elements described.

Uses of the Compounds and Compositions

The bifunctional compounds described herein are useful for degrading BTK in biological samples or in patients via an ubiquitin proteolytic pathway. Thus, an embodiment of this disclosure provides a method of treating a BTK-mediated disease or disorder. As used herein, the term "BTK-mediated disease or disorder" means any disease, disorder, or other deleterious condition in which a BTK is known to play a role. In some instances, a BTK-mediated disease or disorder is a proliferative disorder or an autoimmune disorder. Examples of proliferative disorders include cancer.

In one aspect, provided herein are methods of treating or preventing cancer in a subject in need thereof. In certain embodiments, the methods comprise the step of orally administering to the subject an amount of a bifunctional compound capable of inducing proteolytic degradation of Bruton's tyrosine kinase. In certain embodiments, the amount is effective to treat or prevent the cancer.

In certain embodiments, the cancer is any cancer described below. In particular embodiments, the cancer comprises a solid tumor. In certain embodiments, the cancer is a B cell malignancy. In certain embodiments, the cancer is selected from the group consisting of chronic lymphocytic leukemia (CLL), small lymphocytic lymphoma (SLL), transformed CLL or Richter's transformation, small cell lymphoma, follicular lymphoma (FL), diffuse large B-cell lymphoma (DLBCL), non-Hodgkin lymphoma, mantle cell lymphoma (MCL), marginal zone lymphoma (MZL), Waldenstrom macroglobulinemia (WM), and central nervous system (CNS) lymphoma. In certain embodiments, the cancer is chronic lymphocytic leukemia. In certain embodiments, the cancer is small cell lymphoma. In certain embodiments, the cancer is follicular lymphoma. In certain embodiments, the cancer is diffuse large B-cell lymphoma. In certain embodiments, the cancer is non-Hodgkin lymphoma. In certain embodiments, the cancer is mantle cell lymphoma. In certain embodiments, the cancer is marginal zone lymphoma. In certain embodiments, the cancer is Waldenstrom macroglobulinemia. In certain embodiments, the cancer is small lymphocytic lymphoma (SLL). In certain embodiments, the cancer is CNS lymphoma. In certain embodiments, the cancer is transformed CLL or Richter's transformation.

In certain embodiments, the subject has a mutant Bruton's tyrosine kinase. In certain embodiments, the subject has a C481 mutant Bruton's tyrosine kinase. In certain embodiments, the subject has a C481S mutant Bruton's tyrosine kinase. In certain embodiments, the cancer is resistant to ibrutinib. Those of skill will recognize that certain ibrutinib-resistant cancers express a C481 mutant Bruton's tyrosine kinase, for instance C481S Bruton's tyrosine kinase. For example, in certain embodiments, the subject has a C481 mutant Bruton's tyrosine kinase and the cancer is chronic lymphocytic leukemia (CLL).

In another aspect, provided herein are methods of degrading Bruton's tyrosine kinase in a subject in need thereof. The methods comprise the step of orally administering to the subject an amount of a bifunctional compound capable of inducing proteolytic degradation of Bruton's tyrosine kinase. In certain embodiments, the amount is effective to degrade Bruton's tyrosine kinase in the subject. The Bruton's tyrosine kinase can be expressed in any cells or tissues of the subject. In certain embodiments, the Bruton's tyrosine kinase is expressed in splenocytes. In certain embodiments, the Bruton's tyrosine kinase is expressed in peripheral blood mononuclear cells.

In certain embodiments, the Bruton's tyrosine kinase is a mutant form. In certain embodiments, Bruton's tyrosine kinase comprises a C481 mutation. In certain embodiments, the Bruton's tyrosine kinase comprises a C481S mutation. In certain embodiments, the Bruton's tyrosine kinase is resistant to ibrutinib.

In another aspect, provided herein are methods of preventing B cell activation in a subject in need thereof. The methods comprise the step of orally administering to the subject an amount of a bifunctional compound capable of inducing proteolytic degradation of Bruton's tyrosine kinase. In certain embodiments, the amount is effective to prevent B cell activation. In certain embodiments, the B cell expresses CD69. In certain embodiments, the B cell expresses CD86. In certain embodiments, the B cell expresses CD69 and CD86.

In another aspect, provided herein are methods of degrading a mutant Bruton's tyrosine kinase. The methods comprise the step of contacting a cell expressing the mutant Bruton's tyrosine kinase with an amount of a bifunctional compound capable of inducing proteolytic degradation of Bruton's tyrosine kinase. In certain embodiments, the amount is effective to degrade the mutant Bruton's tyrosine kinase. In certain embodiments, the mutant Bruton's tyrosine kinase is a C481 mutant. In certain embodiments, the mutant Bruton's tyrosine kinase is a C481S mutant.

In the methods, the bifunctional compounds comprise a moiety capable of specifically binding BTK and further comprise a moiety capable of recruiting an ubiquitin ligase to degrade the BTK. Particular compounds are described herein. The compounds can be administered in any form, including pharmaceutically acceptable salts and pharmaceutical compositions.

The bifunctional compound can be administered in any dose deemed suitable by the practitioner of skill. In certain embodiments, the dose is 0.1-1000 mg/kg. In certain embodiments, the dose is 0.1-900 mg/kg. In certain embodiments, the dose is 0.1-800 mg/kg. In certain embodiments, the dose is 0.1-700 mg/kg. In certain embodiments, the dose is 0.1-600 mg/kg. In certain embodiments, the dose is 0.1-500 mg/kg. In certain embodiments, the dose is 0.1-400 mg/kg. In certain embodiments, the dose is 0.1-300 mg/kg. In certain embodiments, the dose is 0.1-200 mg/kg. In certain embodiments, the dose is 0.1-100 mg/kg. In certain embodiments, the dose is selected from the group consisting of 100 mg/kg, 200 mg/kg, 300 mg/kg, 450 mg/kg, 600 mg/kg, 800 mg/kg, and 1000 mg/kg. In certain embodiments, the dose is about 25 mg/kg. In certain embodiments, the dose is about 50 mg/kg. In certain embodiments, the dose is about 75 mg/kg. In certain embodiments, the dose is about 100 mg/kg. In certain embodiments, the dose is about 150 mg/kg. In certain embodiments, the dose is about 200 mg/kg. In certain embodiments, the dose is about 250 mg/kg. In certain embodiments, the dose is about 300 mg/kg. In certain embodiments, the dose is about 400 mg/kg. In certain embodiments, the dose is about 450 mg/kg. In certain embodiments, the dose is about 500 mg/kg. In certain embodiments, the dose is about 600 mg/kg. In certain embodiments, the dose is about 700 mg/kg. In certain embodiments, the dose is about 750 mg/kg. In certain embodiments, the dose is about 800 mg/kg. In certain embodiments, the dose is about 900 mg/kg. In certain embodiments, the dose is about 1000 mg/kg.

The dose can be administered on a schedule deemed suitable by the person of skill in the art. In certain embodiments, the dose is administered once per day. In certain embodiments, the dose is administered twice per day. In certain embodiments, the dose is administered three times per day. In certain embodiments, the dose is administered four times per day. In certain embodiments, the dose is administered in divided doses. In certain embodiments, the dose is administered in two divided doses per day. In certain embodiments, the dose is administered in three divided doses per day. In certain embodiments, the dose is administered in four divided doses per day.

Dosing can continue for any length of time deemed suitable by the person of skill in the art. In certain embodiments, the dose is administered daily for fourteen days. In certain embodiments, the dose is administered daily for thirteen days. In certain embodiments, the dose is administered daily for twelve days. In certain embodiments, the dose is administered daily for eleven days. In certain embodiments, the dose is administered daily for ten days. In certain embodiments, the dose is administered daily for nine days. In certain embodiments, the dose is administered daily for eight days. In certain embodiments, the dose is administered daily for seven days. In certain embodiments, the dose is administered daily for six days. In certain embodiments, the dose is administered daily for five days. In certain embodiments, the dose is administered daily for four days. In certain embodiments, the dose is administered daily for three days. In certain embodiments, the dose is administered daily for two days. In certain embodiments, the dose is administered for one day.

In the dosing schedule, the doses can be administered on consecutive days or cyclicly, according to the judgment of the practioner of skill. In certain embodiments, the doses are administered on consecutive days. In certain embodiments, the doses are administered with an interval between doses. In certain embodiments, the interval is one day. In certain embodiments, the interval is two days. In certain embodiments, the interval is three days. In certain embodiments, the interval is four days. In certain embodiments, the interval is five days. In certain embodiments, the interval is six days.

In certain embodiments, the dose is administered weekly. In certain embodiments, the dose is administered twice per week. In certain embodiments, the dose is administered three times per week.

In certain embodiments, the dose(s) are administered for a period of time with a first interval between dose(s), and then the dose(s) are re-administered for a period of time following the first interval between dose(s), wherein this dosing regimen can be repeated (i.e., cyclicly or cyclically, for example, after a second, third, etc. interval between subsequent administrations of dose(s)) according to the judgment of the practitioner of skill. For example, in one embodiment, a first dose is administered for one week, followed by a first interval of one week without the first dose administration; then, a second dose is re-administered for another week, followed by a second interval of one week without the first or second dose administration, and so on cyclically. Other perturbations for first, second, third, etc. dose(s) followed by perturbations for first, second, third, etc. interval(s), and combinations thereof, are contemplated herein as would be appreciated by the practitioner of skill and the need of the patient. For example, in one embodiment, a first dose is administered daily for one week, followed by a first interval of three weeks without the first daily dose administration; then, a second dose is re-administered biweekly for another week, followed by a second interval of four weeks without the first daily or second biweekly dose administration, and so on cyclically.

The compound can be administered by any route of administration deemed suitable by the practioner of skill. In certain embodiments, the dose is administered orally. Formulations and techniques for administration are described in detail below.

In certain embodiments, term "cancer" includes, but is not limited to, the following cancers: epidermoid Oral: buccal cavity, lip, tongue, mouth, pharynx, squamous cell carcinoma of the head and neck (HNSCC); Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell lung cancer (NSCLC); Gastrointestinal: gastric cancer, esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, microsatellite stable colorectal cancer (MSS CRC), rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma), metastatic castrate-resistant prostate cancer (mCRPC), muscle-invasive urothelial cancer; Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma (MM), malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical cancer, cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast, triple-negative breast cancer (TNBC), platinum-resistant epithelial ovarian cancer (EOC); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders (e.g., mantle cell lymphoma, Waldenstrom's macroglobulinemia, Marginal zone lymphoma, and Follicular lymphoma); Skin: malilymphgnant melanoma, basal cell carcinoma, squamous cell carcinoma, Karposi's sarcoma, keratoacanthoma, moles dysplastic nevi, lipoma, angioma, dermatofibroma, keloids, psoriasis; Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; Adrenal glands: neuroblastoma; and metatstaic melanoma.

Examples of autoimmune disorders include uticaria, graft-versus-host disease (GVHD), acute graft-versus-host disease, pemphigus vulgaris, achalasia, Addison's disease, Adult Still's disease, agammaglobulinemia, alopecia areata, amyloidosis, ankylosing spondylitis, anti-GBM/anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, axonal and neuronal neuropathy (AMAN), Baló disease, Behcet's disease, benign mucosal pemphigoid, bullous pemphigoid, Castleman disease (CD), Celiac disease, Chagas disease, chronic inflammatory demyelinating polyneuropathy (CIDP), chronic recurrent multifocal osteomyelitis (CRMO), Churg-Strauss Syndrome (CSS) or Eosinophilic Granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), herpes gestationis or pemphigoid gestationis (PG), hidradenitis suppurativa (HS) (Acne Inversa), hypogammalglobulinemia, IgA nephropathy, IgG4-related sclerosing disease, immune thrombocytopenic purpura (ITP), inclusion body myositis (IBM), interstitial cystitis (IC), juvenile arthritis, juvenile diabetes (Type 1 diabetes), juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, Multifocal Motor Neuropathy (MMN) or MMNCB, multiple sclerosis, myasthenia gravis, myositis, narcolepsy, neonatal lupus, neuromyelitis optica, neutropenia, ocular cicatricial pemphigoid, optic neuritis, palindromic rheumatism (PR), PANDAS, paraneoplastic cerebellar degeneration (PCD), paroxysmal nocturnal hemoglobinuria (PNH), Parry Romberg syndrome, pars planitis (peripheral uveitis), Parsonnage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive Arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjogren's syndrome, sperm and testicular autoimmunity, stiff person syndrome (SPS), subacute bacterial endocarditis (SBE), Susac's syndrome, sympathetic ophthalmia (SO), Takayasu's arteritis, temporal arteritis (giant cell arteritis), thrombocytopenic purpura (TTP), Tolosa-Hunt syndrome (THS), transverse myelitis, Type 1 diabetes, ulcerative colitis (UC), undifferentiated connective tissue disease (UCTD), uveitis, vasculitis, vitiligo, Vogt-Koyanagi-Harada Disease, and Wegener's granulomatosis (or Granulomatosis with Polyangiitis (GPA)).

In certain embodiments, provided herein are methods of degrading a mutant Bruton's tyrosine kinase. The methods comprise the step of contacting a cell expressing the mutant Bruton's tyrosine kinase with an amount of a bifunctional compound capable of inducing proteolytic degradation of Bruton's tyrosine kinase. In certain embodiments, the amount of a bifunctional compound capable of inducing proteolytic degradation of Bruton's tyrosine kinase is the amount effective to degrade the mutant Bruton's tyrosine kinase. In certain embodiments, the mutant Bruton's tyrosine kinase is a C481 mutant. In certain embodiments, the mutant Bruton's tyrosine kinase is a C481S mutant. The contacting can be in vitro or in vivo. In certain embodiments, the contacting is in vitro. In certain embodiments, the contacting is in vivo. In certain embodiments, the contacting is in a subject in need thereof.

Bifunctional Compounds

The methods provided herein comprise administration of a bifunctional compound. The bifunctional compound can be any compound described herein. In certain embodiments, the bifunctional compound comprises at least two moieties. One moiety is capable of specifically binding Bruton's tyrosine kinase (BTK). The other moiety is capable of recruiting an ubiquitin ligase to degrade the BTK. In certain embodiments, the ubiquitin ligase is an E3 ligase. In certain embodiments, the ubiquitin ligase is cereblon (CRBN) or comprises cereblon as a component.

In the methods, the compound can be a compound of Formula (A1)

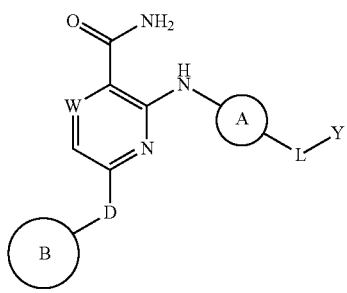

(A1)

or a pharmaceutically acceptable salt thereof, wherein W is CH or N; D is a bond or a linker; Ring A is aryl or heteroaryl; Ring B is aryl or heteroaryl; L is a bond or a linker; and Y is a moiety capable of binding an ubiquitin ligase.

In the methods, the compound can be a compound of Formula (A)

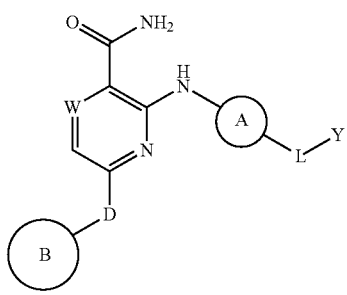

(A)

or a pharmaceutically acceptable salt thereof, wherein W is CH or N; D is a bond or —NH—; Ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of Ring A each possess one to three heteroatoms independently selected from N, O, or S, wherein Ring A is optionally and independently substituted with up to three substituents selected from halo, —CN, —COOH, $NH_2$, and optionally substituted $C_{1-6}$ alkyl; Ring B is a phenyl, a 5-6 membered heteroaryl, a 4-6 membered heterocycloalkyl, or a 8-10 membered (e.g., 8-9 membered or 9-10 membered) spiro bicyclic heterocycle, wherein Ring B is optionally substituted, and wherein the heteroaryl and heterocycloalkyl of Ring B has one to three heteroatoms independently selected from N, O, or S; L is —$X^1$-$X^2$-$X^3$-$X^4$-$X^5$—; $X^1$ is a bond, —C(O)—N(R), —N(R)—C(O), —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro or fused bicyclic heterocycloalkyl having one to three heteroatoms independently selected from N, O, or S, or 4-6 membered monocyclic heterocycloalkyl having one to two heteroatoms independently selected from N, O, or S, wherein each of the monocyclic and bicyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having one to two heteroatoms independently selected from N, O, or S; $X^3$ is a bond, —$C_{1-8}$ alkyl-, —C≡C—, 4-6 membered cycloalkyl, —N(R)—, —N(R)—C(O)—, —(O—$CH_2$—$CH_2$)$_p$—, —($CH_2$—$CH_2$—O)$_p$—, 4-6 membered heterocycloalkyl having one to two heteroatoms independently selected from N, O, or S, wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—$CH_2$—$CH_2$)$_m$—, a 5-6 membered saturated, partially unsaturated, or fully unsaturated carbocycle, or a 5-6 membered saturated, partially unsaturated, or fully unsaturated heterocycle having one to three heteroatoms independently selected from N, O, or S; $X^5$ is a bond, —$C_{1-4}$ alkyl-, —N(R)—, —O—, —C(O)—, or —C(O)—N(R)—; each R is independently —H or —$C_{1-3}$ alkyl (e.g., methyl, ethyl, propyl, or iso-propyl); and each of m, n, and p is independently an integer from one to three (e.g., one, two, or three); and Y is

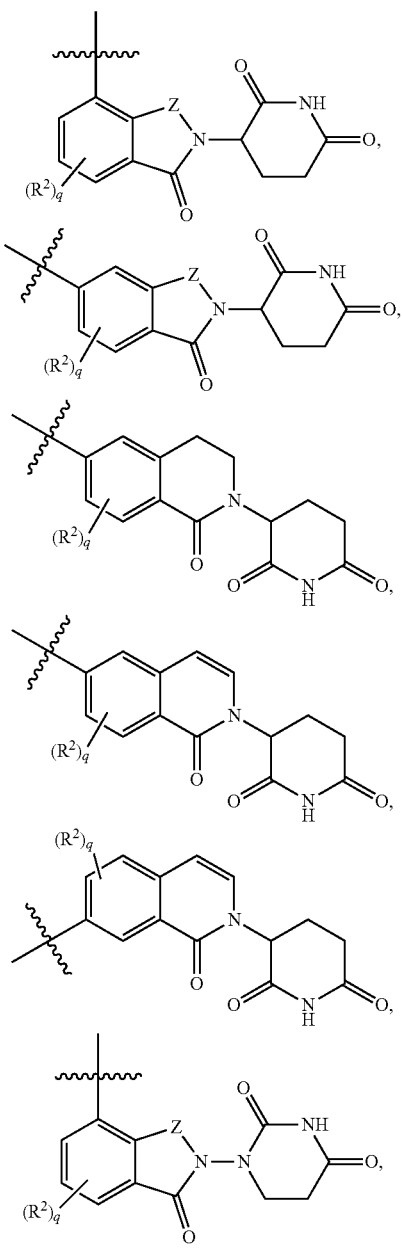

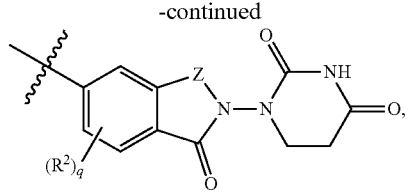
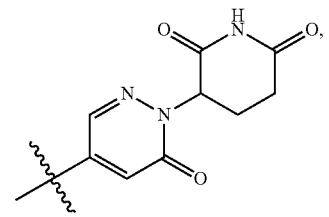
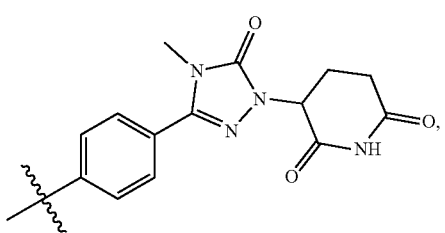
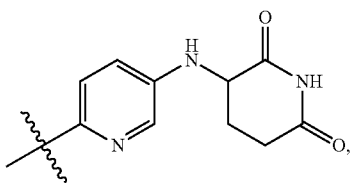
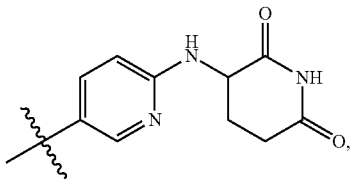
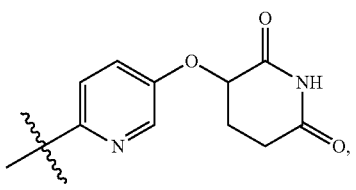
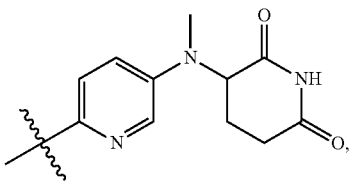
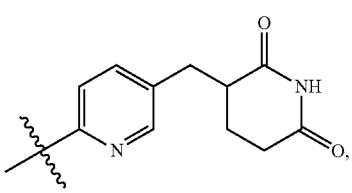
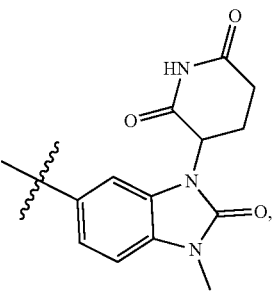
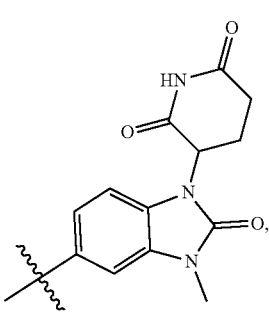
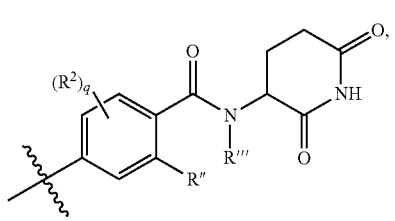
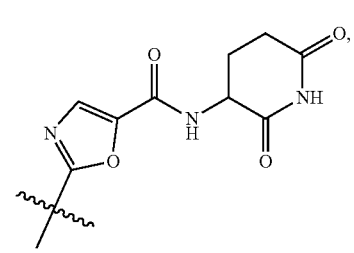
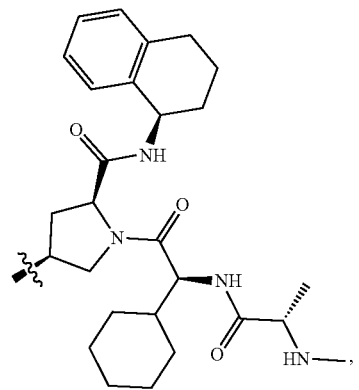

-continued

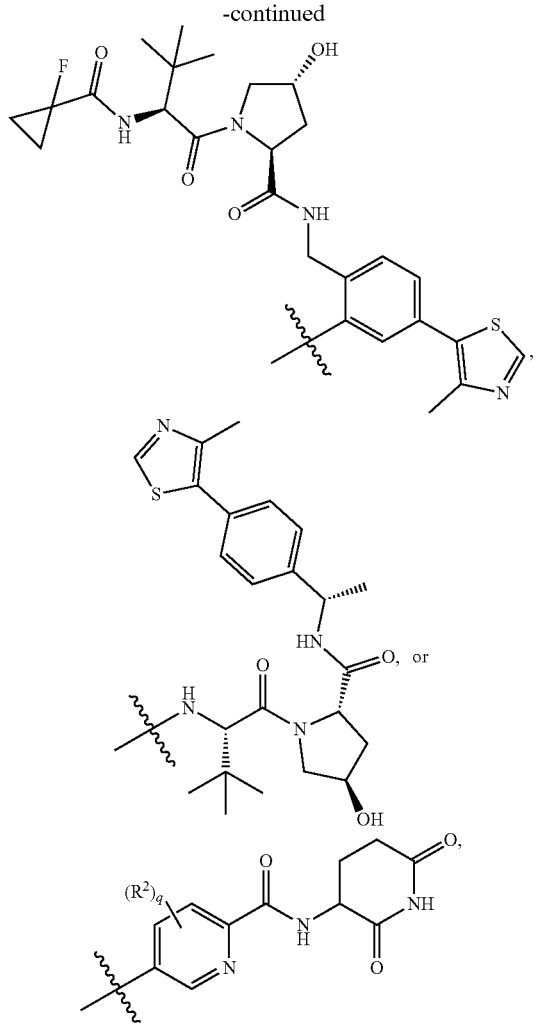

wherein each R² is independently halo, —CN, or —C$_{1-4}$ alkyl, wherein each C$_{1-4}$ alkyl is optionally and independently substituted with up to three instances of halo, —CN, —COOH, —COONH₂, —NH₂, or —CF₃; each R" and R'" are independently hydrogen (H or —H) or, together with the atoms to which they are attached, form a 5-6 membered partially unsaturated or fully unsaturated benzofuzed heterocycle; each Z is —C(R$^A$)₂— or —C(O)—; each R$^A$ is independently —H or —C$_{1-4}$ alkyl; and q is zero, one, or two.

With the exception of the moieties of group R, all moieties of the linking group L as defined in the compound of Formula (A) are bivalent moieties unless otherwise specified. For example, any alkyl (e.g., n-propyl, n-butyl, n-hexyl, and the like), aryl (e.g., phenyl), cycloalkyl (e.g., cyclopropyl, cyclohexyl, and the like), heteroaryl, heterocylcoalkyl (e.g., piperidine, piperazine, and the like) that is present in L is bivalent unless otherwise specified.

In some embodiments, Ring B is an optionally substituted 5-6 membered heterocycloalkyl having one to two nitrogen atoms. For example, Ring B is piperidine-yl, piperizine-yl, or pyrrolidine-yl, any of which is optionally substituted.

In some embodiments, Ring B is an optionally substituted 5-6 membered heteroaryl having one to two heteroatoms independently selected from N and S. For example, Ring B is pyridine-yl, pyrazine-yl, or pyrimidine, any of which is optionally substituted.

In some embodiments, Ring B is

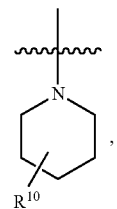

wherein R$^{10}$ is halo, —H, —C$_{1-5}$ alkyl (e.g., —C$_{1-3}$ alkyl), 3-6 membered cycloalkyl, 5-6 membered heterocycloalkyl, —CN, —OH, —CF₃, —CH₂OH, —CH₂CH₂OH, —C(O)OH,

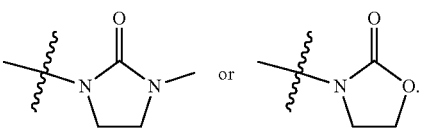

In some embodiments, Ring B is

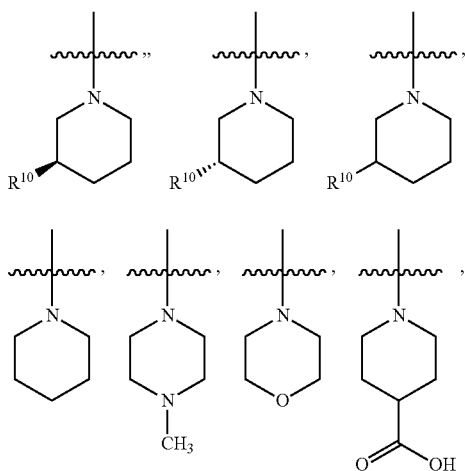

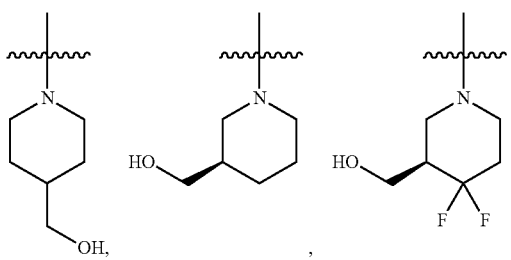

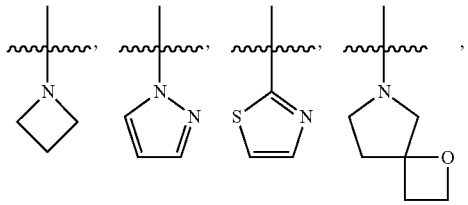

-continued

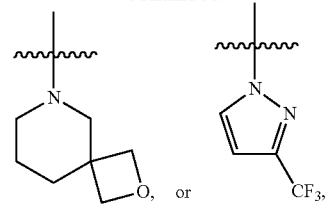

wherein $R^{10}$ is

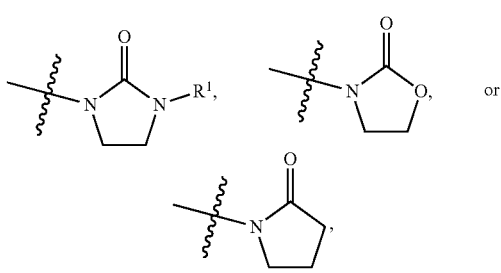

and wherein $R^1$ is a $C_{1-4}$ alkyl group. For example, Ring B is

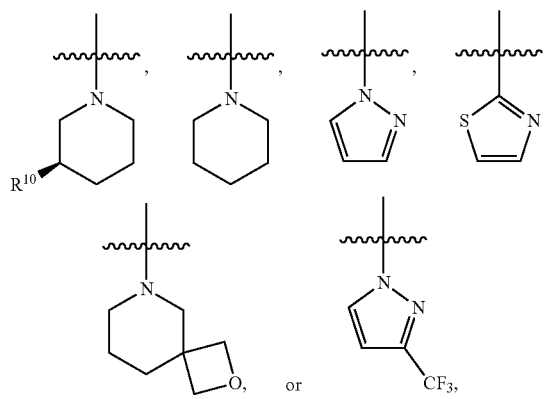

wherein $R^{10}$ is

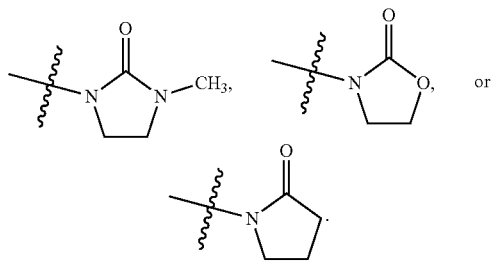

And, in some instances, Ring B is

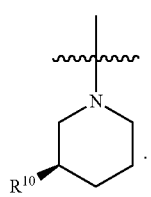

In other instances, $R^{10}$ is

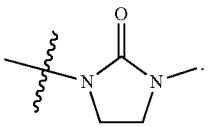 [SMILES: *N1CCN(C)C1=O]

In some embodiments Ring A is

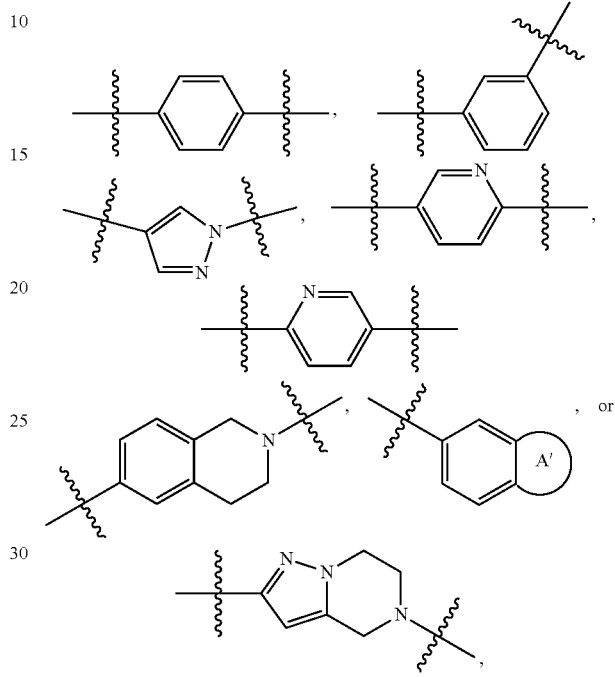

wherein Ring A' together with the phenyl ring to which Ring A' is fused form a 9-10 membered bicyclic aryl or a 9-10 membered bicyclic heteroaryl wherein the bicyclic heteroaryl (i.e., the bicyclic heteroaryl including Ring A') has one to three heteroatoms independently selected from N, O, or S. For example, Ring A is

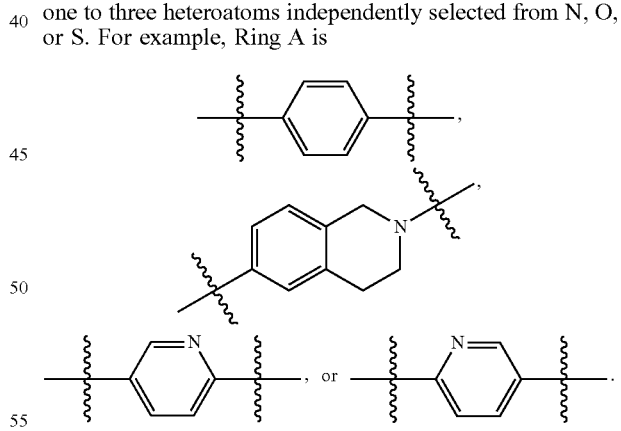

In some embodiments, at least one of $X^1$, $X^2$, and $X^5$ is —N(R)—, —C(O)—N(R)—, or —CH$_2$—.
In some embodiments, $X^1$ is —C(O)—N(R)—.
In some embodiments, $X^2$ is —(O—CH$_2$—CH$_2$)$_n$—, —(CH$_2$—CH$_2$—O)$_n$—, or —C$_{1-5}$ alkyl-.
In some embodiments, $X^3$ is a bond, —C≡C—, —C$_{1-4}$ alkyl-, or —N(R)—.
In some embodiments, $X^4$ is a bond, —CH$_2$—, or —N(R)—.
In some embodiments, $X^5$ is a bond.
In some embodiments, $X^1$ is —(O—CH$_2$—CH$_2$—CH$_2$)$_m$—, m is one, and $X^2$ is —C(O)—N(R)—.

In some embodiments, $X^1$ is —$CH_2$—, —C(O)—,
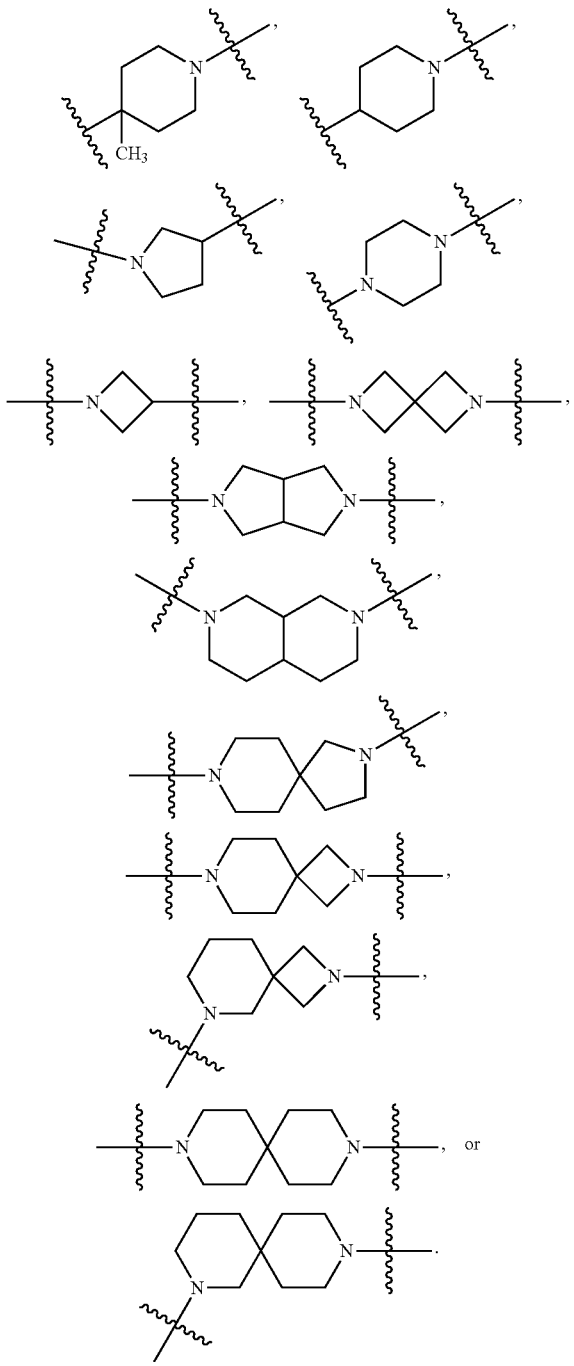
In some embodiments, $X^2$ is a bond, —C(O)—, —$C_{1-5}$ alkyl-,
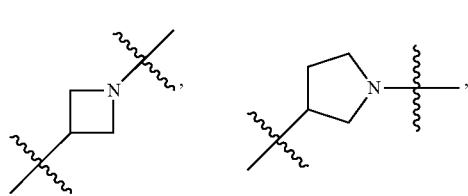
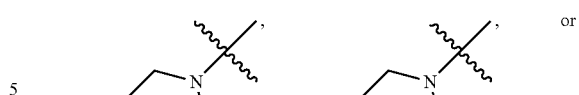

In some embodiments, $X^3$ is bond, —$C_{1-4}$ alkyl-, 4-6 membered cycloalkyl, or —N(R)—.
In some embodiments, $X^3$ is a bond, —$C_{1-4}$ alkyl-, —NH—,
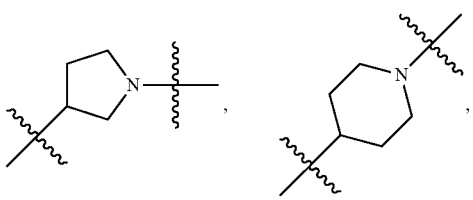
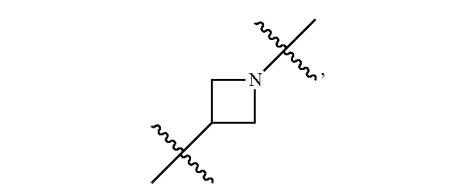
or —C≡C—.
In some embodiments, $X^4$ is a bond,
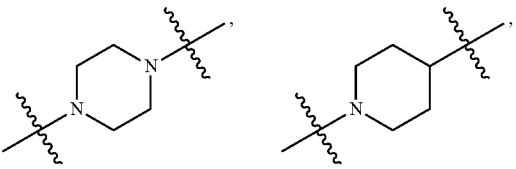
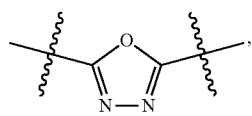
—$C_{1-4}$ alkyl-, —$CH_2$—$CH_2$—N(R)—, or —N(R)—.
In some embodiments, $X^5$ is a bond, —$C_{1-4}$ alkyl-, —N(R)—, or —C(O)—N(R)—.

In some embodiments, L is
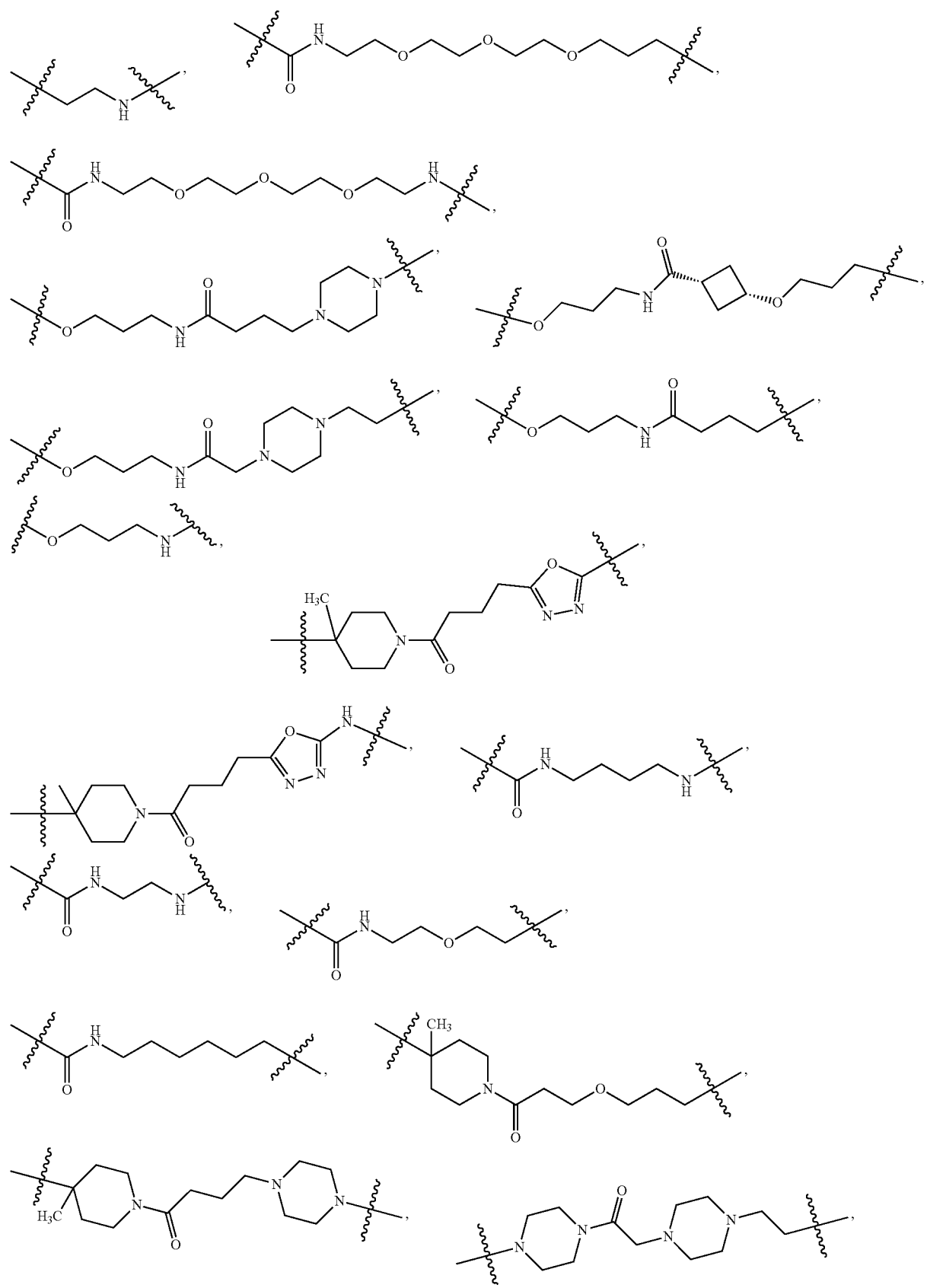

-continued
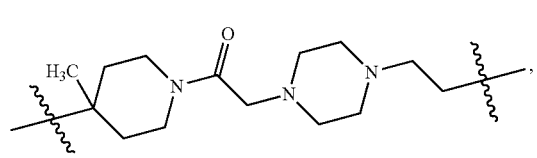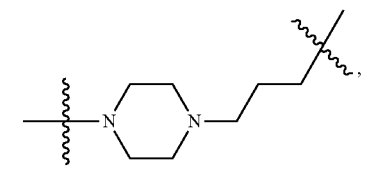
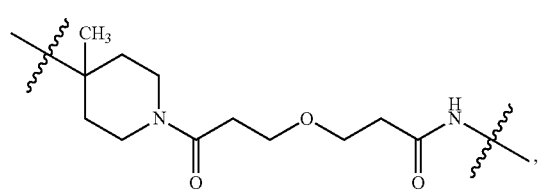
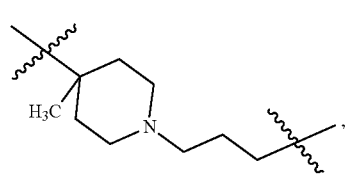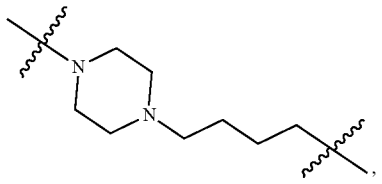
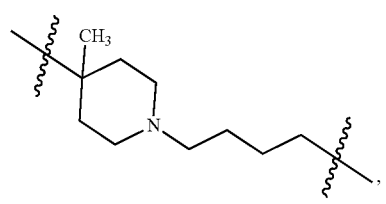
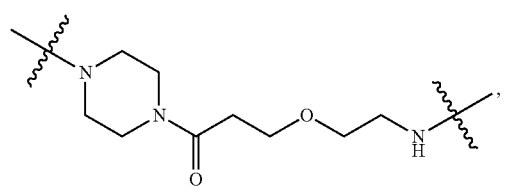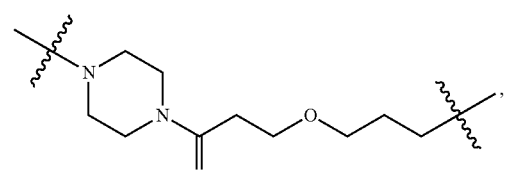
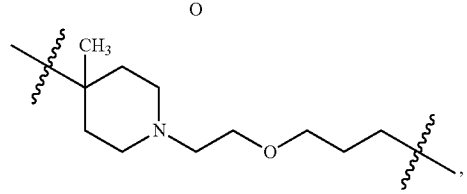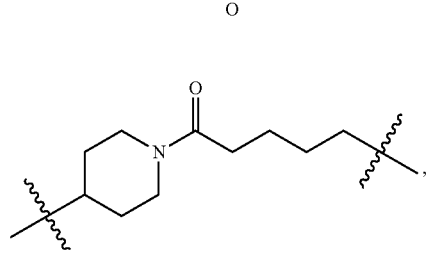
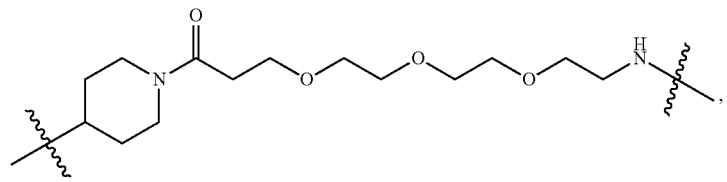
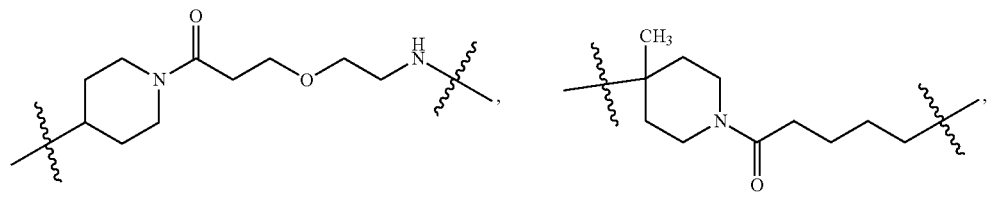

-continued
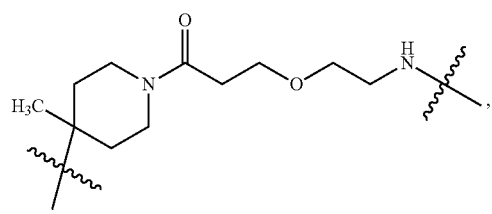 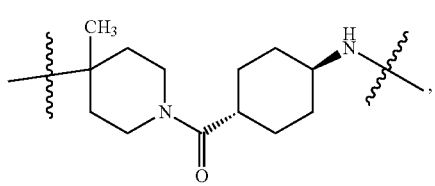
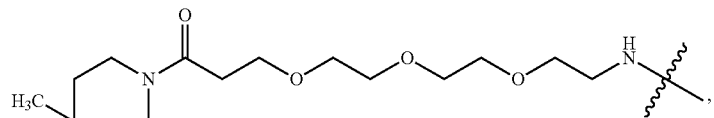
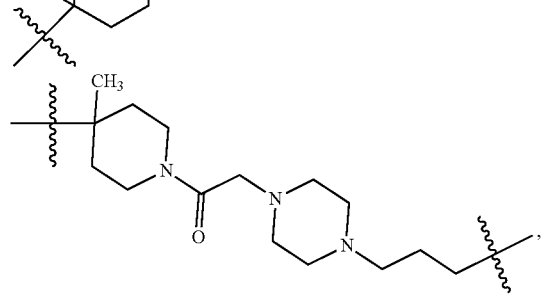 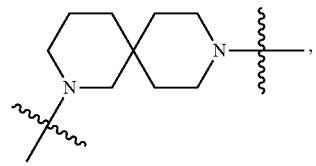
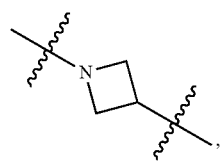 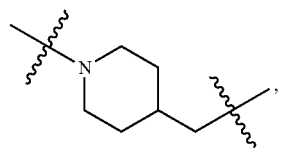
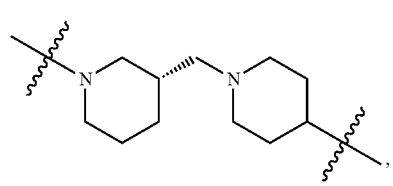 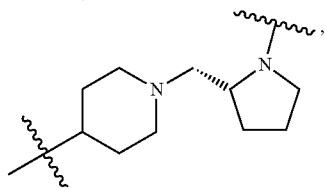
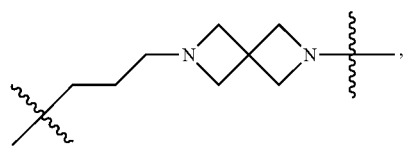 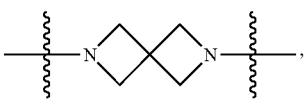
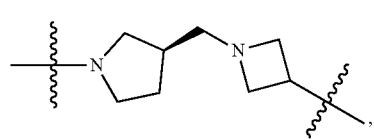 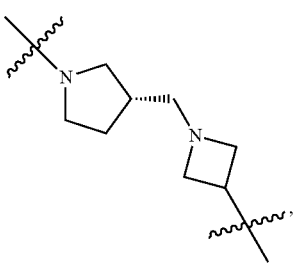
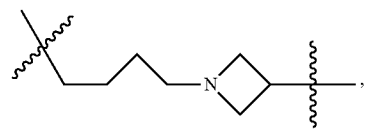 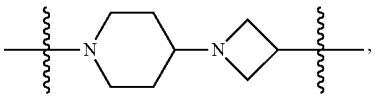

-continued
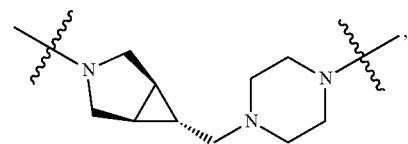 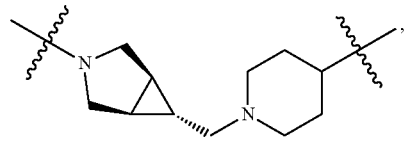
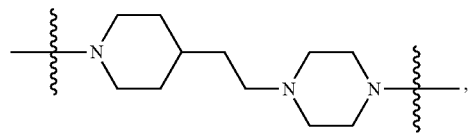 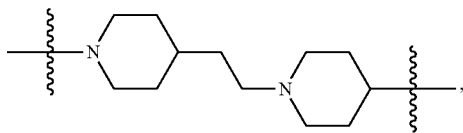
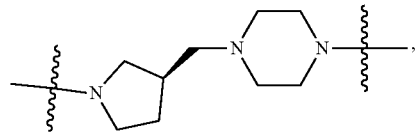 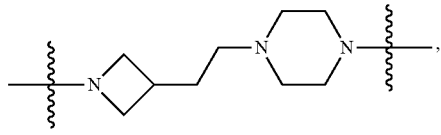
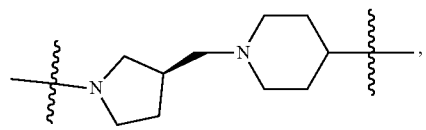 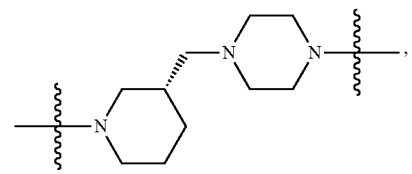
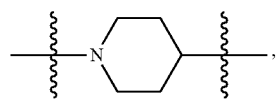
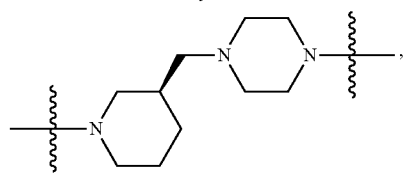
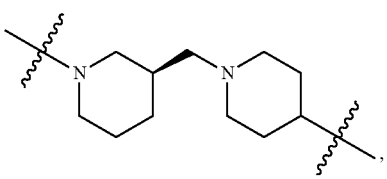
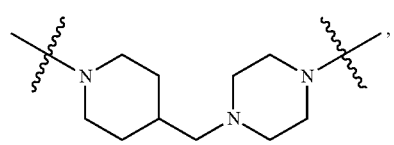
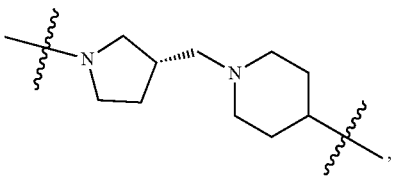
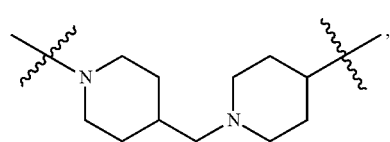
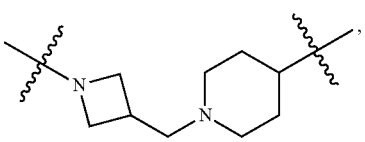
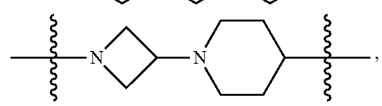
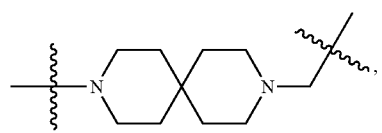 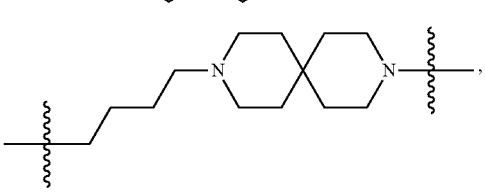

-continued
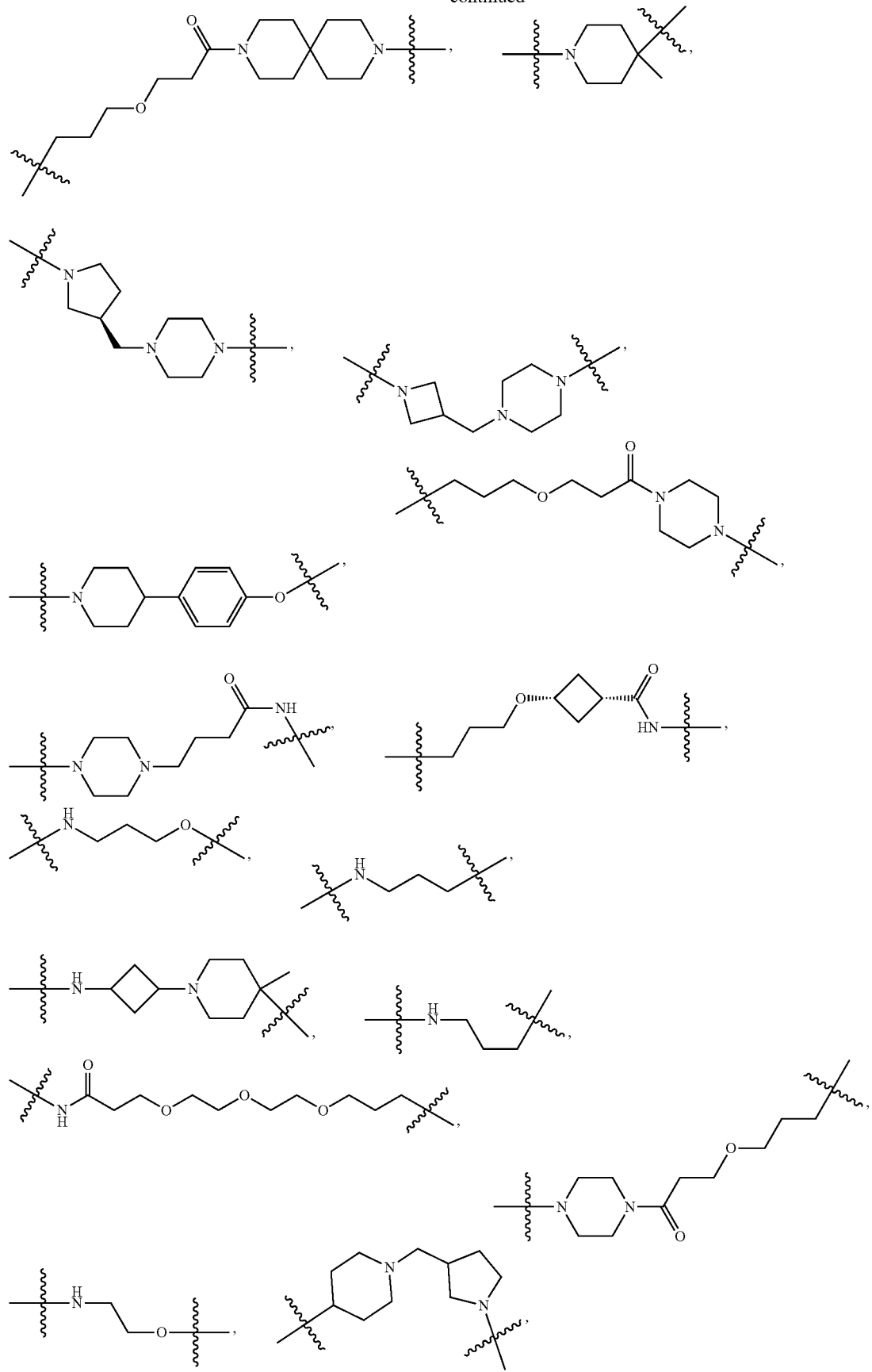

-continued
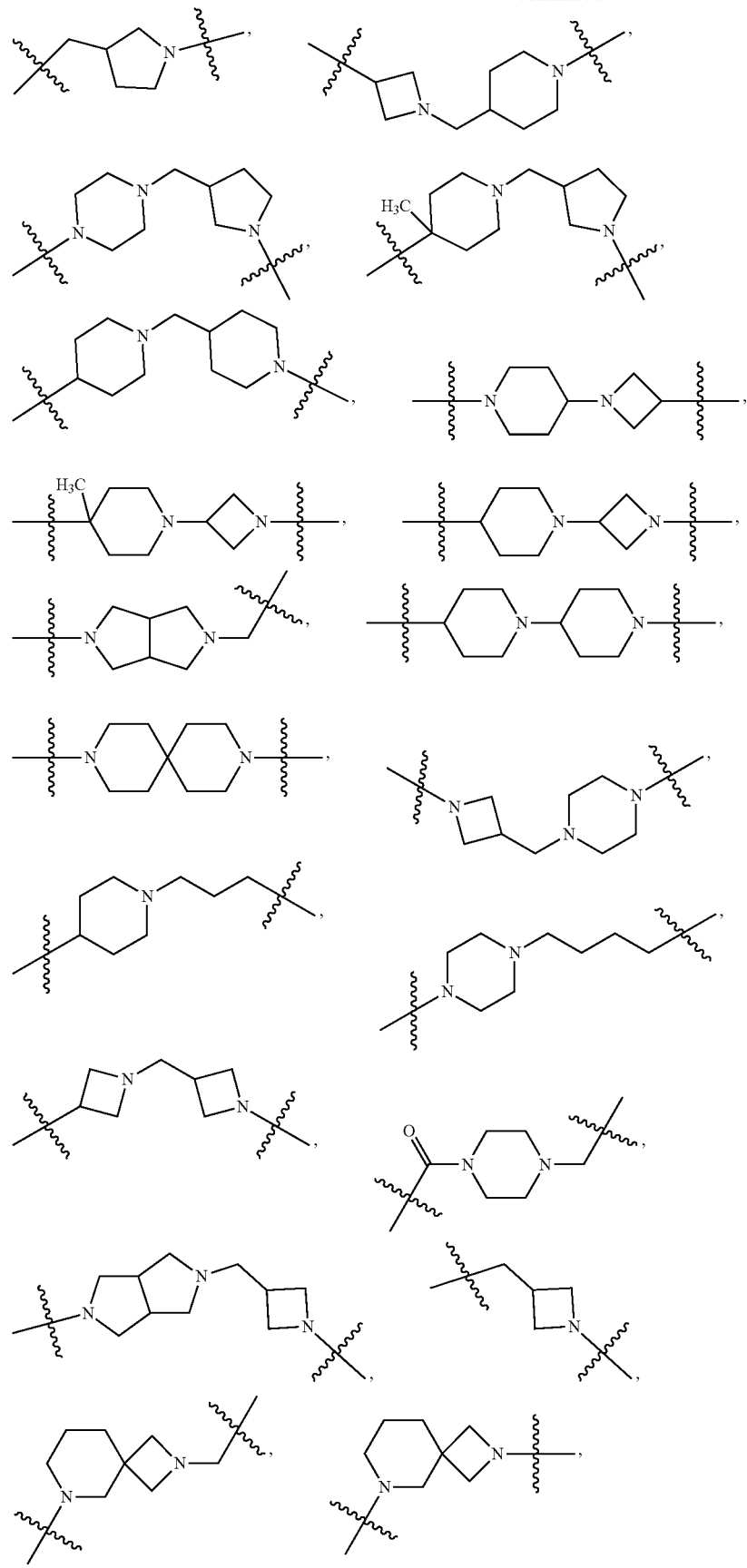

-continued
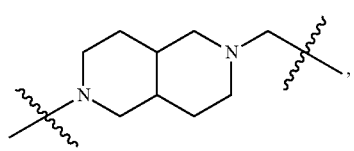
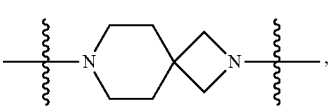
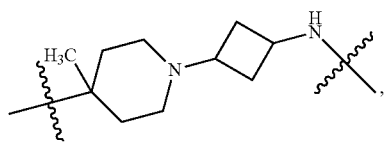
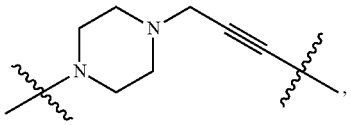
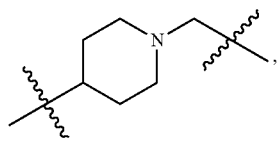
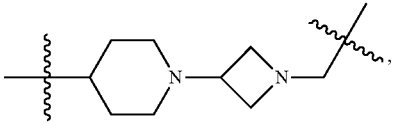
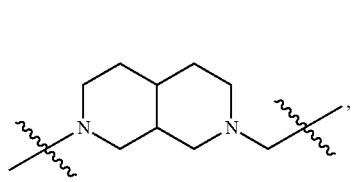
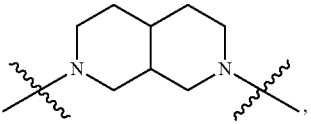
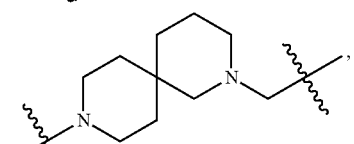
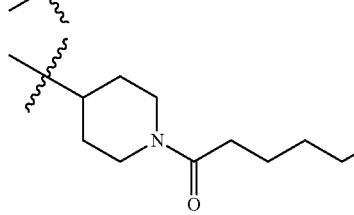
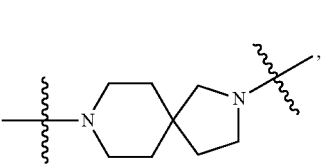
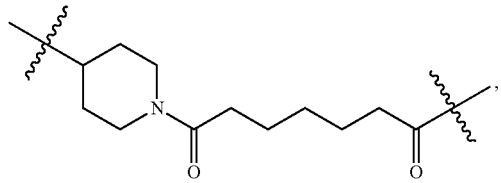
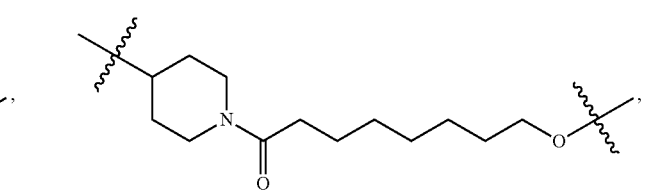
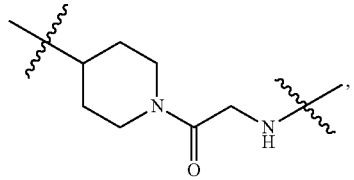
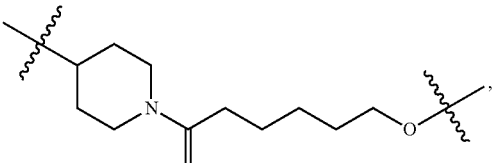
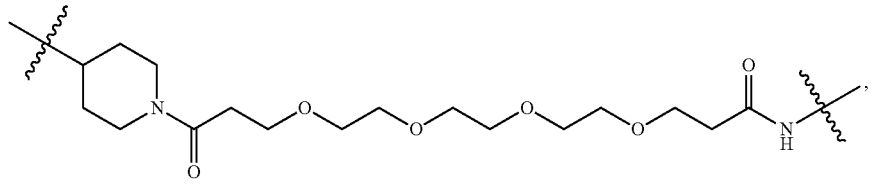
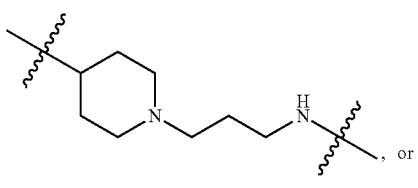
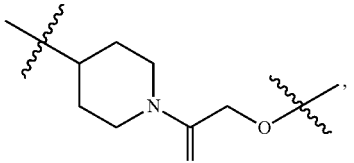, or

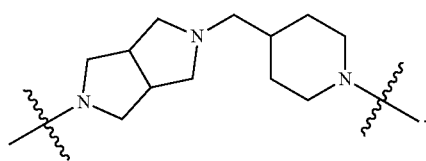
In some embodiments, Y is
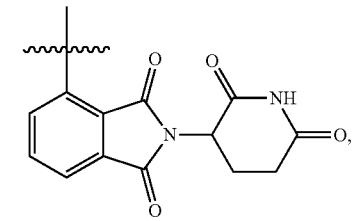
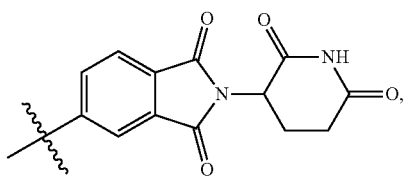
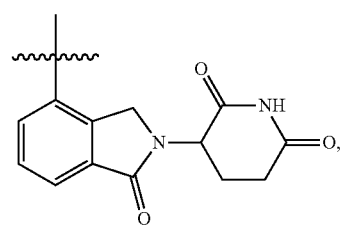
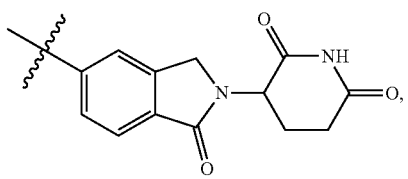
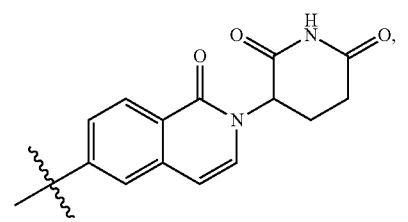
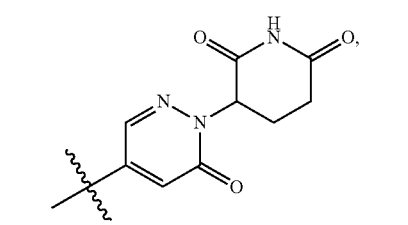
-continued
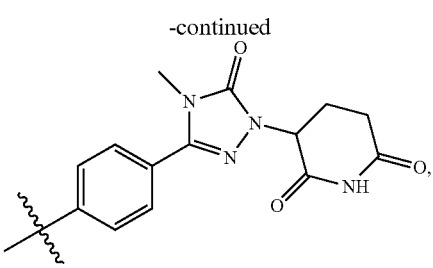
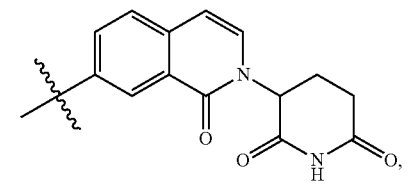
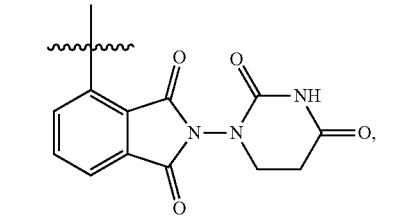
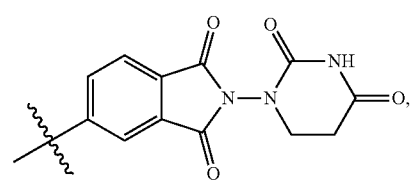
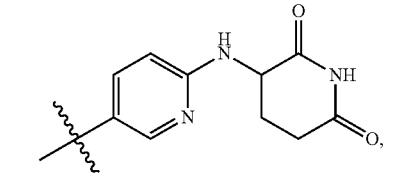

-continued

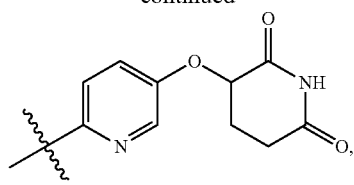

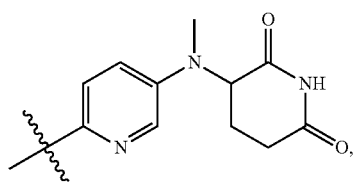

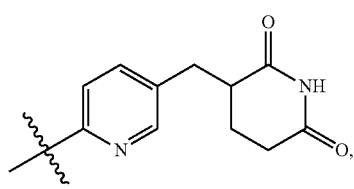

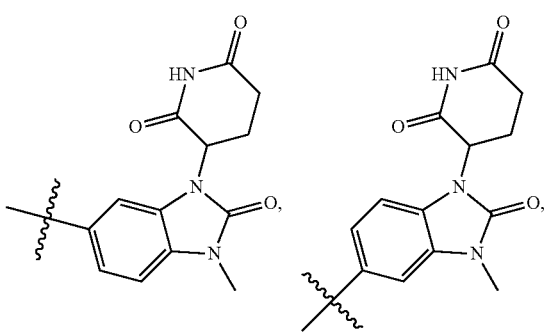

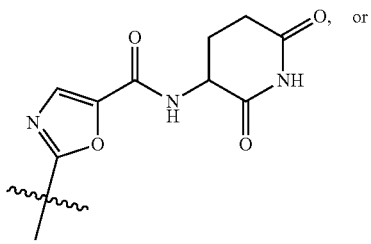

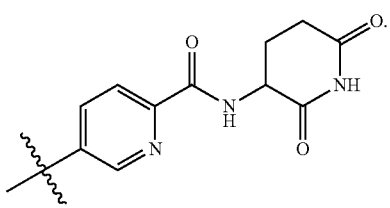

In some embodiments, W is N.
In some embodiments, D is a bond.

This disclosure also provides a compound of Formula (B)

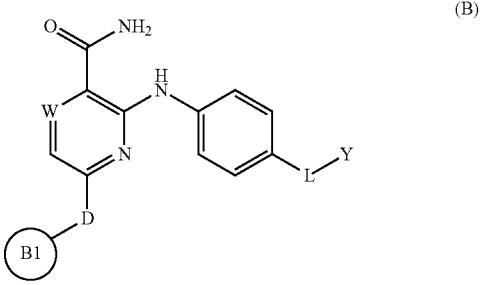

or a pharmaceutically acceptable salt thereof, wherein W is CH or N; D is a bond or —NH—; Ring B1 is a 4-6 membered, fully saturated, partially unsaturated, or fully unsaturated monocyclic heterocycle or a 8-10 membered, fully saturated, spiro bicyclic heterocycle, wherein Ring B1 has one to three heteroatoms independently selected from N, O, or S, and is optionally substituted with one to three groups selected from halo, —CH$_3$, —CF$_3$, —C(O)OH, —CH$_2$OH, or a 5-membered heterocycloalkyl optionally substituted with oxo and having one to two heteroatoms independently selected from N or O; L is —X$^1$-X$^2$-X$^3$—; X$^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having one to three heteroatoms independently selected from N, O, or S, or 4-6 membered monocyclic heterocycloalkyl having one to two heteroatoms independently selected from N, O, or S, wherein each of the monocyclic and bicyclic heterocycloalkyl of X$^1$ is optionally substituted with —CH$_3$; X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having one to two heteroatoms independently selected from N, O, or S; X$^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having one to two heteroatoms independently selected from N, O, or S, wherein the heterocycloalkyl is optionally substituted with —CH$_3$; each R is independently —H or —C$_{1-3}$ alkyl; each of m, n, and p is independently an integer from one to three; and Y is

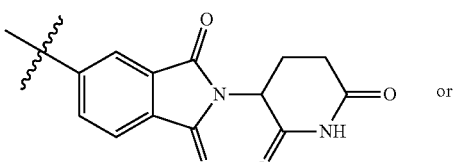 or

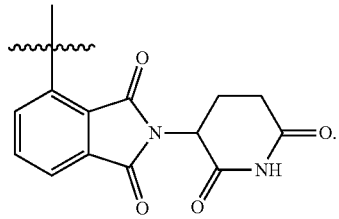

In some embodiments, Ring B1 is

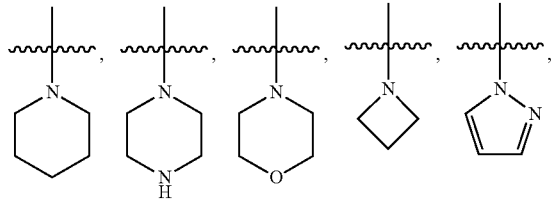

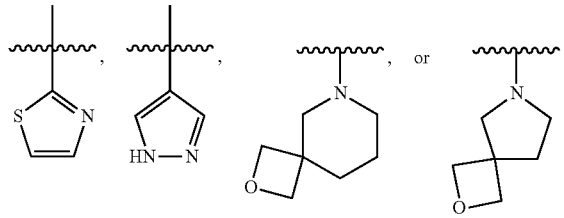

and Ring B1 is optionally substituted one to three groups selected from —CH₃, —CH₂OH, —CH₂CH₂OH, —C(O)OH, —CF₃, —F,

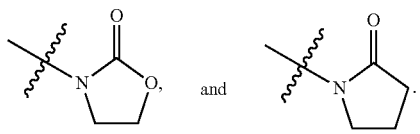 [SMILES: *N1CCOC1=O ; "and" ; *N1CCCC1=O]

For example, Ring B1 is

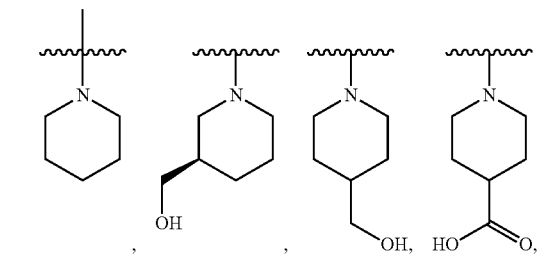

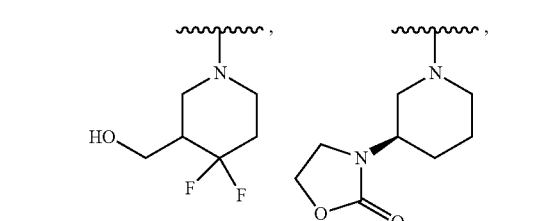

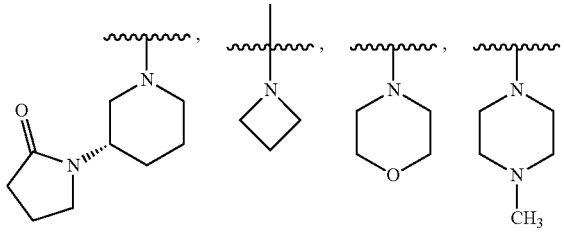

-continued

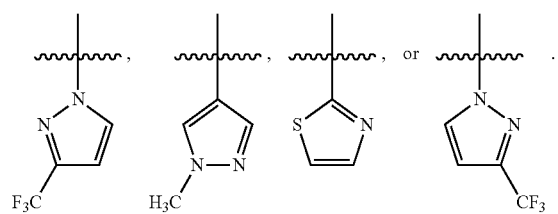

In other examples, Ring B1 is

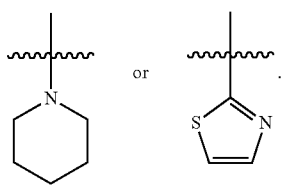 [SMILES: *N1CCCCC1 ; *c1nccs1]

In some embodiments, $X^1$ is

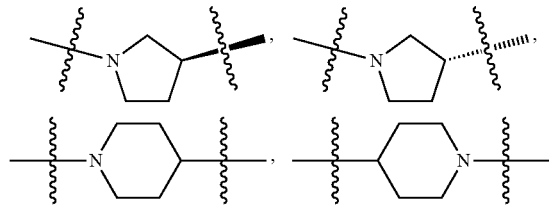

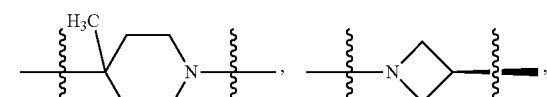

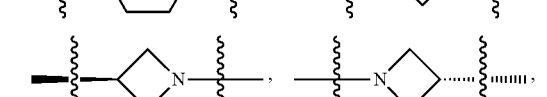

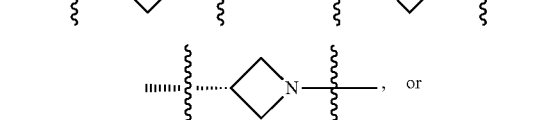

In some embodiments, $X^2$ is a bond, —$C_{1-5}$ alkyl-, 4-6 membered monocyclic cycloalkyl, or 4-6 membered monocyclic heterocycloalkyl having one to two heteroatoms independently selected from N, O, or S. For example, $X^2$ is a bond, —$C_{1-3}$ alkyl-, —C(O)—,

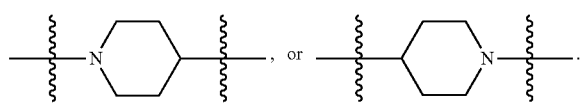 [SMILES: *C1CCN(*)CC1 ; *C1CCN(*)CC1]

In some embodiment, $X^3$ is a bond, $-C_{1-4}$ alkyl-, $-N(R)-$, $-(O-CH_2-CH_2)_p-$, $-(CH_2-CH_2-O)_p-$, or a 4-6 membered heterocycloalkyl having one to two heteroatoms independently selected from N, O, or S, wherein the heterocycloalkyl is optionally substituted with $-CH_3$. For example, $X^3$ is a bond,

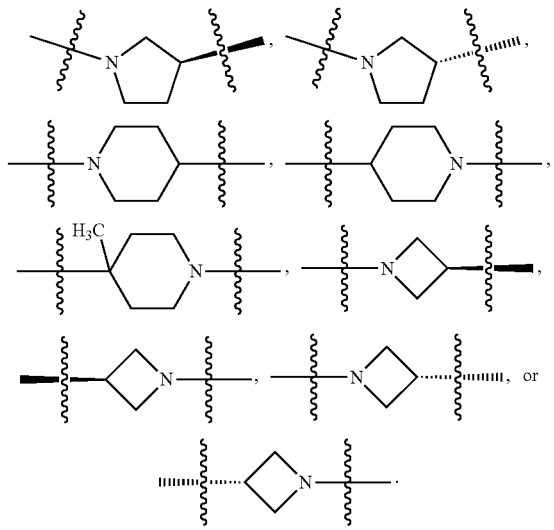

In some embodiments, L is

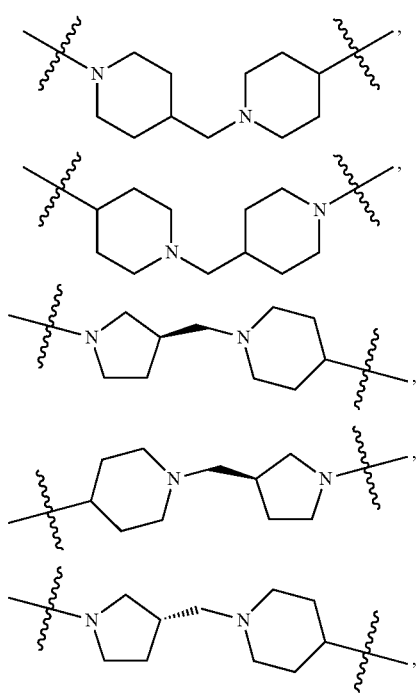

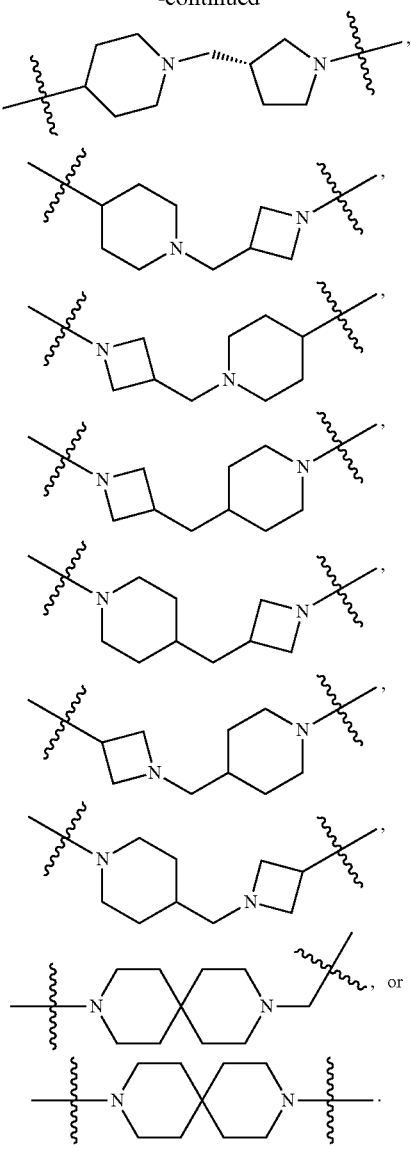

In some embodiments, W is N and D is a bond.
This disclosure also provides a compound of Formula (C)

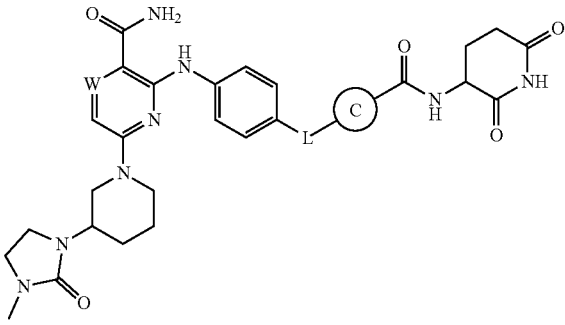

(C)

or a pharmaceutically acceptable salt thereof, wherein W is CH or N; Ring C is phenyl or a saturated, partially unsaturated, or fully unsaturated 5-6 membered monocyclic heterocycle having one to two heteroatoms independently selected from N, O, or S, wherein each of the phenyl and heterocycle of Ring C is optionally substituted; L is —$X^1$-$X^2$-$X^3$—; $X^1$ is —C(O)—N(R), —N(R)—C(O), (O—$CH_2$—$CH_2$)$_m$, O—($C_6H_4$), (O—$CH_2$—$CH_2$—$CH_2$)$_m$—, —$C_{1-5}$ alkyl-, 7-12 membered spiro bicyclic heterocycloalkyl having one to three heteroatoms independently selected from N, O, or S, or 4-6 membered monocyclic heterocycloalkyl having one to two heteroatoms independently selected from N, O, or S, wherein each of the bicyclic heterocycloalkyl and the monocyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having one to two heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having one to two heteroatoms independently selected from N, O, or S, wherein the heterocycloalkyl is optionally substituted with —$CH_3$; each R is independently —H or —$C_{1-3}$ alkyl; and each of m, n, and p is independently an integer from one to three.

In some embodiments, W is N.

In some embodiments, Ring C is

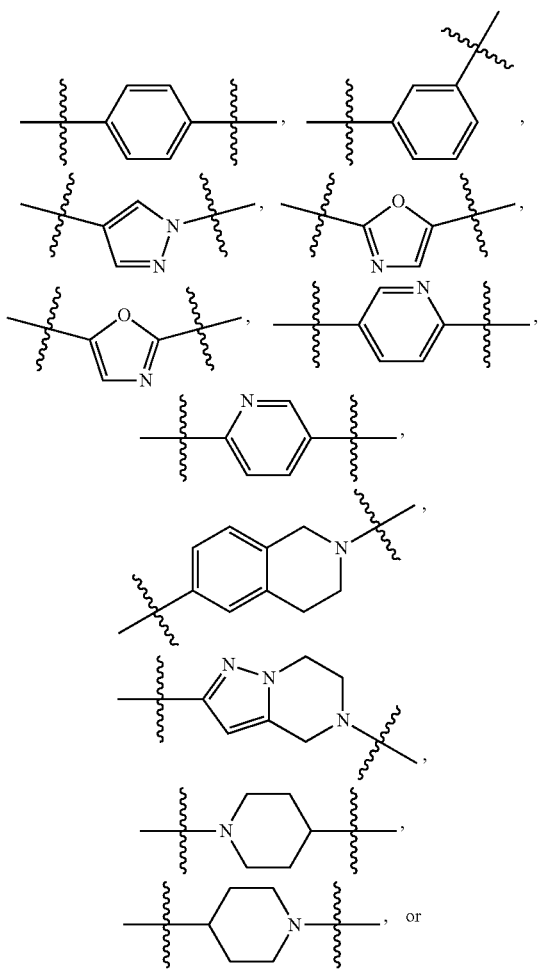

or

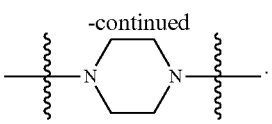

For example, Ring C is

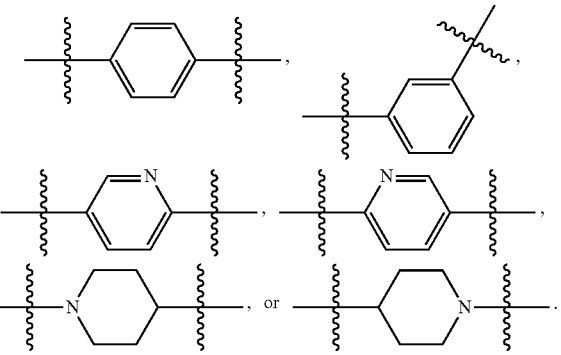

In other examples, Ring C is

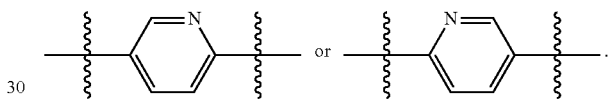

In some embodiments, $X^1$ is a 4-6 membered monocyclic heterocycloalkyl having one to two heteroatoms independently selected from N, O, or S. For example, $X^1$ is

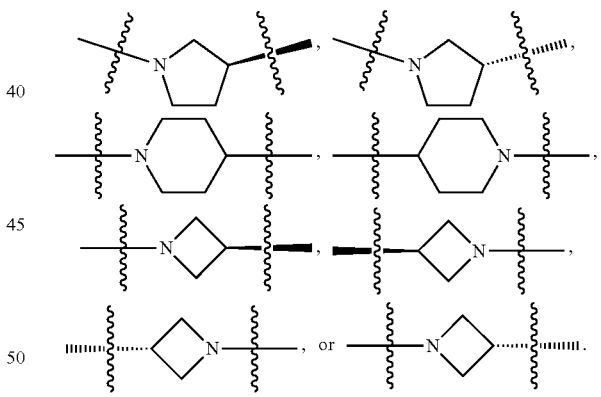

In some examples, $X^1$ is

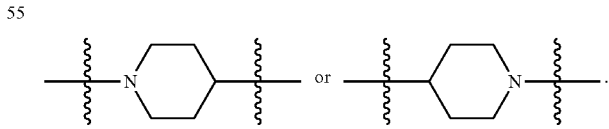

In some embodiments, $X^2$ is a bond, —$C_{1-5}$ alkyl-, 4-6 membered monocyclic cycloalkyl, or 4-6 membered monocyclic heterocycloalkyl having one to two heteroatoms independently selected from N, O, or S. For example, $X^2$ is a bond or —$C_{1-3}$ alkyl- (e.g., —$CH_2$—).

In some embodiments, $X^3$ is a 4-6 membered cycloalkyl, —N(R)—, or a 4-6 membered heterocycloalkyl having one to two heteroatoms independently selected from N, O, or S, wherein the heterocycloalkyl is optionally substituted with —CH₃. For example X³ is

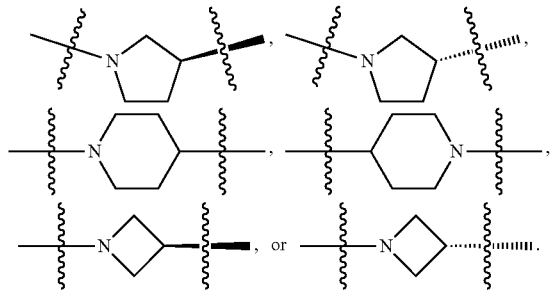

In other embodiments, X³ is

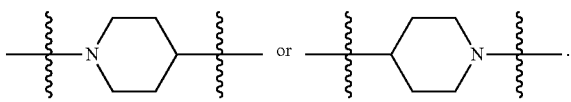

In some embodiments, L is

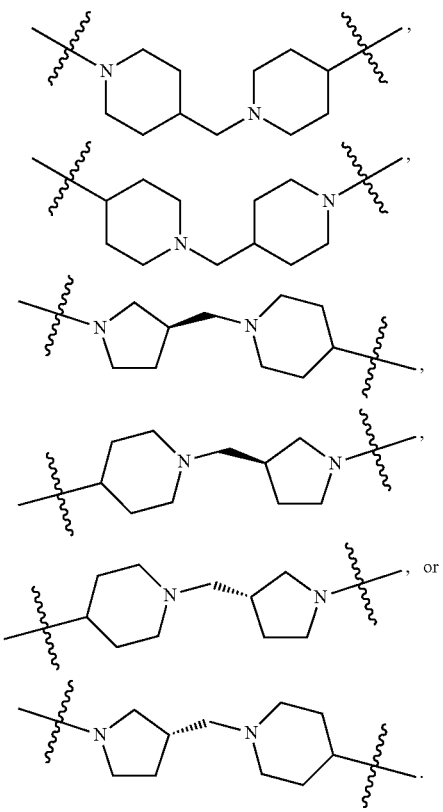

For example, L is

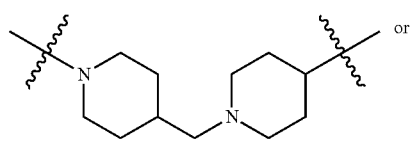

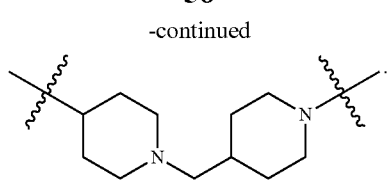

This disclosure also provides a compound of Formula (D)

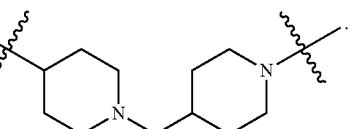

or a pharmaceutically acceptable salt thereof, wherein W is CH or N; Ring A is

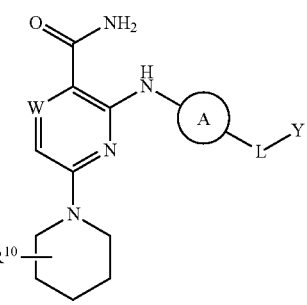

L is —X¹-X²-X³—; X¹ is —$C_{1-5}$ alkyl- or 4-6 membered monocyclic heterocycloalkyl having one to two heteroatoms independently selected from N, O, or S, wherein the monocyclic heterocycloalkyl of X¹ is optionally substituted with —CH₃; X² is a bond, —$C_{1-5}$ alkyl-, or 4-6 membered monocyclic heterocycloalkyl having one to two heteroatoms independently selected from N, O, or S, wherein the monocyclic heterocycloalkyl of X¹ is optionally substituted with —CH₃; X³ is a bond, —$C_{1-4}$ alkyl-, 4-6 membered monocyclic cycloalkyl, or 4-6 membered heterocycloalkyl having one to two heteroatoms independently selected from N, O, or S, wherein the heterocycloalkyl is optionally substituted with —CH₃; Y is

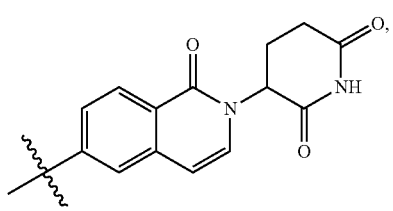

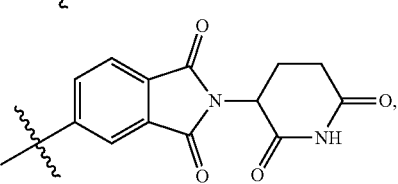

-continued

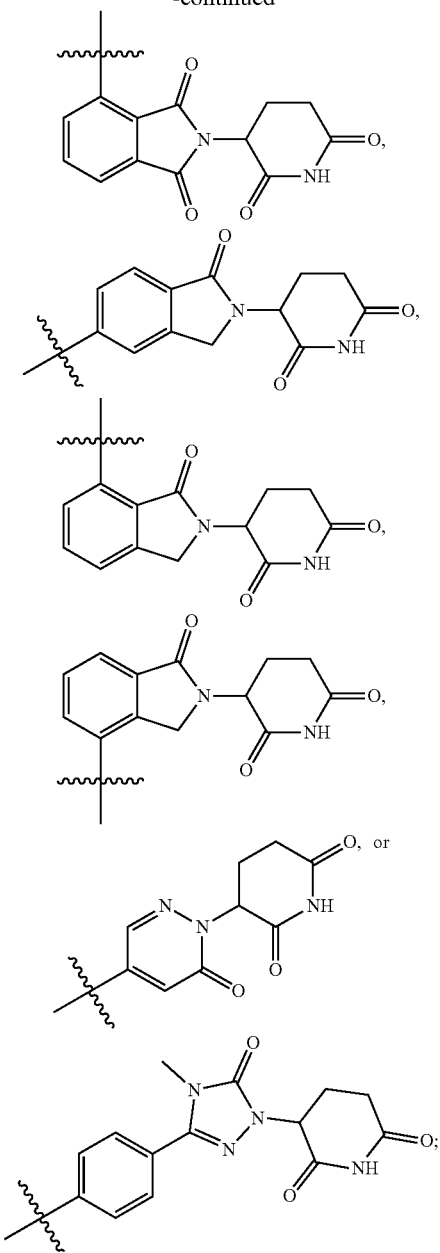

and R[10] is halo, —H, —$C_{1-5}$ alkyl, 3-6 membered cycloalkyl, 5-6 membered heterocycloalkyl, —CN, —OH, —$CF_3$, —$CH_2OH$, —$CH_2CH_2OH$, —C(O)OH,

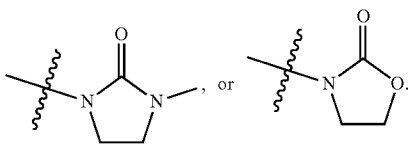

In some embodiments, Ring A is

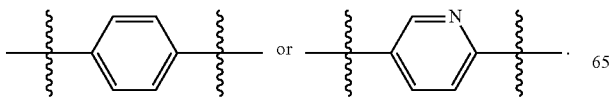

In some embodiments, $X^1$ is a 4-6 membered monocyclic heterocycloalkyl having one to two heteroatoms independently selected from N, O, or S, wherein the monocyclic heterocycloalkyl of $X^1$ is optionally substituted with —$CH_3$. For example $X^1$ is

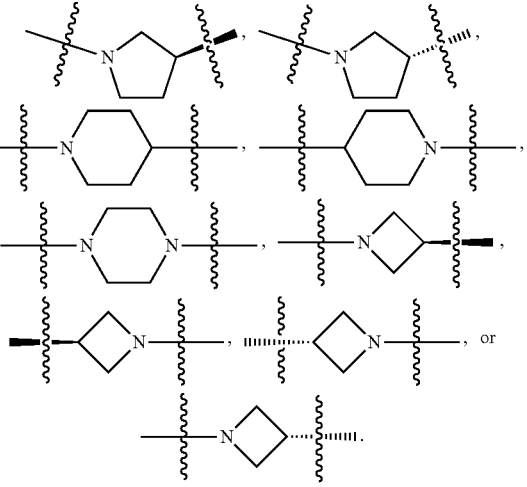

In some embodiments, $X^2$ is a bond, —$C_{1-5}$ alkyl-, 4-6 membered monocyclic cycloalkyl, or 4-6 membered monocyclic heterocycloalkyl having one to two heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having one to two heteroatoms independently selected from N, O, or S. For example, $X^3$ is

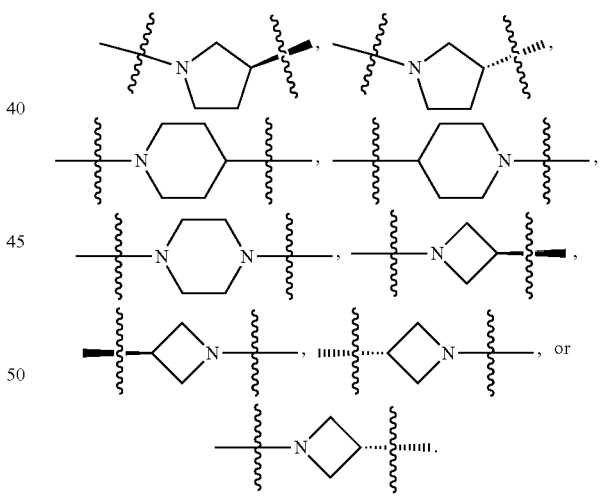

In some embodiments, L is

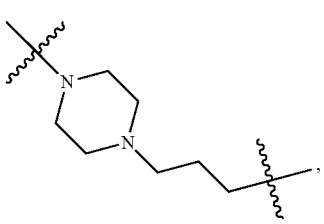

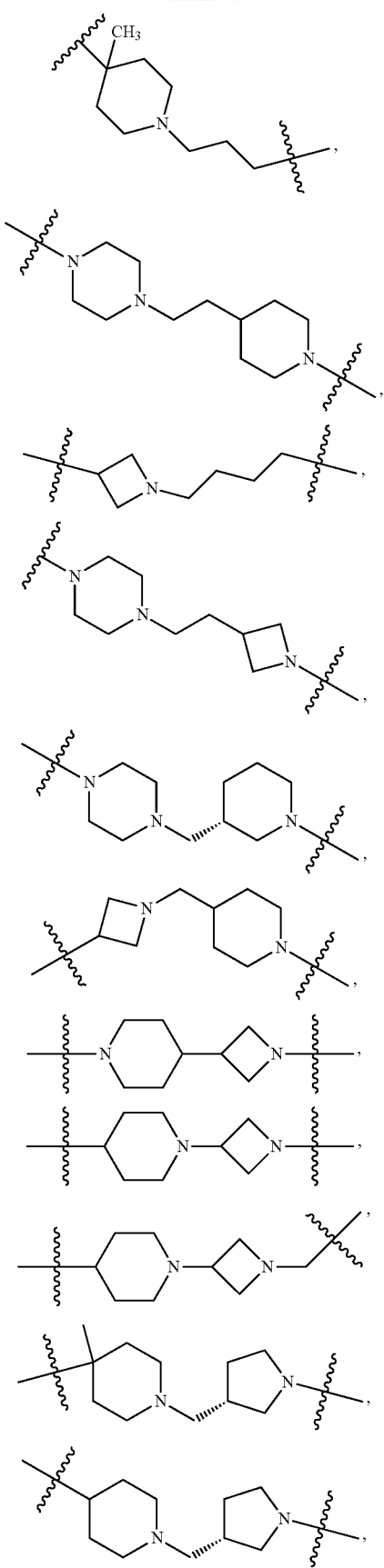
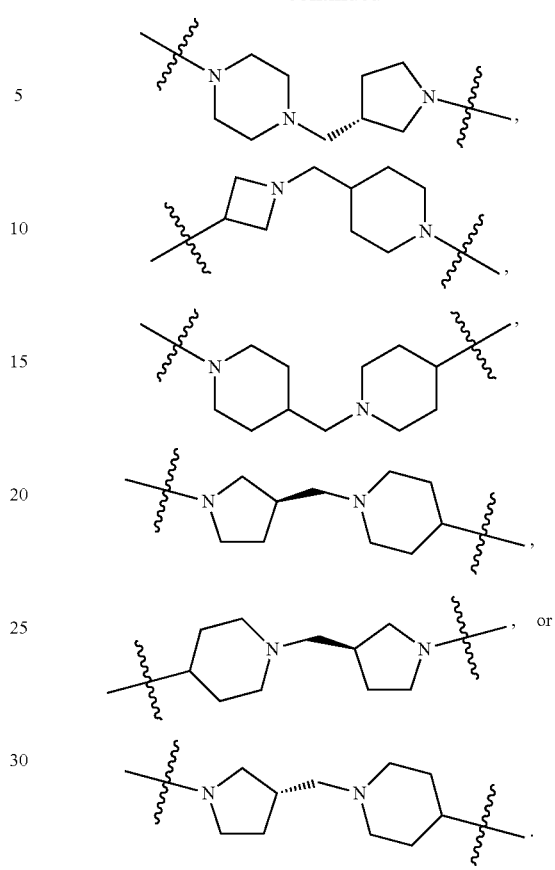
In some embodiments, $R^{10}$ is halo, —H, —$C_{1-5}$ alkyl (e.g., —$C_{1-3}$ alkyl), 3-6 membered cycloalkyl, 5-6 membered heterocycloalkyl, —CN, —OH, —$CF_3$, —$CH_2OH$, —$C(O)OH$, or —$CH_2CH_2OH$. For instance, $R^{10}$ is halo, —H, $C_{1-3}$ alkyl, $CF_3$, —$CH_2OH$, —$C(O)OH$, or —$CH_2CH_2OH$. In other instances, $R^{10}$ is
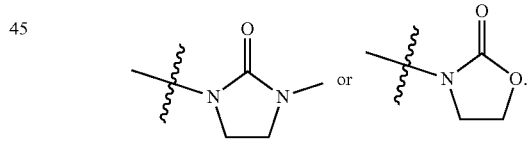
In some embodiments, $R^{10}$ is
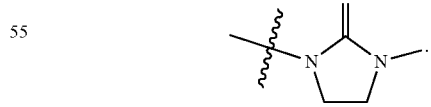
In some embodiments, $R^{10}$ is
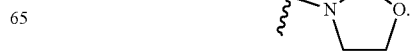

In some embodiments, the compound of Formula (D) is a compound of (D-1)

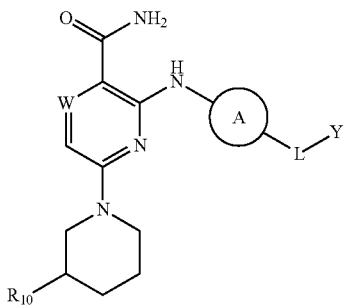
(D-1)

or a pharmaceutically acceptable salt thereof, wherein W is CH or N; Ring A is

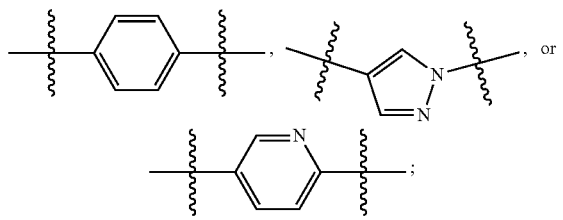
, or

L is —$X^1$-$X^2$-$X^3$—; $X^1$ is —$C_{1-5}$ alkyl- or 4-6 membered monocyclic heterocycloalkyl having one to two heteroatoms independently selected from N, O, or S, wherein the monocyclic heterocycloalkyl of $X^1$ is optionally substituted with —$CH_3$; $X^2$ is a bond, —$C_{1-5}$ alkyl-, or 4-6 membered monocyclic heterocycloalkyl having one to two heteroatoms independently selected from N, O, or S, wherein the monocyclic heterocycloalkyl of $X^1$ is optionally substituted with —$CH_3$; $X^3$ is a bond, —$C_{1-4}$ alkyl-, 4-6 membered monocyclic cycloalkyl, or 4-6 membered heterocycloalkyl having one to two heteroatoms independently selected from N, O, or S, wherein the heterocycloalkyl is optionally substituted with —$CH_3$; Y is

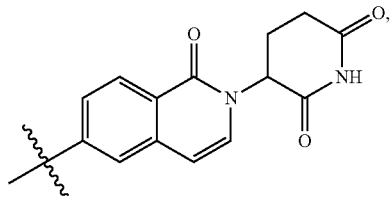

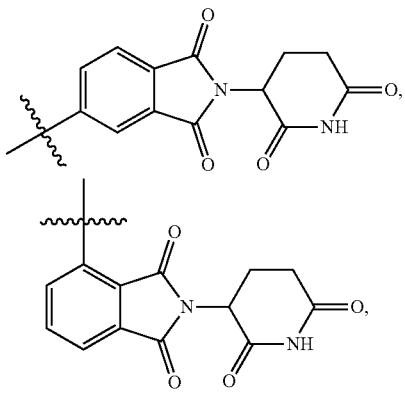

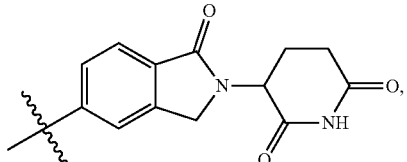

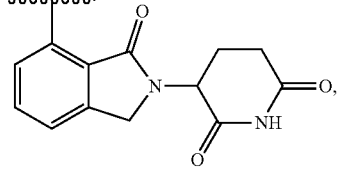

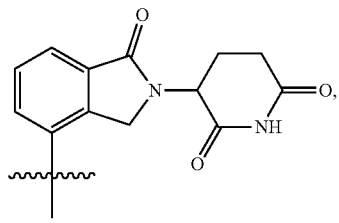

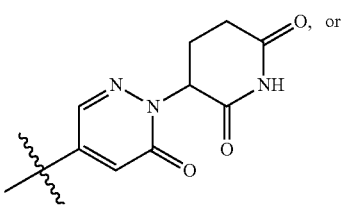

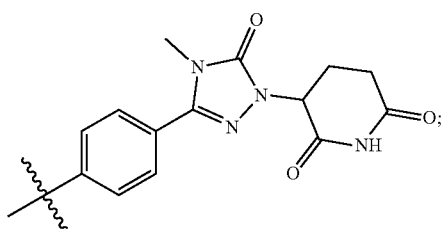

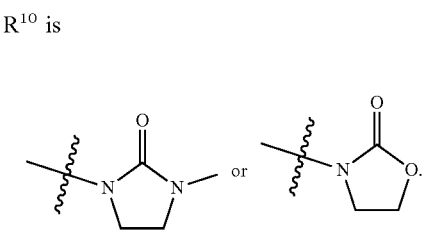

and is $R^{10}$ is

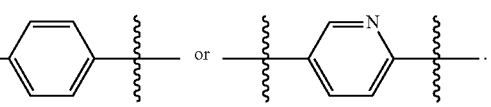

In some embodiments, Ring A is

In some embodiments, $X^1$ is a 4-6 membered monocyclic heterocycloalkyl having one to two heteroatoms independently selected from N, O, or S, wherein the monocyclic heterocycloalkyl of $X^1$ is optionally substituted with —$CH_3$. For example, $X^1$ is

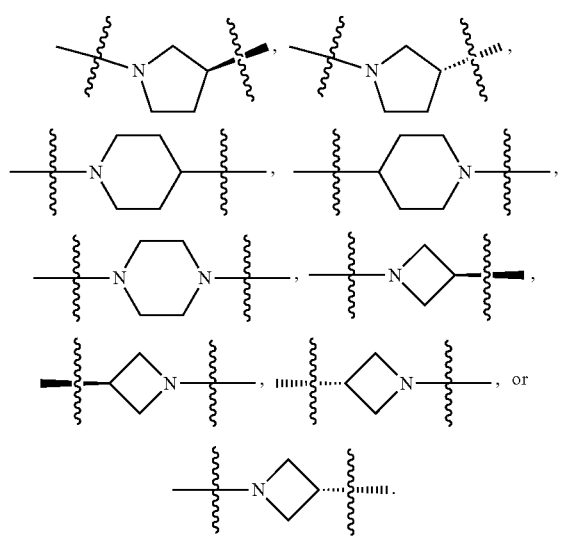

In some embodiments, $X^2$ is a bond, —$C_{1-5}$ alkyl-, 4-6 membered monocyclic cycloalkyl, or 4-6 membered monocyclic heterocycloalkyl having one to two heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having one to two heteroatoms independently selected from N, O, or S. For example, $X^3$ is

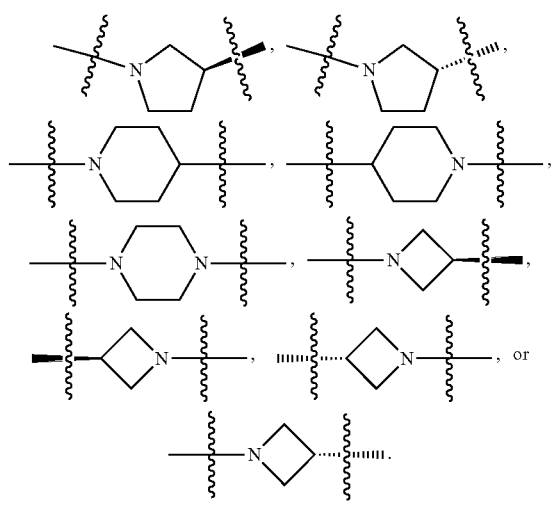

In some embodiments, L is

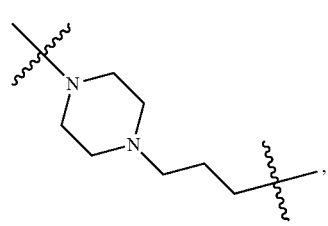

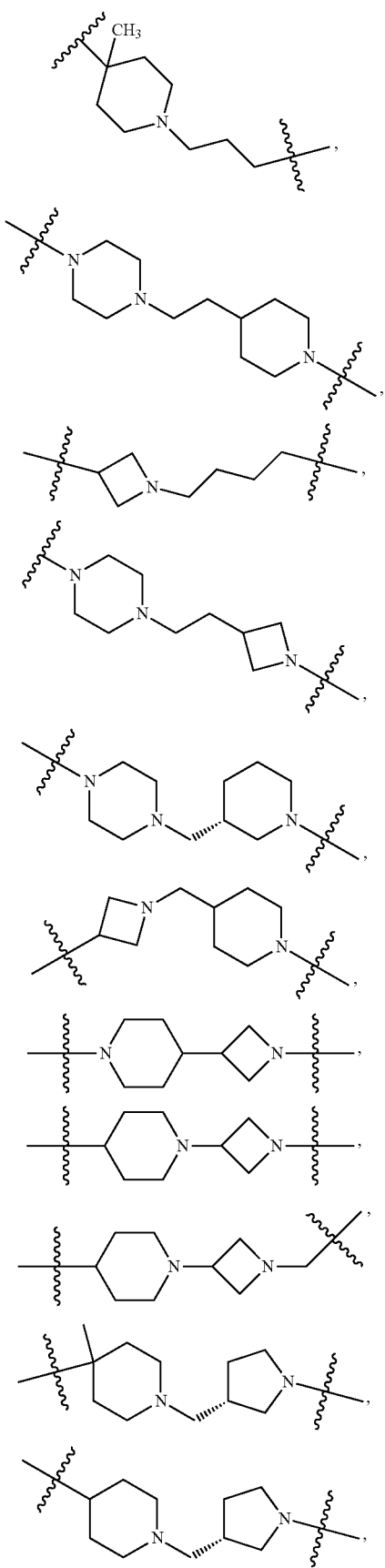

-continued

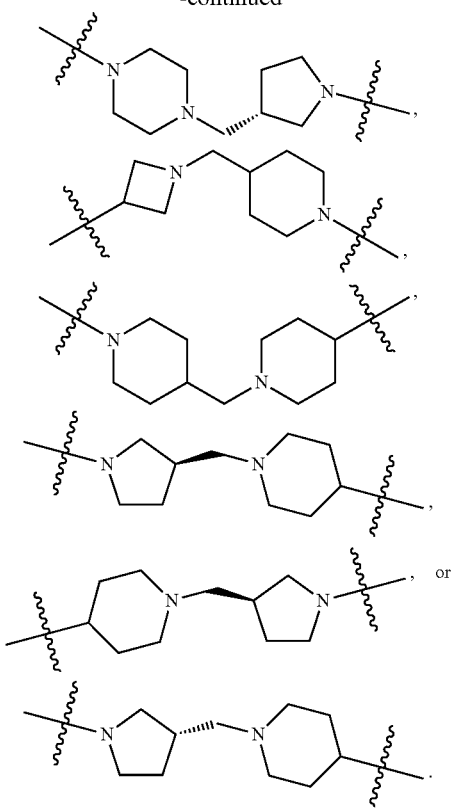

In some embodiments, $R^{10}$ is

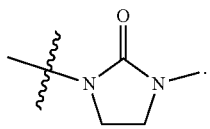 [SMILES: *N1CCN(C)C1=O]

In some embodiments, $R^{10}$ is

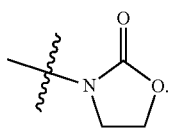

In some embodiments, the compound of Formula (D) or the compound of Formula (D-1) is a compound of Formula (D-2)

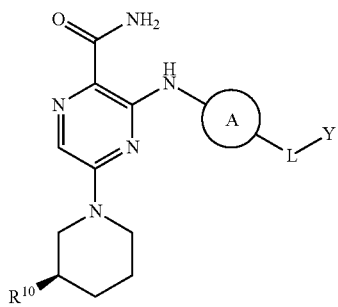

(D-2)

or a pharmaceutically acceptable salt thereof, wherein the terms Ring A, L, Y, and $R^{10}$ are as defined in the compound of Formula (A), the compound of Formula (D), and the compound of Formula (D-1).

In some embodiments, Ring A is

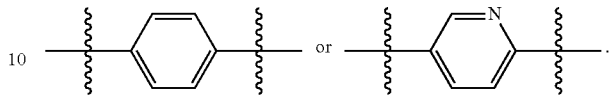

In some embodiments, $X^1$ is a 4-6 membered monocyclic heterocycloalkyl having one to two heteroatoms independently selected from N, O, or S, wherein the monocyclic heterocycloalkyl of $X^1$ is optionally substituted with —$CH_3$. For example, $X^1$ is

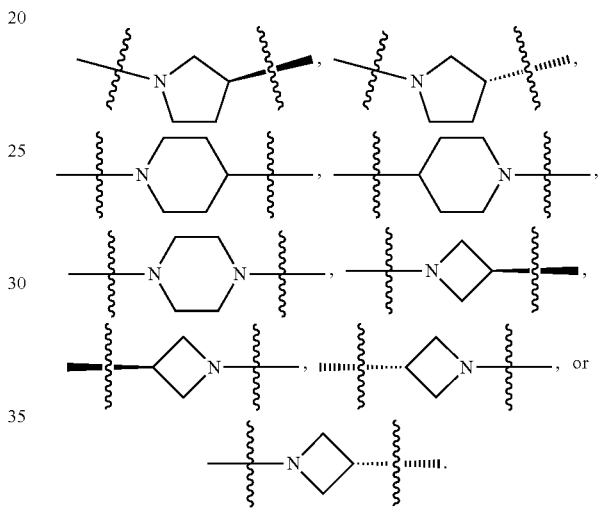

In some embodiments, $X^2$ is a bond, —$C_{1-5}$ alkyl-, 4-6 membered monocyclic cycloalkyl, or 4-6 membered monocyclic heterocycloalkyl having one to two heteroatoms independently selected from N, O, or S. For example, $X^2$ is a bond or —$C_{1-4}$ alkyl-.

In some embodiments, $X^3$ is a bond, a 4-6 membered monocyclic cycloalkyl, or 4-6 membered monocyclic heterocycloalkyl having one to two heteroatoms independently selected from N, O, or S. For example, $X^3$ is

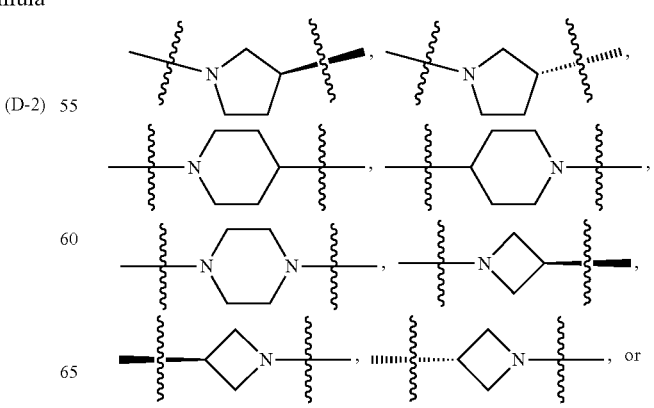

-continued
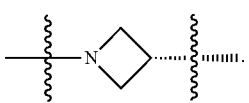
In some embodiments, L is
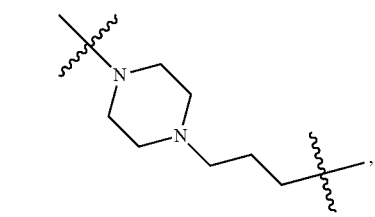
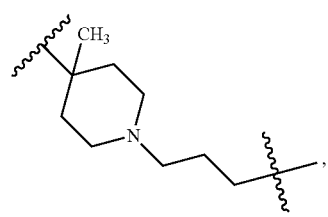
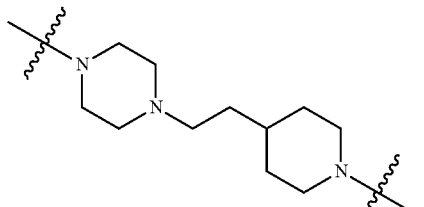
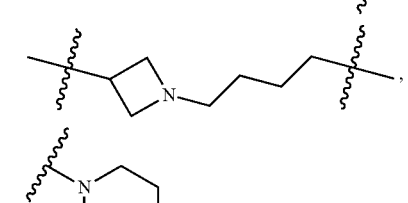
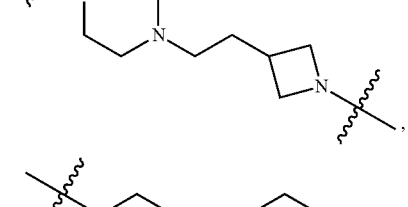
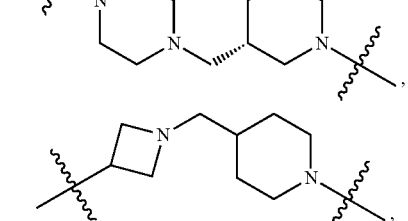
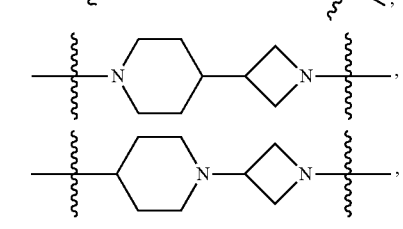
-continued
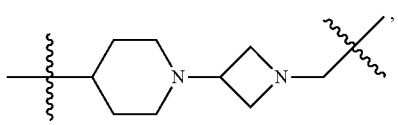
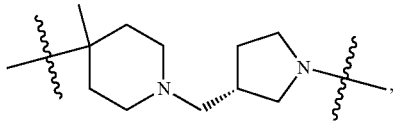
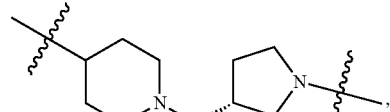
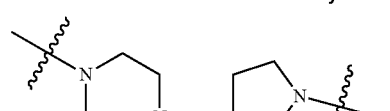
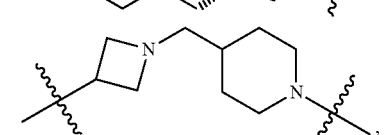
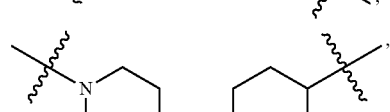
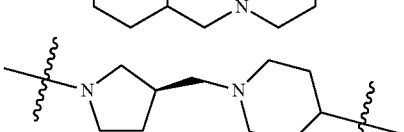
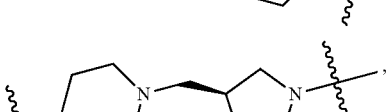, or
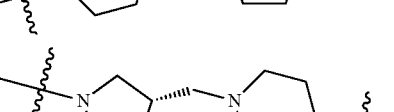.
In some embodiments, $R^{10}$ is
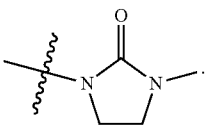 [SMILES: *N1CCN(C)C1=O]
In some embodiments, $R^{10}$ is
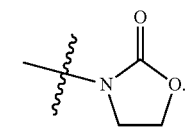

This disclosure also provides a compound of Formula (E)

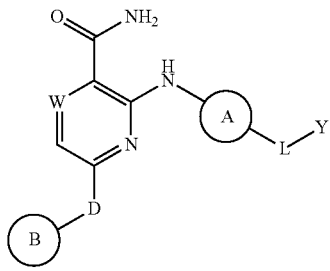

(E)

or a pharmaceutically acceptable salt thereof, wherein D is a bond or —NH—; W is N or CH; Ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of Ring A each possess one to three heteroatoms independently selected from N, O, or S; Ring B is an optionally substituted 5-6 membered saturated, partially unsaturated, or fully unsaturated monocyclic heterocycle, or an optionally substituted 8-10 membered (e.g., 8-9 membered or 9-10 membered) spiro bicyclic heterocycle, wherein Ring B has one to three heteroatoms independently selected from N, O, or S; L is —$X^1$-$X^2$-$X^3$-$X^4$-$X^5$—; $X^1$ is a bond, —C(O)—N(R)—, —N(R)—C(O)—, —(O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having one to three heteroatoms independently selected from N, O, or S, or 4-6 membered monocyclic heterocycloalkyl having one to two heteroatoms independently selected from N, O, or S, wherein each of the monocyclic and bicyclic heterocycloalkyl of $X^1$ is optionally substituted with —$CH_3$; $X^2$ is a bond, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having one to two heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having one to two heteroatoms independently selected from N, O, or S, wherein the heterocycloalkyl is optionally substituted with —$CH_3$; $X^4$ is a bond, —$CH_2$—$CH_2$—N(R)—, —N(R)—, —$C_{1-4}$ alkyl-, —(O—$CH_2$—$CH_2$—$CH_2$)$_m$—, a 5-6 membered saturated, partially unsaturated, or fully unsaturated carbocycle, or a 5-6 membered saturated, partially unsaturated, or fully unsaturated heterocycle having one to three heteroatoms independently selected from N, O, or S; $X^5$ is a bond, —N(R)—, or —C(O)—N(R)—; each R is independently —H or —$C_{1-3}$ alkyl; each of m, n, and p is independently an integer from one to three; and Y is

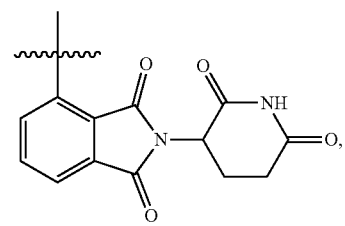

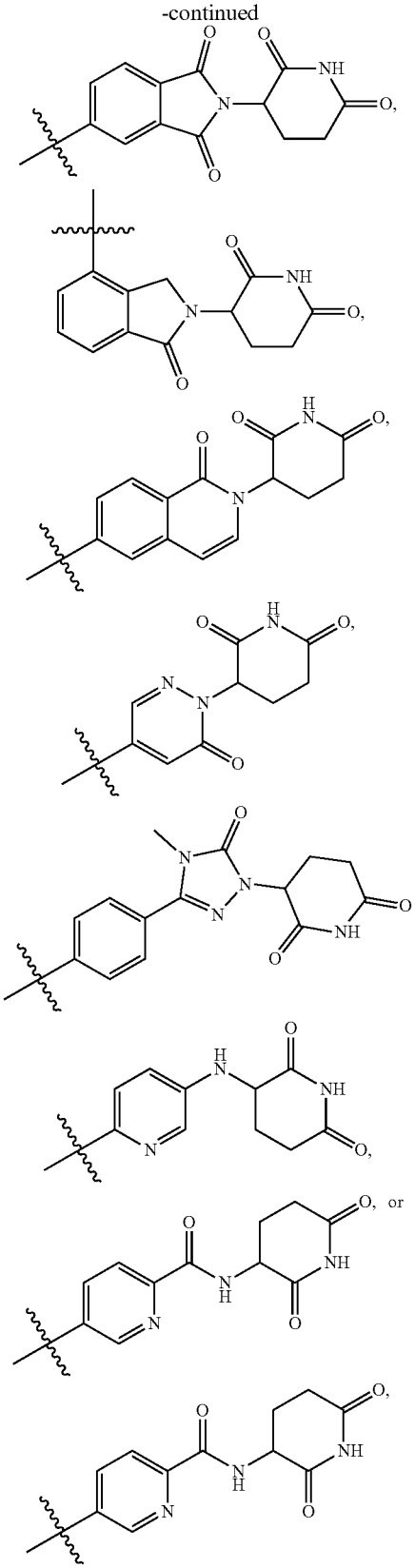

wherein at least one of $X^1$, $X^2$, $X^3$, $X^4$, and $X^5$ has a nitrogen atom, and Y is directly bonded to L at a nitrogen atom of $X^1$, $X^2$, $X^3$, $X^4$, or $X^5$.

In some embodiments, Ring B is
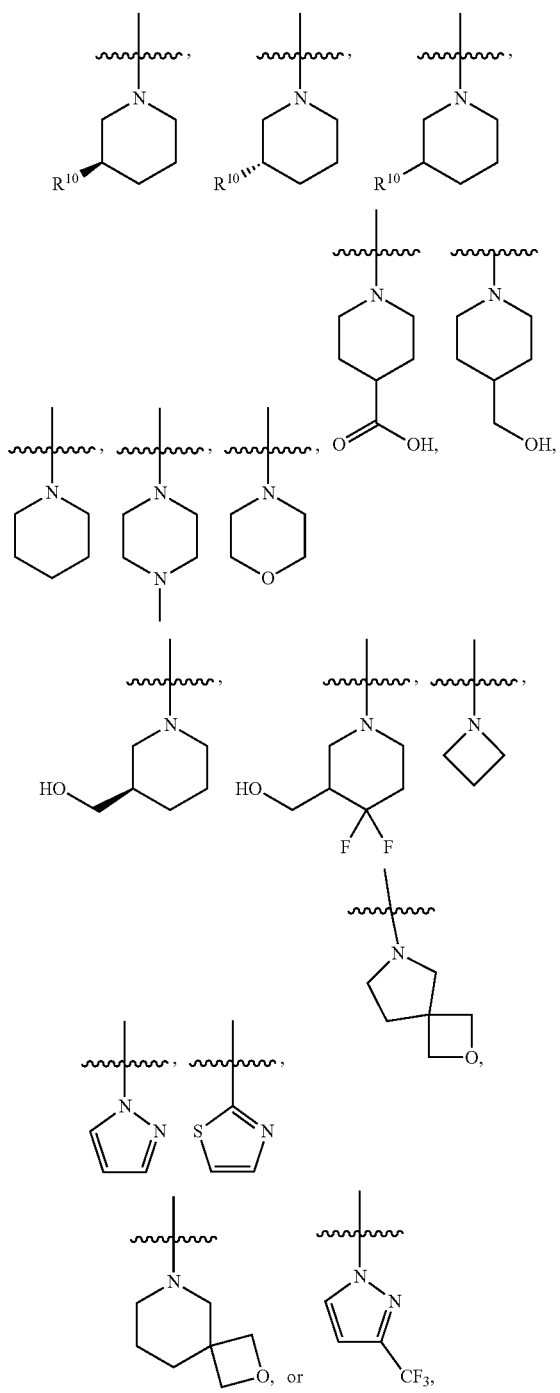
wherein $R^{10}$ is
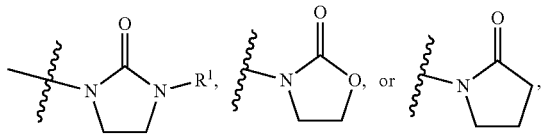
and wherein $R^1$ is a $C_{1-4}$ alkyl group. For example, Ring B is
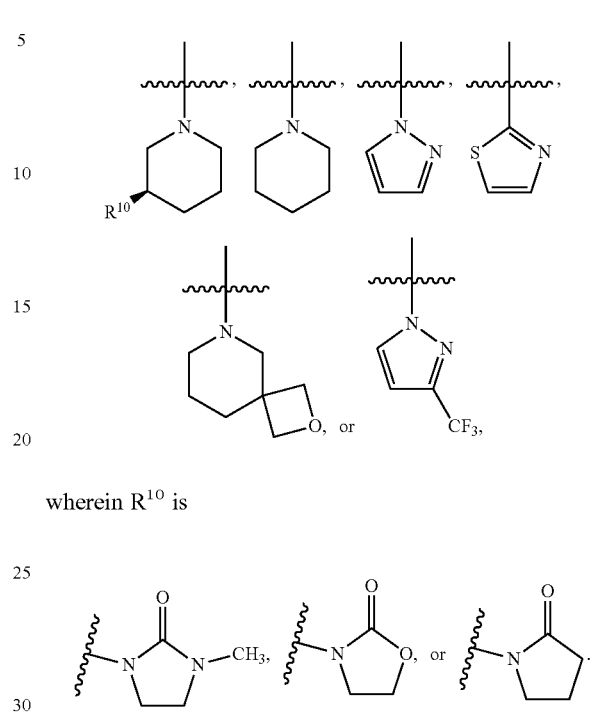
wherein $R^{10}$ is
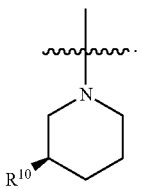
In other examples, Ring B is
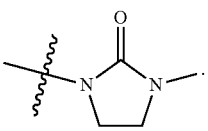 [SMILES: *N1CCN(C)C1=O]
In some embodiments, $R^{10}$ is
In some embodiments, Ring A is
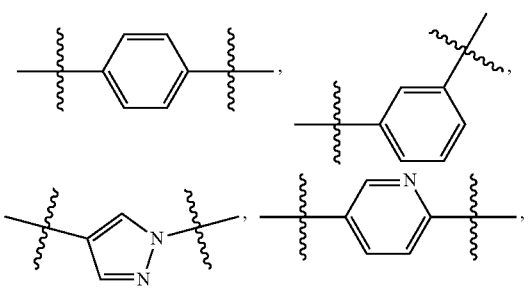

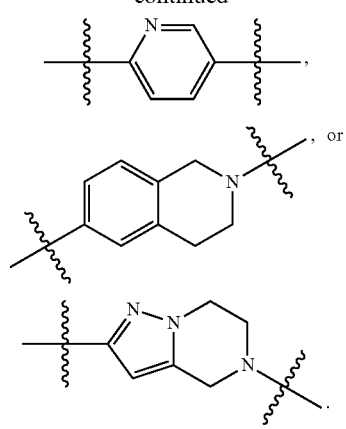
In some embodiments, $X^5$ is —N(R)—.
In some embodiments, $X^5$ is —C(O)—N(R)—.
In some embodiments, $X^5$ is a bond.
In some embodiments, L is
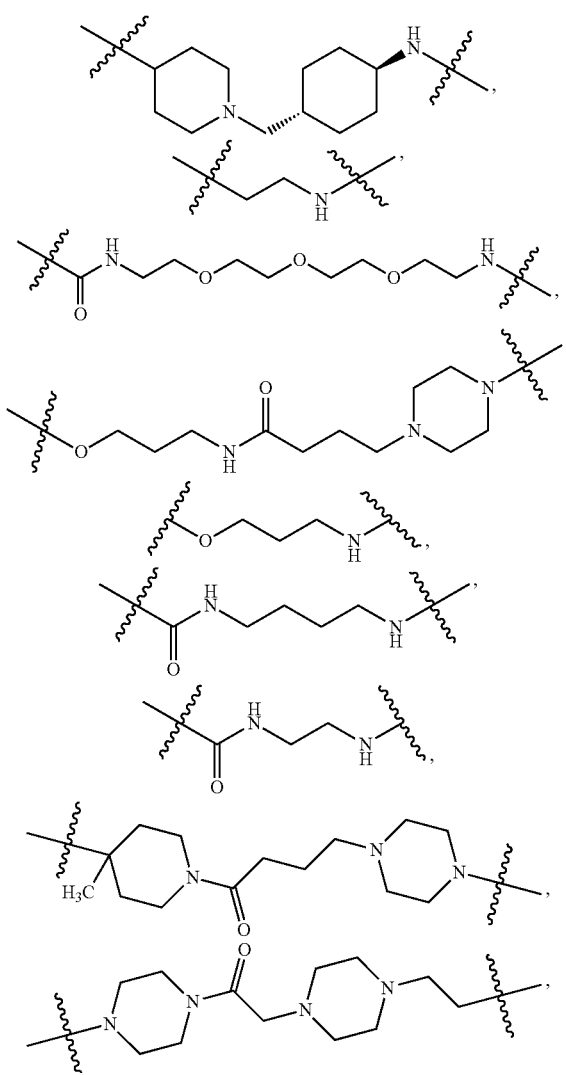
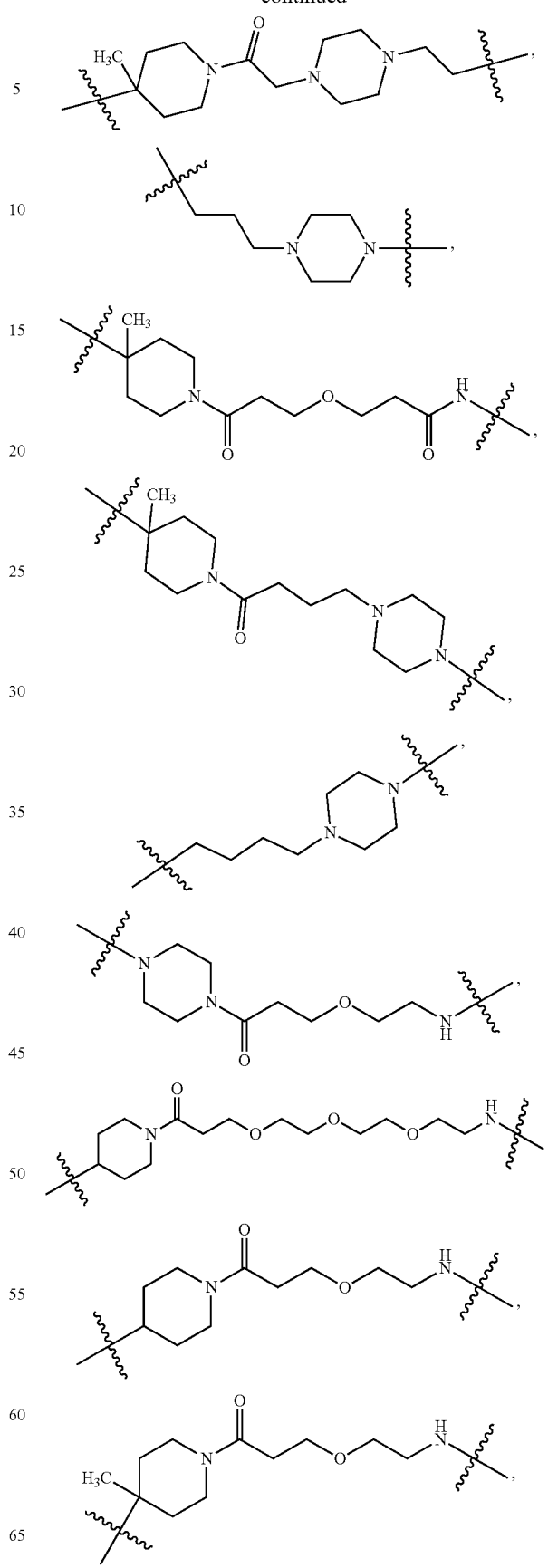

77
-continued
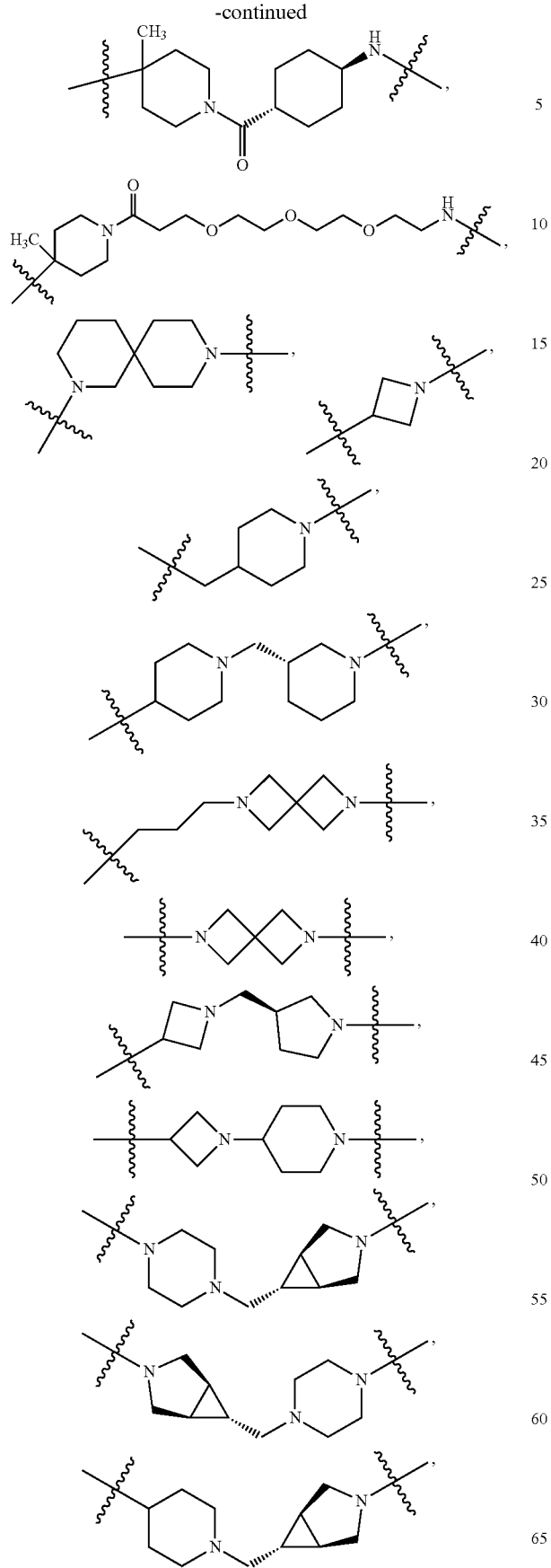
78
-continued
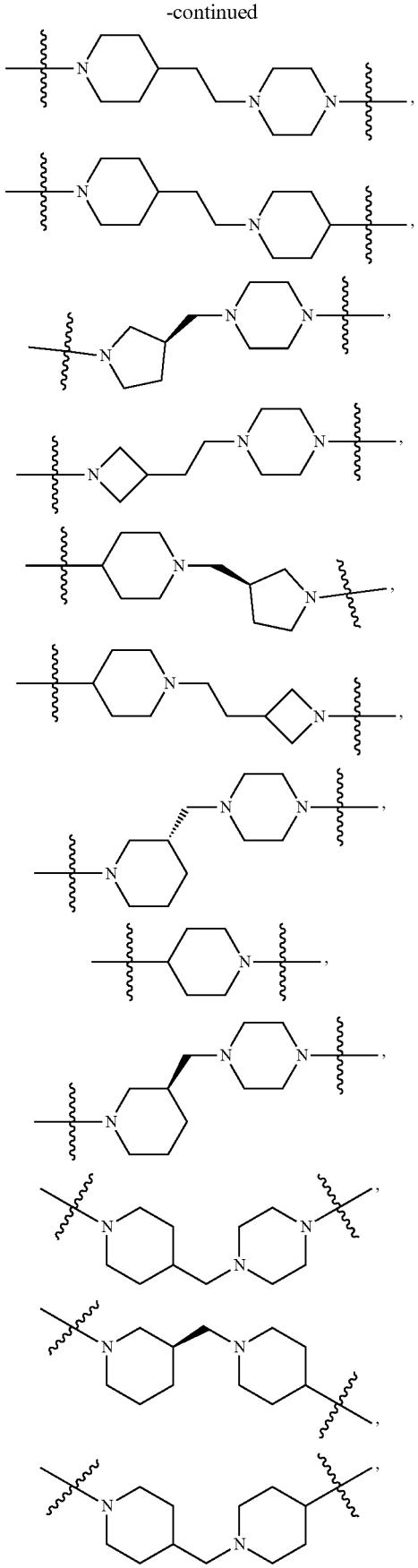

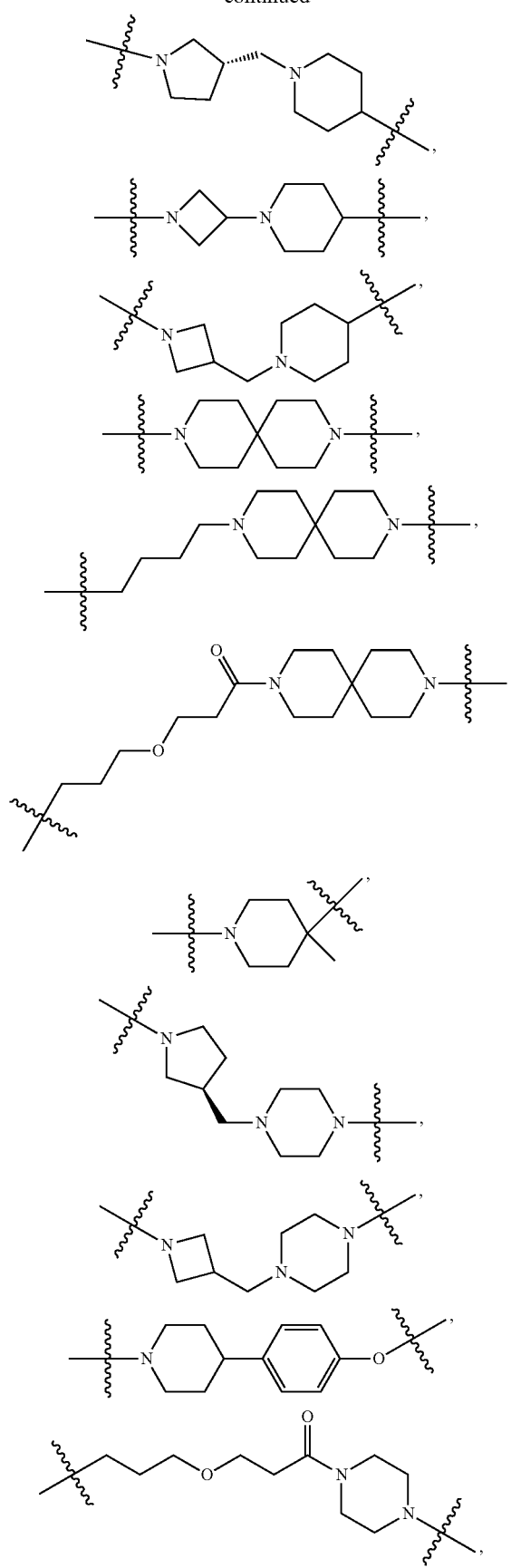
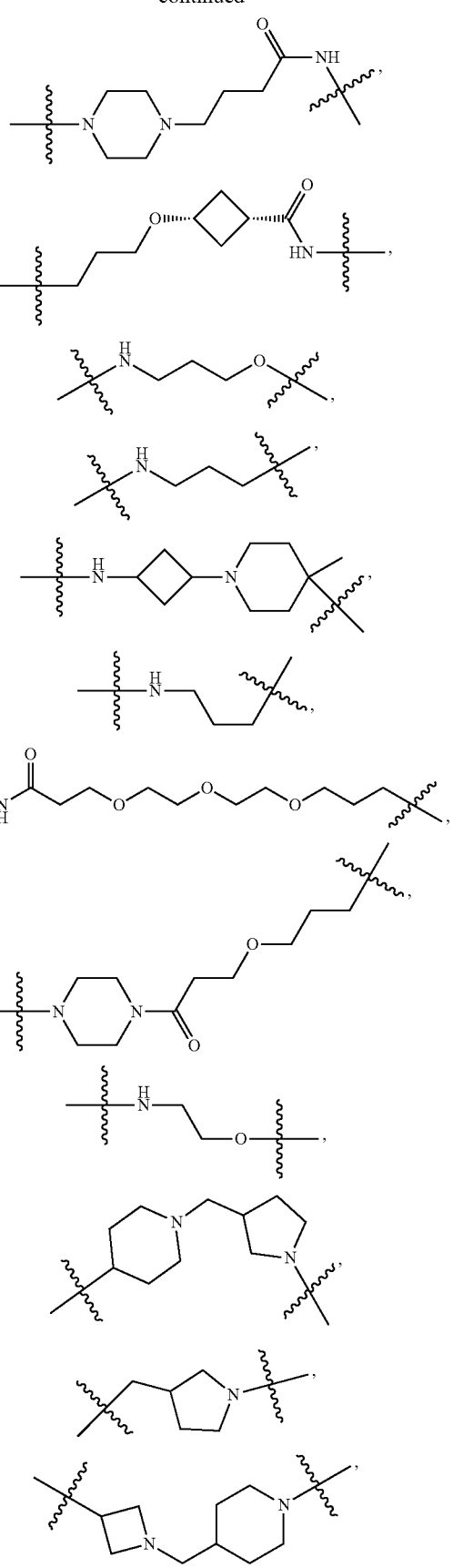

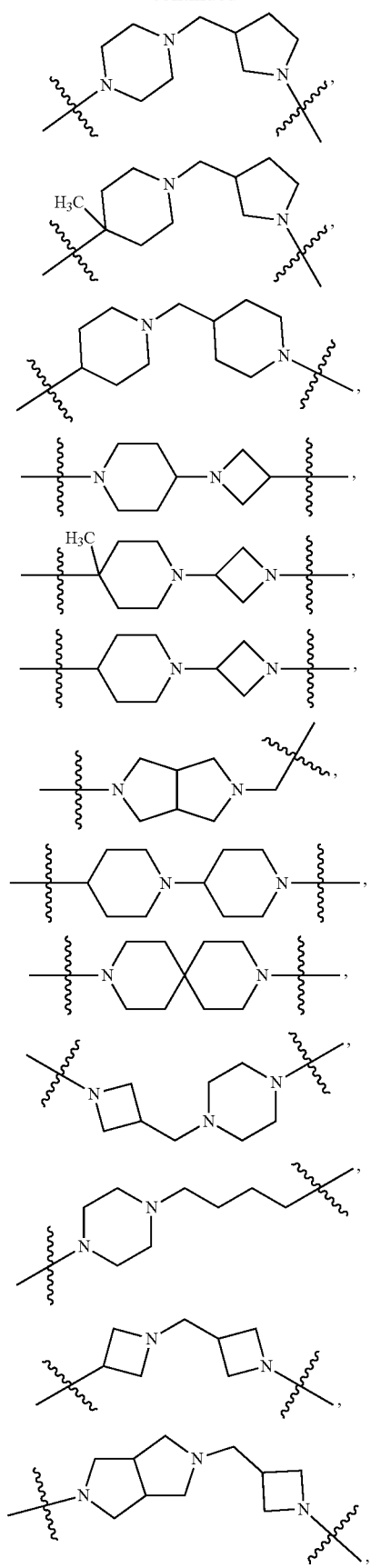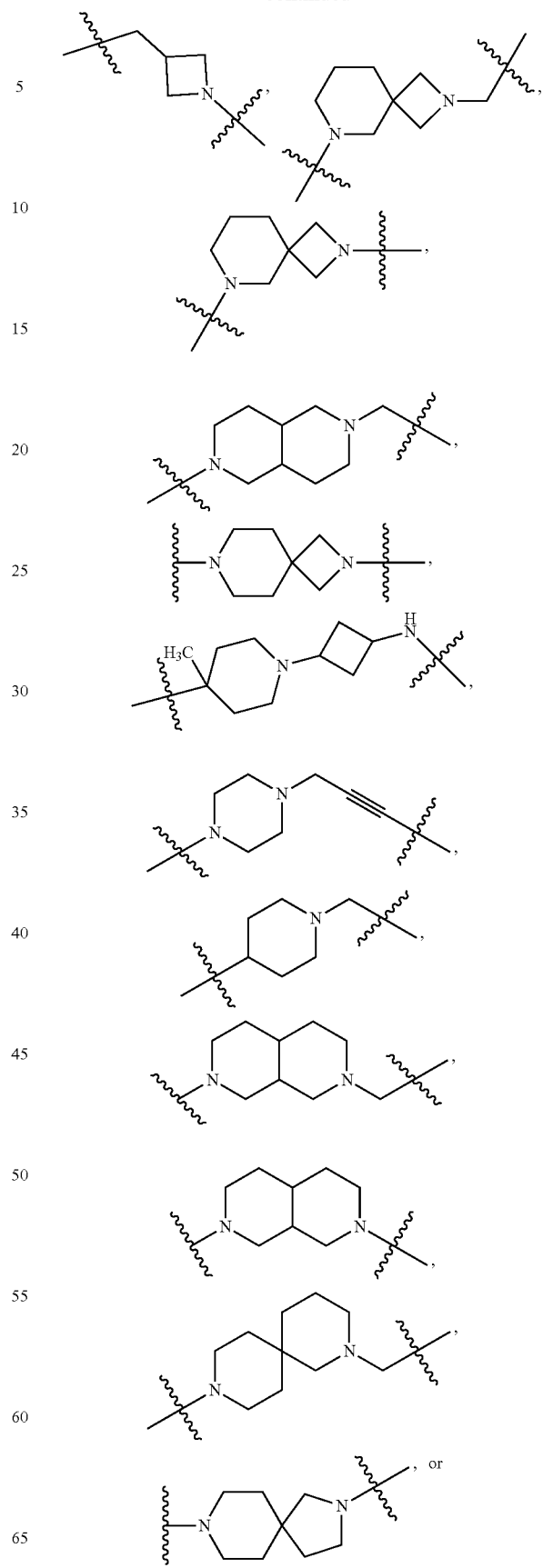

-continued

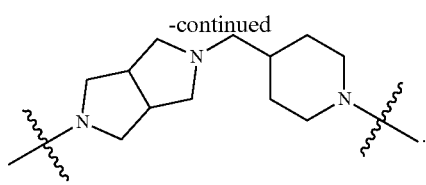

In some embodiments, Y is

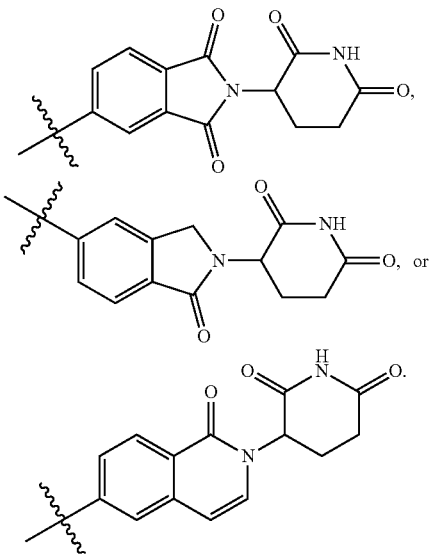

This disclosure also provides a compound of Formula (F)

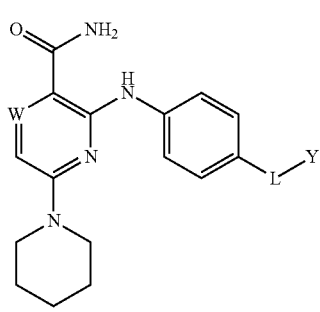

(F)

or a pharmaceutically acceptable salt thereof, wherein W is CH or N; L is —$X^1$-$X^2$-$X^3$—; $X^1$ is —C(O)—N(R), —N(R)—C(O), (O—$CH_2$—$CH_2$)$_m$—, —O($C_6H_4$)—, —(O—$CH_2$—$CH_2$—$CH_2$)$_m$—, —$C_{1-5}$ alkyl-, 7-12 membered spiro bicyclic heterocycloalkyl having one to three heteroatoms independently selected from N, O, or S, or 4-6 membered monocyclic heterocycloalkyl having one to two heteroatoms independently selected from N, O, or S, wherein each of the monocyclic and bicyclic heterocycloalkyl of $X^1$ is optionally substituted with —$CH_3$; $X^2$ is a bond, —$C_{1-5}$ alkyl-, —(O—$CH_2$—$CH_2$)$_n$—, —($CH_2$—$CH_2$—O)$_n$—, —N(R)—C(O)—, —N(R)—, —C(O)—, —$C_{1-5}$ alkyl-, 4-6 membered monocyclic cycloalkyl, or 4-6 membered monocyclic heterocycloalkyl having one to two heteroatoms independently selected from N, O, or S; $X^3$ is a bond, —$C_{1-4}$ alkyl-, —C≡C—, 4-6 membered cycloalkyl, —N(R)—, —(O—$CH_2$—$CH_2$)$_p$—, —($CH_2$—$CH_2$—O)$_p$—, 4-6 membered heterocycloalkyl having one to two heteroatoms independently selected from N, O, or S, wherein the heterocycloalkyl is optionally substituted with —$CH_3$; each R is independently —H or —$C_{1-3}$ alkyl; each of m, n, and p is independently an integer from one to three; and Y is

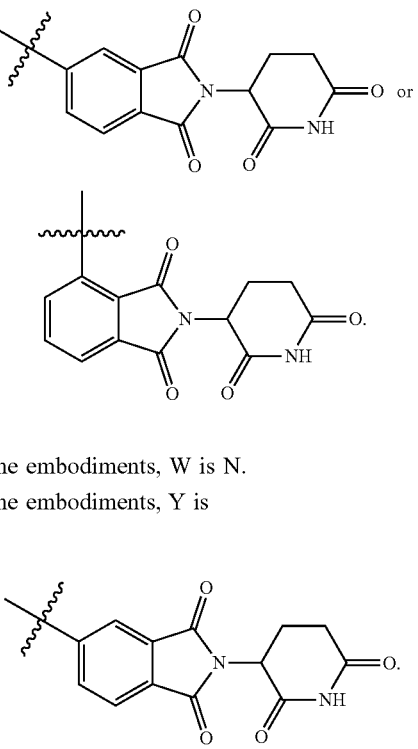

In some embodiments, W is N.
In some embodiments, Y is

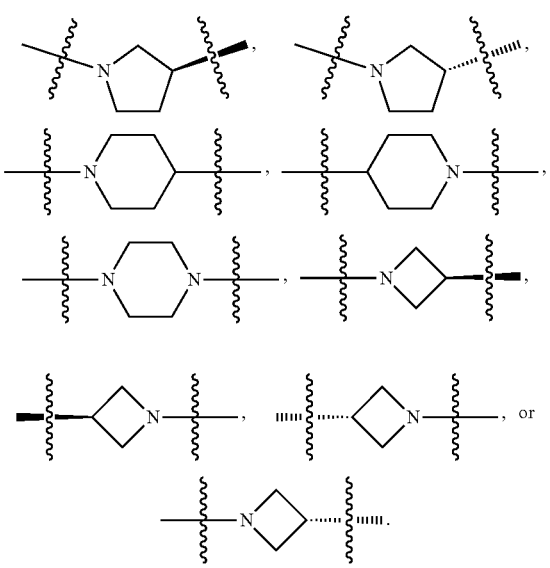

In some embodiments, $X^1$ is a 4-6 membered monocyclic heterocycloalkyl having one to two heteroatoms independently selected from N, O, or S, wherein each of the monocyclic heterocycloalkyl of $X^1$ is optionally substituted with —$CH_3$. For example, $X^1$ In some instances, $X^1$ is
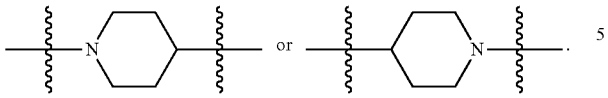
In some embodiments, $X^2$ is a bond or —$C_{1-5}$ alkyl-.
In some embodiments, $X^3$ is a 4-6 membered monocyclic heterocycloalkyl having one to two heteroatoms independently selected from N, O, or S. For example, $X^3$ is
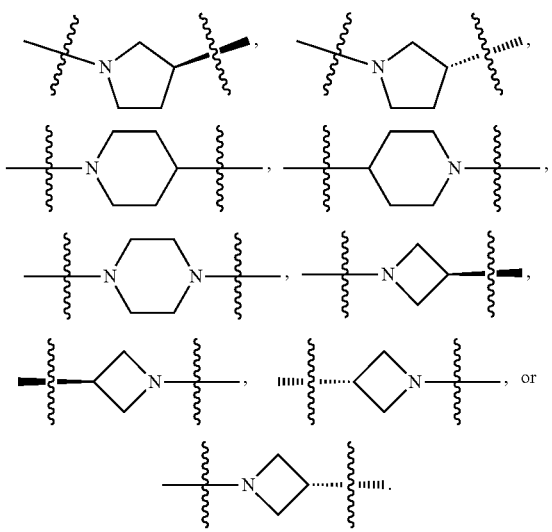
In some instances, $X^3$ is
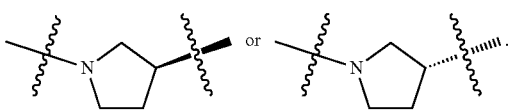
In some embodiments, L is
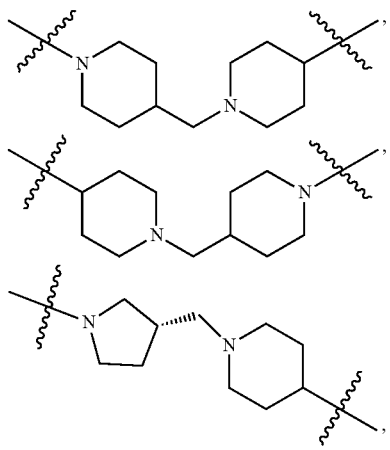
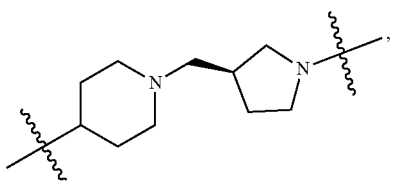
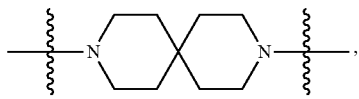
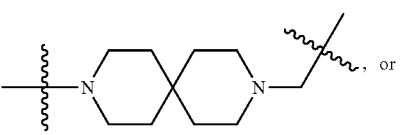, or
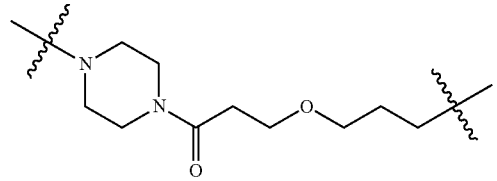
In some embodiments, L is
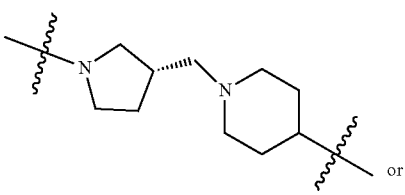
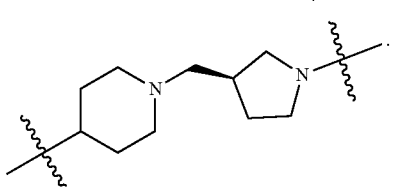
In some embodiments, W is N; an L is
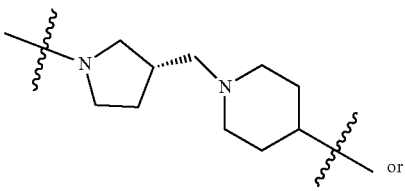
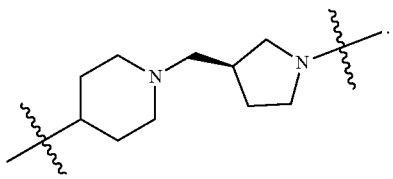

This disclosure also provides a compound of Formula (G)

(G)

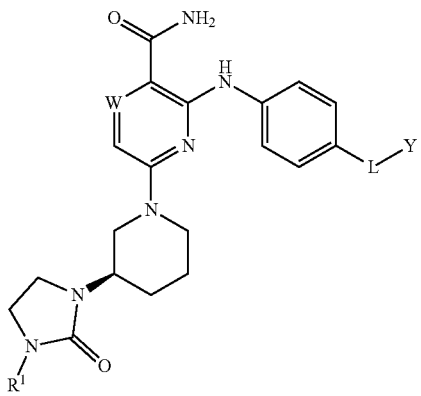

or a pharmaceutically acceptable salt thereof, wherein $R^1$, L, and Y are as defined for compounds of Formula (A).

In some embodiments, $R^1$ is methyl.

In some embodiments, Y is

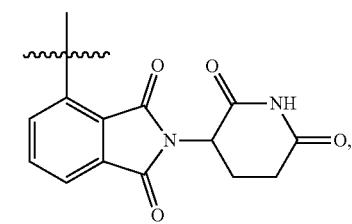

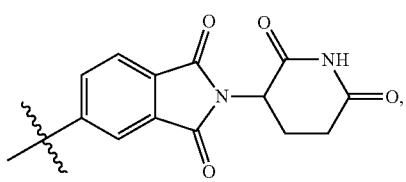

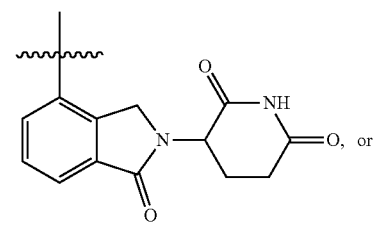

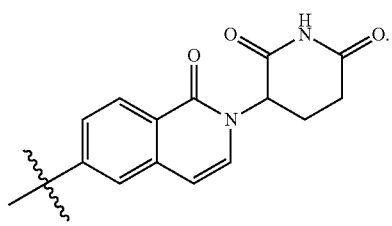

In some embodiments, W is N.

This disclosure also provides a compound of Formula (H)

(H)

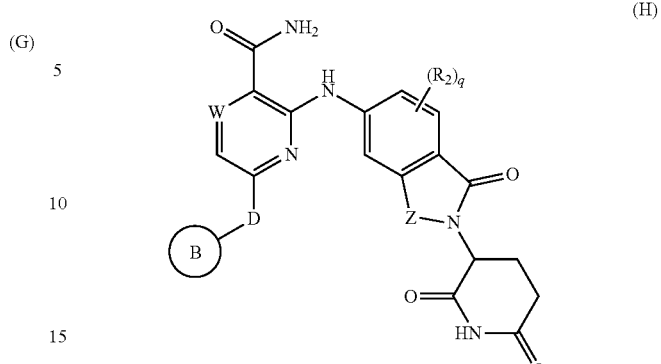

or a pharmaceutically acceptable salt thereof, wherein Ring B, $R^2$, Z, W, D, and q are as defined in the compound of Formula (A).

In some embodiments, q is zero.

This disclosure also provides a compound of Formula (J)

(J)

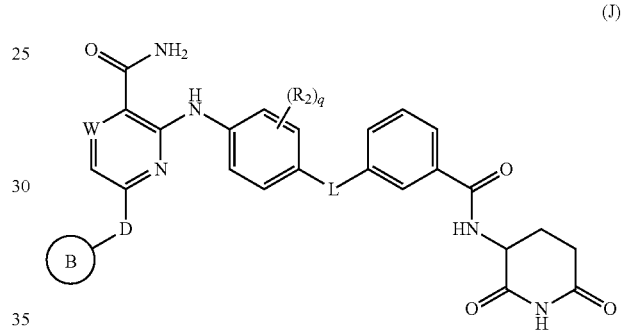

or a pharmaceutically acceptable salt thereof, wherein Ring B, D, W, $R^2$, q, and L are as defined in the compound of Formula (A).

This disclosure also provides a compound of Formula (K)

(K)

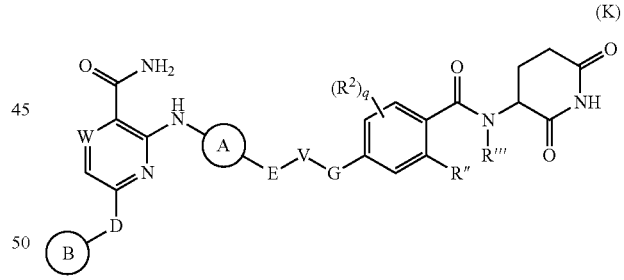

or a pharmaceutically acceptable salt thereof, wherein Ring A is

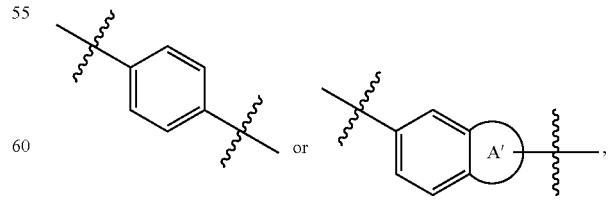

wherein Ring A is optionally and independently substituted with up to three substituents selected from halo, —CN, -carboxyl, —NH$_2$, and optionally substituted —C$_{1-6}$ alkyl (e.g., optionally substituted —C$_{1-3}$ alkyl); V is a bond or —CH$_2$—; and E and G are each independently a 5-6 membered heterocycloalkyl, wherein each heterocycloalkyl contains at least one nitrogen atom. Ring B, W, $R^2$, q, $R'''$, $R''''$, and Ring A' are as defined in the compound of Formula (A). In some embodiments, Ring A' together with the phenyl ring to which Ring A' is fused form a 9-10 membered bicyclic aryl or a 9-10 membered bicyclic heteroaryl wherein the bicyclic heteroaryl has one to three heteroatoms independently selected from N, O, or S.

In some embodiments, D is a bond and W is nitrogen.

This disclosure also provides a compound of Formula (M)

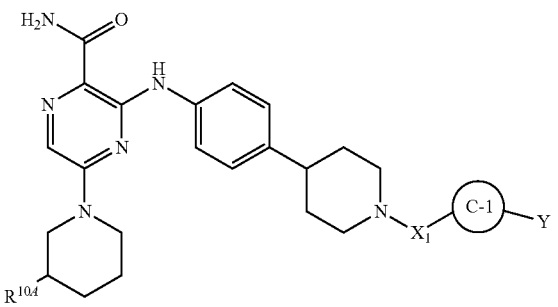

(M)

or a pharmaceutically acceptable salt thereof, wherein $R^{10A}$ is —H,

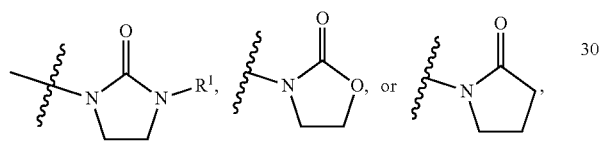

wherein $R^1$ is $C_{1-4}$ alkyl; $X^1$ is —$C_{1-5}$ alkyl-; Ring C-1 is a 5-6 membered heterocycloalkyl having one nitrogen atom; and Y is

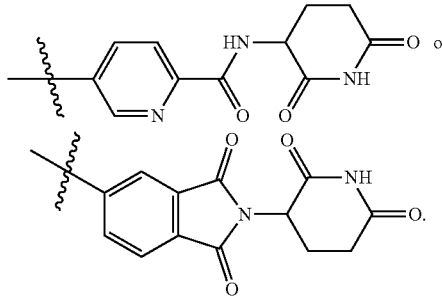

In some embodiments, $R^{10A}$ is —H or

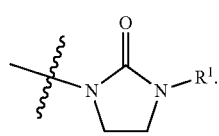

In some embodiments, $R^{10A}$ is

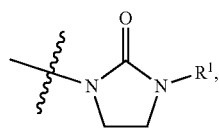

and $R^1$ is methyl, ethyl, propyl, iso-propyl, butyl, sec-butyl, or iso-butyl. For example, $R^1$ is methyl.

In some embodiments, $X^1$ is methylene (—$CH_2$—), ethylene (—$CH_2CH_2$—), or propylene (—$CH_2CH_2CH_2$—). For instance, $X^1$ is methylene (—$CH_2$—).

In some embodiments, Ring C-1 is

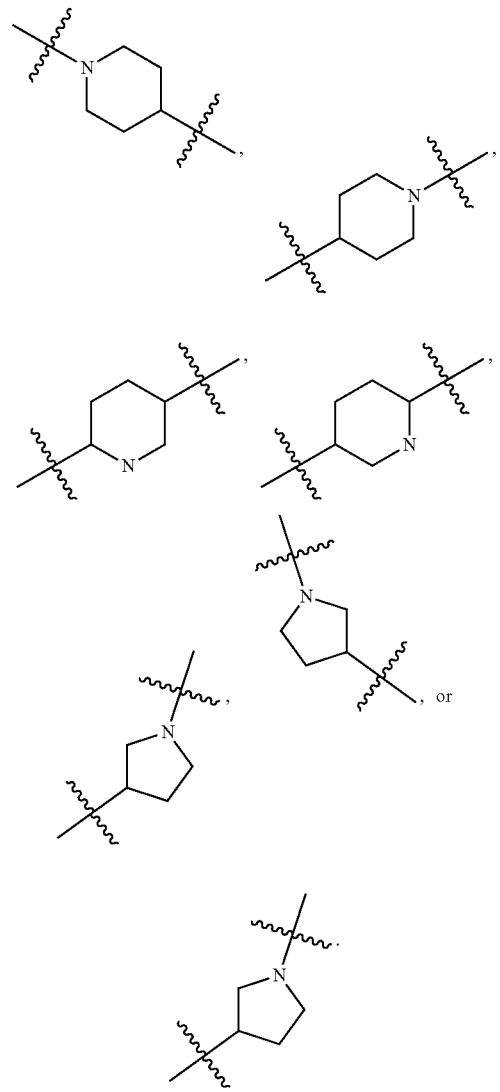

For instance, Ring C-1 is

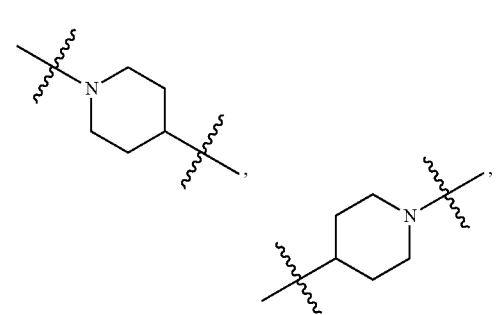

-continued

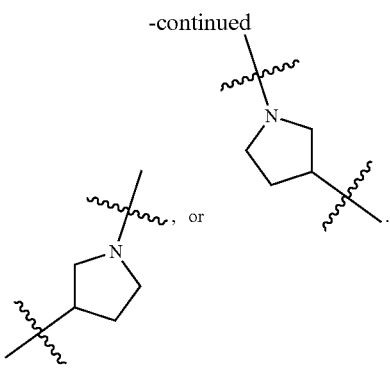

, or

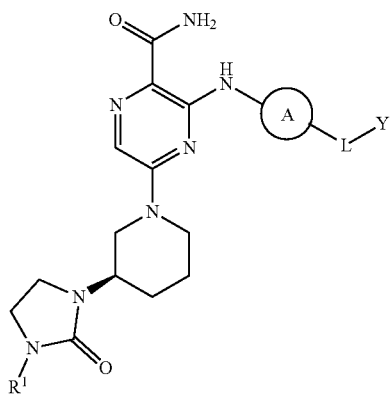

.

This disclosure provides a compound of Formula (X)

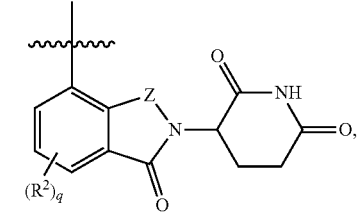

Y is

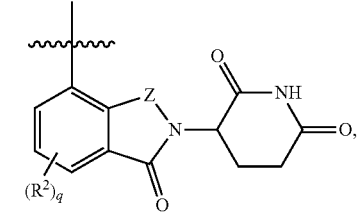

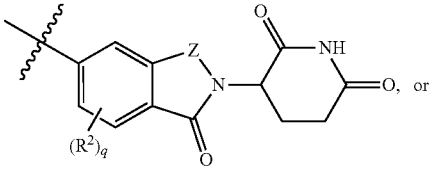

, or

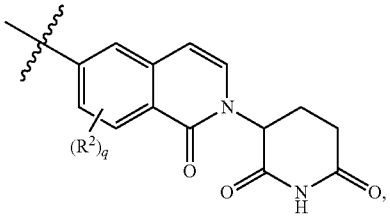

, wherein each $R^2$ is independently halo or $C_{1-4}$ alkyl; each Z is —C($R^A$)$_2$— or —C(O)—; each $R^A$ is independently —H or $C_{1-4}$ alkyl; and q is zero, one, or two.

In some instances, the compound of Formula (X) is a compound of Formula (I)

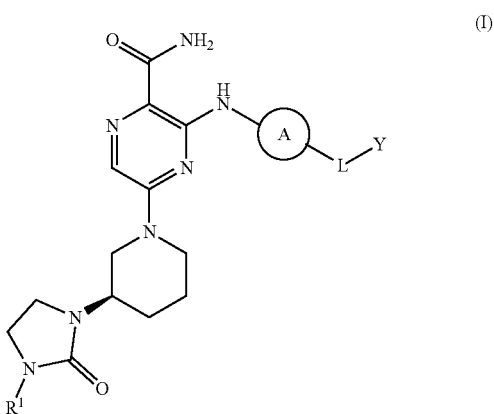

or a pharmaceutically acceptable salt thereof, wherein $R^1$ is $C_{1-3}$ alkyl; Ring A is phenyl, 5-6 membered partially or fully unsaturated monocyclic heterocycle, 9-10 membered bicyclic aryl, or 9-10 membered bicyclic heteroaryl, wherein the heterocycle and the bicyclic heteroaryl of Ring A each independently have one to three heteroatoms independently selected from N, O, or S; L is —$X^1$-$X^2$-$X^3$-$X^4$-$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having one to three heteroatoms independently selected from N, O, or S, wherein the bicyclic heterocycloalkyl of $X^1$ is optionally substituted with —CH$_3$, or 4-6 membered monocyclic heterocycloalkyl having one to two heteroatoms independently selected from N, O, or S, wherein the monocyclic heterocycloalkyl of $X^1$ is optionally substituted with —CH$_3$; $X^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having one to two heteroatoms independently selected from N, O, or S; $X^3$ is a bond, —C$_{1-4}$ alkyl-, —C≡C—, 4-6 membered cycloalkyl, —N(R)—, —(O—CH$_2$—CH$_2$)$_p$—, —(CH$_2$—CH$_2$—O)$_p$—, 4-6 membered heterocycloalkyl having one to two heteroatoms independently selected from N, O, or S, wherein the heterocycloalkyl is optionally substituted with —CH$_3$; $X^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated carbocycle having zero to three heteroatoms independently selected from N, O, or S; $X^5$ is a bond, —C$_{1-4}$ alkyl-, —N(R)—, or —C(O)—N(R)—; each R is independently —H or —C$_{1-3}$ alkyl; each of m, n, and p is independently an integer from one to three;

or a pharmaceutically acceptable salt thereof, wherein $R^1$ is $C_{1-3}$ alkyl; Ring A is phenyl, 9-10 membered bicyclic aryl, or 9-10 membered bicyclic heteroaryl having one to three heteroatoms independently selected from N, O, or S; L is —$X^1$-$X^2$-$X^3$-$X^4$-$X^5$—; $X^1$ is —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro bicyclic heterocycloalkyl having one to three heteroatoms independently selected from N, O, or S, wherein the heterocycloalkyl is optionally substituted with —CH$_3$, or 4-6 membered heterocycloalkyl having one to two heteroatoms independently selected from N, O, or S, wherein the heterocycloalkyl is optionally substituted with —CH$_3$; $X^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered cycloalkyl, or 4-6 membered heterocycloalkyl having one to two heteroatoms independently selected from N, O, or S; X³ is a bond, —C₁₋₄ alkyl-, 4-6 membered cycloalkyl, —N(R)—, —(O—CH₂—CH₂)ₚ—, —(CH₂—CH₂—O)ₚ—, 4-6 membered heterocycloalkyl having one to two heteroatoms independently selected from N, O, or S, wherein the heterocycloalkyl is optionally substituted with —CH₃; X⁴ is a bond, —CH₂—CH₂—N(R)—, —N(R)—, —C₁₋₄ alkyl-, —(O—CH₂—CH₂—CH₂)ₘ—, or 5-6 membered saturated, partially unsaturated, or fully unsaturated heterocycle having one to three heteroatoms independently selected from N, O, or S; X⁵ is a bond, —C₁₋₄ alkyl-, —N(R)—, or —C(O)—N(R)—; each R is independently —H or —C₁₋₃ alkyl; each of m, n, and p is independently an integer from one to three (e.g., one, two, or three);
Y is

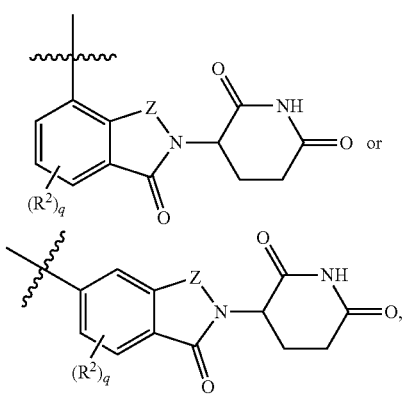 or, wherein each R² is independently halo or —C₁₋₄ alkyl; each Z is —C(Rᴬ)₂— or —C(O)—; each Rᴬ is independently —H or —C₁₋₄ alkyl; and q is zero, one, or two.

In some embodiments, q is zero. In other embodiments, q is one and R² is —F.

In some embodiments, Z is —CH₂— or —C(O)—.

In some embodiments, Y is

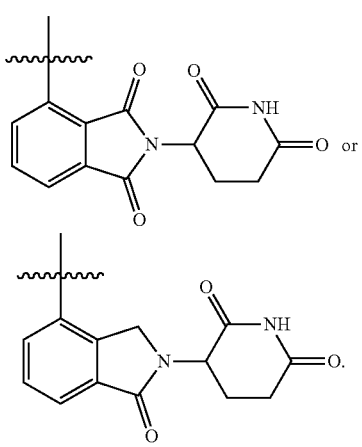 [SMILES: *c1cccc2c1C(=O)N(C1CCC(=O)NC1=O)C2=O ; *c1cccc2c1CN(C1CCC(=O)NC1=O)C2=O] or

In other embodiments, Y is

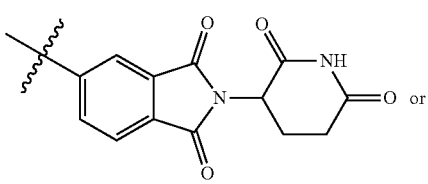

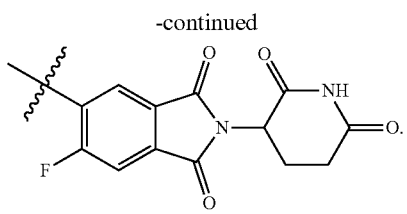

In some embodiments, R¹ is —C₁₋₃ alkyl. For example, R¹ is methyl, ethyl, propyl, or iso-propyl. In other embodiments, R¹ is methyl.

In some embodiments, each R is independently —H or —CH₃. For instance, each R is —H.

In some embodiments, X¹ is —C(O)—N(R)—, —N(R)—C(O)—, —(O—CH₂—CH₂)ₘ—, —O(C₆H₄)—, —(O—CH₂—CH₂—CH₂)ₘ—, —C₁₋₅ alkyl-, 7-12 membered spiro bicyclic heterocycloalkyl having one to three heteroatoms independently selected from N, O, or S, or 4-6 membered heterocycloalkyl having one to two heteroatoms independently selected from N, O, or S, wherein the heterocycloalkyl is optionally substituted with —CH₃. In some embodiments, X¹ is —C(O)—N(R)—. For example, X¹ is —C(O)—N(H)—, —C(O)—N(CH₃)—, or —C(O)—N(CH₂CH₃)—. In other embodiments, X¹ is a 5-6 membered heterocycloalkyl having one to two heteroatoms independently selected from N, O, or S, wherein the heterocycloalkyl is optionally substituted with —CH₃. For example, X¹ is,

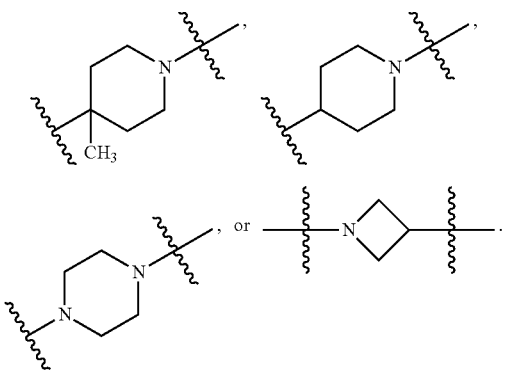

In other examples, X¹ is a 7-10 membered spiro bicyclic heterocycloalkyl ring having one to three heteroatoms independently selected from N, O, or S (e.g., N). For example, X¹ is

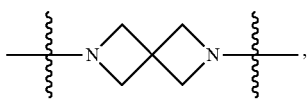

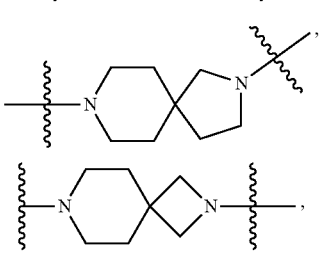

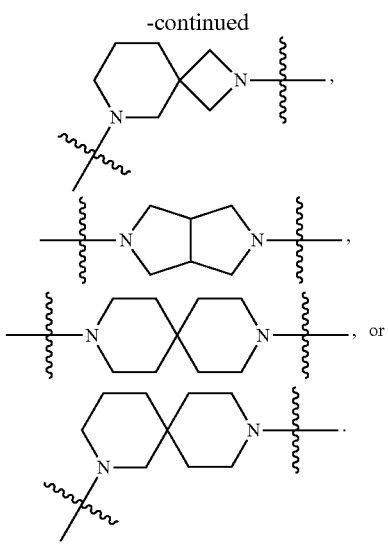

In other embodiments, $X^1$ is $-(O-CH_2-CH_2)_m-$ or $-(O-CH_2-CH_2-CH_2)_m-$, wherein m is one, two, three. For example, $X^1$ is $-(O-CH_2-CH_2)_m-$ or $-(O-CH_2-CH_2-CH_2)_m-$, and m is one. In another example, $X^1$ is $-(O-CH_2-CH_2)_m-$ or $-(O-CH_2-CH_2-CH_2)_m-$, and m is two. In some embodiments, $X^1$ is $-C_{1-5}$ alkyl-. For example, $X^1$ is methylene ($-CH_2-$), ethylene ($-CH_2CH_2-$), propylene ($-CH_2CH_2CH_2-$), butylene ($-CH_2CH_2CH_2CH_2-$), or the like. In some embodiments, $X^1$ is $-CH_2-$, $-C(O)-$,

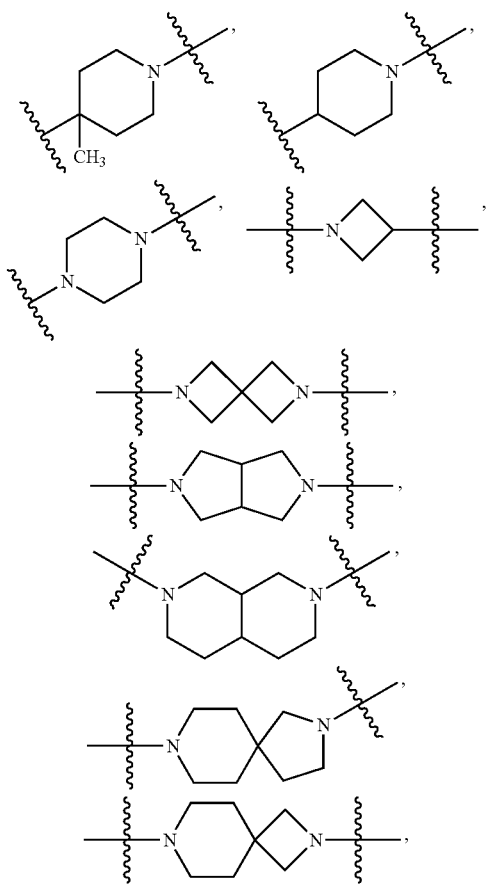

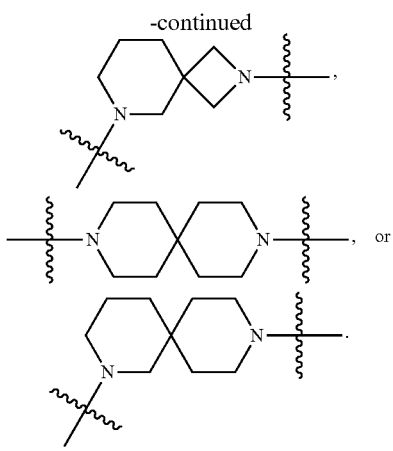

In some embodiments, $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having one to two heteroatoms independently selected from N, O, or S. In some embodiments, $X^2$ is a bond. In some embodiments, $X^2$ is $-(O-CH_2-CH_2)_n-$, $-(CH_2-CH_2-O)_n-$, or $-C_{1-5}$ alkyl-, wherein n is one, two, or three. For example, $X^1$ is $-C(O)-N(R)-$, and $X^2$ is $-(O-CH_2-CH_2)_n-$, $-(CH_2-CH_2-O)_n-$, or $-C_{1-5}$ alkyl-. In some examples, $X^2$ is $-(O-CH_2-CH_2)_n-$ or $-(CH_2-CH_2-O)_n-$, where n is one or two. In other examples, $X^2$ is $-C_{1-5}$ alkyl-. For instance, $X^2$ is methylene ($-CH_2-$), ethylene ($-CH_2CH_2-$), propylene ($-CH_2CH_2CH_2-$), butylene ($-CH_2CH_2CH_2CH_2-$), or the like. In other examples, $X^2$ is a bond, $-CH_2-$, $-CH_2CH_2-$, or $-CH_2CH_2CH_2-$. In some examples, $X^2$ is 4-6 membered cycloalkyl. For instance, $X^2$ is

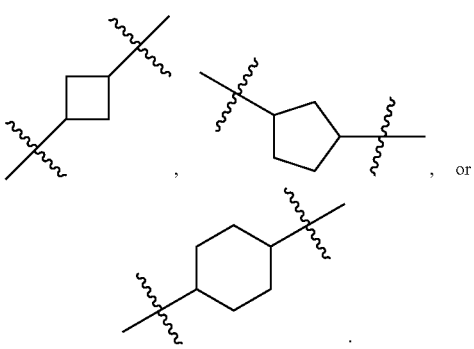

In other examples $X^2$ is 4-6 membered heterocycloalkyl having one to two heteroatoms independently selected from N, O, or S. For instance, $X^2$ is

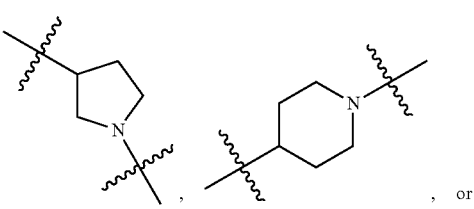

-continued

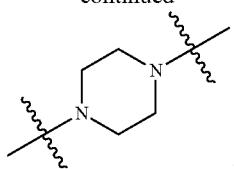

In some embodiments, $X^3$ is a bond, —$C_{1-4}$ alkyl-, 4-6 membered cycloalkyl, —N(R)—, —(O—CH$_2$—CH$_2$)$_p$—, —(CH$_2$—CH$_2$—O)$_p$—, 4-6 membered heterocycloalkyl having one to two heteroatoms independently selected from N, O, or S, wherein the heterocycloalkyl is optionally substituted with —CH$_3$. In some embodiments, $X^3$ is a bond. In some embodiments, $X^3$ is methyl, ethyl, propyl, iso-propyl, butyl, or the like. In some embodiments, $X^3$ is cyclopenty or cyclohexyl. In some embodiments, $X^3$ —N(H)—. And, in other embodiments, $X^3$ is —(O—CH$_2$—CH$_2$)$_p$— or —(CH$_2$—CH$_2$—O)$_p$—, wherein p is one or two.

In some embodiments, $X^4$ is a bond, —CH$_2$—CH$_2$—N(R)—, —N(R)—, —$C_{1-4}$ alkyl-, —(O—CH$_2$—CH$_2$—CH$_2$)$_m$—, or 5-6 membered saturated, partially unsaturated, or fully unsaturated heterocycle having one to three heteroatoms independently selected from N, O, or S. In some embodiments, $X^4$ is a bond,

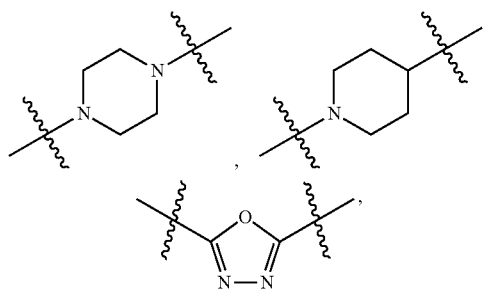

—$C_{1-4}$ alkyl-, —CH$_2$—CH$_2$—N(R)—, or —N(R)—. For example, $X^4$ is —CH$_2$—CH$_2$—N(H)—, or —N(H)—. In other examples, $X^4$ is methyl, ethyl, propyl, iso-propyl, butyl, sec-butyl, or the like.

In some embodiments, $X^5$ is a bond, —$C_{1-4}$ alkyl-, —N(R)—, or —C(O)—N(R)—. In some embodiments, $X^5$ is a bond. In some embodiments, $X^5$ is methyl, ethyl, propyl, iso-propyl, butyl, or the like. In some embodiments, $X^5$ is —N(H)— or —C(O)—N(H)—.

In some embodiments, L is selected from

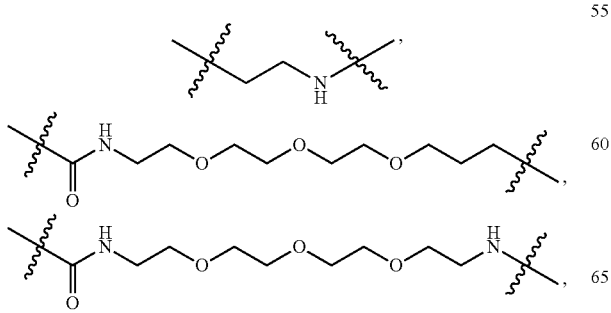

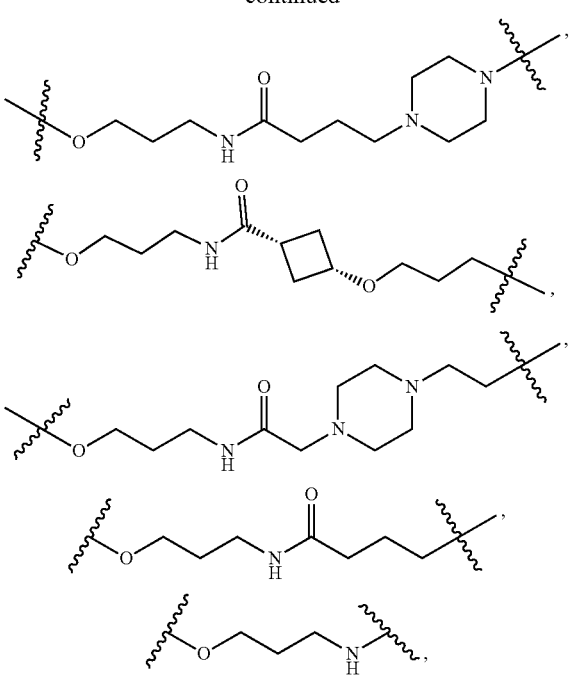

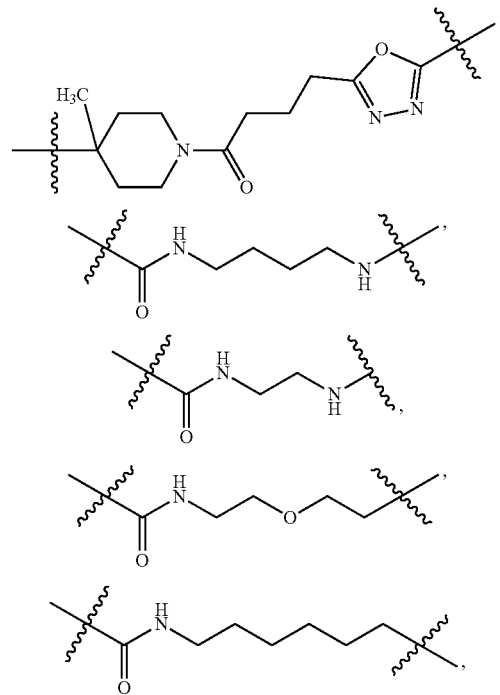

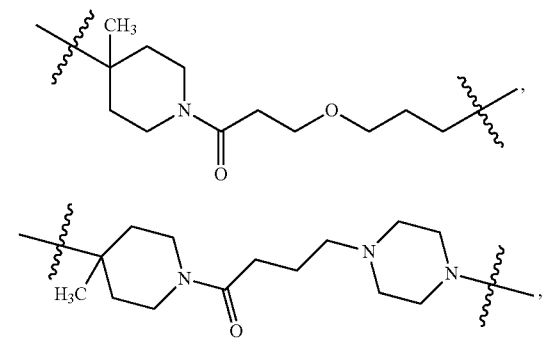

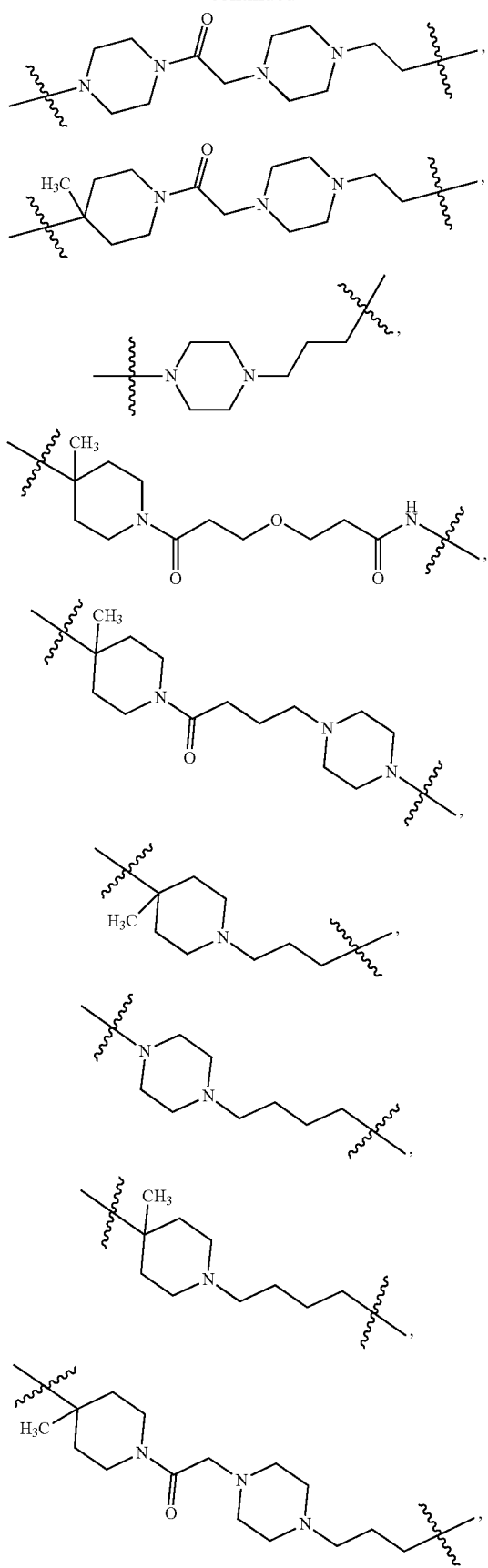
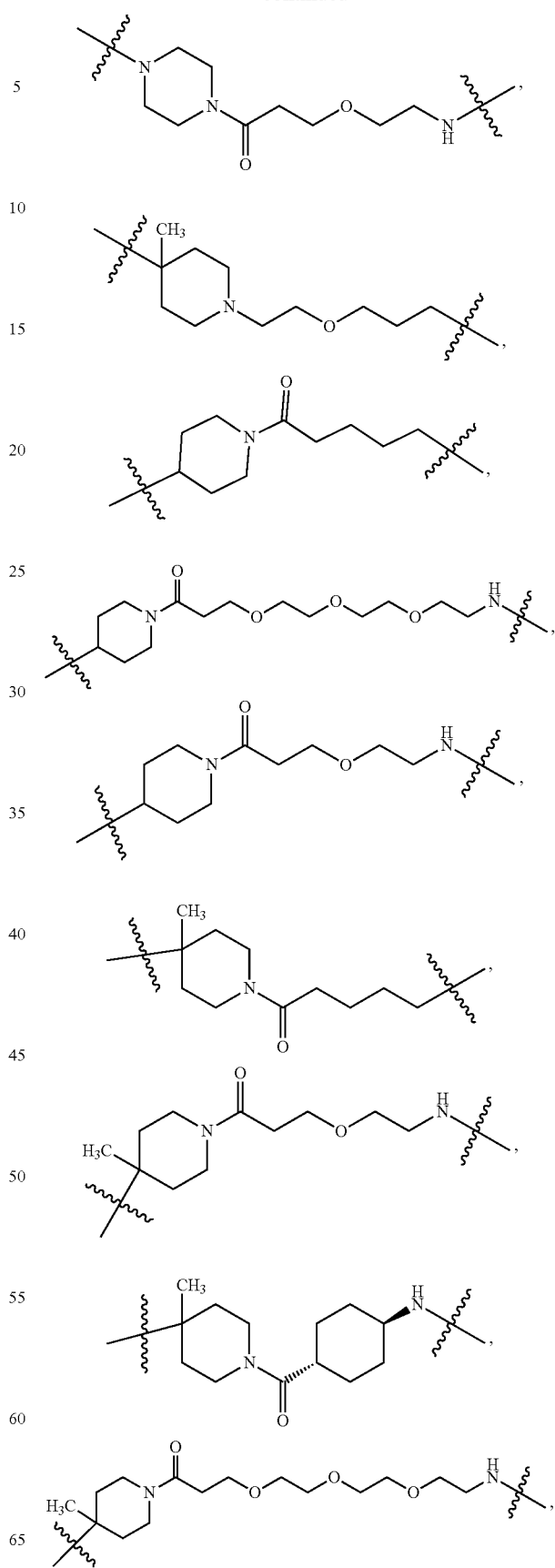

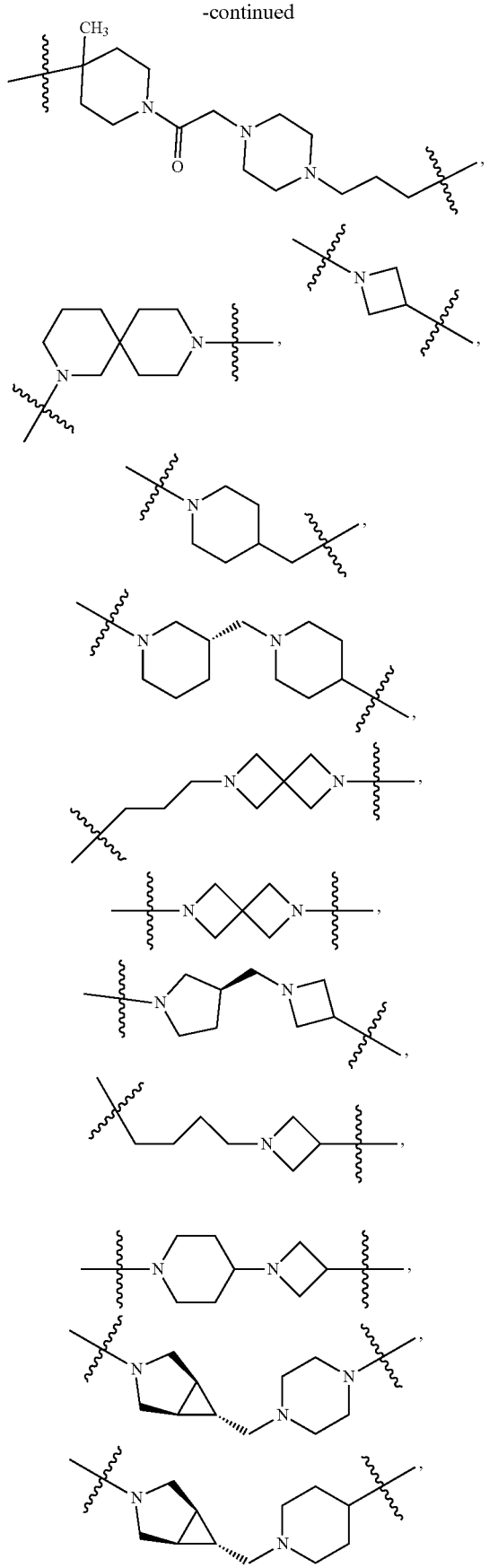
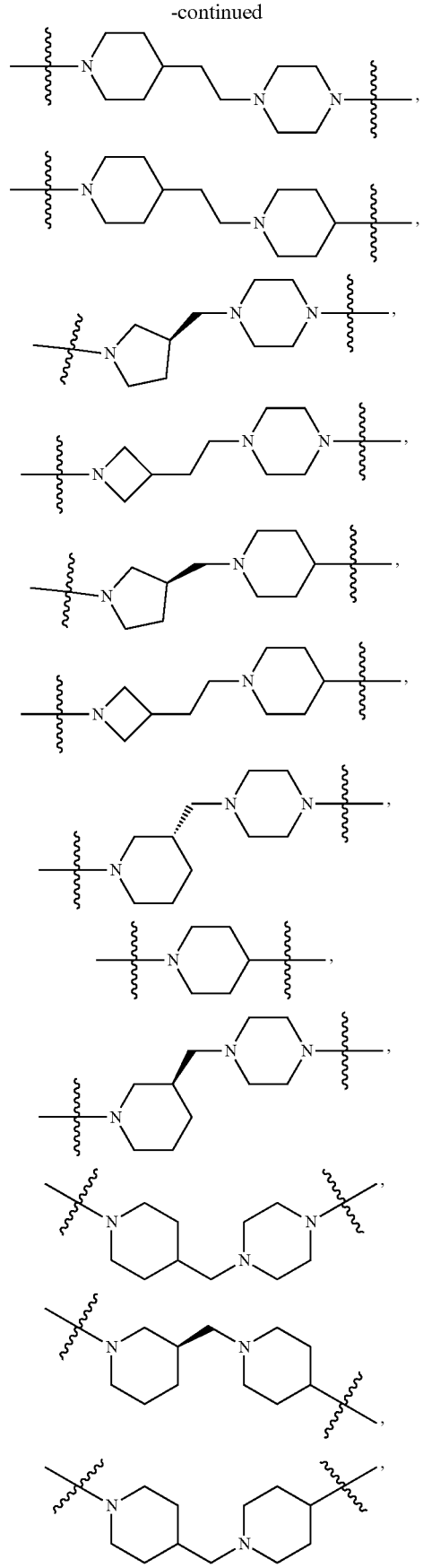

-continued
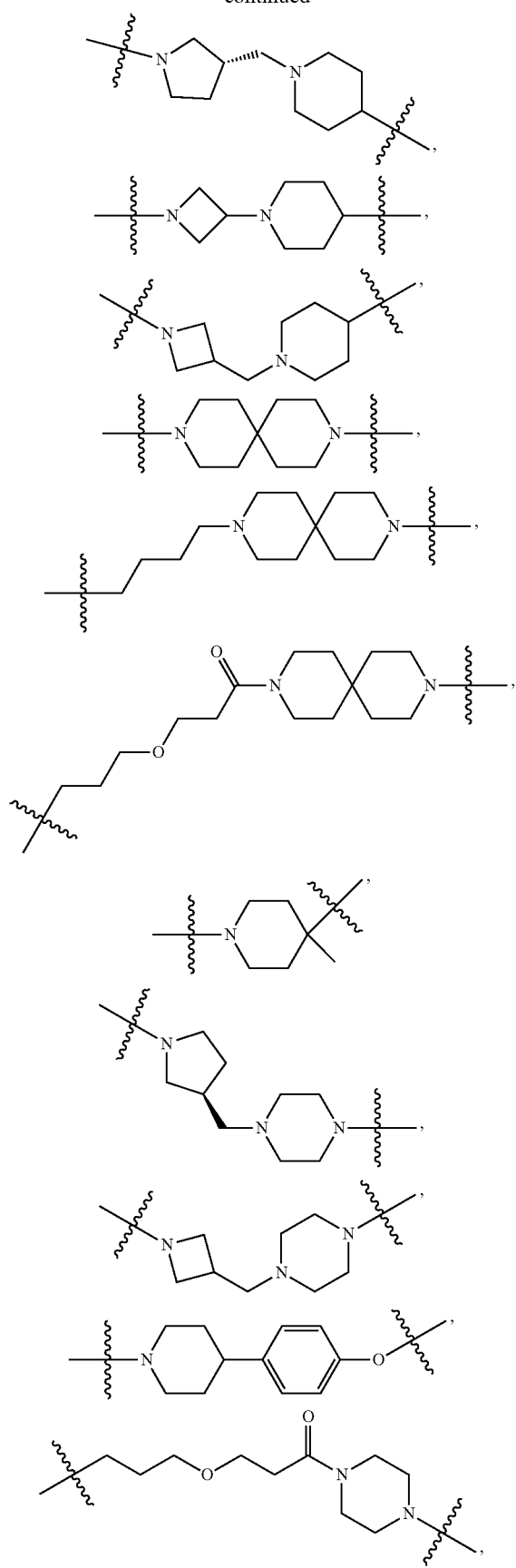
-continued
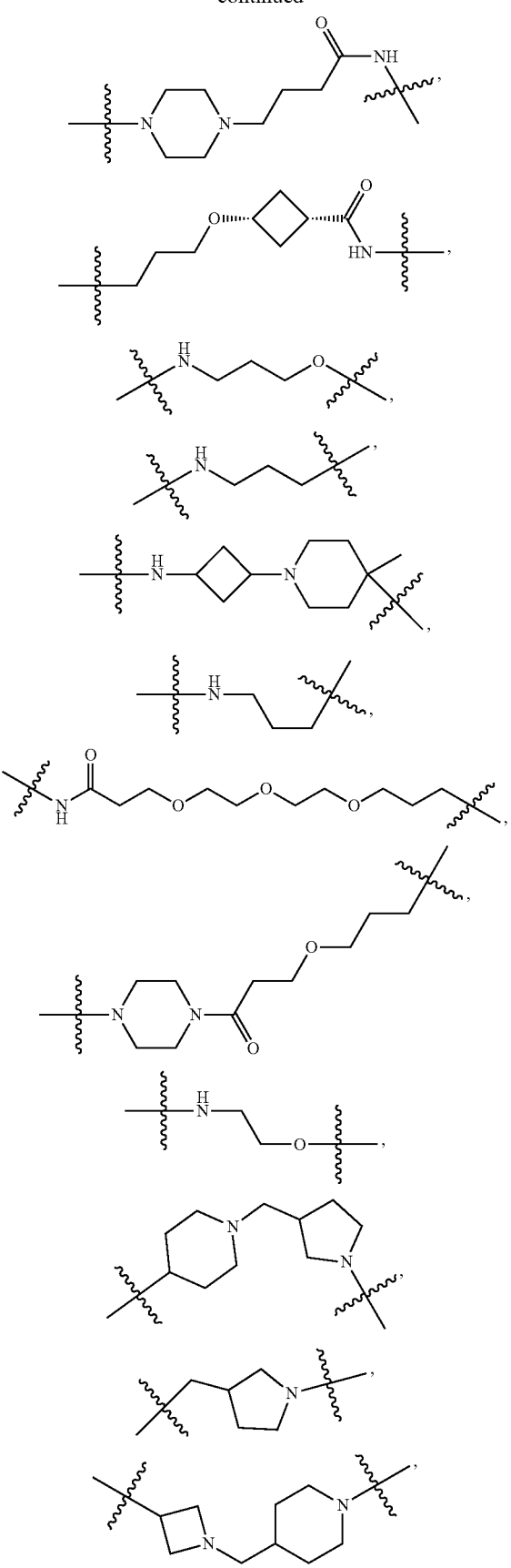

105
-continued
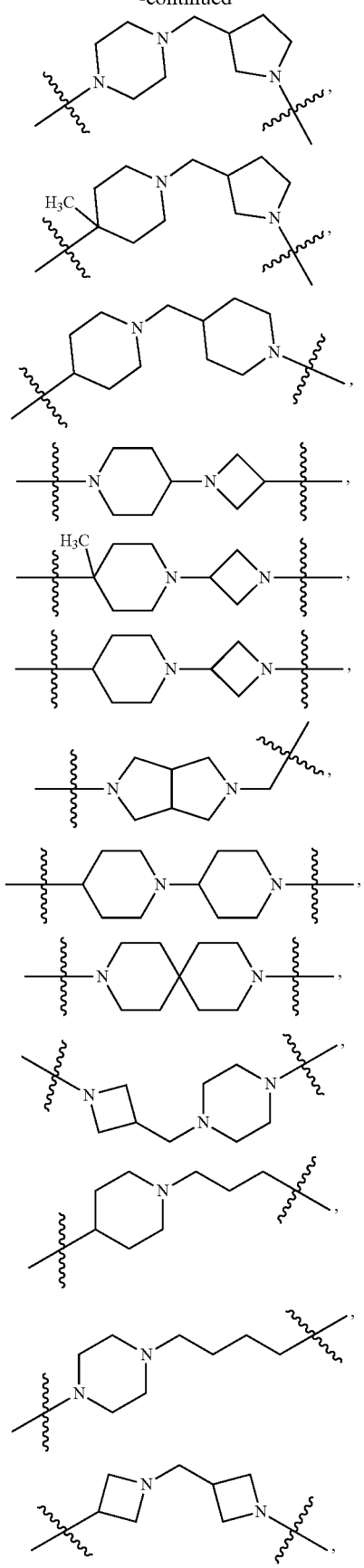
106
-continued
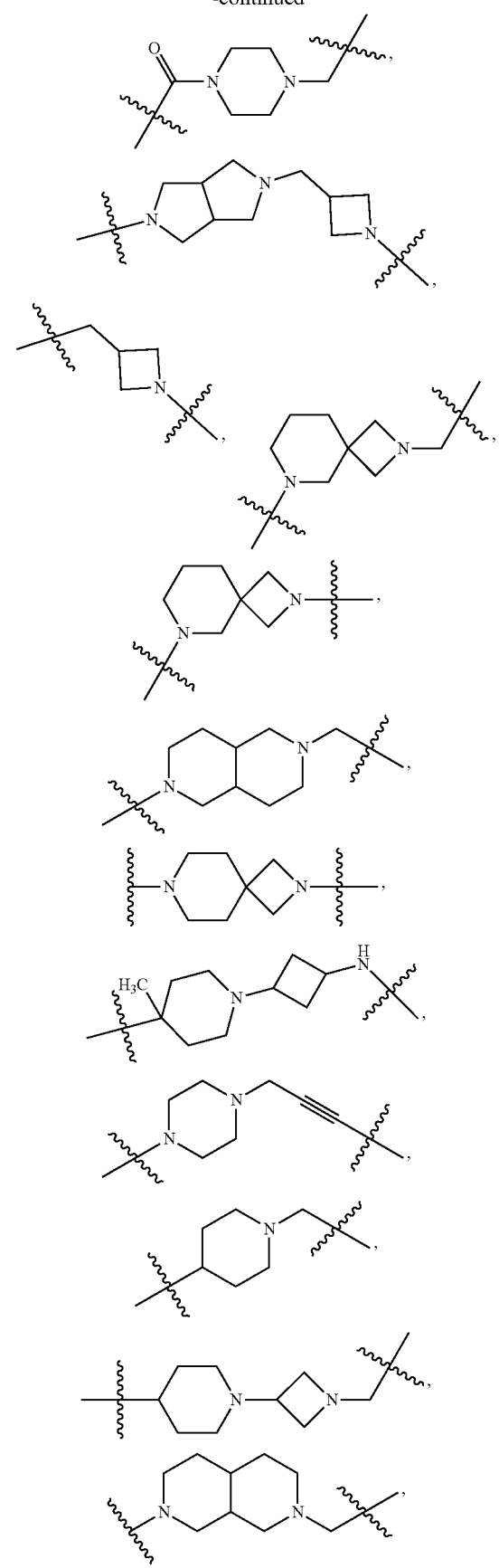

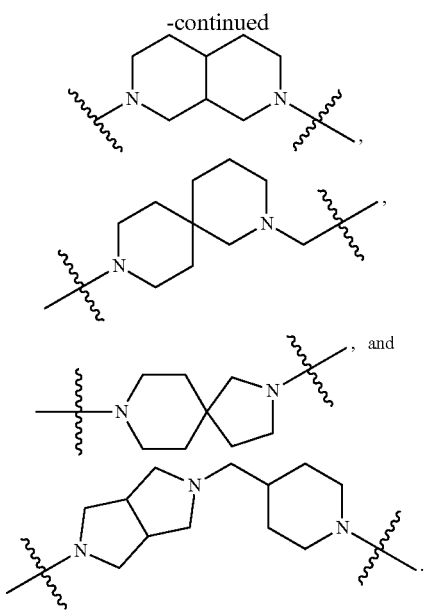

This disclosure also provides a compound of Formula (I-A):

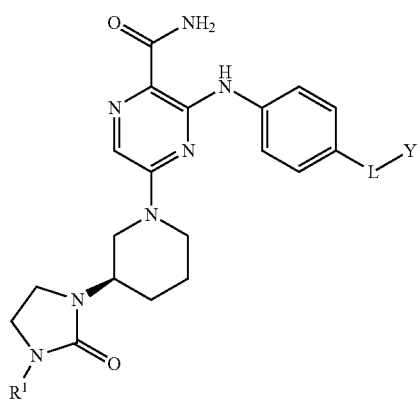

(I-A)

or a pharmaceutically acceptable salt thereof, wherein $R^1$ is $C_{1-3}$ alkyl; L is $-X^1-X^2-X^3-X^4-X^5-$; $X^1$ is $-C(O)-N(R)$, $-N(R)-C(O)-$, $-(O-CH_2-CH_2)_m-$, $-O(C_6H_4)-$, $-(O-CH_2-CH_2-CH_2)_m-$, $-C_{1-5}$ alkyl-, 7-12 membered spiro bicyclic heterocycloalkyl having one to three heteroatoms independently selected from N, O, or S, wherein the heterocycloalkyl is optionally substituted with $-CH_3$, or 4-6 membered heterocycloalkyl having one to two heteroatoms independently selected from N, O, or S, wherein the heterocycloalkyl is optionally substituted with $-CH_3$; $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having one to two heteroatoms independently selected from N, O, or S, wherein the heterocycloalkyl is optionally substituted with $-CH_3$; $X^4$ is a bond, $-CH_2-CH_2-N(R)-$, $-N(R)-$, $-C_{1-4}$ alkyl-, $-(O-CH_2-CH_2)_m-$, or 5-6 membered saturated, partially unsaturated, or fully unsaturated heterocycle having one to three heteroatoms independently selected from N, O, or S; $X^5$ is a bond, $-C_{1-4}$ alkyl-, $-N(R)-$, or $-C(O)-N(R)-$; each R is independently $-H$ or $-C_{1-3}$ alkyl; each of m, n, and p is independently an integer from one to three; Y is

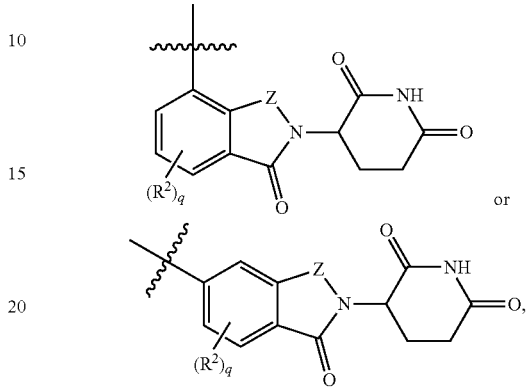

wherein each $R^2$ is independently halo or $-C_{1-4}$ alkyl; each Z is $-C(R^4)_2-$ or $-C(O)-$; each $R^4$ is independently $-H$ or $-C_{1-4}$ alkyl; and q is zero, one, or two.

In other embodiments, each of the variables in Formula (I-A) is as defined herein for the compound of Formula (X) or (I).

This disclosure also provides a compound of Formula (I-B)

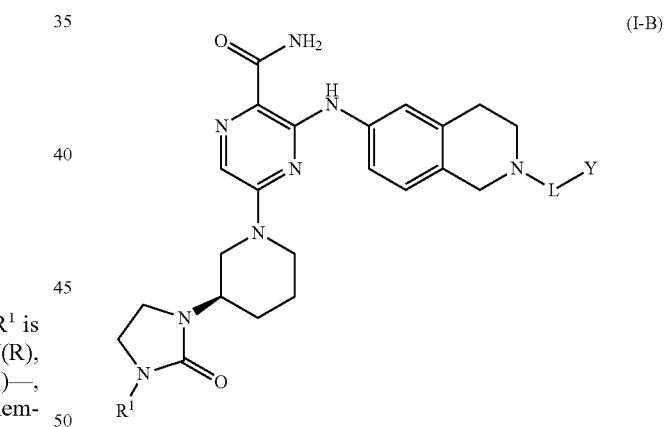

(I-B)

or a pharmaceutically acceptable salt thereof, wherein $R^1$ is $C_{1-3}$ alkyl; L is $-X^1-X^2-X^3-X^4-X^5-$; $X^1$ is $-C(O)-N(R)-$, $-N(R)-C(O)-$, $-(O-CH_2-CH_2)_m-$, $-O(C_6H_4)-$, $-(O-CH_2-CH_2-CH_2)_m-$, $-C_{1-5}$ alkyl-, 7-12 membered spiro bicyclic heterocycloalkyl ring having one to three heteroatoms independently selected from N, O, or S, wherein the heterocycloalkyl is optionally substituted with $-CH_3$, or 4-6 membered heterocycloalkyl having one to two heteroatoms independently selected from N, O, or S, wherein the heterocycloalkyl is optionally substituted with $-CH_3$; $X^2$ is a bond, $-(O-CH_2-CH_2)_n-$, $-(CH_2-CH_2-O)_n-$, $-N(R)-C(O)-$, $-N(R)-$, $-C(O)-$, $-C_{1-5}$ alkyl-, 4-6 membered cycloalkyl, or 4-6 membered heterocycloalkyl having one to two heteroatoms independently selected from N, O, or S; $X^3$ is a bond, $-C_{1-4}$ alkyl-, 4-6 membered cycloalkyl, $-N(R)-$, —(O—CH$_2$—CH$_2$)$_p$—, —(CH$_2$—CH$_2$—O)—, or 4-6 membered heterocycloalkyl having one to two heteroatoms independently selected from N, O, or S, wherein the heterocycloalkyl is optionally substituted with —CH$_3$; X$^4$ is a bond, —CH$_2$—CH$_2$—N(R)—, —N(R)—, —C$_{1-4}$ alkyl-, —(O—CH$_2$—CH$_2$—CH$_2$)$_m$—, or 5-6 membered saturated, partially unsaturated, or fully unsaturated heterocycle having one to three heteroatoms independently selected from N, O, or S; X$^5$ is a bond, —C$_{1-4}$ alkyl-, —N(R)—, or —C(O)—N(R)—; each R is independently —H or —C$_{1-3}$ alkyl; each of m, n, and p is independently an integer from one to three; Y is

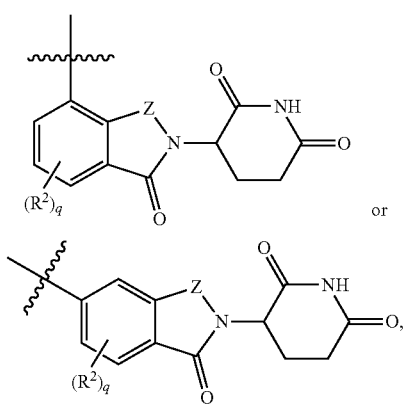

or wherein each R$^2$ is independently halo or C$_{1-4}$ alkyl; each Z is —C(R$^A$)$_2$— or —C(O)—; each R$^A$ is independently —H or C$_{1-4}$ alkyl; and q is zero, one, or two.

In other embodiments, each of the variables in Formula (I-B) is as defined herein for the compound of Formula (X) or (I).

This disclosure also provides a compound of Formula (II)

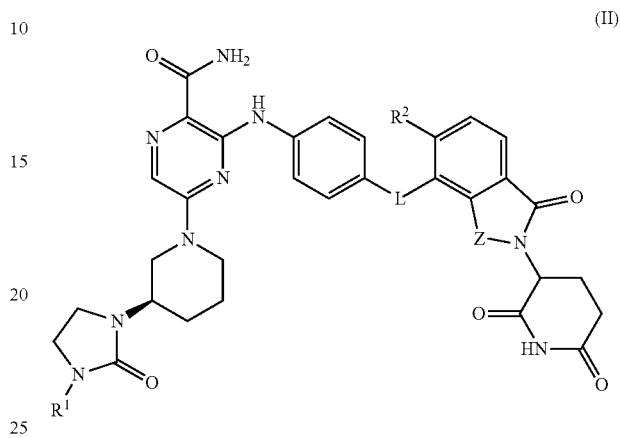

(II)

or a pharmaceutically acceptable salt thereof, wherein each of R$^1$, R$^2$, L, and Z are as defined herein for the compound of Formula (X), (I), (I-A), or (I-B).

In some embodiments, the compound of Formula (II) is a compound of Formulae (II-A) or (II-B)

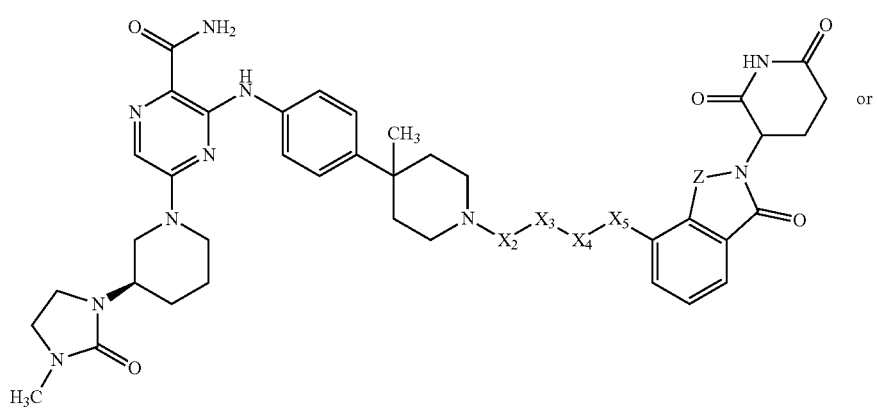

(II-A)

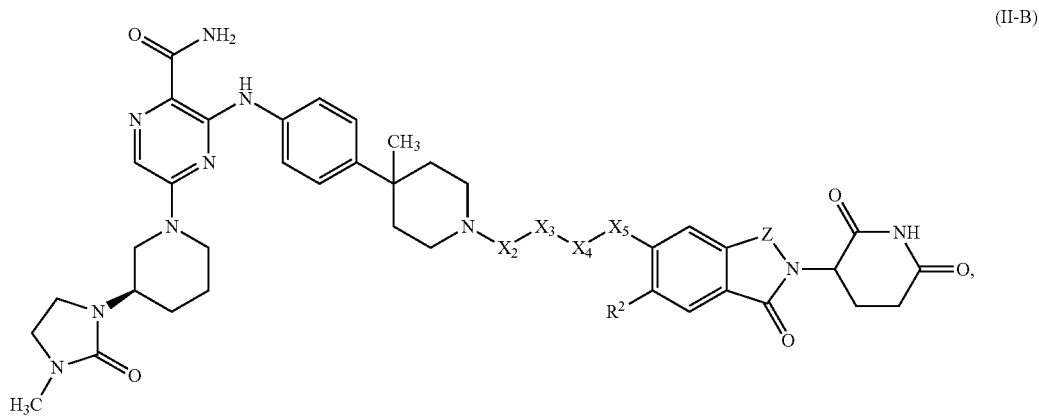

(II-B)

or a pharmaceutically acceptable salt thereof, wherein each of X², X³, X⁴, and X⁵ are as defined herein for the compound of Formula (X), (I), (I-A), (I-B), or (II).

This disclosure also provides a compound of Formula (III)

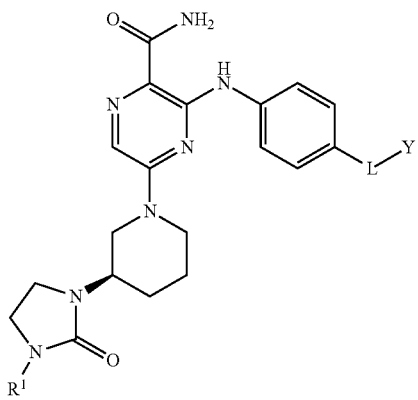

(III)

or a pharmaceutically acceptable salt thereof, wherein R¹ is C₁₋₃ alkyl; L is —X¹-X²-X³—; X¹ is 7-12 membered spiro bicyclic heterocycloalkyl having one to three heteroatoms independently selected from N, O, or S, wherein the heterocycloalkyl is optionally substituted with —CH₃, or 4-6 membered heterocycloalkyl having one to two heteroatoms independently selected from N, O, or S, wherein the heterocycloalkyl is optionally substituted with —CH₃; X² is a bond or —C₁₋₅ alkyl-; X³ is a bond, —C₁₋₄ alkyl-, 4-6 membered heterocycloalkyl having one to two heteroatoms independently selected from N, O, or S, wherein the heterocycloalkyl is optionally substituted with —CH₃; Y is

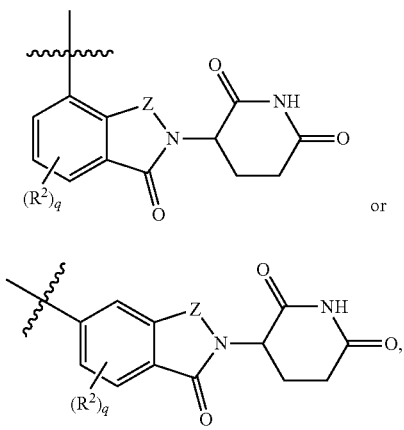

wherein each R² is independently halo or —C₁₋₄ alkyl; each Z is —C(Rᴬ)₂— or —C(O)—; each Rᴬ is independently —H; and q is zero, one, or two.

This disclosure also provides a compound of Formula (IV)

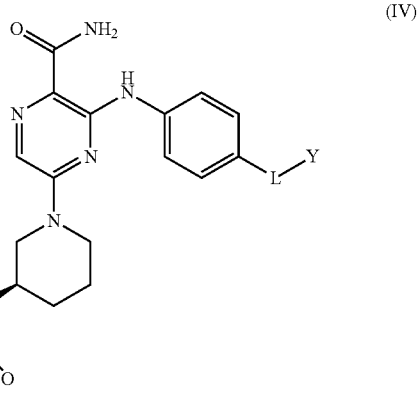

(IV)

or a pharmaceutically acceptable salt thereof, wherein R¹ is C₁₋₃ alkyl; L is —X¹-X²-X³-X⁴-X⁵—; X¹ is —C(O)—N(R)—, —N(R)—C(O)—, —(O—CH₂—CH₂)ₘ—, —O(C₆H₄)—, —(O—CH₂—CH₂—CH₂)ₘ—, —C₁₋₅ alkyl-, 7-12 membered spiro bicyclic heterocycloalkyl having one to three heteroatoms independently selected from N, O, or S, wherein the heterocycloalkyl is optionally substituted with —CH₃, or 4-6 membered heterocycloalkyl having one to two heteroatoms independently selected from N, O, or S, wherein the heterocycloalkyl is optionally substituted with —CH₃; X² is a bond, —(O—CH₂CH₂)ₙ—, —(CH₂—CH₂—O)ₙ—, —N(R)—C(O)—, —N(R)—, —C(O)—, —C₁₋₅ alkyl-, 4-6 membered cycloalkyl, or 4-6 membered heterocycloalkyl having one to two heteroatoms independently selected from N, O, or S; X³ is a bond, —C₁₋₄ alkyl-, 4-6 membered cycloalkyl, —N(R)—, —(O—CH₂—CH₂)ₚ—, —(CH₂—CH₂—O)ₚ—, or 4-6 membered heterocycloalkyl having one to two heteroatoms independently selected from N, O, or S, wherein the heterocycloalkyl is optionally substituted with —CH₃; X⁴ is a bond, —CH₂—CH₂—N(R)—, —N(R)—, —C₁₋₄ alkyl-, —(O—CH₂—CH₂)ₘ—, or 5-6 membered saturated, partially unsaturated, or fully unsaturated heterocycle having one to three heteroatoms independently selected from N, O, or S; X⁵ is a bond, —C₁₋₄ alkyl-, —N(R)—, or —C(O)—N(R)—; each R is independently —H or —C₁₋₃ alkyl; each of m, n, and p is independently an integer from one to three; Y is

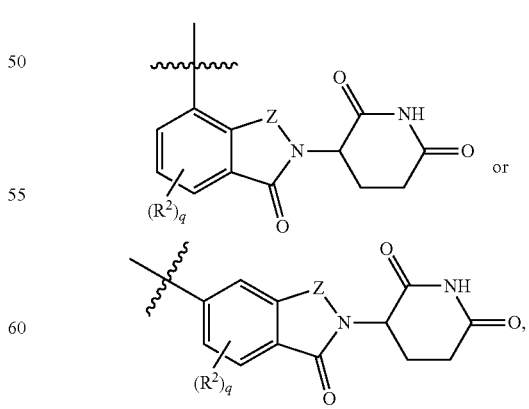

wherein each R² is independently halo or —C₁₋₄ alkyl; each Z is —C(Rᴬ)₂— or —C(O)—; each Rᴬ is independently —H or —C₁₋₄ alkyl; and q is zero, one, or two.

General Synthetic Schemes

Compounds can be prepared or synthesized according to any technique deemed suitable by the person of skill in the art. In certain embodiments, compounds are prepared according to International Application No. PCT/US2019/56112, filed Oct. 14, 2019, incorporated by reference herein in its entirety. Exemplary synthetic schemes are described below.

General Procedure 1: Amide Coupling

A mixture of amine (0.03 mmol), acid (0.03 mmol), HATU (0.04 mmol), DIPEA (0.15 mmol) and DMF was allowed to stir at room temperature for thirty minutes. The mixture was purified by HPLC ($H_2O$/MeCN with 0.1% TFA) to afford the amide product. An exemplary amide coupling is provided in Scheme 1 below where 3-(3-(2-(2,6-dioxopiperidin-3-yl)-1-oxoisoindolin-4-yl)propoxy)propanoic acid, and (R)-3-((4-(3,9-diazaspiro[5.5]undecan-3-yl)phenyl)amino)-5-(3-(3-methyl-2-oxoimidazolidin-1-yl)piperidin-1-yl)pyrazine-2-carboxamide were reacted as described above to provide 3-((4-(9-(3-(3-(2-(2,6-dioxopiperidin-3-yl)-1-oxoisoindolin-4-yl)propoxy)propanoyl)-3,9-diazaspiro[5.5]undecan-3-yl)phenyl)amino)-5-((R)-3-(3-methyl-2-oxoimidazolidin-1-yl)piperidin-1-yl)pyrazine-2-carboxamide (Compound 57).

Scheme 1: Synthesis of Compound 57 via Amide Formation

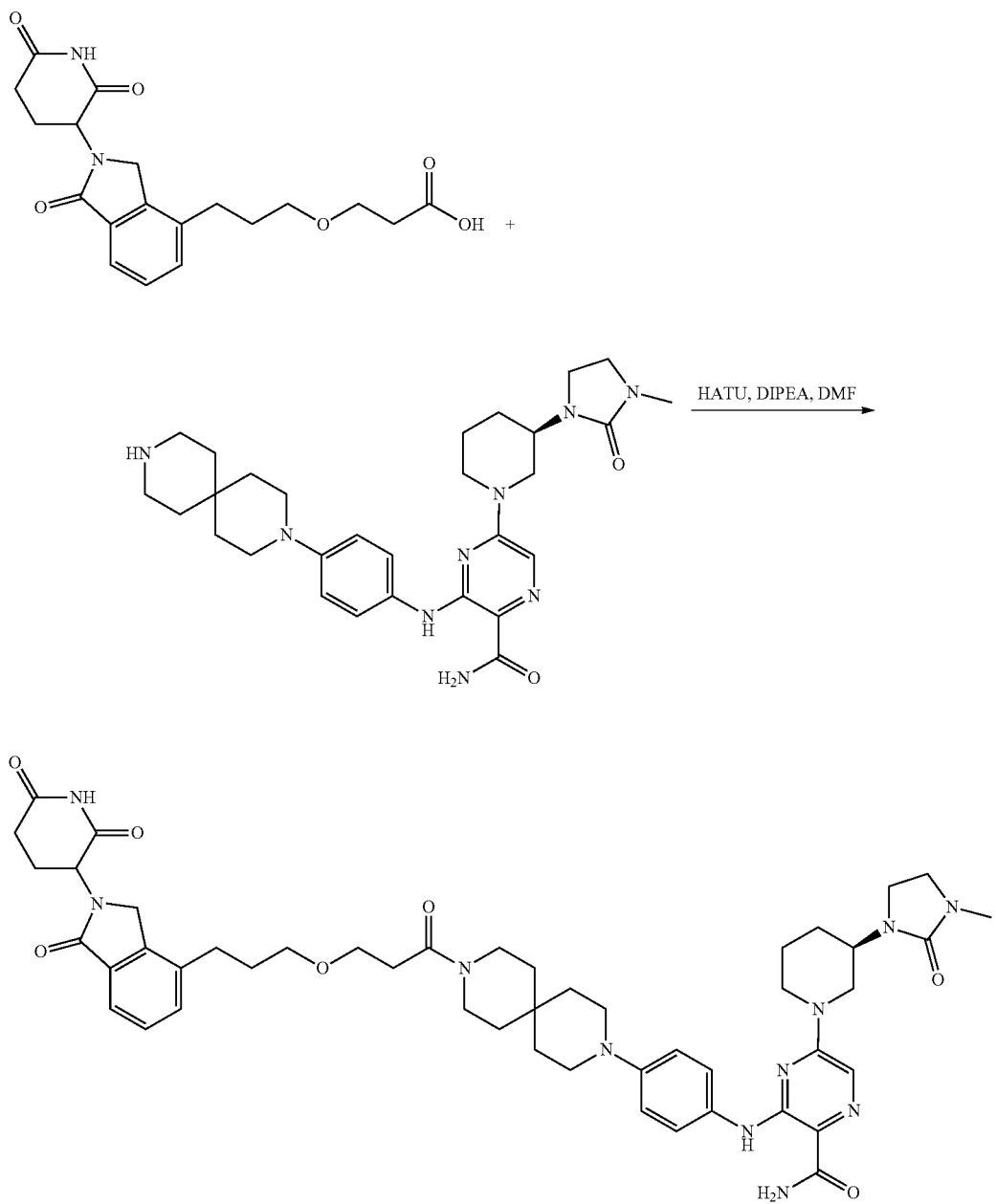

Compound 57

Other amide containing compounds of this description synthesized using General Procedure 1 were Compounds 2-9, 10-14, 19, 20, 22-28, 61, 62, 63, and 67.

General Procedure 2: Reductive Amination

A mixture of amine TFA salt (0.07 mmol), aldehyde (0.1 mmol), triethylamine (0.28 mmol), and DCE were allowed to stir at room temperature for ten minutes. NaBH(OAc)$_3$ (0.14 mmol) was added and the mixture was allowed to stir at room temperature for 2 h. The mixture was filtered through celite, washed with CH$_2$Cl$_2$, concentrated, and purified by HPLC (H$_2$O/MeCN with 0.1% TFA) to afford the amine product. An exemplary reductive amination is provided in Scheme 2 where (R)-5-(3-(3-methyl-2-oxoimidazolidin-1-yl)piperidin-1-yl)-3-((4-(piperidin-4-yl)phenyl)amino)pyrazine-2-carboxamide was treated as described above with (3R)-1-(2-(2,6-dioxopiperidin-3-yl)-1,3-dioxoisoindolin-5-yl)piperidine-3-carbaldehyde to provide 3-((4-(1-(((3S)-1-(2-(2,6-dioxopiperidin-3-yl)-1,3-dioxoisoindolin-5-yl)piperidin-3-yl)methyl)piperidin-4-yl)phenyl)amino)-5-((R)-3-(3-methyl-2-oxoimidazolidin-1-yl)piperidin-1-yl)pyrazine-2-carboxamide (Compound 32).

Other amine containing compounds of this description synthesized using General Procedure 2 were Compounds 33, 46, 56, 15-18, 21, 31, 48-52, 54, 59, 60, 35, 36, and 38-45.

Scheme 3: Synthesis of Compounds of This Disclosure

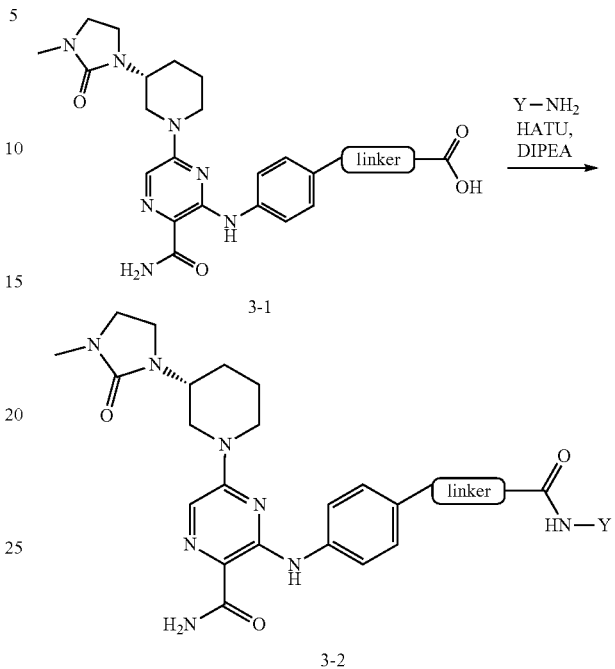

Scheme 2: Synthesis of Compound 32 via Reductive Amination

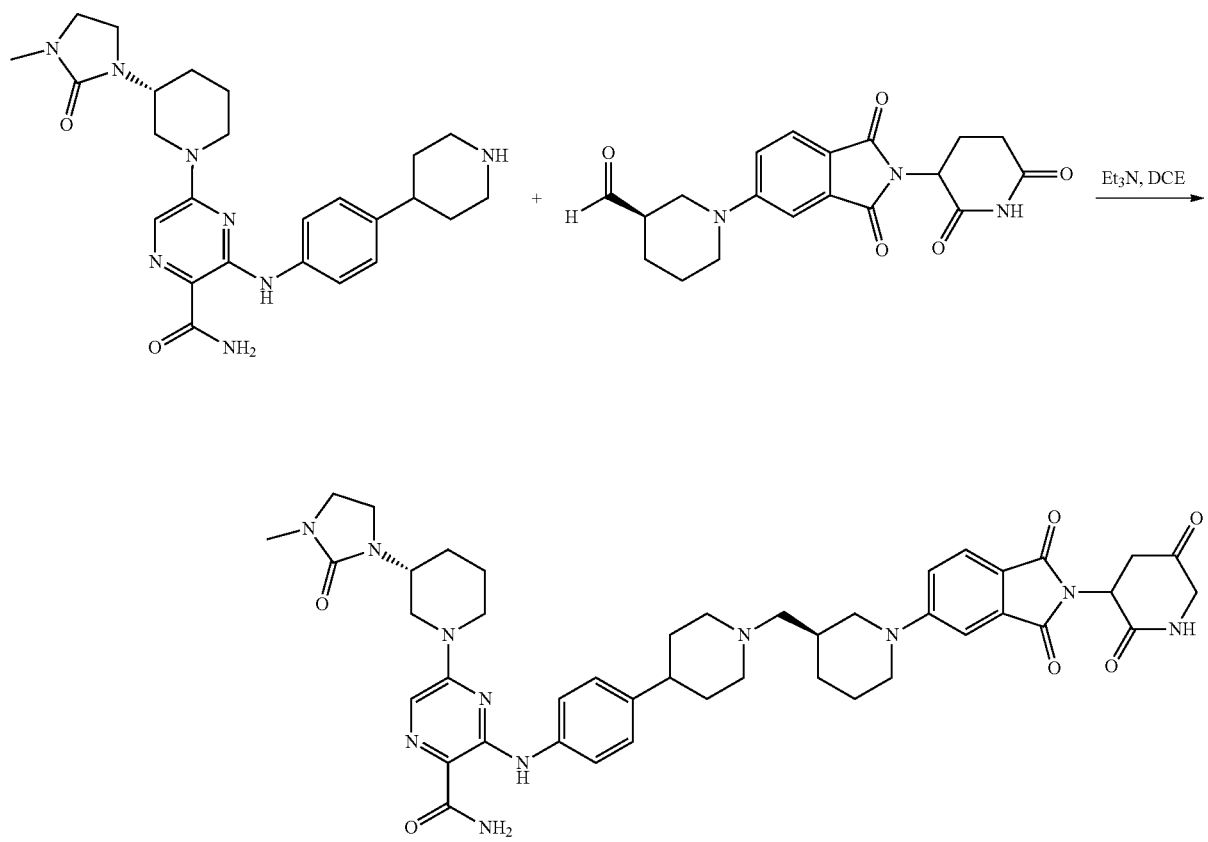

Compound 32

Intermediate (3-1), which can be generated by de-esterifying intermediate (1-6), is treated with amine, Y—NH₂, under coupling conditions to generate compounds of this disclosure (3-2), wherein the terminal linking group of L is an amide.

General Procedure 3: Aryl Fluoride Displacement

A mixture of amine (0.22 mmol), aryl fluoride (0.22 mmol), DIPEA (0.88 mmol) and DMF (1 mL) was allowed to stir at 90° C. for 16 h. The mixture was purified by HPLC (H₂O/MeCN with 0.1% TFA) to afford the desired product. An exemplary aryl fluoride displacement is provided in Scheme 3, where (R)-3-((4-(2,6-diazaspiro[3.3]heptan-2-yl)phenyl)amino)-5-(3-(3-methyl-2-oxoimidazolidin-1-yl)piperidin-1-yl)pyrazine-2-carboxamide is treated as described above with 2-(2,6-dioxopiperidin-3-yl)-5-fluoroisoindoline-1,3-dione to provide 3-((4-(6-(2-(2,6-dioxopiperidin-3-yl)-1,3-dioxoisoindolin-5-yl)-2,6-diazaspiro[3.3]heptan-2-yl)phenyl)amino)-5-((R)-3-(3-methyl-2-oxoimidazolidin-1-yl)piperidin-1-yl)pyrazine-2-carboxamide (Compound 34).

Scheme 3: Synthesis of Compound 34 via Aryl Fluoride Displacement

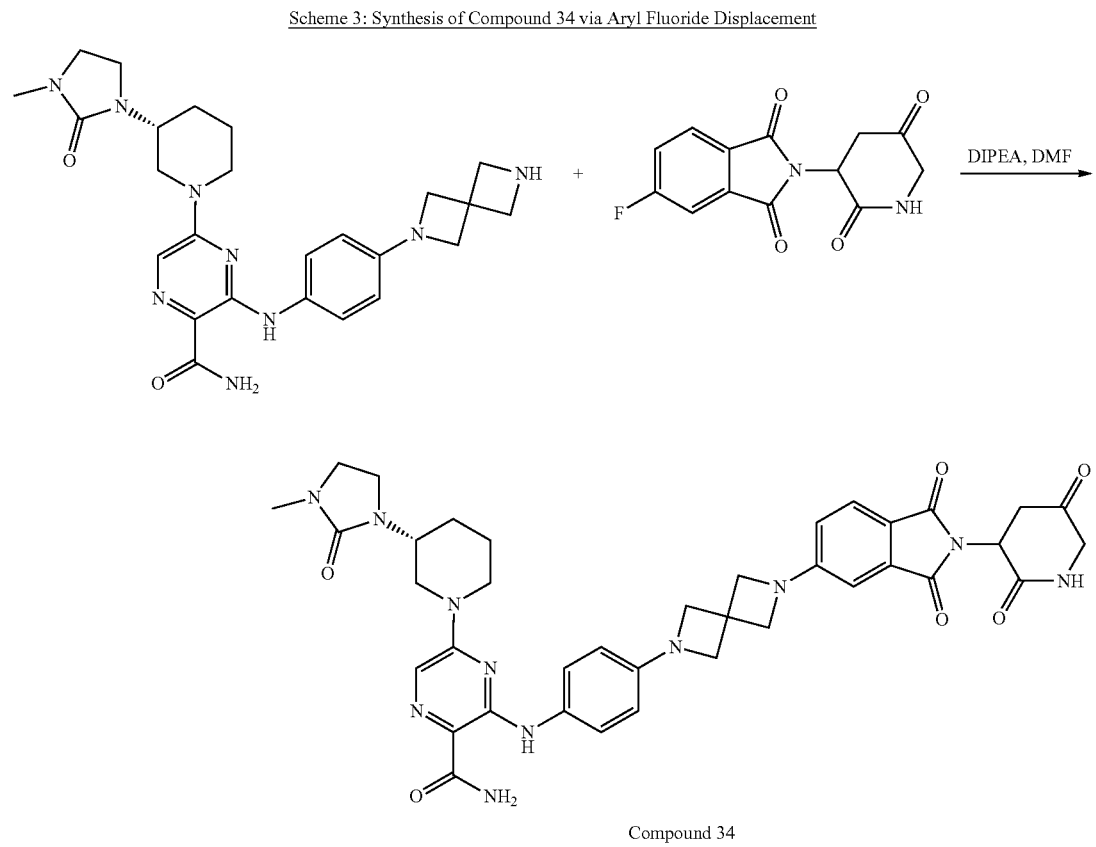 [SMILES: CN1CCN([C@@H]2CCCN(c3cnc(C(N)=O)c(Nc4ccc(N5CC6(CNC6)C5)cc4)n3)C2)C1=O ; O=C1CNC(=O)C(N2C(=O)c3ccc(F)cc3C2=O)C1 ; CN1CCN([C@@H]2CCCN(c3cnc(C(N)=O)c(Nc4ccc(N5CC6(C5)CN(c5ccc7c(c5)C(=O)N(C5CC(=O)CNC5=O)C7=O)C6)cc4)n3)C2)C1=O]

Compound 34

Other aryl amine containing compounds of this description synthesized using General Procedure 3 are Compounds 55, 29, 47, 53, 58, 64-66, 37, and 30.

The abovementioned synthetic schemes were used to synthesize the compounds in Table 1.

TABLE 1
Example compounds and/or pharmaceutically acceptable salts thereof for use in the methods described herein.
| Compound Number | Structure |
|---|---|
| 1 | 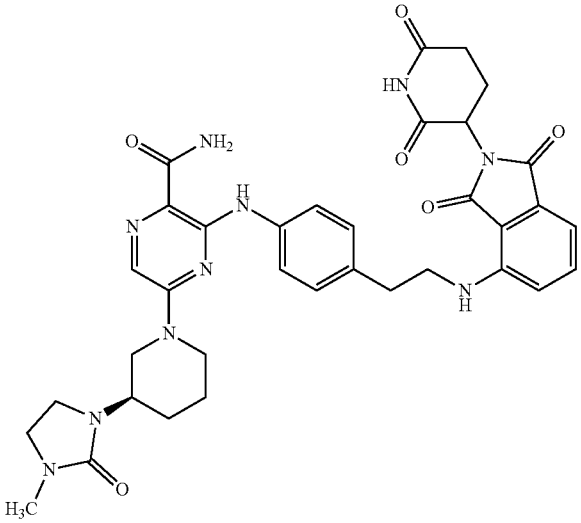 [SMILES: CN1CCN([C@@H]2CCCN(c3cnc(C(N)=O)c(Nc4ccc(CCNc5cccc6c5C(=O)N(C5CCC(=O)NC5=O)C6=O)cc4)n3)C2)C1=O] |
| 2 | 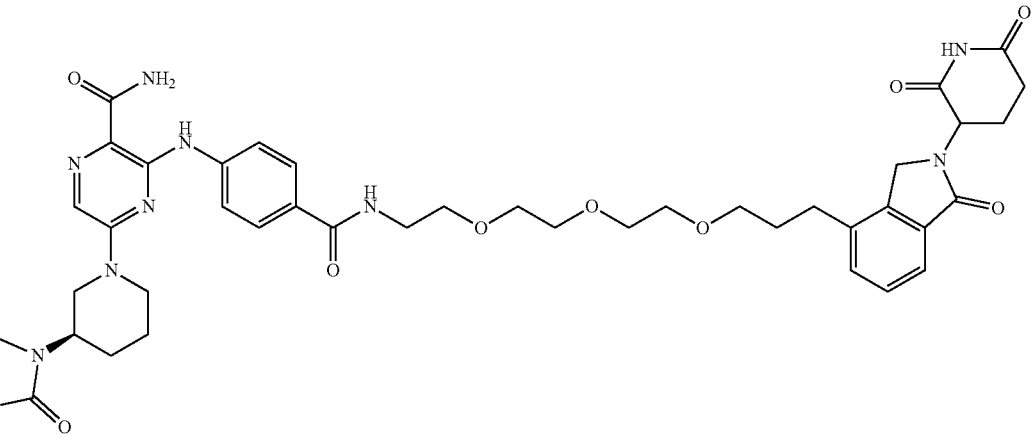 |
| 3 | 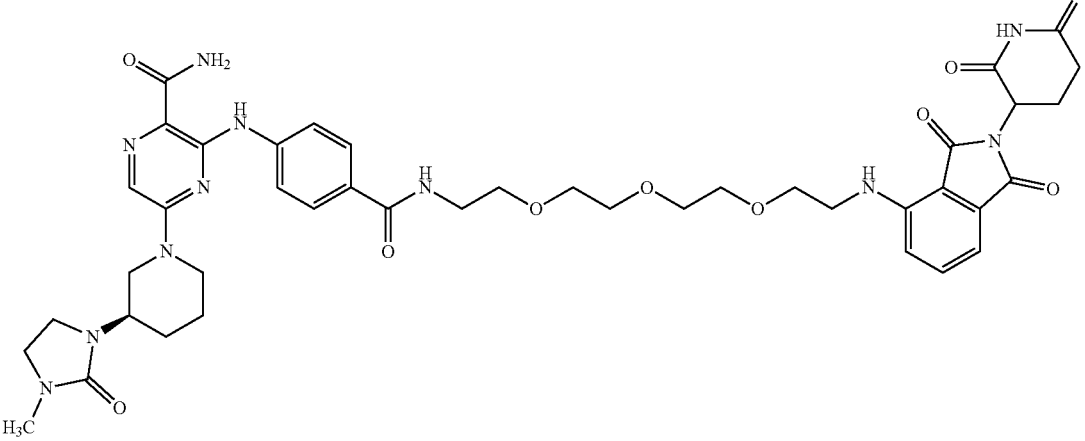 |

TABLE 1-continued

Example compounds and/or pharmaceutically acceptable salts thereof for use in the methods described herein.

| Compound Number | Structure |
| --- | --- |
| 4 | 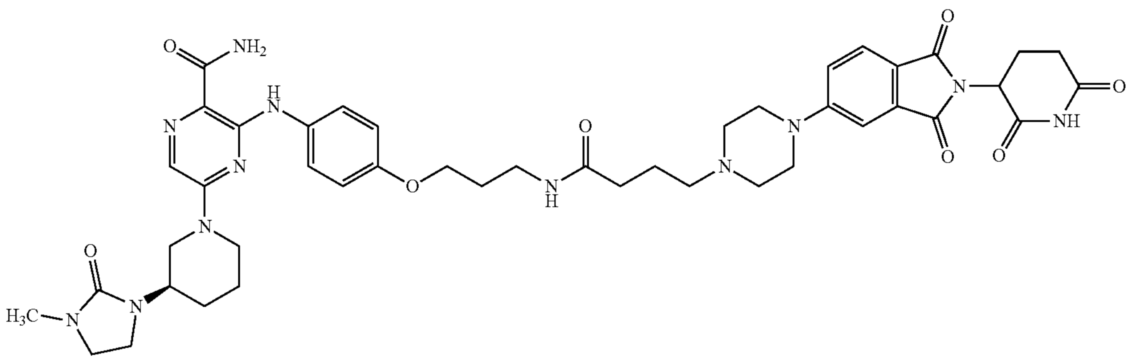 [SMILES: CN1CCN([C@@H]2CCCN(c3cnc(C(N)=O)c(Nc4ccc(OCCCNC(=O)CCCN5CCN(c6ccc7c(c6)C(=O)N(C6CCC(=O)NC6=O)C7=O)CC5)cc4)n3)C2)C1=O] |
| 5 | 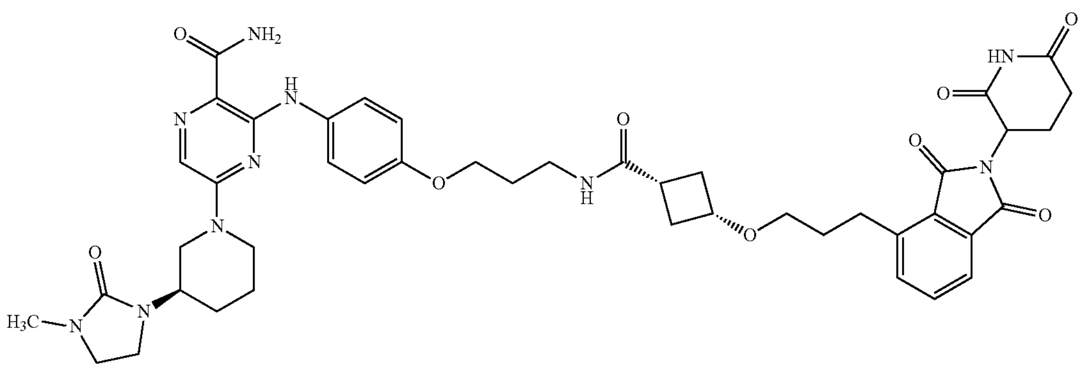 [SMILES: CN1CCN([C@@H]2CCCN(c3cnc(C(N)=O)c(Nc4ccc(OCCCNC(=O)[C@H]5C[C@@H](OCCCc6cccc7c6C(=O)N(C6CCC(=O)NC6=O)C7=O)C5)cc4)n3)C2)C1=O] |
| 6 | 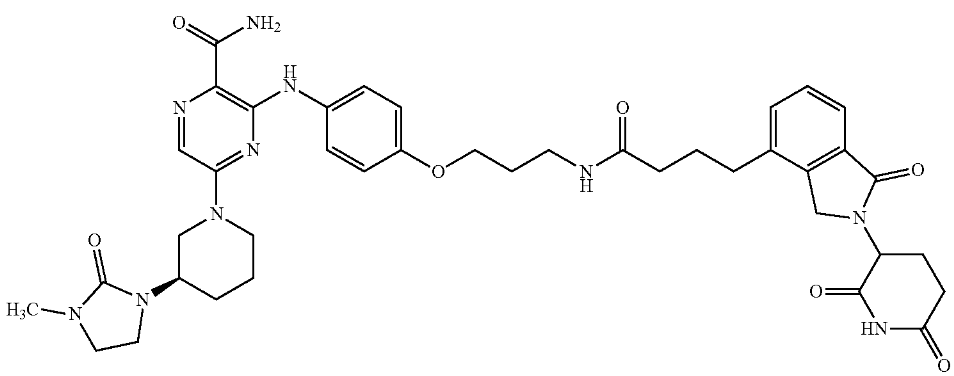 [SMILES: CN1CCN([C@@H]2CCCN(c3cnc(C(N)=O)c(Nc4ccc(OCCCNC(=O)CCCc5cccc6c5CN(C5CCC(=O)NC5=O)C6=O)cc4)n3)C2)C1=O] |
| 7 | 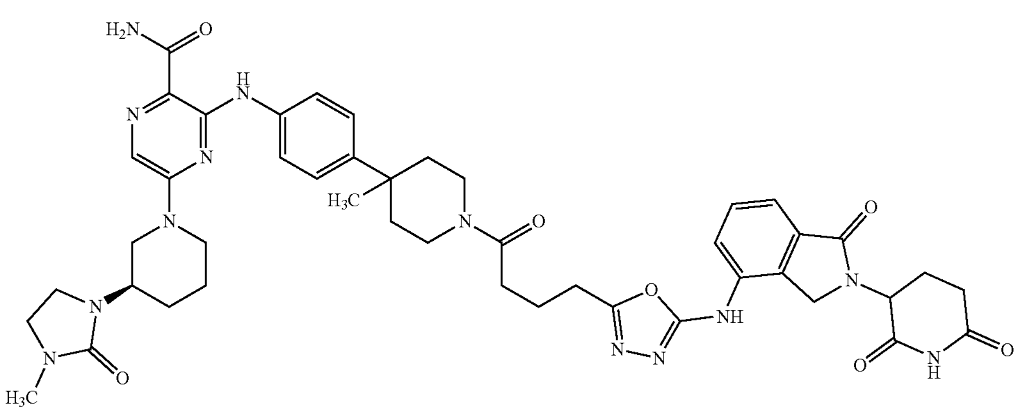 [SMILES: CN1CCN([C@@H]2CCCN(c3cnc(C(N)=O)c(Nc4ccc(C5(C)CCN(C(=O)CCCc6nnc(Nc7cccc8c7CN(C7CCC(=O)NC7=O)C8=O)o6)CC5)cc4)n3)C2)C1=O] |

TABLE 1-continued

Example compounds and/or pharmaceutically acceptable salts thereof for use in the methods described herein.

| Compound Number | Structure |
|---|---|
| 8 | 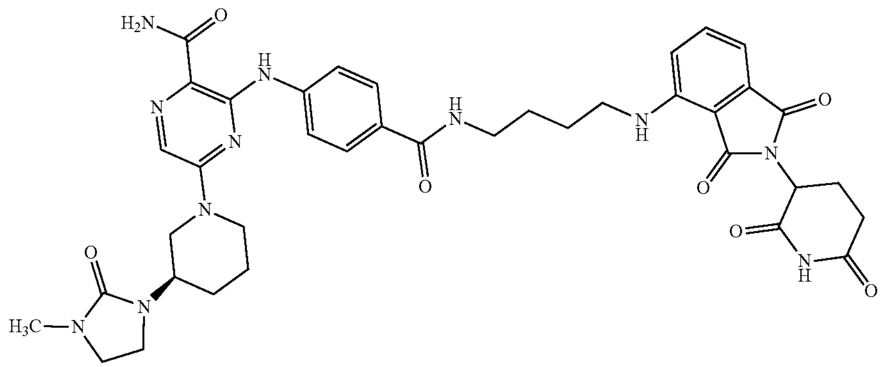 [SMILES: CN1CCN([C@@H]2CCCN(c3cnc(C(N)=O)c(Nc4ccc(C(=O)NCCCCNc5cccc6c5C(=O)N(C5CCC(=O)NC5=O)C6=O)cc4)n3)C2)C1=O] |
| 9 | 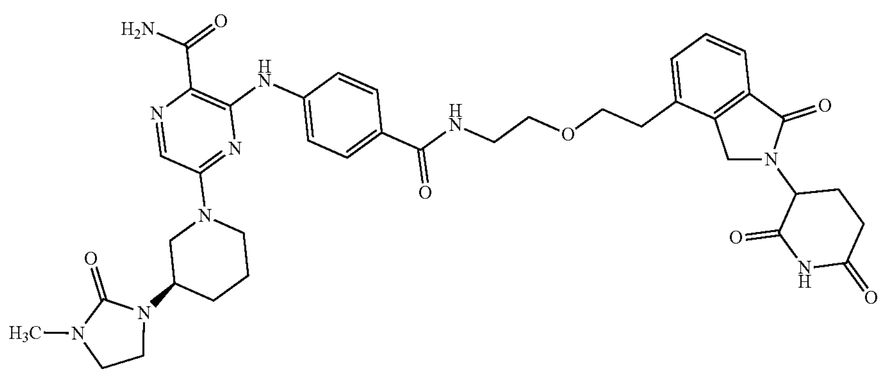 [SMILES: CN1CCN([C@@H]2CCCN(c3cnc(C(N)=O)c(Nc4ccc(C(=O)NCCOCCc5cccc6c5CN(C5CCC(=O)NC5=O)C6=O)cc4)n3)C2)C1=O] |
| 10 | 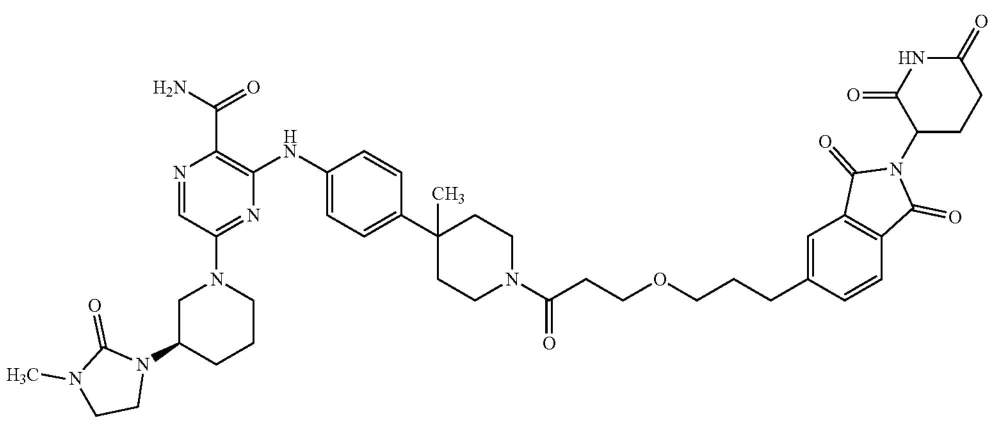 [SMILES: CN1CCN([C@@H]2CCCN(c3cnc(C(N)=O)c(Nc4ccc(C5(C)CCN(C(=O)CCOCCCc6ccc7c(c6)C(=O)N(C6CCC(=O)NC6=O)C7=O)CC5)cc4)n3)C2)C1=O] |

TABLE 1-continued
Example compounds and/or pharmaceutically acceptable salts thereof for use in the methods described herein.
| Compound Number | Structure |
|---|---|
| 11 | 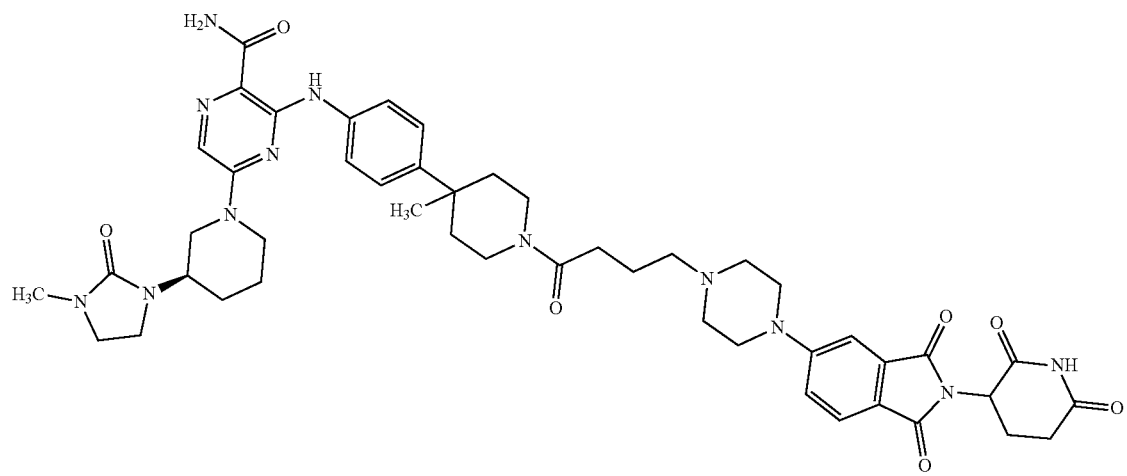 [SMILES: CN1CCN([C@@H]2CCCN(c3cnc(C(N)=O)c(Nc4ccc(C5(C)CCN(C(=O)CCCN6CCN(c7ccc8c(c7)C(=O)N(C7CCC(=O)NC7=O)C8=O)CC6)CC5)cc4)n3)C2)C1=O] |
| 12 | 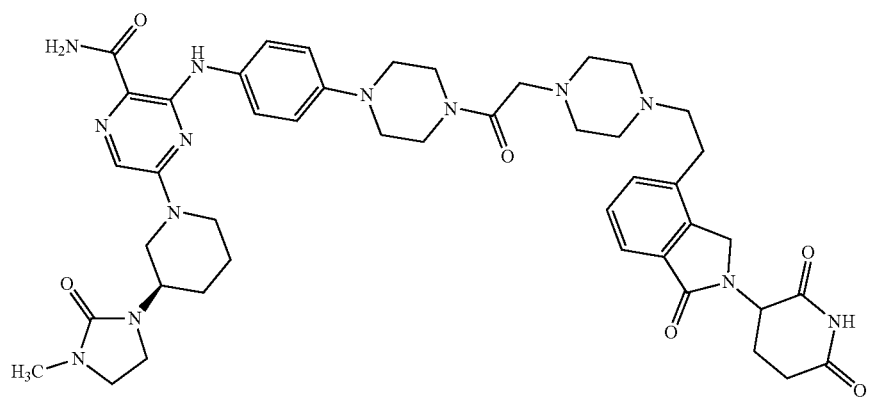 [SMILES: CN1CCN([C@@H]2CCCN(c3cnc(C(N)=O)c(Nc4ccc(N5CCN(C(=O)CN6CCN(CCc7cccc8c7CN(C7CCC(=O)NC7=O)C8=O)CC6)CC5)cc4)n3)C2)C1=O] |
| 13 | 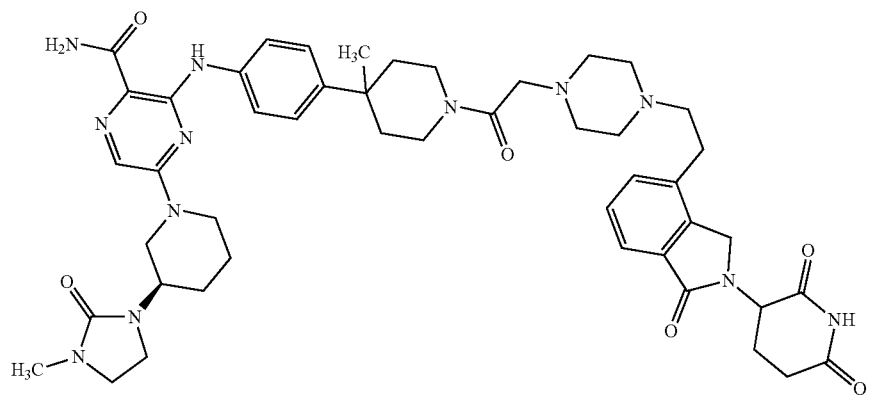 [SMILES: CN1CCN([C@@H]2CCCN(c3cnc(C(N)=O)c(Nc4ccc(C5(C)CCN(C(=O)CN6CCN(CCc7cccc8c7CN(C7CCC(=O)NC7=O)C8=O)CC6)CC5)cc4)n3)C2)C1=O] |

TABLE 1-continued

Example compounds and/or pharmaceutically acceptable salts thereof for use in the methods described herein.

| Compound Number | Structure |
|---|---|
| 14 | 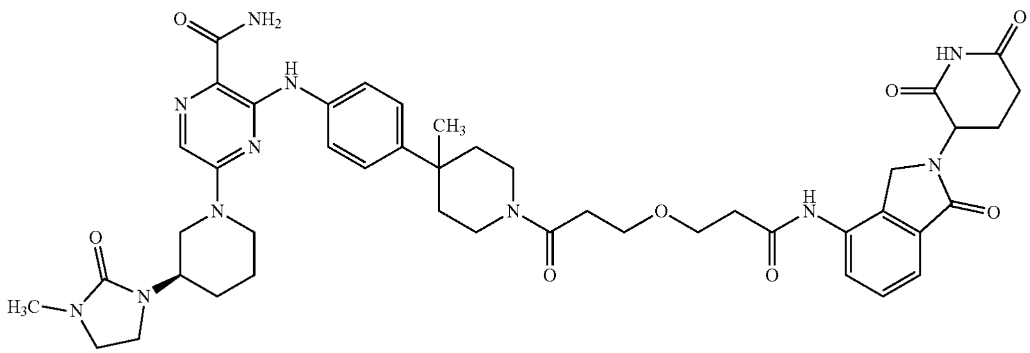 [SMILES: CN1CCN([C@@H]2CCCN(c3cnc(C(N)=O)c(Nc4ccc(C5(C)CCN(C(=O)CCOCCC(=O)Nc6cccc7c6CN(C6CCC(=O)NC6=O)C7=O)CC5)cc4)n3)C2)C1=O] |
| 15 | 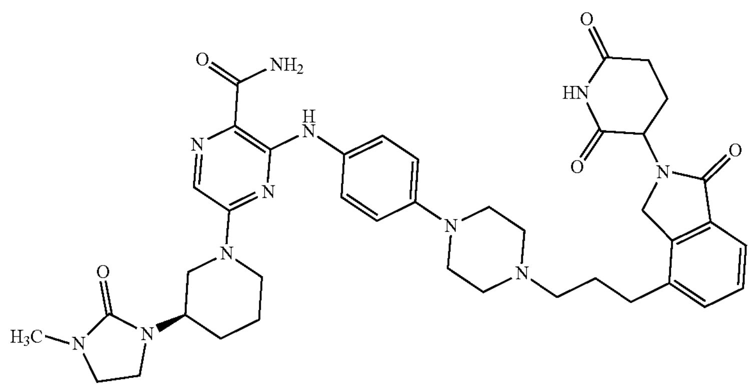 [SMILES: CN1CCN([C@@H]2CCCN(c3cnc(C(N)=O)c(Nc4ccc(N5CCN(CCCc6cccc7c6CN(C6CCC(=O)NC6=O)C7=O)CC5)cc4)n3)C2)C1=O] |
| 16 | 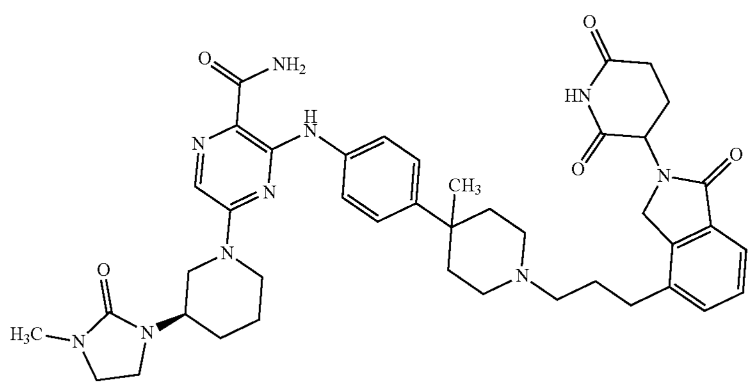 [SMILES: CN1CCN([C@@H]2CCCN(c3cnc(C(N)=O)c(Nc4ccc(C5(C)CCN(CCCc6cccc7c6CN(C6CCC(=O)NC6=O)C7=O)CC5)cc4)n3)C2)C1=O] |
| 17 | 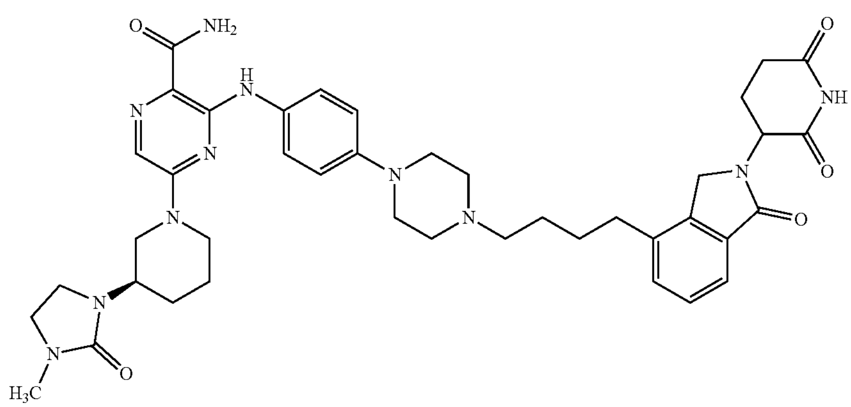 [SMILES: CN1CCN([C@@H]2CCCN(c3cnc(C(N)=O)c(Nc4ccc(N5CCN(CCCCc6cccc7c6CN(C6CCC(=O)NC6=O)C7=O)CC5)cc4)n3)C2)C1=O] |

TABLE 1-continued
Example compounds and/or pharmaceutically acceptable salts thereof for use in the methods described herein.
| Compound Number | Structure |
|---|---|
| 18 | 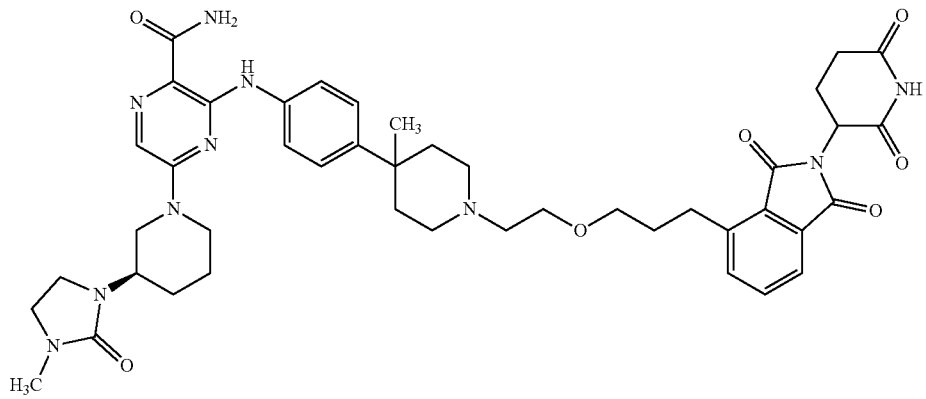 [SMILES: CN1CCN([C@@H]2CCCN(c3cnc(C(N)=O)c(Nc4ccc(C5(C)CCN(CCOCCCc6cccc7c6C(=O)N(C6CCC(=O)NC6=O)C7=O)CC5)cc4)n3)C2)C1=O] |
| 19 | 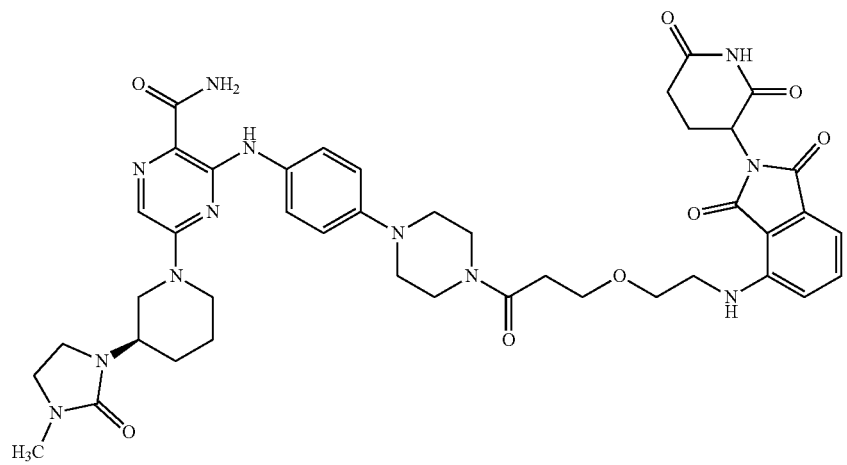 [SMILES: CN1CCN([C@@H]2CCCN(c3cnc(C(N)=O)c(Nc4ccc(N5CCN(C(=O)CCOCCNc6cccc7c6C(=O)N(C6CCC(=O)NC6=O)C7=O)CC5)cc4)n3)C2)C1=O] |
| 20 | 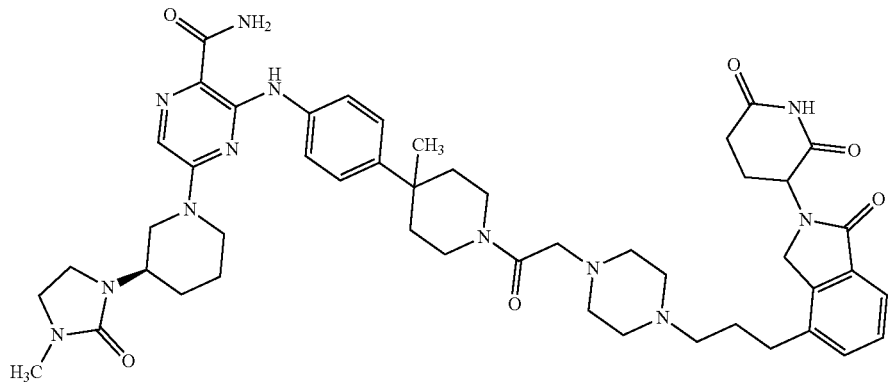 [SMILES: CN1CCN([C@@H]2CCCN(c3cnc(C(N)=O)c(Nc4ccc(C5(C)CCN(C(=O)CN6CCN(CCCc7cccc8c7CN(C7CCC(=O)NC7=O)C8=O)CC6)CC5)cc4)n3)C2)C1=O] |

TABLE 1-continued
Example compounds and/or pharmaceutically acceptable salts thereof for use in the methods described herein.
| Compound Number | Structure |
|---|---|
| 21 | 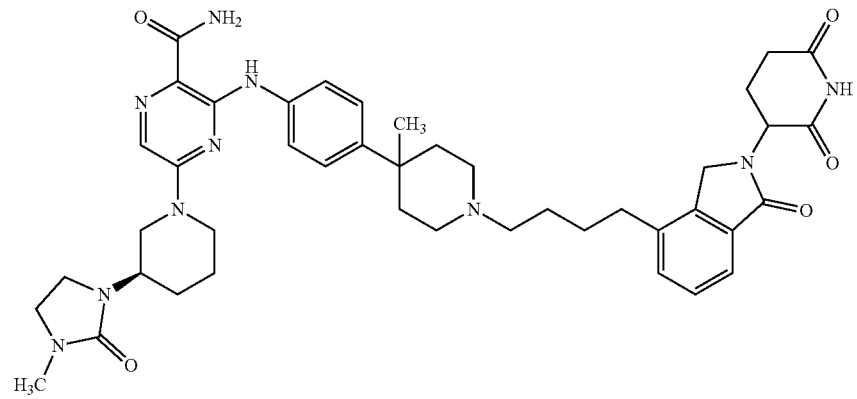 [SMILES: CN1CCN([C@@H]2CCCN(c3cnc(C(N)=O)c(Nc4ccc(C5(C)CCN(CCCCc6cccc7c6CN(C6CCC(=O)NC6=O)C7=O)CC5)cc4)n3)C2)C1=O] |
| 22 | 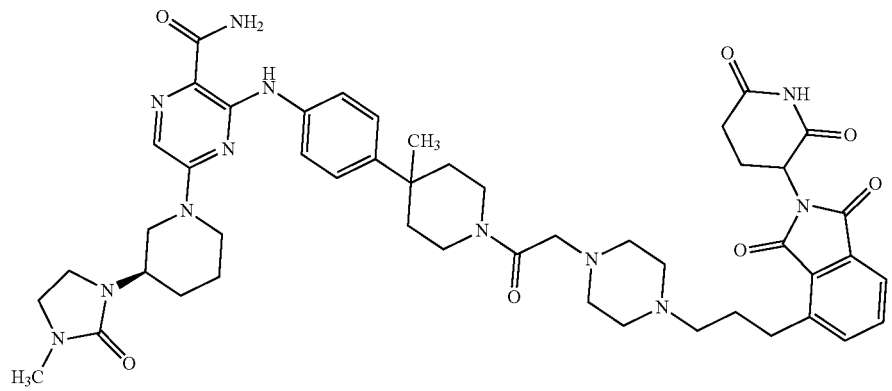 [SMILES: CN1CCN([C@@H]2CCCN(c3cnc(C(N)=O)c(Nc4ccc(C5(C)CCN(C(=O)CN6CCN(CCCc7cccc8c7C(=O)N(C7CCC(=O)NC7=O)C8=O)CC6)CC5)cc4)n3)C2)C1=O] |
| 23 | 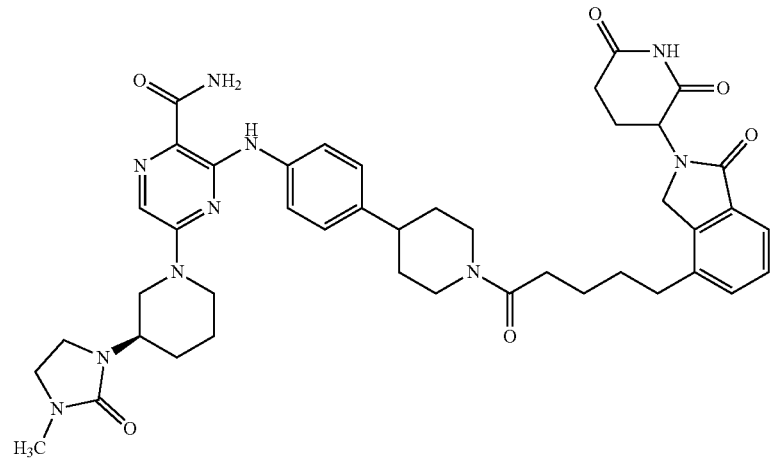 [SMILES: CN1CCN([C@@H]2CCCN(c3cnc(C(N)=O)c(Nc4ccc(C5CCN(C(=O)CCCCc6cccc7c6CN(C6CCC(=O)NC6=O)C7=O)CC5)cc4)n3)C2)C1=O] |

TABLE 1-continued
Example compounds and/or pharmaceutically acceptable salts thereof for use in the methods described herein.
| Compound Number | Structure |
|---|---|
| 24 | 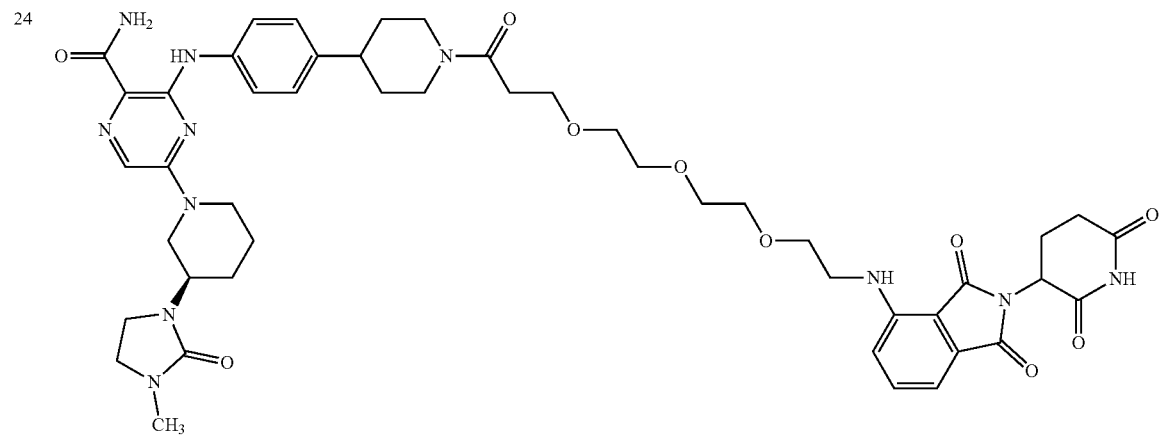 |
| 25 | 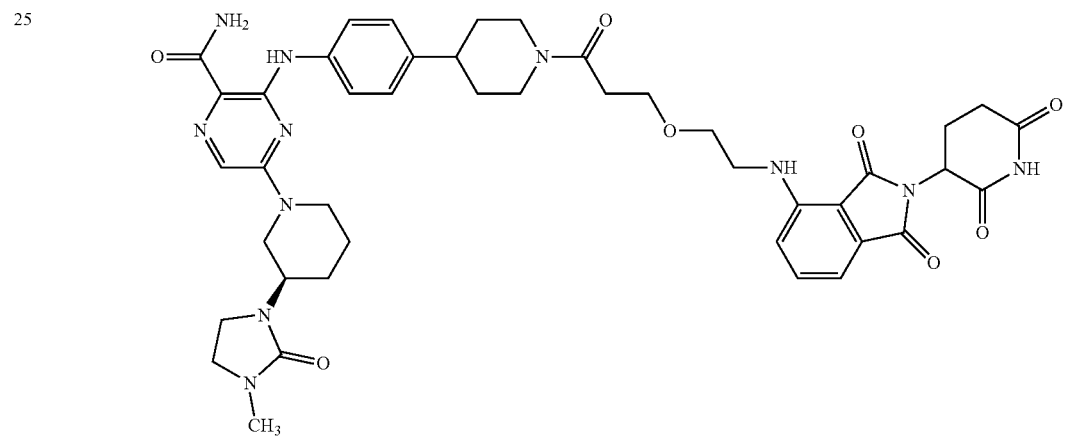 |
| 26 | 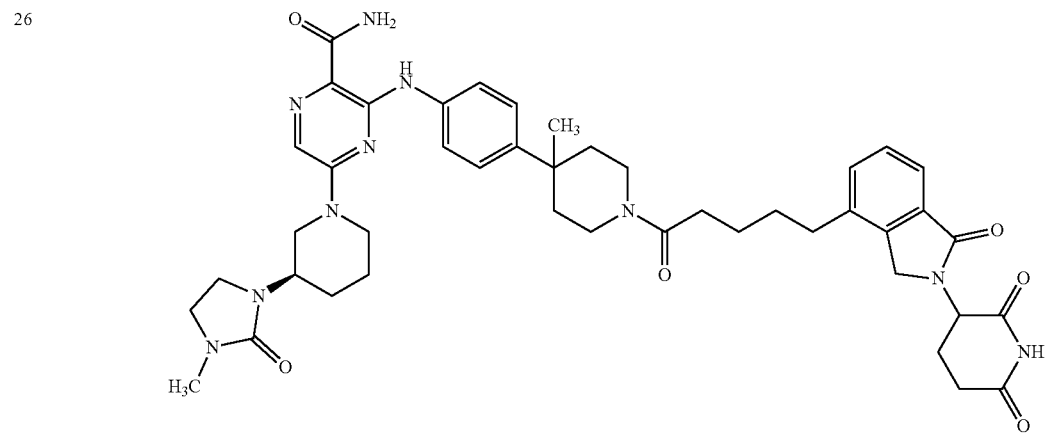 |

135 136
TABLE 1-continued
Example compounds and/or pharmaceutically acceptable salts thereof for use in the methods described herein.
| Compound Number | Structure |
|---|---|
| 27 | 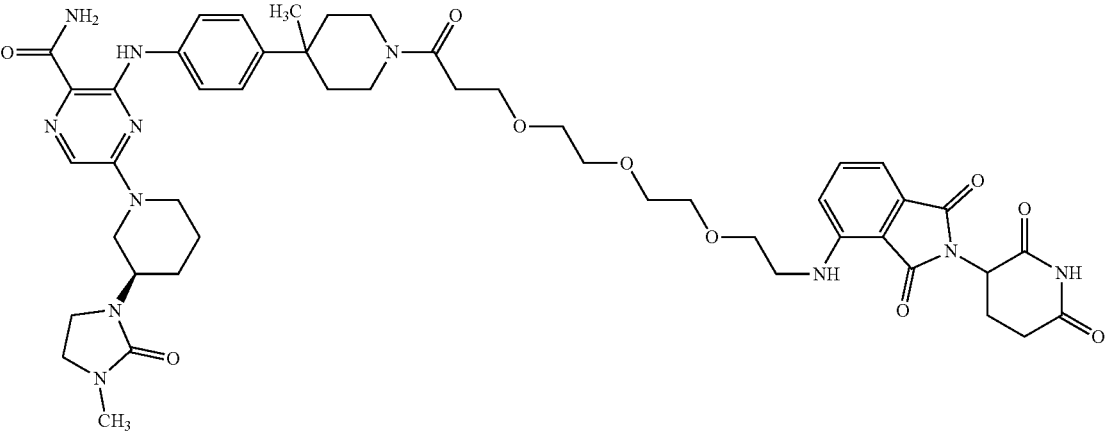 [SMILES: CN1CCN([C@@H]2CCCN(c3cnc(C(N)=O)c(Nc4ccc(C5(C)CCN(C(=O)CCOCCOCCOCCNc6cccc7c6C(=O)N(C6CCC(=O)NC6=O)C7=O)CC5)cc4)n3)C2)C1=O] |
| 28 | 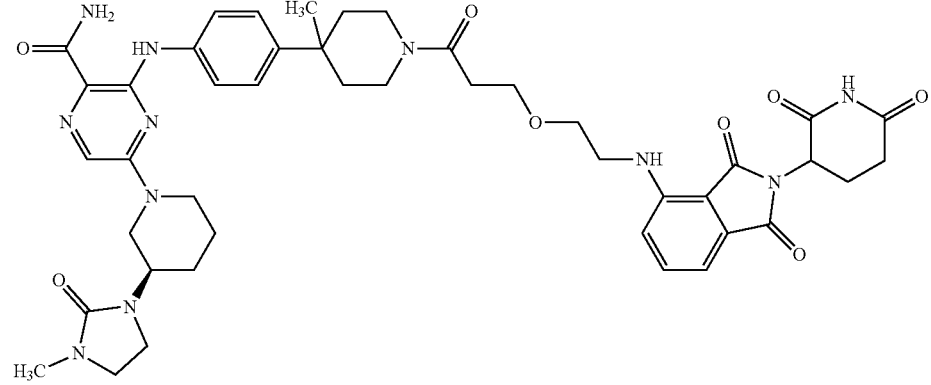 [SMILES: CN1CCN([C@@H]2CCCN(c3cnc(C(N)=O)c(Nc4ccc(C5(C)CCN(C(=O)CCOCCNc6cccc7c6C(=O)N(C6CCC(=O)NC6=O)C7=O)CC5)cc4)n3)C2)C1=O] |
| 29 | 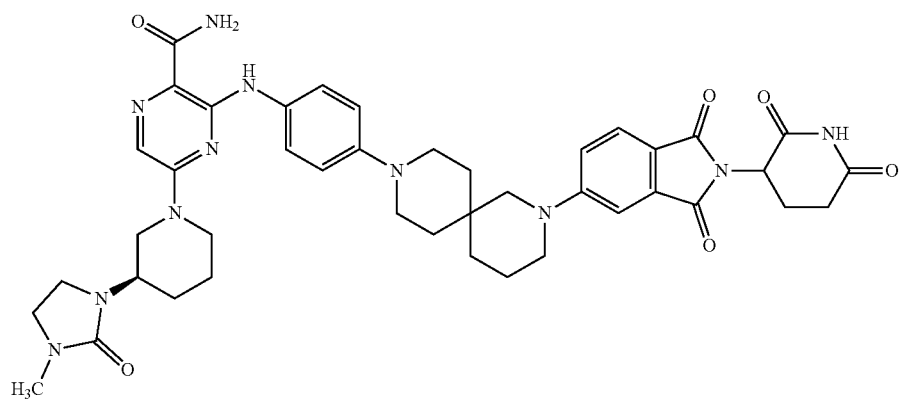 [SMILES: CN1CCN([C@@H]2CCCN(c3cnc(C(N)=O)c(Nc4ccc(N5CCC6(CCCN(c7ccc8c(c7)C(=O)N(C7CCC(=O)NC7=O)C8=O)C6)CC5)cc4)n3)C2)C1=O] |

TABLE 1-continued

Example compounds and/or pharmaceutically acceptable salts thereof for use in the methods described herein.

| Compound Number | Structure |
| --- | --- |
| 30 | 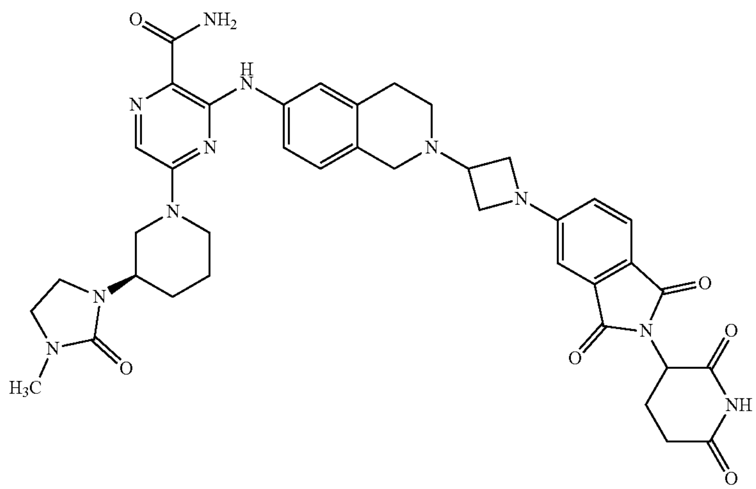 [SMILES: CN1CCN([C@@H]2CCCN(c3cnc(C(N)=O)c(Nc4ccc5c(c4)CCN(C4CN(c6ccc7c(c6)C(=O)N(C6CCC(=O)NC6=O)C7=O)C4)C5)n3)C2)C1=O] |
| 31 | 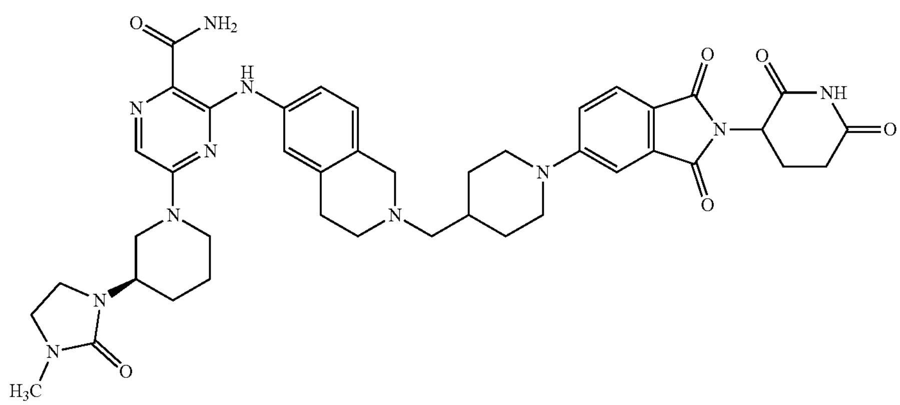 [SMILES: CN1CCN([C@@H]2CCCN(c3cnc(C(N)=O)c(Nc4ccc5c(c4)CCN(CC4CCN(c6ccc7c(c6)C(=O)N(C6CCC(=O)NC6=O)C7=O)CC4)C5)n3)C2)C1=O] |
| 32 | 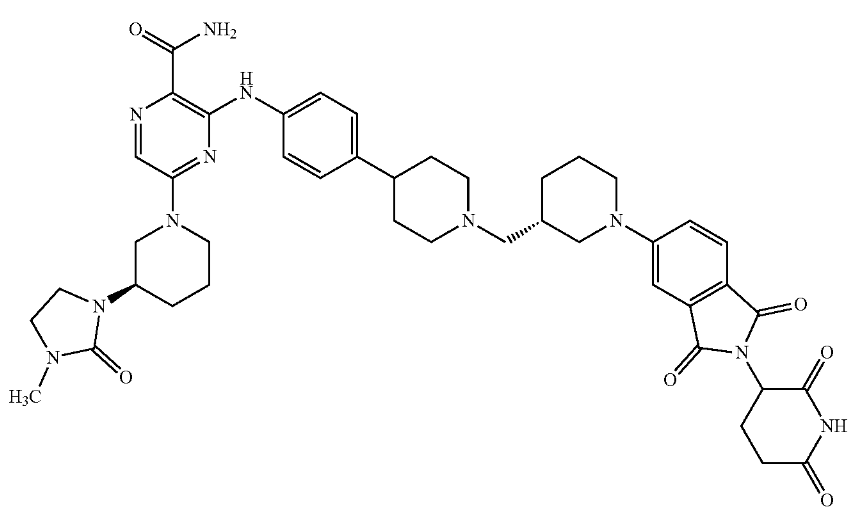 [SMILES: CN1CCN([C@@H]2CCCN(c3cnc(C(N)=O)c(Nc4ccc(C5CCN(C[C@@H]6CCCN(c7ccc8c(c7)C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
| --- | --- |
| 33 | 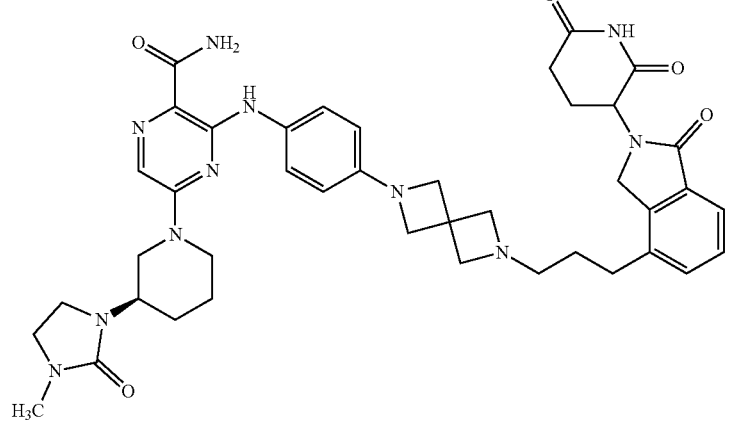 |
| 34 | 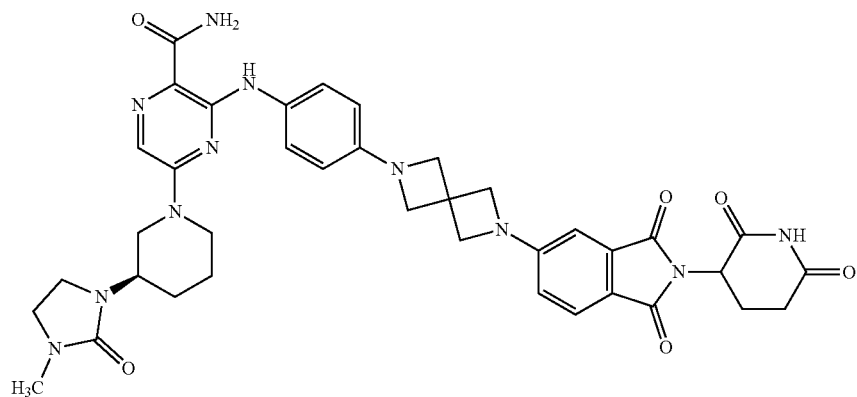 [SMILES: CN1CCN([C@@H]2CCCN(c3cnc(C(N)=O)c(Nc4ccc(N5CC6(C5)CN(c5ccc7c(c5)C(=O)N(C5CCC(=O)NC5=O)C7=O)C6)cc4)n3)C2)C1=O] |
| 35 | 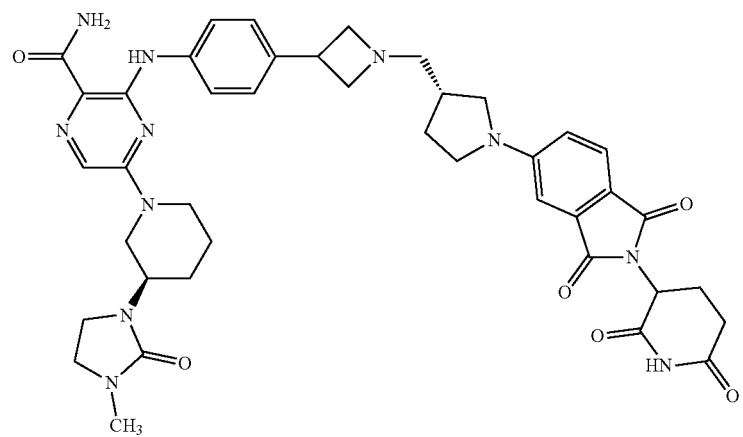 [SMILES: CN1CCN([C@@H]2CCCN(c3cnc(C(N)=O)c(Nc4ccc(C5CN(C[C@H]6CCN(c7ccc8c(c7)C(=O)N(C7CCC(=O)NC7=O)C8=O)C6)C5)cc4)n3)C2)C1=O] |

TABLE 1-continued
Example compounds and/or pharmaceutically acceptable salts thereof for use in the methods described herein.
| Compound Number | Structure |
| --- | --- |
| 36 | 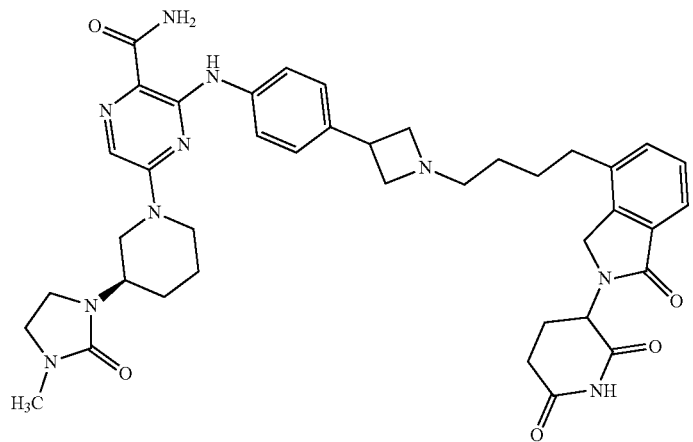 [SMILES: CN1CCN([C@@H]2CCCN(c3cnc(C(N)=O)c(Nc4ccc(C5CN(CCCCc6cccc7c6CN(C6CCC(=O)NC6=O)C7=O)C5)cc4)n3)C2)C1=O] |
| 37 | 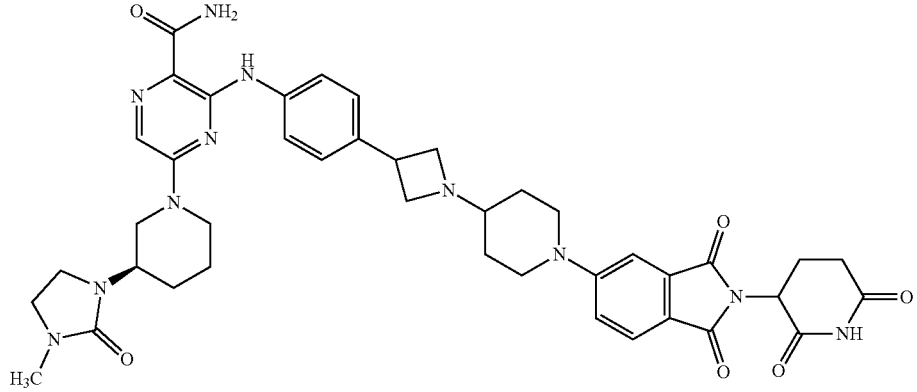 [SMILES: CN1CCN([C@@H]2CCCN(c3cnc(C(N)=O)c(Nc4ccc(C5CN(C6CCN(c7ccc8c(c7)C(=O)N(C7CCC(=O)NC7=O)C8=O)CC6)C5)cc4)n3)C2)C1=O] |
| 38 | 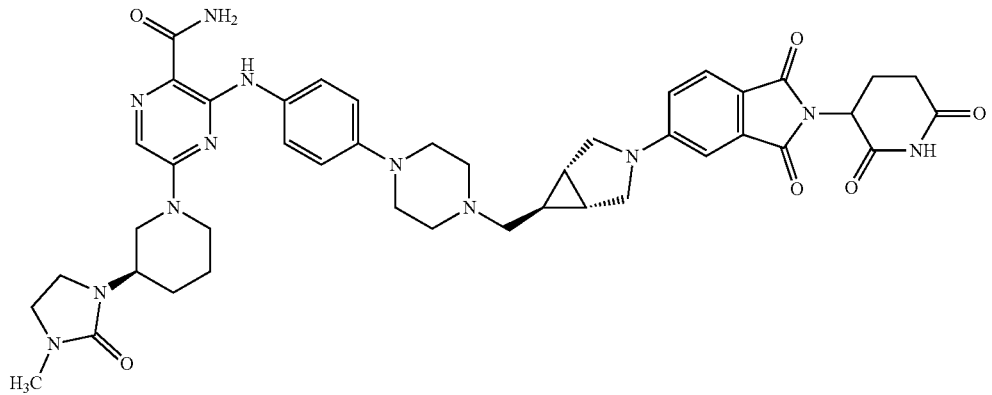 [SMILES: CN1CCN([C@@H]2CCCN(c3cnc(C(N)=O)c(Nc4ccc(N5CCN(C[C@@H]6[C@H]7CN(c8ccc9c(c8)C(=O)N(C8CCC(=O)NC8=O)C9=O)C[C@@H]67)CC5)cc4)n3)C2)C1=O] |

TABLE 1-continued
Example compounds and/or pharmaceutically acceptable salts thereof for use in the methods described herein.
| Compound Number | Structure |
|---|---|
| 39 | 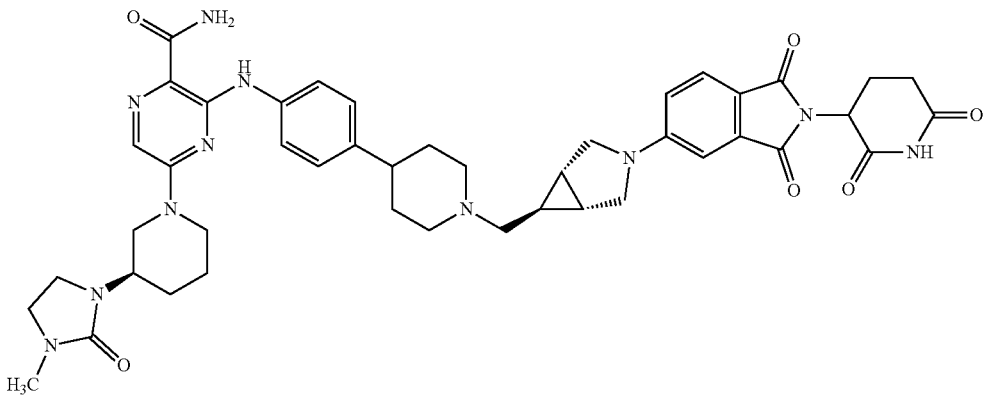 |
| 40 | 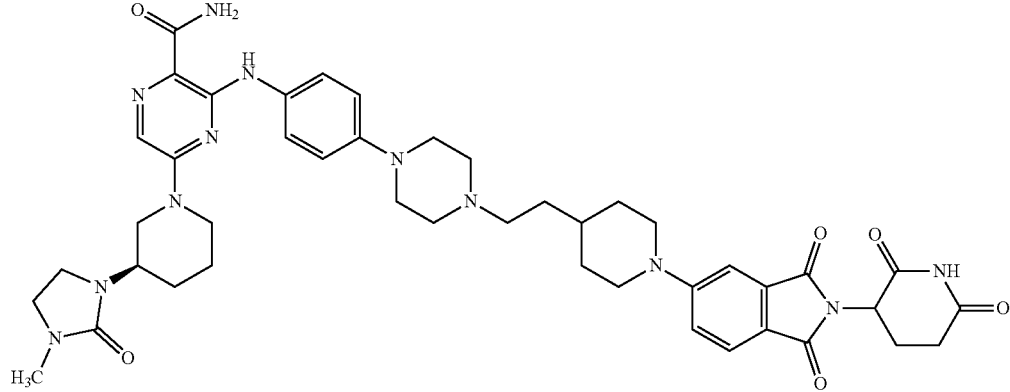 [SMILES: CN1CCN([C@@H]2CCCN(c3cnc(C(N)=O)c(Nc4ccc(N5CCN(CCC6CCN(c7ccc8c(c7)C(=O)N(C7CCC(=O)NC7=O)C8=O)CC6)CC5)cc4)n3)C2)C1=O] |
| 41 | 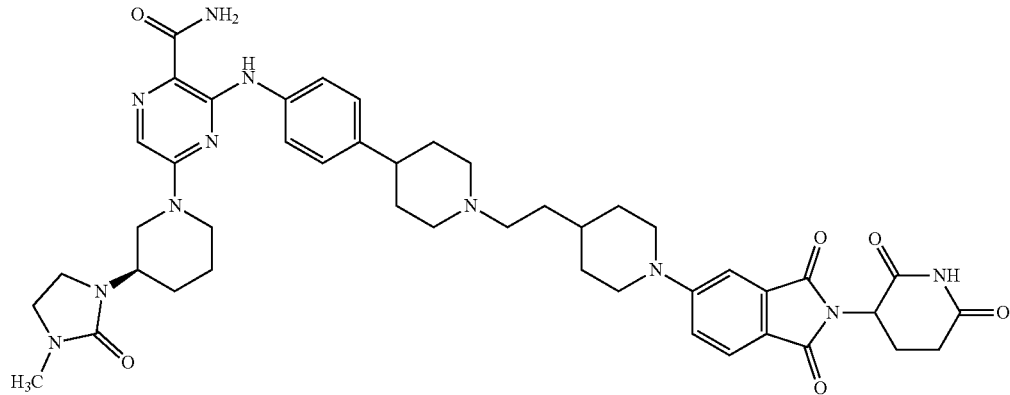 [SMILES: CN1CCN([C@@H]2CCCN(c3cnc(C(N)=O)c(Nc4ccc(C5CCN(CCC6CCN(c7ccc8c(c7)C(=O)N(C7CCC(=O)NC7=O)C8=O)CC6)CC5)cc4)n3)C2)C1=O] |

US 11,820,781 B2
145                                                                 146
TABLE 1-continued
Example compounds and/or pharmaceutically acceptable salts thereof for use in the methods described herein.
| Compound Number | Structure |
|---|---|
| 42 | 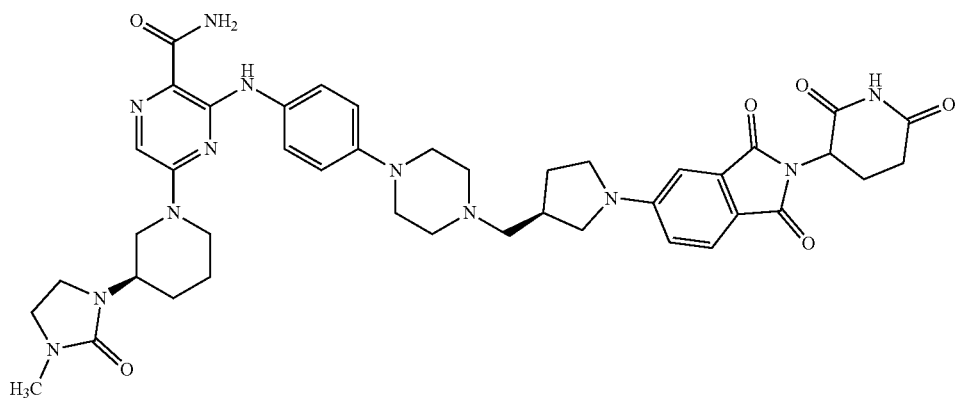 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)cc4)n3)C2)C1=O] |
| 43 | 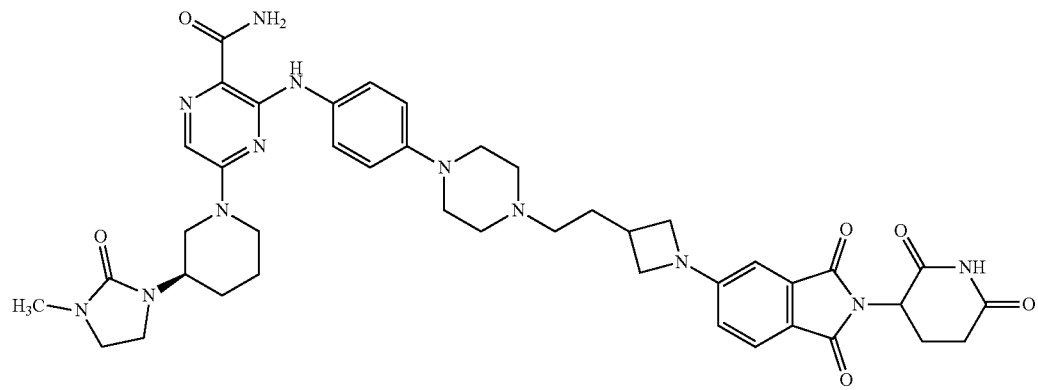 [SMILES: CN1CCN([C@@H]2CCCN(c3cnc(C(N)=O)c(Nc4ccc(N5CCN(CCC6CN(c7ccc8c(c7)C(=O)N(C7CCC(=O)NC7=O)C8=O)C6)CC5)cc4)n3)C2)C1=O] |
| 44 | 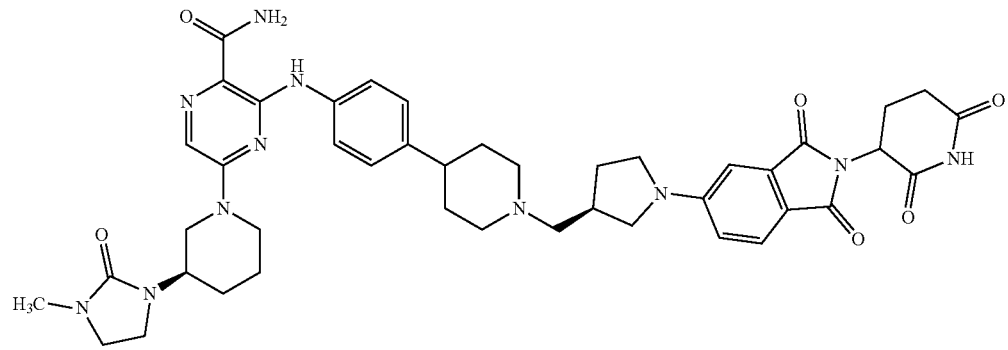 [SMILES: CN1CCN([C@@H]2CCCN(c3cnc(C(N)=O)c(Nc4ccc(C5CCN(C[C@H]6CCN(c7ccc8c(c7)C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
|---|---|
| 45 | 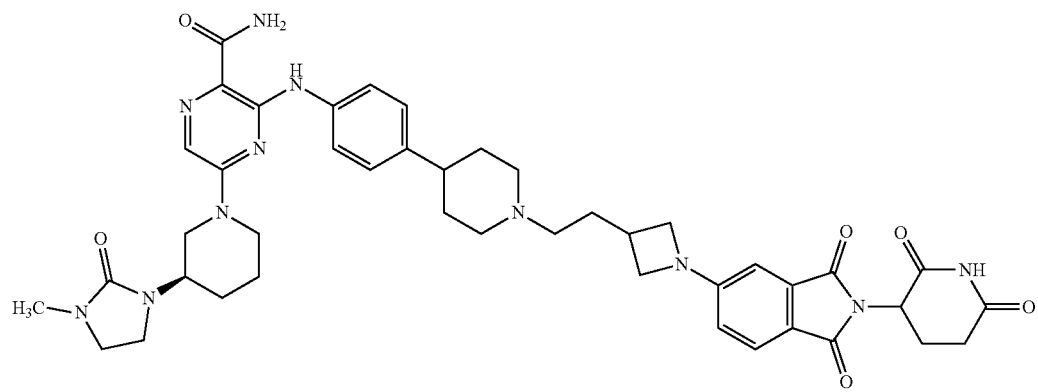 [SMILES: CN1CCN([C@@H]2CCCN(c3cnc(C(N)=O)c(Nc4ccc(C5CCN(CCC6CN(c7ccc8c(c7)C(=O)N(C7CCC(=O)NC7=O)C8=O)C6)CC5)cc4)n3)C2)C1=O] |
| 46 | 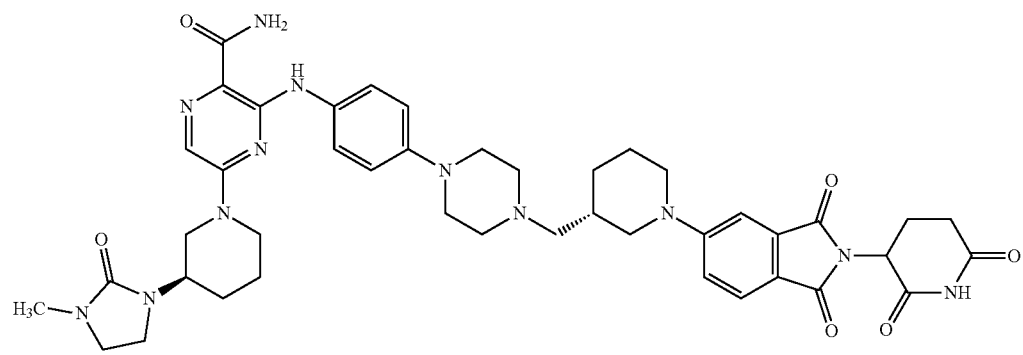 [SMILES: CN1CCN([C@@H]2CCCN(c3cnc(C(N)=O)c(Nc4ccc(N5CCN(C[C@@H]6CCCN(c7ccc8c(c7)C(=O)N(C7CCC(=O)NC7=O)C8=O)C6)CC5)cc4)n3)C2)C1=O] |
| 47 | 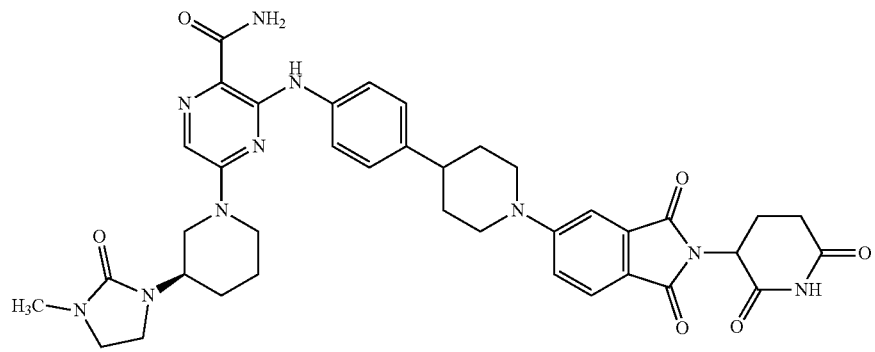 [SMILES: CN1CCN([C@@H]2CCCN(c3cnc(C(N)=O)c(Nc4ccc(C5CCN(c6ccc7c(c6)C(=O)N(C6CCC(=O)NC6=O)C7=O)CC5)cc4)n3)C2)C1=O] |
| 48 | 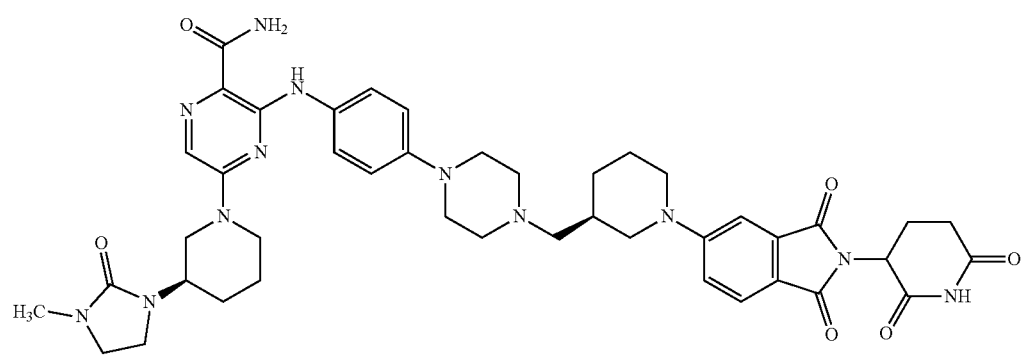 [SMILES: CN1CCN([C@@H]2CCCN(c3cnc(C(N)=O)c(Nc4ccc(N5CCN(C[C@H]6CCCN(c7ccc8c(c7)C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
|---|---|
| 49 | 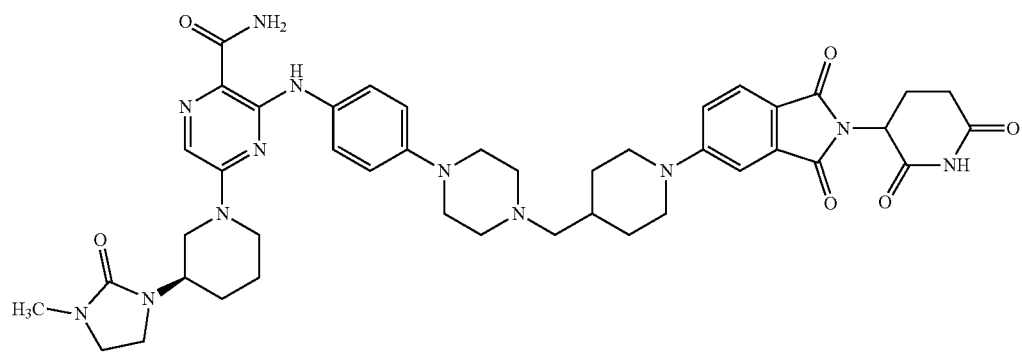 |
| 50 | 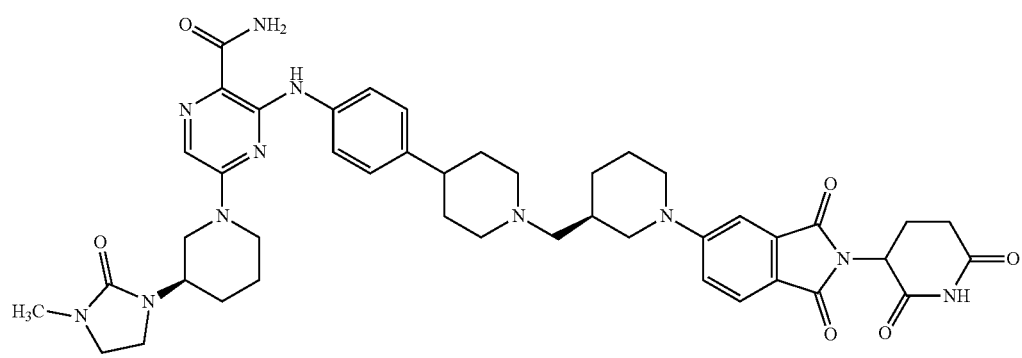 |
| 51 | 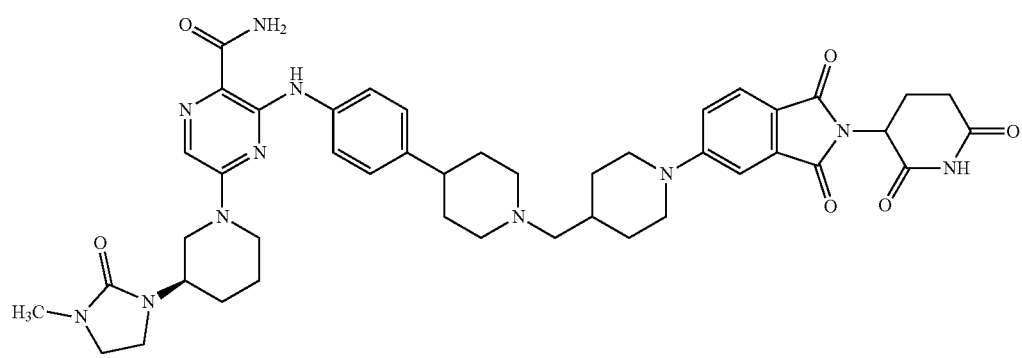 [SMILES: CN1CCN([C@@H]2CCCN(c3cnc(C(N)=O)c(Nc4ccc(C5CCN(CC6CCN(c7ccc8c(c7)C(=O)N(C7CCC(=O)NC7=O)C8=O)CC6)CC5)cc4)n3)C2)C1=O] |
| 52 | 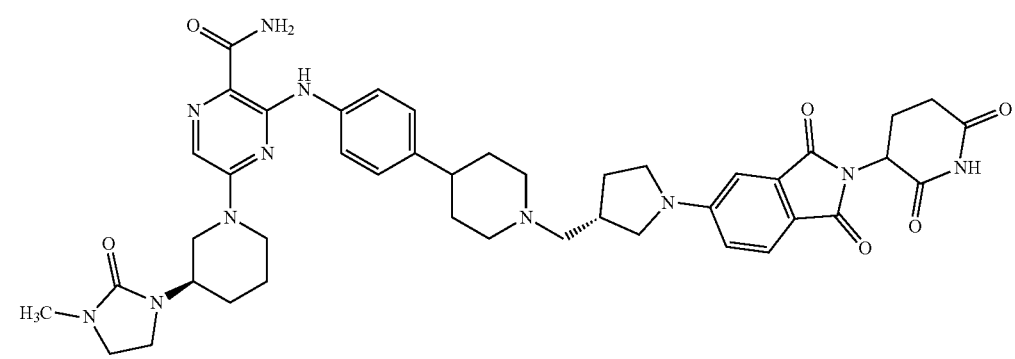 [SMILES: CN1CCN([C@@H]2CCCN(c3cnc(C(N)=O)c(Nc4ccc(C5CCN(C[C@@H]6CCN(c7ccc8c(c7)C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
|---|---|
| 53 | 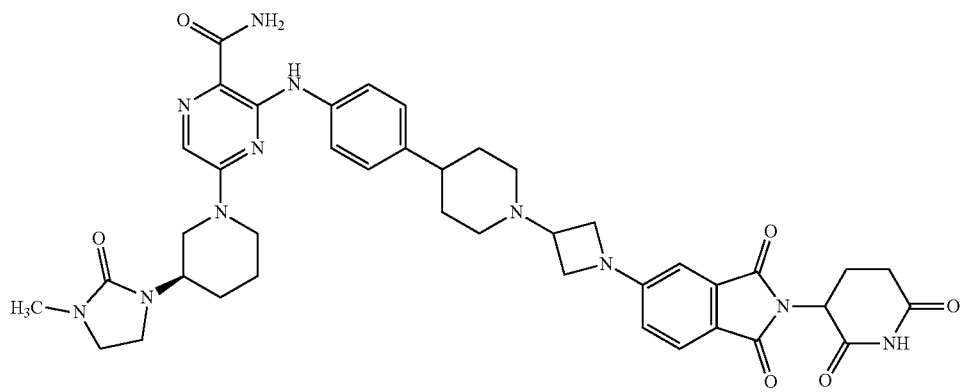 [SMILES: CN1CCN([C@@H]2CCCN(c3cnc(C(N)=O)c(Nc4ccc(C5CCN(C6CN(c7ccc8c(c7)C(=O)N(C7CCC(=O)NC7=O)C8=O)C6)CC5)cc4)n3)C2)C1=O] |
| 54 | 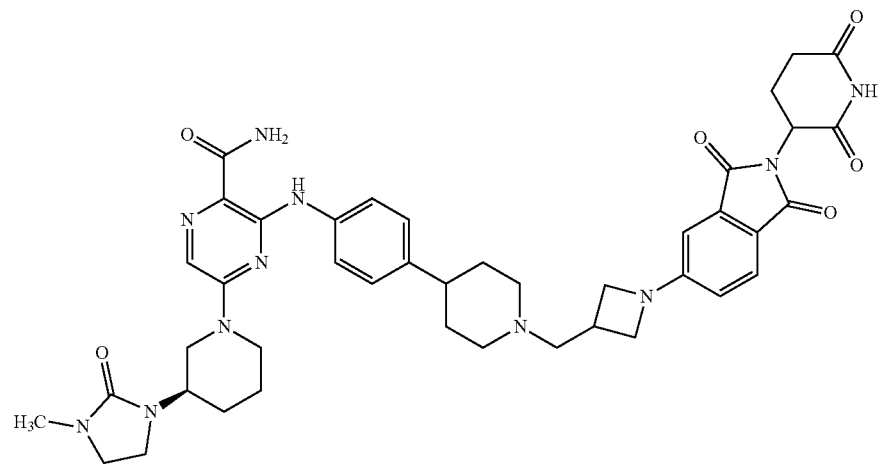 [SMILES: CN1CCN([C@@H]2CCCN(c3cnc(C(N)=O)c(Nc4ccc(C5CCN(CC6CN(c7ccc8c(c7)C(=O)N(C7CCC(=O)NC7=O)C8=O)C6)CC5)cc4)n3)C2)C1=O] |
| 55 | 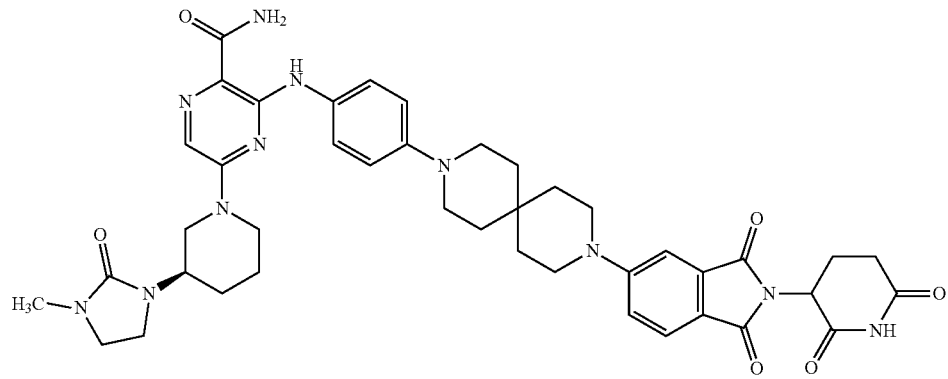 [SMILES: CN1CCN([C@@H]2CCCN(c3cnc(C(N)=O)c(Nc4ccc(N5CCC6(CC5)CCN(c5ccc7c(c5)C(=O)N(C5CCC(=O)NC5=O)C7=O)CC6)cc4)n3)C2)C1=O] |

TABLE 1-continued

Example compounds and/or pharmaceutically acceptable salts thereof for use in the methods described herein.

| Compound Number | Structure |
|---|---|
| 56 | 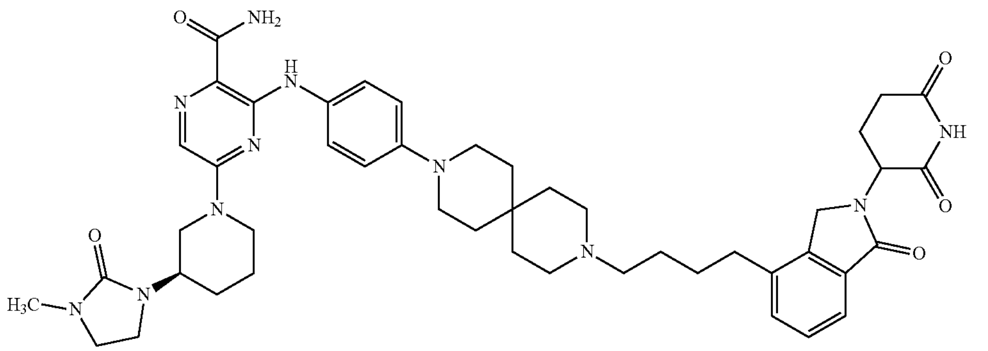 [SMILES: CN1CCN([C@@H]2CCCN(c3cnc(C(N)=O)c(Nc4ccc(N5CCC6(CCN(CCCCc7cccc8c7CN(C7CCC(=O)NC7=O)C8=O)CC6)CC5)cc4)n3)C2)C1=O] |
| 57 | 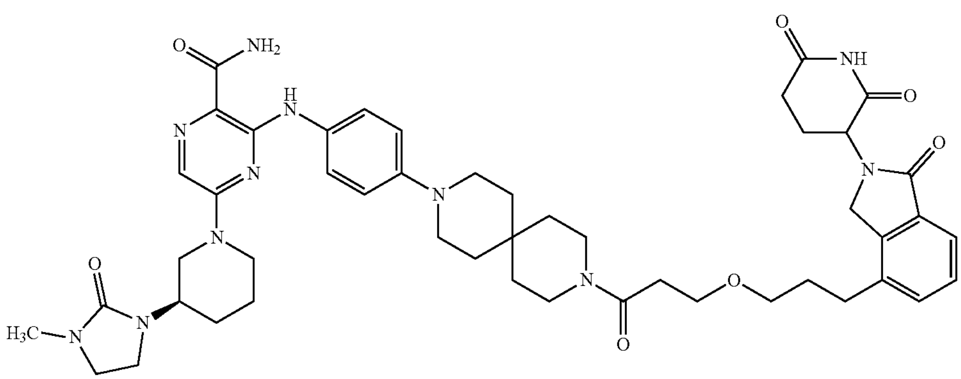 [SMILES: CN1CCN([C@@H]2CCCN(c3cnc(C(N)=O)c(Nc4ccc(N5CCC6(CCN(C(=O)CCOCCCc7cccc8c7CN(C7CCC(=O)NC7=O)C8=O)CC6)CC5)cc4)n3)C2)C1=O] |
| 58 | 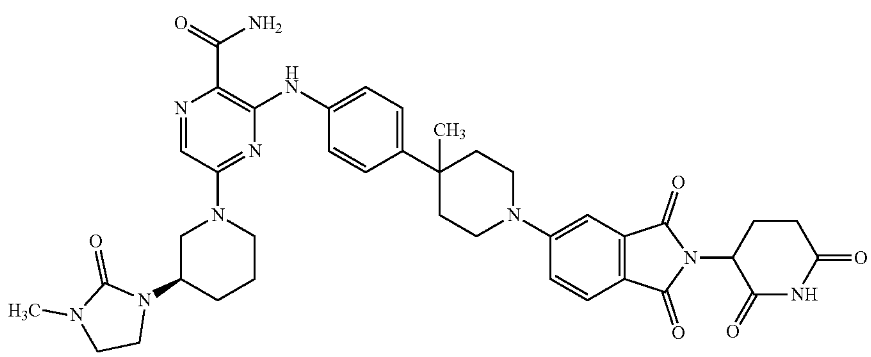 [SMILES: CN1CCN([C@@H]2CCCN(c3cnc(C(N)=O)c(Nc4ccc(C5(C)CCN(c6ccc7c(c6)C(=O)N(C6CCC(=O)NC6=O)C7=O)CC5)cc4)n3)C2)C1=O] |
| 59 | 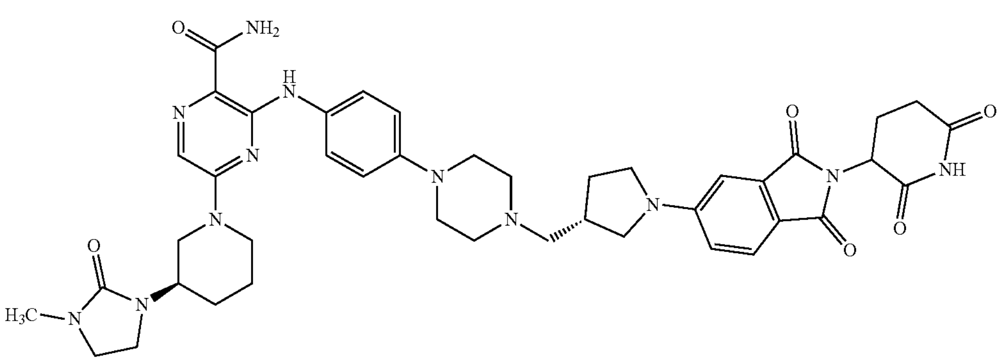 [SMILES: CN1CCN([C@@H]2CCCN(c3cnc(C(N)=O)c(Nc4ccc(N5CCN(C[C@@H]6CCN(c7ccc8c(c7)C(=O)N(C7CCC(=O)NC7=O)C8=O)C6)CC5)cc4)n3)C2)C1=O] |

US 11,820,781 B2
155              156
TABLE 1-continued
Example compounds and/or pharmaceutically acceptable salts thereof for use in the methods described herein.
| Compound Number | Structure |
|---|---|
| 60 | 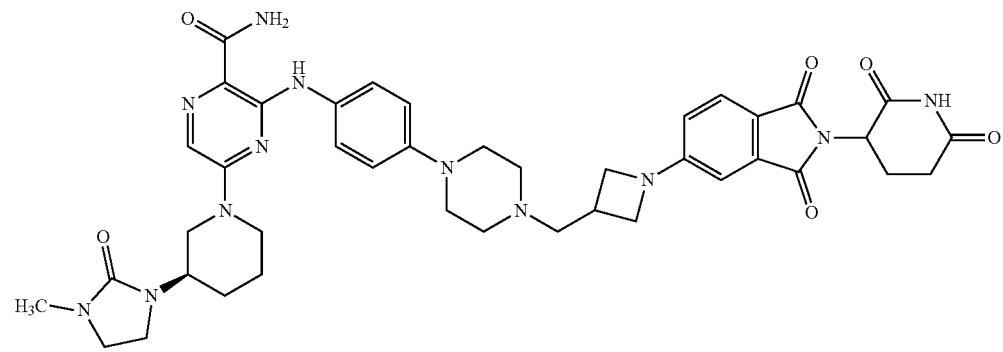 [SMILES: CN1CCN([C@@H]2CCCN(c3cnc(C(N)=O)c(Nc4ccc(N5CCN(CC6CN(c7ccc8c(c7)C(=O)N(C7CCC(=O)NC7=O)C8=O)C6)CC5)cc4)n3)C2)C1=O] |
| 61 | 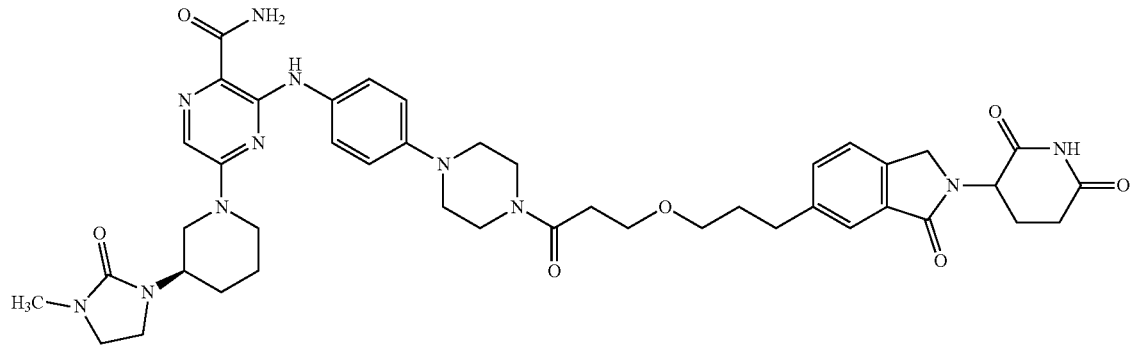 [SMILES: CN1CCN([C@@H]2CCCN(c3cnc(C(N)=O)c(Nc4ccc(N5CCN(C(=O)CCOCCCc6ccc7c(c6)C(=O)N(C6CCC(=O)NC6=O)C7)CC5)cc4)n3)C2)C1=O] |
| 62 | 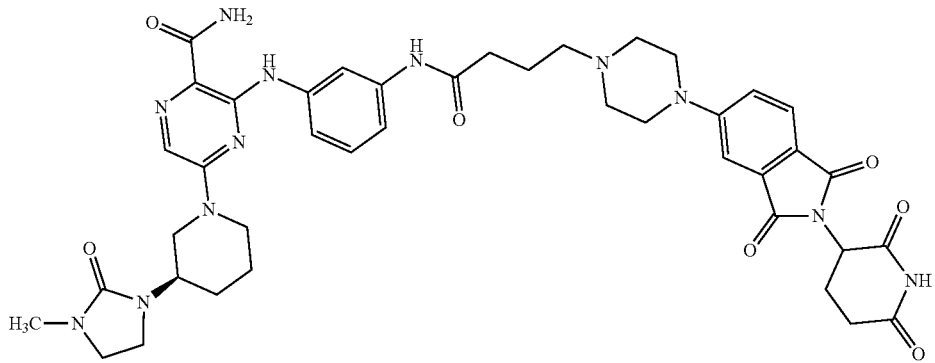 [SMILES: CN1CCN([C@@H]2CCCN(c3cnc(C(N)=O)c(Nc4cccc(NC(=O)CCCN5CCN(c6ccc7c(c6)C(=O)N(C6CCC(=O)NC6=O)C7=O)CC5)c4)n3)C2)C1=O] |
| 63 | 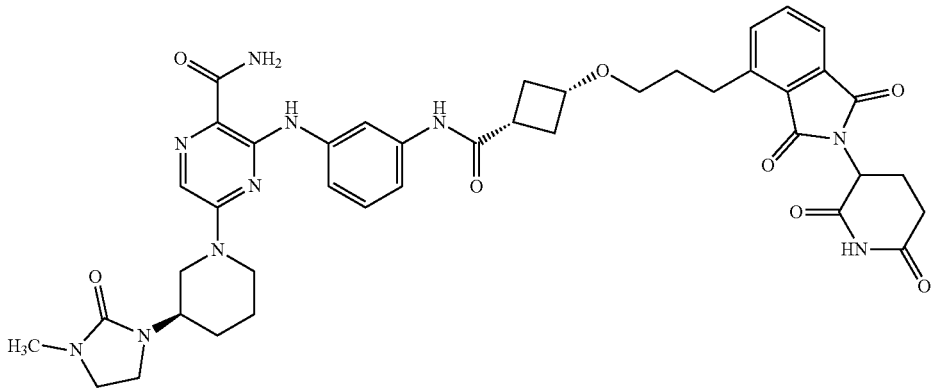 [SMILES: CN1CCN([C@@H]2CCCN(c3cnc(C(N)=O)c(Nc4cccc(NC(=O)[C@H]5C[C@@H](OCCCc6cccc7c6C(=O)N(C6CCC(=O)NC6=O)C7=O)C5)c4)n3)C2)C1=O] |

TABLE 1-continued
Example compounds and/or pharmaceutically acceptable salts thereof for use in the methods described herein.
| Compound Number | Structure |
|---|---|
| 64 | 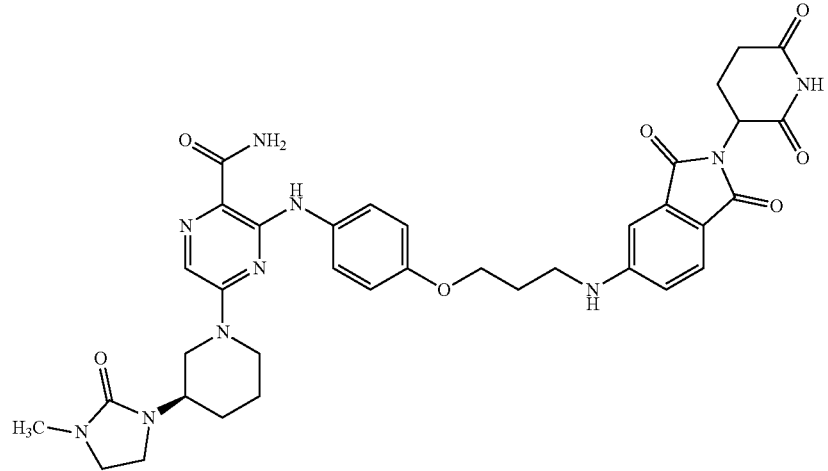 [SMILES: CN1CCN([C@@H]2CCCN(c3cnc(C(N)=O)c(Nc4ccc(OCCCNc5ccc6c(c5)C(=O)N(C5CCC(=O)NC5=O)C6=O)cc4)n3)C2)C1=O] |
| 65 | 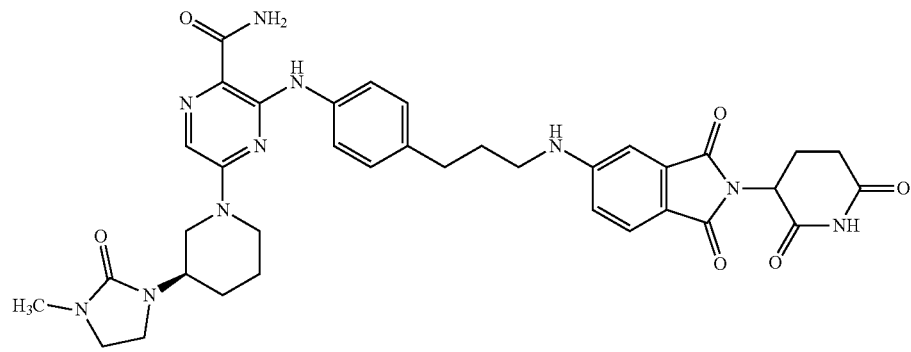 [SMILES: CN1CCN([C@@H]2CCCN(c3cnc(C(N)=O)c(Nc4ccc(CCCNc5ccc6c(c5)C(=O)N(C5CCC(=O)NC5=O)C6=O)cc4)n3)C2)C1=O] |
| 66 | 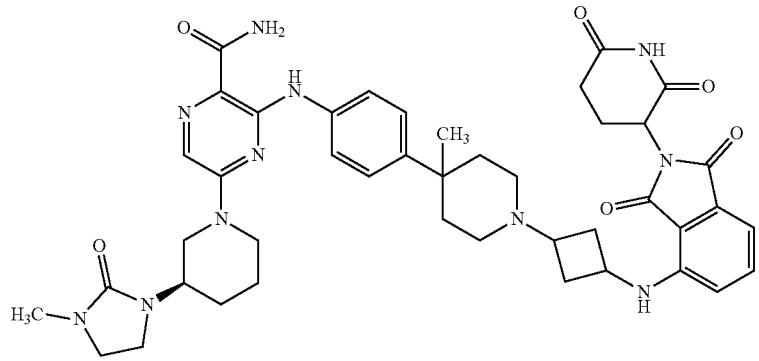 [SMILES: CN1CCN([C@@H]2CCCN(c3cnc(C(N)=O)c(Nc4ccc(C5(C)CCN(C6CC(Nc7cccc8c7C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
|---|---|
| 67 | 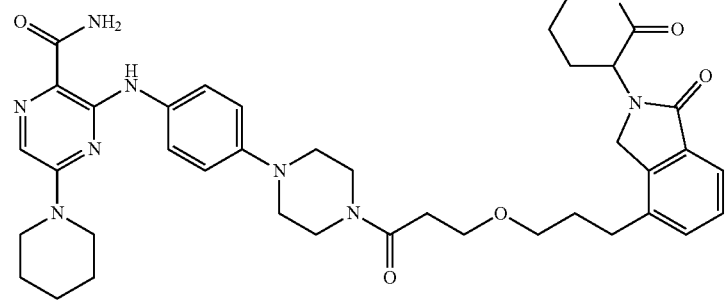 |
| 68 | 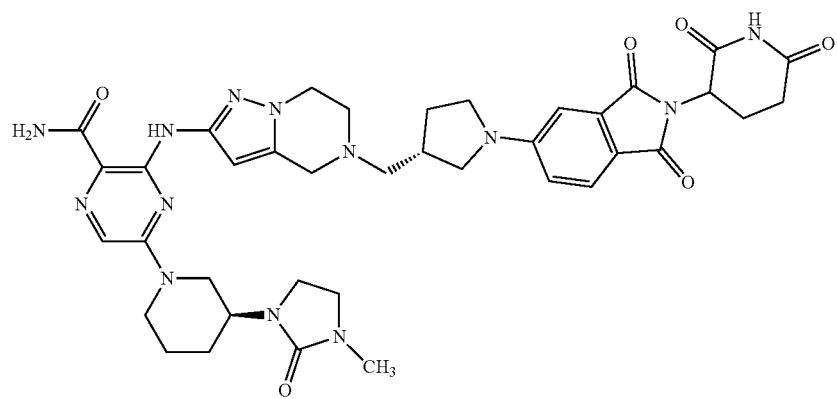 [SMILES: CN1CCN([C@H]2CCCN(c3cnc(C(N)=O)c(Nc4cc5n(n4)CCN(C[C@@H]4CCN(c6ccc7c(c6)C(=O)N(C6CCC(=O)NC6=O)C7=O)C4)C5)n3)C2)C1=O] |
| 69 | 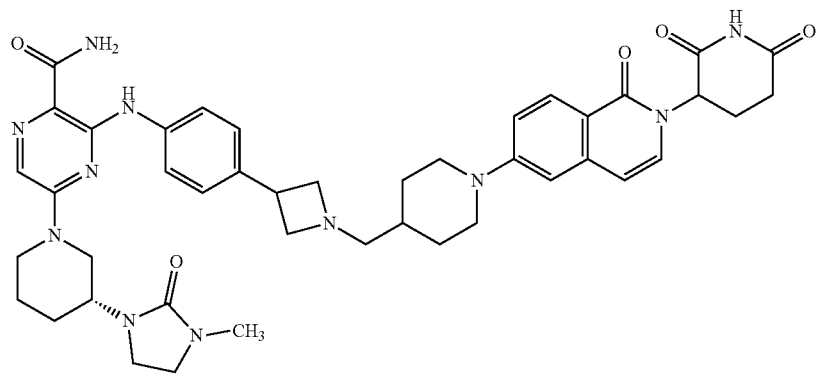 [SMILES: CN1CCN([C@@H]2CCCN(c3cnc(C(N)=O)c(Nc4ccc(C5CN(CC6CCN(c7ccc8c(=O)n(C9CCC(=O)NC9=O)ccc8c7)CC6)C5)cc4)n3)C2)C1=O] |

TABLE 1-continued
Example compounds and/or pharmaceutically acceptable salts thereof for use in the methods described herein.
| Compound Number | Structure |
|---|---|
| 70 | 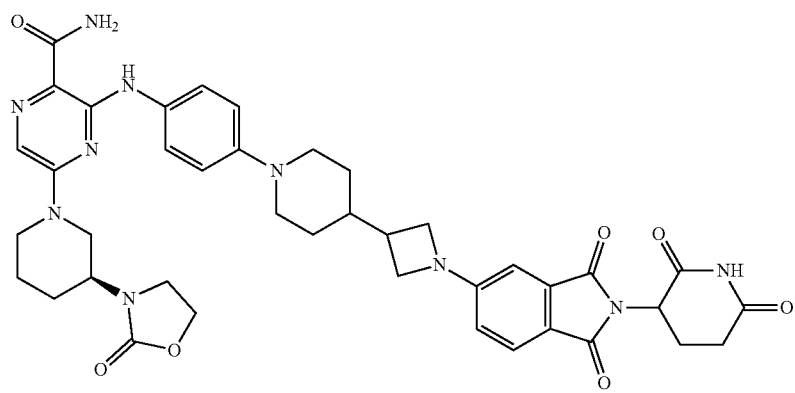 [SMILES: NC(=O)c1ncc(N2CCC[C@H](N3CCOC3=O)C2)nc1Nc1ccc(N2CCC(C3CN(c4ccc5c(c4)C(=O)N(C4CCC(=O)NC4=O)C5=O)C3)CC2)cc1] |
| 71 | 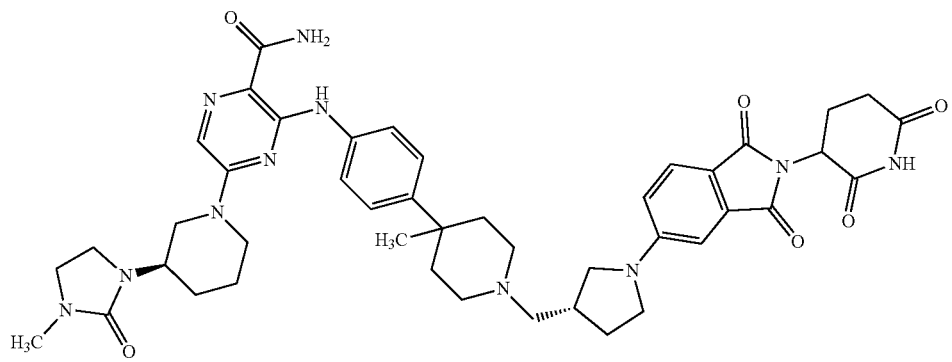 [SMILES: CN1CCN([C@@H]2CCCN(c3cnc(C(N)=O)c(Nc4ccc(C5(C)CCN(C[C@H]6CCN(c7ccc8c(c7)C(=O)N(C7CCC(=O)NC7=O)C8=O)C6)CC5)cc4)n3)C2)C1=O] |
| 72 | 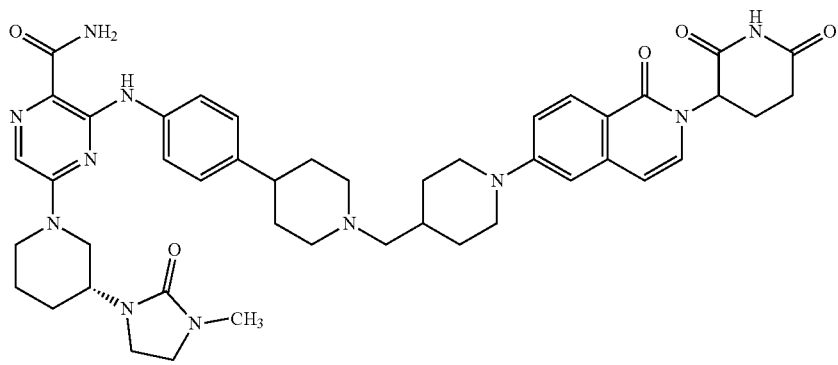 [SMILES: CN1CCN([C@@H]2CCCN(c3cnc(C(N)=O)c(Nc4ccc(C5CCN(CC6CCN(c7ccc8c(=O)n(C9CCC(=O)NC9=O)ccc8c7)CC6)CC5)cc4)n3)C2)C1=O] |
| 73 | 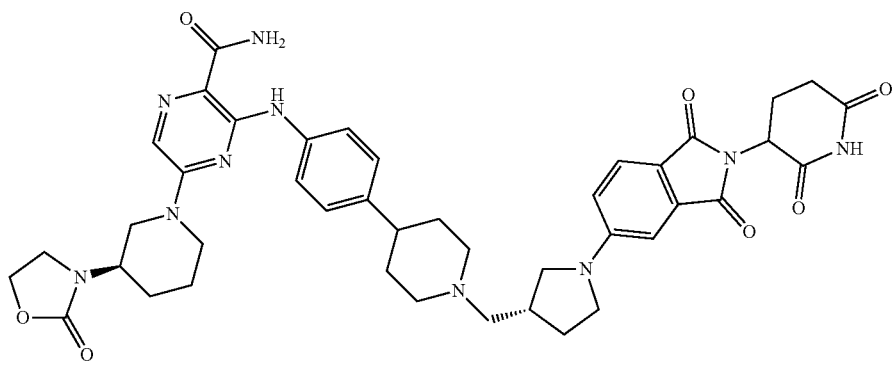 [SMILES: NC(=O)c1ncc(N2CCC[C@@H](N3CCOC3=O)C2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued
Example compounds and/or pharmaceutically acceptable salts thereof for use in the methods described herein.
| Compound Number | Structure |
|---|---|
| 74 | 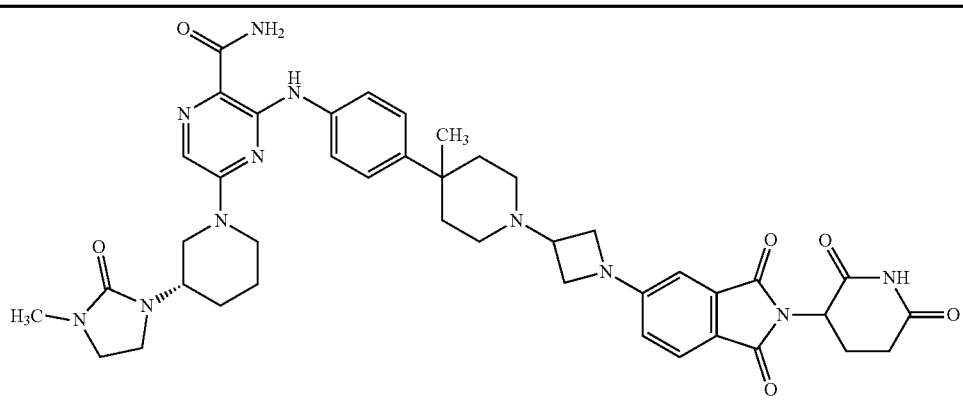 |
| 75 | 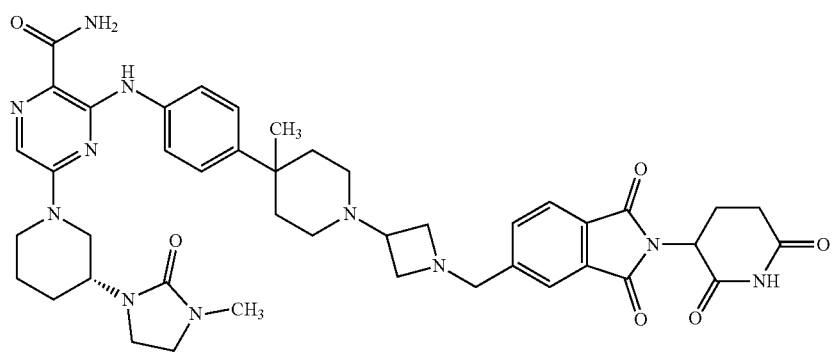 [SMILES: CN1CCN([C@@H]2CCCN(c3cnc(C(N)=O)c(Nc4ccc(C5(C)CCN(C6CN(Cc7ccc8c(c7)C(=O)N(C7CCC(=O)NC7=O)C8=O)C6)CC5)cc4)n3)C2)C1=O] |
| 76 | 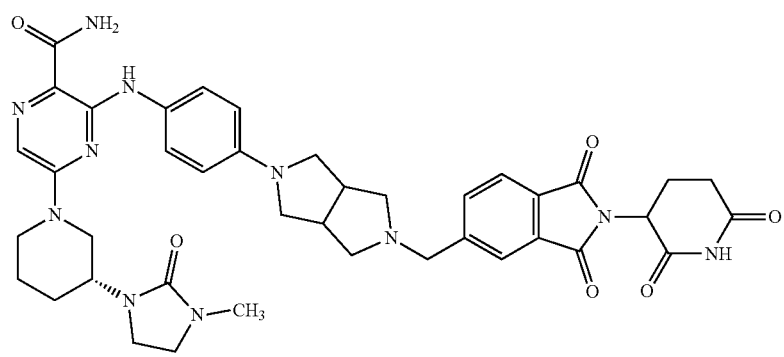 [SMILES: CN1CCN([C@@H]2CCCN(c3cnc(C(N)=O)c(Nc4ccc(N5CC6CN(Cc7ccc8c(c7)C(=O)N(C7CCC(=O)NC7=O)C8=O)CC6C5)cc4)n3)C2)C1=O] |
| 77 | 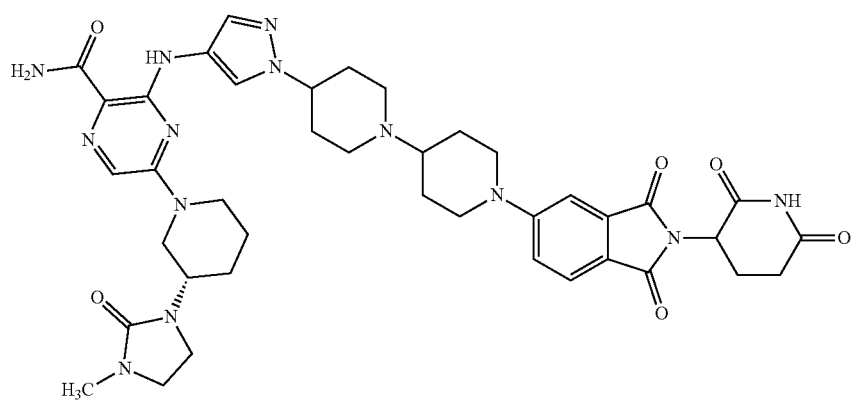 [SMILES: CN1CCN([C@H]2CCCN(c3cnc(C(N)=O)c(Nc4cnn(C5CCN(C6CCN(c7ccc8c(c7)C(=O)N(C7CCC(=O)NC7=O)C8=O)CC6)CC5)c4)n3)C2)C1=O] |

TABLE 1-continued
Example compounds and/or pharmaceutically acceptable salts thereof for use in the methods described herein.
| Compound Number | Structure |
|---|---|
| 78 | 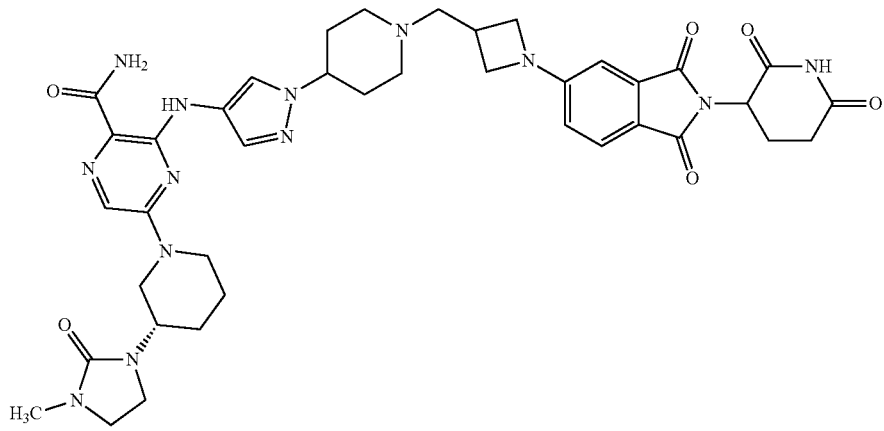 [SMILES: CN1CCN([C@H]2CCCN(c3cnc(C(N)=O)c(Nc4cnn(C5CCN(CC6CN(c7ccc8c(c7)C(=O)N(C7CCC(=O)NC7=O)C8=O)C6)CC5)c4)n3)C2)C1=O] |
| 79 | 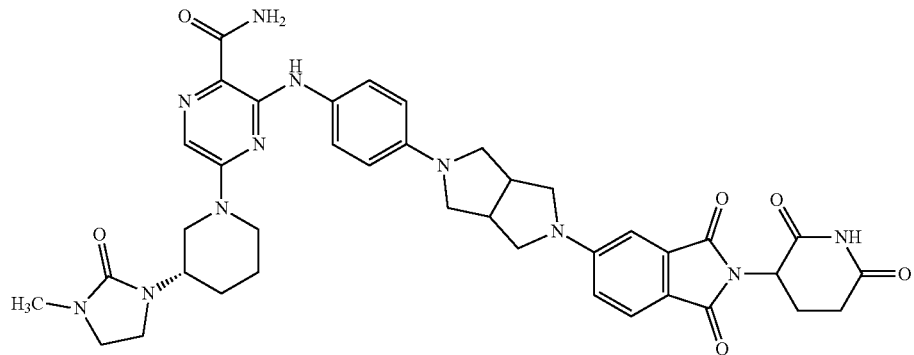 [SMILES: CN1CCN([C@H]2CCCN(c3cnc(C(N)=O)c(Nc4ccc(N5CC6CN(c7ccc8c(c7)C(=O)N(C7CCC(=O)NC7=O)C8=O)CC6C5)cc4)n3)C2)C1=O] |
| 80 | 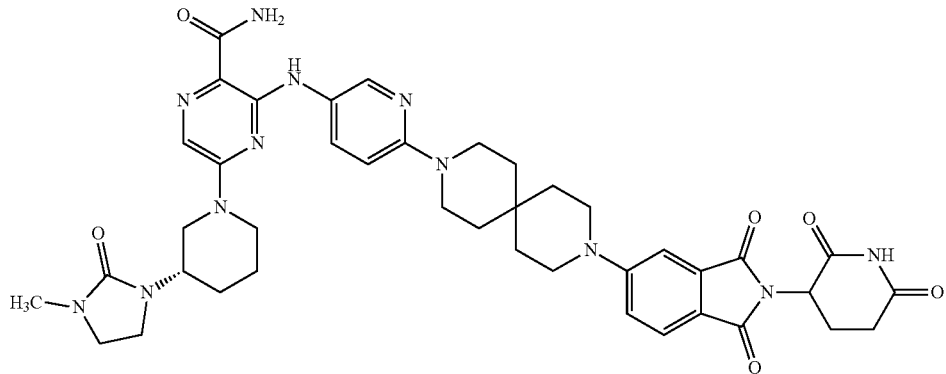 [SMILES: CN1CCN([C@H]2CCCN(c3cnc(C(N)=O)c(Nc4ccc(N5CCC6(CCN(c7ccc8c(c7)C(=O)N(C7CCC(=O)NC7=O)C8=O)CC6)CC5)nc4)n3)C2)C1=O] |

TABLE 1-continued

Example compounds and/or pharmaceutically acceptable salts thereof for use in the methods described herein.

| Compound Number | Structure |
|---|---|
| 81 | 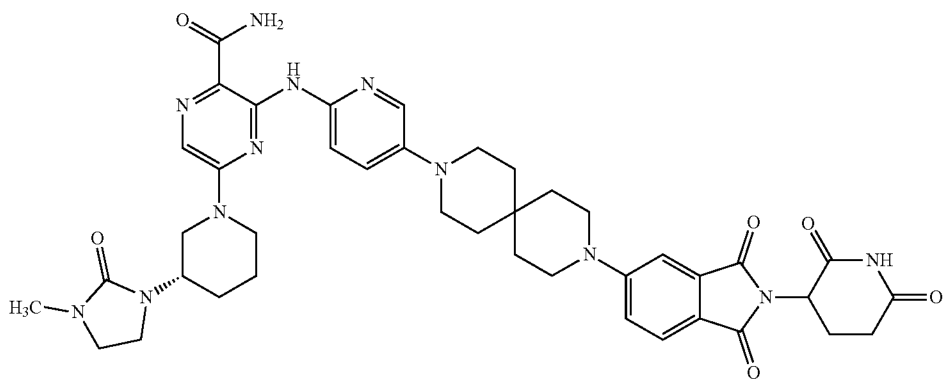 [SMILES: CN1CCN([C@H]2CCCN(c3cnc(C(N)=O)c(Nc4ccc(N5CCC6(CC5)CCN(c5ccc7c(c5)C(=O)N(C5CCC(=O)NC5=O)C7=O)CC6)cn4)n3)C2)C1=O] |
| 82 | 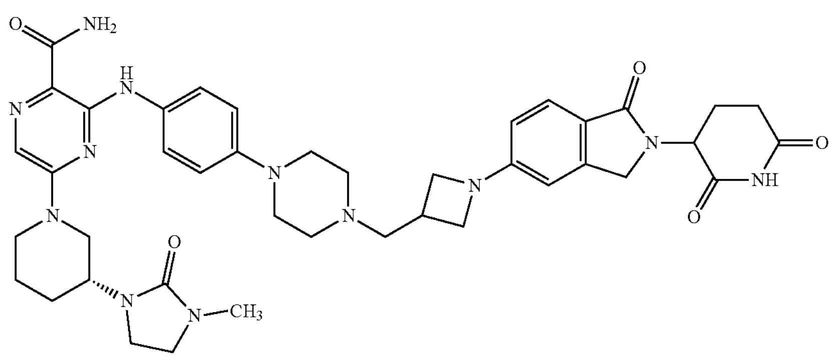 [SMILES: CN1CCN([C@@H]2CCCN(c3cnc(C(N)=O)c(Nc4ccc(N5CCN(CC6CN(c7ccc8c(c7)CN(C7CCC(=O)NC7=O)C8=O)C6)CC5)cc4)n3)C2)C1=O] |
| 83 | 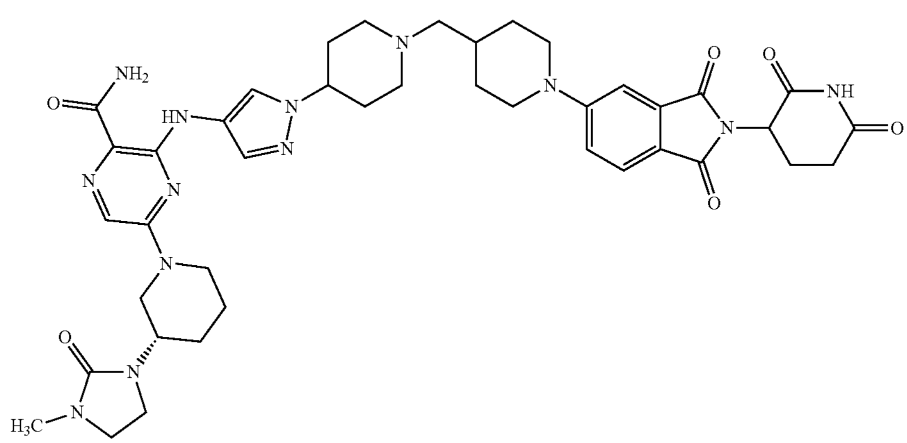 [SMILES: CN1CCN([C@H]2CCCN(c3cnc(C(N)=O)c(Nc4cnn(C5CCN(CC6CCN(c7ccc8c(c7)C(=O)N(C7CCC(=O)NC7=O)C8=O)CC6)CC5)c4)n3)C2)C1=O] |

TABLE 1-continued
Example compounds and/or pharmaceutically acceptable salts thereof for use in the methods described herein.
| Compound Number | Structure |
|---|---|
| 84 | 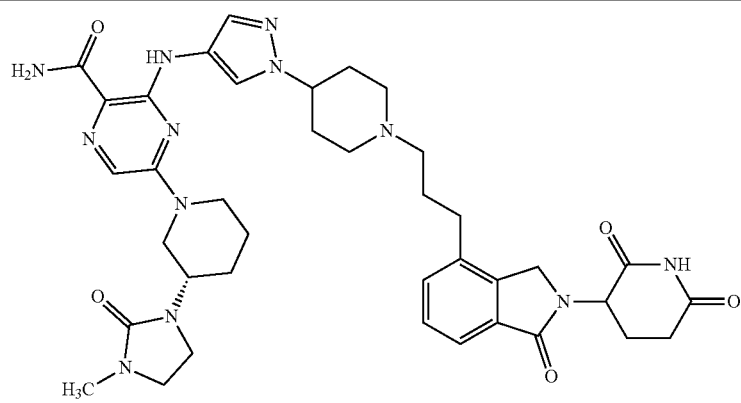 |
| 85 | 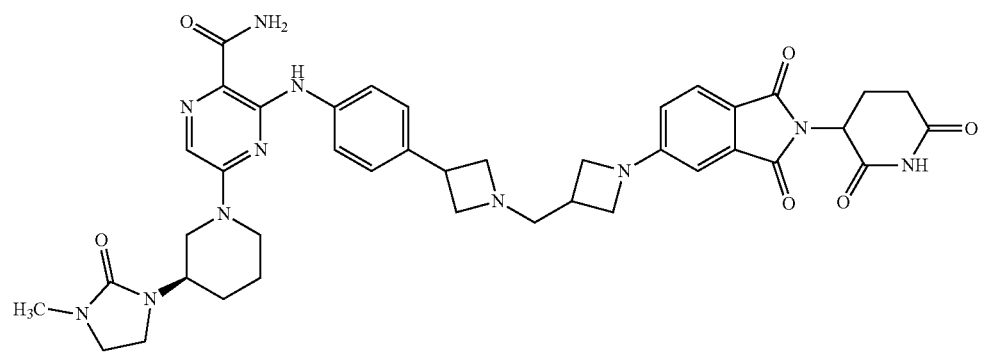 [SMILES: CN1CCN([C@@H]2CCCN(c3cnc(C(N)=O)c(Nc4ccc(C5CN(CC6CN(c7ccc8c(c7)C(=O)N(C7CCC(=O)NC7=O)C8=O)C6)C5)cc4)n3)C2)C1=O] |
| 86 | 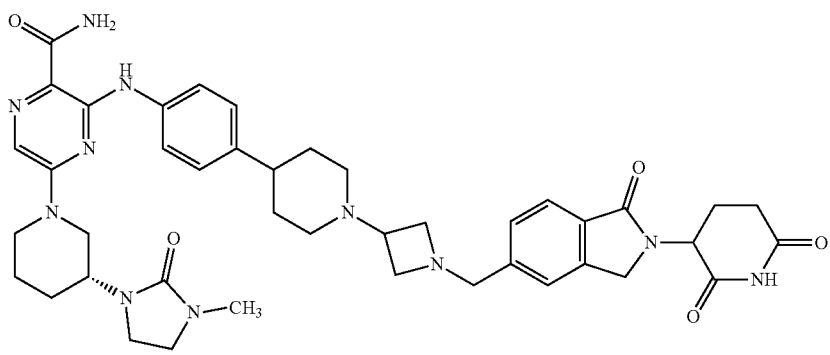 [SMILES: CN1CCN([C@@H]2CCCN(c3cnc(C(N)=O)c(Nc4ccc(C5CCN(C6CN(Cc7ccc8c(c7)CN(C7CCC(=O)NC7=O)C8=O)C6)CC5)cc4)n3)C2)C1=O] |
| 87 | 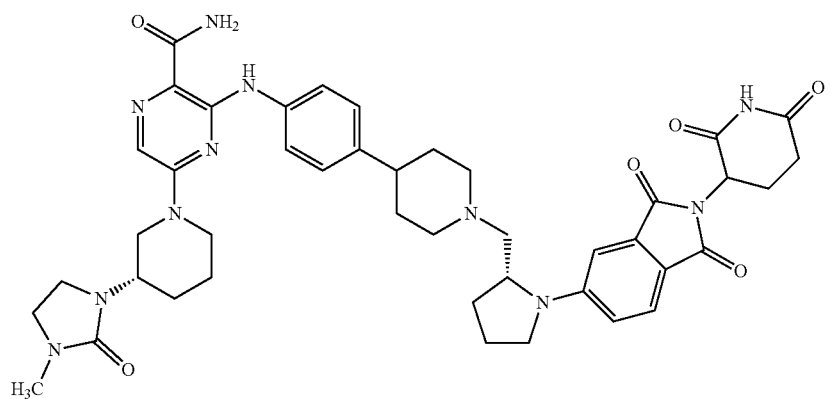 [SMILES: CN1CCN([C@H]2CCCN(c3cnc(C(N)=O)c(Nc4ccc(C5CCN(C[C@H]6CCCN6c6ccc7c(c6)C(=O)N(C6CCC(=O)NC6=O)C7=O)CC5)cc4)n3)C2)C1=O] |

TABLE 1-continued
Example compounds and/or pharmaceutically acceptable salts thereof for use in the methods described herein.
| Compound Number | Structure |
|---|---|
| 88 | 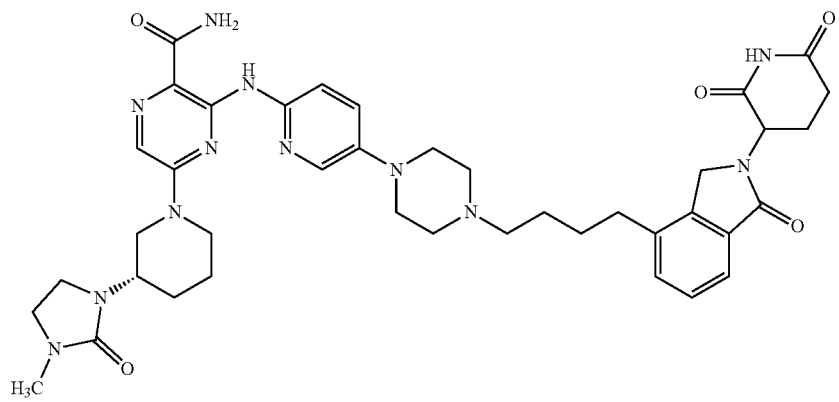 [SMILES: CN1CCN([C@H]2CCCN(c3cnc(C(N)=O)c(Nc4ccc(N5CCN(CCCCc6cccc7c6CN(C6CCC(=O)NC6=O)C7=O)CC5)cn4)n3)C2)C1=O] |
| 89 | 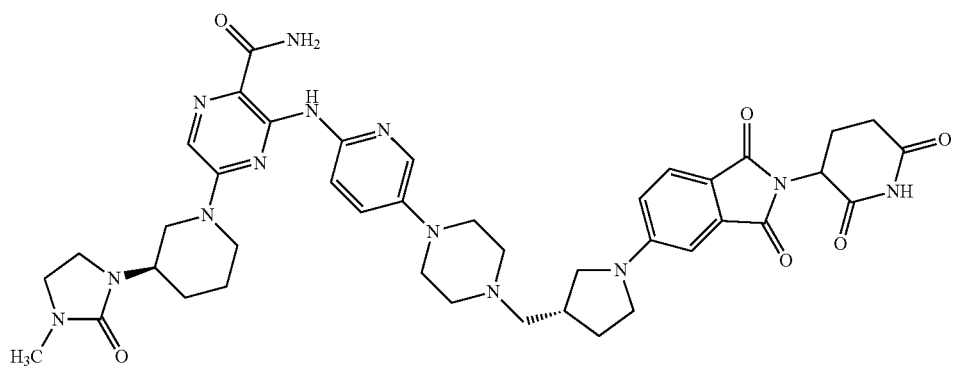 [SMILES: CN1CCN([C@@H]2CCCN(c3cnc(C(N)=O)c(Nc4ccc(N5CCN(C[C@H]6CCN(c7ccc8c(c7)C(=O)N(C7CCC(=O)NC7=O)C8=O)C6)CC5)cn4)n3)C2)C1=O] |
| 90 | 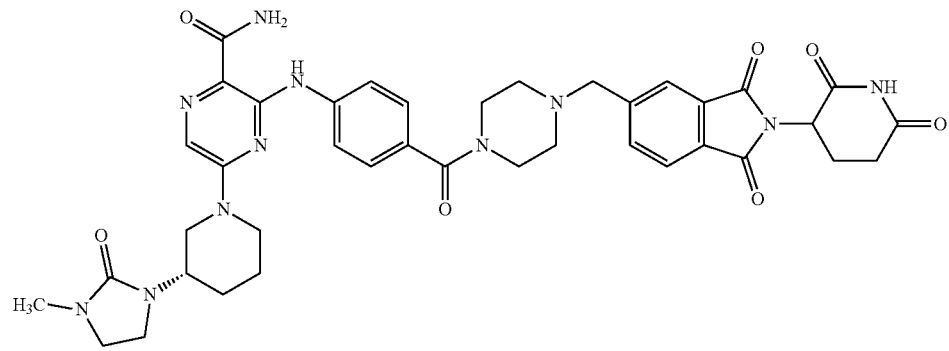 [SMILES: CN1CCN([C@H]2CCCN(c3cnc(C(N)=O)c(Nc4ccc(C(=O)N5CCN(Cc6ccc7c(c6)C(=O)N(C6CCC(=O)NC6=O)C7=O)CC5)cc4)n3)C2)C1=O] |
| 91 | 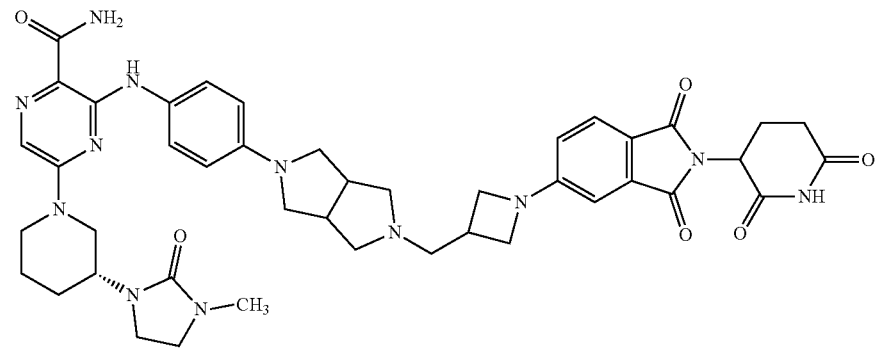 [SMILES: CN1CCN([C@@H]2CCCN(c3cnc(C(N)=O)c(Nc4ccc(N5CC6CN(CC7CN(c8ccc9c(c8)C(=O)N(C8CCC(=O)NC8=O)C9=O)C7)CC6C5)cc4)n3)C2)C1=O] |

TABLE 1-continued
Example compounds and/or pharmaceutically acceptable salts thereof for use in the methods described herein.
| Compound Number | Structure |
|---|---|
| 92 | 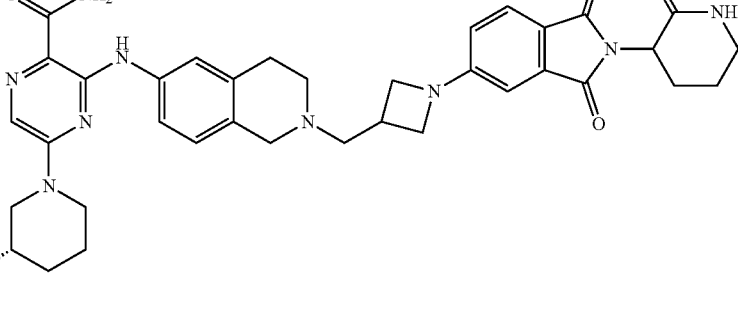 |
| 93 | 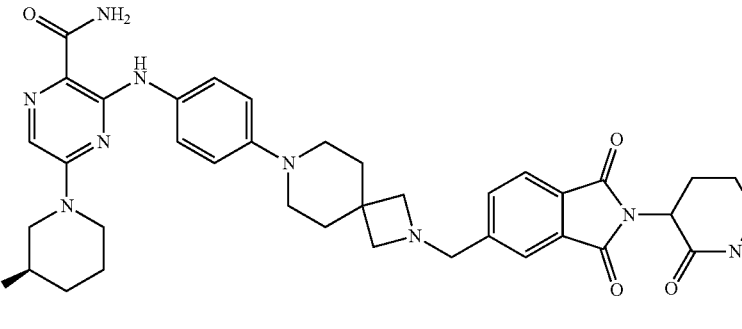 |
| 94 | 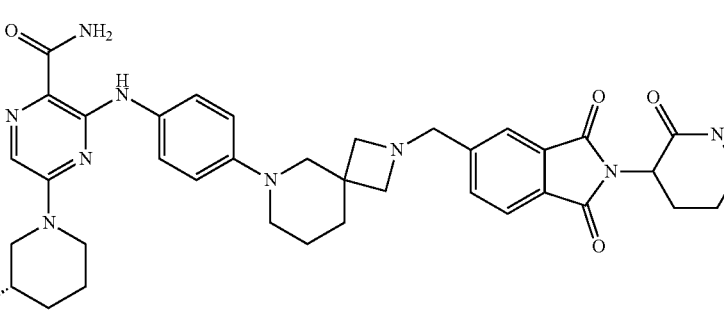 |
| 95 | 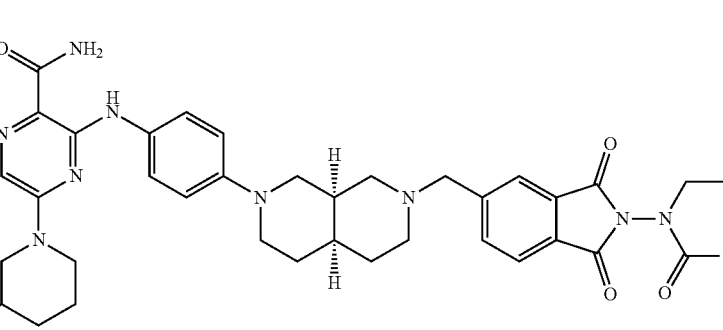 |

TABLE 1-continued
Example compounds and/or pharmaceutically acceptable salts thereof for use in the methods described herein.
| Compound Number | Structure |
|---|---|
| 96 | 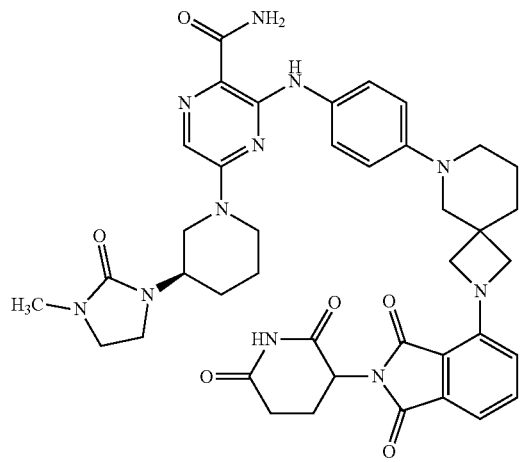 [SMILES: CN1CCN([C@@H]2CCCN(c3cnc(C(N)=O)c(Nc4ccc(N5CCCC6(C5)CN(c5cccc7c5C(=O)N(C5CCC(=O)NC5=O)C7=O)C6)cc4)n3)C2)C1=O] |
| 97 | 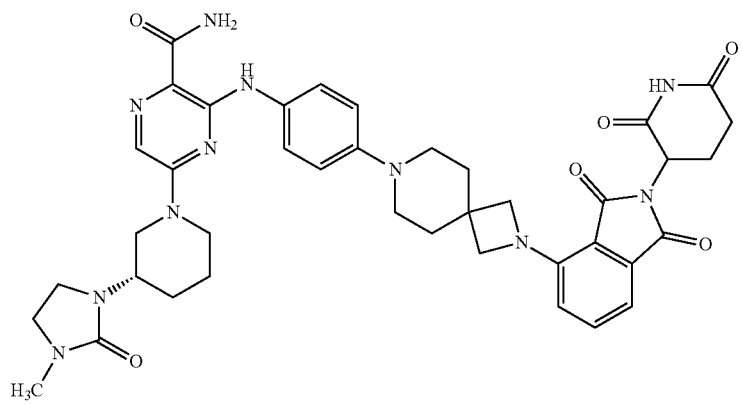 [SMILES: CN1CCN([C@H]2CCCN(c3cnc(C(N)=O)c(Nc4ccc(N5CCC6(CC5)CN(c5cccc7c5C(=O)N(C5CCC(=O)NC5=O)C7=O)C6)cc4)n3)C2)C1=O] |
| 98 | 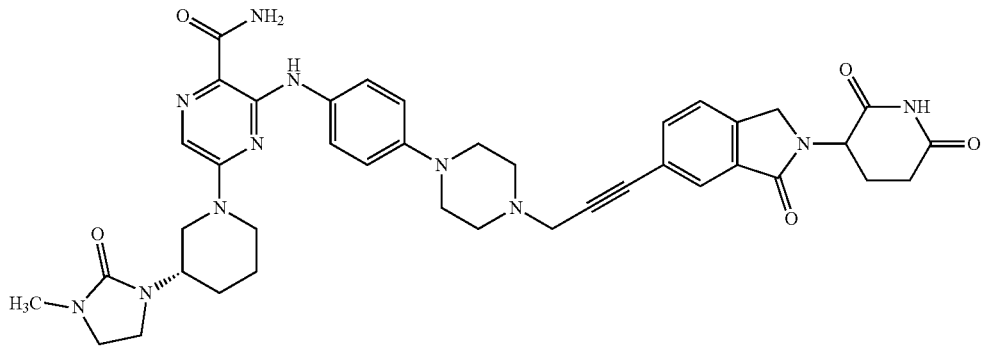 [SMILES: CN1CCN([C@H]2CCCN(c3cnc(C(N)=O)c(Nc4ccc(N5CCN(CC#Cc6ccc7c(c6)C(=O)N(C6CCC(=O)NC6=O)C7)CC5)cc4)n3)C2)C1=O] |

TABLE 1-continued
Example compounds and/or pharmaceutically acceptable salts thereof for use in the methods described herein.
| Compound Number | Structure |
|---|---|
| 99 | 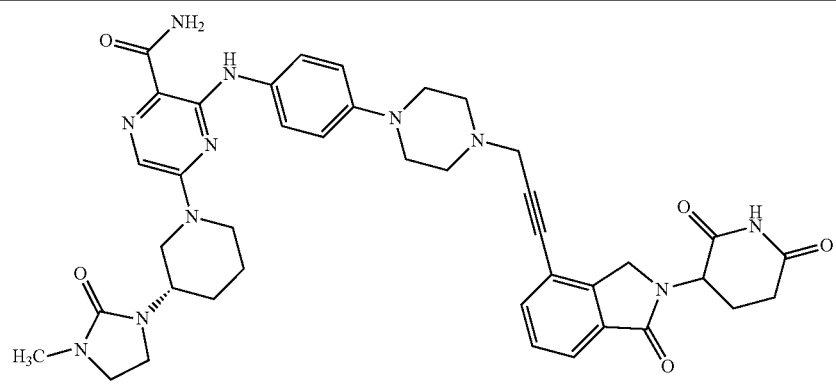 |
| 100 | 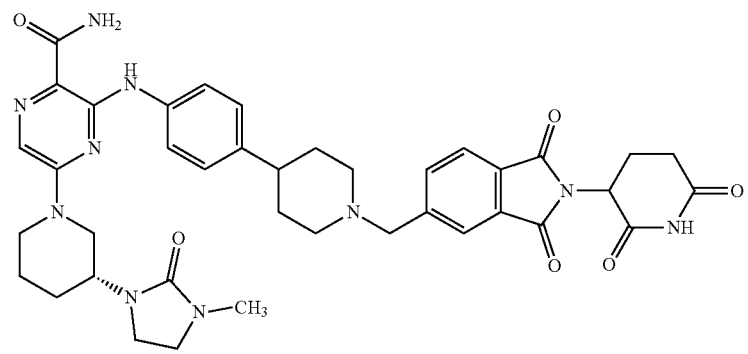 [SMILES: CN1CCN([C@@H]2CCCN(c3cnc(C(N)=O)c(Nc4ccc(C5CCN(Cc6ccc7c(c6)C(=O)N(C6CCC(=O)NC6=O)C7=O)CC5)cc4)n3)C2)C1=O] |
| 101 | 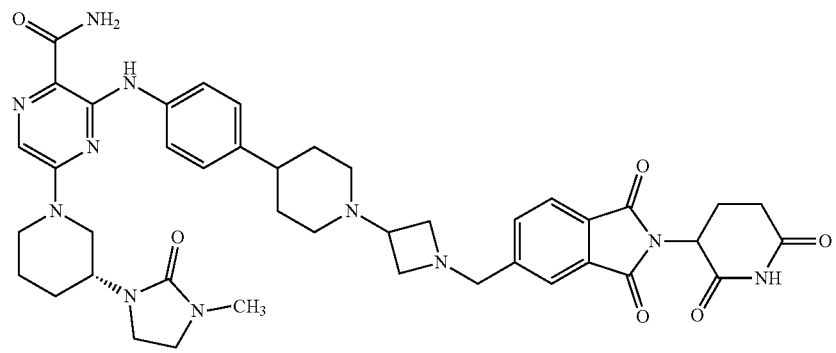 [SMILES: CN1CCN([C@@H]2CCCN(c3cnc(C(N)=O)c(Nc4ccc(C5CCN(C6CN(Cc7ccc8c(c7)C(=O)N(C7CCC(=O)NC7=O)C8=O)C6)CC5)cc4)n3)C2)C1=O] |
| 102 | 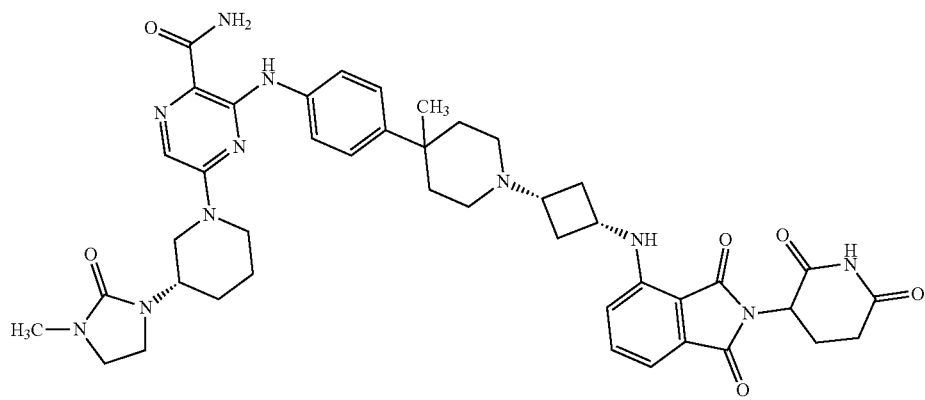 [SMILES: CN1CCN([C@H]2CCCN(c3cnc(C(N)=O)c(Nc4ccc(C5(C)CCN([C@H]6C[C@@H](Nc7cccc8c7C(=O)N(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
| --- | --- |
| 103 | 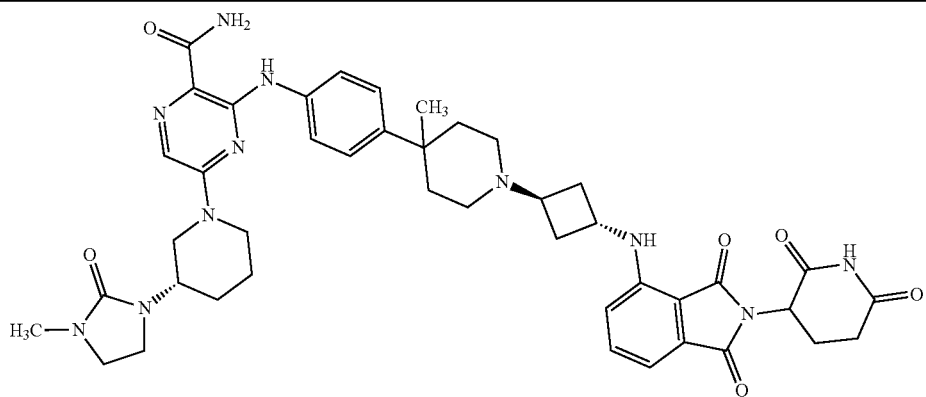 |
| 104 | 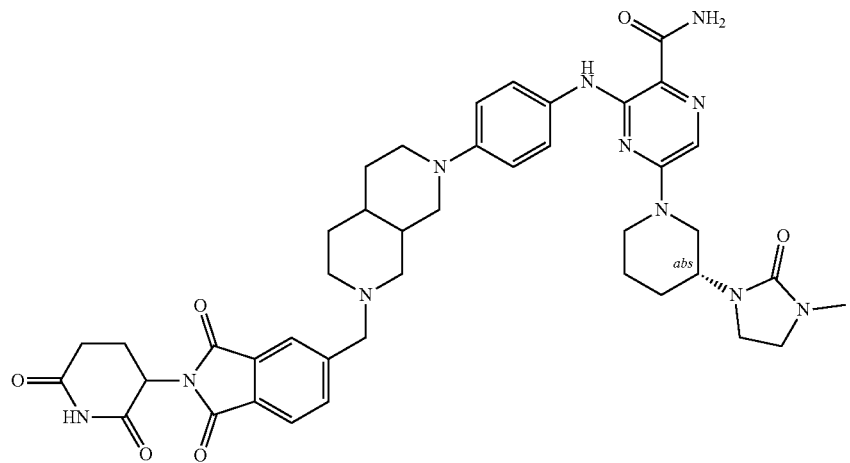 |
| 105 | 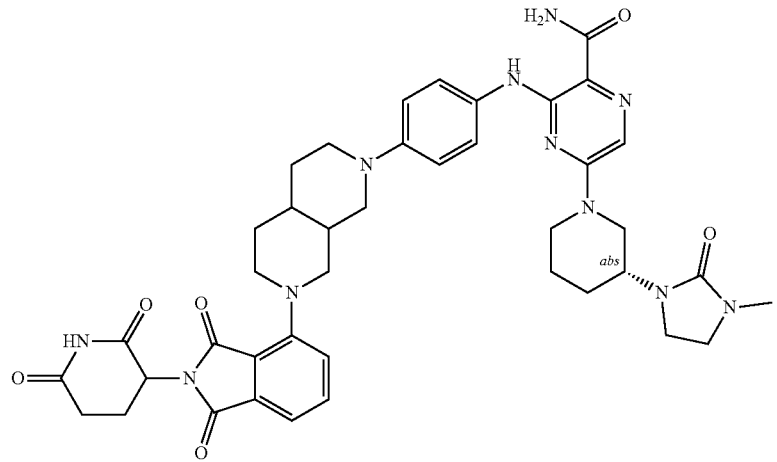 |

TABLE 1-continued

Example compounds and/or pharmaceutically acceptable salts thereof for use in the methods described herein.

| Compound Number | Structure |
|---|---|
| 106 | 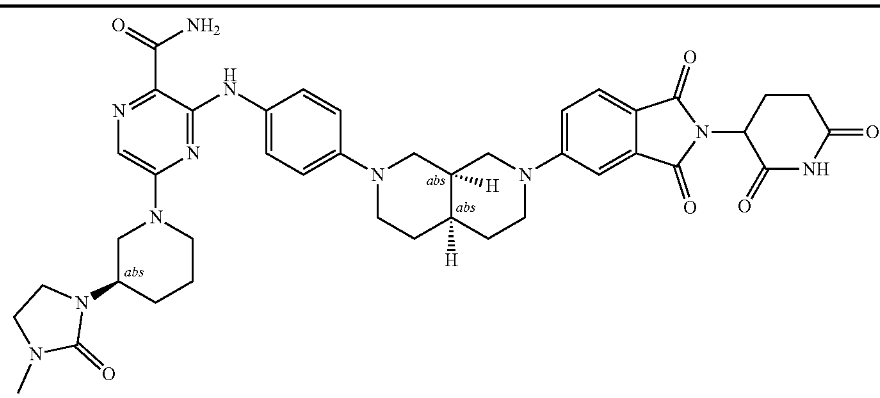 |
| 107 | 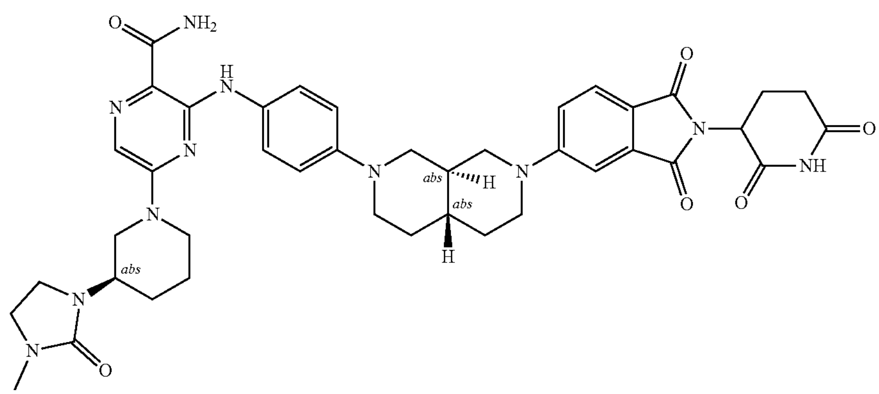 |
| 108 | 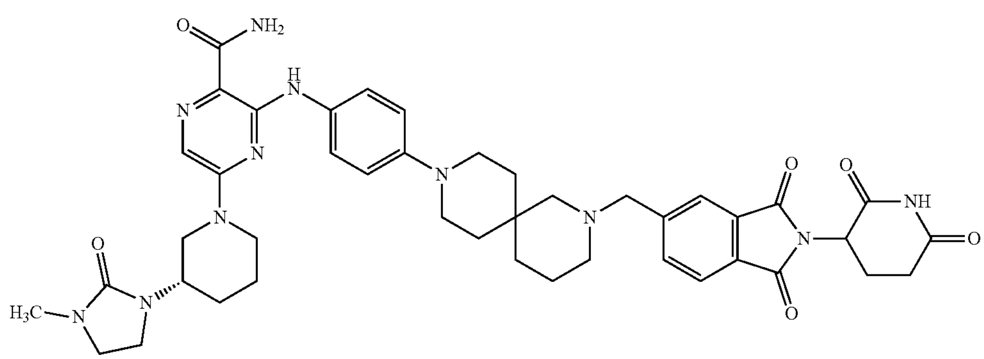 [SMILES: CN1CCN([C@H]2CCCN(c3cnc(C(N)=O)c(Nc4ccc(N5CCC6(CCCN(Cc7ccc8c(c7)C(=O)N(C7CCC(=O)NC7=O)C8=O)C6)CC5)cc4)n3)C2)C1=O] |
| 109 | 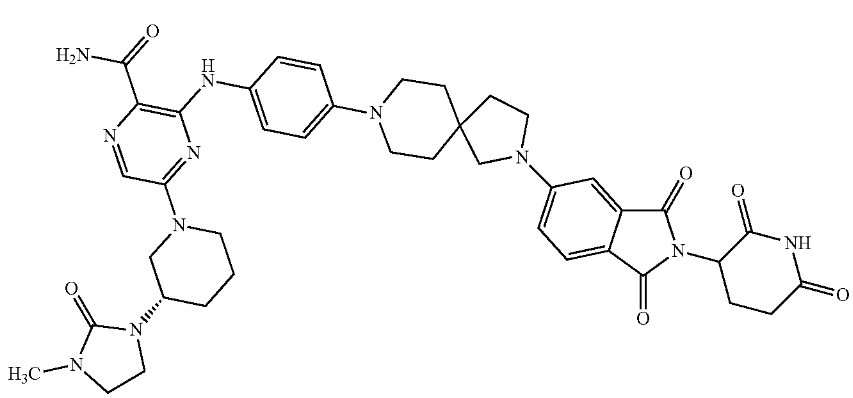 [SMILES: CN1CCN([C@H]2CCCN(c3cnc(C(N)=O)c(Nc4ccc(N5CCC6(CC5)CCN(c5ccc7c(c5)C(=O)N(C5CCC(=O)NC5=O)C7=O)C6)cc4)n3)C2)C1=O] |

TABLE 1-continued
Example compounds and/or pharmaceutically acceptable salts thereof for use in the methods described herein.
| Compound Number | Structure |
|---|---|
| 110 | 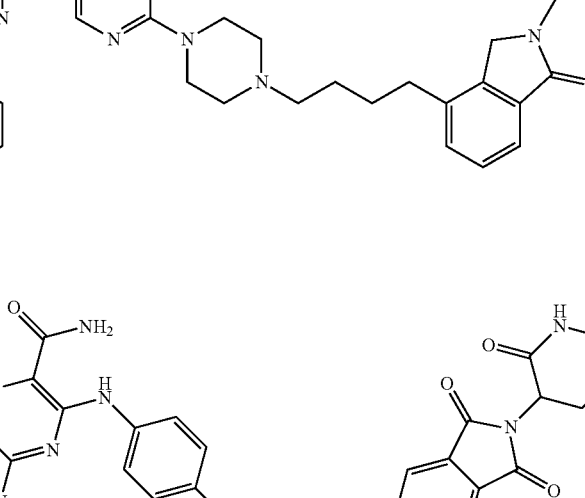 |
| 111 | 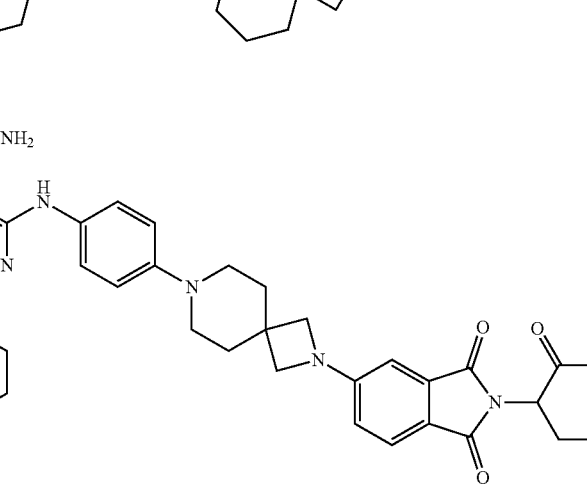 |
| 112 | 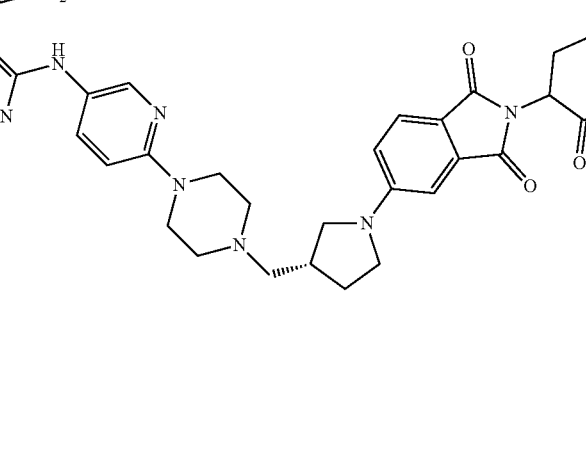 |
| 113 | 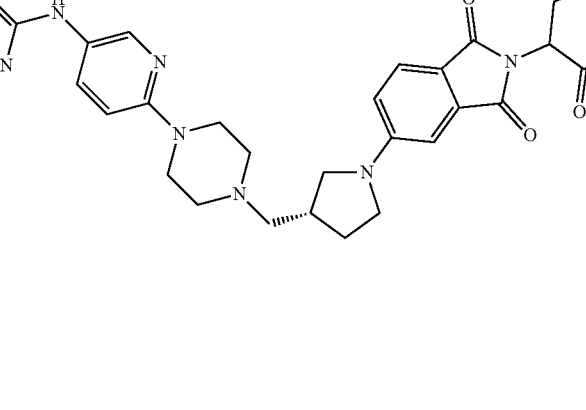 |

TABLE 1-continued
Example compounds and/or pharmaceutically acceptable salts thereof for use in the methods described herein.
| Compound Number | Structure |
|---|---|
| 114 | 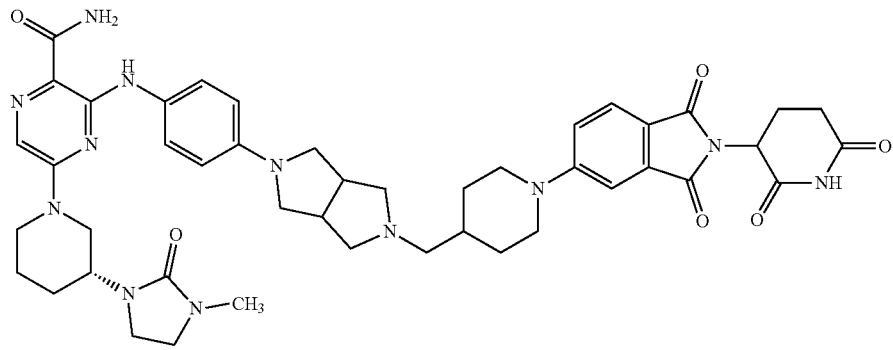 [SMILES: CN1CCN([C@@H]2CCCN(c3cnc(C(N)=O)c(Nc4ccc(N5CC6CN(CC7CCN(c8ccc9c(c8)C(=O)N(C8CCC(=O)NC8=O)C9=O)CC7)CC6C5)cc4)n3)C2)C1=O] |
| 115 | 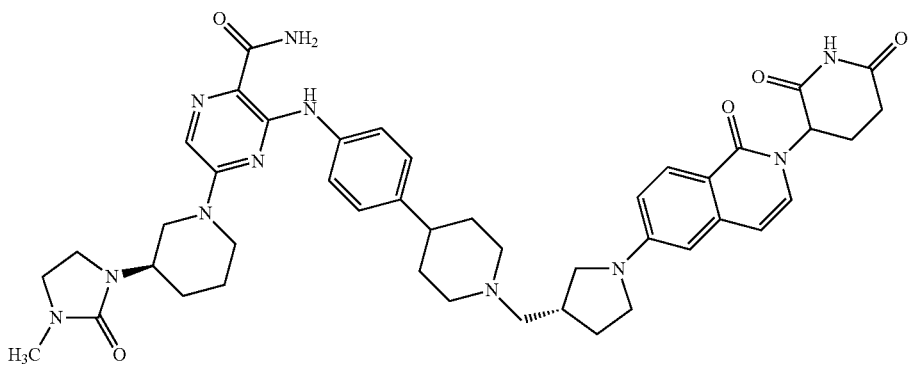 [SMILES: CN1CCN([C@@H]2CCCN(c3cnc(C(N)=O)c(Nc4ccc(C5CCN(C[C@H]6CCN(c7ccc8c(=O)n(C9CCC(=O)NC9=O)ccc8c7)C6)CC5)cc4)n3)C2)C1=O] |
| 116 | 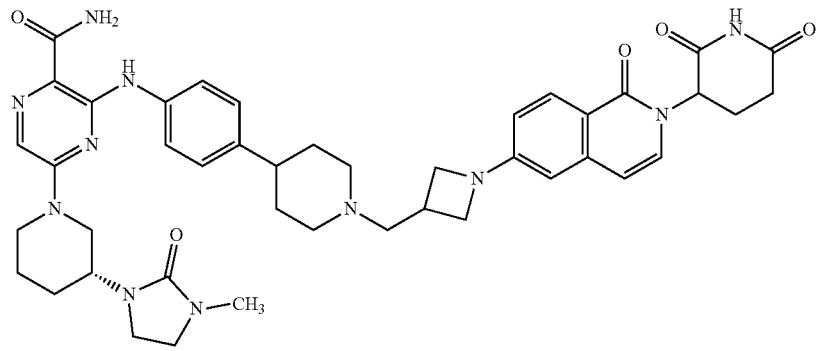 [SMILES: CN1CCN([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |
| 117 | 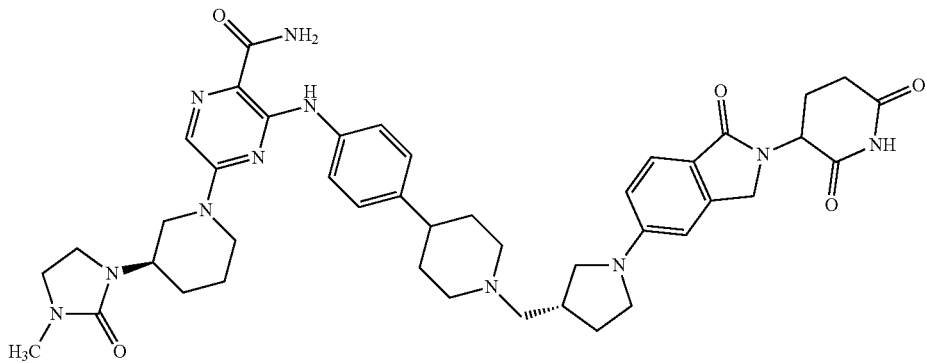 [SMILES: CN1CCN([C@@H]2CCCN(c3cnc(C(N)=O)c(Nc4ccc(C5CCN(C[C@H]6CCN(c7ccc8c(c7)CN(C7CCC(=O)NC7=O)C8=O)C6)CC5)cc4)n3)C2)C1=O] |

TABLE 1-continued
Example compounds and/or pharmaceutically acceptable salts thereof for use in the methods described herein.
| Compound Number | Structure |
|---|---|
| 118 | 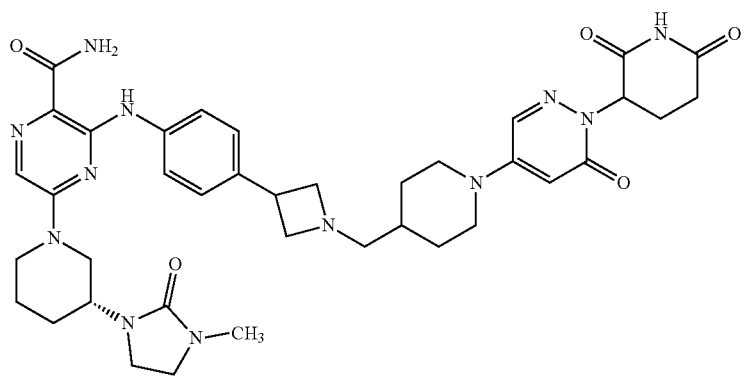 [SMILES: CN1CCN([C@@H]2CCCN(c3cnc(C(N)=O)c(Nc4ccc(C5CN(CC6CCN(c7cnn(C8CCC(=O)NC8=O)c(=O)c7)CC6)C5)cc4)n3)C2)C1=O] |
| 119 | 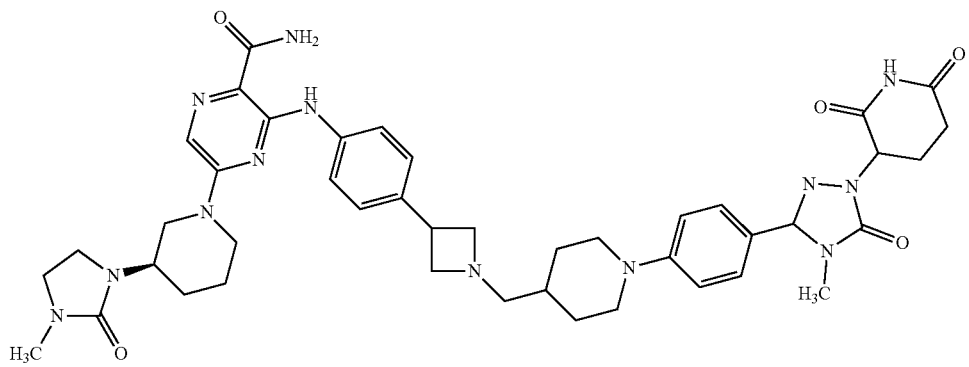 [SMILES: CN1CCN([C@@H]2CCCN(c3cnc(C(N)=O)c(Nc4ccc(C5CN(CC6CCN(c7ccc(C8NN(C9CCC(=O)NC9=O)C(=O)N8C)cc7)CC6)C5)cc4)n3)C2)C1=O] |
| 120 | 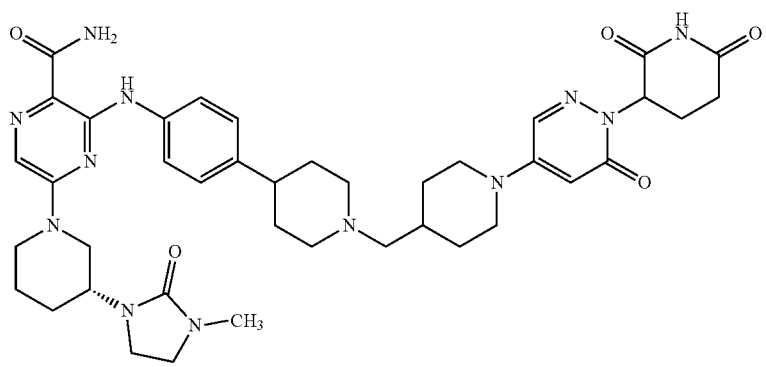 [SMILES: CN1CCN([C@@H]2CCCN(c3cnc(C(N)=O)c(Nc4ccc(C5CCN(CC6CCN(c7cnn(C8CCC(=O)NC8=O)c(=O)c7)CC6)CC5)cc4)n3)C2)C1=O] |
| 121 | 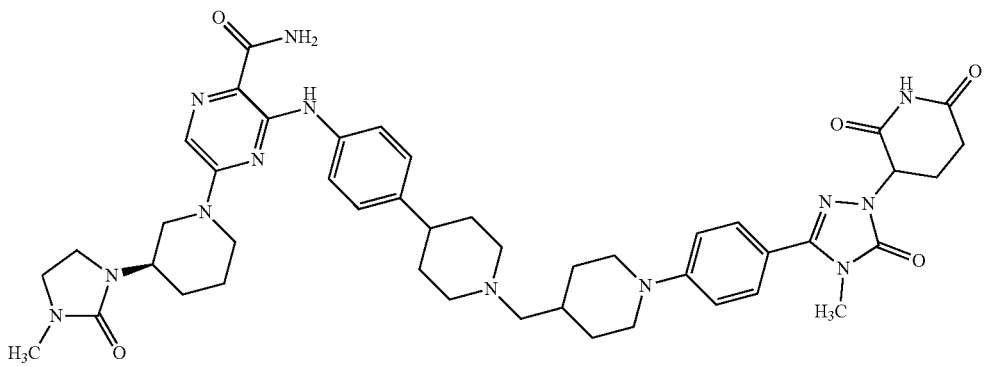 [SMILES: CN1CCN([C@@H]2CCCN(c3cnc(C(N)=O)c(Nc4ccc(C5CCN(CC6CCN(c7ccc(-c8nn(C9CCC(=O)NC9=O)c(=O)n8C)cc7)CC6)CC5)cc4)n3)C2)C1=O] |

TABLE 1-continued
Example compounds and/or pharmaceutically acceptable salts thereof for use in the methods described herein.
| Compound Number | Structure |
|---|---|
| 122 | 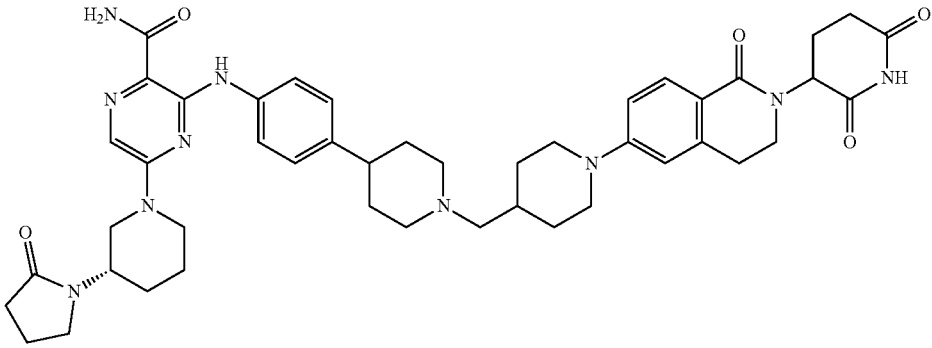 [SMILES: NC(=O)c1ncc(N2CCC[C@H](N3CCCC3=O)C2)nc1Nc1ccc(C2CCN(CC3CCN(c4ccc5c(c4)CCN(C4CCC(=O)NC4=O)C5=O)CC3)CC2)cc1] |
| 123 | 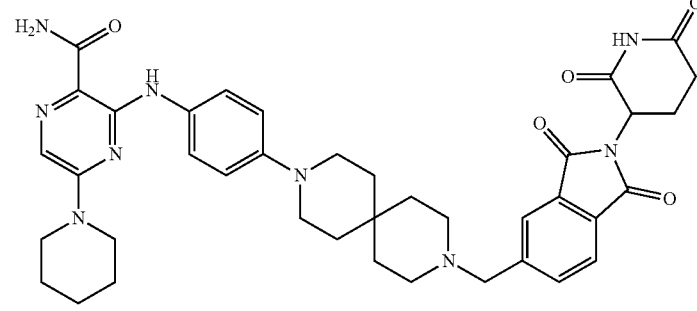 |
| 124 | 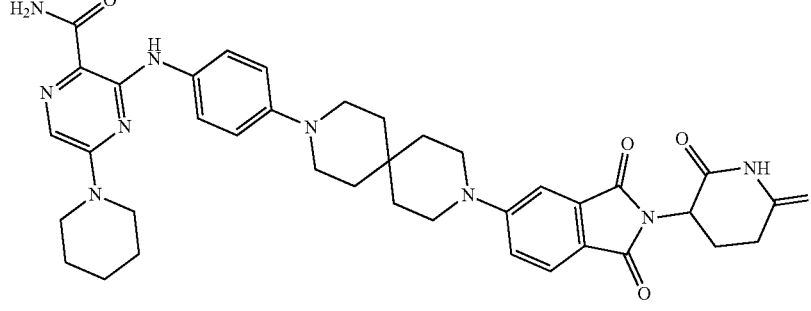 |
| 125 | 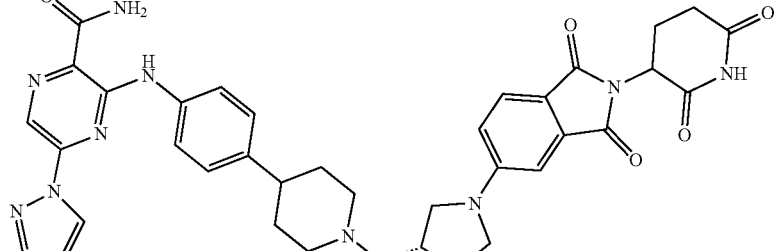 |

TABLE 1-continued
Example compounds and/or pharmaceutically acceptable salts thereof for use in the methods described herein.
| Compound Number | Structure |
|---|---|
| 126 | 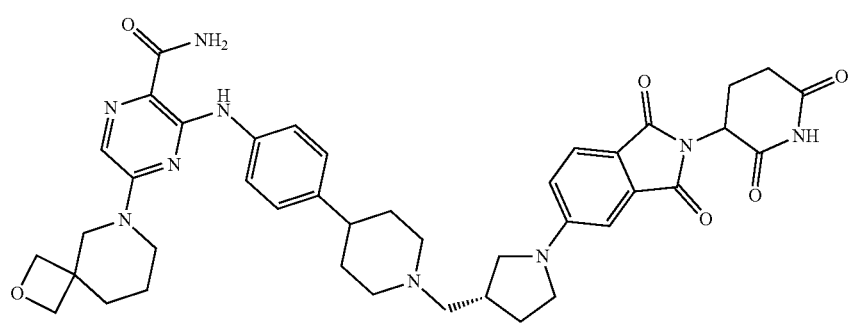 [SMILES: NC(=O)c1ncc(N2CCCC3(COC3)C2)nc1Nc1ccc(C2CCN(C[C@H]3CCN(c4ccc5c(c4)C(=O)N(C4CCC(=O)NC4=O)C5=O)C3)CC2)cc1] |
| 127 | 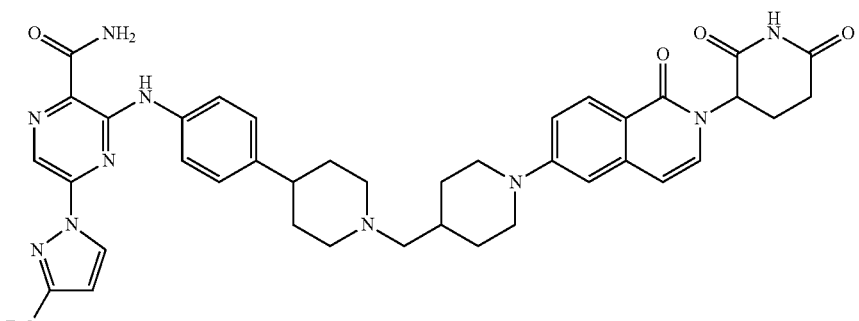 |
| 128 | 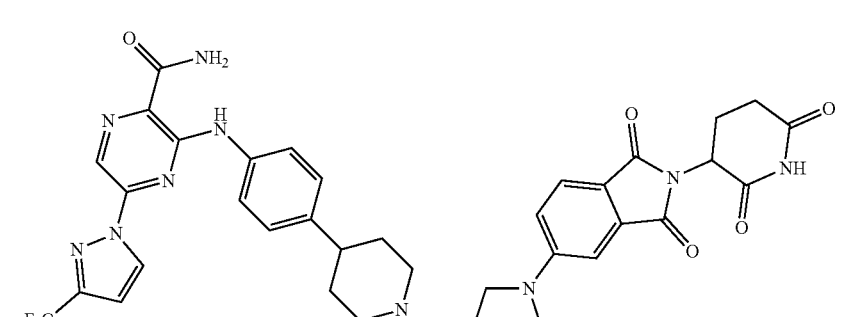 |
| 129 | 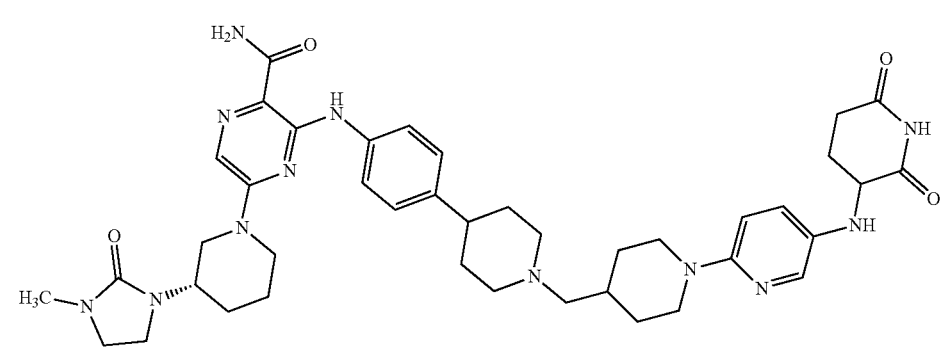 [SMILES: CN1CCN([C@H]2CCCN(c3cnc(C(N)=O)c(Nc4ccc(C5CCN(CC6CCN(c7ccc(NC8CCC(=O)NC8=O)cn7)CC6)CC5)cc4)n3)C2)C1=O] |

TABLE 1-continued
Example compounds and/or pharmaceutically acceptable salts thereof for use in the methods described herein.
| Compound Number | Structure |
|---|---|
| 130 | 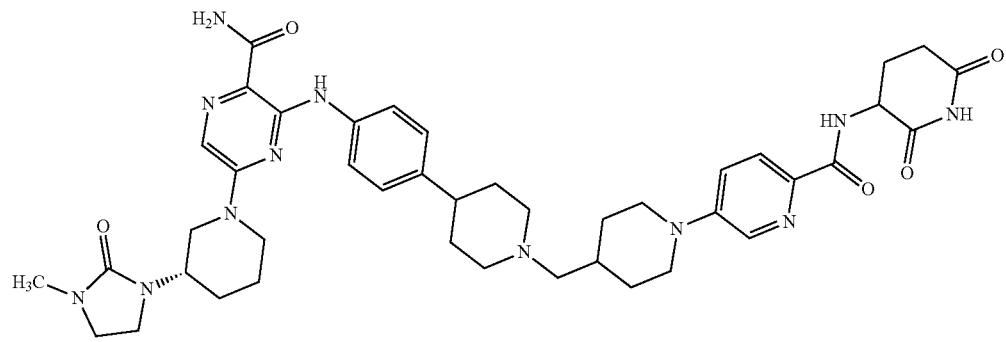 [SMILES: CN1CCN([C@H]2CCCN(c3cnc(C(N)=O)c(Nc4ccc(C5CCN(CC6CCN(c7ccc(C(=O)NC8CCC(=O)NC8=O)nc7)CC6)CC5)cc4)n3)C2)C1=O] |
| 131 | 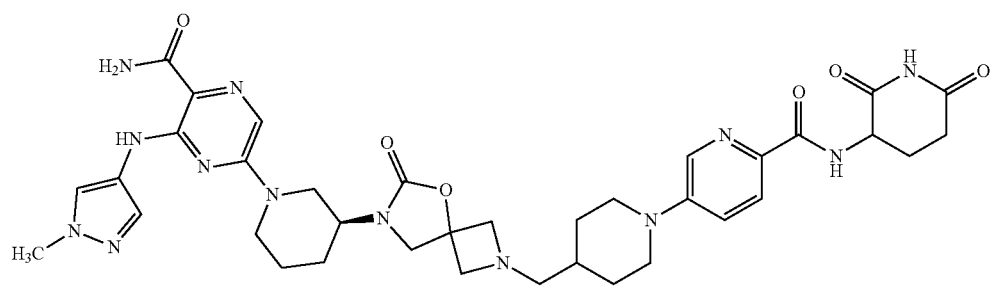 [SMILES: Cn1cc(Nc2nc(N3CCC[C@H](N4CC5(CN(CC6CCN(c7ccc(C(=O)NC8CCC(=O)NC8=O)nc7)CC6)C5)OC4=O)C3)cnc2C(N)=O)cn1] |
| 132 | 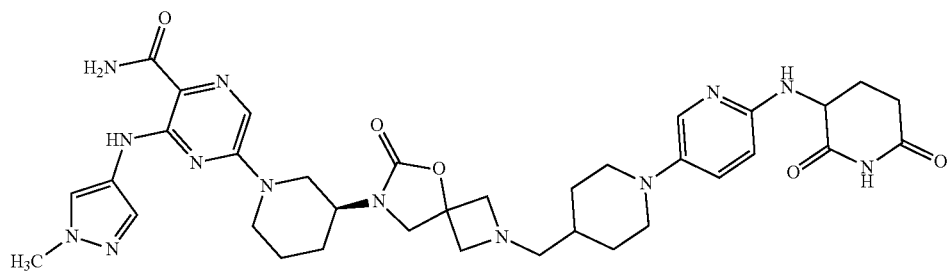 [SMILES: Cn1cc(Nc2nc(N3CCC[C@H](N4CC5(CN(CC6CCN(c7ccc(NC8CCC(=O)NC8=O)nc7)CC6)C5)OC4=O)C3)cnc2C(N)=O)cn1] |
| 133 | 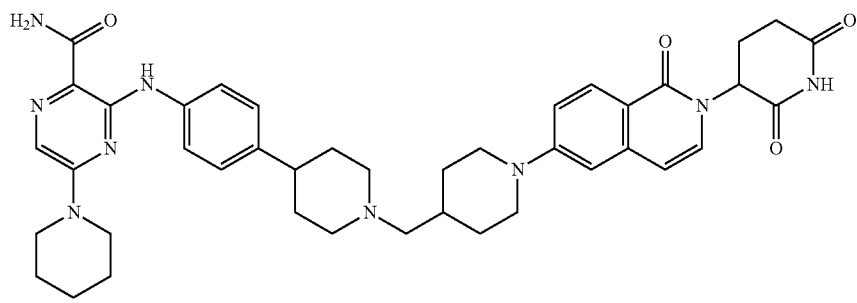 [SMILES: NC(=O)c1ncc(N2CCCCC2)nc1Nc1ccc(C2CCN(CC3CCN(c4ccc5c(=O)n(C6CCC(=O)NC6=O)ccc5c4)CC3)CC2)cc1] |

TABLE 1-continued
Example compounds and/or pharmaceutically acceptable salts thereof for use in the methods described herein.
| Compound Number | Structure |
|---|---|
| 134 | 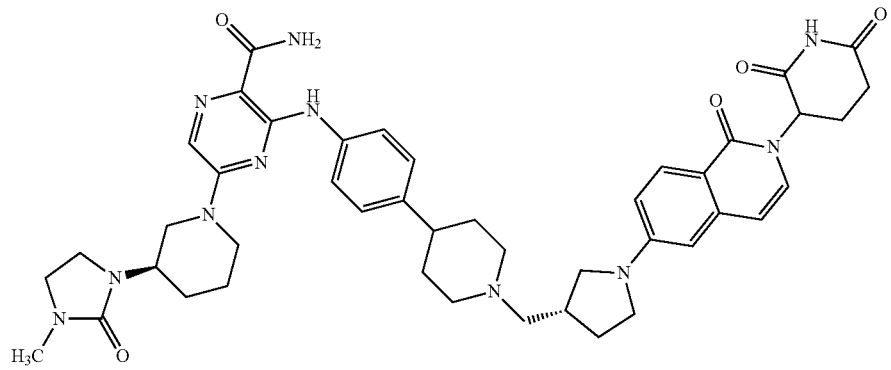 [SMILES: CN1CCN([C@@H]2CCCN(c3cnc(C(N)=O)c(Nc4ccc(C5CCN(C[C@H]6CCN(c7ccc8c(=O)n(C9CCC(=O)NC9=O)ccc8c7)C6)CC5)cc4)n3)C2)C1=O] |
| 135 | 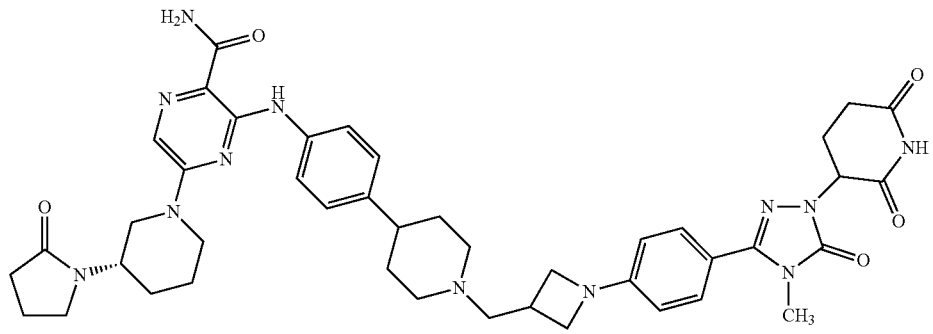 [SMILES: Cn1c(-c2ccc(N3CC(CN4CCC(c5ccc(Nc6nc(N7CCC[C@H](N8CCCC8=O)C7)cnc6C(N)=O)cc5)CC4)C3)cc2)nn(C2CCC(=O)NC2=O)c1=O] |
| 136 | 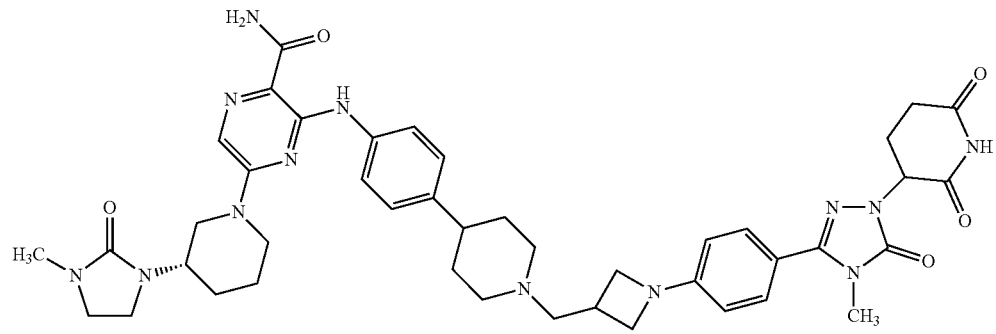 [SMILES: CN1CCN([C@H]2CCCN(c3cnc(C(N)=O)c(Nc4ccc(C5CCN(CC6CN(c7ccc(-c8nn(C9CCC(=O)NC9=O)c(=O)n8C)cc7)C6)CC5)cc4)n3)C2)C1=O] |
| 137 | 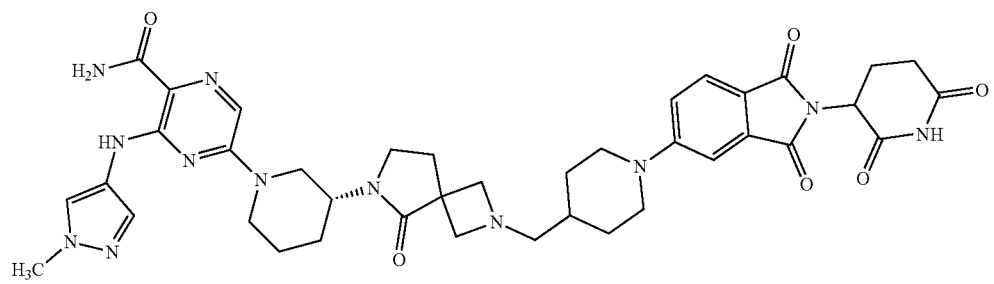 [SMILES: Cn1cc(Nc2nc(N3CCC[C@@H](N4CCC5(CN(CC6CCN(c7ccc8c(c7)C(=O)N(C7CCC(=O)NC7=O)C8=O)CC6)C5)C4=O)C3)cnc2C(N)=O)cn1] |

TABLE 1-continued
Example compounds and/or pharmaceutically acceptable salts thereof for use in the methods described herein.
| Compound Number | Structure |
|---|---|
| 138 | 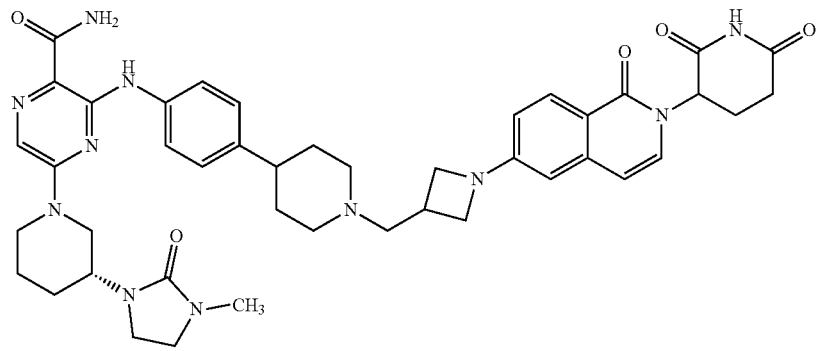 [SMILES: CN1CCN([C@@H]2CCCN(c3cnc(C(N)=O)c(Nc4ccc(C5CCN(CC6CN(c7ccc8c(=O)n(C9CCC(=O)NC9=O)ccc8c7)C6)CC5)cc4)n3)C2)C1=O] |
| 139 | 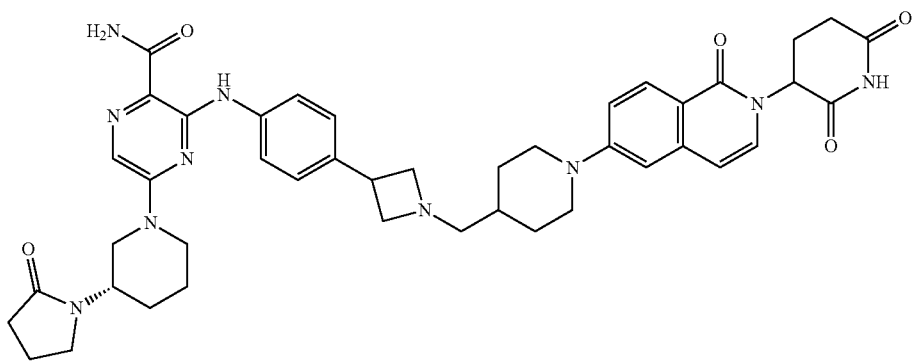 [SMILES: NC(=O)c1ncc(N2CCC[C@H](N3CCCC3=O)C2)nc1Nc1ccc(C2CN(CC3CCN(c4ccc5c(=O)n(C6CCC(=O)NC6=O)ccc5c4)CC3)C2)cc1] |
| 140 | 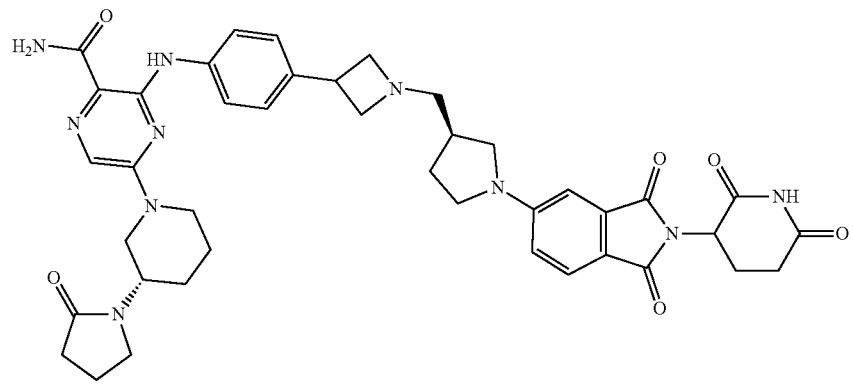 [SMILES: NC(=O)c1ncc(N2CCC[C@H](N3CCCC3=O)C2)nc1Nc1ccc(C2CN(C[C@@H]3CCN(c4ccc5c(c4)C(=O)N(C4CCC(=O)NC4=O)C5=O)C3)C2)cc1] |
| 141 | 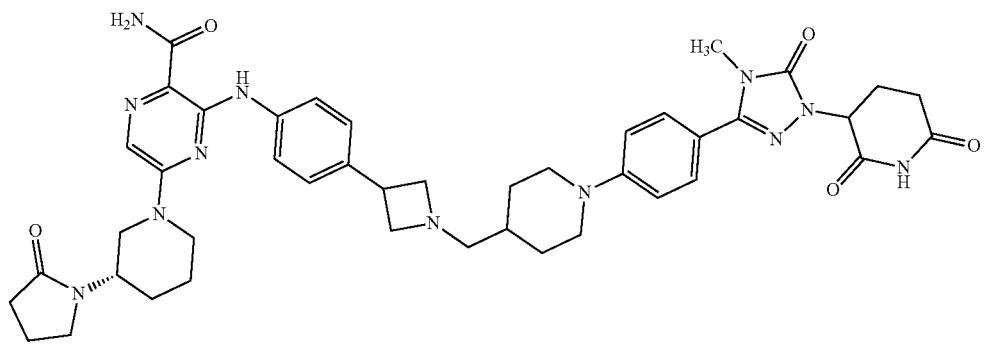 [SMILES: Cn1c(-c2ccc(N3CCC(CN4CC(c5ccc(Nc6nc(N7CCC[C@H](N8CCCC8=O)C7)cnc6C(N)=O)cc5)C4)CC3)cc2)nn(C2CCC(=O)NC2=O)c1=O] |

TABLE 1-continued

Example compounds and/or pharmaceutically acceptable salts thereof for use in the methods described herein.

| Compound Number | Structure |
|---|---|
| 142 | 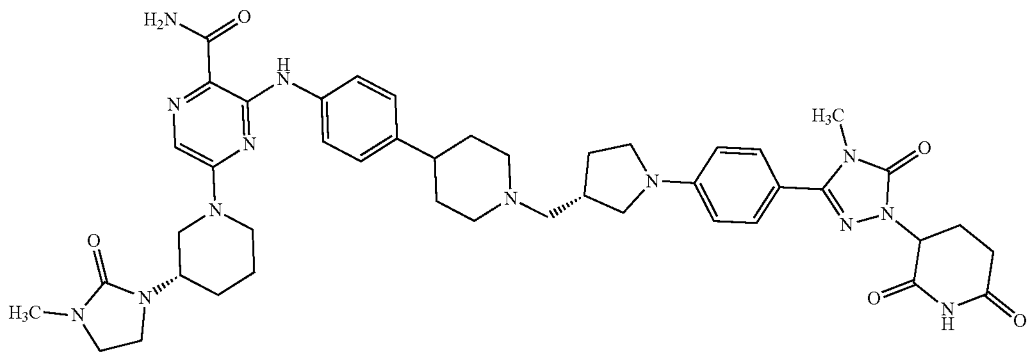 [SMILES: CN1CCN([C@H]2CCCN(c3cnc(C(N)=O)c(Nc4ccc(C5CCN(C[C@@H]6CCN(c7ccc(-c8nn(C9CCC(=O)NC9=O)c(=O)n8C)cc7)C6)CC5)cc4)n3)C2)C1=O] |
| 143 | 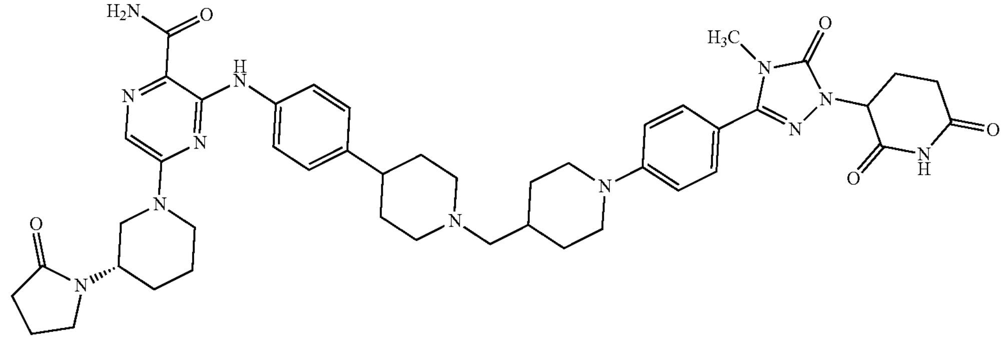 [SMILES: Cn1c(-c2ccc(N3CCC(CN4CCC(c5ccc(Nc6nc(N7CCC[C@H](N8CCCC8=O)C7)cnc6C(N)=O)cc5)CC4)CC3)cc2)nn(C2CCC(=O)NC2=O)c1=O] |
| 144 | 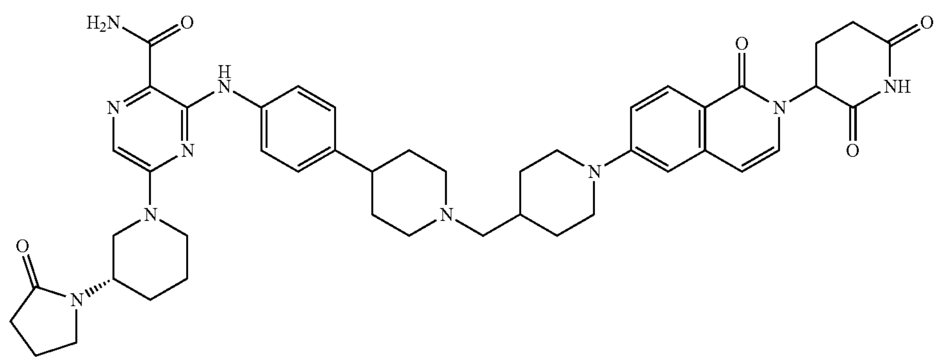 [SMILES: NC(=O)c1ncc(N2CCC[C@H](N3CCCC3=O)C2)nc1Nc1ccc(C2CCN(CC3CCN(c4ccc5c(=O)n(C6CCC(=O)NC6=O)ccc5c4)CC3)CC2)cc1] |
| 145 | 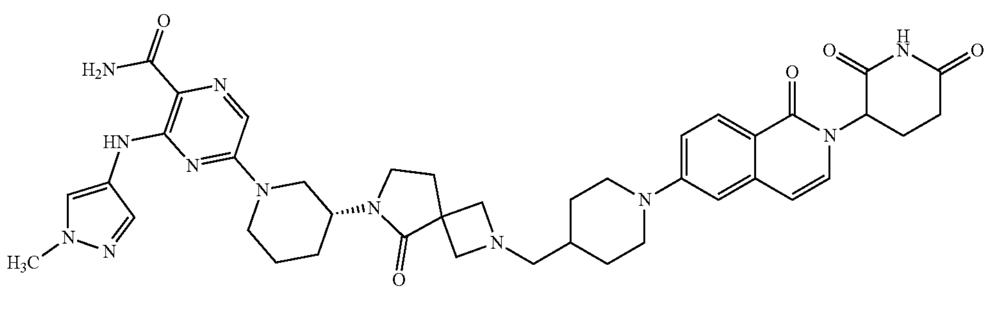 [SMILES: Cn1cc(Nc2nc(N3CCC[C@@H](N4CCC5(CN(CC6CCN(c7ccc8c(=O)n(C9CCC(=O)NC9=O)ccc8c7)CC6)C5)C4=O)C3)cnc2C(N)=O)cn1] |

TABLE 1-continued
Example compounds and/or pharmaceutically acceptable salts thereof for use in the methods described herein.
| Compound Number | Structure |
|---|---|
| 146 | 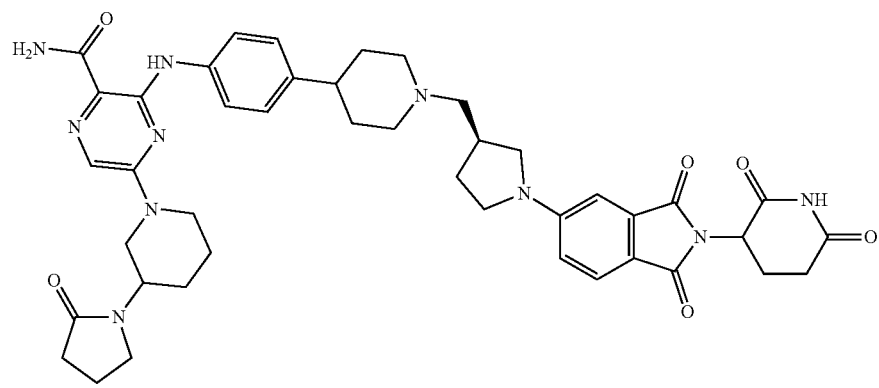 [SMILES: NC(=O)c1ncc(N2CCCC(N3CCCC3=O)C2)nc1Nc1ccc(C2CCN(C[C@@H]3CCN(c4ccc5c(c4)C(=O)N(C4CCC(=O)NC4=O)C5=O)C3)CC2)cc1] |
| 147 | 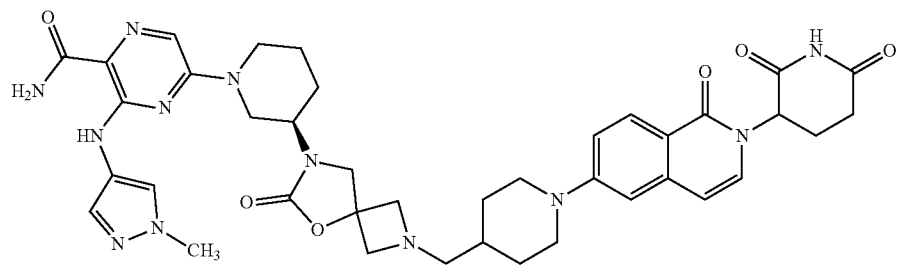 [SMILES: Cn1cc(Nc2nc(N3CCC[C@@H](N4CC5(CN(CC6CCN(c7ccc8c(=O)n(C9CCC(=O)NC9=O)ccc8c7)CC6)C5)OC4=O)C3)cnc2C(N)=O)cn1] |
| 148 | 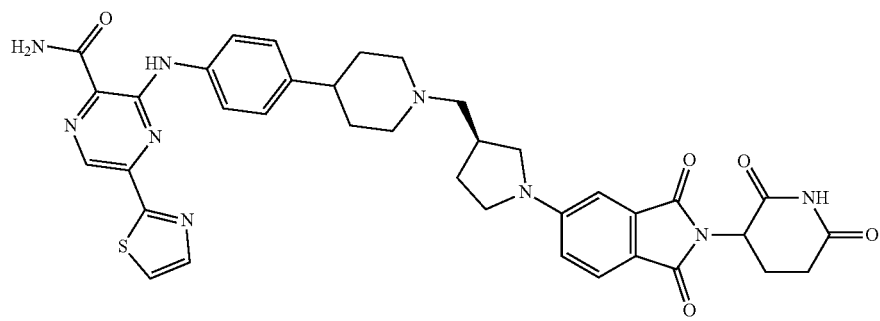 [SMILES: NC(=O)c1ncc(-c2nccs2)nc1Nc1ccc(C2CCN(C[C@@H]3CCN(c4ccc5c(c4)C(=O)N(C4CCC(=O)NC4=O)C5=O)C3)CC2)cc1] |
| 149 | 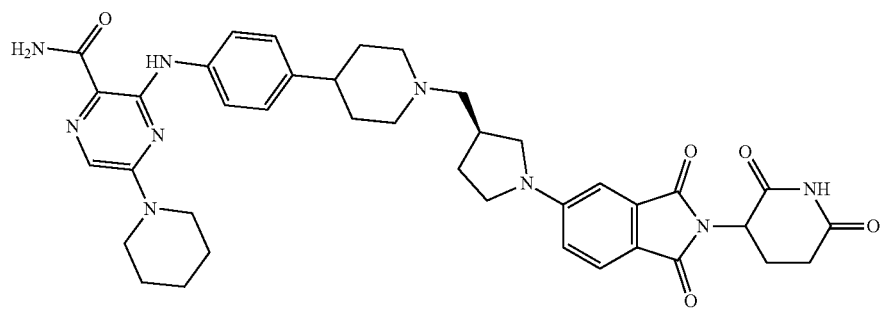 [SMILES: NC(=O)c1ncc(N2CCCCC2)nc1Nc1ccc(C2CCN(C[C@@H]3CCN(c4ccc5c(c4)C(=O)N(C4CCC(=O)NC4=O)C5=O)C3)CC2)cc1] |

TABLE 1-continued
Example compounds and/or pharmaceutically acceptable salts thereof for use in the methods described herein.
| Compound Number | Structure |
|---|---|
| 150 | 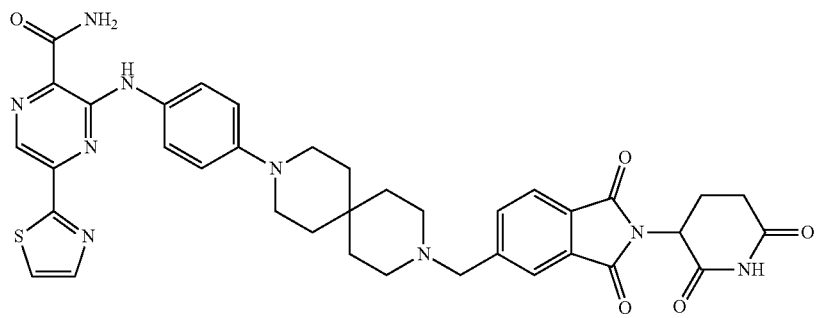 [SMILES: NC(=O)c1ncc(-c2nccs2)nc1Nc1ccc(N2CCC3(CCN(Cc4ccc5c(c4)C(=O)N(C4CCC(=O)NC4=O)C5=O)CC3)CC2)cc1] |
| 151 | 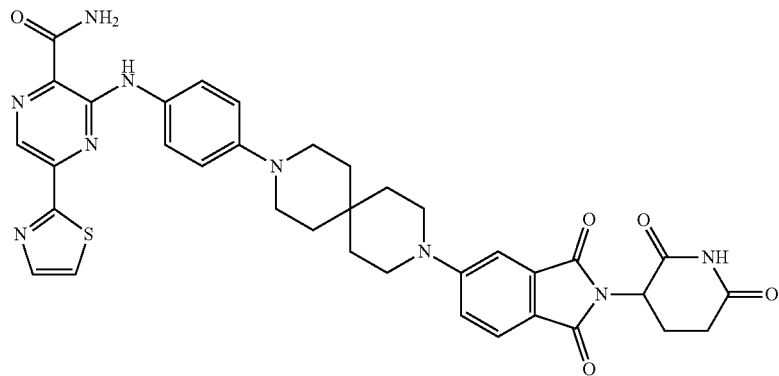 [SMILES: NC(=O)c1ncc(-c2nccs2)nc1Nc1ccc(N2CCC3(CC2)CCN(c2ccc4c(c2)C(=O)N(C2CCC(=O)NC2=O)C4=O)CC3)cc1] |
| 152 | 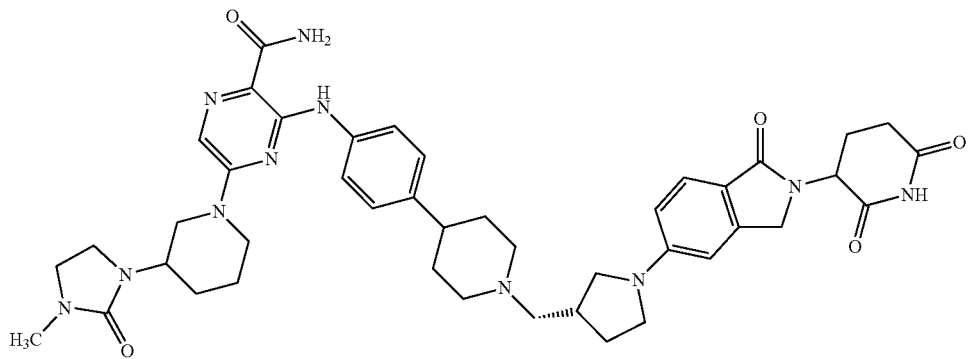 |
| 153 | 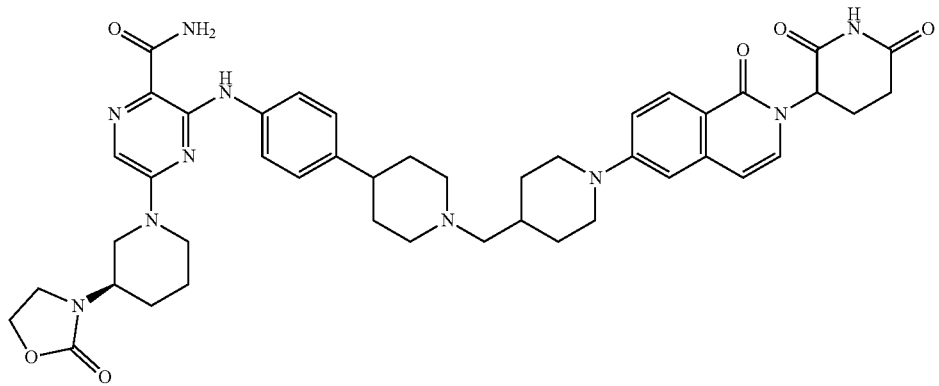 [SMILES: NC(=O)c1ncc(N2CCC[C@@H](N3CCOC3=O)C2)nc1Nc1ccc(C2CCN(CC3CCN(c4ccc5c(=O)n(C6CCC(=O)NC6=O)ccc5c4)CC3)CC2)cc1] |

TABLE 1-continued

Example compounds and/or pharmaceutically acceptable salts thereof for use in the methods described herein.

| Compound Number | Structure |
|---|---|
| 154 | 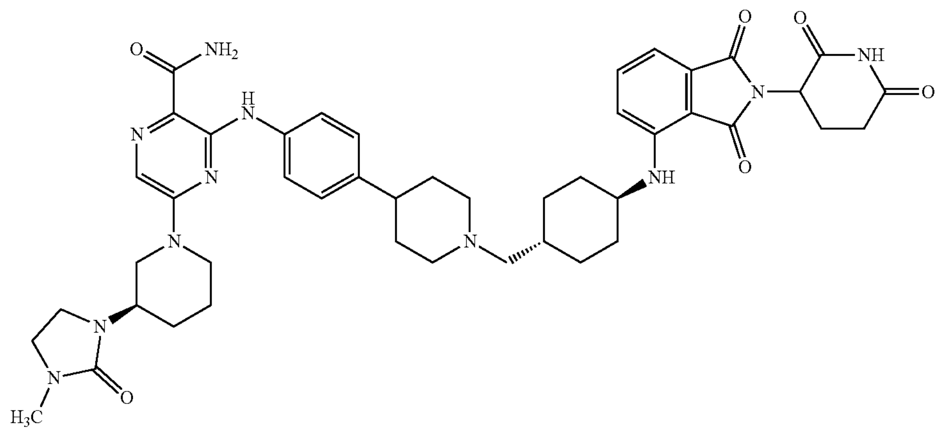 [SMILES: CN1CCN([C@@H]2CCCN(c3cnc(C(N)=O)c(Nc4ccc(C5CCN(C[C@H]6CC[C@H](Nc7cccc8c7C(=O)N(C7CCC(=O)NC7=O)C8=O)CC6)CC5)cc4)n3)C2)C1=O] |
| 155 | 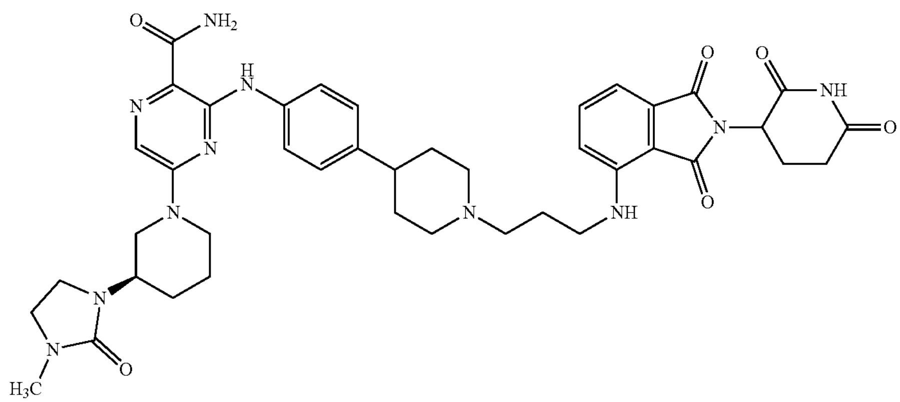 [SMILES: CN1CCN([C@@H]2CCCN(c3cnc(C(N)=O)c(Nc4ccc(C5CCN(CCCNc6cccc7c6C(=O)N(C6CCC(=O)NC6=O)C7=O)CC5)cc4)n3)C2)C1=O] |
| 156 | 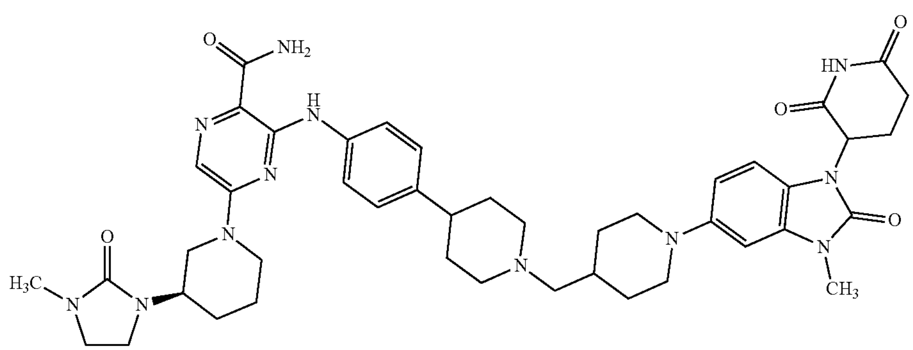 [SMILES: CN1CCN([C@@H]2CCCN(c3cnc(C(N)=O)c(Nc4ccc(C5CCN(CC6CCN(c7ccc8c(c7)n(C)c(=O)n8C7CCC(=O)NC7=O)CC6)CC5)cc4)n3)C2)C1=O] |
| 157 | 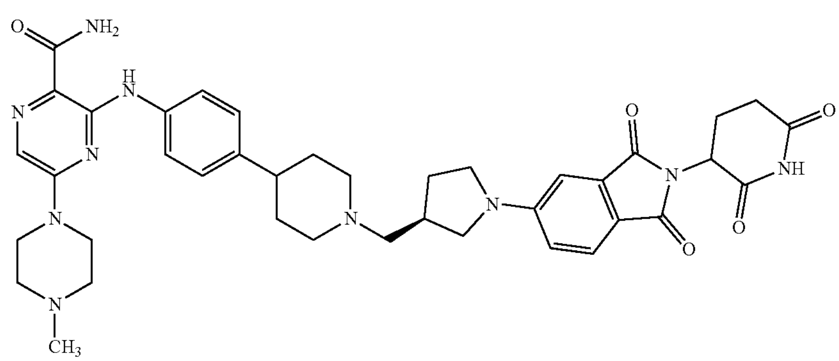 [SMILES: CN1CCN(c2cnc(C(N)=O)c(Nc3ccc(C4CCN(C[C@H]5CCN(c6ccc7c(c6)C(=O)N(C6CCC(=O)NC6=O)C7=O)C5)CC4)cc3)n2)CC1] |

TABLE 1-continued
Example compounds and/or pharmaceutically acceptable salts thereof for use in the methods described herein.
| Compound Number | Structure |
|---|---|
| 158 | 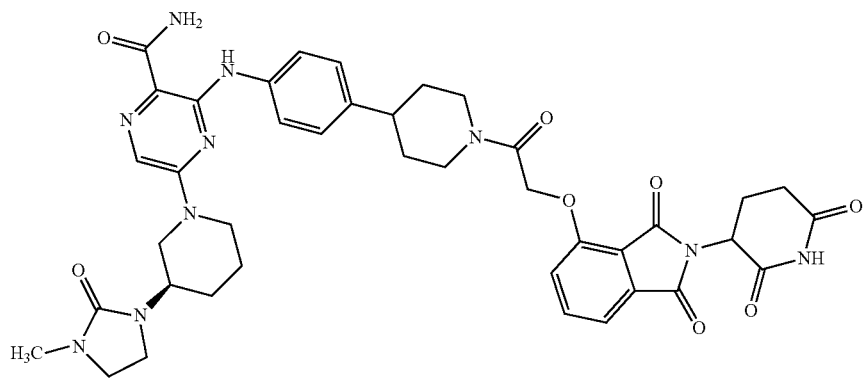 [SMILES: CN1CCN([C@@H]2CCCN(c3cnc(C(N)=O)c(Nc4ccc(C5CCN(C(=O)COc6cccc7c6C(=O)N(C6CCC(=O)NC6=O)C7=O)CC5)cc4)n3)C2)C1=O] |
| 159 | 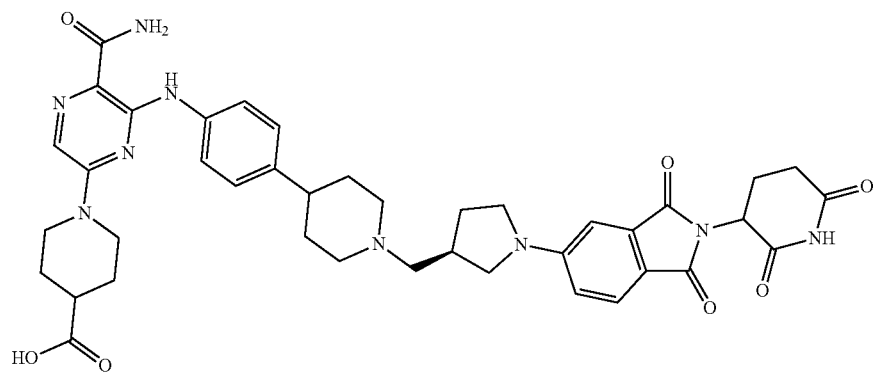 [SMILES: NC(=O)c1ncc(N2CCC(C(=O)O)CC2)nc1Nc1ccc(C2CCN(C[C@H]3CCN(c4ccc5c(c4)C(=O)N(C4CCC(=O)NC4=O)C5=O)C3)CC2)cc1] |
| 160 | 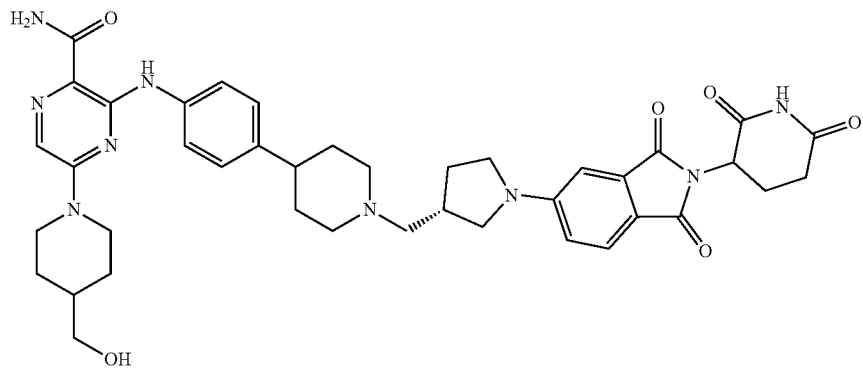 [SMILES: NC(=O)c1ncc(N2CCC(CO)CC2)nc1Nc1ccc(C2CCN(C[C@@H]3CCN(c4ccc5c(c4)C(=O)N(C4CCC(=O)NC4=O)C5=O)C3)CC2)cc1] |
| 161 | 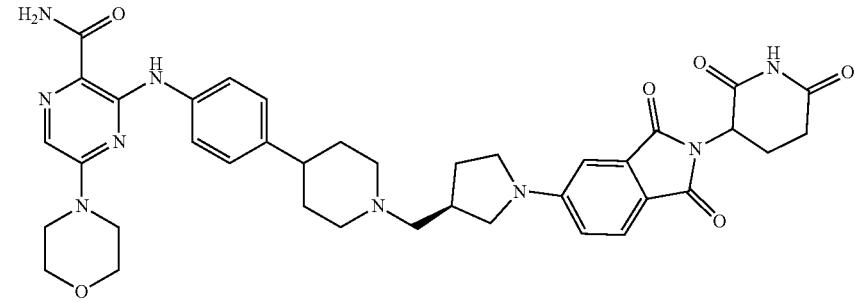 [SMILES: NC(=O)c1ncc(N2CCOCC2)nc1Nc1ccc(C2CCN(C[C@H]3CCN(c4ccc5c(c4)C(=O)N(C4CCC(=O)NC4=O)C5=O)C3)CC2)cc1] |

TABLE 1-continued
Example compounds and/or pharmaceutically acceptable salts thereof for use in the methods described herein.
| Compound Number | Structure |
|---|---|
| 162 | 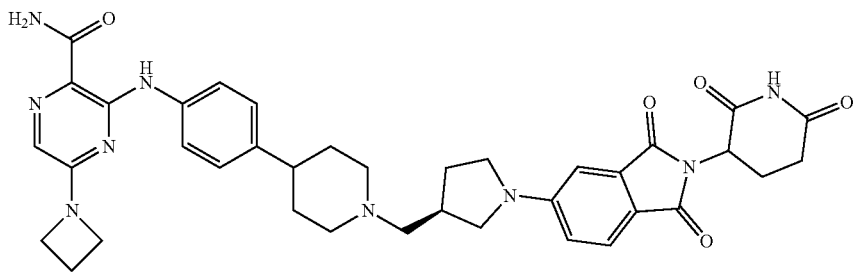 [SMILES: NC(=O)c1ncc(N2CCC2)nc1Nc1ccc(C2CCN(C[C@H]3CCN(c4ccc5c(c4)C(=O)N(C4CCC(=O)NC4=O)C5=O)C3)CC2)cc1] |
| 163 | 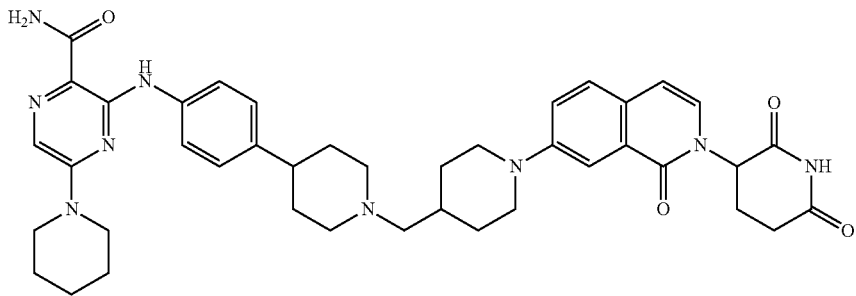 [SMILES: NC(=O)c1ncc(N2CCCCC2)nc1Nc1ccc(C2CCN(CC3CCN(c4ccc5ccn(C6CCC(=O)NC6=O)c(=O)c5c4)CC3)CC2)cc1] |
| 164 | 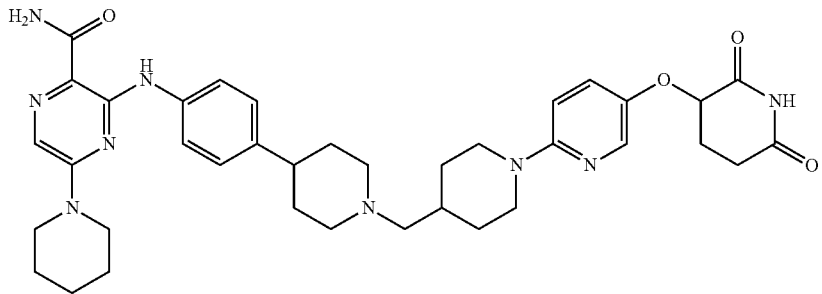 [SMILES: NC(=O)c1ncc(N2CCCCC2)nc1Nc1ccc(C2CCN(CC3CCN(c4ccc(OC5CCC(=O)NC5=O)cn4)CC3)CC2)cc1] |
| 165 | 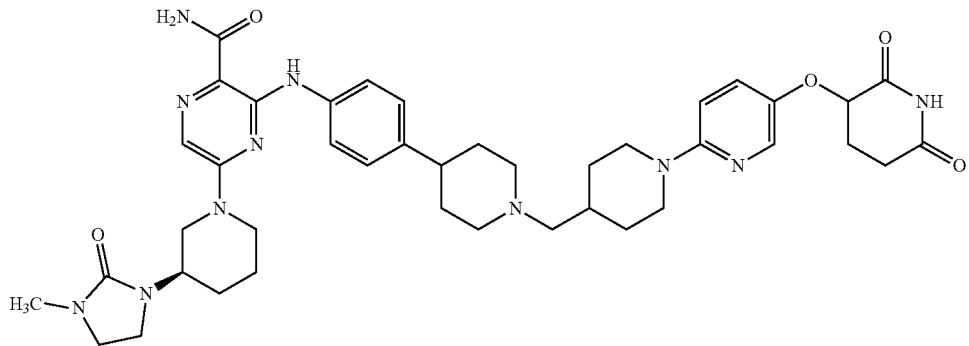 [SMILES: CN1CCN([C@@H]2CCCN(c3cnc(C(N)=O)c(Nc4ccc(C5CCN(CC6CCN(c7ccc(OC8CCC(=O)NC8=O)cn7)CC6)CC5)cc4)n3)C2)C1=O] |

TABLE 1-continued
Example compounds and/or pharmaceutically acceptable salts thereof for use in the methods described herein.
| Compound Number | Structure |
|---|---|
| 166 | 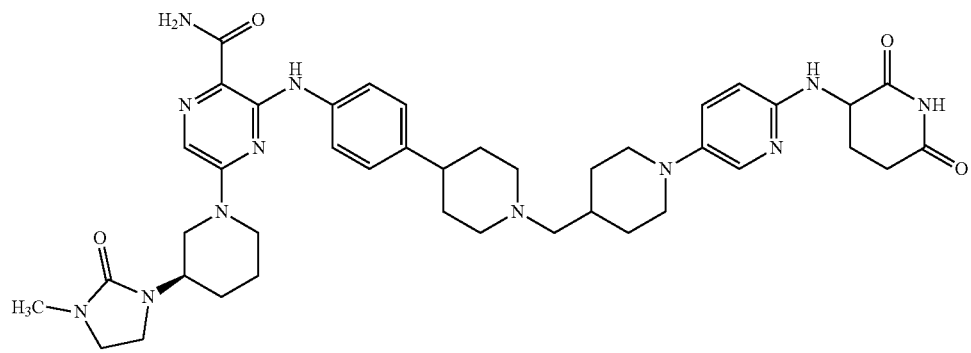 [SMILES: CN1CCN([C@@H]2CCCN(c3cnc(C(N)=O)c(Nc4ccc(C5CCN(CC6CCN(c7ccc(NC8CCC(=O)NC8=O)nc7)CC6)CC5)cc4)n3)C2)C1=O] |
| 167 | 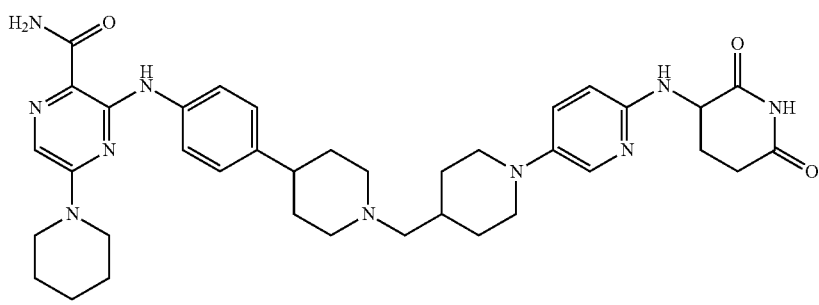 [SMILES: NC(=O)c1ncc(N2CCCCC2)nc1Nc1ccc(C2CCN(CC3CCN(c4ccc(NC5CCC(=O)NC5=O)nc4)CC3)CC2)cc1] |
| 168 | 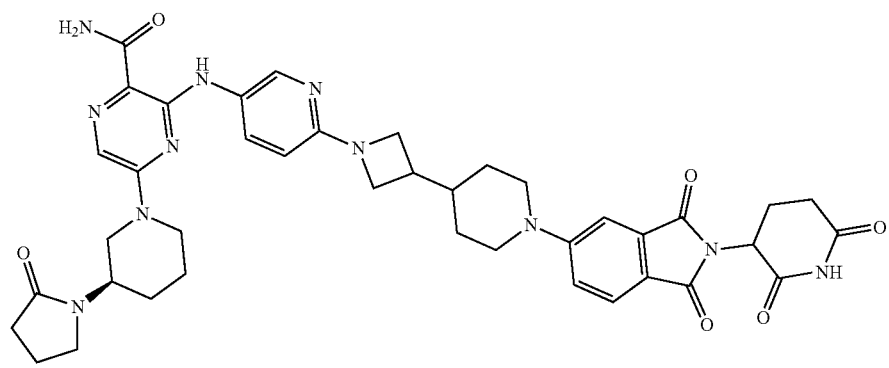 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)nc1] |
| 169 | 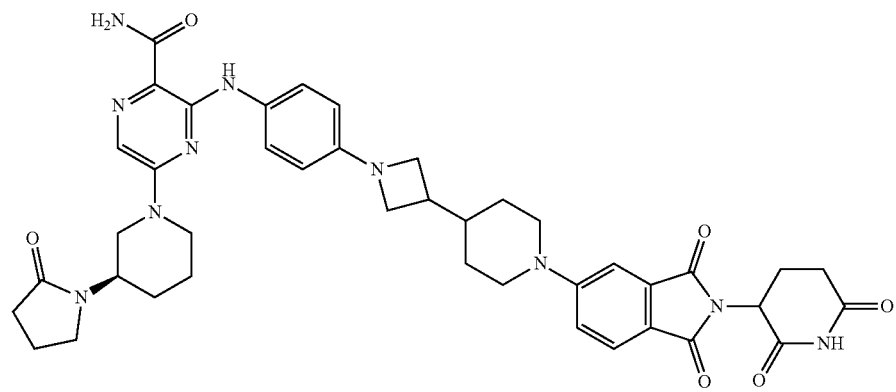 [SMILES: NC(=O)c1ncc(N2CCC[C@@H](N3CCCC3=O)C2)nc1Nc1ccc(N2CC(C3CCN(c4ccc5c(c4)C(=O)N(C4CCC(=O)NC4=O)C5=O)CC3)C2)cc1] |

TABLE 1-continued

Example compounds and/or pharmaceutically acceptable salts thereof for use in the methods described herein.

| Compound Number | Structure |
|---|---|
| 170 | 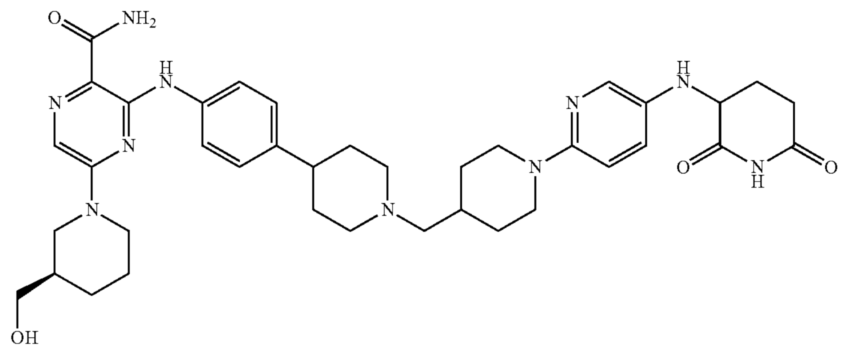 [SMILES: NC(=O)c1ncc(N2CCC[C@@H](CO)C2)nc1Nc1ccc(C2CCN(CC3CCN(c4ccc(NC5CCC(=O)NC5=O)cn4)CC3)CC2)cc1] |
| 171 | 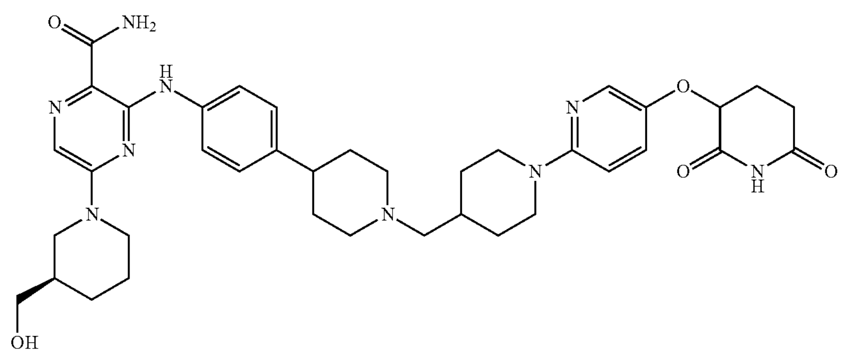 [SMILES: NC(=O)c1ncc(N2CCC[C@@H](CO)C2)nc1Nc1ccc(C2CCN(CC3CCN(c4ccc(OC5CCC(=O)NC5=O)cn4)CC3)CC2)cc1] |
| 172 | 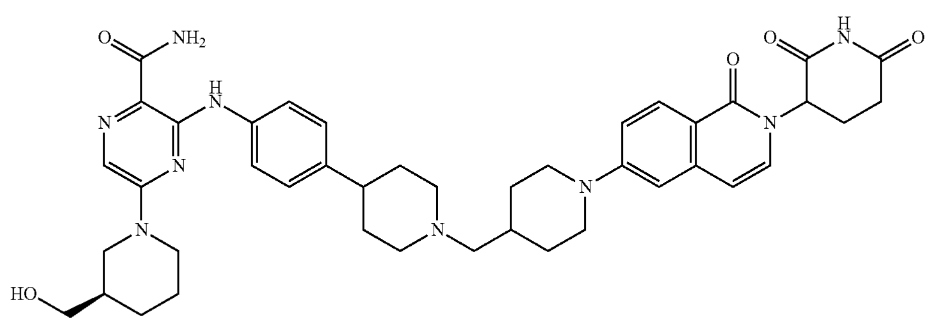 [SMILES: NC(=O)c1ncc(N2CCC[C@@H](CO)C2)nc1Nc1ccc(C2CCN(CC3CCN(c4ccc5c(=O)n(C6CCC(=O)NC6=O)ccc5c4)CC3)CC2)cc1] |
| 173 | 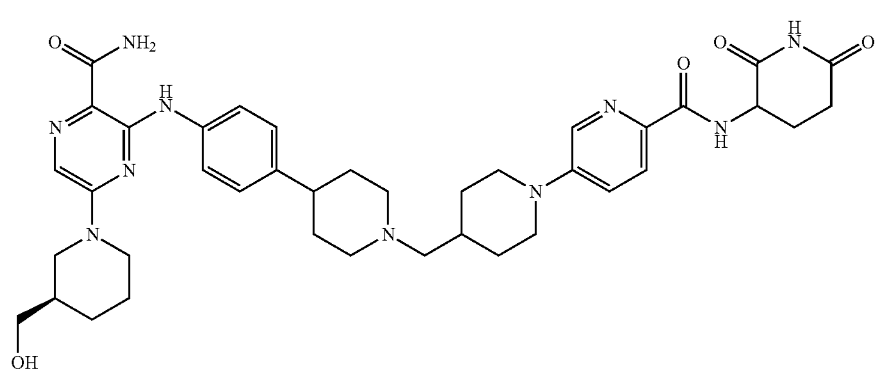 [SMILES: NC(=O)c1ncc(N2CCC[C@@H](CO)C2)nc1Nc1ccc(C2CCN(CC3CCN(c4ccc(C(=O)NC5CCC(=O)NC5=O)nc4)CC3)CC2)cc1] |

TABLE 1-continued
Example compounds and/or pharmaceutically acceptable salts thereof for use in the methods described herein.
| Compound Number | Structure |
|---|---|
| 174 | 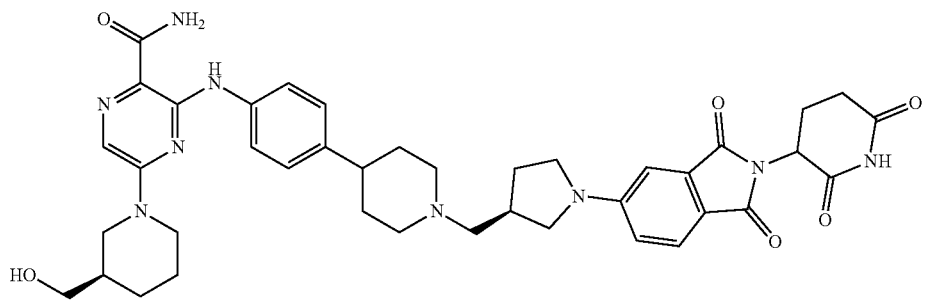 [SMILES: NC(=O)c1ncc(N2CCC[C@@H](CO)C2)nc1Nc1ccc(C2CCN(C[C@H]3CCN(c4ccc5c(c4)C(=O)N(C4CCC(=O)NC4=O)C5=O)C3)CC2)cc1] |
| 175 | 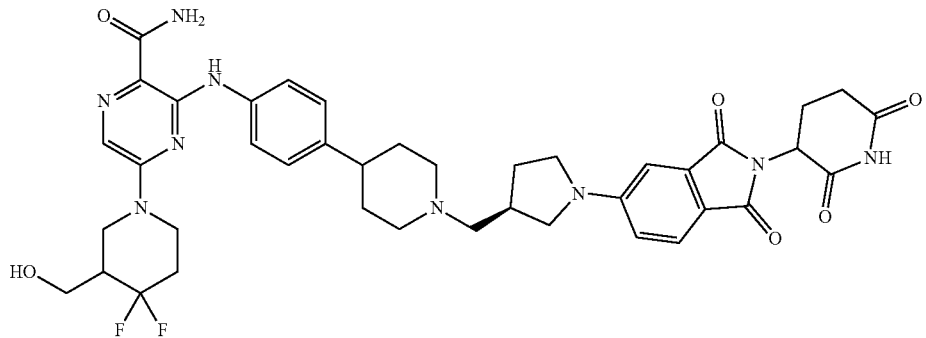 [SMILES: NC(=O)c1ncc(N2CCC(F)(F)C(CO)C2)nc1Nc1ccc(C2CCN(C[C@H]3CCN(c4ccc5c(c4)C(=O)N(C4CCC(=O)NC4=O)C5=O)C3)CC2)cc1] |
| 176 | 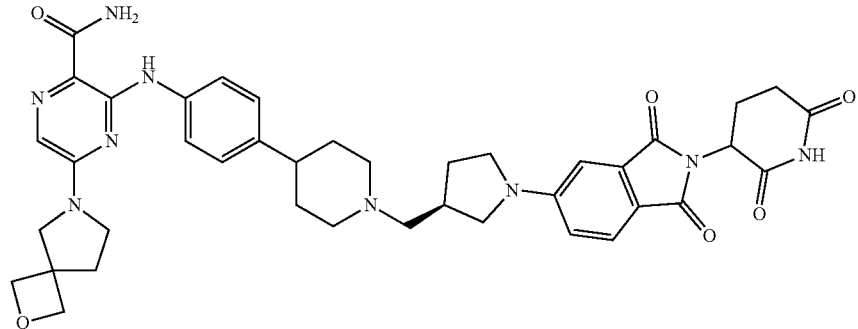 [SMILES: NC(=O)c1ncc(N2CCC3(COC3)C2)nc1Nc1ccc(C2CCN(C[C@H]3CCN(c4ccc5c(c4)C(=O)N(C4CCC(=O)NC4=O)C5=O)C3)CC2)cc1] |
| 177 | 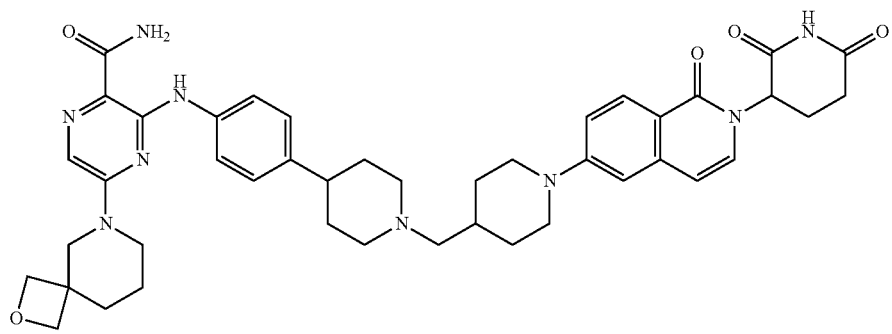 [SMILES: NC(=O)c1ncc(N2CCCC3(COC3)C2)nc1Nc1ccc(C2CCN(CC3CCN(c4ccc5c(=O)n(C6CCC(=O)NC6=O)ccc5c4)CC3)CC2)cc1] |

TABLE 1-continued
Example compounds and/or pharmaceutically acceptable salts thereof for use in the methods described herein.
| Compound Number | Structure |
|---|---|
| 178 | 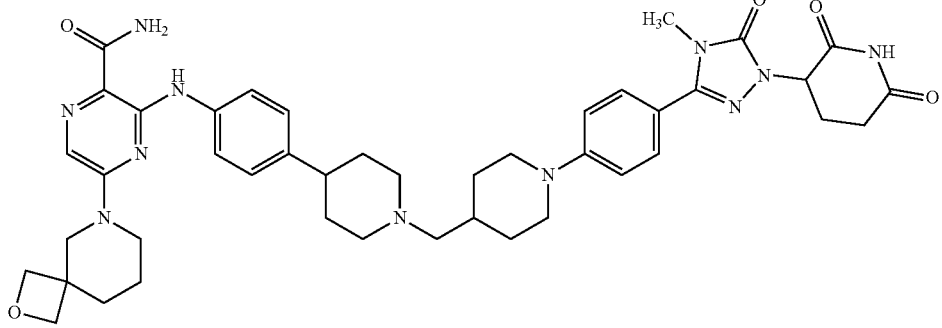 |
| 179 | 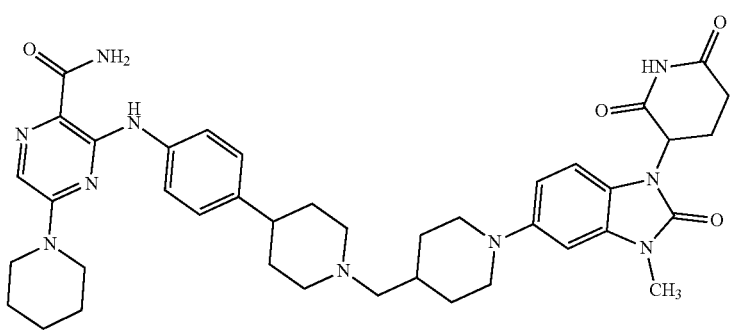 [SMILES: Cn1c(=O)n(C2CCC(=O)NC2=O)c2ccc(N3CCC(CN4CCC(c5ccc(Nc6nc(N7CCCCC7)cnc6C(N)=O)cc5)CC4)CC3)cc21] |
| 180 | 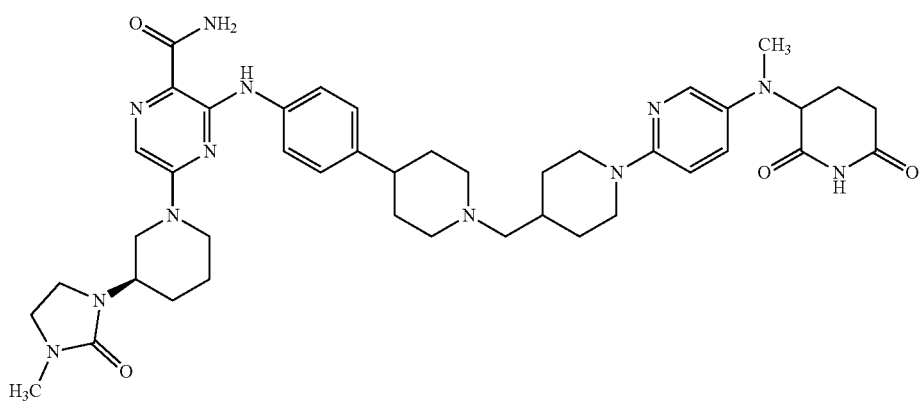 [SMILES: CN1CCN([C@@H]2CCCN(c3cnc(C(N)=O)c(Nc4ccc(C5CCN(CC6CCN(c7ccc(N(C)C8CCC(=O)NC8=O)cn7)CC6)CC5)cc4)n3)C2)C1=O] |
| 181 | 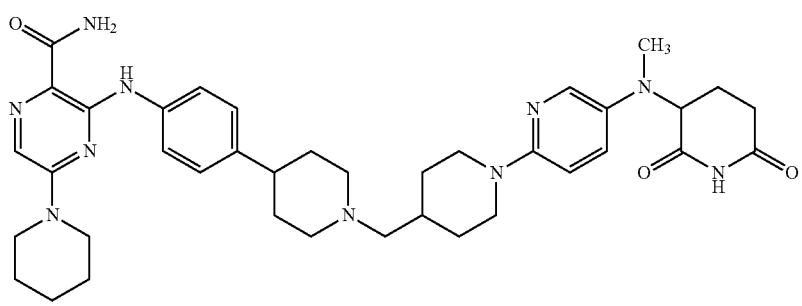 [SMILES: CN(c1ccc(N2CCC(CN3CCC(c4ccc(Nc5nc(N6CCCCC6)cnc5C(N)=O)cc4)CC3)CC2)nc1)C1CCC(=O)NC1=O] |

TABLE 1-continued
Example compounds and/or pharmaceutically acceptable salts thereof for use in the methods described herein.
| Compound Number | Structure |
|---|---|
| 182 | 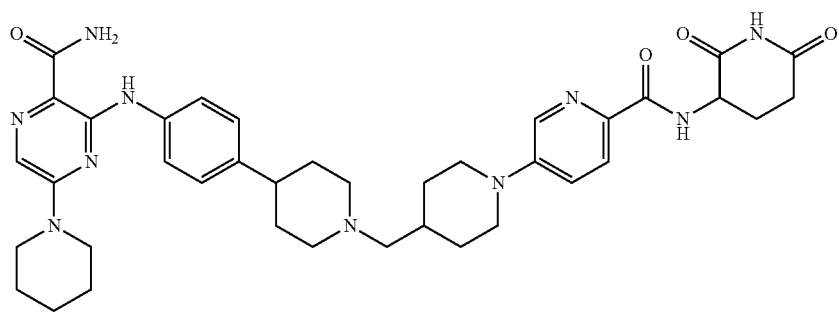 [SMILES: NC(=O)c1ncc(N2CCCCC2)nc1Nc1ccc(C2CCN(CC3CCN(c4ccc(C(=O)NC5CCC(=O)NC5=O)nc4)CC3)CC2)cc1] |
| 183 | 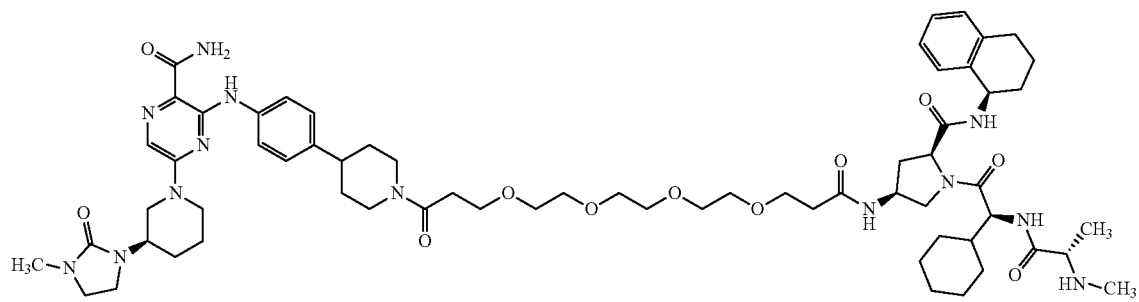 |
| 184 | 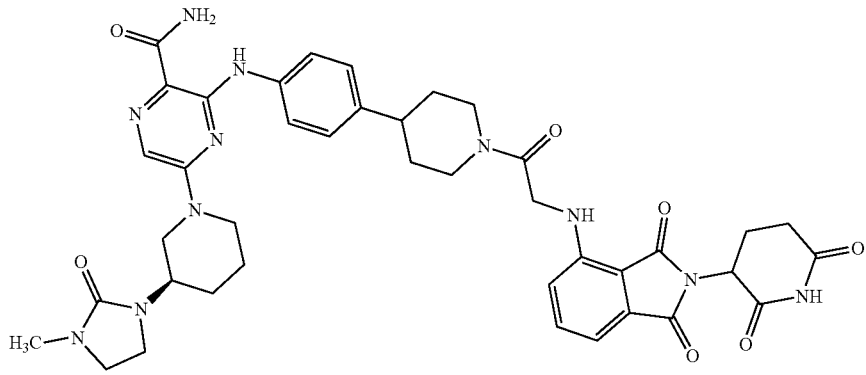 [SMILES: CN1CCN([C@@H]2CCCN(c3cnc(C(N)=O)c(Nc4ccc(C5CCN(C(=O)CNc6cccc7c6C(=O)N(C6CCC(=O)NC6=O)C7=O)CC5)cc4)n3)C2)C1=O] |
| 185 | 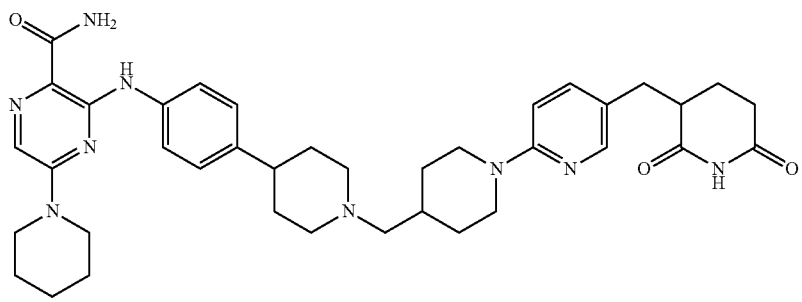 [SMILES: NC(=O)c1ncc(N2CCCCC2)nc1Nc1ccc(C2CCN(CC3CCN(c4ccc(CC5CCC(=O)NC5=O)cn4)CC3)CC2)cc1] |

TABLE 1-continued
Example compounds and/or pharmaceutically acceptable salts thereof for use in the methods described herein.
| Compound Number | Structure |
|---|---|
| 186 | 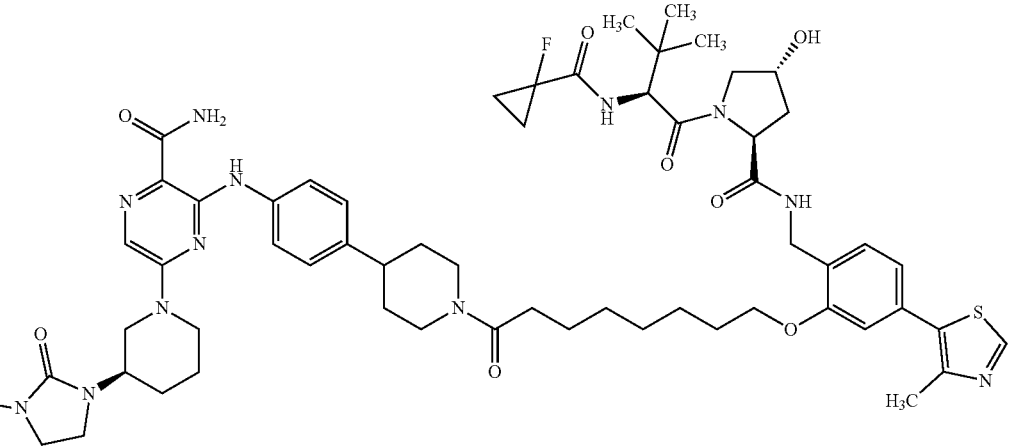 |
| 187 | 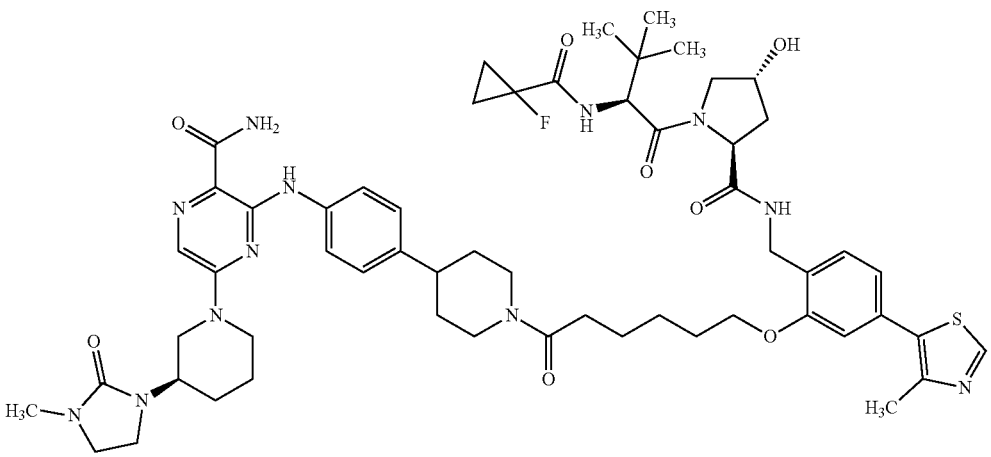 [SMILES: Cc1ncsc1-c1ccc(CNC(=O)[C@@H]2C[C@@H](O)CN2C(=O)[C@@H](NC(=O)C2(F)CC2)C(C)(C)C)c(OCCCCCC(=O)N2CCC(c3ccc(Nc4nc(N5CCC[C@@H](N6CCN(C)C6=O)C5)cnc4C(N)=O)cc3)CC2)c1] |
| 188 | 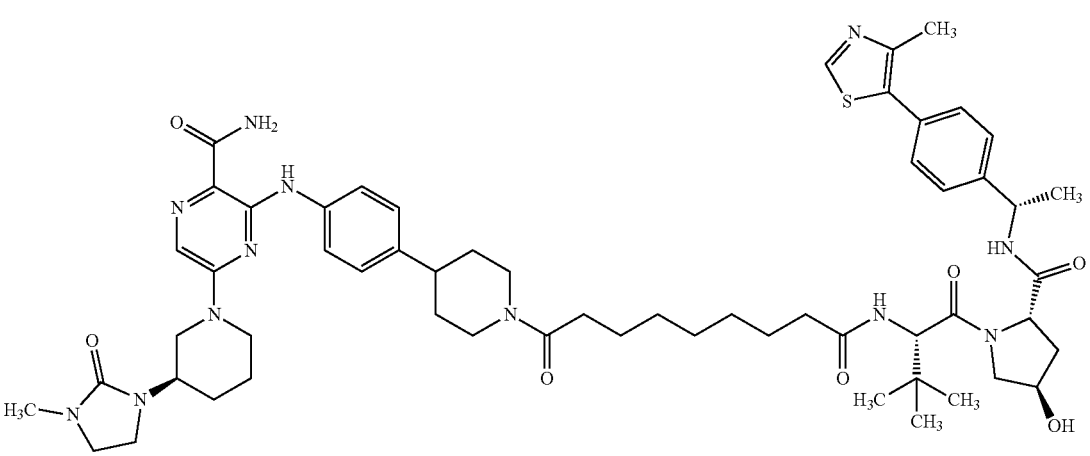 [SMILES: Cc1ncsc1-c1ccc([C@H](C)NC(=O)[C@@H]2C[C@@H](O)CN2C(=O)[C@@H](NC(=O)CCCCCCCC(=O)N2CCC(c3ccc(Nc4nc(N5CCC[C@@H](N6CCN(C)C6=O)C5)cnc4C(N)=O)cc3)CC2)C(C)(C)C)cc1] |

TABLE 1-continued
Example compounds and/or pharmaceutically acceptable salts thereof for use in the methods described herein.
| Compound Number | Structure |
|---|---|
| 189 | 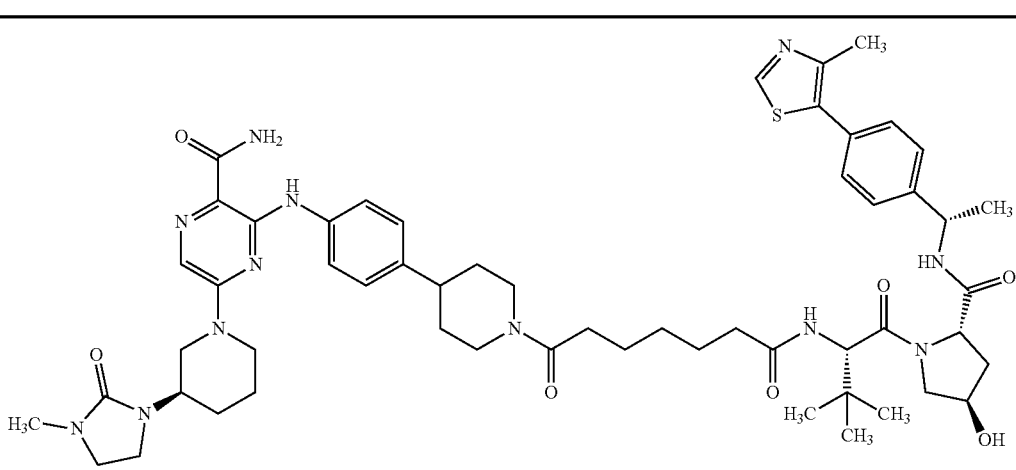 |
| 190 | 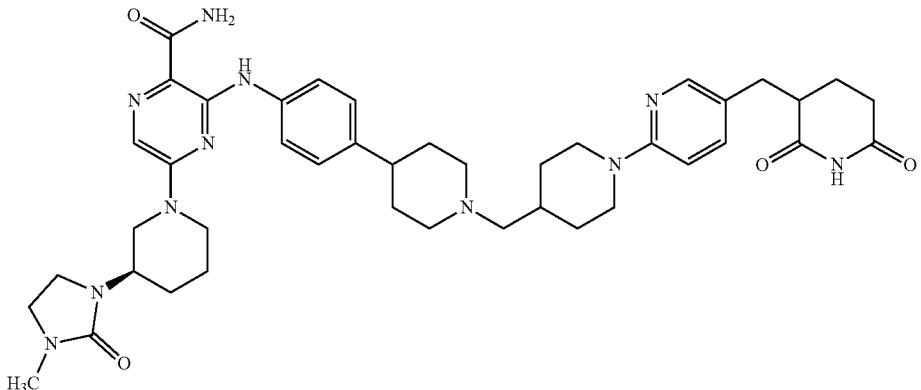 |
| 191 | 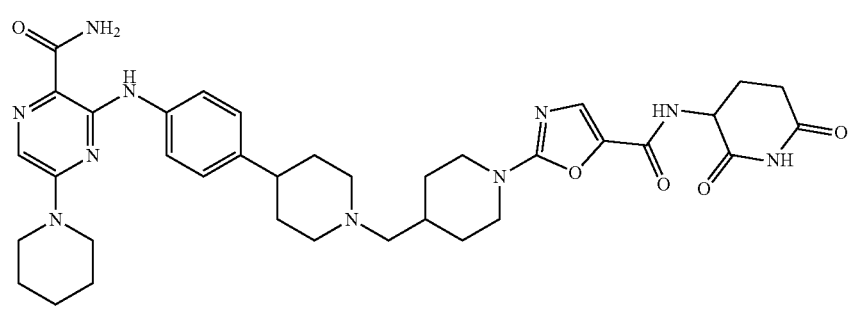 [SMILES: NC(=O)c1ncc(N2CCCCC2)nc1Nc1ccc(C2CCN(CC3CCN(c4ncc(C(=O)NC5CCC(=O)NC5=O)o4)CC3)CC2)cc1] |

TABLE 1-continued
Example compounds and/or pharmaceutically acceptable salts thereof for use in the methods described herein.
| Compound Number | Structure |
|---|---|
| 192 | 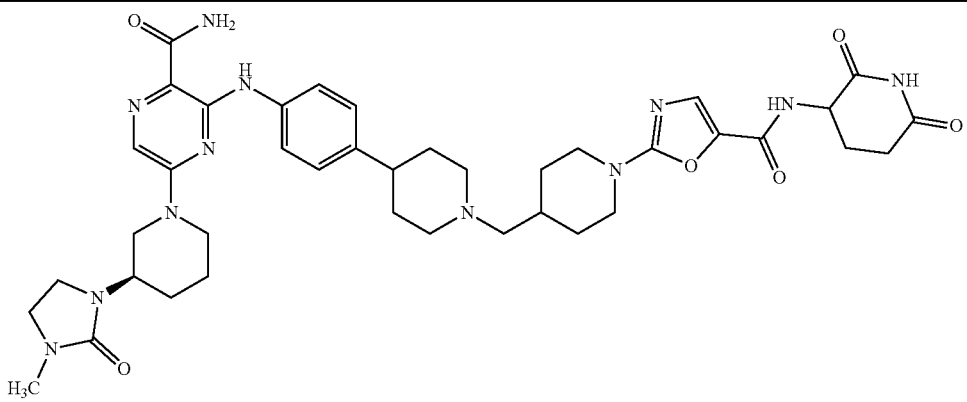 |
| 193 | 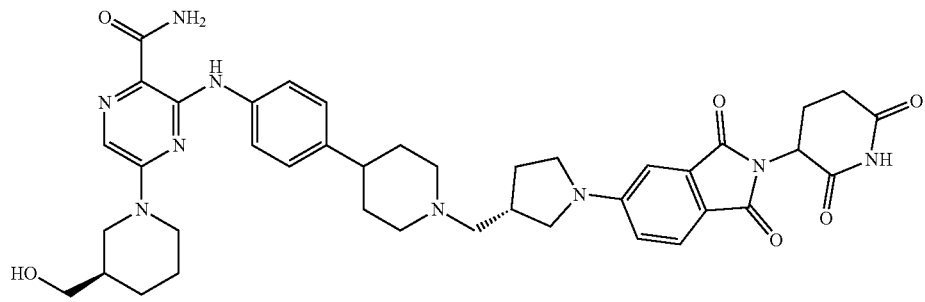 [SMILES: NC(=O)c1ncc(N2CCC[C@@H](CO)C2)nc1Nc1ccc(C2CCN(C[C@@H]3CCN(c4ccc5c(c4)C(=O)N(C4CCC(=O)NC4=O)C5=O)C3)CC2)cc1] |
| 194 | 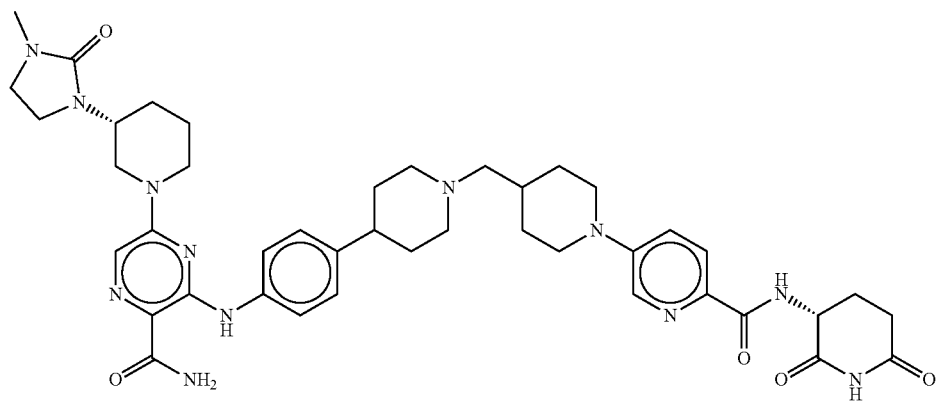 |
| 195 | 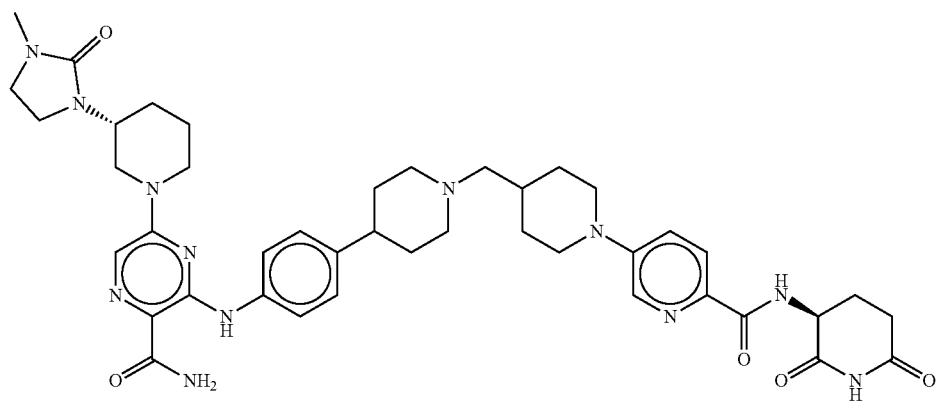 |

TABLE 1-continued
Example compounds and/or pharmaceutically acceptable salts thereof for use in the methods described herein.
| Compound Number | Structure |
|---|---|
| 196 | 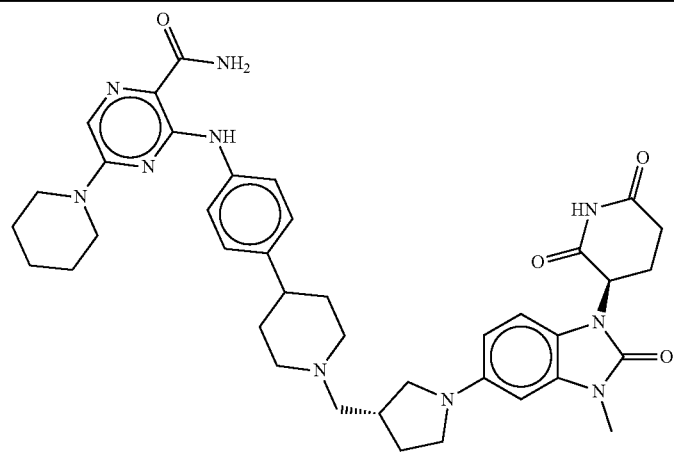 |
| 197 | 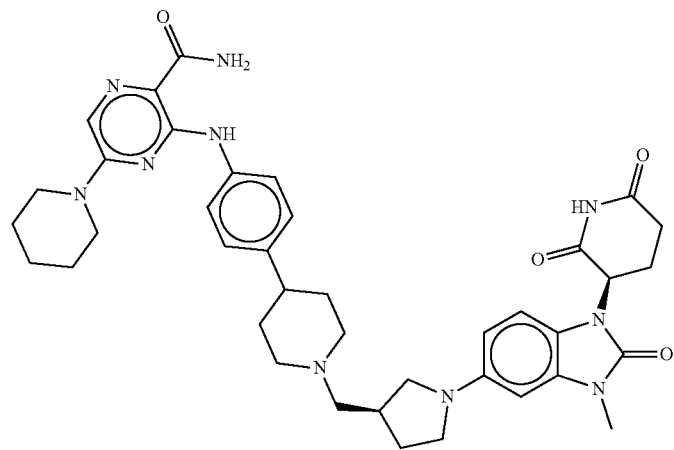 |
| 198 | 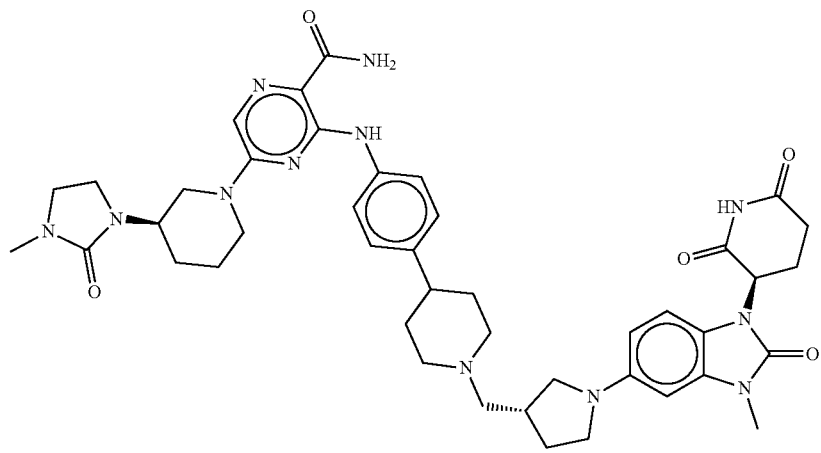 |

TABLE 1-continued
Example compounds and/or pharmaceutically acceptable salts thereof for use in the methods described herein.
| Compound Number | Structure |
|---|---|
| 199 | 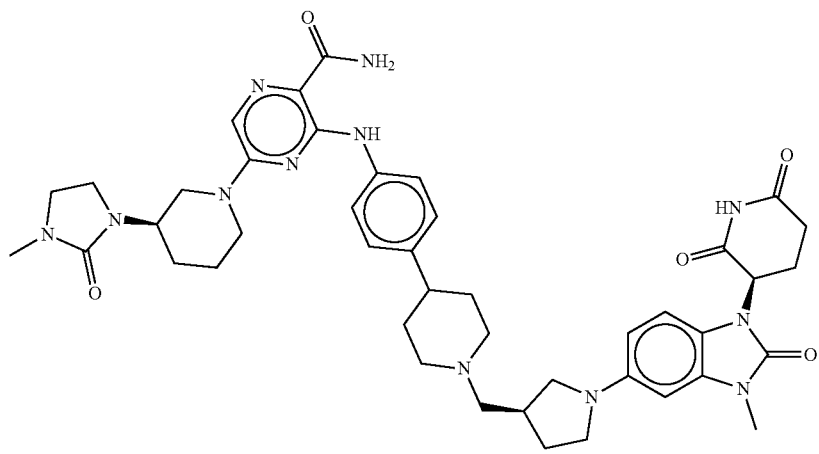 |
| 200 | 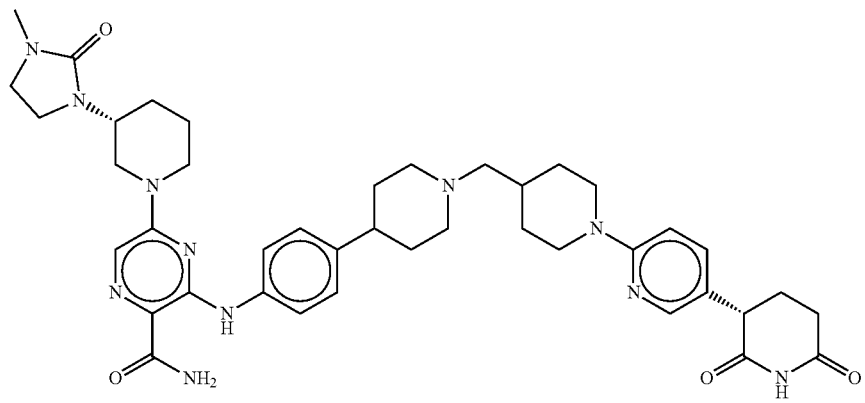 |
| 201 | 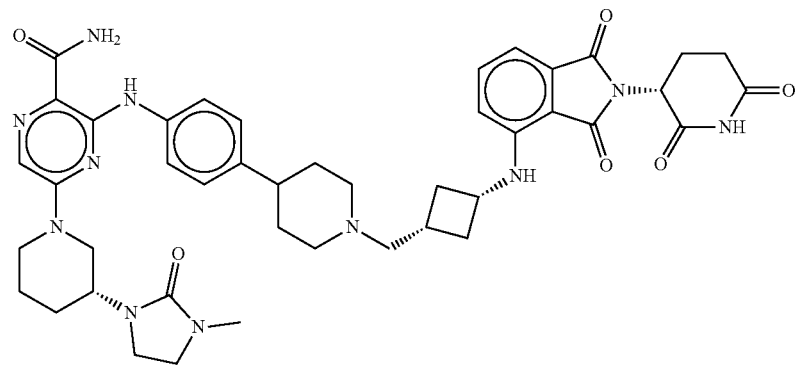 |

TABLE 1-continued
Example compounds and/or pharmaceutically acceptable salts thereof for use in the methods described herein.
| Compound Number | Structure |
|---|---|
| 202 | 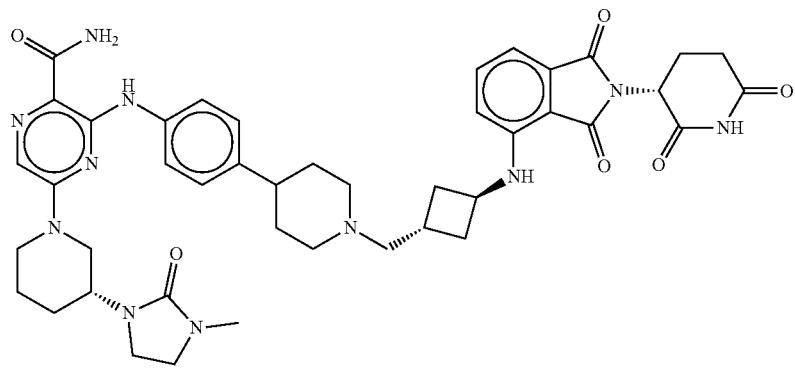 |
| 203 | 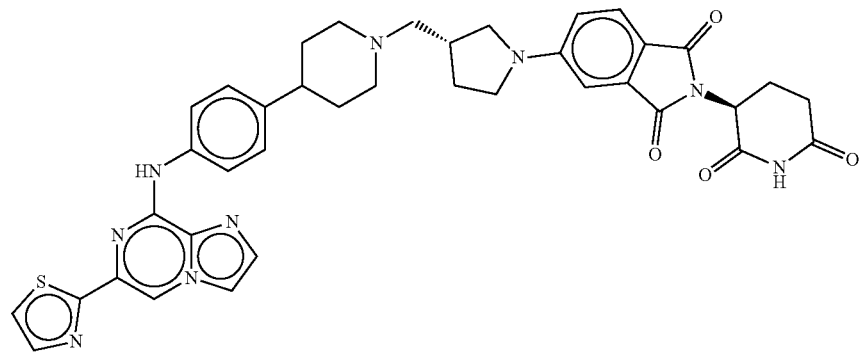 |
| 204 | 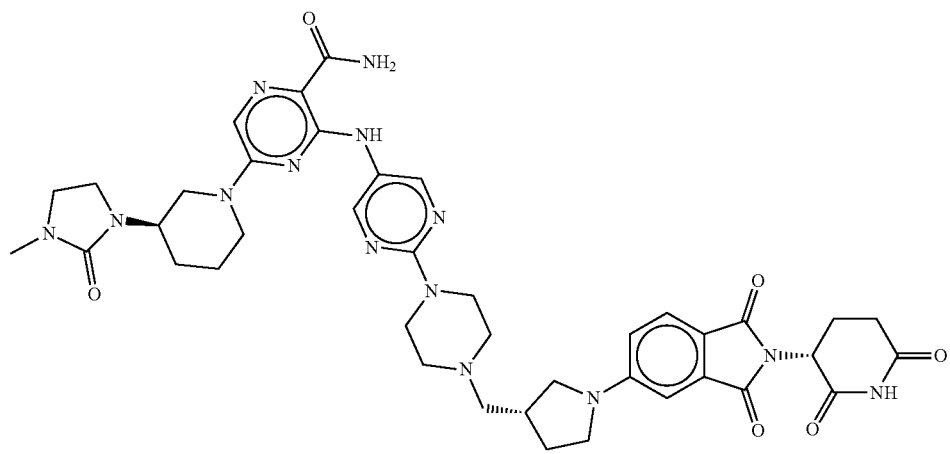 |
| 205 | 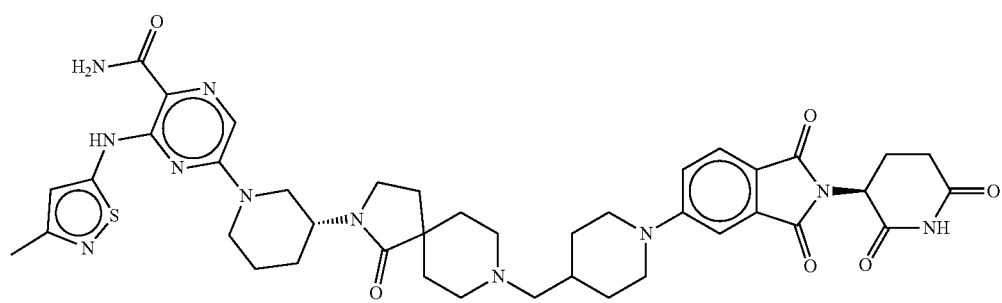 |

US 11,820,781 B2
233 234
TABLE 1-continued
Example compounds and/or pharmaceutically acceptable salts thereof for use in the methods described herein.
| Compound Number | Structure |
|---|---|
| 206 | 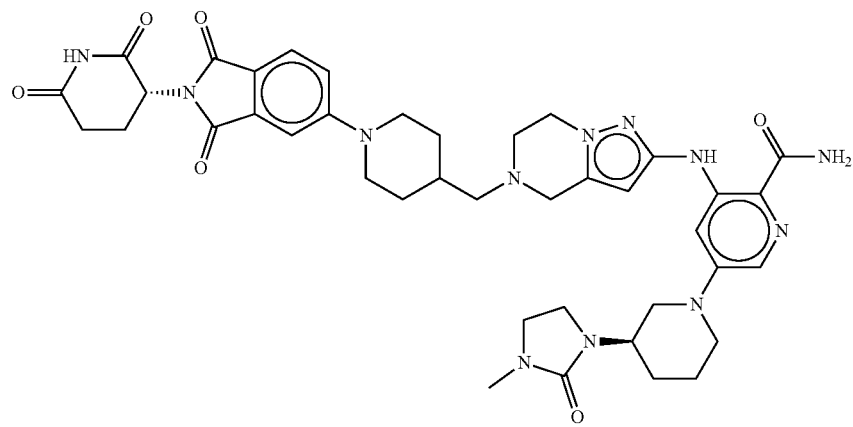 |
| 207 | 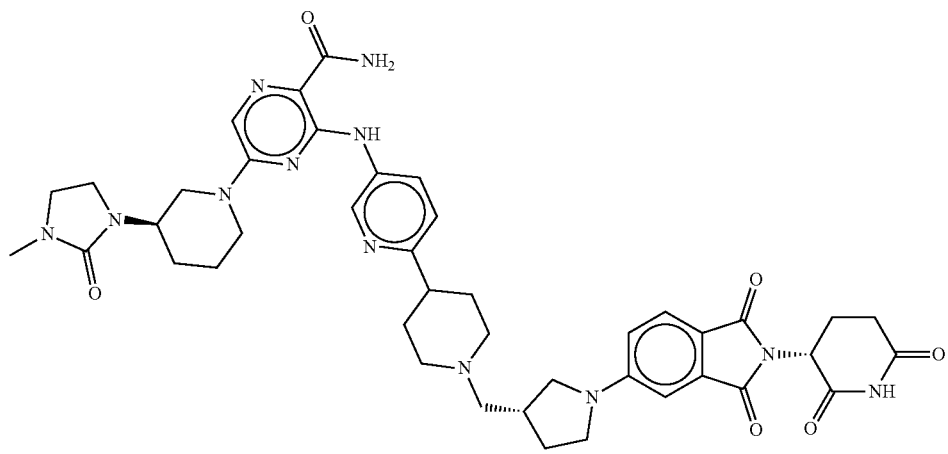 |
| 208 | 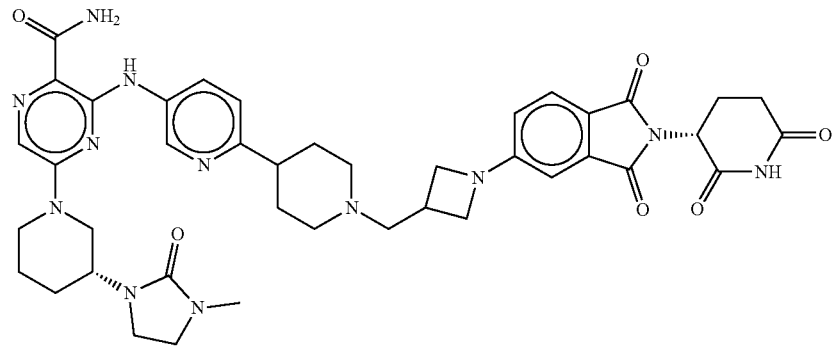 |

235
236
TABLE 1-continued
Example compounds and/or pharmaceutically acceptable salts thereof for use in the methods described herein.
| Compound Number | Structure |
|---|---|
| 209 | 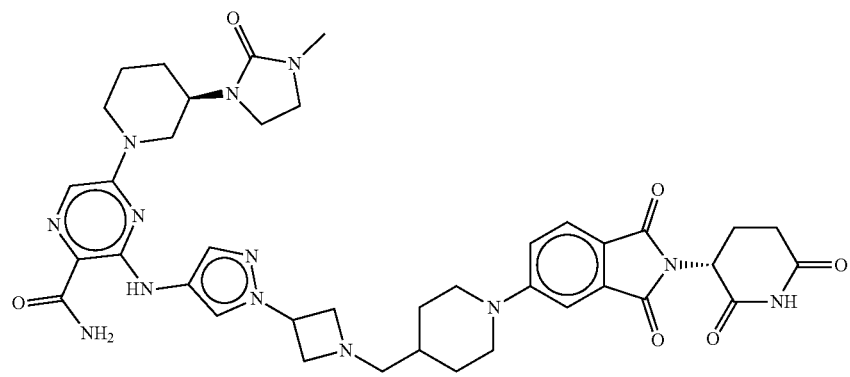 |
| 210 | 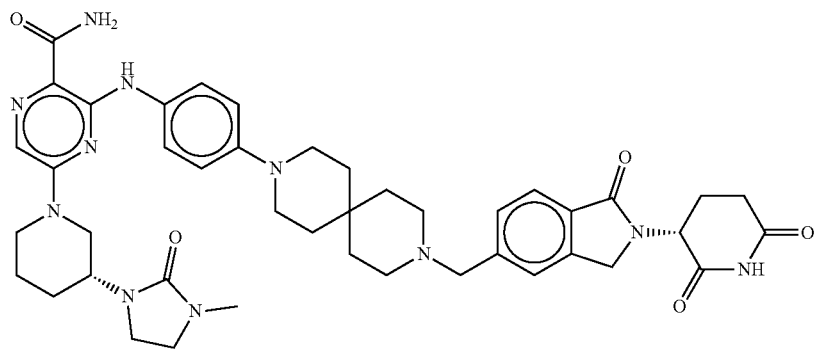 |
| 211 | 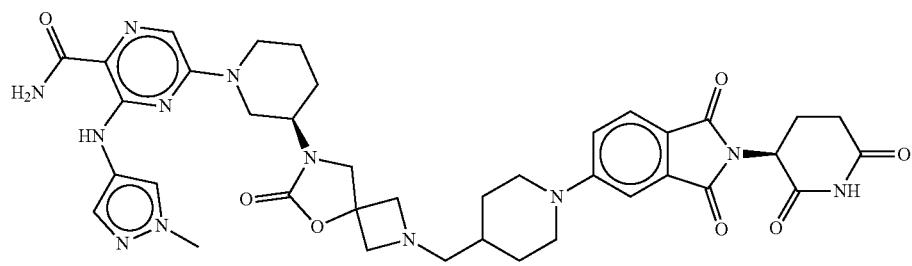 |
| 212 | 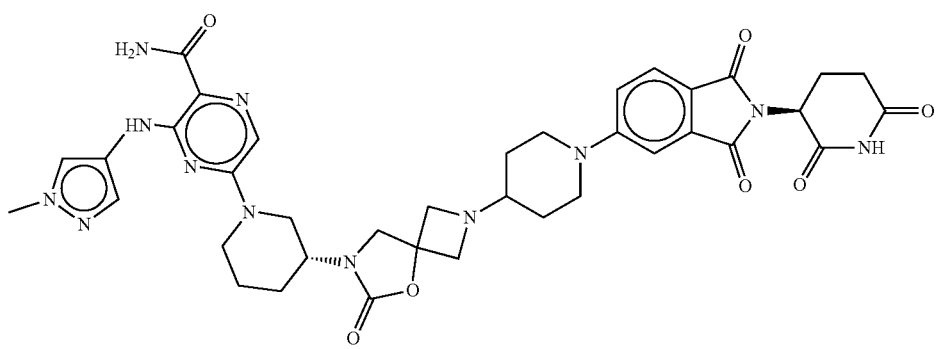 |

TABLE 1-continued
Example compounds and/or pharmaceutically acceptable salts thereof for use in the methods described herein.
| Compound Number | Structure |
| --- | --- |
| 213 | 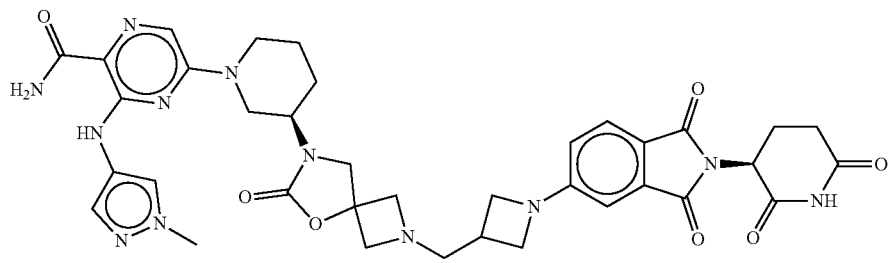 |
| 214 | 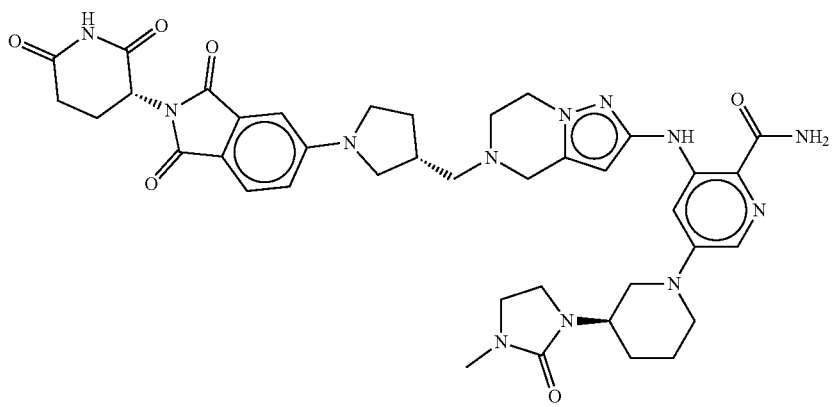 |
| 215 | 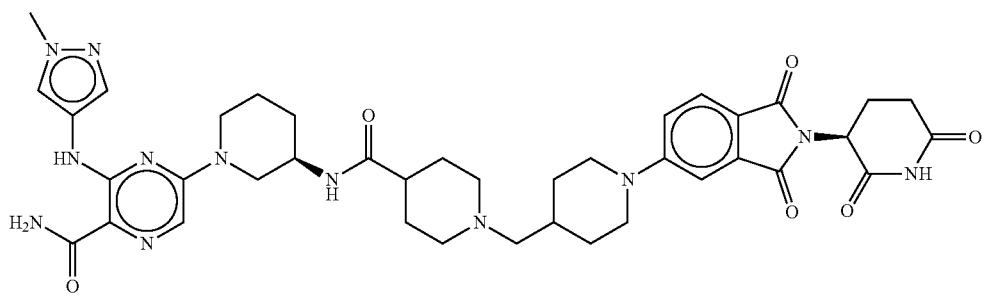 |
| 216 | 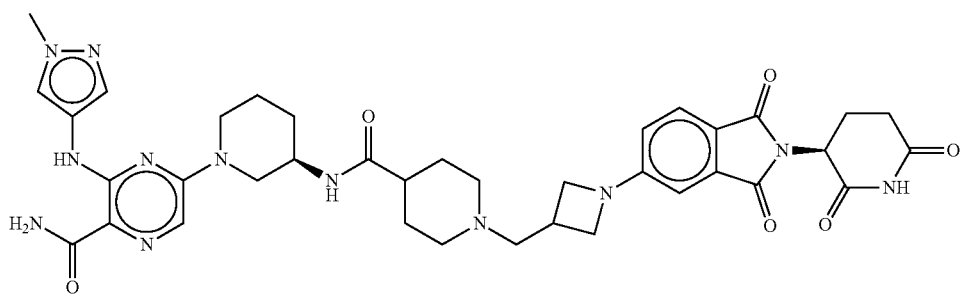 |

TABLE 1-continued

Example compounds and/or pharmaceutically acceptable salts thereof for use in the methods described herein.

| Compound Number | Structure |
|---|---|
| 217 | 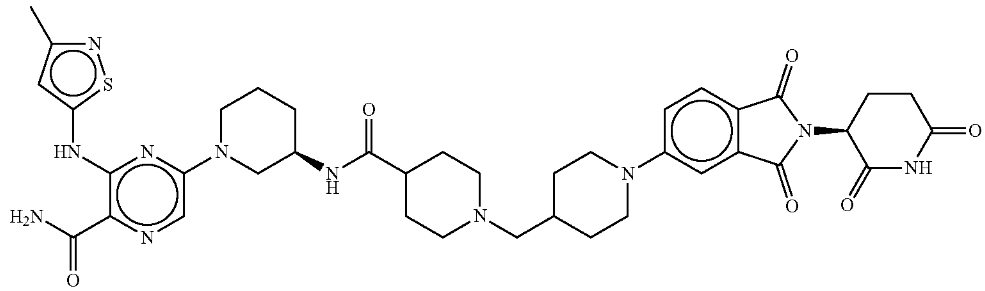 |
| 218 | 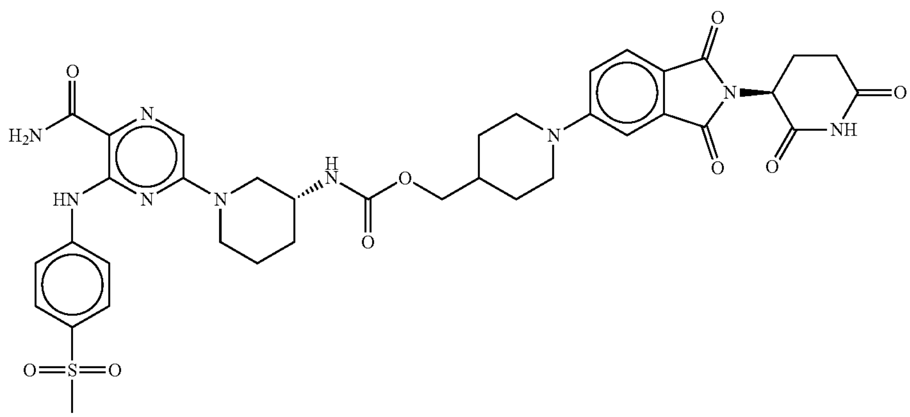 |

Formulations and Administration

Pharmaceutical Compositions

The compounds described herein can be formulated into pharmaceutical compositions that further comprise a pharmaceutically acceptable carrier, diluent, adjuvant, or vehicle. In one embodiment, this disclosure provides a pharmaceutical composition comprising a compound described above, and a pharmaceutically acceptable carrier, diluent, adjuvant, or vehicle. In one embodiment, this disclosure is a pharmaceutical composition comprising an effective amount of a compound of this disclosure or a pharmaceutically acceptable salt thereof and a pharmaceutically acceptable carrier, diluent, adjuvant, or vehicle. Pharmaceutically acceptable carriers include, for example, pharmaceutical diluents, excipients, or carriers suitably selected with respect to the intended form of administration, and consistent with conventional pharmaceutical practices.

According to another embodiment, the description provides a composition comprising a compound herein or a pharmaceutically acceptable salt thereof and a pharmaceutically acceptable carrier, adjuvant, or vehicle. Pharmaceutical compositions of this description comprise a therapeutically effective amount of a compound of Formula (A1), (A), (B), (C), (D), (D-1), (D-2), (E), (F), (G), (H), (J), (K), (M), (I), (I-A), (I-B), (II), (II-A), (II-B), (III), (IV), and/or (X) wherein a "therapeutically effective amount" is an amount that is (a) effective to measurably degrade BTK (or reduce the amount of BTK) in a biological sample or in a patient; or (b) effective in treating and/or ameliorating a disease or disorder that is mediated by BTK.

The term "patient," as used herein, means an animal, alternatively a mammal, and alternatively a human.

It also will be appreciated that certain compounds of this disclosure can exist in free form for treatment, or where appropriate, as a pharmaceutically acceptable derivative (e.g., a salt) thereof. According to this disclosure, a pharmaceutically acceptable derivative includes, but is not limited to, pharmaceutically acceptable prodrugs, salts, esters, salts of such esters, or any other adduct/educt or derivative that upon administration to a patient in need is capable of providing, directly or indirectly, a compound as otherwise described herein, or a metabolite or residue thereof.

As used herein, the term "pharmaceutically acceptable salt" refers to those salts that are, within the scope of sound medical judgement, suitable for use in contact with the tissues of humans and lower animals without undue toxicity, irritation, allergic response, and the like.

Pharmaceutically acceptable salts are well known in the art. For example, S. M. Berge et al., describe pharmaceutically acceptable salts in detail in *J. Pharmaceutical Sciences* 1977, 66, 1-19, incorporated herein by reference. Pharmaceutically acceptable salts of the compounds of this description include those derived from suitable inorganic and organic acids and bases. Examples of pharmaceutically acceptable, nontoxic acid addition salts include salts of an amino group formed with inorganic acids such as hydrochloric acid, hydrobromic acid, phosphoric acid, sulfuric acid, and perchloric acid; or with organic acids such as acetic acid, oxalic acid, maleic acid, tartaric acid, citric acid, succinic acid, or malonic acid; or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4} \text{ alkyl})_4$ salts. This description also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A pharmaceutically acceptable carrier may contain inert ingredients that do not unduly inhibit the biological activity of the compounds. The pharmaceutically acceptable carriers should be biocompatible, for example, non-toxic, non-inflammatory, non-immunogenic, or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants, and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, the use of such conventional carrier medium is contemplated to be within the scope of this description. As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful, uncomfortable, or risky. Side effects include, but are not limited to, fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain, and headache), hair loss, asthenia, dizziness, extra-pyramidal symptoms, akathisia, cardiovascular disturbances, and sexual dysfunction.

Some examples of materials that can serve as pharmaceutically acceptable carriers include, but are not limited to, ion exchangers, alumina, aluminum stearate, lecithin, serum proteins (such as human serum albumin), buffer substances (such as tween 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring, and perfuming agents. Preservatives and antioxidants can also be present in the composition, according to the judgment of the formulator.

As used herein, the term "measurably degrade," means a measurable reduction in (a) BTK activity, between a sample comprising a compound of this description and a BTK and an equivalent sample comprising a BTK in the absence of said compound; or (b) the concentration of the BTK in a sample over time.

Administration

The compositions of this disclosure are administered orally. The pharmaceutically acceptable compositions of this description may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents also may be added.

Liquid dosage forms for oral administration include, but are not limited to, pharmaceutically acceptable emulsions, microemulsions, solutions, suspensions, syrups, and elixirs. In addition to the active compounds herein, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions also can include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound herein is mixed with at least one inert, pharmaceutically acceptable excipient or carrier such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets, and pills, the dosage form also may comprise buffering agents.

Solid compositions of a similar type also may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Solid dosage forms optionally may contain opacifying agents. These solid dosage forms also can be of a composition such that they release the active ingredient(s) only, for example, in a certain part of the intestinal tract, optionally, in a delayed manner. Examples of embedding compositions that can be used include polymeric substances and waxes. Solid compositions of a similar type also may be employed as fillers in soft and hard-filled gelatin capsules using such excipients as lactose or milk sugar as well as high molecular weight polyethylene glycols and the like.

The active compounds herein also can be in microencapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active compound may be admixed with at least one inert diluent such as sucrose, lactose, or starch. Such dosage forms also may comprise, as is normal practice, additional substances other than inert diluents, for example, tableting lubricants and other tableting aids such a magnesium stearate and microcrystalline cellulose. In the case of capsules, tablets and pills, the dosage forms also may comprise buffering agents. They may optionally contain opacifying agents and also can be of a composition such that they release the active ingredient(s) only, for example, in a certain part of the intestinal tract, optionally, in a delayed manner. Examples of embedding compositions that can be used include polymeric substances and waxes.

The compounds of the description are formulated in dosage unit form for ease of administration and uniformity of dosage. As used herein, the phrase "dosage unit form" refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed, and like factors well known in the medical arts.

The amount of the compounds of this disclosure that may be combined with the carrier materials to produce a composition in a single dosage form will vary depending upon the host treated, the particular mode of administration, and other factors. The compositions should be formulated so that a dosage of between 0.01-100 mg/kg body weight/day of the compound or inhibitor can be administered to a patient receiving these compositions.

Depending upon the particular condition, or disease, to be treated or prevented, additional therapeutic agents, which are normally administered to treat or prevent that condition, also may be present in the compositions of this disclosure. As used herein, additional therapeutic agents that are normally administered to treat or prevent a particular disease, or condition, are known as "appropriate for the disease, or condition, being treated."

For example, chemotherapeutic agents or other anti-proliferative agents may be combined with the compounds of this disclosure to treat proliferative diseases and cancer. Examples of known chemotherapeutic agents include, but are not limited to, PI3K inhibitors (e.g., idelalisib and copanlisib), BCL-2 inhibitors (e.g., venetoclax), BTK inhibitors (e.g., ibrutinib and acalabrutinib), etoposide, CD20 antibodies (e.g., rituximab, ocrelizumab, obinutuzumab, ofatumumab, ibritumomab tiuxetan, tositumomab, and ublituximab), aletuzumab, bendamustine, cladribine, doxorubicin, chlorambucil, prednisone, midostaurin, lenalidomide, pomalidomide, checkpoint inhibitors (e.g., ipilimumab, nivolumab, pembolizumab, atezolizumab, avelumab, durvalumab), engineered cell therapy (e.g., CAR-T therapy—Kymriah®, Yescarta®), Gleevec™, adriamycin, dexamethasone, vincristine, cyclophosphamide, fluorouracil, topotecan, taxol, interferons, and platinum derivatives.

And, in some instances, radiation therapy is administered during the treatment course wherein a compound of this disclosure (or a pharmaceutically acceptable salt thereof) is administered to a patient in need thereof.

Other examples of agents with which the compounds or inhibitors of this disclosure also may be combined include, without limitation, treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this disclosure will be no more than the amount that would normally be administered in a composition comprising that therapeutic agent as the only active agent. The amount of additional therapeutic agent in the presently disclosed compositions will range from about 50% to 100% of the amount normally present in a composition comprising that agent as the only therapeutically active agent.

EXAMPLES

Additional embodiments are disclosed in further detail in the following examples, which are not in any way intended to limit the scope of the claims.

Example 1

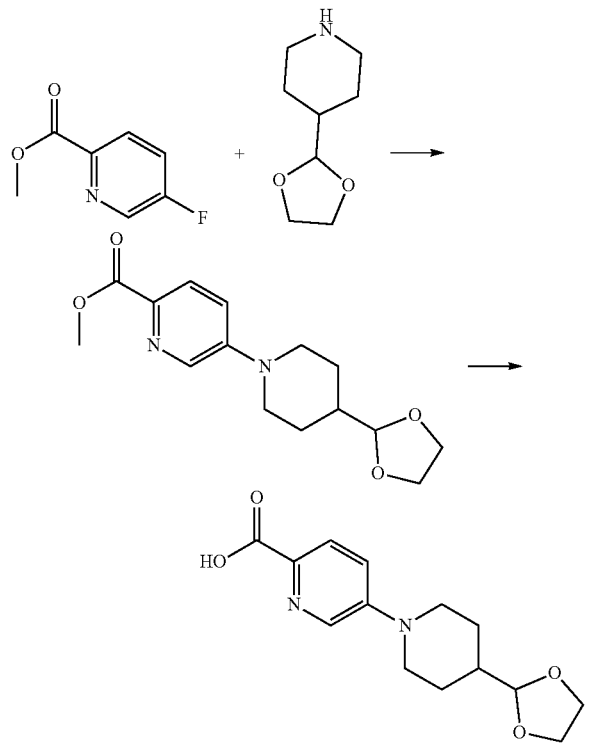

Synthesis of methyl 5-(4-(1,3-dioxolan-2-yl)piperidin-1-yl)picolinate

A mixture of methyl 5-fluoropyridine-2-carboxylate (1020 mg, 6.58 mmol), 4-(1,3-dioxolan-2-yl)piperidine (1033 mg, 6.58 mmol), N,N-diisopropylethylamine (2.29 mL, 13.15 mmol) and DMSO (6.5 mL) was allowed to stir at 100° C. overnight. The mixture was cooled to room temperature. H$_2$O (8.1 mL) was added and the mixture was filtered. The solids were collected and dried to afford methyl 5-[4-(1,3-dioxolan-2-yl)piperidin-1-yl]pyridine-2-carboxylate (1.90 g, 98.8%). LCMS: C$_{15}$H$_{20}$N$_2$O$_4$ requires: 292, found: m/z=293 [M+H]$^+$.

Synthesis of 5-(4-(1,3-dioxolan-2-yl)piperidin-1-yl) picolinic acid

A mixture of methyl 5-[4-(1,3-dioxolan-2-yl)piperidin-1-yl]pyridine-2-carboxylate (1.90 g, 6.50 mmol), sodium hydroxide (324.95 mg, 8.12 mmol), THF (8.4 mL) and water (8.4 mL) were allowed to stir at rt for 2 h. The volatiles were removed. MeCN (11.8 mL) was added and the mixture was stirred at rt for 20 min. The mixture was filtered and the solids were collected to yield 5-[4-(1,3-dioxolan-2-yl)piperidin-1-yl]pyridine-2-carboxylic acid (1.68 g, 92.9%). LCMS: C$_{14}$H$_{18}$N$_2$O$_4$ requires: 278, found: m/z=279 [M+H]$^+$.

Example 2

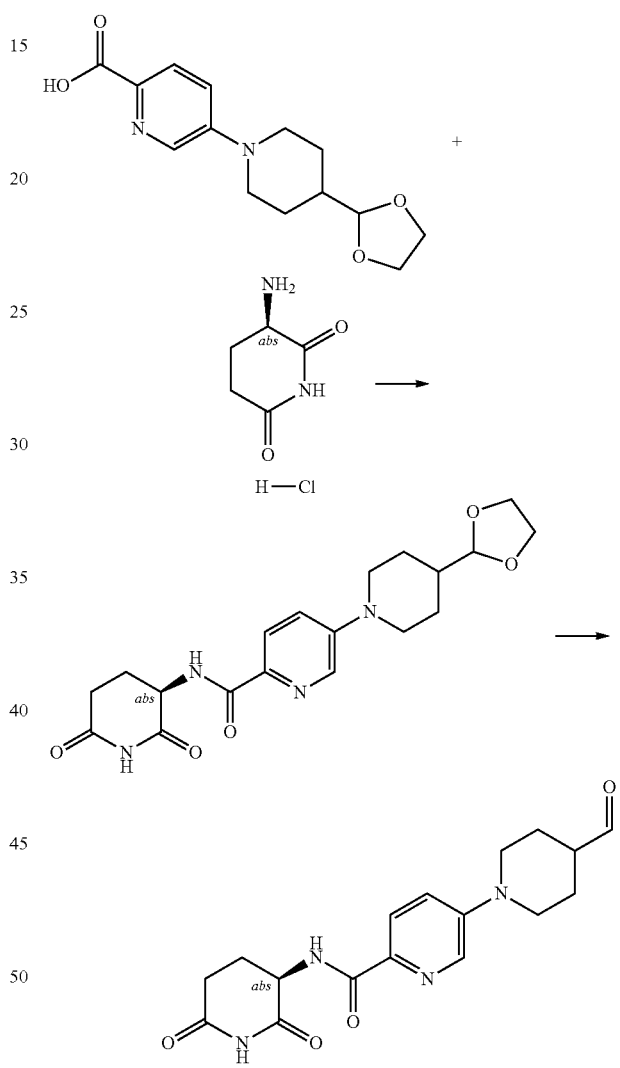

Synthesis of (R)-5-(4-(1,3-dioxolan-2-yl)piperidin-1-yl)-N-(2,6-dioxopiperidin-3-yl)picolinamide A mixture of 5-[4-(1,3-dioxolan-2-yl)piperidin-1-yl]pyridine-2-carboxylic acid (196 mg, 0.70 mmol), (3R)-3-aminopiperidine-2,6-dione hydrochloride (115 mg, 0.70 mmol), [(dimethylamino)({[1,2,3]triazolo[4,5-b]pyridin-3-yloxy}) methylidene]dimethylazanium; hexafluoro-lambda5-phosphanuide (535 mg, 1.41 mmol), N,N-diisopropylethylamine (0.31 mL, 1.76 mmol), and DMF (2 mL) was allowed to stir at rt for 30 min. 0.1 M HCl (1 mL) in water was added and the mixture was allowed to stir at rt for 15 min. The mixture was filtered, washing with cold H$_2$O. The solids were collected to afford 5-[4-(1,3-dioxolan-2-yl)piperidin-1-yl]-N-[(3R)-2,6-dioxopiperidin-3-yl]pyridine-2-carboxamide (0.272 g, 99.4%). LCMS: C$_{19}$H$_{24}$N$_4$O$_5$ requires: 388, found: m/z=389 [M+H]$^+$.

Synthesis of (R)—N-(2,6-dioxopiperidin-3-yl)-5-(4-formylpiperidin-1-yl)picolinamide A mixture of 5-[4-(1,3-dioxolan-2-yl)piperidin-1-yl]-N-[(3R)-2,6-dioxopiperidin-3-yl]pyridine-2-carboxamide (259 mg, 0.67 mmol), THF (3 mL) and 2 M HCl (3 mL) was allowed to stir at 50° C. for 1 h. Saturated aq. NaHCO$_3$ was added until pH-7-8. CHCl$_3$/iPrOH was added, and the organic layer was dried with MgSO$_4$, filtered, and concentrated. MeCN was added and the mixture was sonicated for ~10 min. The mixture was filtered and the solids were collected to afford (R)—N-(2,6-dioxopiperidin-3-yl)-5-(4-formylpiperidin-1-yl)picolinamide (0.155 g, 68%). LCMS: C$_{17}$H$_{20}$N$_4$O$_4$ requires: 344, found: m/z=345 [M+H]$^+$.

Example 3

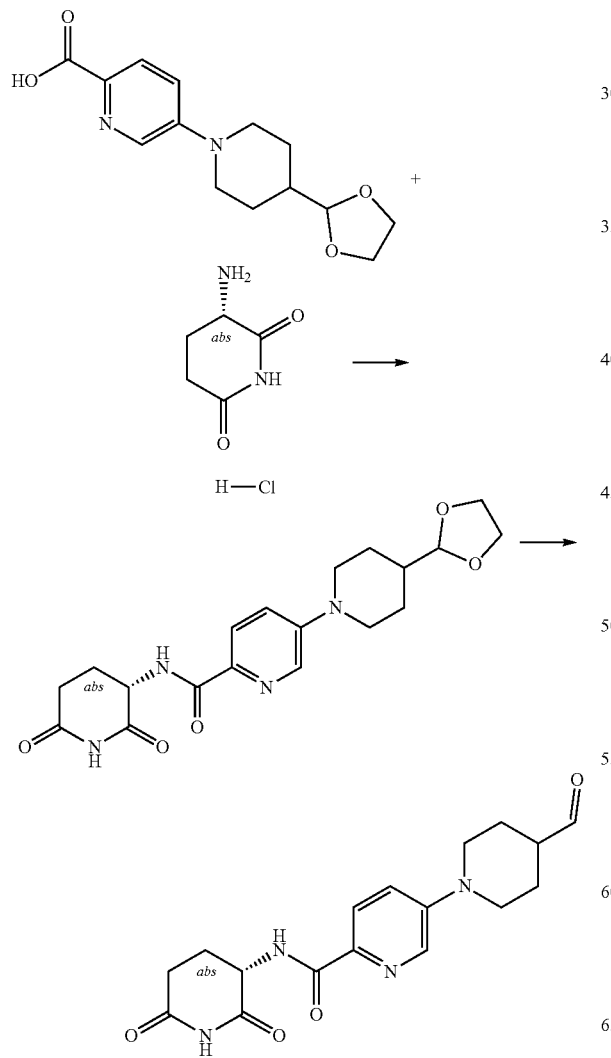

Synthesis of (S)-5-(4-(1,3-dioxolan-2-yl)piperidin-1-yl)-N-(2,6-dioxopiperidin-3-yl)picolinamide A mixture of (3S)-3-aminopiperidine-2,6-dione hydrochloride (118.28 mg, 0.72 mmol), 5-[4-(1,3-dioxolan-2-yl)piperidin-1-yl]pyridine-2-carboxylic acid (200 mg, 0.72 mmol), [(dimethylamino)({[1,2,3]triazolo[4,5-b]pyridin-3-yloxy})methylidene]dimethylazanium; hexafluoro-lambda5-phosphanuide (546 mg, 1.44 mmol), N,N-diisopropylethylamine (0.32 mL, 1.80 mmol), and DMF (2 mL) was allowed to stir at rt for 30 min. Aq. 1M HCl was added and the mixture was stirred at rt for 15 min. The mixture was filtered and the solids were collected as 5-[4-(1,3-dioxolan-2-yl)piperidin-1-yl]-N-[(3S)-2,6-dioxopiperidin-3-yl]pyridine-2-carboxamide (0.2750 g, 99%). LCMS: C$_{19}$H$_{24}$N$_4$O$_5$ requires: 388, found: m/z=389 [M+H]$^+$.

Synthesis of (S)—N-(2,6-dioxopiperidin-3-yl)-5-(4-formylpiperidin-1-yl)picolinamide A mixture of 5-[4-(1,3-dioxolan-2-yl)piperidin-1-yl]-N-[(3S)-2,6-dioxopiperidin-3-yl]pyridine-2-carboxamide (332 mg, 0.85 mmol), THF (3 mL), and 2M HCl (3 mL) was allowed to stir at 50° C. for 1 h. Saturated aq. NaHCO$_3$ was added until pH-7-8. CHCl$_3$/iPrOH was added, and the organic layer was dried with MgSO$_4$, filtered, and concentrated. MeCN was added and the mixture was sonicated for ~10 min. The mixture was filtered and the solids were collected to afford (S)—N-(2,6-dioxopiperidin-3-yl)-5-(4-formylpiperidin-1-yl)picolinamide (175 mg, 60%). LCMS: C$_{17}$H$_{20}$N$_4$O$_4$ requires: 344, found: m/z=345 [M+H]$^+$.

Example 4

Synthesis of 5-[(3R)-3-(3-methyl-2-oxoimidazolidin-1-yl)piperidin-1-yl]-3-{[4-(piperazin-1-yl)phenyl]amino}pyrazine-2-carboxamide tert-butyl(3R)-3-{[(2-chloroethyl)carbamoyl]amino}piperidine-1-carboxylate

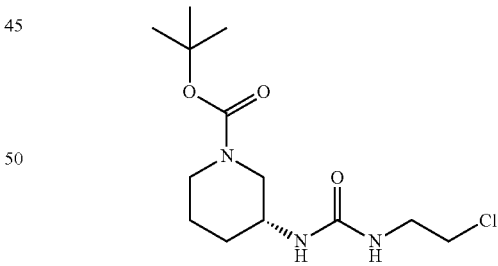

To a mixture of tert-butyl (3R)-3-aminopiperidine-1-carboxylate (25.0 g, 125 mmol) and triethylamine (34.8 mL, 25.3 g, 250 mmol) in DCM (250 mL) was added 1-chloro-2-isocyanatoethane (12.8 mL, 15.8 g, 150 mmol) over 25 minutes. A mild exotherm was observed. After four hours, 100 mL water was added. The layers were separated. The organic layer was dried over Na$_2$SO$_4$ and concentrated. The mixture was dissolved in ethyl acetate and filtered through 1000 cc of silica gel in a 2000 mL Buchner funnel eluted with ethyl acetate. The resulting solution was concentrated in vacuo to provide tert-butyl (3R)-3-{[(2-chloroethyl)carbamoyl]amino}piperidine-1-carboxylate (40.6 g, 106%)

which was used without further purification. LCMS: $C_{13}H_{24}ClN_3O_3$ requires 305, found: m/z=306 [M+H]$^+$.

tert-butyl (3R)-3-(2-oxoimidazolidin-1-yl)piperidine-1-carboxylate

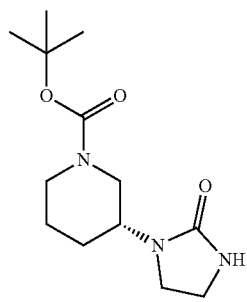 [SMILES: CC(C)(C)OC(=O)N1CCC[C@@H](N2CCNC2=O)C1]

To an ice cooled mixture of tert-butyl (3R)-3-{[(2-chloroethyl)carbamoyl]amino}piperidine-1-carboxylate (40.3 g, 132 mmol) in THF (400 mL) was added 60% sodium hydride (10.6 g, 264 mmol) in portions. The cooling bath was allowed to melt and the reaction was stirred at room temperature overnight. Another portion of 60% sodium hydride (5.65 g, 141 mmol) was added. The mixture bubbled. After ten minutes, a mild exotherm was observed. After two hours, the reaction was quenched by the addition of 75 mL water. The layers were separated. The aqueous layer was extracted with two 50 mL portions of DCM. The combined organic layers were washed with brine, dried over anhydrous Na$_2$SO$_4$, and concentrated in vacuo. The resulting material was partitioned between acetonitrile and hexanes. The acetonitrile layer was concentrated in vacuo to provide tert-butyl (3R)-3-(2-oxoimidazolidin-1-yl)piperidine-1-carboxylate (33.9 g, 95.4%). LCMS: $C_{13}H_{23}N_3O_3$ requires 269, found: m/z=270 [M+H]$^+$.

tert-butyl(3R)-3-(3-methyl-2-oxoimidazolidin-1-yl)piperidine-1-carboxylate

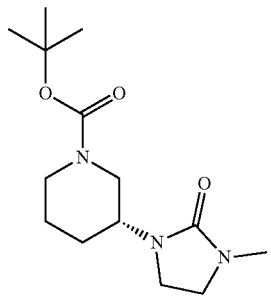 [SMILES: CN1CCN([C@@H]2CCCN(C(=O)OC(C)(C)C)C2)C1=O]

To an ice cooled mixture of tert-butyl (3R)-3-(2-oxoimidazolidin-1-yl)piperidine-1-carboxylate (33.8 g, 126 mmol) in THF (300 mL) was added 60% sodium hydride (10.1 g, 251 mmol) in portions. After five minutes, the cooling bath was removed. The mixture bubbled for one hour. The mixture was cooled in an ice bath. Methyl iodide (11.7 mL, 26.7 g, 188 mmol) was added over five minutes. The mixture bubbled. The cooling bath was allowed to warm to room temperature. After stirring for 16 hours at room temperature, the reaction was quenched with water (75 mL). The layers were separated. The organic layer was washed with brine. The combined aqueous layers were extracted twice with DCM. The combined organic layers were dried over anhydrous Na$_2$SO$_4$ and concentrated. The resulting material was partitioned between acetonitrile and hexane. The acetonitrile layer was filtered and concentrated in vacuo to provide tert-butyl (3R)-3-(3-methyl-2-oxoimidazolidin-1-yl)piperidine-1-carboxylate (38.4 g, 108%) which was used crude without further purification. LCMS: $C_{14}H_{25}N_3O_3$ requires 283, found: m/z=306 [M+Na]$^+$.

1-methyl-3-[(3R)-piperidin-3-yl]imidazolidin-2-one hydrochloride

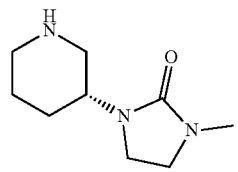

tert-butyl (3R)-3-(3-methyl-2-oxoimidazolidin-1-yl)piperidine-1-carboxylate (35.1 g, 124 mmol) was stirred in hydrogen chloride 4M solution in dioxane (310 mL, 1.24 mol) for two hours. The mixture was concentrated in vacuo to provide 1-methyl-3-[(3R)-piperidin-3-yl]imidazolidin-2-one hydrochloride (35.0 g, 128%) which was used crude without further purification. LCMS: $C_9H_{17}N_3O$ requires 183, found: m/z=184 [M+H]$^+$.

3-chloro-5-[(3R)-3-(3-methyl-2-oxoimidazolidin-1-yl)piperidin-1-yl]pyrazine-2-carbonitrile

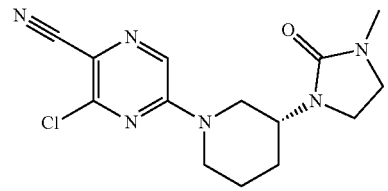 [SMILES: CN1CCN([C@@H]2CCCN(c3cnc(C#N)c(Cl)n3)C2)C1=O]

3,5-dichloropyrazine-2-carbonitrile (21.6 g, 124 mmol) was added to an ice-cold mixture of 1-methyl-3-[(3R)-piperidin-3-yl]imidazolidin-2-one hydrochloride (27.2 g, 124 mmol) and N,N-diisopropylethylamine (86.3 mL, 495 mmol) in DMF (300 mL). After 15 minutes, the cooling bath was removed. After stirring for 16 hours, the mixture was diluted with 800 mL water. The mixture was extracted with ethyl acetate. The organic layer was washed twice with water and washed once with brine. The organic layer was dried over anhydrous Na$_2$SO$_4$ and concentrated in vacuo. The crude residue was purified by flash chromatography on a 330 g silica gel column eluted with zero to 3% MeOH/DCM gradient to provide 3-chloro-5-[(3R)-3-(3-methyl-2-oxoimidazolidin-1-yl)piperidin-1-yl]pyrazine-2-carbonitrile (22.1 g, 55.6%). LCMS: $C_{14}H_{17}ClN_6O$ requires 320, found: m/z=320 [M+H]$^+$.

tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate

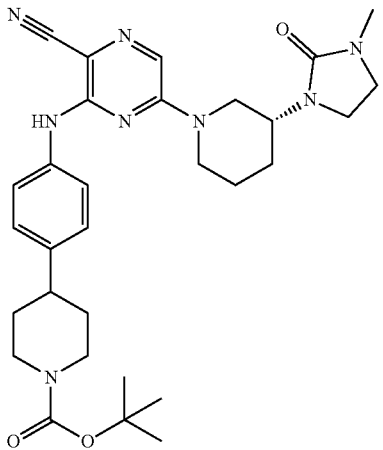 [SMILES: CN1CCN([C@@H]2CCCN(c3cnc(C#N)c(Nc4ccc(C5CCN(C(=O)OC(C)(C)C)CC5)cc4)n3)C2)C1=O]

A mixture of 3-chloro-5-[(3R)-3-(3-methyl-2-oxoimidazolidin-1-yl)piperidin-1-yl]pyrazine-2-carbonitrile (244 mg, 0.76 mmol), tert-butyl 4-(4-aminophenyl)piperidine-1-carboxylate (211 mg, 0.76 mmol), Pd(OAc)$_2$ (56.4 mg, 0.25 mmol), BINAP (156.3 mg, 0.25 mmol), and Cs$_2$CO$_3$ (7434 mg, 2.28 mmol) was degassed and backfilled with N$_2$ five times. The mixture was allowed to stir at 100° C. for 90 min. The mixture was filtered through celite washing with MeOH/EtOAc, concentrated, and purified by MPLC (0-100% EtOAc in CH$_2$Cl$_2$) to afford tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate (259 mg, 60.7%). LCMS: C$_3$H$_{40}$N$_8$O$_3$ requires 560, found m/z=561 [M+H]$^+$.

tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate

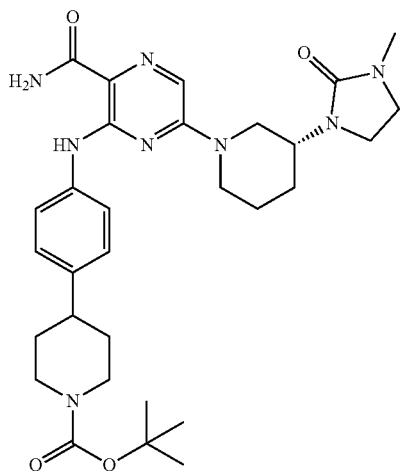 [SMILES: CN1CCN([C@@H]2CCCN(c3cnc(C(N)=O)c(Nc4ccc(C5CCN(C(=O)OC(C)(C)C)CC5)cc4)n3)C2)C1=O]

H$_2$O$_2$ (30% in water, 2.50 mL, 0.24 mmol) was added to a mixture of tert-butyl 4-[4-({3-cyano-6-[(3R)-3-(3-methyl-2-oxoimidazolidin-1-yl)piperidin-1-yl]pyrazin-2-yl}amino)phenyl]piperidine-1-carboxylate (259 mg, 0.46 mmol), Cs$_2$CO$_3$ (150.5 mg, 0.46 mmol), MeOH (9 mL), and DMSO (0.5 mL). The mixture was allowed to stir at rt for 30 min. The mixture was concentrated. EtOAc was added and the organic phase was washed with H$_2$O and brine. The organic layer was dried with MgSO$_4$, filtered, concentrated, and purified by MPLC (0-10% MeOH in CH$_2$Cl$_2$) to afford tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate (252 mg, 94%). LCMS: C$_{30}$H$_{42}$N$_8$O$_4$ requires 578, found m/z=579 [M+H]$^+$.

5-[(3R)-3-(3-methyl-2-oxoimidazolidin-1-yl)piperidin-1-yl]-3-{[4-(piperazin-1-yl)phenyl]amino}pyrazine-2-carboxamide

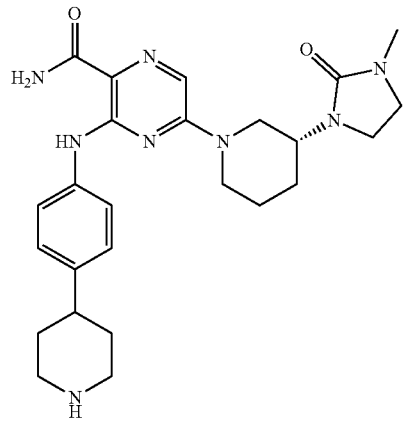 [SMILES: CN1CCN([C@@H]2CCCN(c3cnc(C(N)=O)c(Nc4ccc(C5CCNCC5)cc4)n3)C2)C1=O]

A mixture of tert-butyl 4-[4-({3-carbamoyl-6-[(3R)-3-(3-methyl-2-oxoimidazolidin-1-yl)piperidin-1-yl]pyrazin-2-yl}amino)phenyl]piperidine-1-carboxylate (252 mg, 0.44 mmol), hydrogen chloride (4M in dioxane, 2.72 mL, 10.89 mmol), and THF (2 mL) was allowed to stir at room temperature for 2 h. The volatiles were removed to afford 5-[(3R)-3-(3-methyl-2-oxoimidazolidin-1-yl)piperidin-1-yl]-3-{[4-(piperidin-4-yl)phenyl]amino}pyrazine-2-carboxamide (209 mg, quant).

Example 5

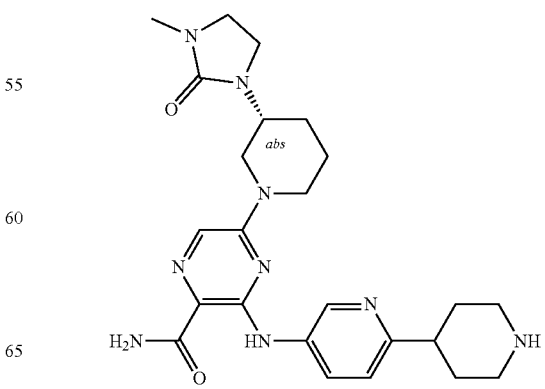

Synthesis of (R)-5-(3-(3-methyl-2-oxoimidazolidin-1-yl)piperidin-1-yl)-3-((6-(piperidin-4-yl)pyridin-3-yl)amino)pyrazine-2-carboxamide Prepared in a manner analogous to the preparation of 5-[(3R)-3-(3-methyl-2-oxoimidazolidin-1-yl)piperidin-1-yl]-3-{[4-(piperidin-4-yl)phenyl]amino}pyrazine-2-carboxamide with tert-butyl 4-(5-aminopyridin-2-yl)piperidine-1-carboxylate in place of tert-butyl 4-(4-aminophenyl)piperidine-1-carboxylate.

Example 6

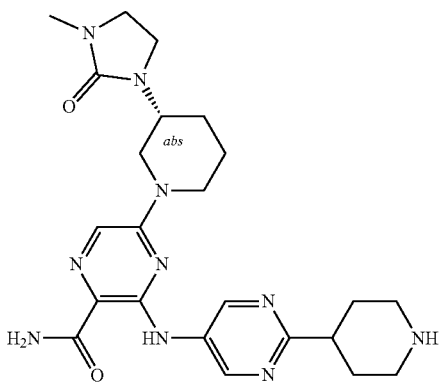 [SMILES: CN1CCN([C@@H]2CCCN(c3cnc(C(N)=O)c(Nc4cnc(C5CCNCC5)nc4)n3)C2)C1=O]

Synthesis of (R)-5-(3-(3-methyl-2-oxoimidazolidin-1-yl)piperidin-1-yl)-3-((2-(piperidin-4-yl)pyrimidin-5-yl)amino)pyrazine-2-carboxamide Prepared in a manner analogous to the preparation of 5-[(3R)-3-(3-methyl-2-oxoimidazolidin-1-yl)piperidin-1-yl]-3-{[4-(piperidin-4-yl)phenyl]amino}pyrazine-2-carboxamide with tert-butyl 4-(5-aminopyrimidin-2-yl)piperidine-1-carboxylate in place of tert-butyl 4-(4-aminophenyl)piperidine-1-carboxylate.

Example 7

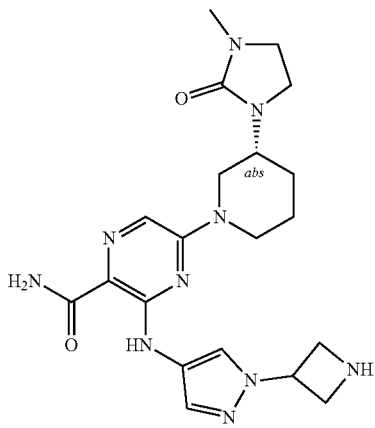 [SMILES: CN1CCN([C@@H]2CCCN(c3cnc(C(N)=O)c(Nc4cnn(C5CNC5)c4)n3)C2)C1=O]

Synthesis of (R)-3-((1-(azetidin-3-yl)-1H-pyrazol-4-yl)amino)-5-(3-(3-methyl-2-oxoimidazolidin-1-yl)piperidin-1-yl)pyrazine-2-carboxamide Prepared in a manner analogous to the preparation of 5-[(3R)-3-(3-methyl-2-oxoimidazolidin-1-yl)piperidin-1-yl]-3-{[4-(piperidin-4-yl)phenyl]amino}pyrazine-2-carboxamide with tert-butyl 3-(4-amino-1H-pyrazol-1-yl)azetidine-1-carboxylate in place of tert-butyl 4-(4-aminophenyl)piperidine-1-carboxylate.

Example 8

Synthesis of (R)-3-((4-(3,9-diazaspiro[5.5]undecan-3-yl)phenyl)amino)-5-(3-(3-methyl-2-oxoimidazolidin-1-yl)piperidin-1-yl)pyrazine-2-carboxamide

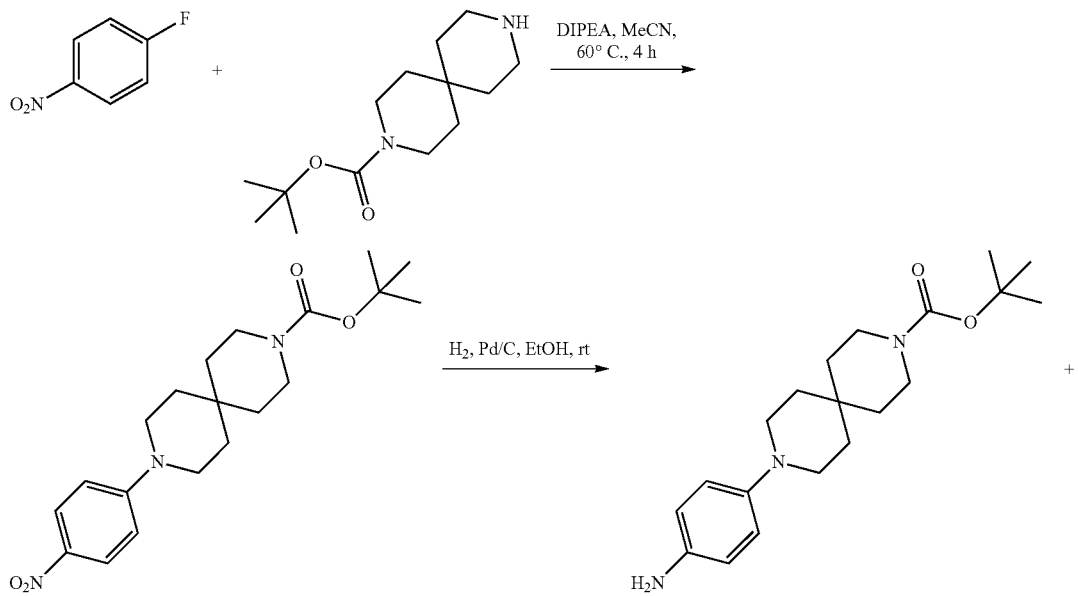

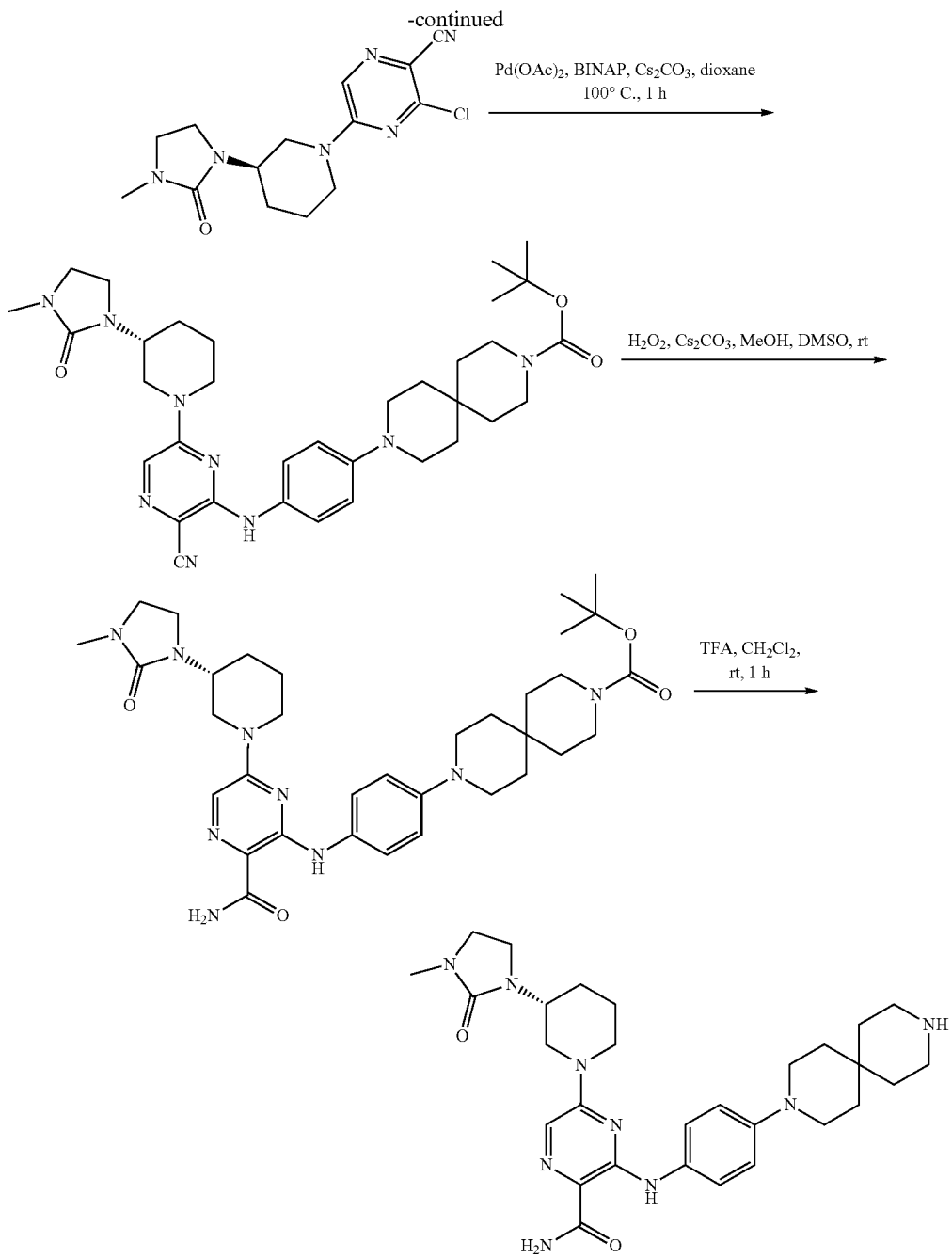

Synthesis of tert-butyl 9-(4-nitrophenyl)-3,9-diazaspiro[5.5]undecane-3-carboxylate A mixture of 4-fluoronitrobenzene (554.7 mg, 3.93 mmol), DMF (20 mL), ethylbis(propan-2-yl)amine (2.74 mL, 15.7 mmol) and tert-butyl 3,9-diazaspiro[5.5]undecane-3-carboxylate (1000 mg, 3.93 mmol) was allowed to stir at 90° C. overnight. EtOAc and $H_2O$ were added. The organic layer was dried with $MgSO_4$, filtered, concentrated, and purified by MPLC (0-50% EtOAc in hexanes) to afford tert-butyl 9-(4-nitrophenyl)-3,9-diazaspiro[5.5]undecane-3-carboxylate (1287.00 mg, 87.2%). $C_{20}H_{29}N_3O_4$ requires 375, found: m/z=376 [M+H]$^+$.

Synthesis of tert-butyl 9-(4-aminophenyl)-3,9-diazaspiro[5.5]undecane-3-carboxylate A mixture of tert-butyl 9-(4-nitrophenyl)-3,9-diazaspiro[5.5]undecane-3-carboxylate (1.29 g, 3.43 mmol), Pd/C (36 mg, 0.34 mmol), and EtOH (30 mL) was evacuated and backfilled with $H_2$ five times. The mixture was allowed to stir at room temperature for 2 h.

The mixture was filtered through celite washing with EtOAc/MeOH and concentrated to afford tert-butyl 9-(4-aminophenyl)-3,9-diazaspiro[5.5]undecane-3-carboxylate (871 mg, 73.5%). LCMS: $C_{20}H_{31}N_3O_2$ requires 345, found: m/z=346 [M+H]$^+$.

Synthesis of tert-butyl(R)-9-(4-((3-cyano-6-(3-(3-methyl-2-oxoimidazolidin-1-yl)piperidin-1-yl)pyrazin-2-yl)amino)phenyl)-3,9-diazaspiro[5.5]undecane-3-carboxylate A mixture of tert-butyl 9-(4-aminophenyl)-3,9-diazaspiro[5.5]undecane-3-carboxylate (162.6 mg, 0.47 mmol), 3-chloro-5-[(3R)-3-(3-methyl-2-oxoimidazolidin-1-yl)piperidin-1-yl]pyrazine-2-carbonitrile (151 mg, 0.47 mmol), Pd(OAc)$_2$ (34.9 mg, 0.16 mmol), [2'-(diphenylphosphanyl)-[1,1'-binaphthalen]-2-yl]diphenylphosphane (96.7 mg, 0.16 mmol), and cesium carbonate (460 mg, 1.41 mmol) was degassed and backfilled with N$_2$ five times. The mixture was allowed to stir at 100° C. for 90 min. The mixture was filtered through celite washing with MeOH/EtOAc, concentrated, and purified by MPLC (0-100% EtOAc in CH$_2$Cl$_2$) to afford tert-butyl 9-[4-({3-cyano-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (204 mg, 68.8%). LCMS: C$_{34}$H$_{47}$N$_9$O$_3$ requires 629, found: m/z=630 [M+H]$^+$.

Synthesis of tert-butyl (R)-9-(4-((3-carbamoyl-6-(3-(3-methyl-2-oxoimidazolidin-1-yl)piperidin-1-yl)pyrazin-2-yl)amino)phenyl)-3,9-diazaspiro[5.5]undecane-3-carboxylate H$_2$O$_2$ (30% in H$_2$O, 0.55 mL, 0.05 mmol) was added to a mixture of tert-butyl 9-[4-({3-cyano-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (204 mg, 0.32 mmol), cesium carbonate (106 mg, 0.32 mmol), MeOH (6 mL), and DMSO (0.3 mL). The mixture was allowed to stir at room temperature for 30 min. The mixture was concentrated. EtOAc was added and the organic phase was washed with H$_2$O and brine. The organic layer was dried with MgSO$_4$, filtered, concentrated, and purified by MPLC (0-10% MeOH in CH$_2$Cl$_2$) to afford tert-butyl 9-[4-({3-carbamoyl-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (95.00 mg, 45%). LCMS: C$_{34}$H$_{49}$N$_9$O$_4$ requires 647, found: m/z=648 [M+H]$^+$.

Synthesis of (R)-3-((4-(3,9-diazaspiro[5.5]undecan-3-yl)phenyl)amino)-5-(3-(3-methyl-2-oxoimidazolidin-1-yl)piperidin-1-yl)pyrazine-2-carboxamide A mixture of tert-butyl 9-[4-({3-carbamoyl-6-[(3R)-3-(3-methyl-2-oxoimidazolidin-1-yl)piperidin-1-yl]pyrazin-2-yl}amino)phenyl]-3,9-diazaspiro[5.5]undecane-3-carboxylate (25 mg, 0.04 mmol), CH$_2$Cl$_2$ (1 mL), and TFA (0.2 mL) was allowed to stir at room temperature for 1 h. The volatiles were removed to afford 3-[(4-{3,9-diazaspiro[5.5]undecan-3-yl}phenyl)amino]-5-[(3R)-3-(3-methyl-2-oxoimidazolidin-1-yl)piperidin-1-yl]pyrazine-2-carboxamide (21.00 mg, 99.4%). LCMS: C$_{29}$H$_{41}$N$_9$O$_2$ requires 547, found: m/z=548 [M+H]$^+$.

Example 9

General Procedure B

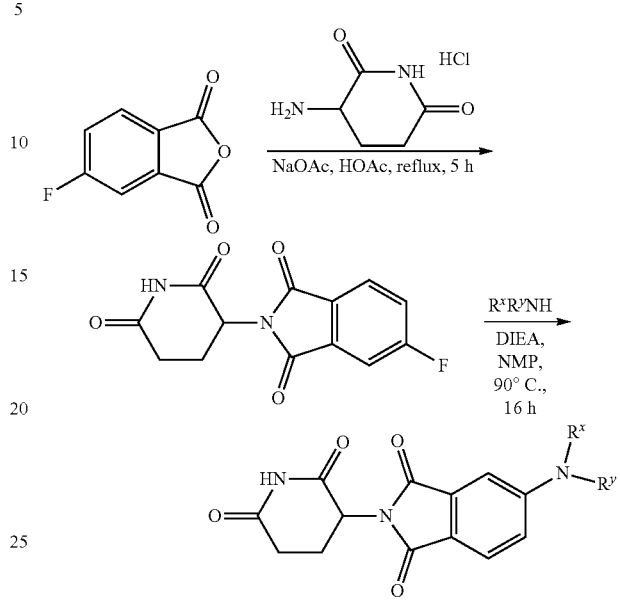

Step 1: Synthesis of 2-(2,6-dioxopiperidin-3-yl)-5-fluoroisoindoline-1,3-dione

A mixture of 5-fluoro-1,3-dihydro-2-benzofuran-1,3-dione (5.0 g, 30.10 mmol), 3-aminopiperidine-2,6-dione hydrochloride (6.9 g, 42.14 mmol), and NaOAc (4.2 g, 51.17 mmol) in HOAc (50 mL) was stirred at 120° C. for 5 h before concentration under vacuum. The residue was washed with water and the solid was collected by filtration. The crude product was washed with water twice, ethyl acetate twice, and dried in an oven to afford 2-(2,6-dioxopiperidin-3-yl)-5-fluoroisoindoline-1,3-dione (7.7 g, 92%) as a light brown solid. $^1$H NMR (300 MHz, DMSO-d$_6$) δ 11.16 (s, 1H), 8.03-8.00 (m, 1H), 7.87-7.85 (m, 1H), 7.75-7.70 (m, 1H), 5.19-5.15 (m, 1H), 2.94-2.86 (m, 1H), 2.63-2.48 (m, 2H), 2.12-2.06 (m, 1H). $^{19}$F NMR (300 MHz, DMSO-d$_6$) δ −102.078.

Step 2: Amine Displacement of Aryl Fluoride

To a solution of 2-(2,6-dioxopiperidin-3-yl)-5-fluoro-2,3-dihydro-H-isoindole-1,3-dione (1.0 g, 3.62 mmol) in N-methyl pyrrolidone (10 mL) were added R$^x$R$^y$NH (3.60 mmol) and DIEA (1.4 g, 10.83 mmol). The resulting solution was stirred at 80° C. for 16 h. The reaction mixture was cooled to room temperature and purified by reverse phase flash chromatography to afford the corresponding final product. R$^x$R$^y$ correspond to any amine R groups defined elsewhere herein.

Step 3: Alcohol Oxidation

Dess-Martin periodinane (1.54 mmol) was added to a mixture of the alkyl alcohol (0.77 mmol) and CH$_2$Cl$_2$ (10 mL). The mixture was allowed to stir at room temperature for one hour. CH$_2$Cl$_2$ and aqueous Na$_2$SO$_3$ were added. The organic layer was dried with MgSO$_4$, filtered, concentrated, and purified by MPLC (20-100% EtOAc in hexanes) to afford the aldehyde.

Example 10

Synthesis of 2-(2,6-dioxopiperidin-3-yl)-5-(4-(hydroxymethyl)piperidin-1-yl)isoindoline-1,3-dione

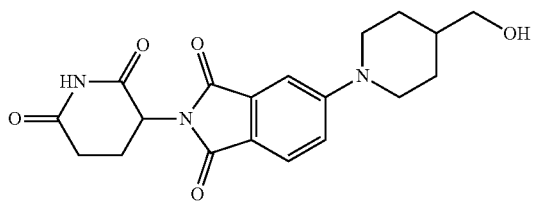 [SMILES: O=C1CCC(N2C(=O)c3ccc(N4CCC(CO)CC4)cc3C2=O)C(=O)N1]

General Procedure B was used with piperidin-4-ylmethanol to afford 2-(2,6-dioxopiperidin-3-yl)-5-(4-(hydroxymethyl)piperidin-1-yl)isoindoline-1,3-dione (938.7 mg, 70%) as a yellow solid. $^1$H NMR (300 MHz, DMSO-d$_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.51 (t, J=5.1 Hz, 1H), 4.07 (d, J=13.2 Hz, 2H), 3.27 (t, J=5.7 Hz, 2H), 2.99-2.80 (m, 3H), 2.62-2.55 (m, 2H), 2.17-1.95 (m, 1H), 1.76-1.67 (m, 3H), 1.24-1.12 (m, 2H). MS (ESI) calc'd for (C$_{19}$H$_2$N$_3$O$_5$) [M+H]$^+$, 372.1; found 372.2.

Example 11

Synthesis of 1-(2-(2,6-dioxopiperidin-3-yl)-1,3-dioxoisoindolin-5-yl)piperidine-4-carbaldehyde

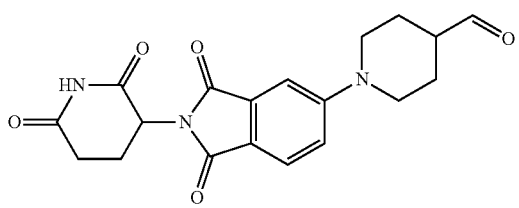 [SMILES: O=CC1CCN(c2ccc3c(c2)C(=O)N(C2CCC(=O)NC2=O)C3=O)CC1]

General Procedure B was used with 2-(2,6-dioxopiperidin-3-yl)-5-(4-(hydroxymethyl)piperidin-1-yl)isoindoline-1,3-dione to afford 1-(2-(2,6-dioxopiperidin-3-yl)-1,3-dioxoisoindolin-5-yl)piperidine-4-carbaldehyde. MS (ESI) calc'd for (C$_{19}$H$_{19}$N$_3$O$_5$) [M+H]$^+$, 370; found 370.

Example 12

Synthesis of 2-(2,6-dioxopiperidin-3-yl)-5-(3-(hydroxymethyl)azetidin-1-yl)isoindoline-1,3-dione

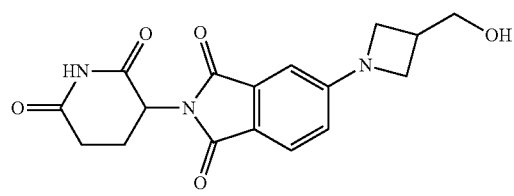 [SMILES: O=C1CCC(N2C(=O)c3ccc(N4CC(CO)C4)cc3C2=O)C(=O)N1]

General Procedure B was used with azetidin-3-ylmethanol hydrochloride to afford 2-(2,6-dioxopiperidin-3-yl)-5-(3-(hydroxymethyl)azetidin-1-yl)isoindoline-1,3-dione (1.85 g, 68%) as a yellow solid. $^1$H NMR (400 MHz, DMSO-d$_6$) δ 11.09 (s, 1H), 7.63 (d, J=8.4 Hz, 1H), 6.76 (d, J=2.0 Hz, 1H), 6.62 (dd, J=8.4, 2.0 Hz, 1H), 5.06 (dd, J=12.4, 5.2 Hz, 1H), 4.86 (t, J 5.2 Hz, 1H), 4.05 (t, J=8.4 Hz, 2H), 3.77 (dd, J=8.4, 5.2 Hz, 2H), 3.60 (t, J=5.2 Hz, 2H), 3.00-2.81 (m, 2H), 2.65-2.53 (m, 2H), 2.06-1.96 (m, 1H). MS (ESI) calc'd for (C$_{17}$H$_{17}$N$_3$O$_5$) [M+H]$^+$, 344.1; found 344.4.

Example 13

Synthesis of 1-(2-(2,6-dioxopiperidin-3-yl)-1,3-dioxoisoindolin-5-yl)azetidine-3-carbaldehyde

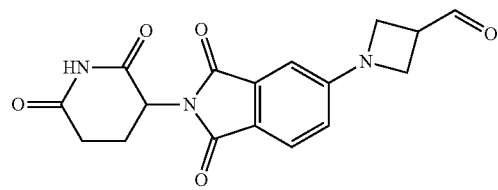 [SMILES: O=CC1CN(c2ccc3c(c2)C(=O)N(C2CCC(=O)NC2=O)C3=O)C1]

General Procedure B was used with 2-(2,6-dioxopiperidin-3-yl)-5-(3-(hydroxymethyl)azetidin-1-yl)isoindoline-1,3-dione to afford 1-(2-(2,6-dioxopiperidin-3-yl)-1,3-dioxoisoindolin-5-yl)azetidine-3-carbaldehyde. MS (ESI) calc'd for (C$_{17}$H$_{15}$N$_3$O$_5$) [M+H]$^+$, 342; found 342.

Example 14

Synthesis of 2-(2,6-dioxopiperidin-3-yl)-5-((S)-3-(hydroxymethyl)pyrrolidin-1-yl)isoindoline-1,3-dione

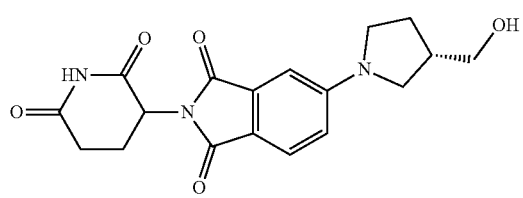 [SMILES: O=C1CCC(N2C(=O)c3ccc(N4CC[C@H](CO)C4)cc3C2=O)C(=O)N1]

General Procedure B was used with (S)-pyrrolidin-3-ylmethanol to afford 2-(2,6-dioxopiperidin-3-yl)-5-((S)-3-(hydroxymethyl)pyrrolidin-1-yl)isoindoline-1,3-dione (643.1 mg, 33%) as a yellow solid. $^1$H NMR (300 MHz, DMSO-d$_6$) δ 11.08 (s, 1H), 7.64 (d, J=8.4 Hz, 1H), 6.89 (d, J=2.1 Hz, 1H), 6.80 (dd, J=8.4, 2.1 Hz, 1H), 5.06 (dd, J=12.9, 5.4 Hz, 1H), 4.78 (t, J 5.4 Hz, 1H), 3.59-3.41 (m, 5H), 3.22-3.17 (m, 1H), 2.95-2.83 (m, 1H), 2.67-2.44 (m, 3H), 2.12-1.88 (m, 2H), 1.87-1.76 (m, 1H). MS (ESI) calc'd for (C$_{18}$H$_{19}$N$_3$O$_5$) [M+H]$^+$, 358.1; found 358.1.

Example 15

Synthesis of (3S)-1-(2-(2,6-dioxopiperidin-3-yl)-1,3-dioxoisoindolin-5-yl)pyrrolidine-3-carbaldehyde

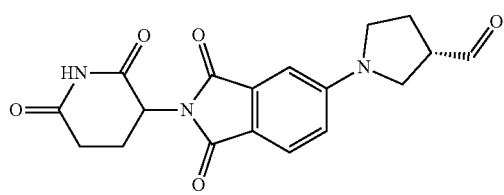 [SMILES: O=C[C@H]1CCN(c2ccc3c(c2)C(=O)N(C2CCC(=O)NC2=O)C3=O)C1]

General Procedure B was used with (2,6-dioxopiperidin-3-yl)-5-((S)-3-(hydroxymethyl)pyrrolidin-1-yl)isoindoline-1,3-dione to afford (3S)-1-(2-(2,6-dioxopiperidin-3-yl)-1,3-dioxoisoindolin-5-yl)pyrrolidine-3-carbaldehyde. MS (ESI) calc'd for ($C_{18}H_{17}N_3O_5$) [M+H]$^+$, 356; found 356.

Example 16

Synthesis of N-(4-(piperidin-4-yl)phenyl)-6-(thiazol-2-yl)imidazo[1,2-a]pyrazin-8-amine

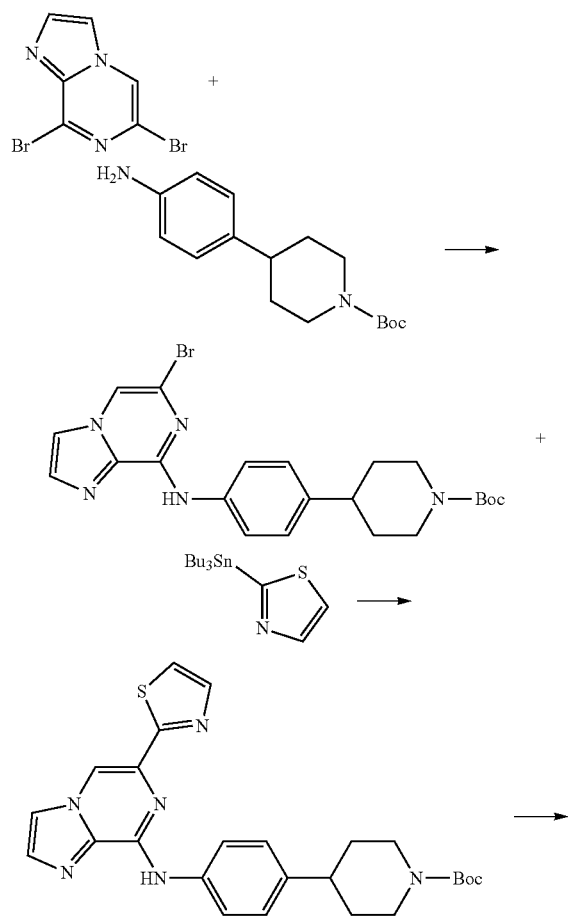

Synthesis of tert-butyl 4-(4-((6-bromoimidazo[1,2-a]pyrazin-8-yl)amino)phenyl)piperidine-1-carboxylate

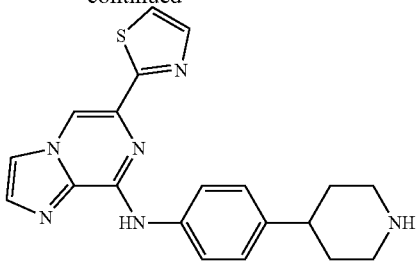

A mixture of 6,8-dibromoimidazo[1,2-a]pyrazine (1 g), tert-butyl 4-(4-aminophenyl)piperidine-1-carboxylate (1.1 g), DIEA (1.3 mL), and iPrOH (10 mL) was allowed to stir at 80° C. overnight. The mixture was poured into water, and the mixture was filtered. After washing with water and Et$_2$O, tert-butyl 4-(4-((6-bromoimidazo[1,2-a]pyrazin-8-yl)amino)phenyl)piperidine-1-carboxylate (0.70 g, 41%) was obtained. LCMS: $C_{22}H_{26}BrN_5O_2$ requires 471, found: m/z=472 [M+H]$^+$.

Synthesis of tert-butyl 4-(4-((6-(thiazol-2-yl)imidazo[1,2-a]pyrazin-8-yl)amino)phenyl)piperidine-1-carboxylate A mixture of tert-butyl 4-[4-({6-bromoimidazo[1,2-a]pyrazin-8-yl}amino)phenyl]piperidine-1-carboxylate (50 mg), tetrakis(triphenylphosphine)palladium(0)(25 mg), sodium carbonate (23 mg), 2-(tributylstannyl)-1,3-thiazole (40 mg) and 1,4-dioxane (1 mL) was allowed to stir at 50° C. overnight. EtOAc and H$_2$O were added, and the organic layer was dried with MgSO$_4$, filtered, concentrated, and purified by HPLC (5-95 MeCN in H$_2$O) to afford tert-butyl 4-(4-((6-(thiazol-2-yl)imidazo[1,2-a]pyrazin-8-yl)amino) phenyl)piperidine-1-carboxylate (24 mg, 48%).

Synthesis of N-(4-(piperidin-4-yl)phenyl)-6-(thiazol-2-yl)imidazo[1,2-a]pyrazin-8-amine A mixture of tert-butyl 4-(4-((6-(thiazol-2-yl)imidazo[1,2-a]pyrazin-8-yl)amino)phenyl)piperidine-1-carboxylate (24 mg), TFA (0.5 mL) and CH$_2$Cl$_2$ (0.5 mL) was allowed to stir at rt for one hour. The volatiles were removed to afford N-(4-(piperidin-4-yl)phenyl)-6-(thiazol-2-yl)imidazo[1,2-a]pyrazin-8-amine.

Example 17

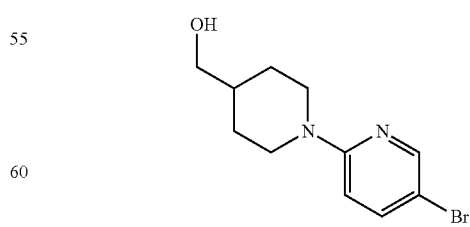

[1-(5-bromopyridin-2-yl)piperidin-4-yl]methanol

To a mixture of 5-bromo-2-fluoropyridine (559 mg, 3.18 mmol) in DMF (7.00 mL) was added piperidin-4-ylmethanol (366 mg, 3.18 mmol) and potassium carbonate (0.88 g, 6.35 mmol). The mixture was stirred at 90° C. overnight. The mixture was diluted with water and extracted with ethyl acetate. The organic layer was washed with water, dried over anhydrous $Na_2SO_4$, and concentrated in vacuo. The crude residue was purified by flash chromatography on a 40 g column eluted with zero to 10% MeOH/DCM to provide [1-(5-bromopyridin-2-yl)piperidin-4-yl]methanol (0.841 g, 97.6%). LCMS: $C_{11}H_{15}BrN_2O$ requires 270, found: m/z=271 $[M+H]^+$.

Example 18

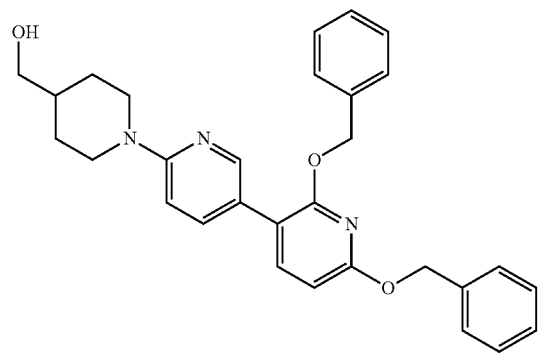 [SMILES: OCC1CCN(c2ccc(-c3ccc(OCc4ccccc4)nc3OCc3ccccc3)cn2)CC1]

{1-[2',6'-bis(benzyloxy)-[3,3'-bipyridin]-6-yl]piperidin-4-yl}methanol

[1-(5-bromopyridin-2-yl)piperidin-4-yl]methanol (93.0 mg, 0.34 mmol), 2,6-bis(benzyloxy)pyridin-3-ylboronic acid (172 mg, 0.51 mmol), tetrakis(triphenylphosphine)palladium(0) (39.6 mg, 0.03 mmol), and potassium carbonate (94.8 mg, 0.69 mmol) were deposited in a microwave vial in THF (3.00 mL) and water (1.00 mL). The mixture was microwaved at 120° C. for 40 minutes. The organic layer was loaded directly onto a silica gel cartridge and the mixture was purified by flash chromatography on a 24 g column eluted with zero to 10% MeOH/DCM. The resulting material was repurified by flash chromatography on a 24 g column eluted with zero to 50% ethylacetate/DCM to provide {1-[2',6'-bis(benzyloxy)-[3,3'-bipyridin]-6-yl]piperidin-4-yl}methanol (0.097 g, 58.7%). LCMS: $C_3H_{31}N_3O_3$ requires 481, found: m/z=482 $[M+H]^+$.

Example 19

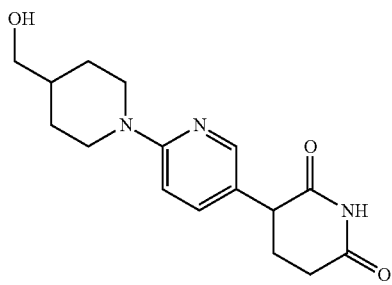 [SMILES: O=C1CCC(c2ccc(N3CCC(CO)CC3)nc2)C(=O)N1]

3-{6-[4-(hydroxymethyl)piperidin-1-yl]pyridin-3-yl}piperidine-2,6-dione

To a mixture of {1-[2',6'-bis(benzyloxy)-[3,3'-bipyridin]-6-yl]piperidin-4-yl}methanol (97.0 mg, 0.20 mmol) in ethanol (3.00 mL) was added 10% palladium on carbon (97.0 mg). The mixture was stirred under an atmosphere of $H_2$ for three hours. The mixture was filtered through a pad of celite which was washed with 50 mL DCM. The resulting solution was concentrated then purified by flash chromatography on a 24 g column eluted with zero to 20% MeOH/DCM to provide 3-{6-[4-(hydroxymethyl)piperidin-1-yl]pyridin-3-yl}piperidine-2,6-dione (0.0214 g, 34.3%). LCMS: $C_{16}H_{21}N_3O_3$ requires 303, found: m/z=304 $[M+H]^+$.

Example 20

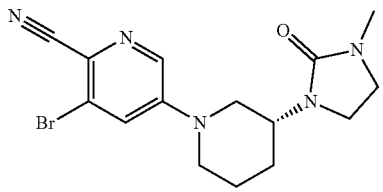 [SMILES: CN1CCN([C@@H]2CCCN(c3cnc(C#N)c(Br)c3)C2)C1=O]

3-bromo-5-[(3R)-3-(3-methyl-2-oxoimidazolidin-1-yl)piperidin-1-yl]pyridine-2-carbonitrile 1-methyl-3-[(3R)-piperidin-3-yl]imidazolidin-2-one trifluoroacetate (1.40 g, 4.72 mmol), 3-bromo-5-fluoropyridine-2-carbonitrile (948 mg, 4.72 mmol), and N,N-diisopropylethylamine (2.46 mL, 1.83 g, 14.2 mmol) were stirred in DMF (12.00 mL) at 90° C. for two hours. The mixture was poured into ice water. The mixture was extracted with ethyl acetate. The organic layer was washed twice with water, dried over $Na_2SO_4$, and concentrated in vacuo. The crude residue was purified by flash chromatography on a 40 g column eluted with zero to 10% MeOH/DCM to provide 3-bromo-5-[(3R)-3-(3-methyl-2-oxoimidazolidin-1-yl)piperidin-1-yl]pyridine-2-carbonitrile (828 mg, 48.2%). LCMS: $C_{15}H_{18}BrN_5O$ requires 363, found: m/z=364 $[M+H]^+$.

Example 21

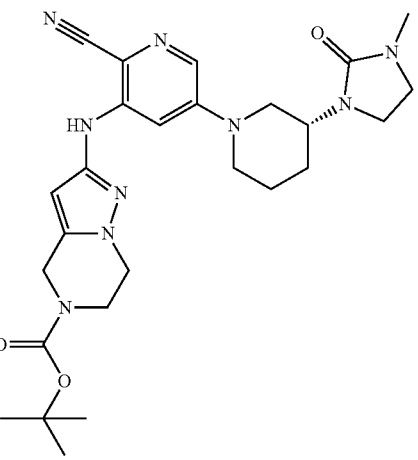

3-bromo-5-[(3R)-3-(3-methyl-2-oxoimidazolidin-1-yl)piperidin-1-yl]pyridine-2-carbonitrile 3-bromo-5-[(3R)-3-(3-methyl-2-oxoimidazolidin-1-yl)piperidin-1-yl]pyridine-2-carbonitrile (283 mg, 0.78 mmol), tert-butyl 2-amino-4H,6H,7H-pyrazolo[1,5-a]pyrazine-5-carboxylate (185 mg, 0.78 mmol), and cesium carbonate (1.01 g, 3.11 mmol) were suspended in dioxane (6.00 mL). A vacuum was applied on the vial until the contents bubbled, and the headspace was backfilled with argon for five cycles. (Acetyloxy)palladio acetate (34.89 mg, 0.16 mmol) and BINAP (96.8 mg, 0.16 mmol) were added. A vacuum was applied on the vial until the contents bubbled, and the headspace was backfilled with argon for five cycles. The mixture was heated at 90° C. overnight. The mixture was cooled, diluted with DCM, and filtered. The resulting solution was concentrated in vacuo then purified by flash chromatography on a 40 g column eluted with zero to 10% MeOH/DCM to provide tert-butyl 2-({2-cyano-5-[(3R)-3-(3-methyl-2-oxoimidazolidin-1-yl)piperidin-1-yl]pyridin-3-yl}amino)-4H,6H,7H-pyrazolo[1,5-a]pyrazine-5-carboxylate (253 mg, 62.4%). LCMS: $C_{26}H_{35}N_9O_3$ requires 521, found: m/z=522 [M+H]$^+$.

Example 22

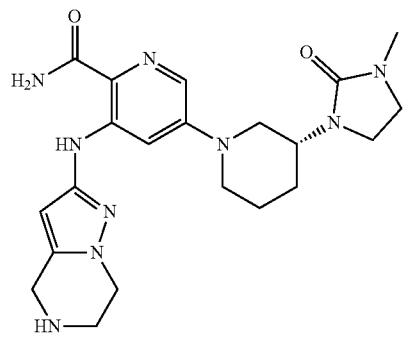 [SMILES: CN1CCN([C@@H]2CCCN(c3cnc(C(N)=O)c(Nc4cc5n(n4)CCNC5)c3)C2)C1=O]

5-[(3R)-3-(3-methyl-2-oxoimidazolidin-1-yl)piperidin-1-yl]-3-{4H,5H,6H,7H-pyrazolo[1,5-a]pyrazin-2-ylamino}pyridine-2-carboxamide trifluoroacetate tert-butyl 2-({2-carbamoyl-5-[(3R)-3-(3-methyl-2-oxoimidazolidin-1-yl)piperidin-1-yl]pyridin-3-yl}amino)-4H,6H,7H-pyrazolo[1,5-a]pyrazine-5-carboxylate (20.00 mg, 0.04 mmol) was stirred in DCM (1.00 mL) and hydrogen chloride (4M in dioxane, 1.00 mL, 0.15 g, 4.00 mmol) for one hour. The mixture was concentrated to provide 5-[(3R)-3-(3-methyl-2-oxoimidazolidin-1-yl)piperidin-1-yl]-3-{4H,5H,6H,7H-pyrazolo[1,5-a]pyrazin-2-ylamino}pyridine-2-carboxamide trifluoroacetate (0.021 g, 100%). LCMS: $C_{21}H_{29}N_9O_2$ requires 439, found: m/z=440 [M+H]$^+$.

Example 23

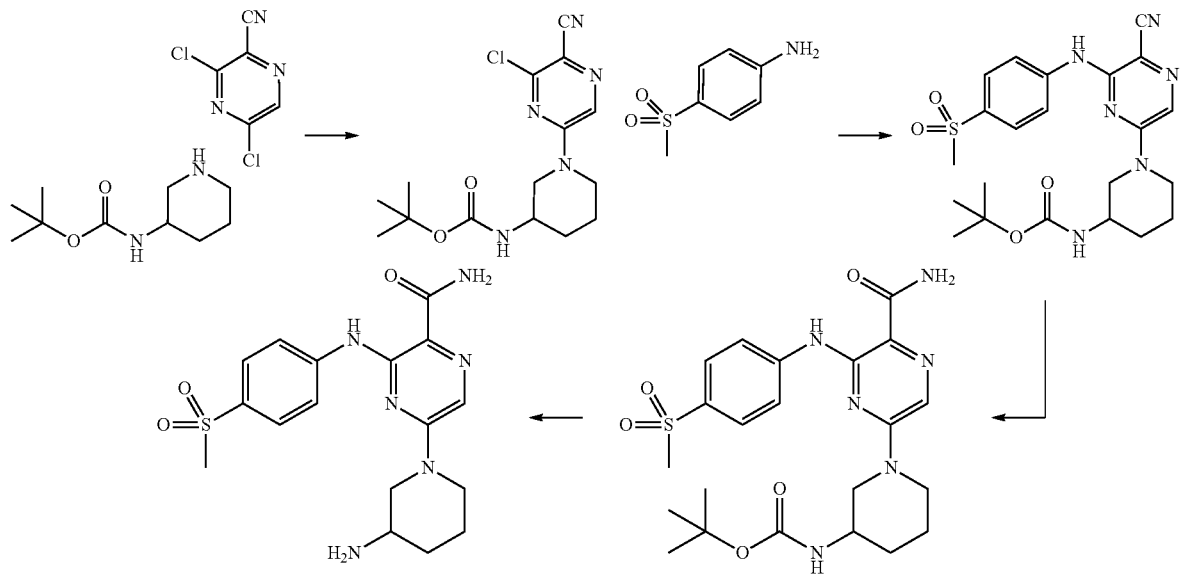

A:

A mixture of of 3,5-dichloropyrazine-2-carbonitrile (1.5 g, 8.62 mmol), t-butyl N-piperidinylcarbamate (2.07 g, 10.4 mmol), and i-Pr$_2$NEt (3 mL, 17.2 mmol) was dissolved in DMF (10 mL) and stirred for 1.5 h at r. The reaction mixture was diluted with EtOAc (20 mL) and washed with H$_2$O (2×30 mL) before being concentrated to a yellow oil. Flash chromatography (SiO$_2$, 10→15% CH$_2$Cl$_2$/EtOAc) afforded tert-butyl (R)-(1-(6-chloro-5-cyanopyrazin-2-yl)piperidin-3-yl)carbamate (2.5 g, 86%) as a white solid. LCMS: $C_1H_{20}ClN_5O_2$ requires: 338, found: m/z=339 [M+H]$^+$.

B:

A mixture of tert-butyl (R)-(1-(6-chloro-5-cyanopyrazin-2-yl)piperidin-3-yl)carbamate (800 mg, 2.37 mmol), 4-methylsulfonylaniline (405 mg, 2.37 mmol), (acetyloxy)palladio acetate (106 mg, 0.47 mmol), BINAP (295 mg, 0.47 mmol), and $Cs_2CO_3$ (3.09 g, 9.47 mmol) were suspended in DCE (35 mL) and the mixture was degassed under a stream of $N_2$ for five min. The reaction mixture was heated to 110° C. for 2.5 h before being cooled and diluted with EtOAc (50 mL), filtered over celite, and concentrated. Purification ($SiO_2$, 10→65% EtOAc/$CH_2Cl_2$) afforded tert-butyl (R)-(1-(5-cyano-6-((4-(methylsulfonyl)phenyl)amino)pyrazin-2-yl)piperidin-3-yl)carbamate (760 mg, 68%). LCMS: $C_{22}H_{28}N_6O_4S$ requires: 472, found: m/z=473 $[M+H]^+$.

C:

tert-butyl N-[(3R)-1-{5-cyano-6-[(4-methanesulfonylphenyl)amino]pyrazin-2-yl}piperidin-3-yl]carbamate (760 mg, 1.61 mmol) was dissolved in MeOH (5 mL) and NaOH (100 mg) and $H_2O_2$ (33% aq, one mL) were added. The reaction mixture was stirred for 20 min before being diluted with ACN (2 mL) and stirred for an additional 10 min. An exotherm was observed upon ACN addition. The mixture was concentrated before being diluted with 50 mL EtOAc and the organic phase was washed with $H_2O$ (2×15 mL). The combined organic extracts were dried ($MgSO_4$), filtered, and concentrated to afford tert-butyl (R)-(1-(5-carbamoyl-6-((4-(methylsulfonyl)phenyl)amino)pyrazin-2-yl)piperidin-3-yl)carbamate after purification ($SiO_2$, 0→10% MeOH/$CH_2Cl_2$). LCMS: $C_{22}H_{30}N_6O_5S$ requires: 490, found: m/z=491 $[M+H]^+$.

D:

tert-butyl N-[(3R)-1-{5-carbamoyl-6-[(4-methanesulfonylphenyl)amino]pyrazin-2-yl}piperidin-3-yl]carbamate was dissolved in $CH_2Cl_2$ (5 mL) and TFA (2 mL) was added at rt. After one h the reaction mixture was concentrated to a thick oil before being dissolved in ACN/$H_2O$ and lyophilized to afford (R)-5-(3-aminopiperidin-1-yl)-3-((4-(methylsulfonyl)phenyl)amino)pyrazine-2-carboxamide (402 mg, 44%, 3 steps) as a TFA salt. LCMS: $C_{17}H_{22}N_6O_3S$ requires: 390, found: m/z=391 $[M+H]^+$.

Example 24

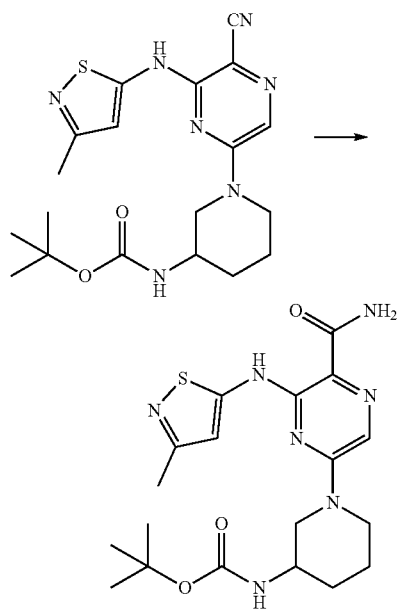

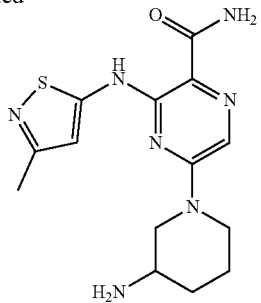

Procedure B was followed to afford tert-butyl (R)-(1-(5-cyano-6-((3-methylisothiazol-5-yl)amino)pyrazin-2-yl)piperidin-3-yl)carbamate (5.6 g, 89%). LCMS: $C_{19}H_{25}N_7O_2S$ requires: 415, found: m/z=416 $[M+H]^+$.

Procedure C was followed to afford tert-butyl (R)-(1-(5-carbamoyl-6-((3-methylisothiazol-5-yl)amino)pyrazin-2-yl)piperidin-3-yl)carbamate (850 mg, 82%). LCMS: $C_{19}H_{27}N_7O_3S$ requires: 433, found: m/z=434 $[M+H]^+$.

Procedure D was followed to afford (R)-5-(3-aminopiperidin-1-yl)-3-((3-methylisothiazol-5-yl)amino)pyrazine-2-carboxamide (600 mg, 74%). LCMS: $C_{14}H_{19}N_7OS$ requires: 333, found: m/z=334 $[M+H]^+$.

Example 25

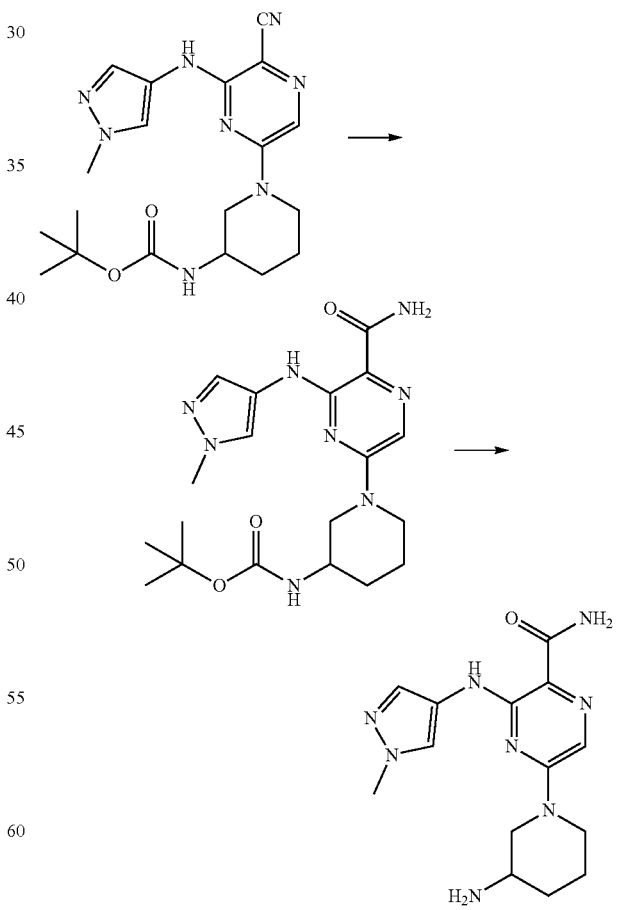

Procedure B was followed to afford tert-butyl (R)-(1-(5-cyano-6-((1-methyl-1H-pyrazol-4-yl)amino)pyrazin-2-yl)piperidin-3-yl)carbamate (941 mg, 80%). LCMS: $C_{19}H_{26}N_8O_2$ requires: 398, found: m/z=399 $[M+H]^+$.

Procedure C was followed to afford tert-butyl (R)-(1-(5-carbamoyl-6-((1-methyl-1H-pyrazol-4-yl)amino)pyrazin-2-yl)piperidin-3-yl)carbamate (297 mg, 95%). LCMS: $C_{19}H_{28}N_8O_3$ requires: 416, found: m/z=417 [M+H]$^+$.

Procedure D was followed to afford (R)-5-(3-aminopiperidin-1-yl)-3-((1-methyl-1H-pyrazol-4-yl)amino)pyrazine-2-carboxamide. LCMS: $C_{14}H_{20}N_8O$ requires: 316, found: m/z=317 [M+H]$^+$.

Procedure D was followed to afford (R)-5-(3-aminopiperidin-1-yl)-3-((1-methyl-1H-pyrazol-4-yl)amino)pyrazine-2-carboxamide. LCMS: $C_{14}H_{20}N_8O$ requires: 4=316, found: m/z=317 [M+H]$^+$.

Example 26

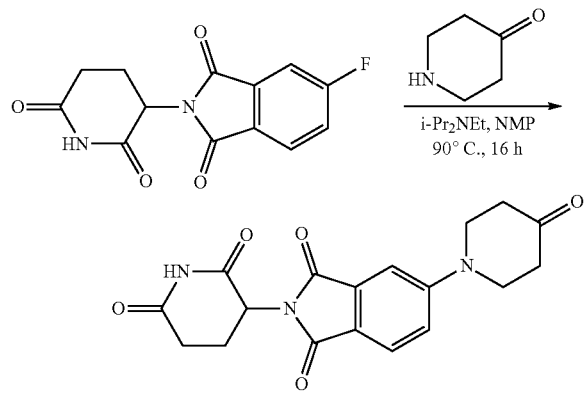

E:

2-(2,6-dioxopiperidin-3-yl)-5-fluoroisoindole-1,3-dione (500 mg, 1.81 mmol) and 4-piperidinone hydrochloride (245 mg, 1.81 mmol) were dissolved in NMP (3 mL) and i-Pr$_2$NEt (703 mg, 5.43 mmol) was added. The mixture was heated at 90° C. for 16 h before being diluted with EtOAc. The organic phase was washed (2×H$_2$O, sat. aq. NaCl), dried (Na$_2$SO$_4$), concentrated, and purified (SiO$_2$, 10→100% EtOAc/hexanes) to provide 2-(2,6-dioxopiperidin-3-yl)-5-(4-oxopiperidin-1-yl)isoindole-1,3-dione (131 mg, 20%). LCMS: $C_1H_{17}N_3O_5$ requires 355, found: m/z=356 [M+H]$^+$.

Example 27

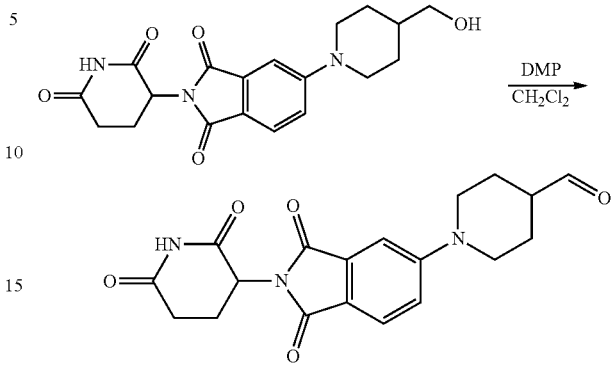

Procedure E was used with piperidin-4-ylmethanol to afford 2-(2,6-dioxopiperidin-3-yl)-5-(4-(hydroxymethyl)piperidin-1-yl)isoindoline-1,3-dione (939 mg, 70%) as a yellow solid. $^1$H NMR (300 MHz, DMSO-d$_6$) δ 11.09 (s, 1H), 7.65 (d, J=8.4 Hz, 1H), 7.30 (d, J=2.4 Hz, 1H), 7.23 (dd, J=8.4, 2.4 Hz, 1H), 5.07 (dd, J=12.6, 5.4 Hz, 1H), 4.51 (t, J=5.1 Hz, 1H), 4.07 (d, J 13.2 Hz, 2H), 3.27 (t, J=5.7 Hz, 2H), 2.99-2.80 (m, 3H), 2.62-2.55 (m, 2H), 2.17-1.95 (m, 1H), 1.76-1.67 (m, 3H), 1.24-1.12 (m, 2H). LCMS: $C_{19}H_{21}N_3O_5$ requires: 371, found: m/z=372 [M+H]$^+$.

F:

2-(2,6-dioxopiperidin-3-yl)-5-[4-(hydroxymethyl)piperidin-1-yl]isoindole-1,3-dione (1.50 g, 4.04 mmol) was dissolved in CH$_2$Cl$_2$ (15 mL) and 1,1-bis(acetyloxy)-3-oxo-1lambda5,2-benziodaoxol-1-yl acetate (1.88 g, 4.44 mmol) was added in one portion at rt. After five hours, the reaction mixture was diluted with NaHCO$_3$ (2 mL sat. aq.), Na$_2$S$_2$O$_3$ (sat. aq.) was added, and the mixture was stirred for 30 min. The organic phase was removed. The aqueous layer was extracted (2×20 mL CH$_2$Cl$_2$) and the combined organic phases were dried (Na$_2$SO$_4$), filtered, and concentrated. Purification (SiO$_2$, 2-6% MeOH in CH$_2$Cl$_2$) afforded 1-[2-(2,6-dioxopiperidin-3-yl)-1,3-dioxoisoindol-5-yl]piperidine-4-carbaldehyde (1.20 g, 80%). LCMS: $C_{19}H_{19}N_3O_5$ requires: 369, found: m/z=370 [M+H]$^+$.

Example 28

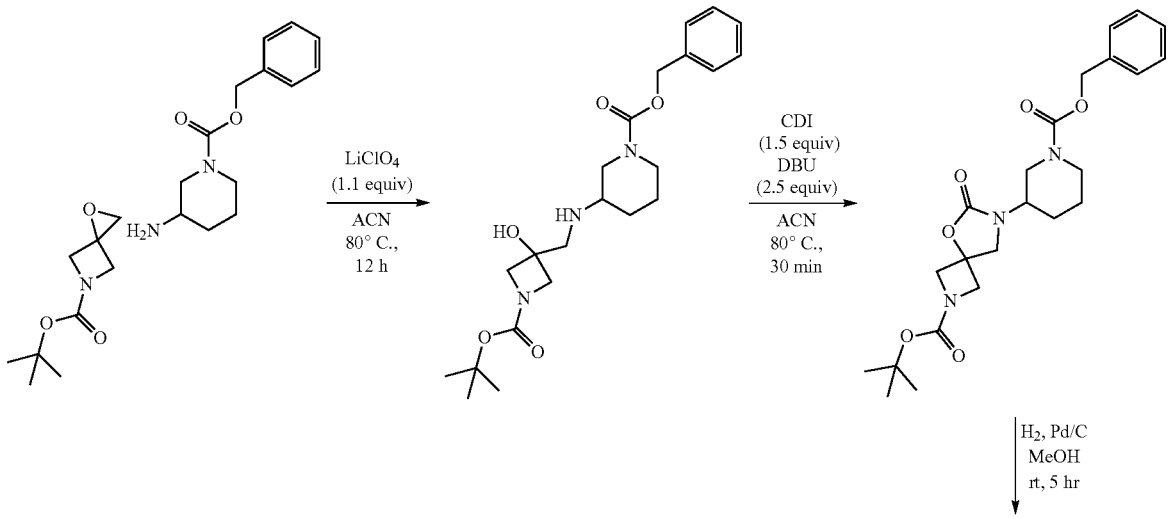

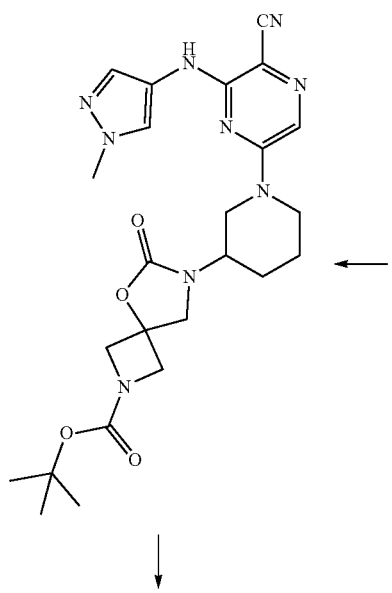
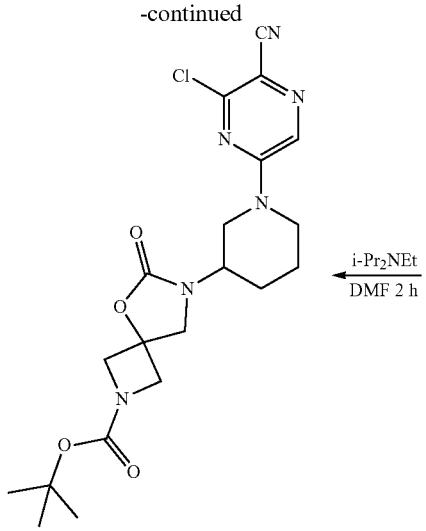
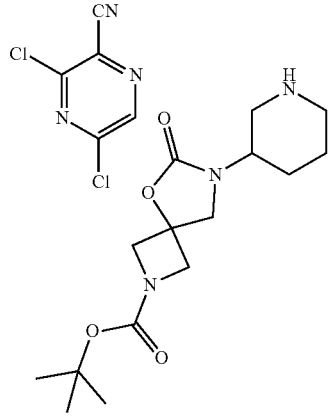
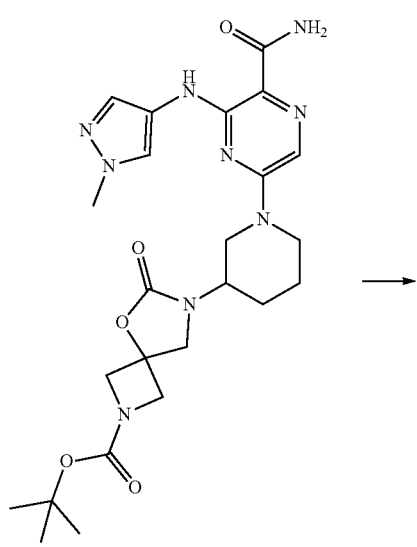
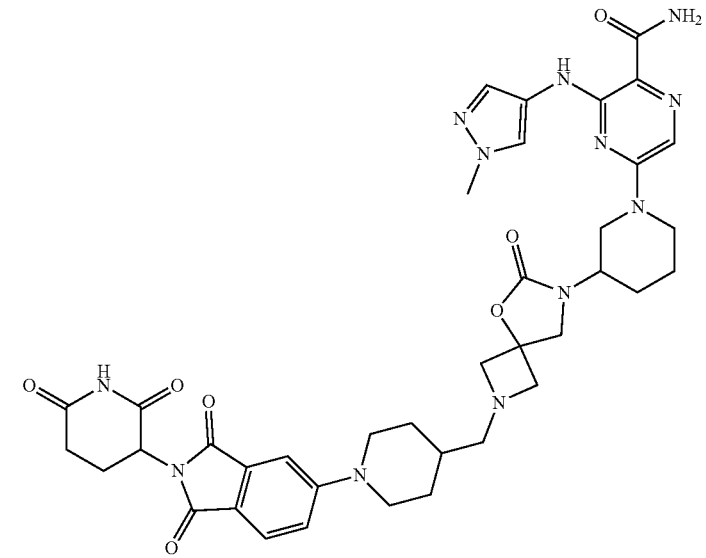

(R)-3-amino-1-N-Cbz-piperidine (253 mg, 1.08 mmol) and LiClO$_4$ (126 mg, 1.19 mmol) were added sequentially to a solution of tert-butyl 1-oxa-5-azaspiro[2.3]hexane-5-carboxylate (200 mg, 1.08 mmol) in ACN (10 mL). After stirring at 80° C. for 16 h the reaction mixture was concentrated under reduced pressure. Purification (SiO$_2$, 0-5% MeOH/CH$_2$Cl$_2$) afforded the desired product (441 mg, 97%). LCMS: C$_{22}$H$_{33}$N$_3$O$_5$ requires: 419, found: m/z=420 [M+H]$^+$.

CDI (255 mg, 1.57 mmol) and DBU (392 µL, 2.62 mmol) were added sequentially to a solution of benzyl (3R)-3-({[1-(tert-butoxycarbonyl)-3-hydroxyazetidin-3-yl]methyl}amino)piperidine-1-carboxylate (440 mg, 1.05 mmol) in ACN (2.6 mL). After stirring at 80° C. for 30 min, the reaction mixture was concentrated under reduced pressure. Purification (SiO$_2$, 0→5% MeOH/CH$_2$Cl$_2$) afforded the desired product (363 mg, 78%). LCMS: C$_{23}$H$_{31}$N$_3$O$_6$ requires: 445, found: m/z=446 [M+H]$^+$.

A solution of tert-butyl 7-[(3R)-1-[(benzyloxy)carbonyl]piperidin-3-yl]-6-oxo-5-oxa-2,7-diazaspiro[3.4]octane-2-carboxylate (363 mg, 0.81 mmol, 1 equiv) in MeOH (8.1 mL) was stirred with Pd/C (36.3 mg, 10 wt %) under a balloon of H$_2$. After stirring for 2 h, the reaction mixture was filtered through Celite and concentrated under reduced pressure to afford tert-butyl (R)-6-oxo-7-(piperidin-3-yl)-5-oxa-2,7-diazaspiro[3.4]octane-2-carboxylate. LCMS: C$_{15}$H$_{25}$N$_3$O$_4$ requires: 311, found: m/z=312 [M+H]$^+$.

Procedure A was followed to afford tert-butyl 7-[(3R)-1-(6-chloro-5-cyanopyrazin-2-yl)piperidin-3-yl]-6-oxo-5-oxa-2,7-diazaspiro[3.4]octane-2-carboxylate (364 mg, 95%, 2 steps). LCMS: C$_{20}$H$_{25}$ClN$_6$O$_4$ requires: 448, found: m/z=449 [M+H]$^+$.

Procedure B was followed to afford tert-butyl (R)-7-(1-(5-cyano-6-((1-methyl-1H-pyrazol-4-yl)amino)pyrazin-2-yl)piperidin-3-yl)-6-oxo-5-oxa-2,7-diazaspiro[3.4]octane-2-carboxylate (131 mg, 56%). LCMS: $C_{24}H_{31}N_9O_4$ requires: 509, found: m/z=510 [M+H]$^+$.

Procedure C was followed to afford tert-butyl (R)-7-(1-(5-carbamoyl-6-((1-methyl-1H-pyrazol-4-yl)amino)pyrazin-2-yl)piperidin-3-yl)-6-oxo-5-oxa-2,7-diazaspiro[3.4]octane-2-carboxylate (121 mg, 89%). LCMS: $C_{24}H_{33}N_9O_5$ requires: 527, found: m/z=528 [M+H]$^+$.

Compound 211: Procedure D was followed to afford a crude amine that was subjected to Procedure Q to afford 5-[(3R)-3-[2-({1-[2-(2,6-dioxopiperidin-3-yl)-1,3-dioxoisoindol-5-yl]piperidin-4-yl}methyl)-6-oxo-5-oxa-2,7-diazaspiro[3.4]octan-7-yl]piperidin-1-yl]-3-[(1-methylpyrazol-4-yl)amino]pyrazine-2-carboxamide (13.8 mg, 49%, 2 steps). $^1$H NMR (500 MHz, Acetonitrile-d$_3$) δ 10.74 (s, 1H), 8.94 (s, 1H), 7.87 (s, 1H), 7.65 (d, J=8.6 Hz, 1H), 7.50 (s, 1H), 7.47 (d, J=0.8 Hz, 1H), 7.37 (s, 1H), 7.31 (d, J=2.4 Hz, 1H), 7.17 (dd, J=8.7, 2.4 Hz, 1H), 5.79 (s, 1H), 5.07-4.88 (m, 1H), 4.50 (d, J=12.8 Hz, 1H), 4.19 (d, J=13.6 Hz, 1H), 4.00 (d, J=13.1 Hz, 2H), 3.84 (s, 3H), 3.78 (dd, J=19.2, 10.2 Hz, 2H), 3.45 (d, J=8.1 Hz, 1H), 3.39 (d, J=8.1 Hz, 1H), 3.34 (d, J=8.1 Hz, 1H), 3.31-3.25 (m, 1H), 3.17 (dd, J=12.9, 10.4 Hz, 1H), 3.14-3.07 (m, 1H), 2.97 (td, J=12.8, 2.7 Hz, 2H), 2.87-2.63 (m, 3H), 2.39 (d, J=6.9 Hz, 2H), 2.31-2.26 (m, 1H), 2.15-2.08 (m, 1H), 1.91 (dt, J=13.3, 3.5 Hz, 1H), 1.88-1.84 (m, 1H), 1.81 (dd, J=12.1, 3.6 Hz, 3H), 1.70 (tt, J=11.1, 3.9 Hz, 1H), 1.61 (dtd, J=11.6, 7.4, 4.0 Hz, 1H), 0.90 (dq, J=7.8, 6.0, 5.5 Hz, 3H). LCMS: $C_{38}H_{44}N_{12}O_7$ requires: 780, found: m/z=781 [M+H]$^+$.

Example 29

Compound 212

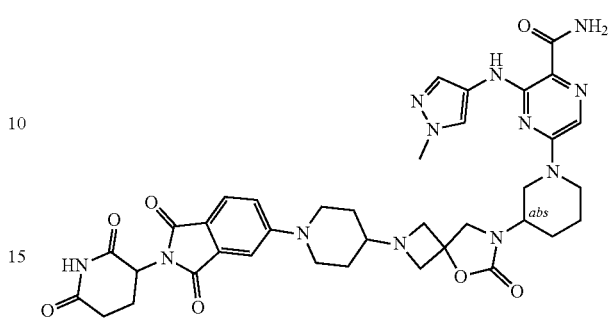

Procedure D was followed to afford a crude amine that was subjected to Procedure Q to afford 5-[(3R)-3-(2-{1-[2-(2,6-dioxopiperidin-3-yl)-1,3-dioxoisoindol-5-yl]piperidin-4-yl}-6-oxo-5-oxa-2,7-diazaspiro[3.4]octan-7-yl)piperidin-1-yl]-3-[(1-methylpyrazol-4-yl)amino]pyrazine-2-carboxamide (9.5 mg, 34%, 2 steps). $^1$H NMR (500 MHz, Acetonitrile-d$_3$) δ 10.71 (s, 1H), 8.90 (s, 1H), 7.84 (s, 1H), 7.63 (d, J=8.5 Hz, 1H), 7.47 (s, 1H), 7.44 (s, 1H), 7.34 (s, 1H), 7.28 (d, J=2.4 Hz, 1H), 7.15 (dd, J=8.6, 2.4 Hz, 1H), 5.75 (s, 1H), 4.93 (dd, J=12.3, 5.4 Hz, 1H), 4.50 (dd, J=13.1, 4.1 Hz, 1H), 4.18 (d, J=13.6 Hz, 1H), 3.81 (s, 3H), 3.81-3.66 (m, 3H), 3.44 (d, J=8.0 Hz, 1H), 3.40 (d, J=8.0 Hz, 1H), 3.34 (d, J=7.9 Hz, 1H), 3.31 (d, J=7.8 Hz, 1H), 3.17-3.00 (m, 4H), 2.83-2.60 (m, 3H), 2.36 (tt, J=8.3, 3.7 Hz, 1H), 2.12-2.05 (m, 2H), 1.96 (s, 1H), 1.87 (dq, J=13.4, 3.3 Hz, 1H), 1.79 (ddd, J=16.5, 10.2, 4.2 Hz, 3H), 1.70-1.59 (m, 1H), 1.33 (qd, J=9.6, 5.0 Hz, 1H), 0.87 (dt, J=11.1, 5.7 Hz, 2H). LCMS: $C_{37}H_{42}N_{12}O_7$ requires: 766, found: m/z=767 [M+H]$^+$.

Example 30

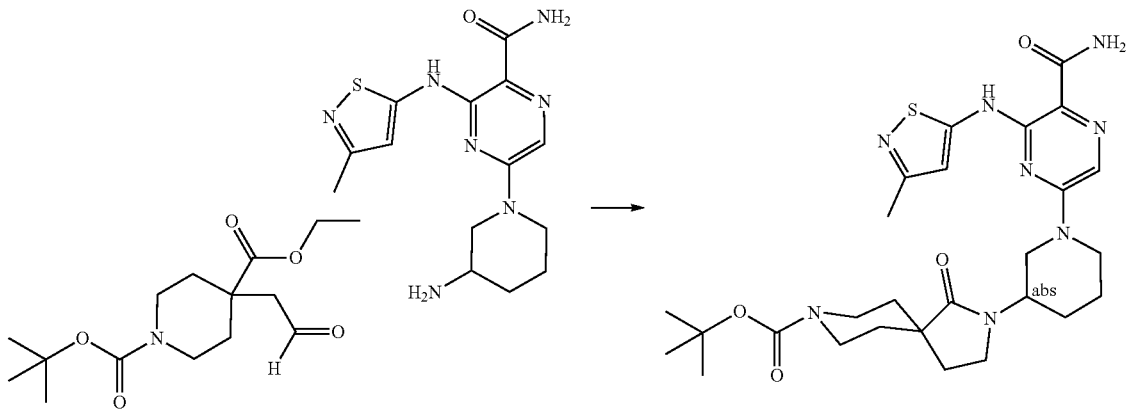

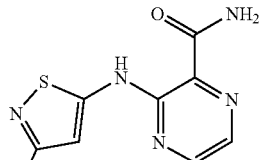

-continued

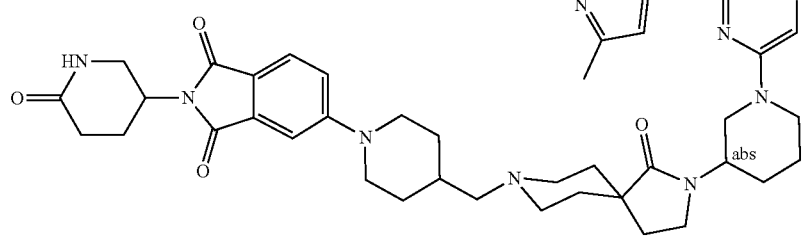

Q:

A mixture of 4-(2-oxoethyl)-piperidine-1,4-dicarboxylic acid 1-tert-butyl ester 4-ethyl ester (23.7 mg, 79 µmol) and (R)-5-(3-aminopiperidin-1-yl)-3-((3-methylisothiazol-5-yl)amino)pyrazine-2-carboxamide (41 mg, 103 µmol, TFA salt) was dissolved in DCE (1 mL) and stirred at rt for 5 min before NaBH(OAc)$_3$ (33 mg, 160 µmol) was added in one portion. After 16 h the mixture was diluted with CH$_2$Cl$_2$ and NaHCO$_3$ (sat. aq.) and the aqueous phase was extracted (3×5 mL CH$_2$Cl$_2$). The combined organic extracts were dried (Na$_2$SO$_4$), filtered, and concentrated. The crude residue was purified (RP-HPLC) to afford tert-butyl 2-[(3R)-1-{5-carbamoyl-6-[(3-methyl-1,2-thiazol-5-yl)amino]pyrazin-2-yl}piperidin-3-yl]-1-oxo-2,8-diazaspiro[4.5]decane-8-carboxylate (40 mg, 68%). LCMS: C$_{27}$H$_{38}$N$_8$O$_4$S requires: 570, found: m/z=571.

Compound 205: Procedure D was followed to afford a crude amine that was subjected to Procedure Q to afford 5-[(3R)-3-[8-({1-[2-(2,6-dioxopiperidin-3-yl)-1,3-dioxoisoindol-5-yl]piperidin-4-yl}methyl)-1-oxo-2,8-diazaspiro[4.5]decan-2-yl]piperidin-1-yl]-3-[(3-methyl-1,2-thiazol-5-yl)amino]pyrazine-2-carboxamide (29.7 mg, 49%). $^1$H NMR (500 MHz, DMSO-d$_6$) δ 12.29 (s, 1H), 11.08 (s, 1H), 7.92 (s, 1H), 7.84 (s, 1H), 7.66 (d, J=8.5 Hz, 1H), 7.58 (s, 1H), 7.32 (d, J=2.3 Hz, 1H), 7.24 (dd, J=8.8, 2.3 Hz, 1H), 6.86 (s, 1H), 5.07 (dd, J=12.8, 5.4 Hz, 1H), 4.46 (s, 2H), 4.05 (d, J=13.0 Hz, 2H), 3.83 (d, J=10.9 Hz, 1H), 3.12 (t, J=12.6 Hz, 1H), 2.98 (t, J=12.4 Hz, 2H), 2.89 (t, J=12.9 Hz, 1H), 2.76 (d, J=9.1 Hz, 2H), 2.71-2.55 (m, 3H), 2.30 (s, 3H), 2.15 (d, J=6.9 Hz, 2H), 2.09-1.94 (m, 3H), 1.94-1.69 (m, 9H), 1.62 (d, J=13.1 Hz, 1H), 1.36 (dd, J=25.7, 12.6 Hz, 2H), 1.25 (s, 1H), 1.15 (d, J=12.5 Hz, 2H). LCMS: C$_{41}$H$_{49}$N$_{11}$O$_6$S requires: 823, found: m/z=824.

Example 31

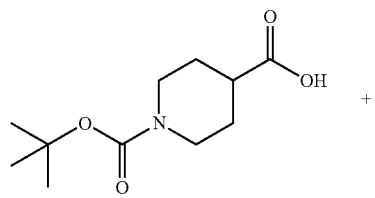 +

-continued

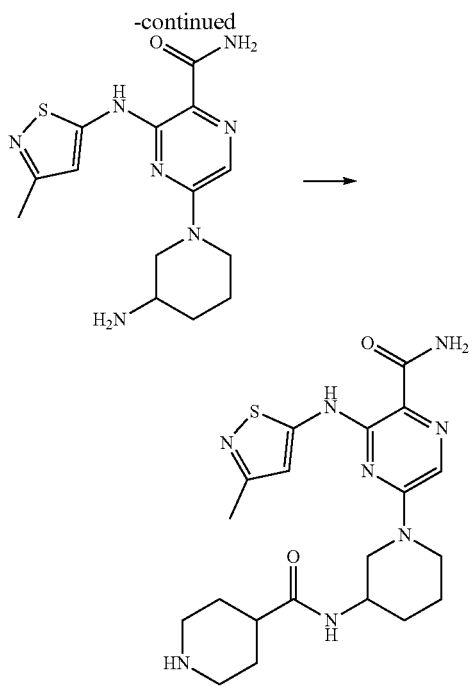

R:

A mixture of 1-(tert-butoxycarbonyl)piperidine-4-carboxylic acid (22.35 mg, 100 µmol) and (1,2,3-benzotriazol-1-yloxy)tris(dimethylamino)phosphanium; hexafluoro-lambda5-phosphanuide (50 mg, 110 µmol), and i-Pr$_2$NEt (65 µL, 370 µmol) was added at rt. After min 5-[(3R)-3-aminopiperidin-1-yl]-3-[(3-methyl-1,2-thiazol-5-yl)amino]pyrazine-2-carboxamide (25.00 mg, 70 µmol) was added and the mixture was stirred for 20 min. The reaction mixture was diluted with H$_2$O and extracted (3×5 mL CH$_2$Cl$_2$). The combined organic extracts were dried (Na$_2$SO$_4$), filtered, and concentrated. The crude residue was purified (SiO$_2$, 0-10% MeOH/CH$_2$Cl$_2$) to afford tert-butyl 4-{[(3R)-1-{5-carbamoyl-6-[(3-methyl-1,2-thiazol-5-yl)amino]pyrazin-2-yl}piperidin-3-yl]carbamoyl}piperidine-1-carboxylate (25 mg, 61%). The product was dissolved in a mixture of CH$_2$Cl$_2$ (1 mL) and TFA (1 mL) and stirred for 30 min before being concentrated to dryness. LCMS: C$_{25}$H$_{36}$N$_8$O$_4$S requires: 544, found: m/z=546.

Example 32

Compound 217

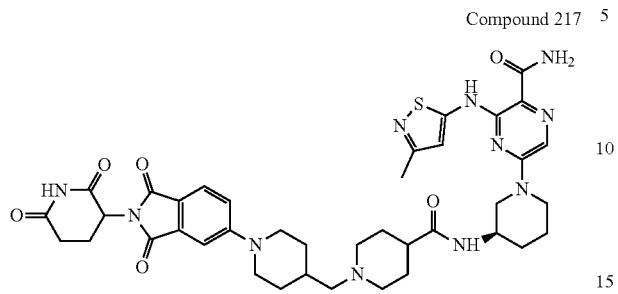

Procedure Q was followed to afford 5-[(3R)-3-[1-({1-[2-(2,6-dioxopiperidin-3-yl)-1,3-dioxoisoindol-5-yl]piperidin-4-yl}methyl)piperidine-4-amido]piperidin-1-yl]-3-[(3-methyl-1,2-thiazol-5-yl)amino]pyrazine-2-carboxamide (18 mg, 19%). $^1$H NMR (500 MHz, DMSO-$d_6$) δ 12.27 (d, J=32.4 Hz, 1H), 11.06 (s, 1H), 8.01 (s, 1H), 7.84 (d, J=18.1 Hz, 1H), 7.63 (d, J=8.4 Hz, 1H), 7.58-7.43 (m, 2H), 7.28 (s, 1H), 7.20 (d, J=9.1 Hz, 1H), 6.85 (d, J=22.5 Hz, 1H), 5.05 (dd, J=12.9, 5.4 Hz, 1H), 4.17 (s, 1H), 4.00 (d, J=14.4 Hz, 2H), 3.74 (d, J=14.2 Hz, 1H), 3.57 (s, 1H), 3.48-3.35 (m, 3H), 3.09-2.77 (m, 3H), 2.72-2.54 (m, 2H), 2.28 (s, 3H), 2.22-2.05 (m, 2H), 2.05-1.90 (m, 3H), 1.80 (s, 3H), 1.70 (d, J=11.6 Hz, 3H), 1.64-1.28 (m, 5H), 1.23 (s, 1H), 1.20-0.96 (m, 3H). LCMS: $C_{38}H_{46}N_{12}O_6S$ requires: 798, found: m/z=799 [M+H]$^+$.

Example 33

Compound 215

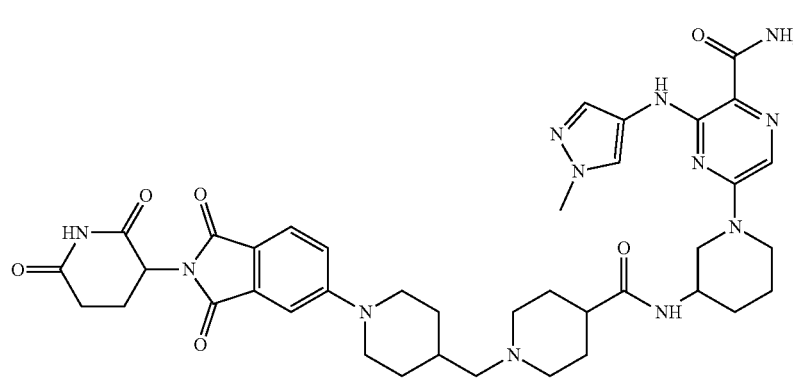

Procedure Q was followed to afford 5-((3R)-3-(1-((1-(2-(2,6-dioxopipendin-3-yl)-1,3-dioxoisoindolin-5-yl)piperidin-4-yl)methyl)piperidine-4-carboxamido)piperidin-1-yl)-3-((1-methyl-1H-pyrazol-4-yl)amino)pyrazine-2-carboxamide (9.7 mg, 33%). $^1$H NMR (500 MHz, DMSO-$d_6$) δ 11.07 (s, 1H), 10.87 (s, 1H), 7.98 (s, 1H), 7.81 (d, J=6.9 Hz, 1H), 7.66 (s, 1H), 7.64 (d, J=8.5 Hz, 1H), 7.55 (s, 1H), 7.48 (s, 1H), 7.30 (d, J=2.1 Hz, 1H), 7.28-7.19 (m, 2H), 5.06 (dd, J=12.8, 5.4 Hz, 1H), 4.29 (s, 1H), 4.04 (d, J=13.0 Hz, 2H), 3.94 (d, J=13.0 Hz, 1H), 3.86 (s, 3H), 3.70 (s, 1H), 3.08 (t, J=10.9 Hz, 1H), 3.01-2.92 (m, 2H), 2.90-2.78 (m, 3H), 2.09 (h, J=6.3 Hz, 3H), 2.00 (dd, J=11.8, 6.0 Hz, 1H), 1.92-1.71 (m, 8H), 1.59 (d, J=24.4 Hz, 7H), 1.12 (d, J=12.5 Hz, 3H). LCMS: $C_{39}H_{48}N_{12}O_6$ requires: 780, found: m/z=781 [M+H]$^+$.

Example 34

Compound 218

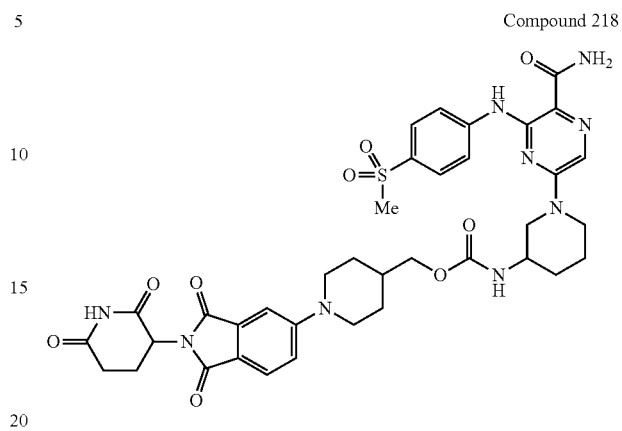

A solution of 2-(2,6-dioxopiperidin-3-yl)-5-(4-(hydroxymethyl)piperidin-1-yl)isoindoline-1,3-dione (37.1 mg, 100 μM) and Et$_3$N (18.1 μL, 13 mg, 130 μmol) in a mixture of CH$_2$Cl$_2$ (1 mL) and NMP (0.1 mL) was cooled to 0° C. before a 100 μL solution of 4-nitrophenyl chloroformate (20.2 mg, 0.10 mmol) was added. After 10 min the ice bath was removed and the reaction mixture was stirred for one hour, diluted with H$_2$O (1 mL) and extracted (2×3 mL CH$_2$Cl$_2$). The combined organic extracts were dried (Na$_2$SO$_4$), filtered, and concentrated. The crude nitrophenyl carbonate and 5-[(3R)-3-aminocyclohexyl]-3-[(4-methanesulfonylphenyl)amino]pyrazine-2-carboxamide (19.5 mg, 50 μmol) was dissolved in DMF (0.5 mL) and Et$_3$N (18.1 μL, 13.1 mg, 130 μmol) was added. The mixture was stirred for one hour at rt before being filtered and purified (RP-HPLC) to afford (1-(2-(2,6-dioxopiperidin-3-yl)-1,3-dioxoisoindolin-5-yl)piperidin-4-yl)methyl ((R)-1-(5-carbamoyl-6-((4-(methylsulfonyl)phenyl)amino)pyrazin-2-yl)piperidin-3-yl)carbamate (17 mg, 39%). $^1$H NMR (500 MHz, chloroform-d) δ 11.60 (s, 1H), 7.99 (d, J=13.7 Hz, 1H), 7.94-7.75 (m, 4H), 7.55 (s, OH), 5.30 (s, 2H), 4.96 (dd, J=12.2, 5.8 Hz, 1H), 4.39-3.12 (m, 13H), 2.89 (t, J=19.6 Hz, 1H), 2.84-2.65 (m, 1H), 2.20-2.10 (m, 1H), 2.10-1.98 (m, 1H), 1.59 (s, 15H). LCMS: $C_{37}H_{41}N_9O_9S$ requires: 787, found: m/z=788 [M+H]$^+$.

279
Example 35
280
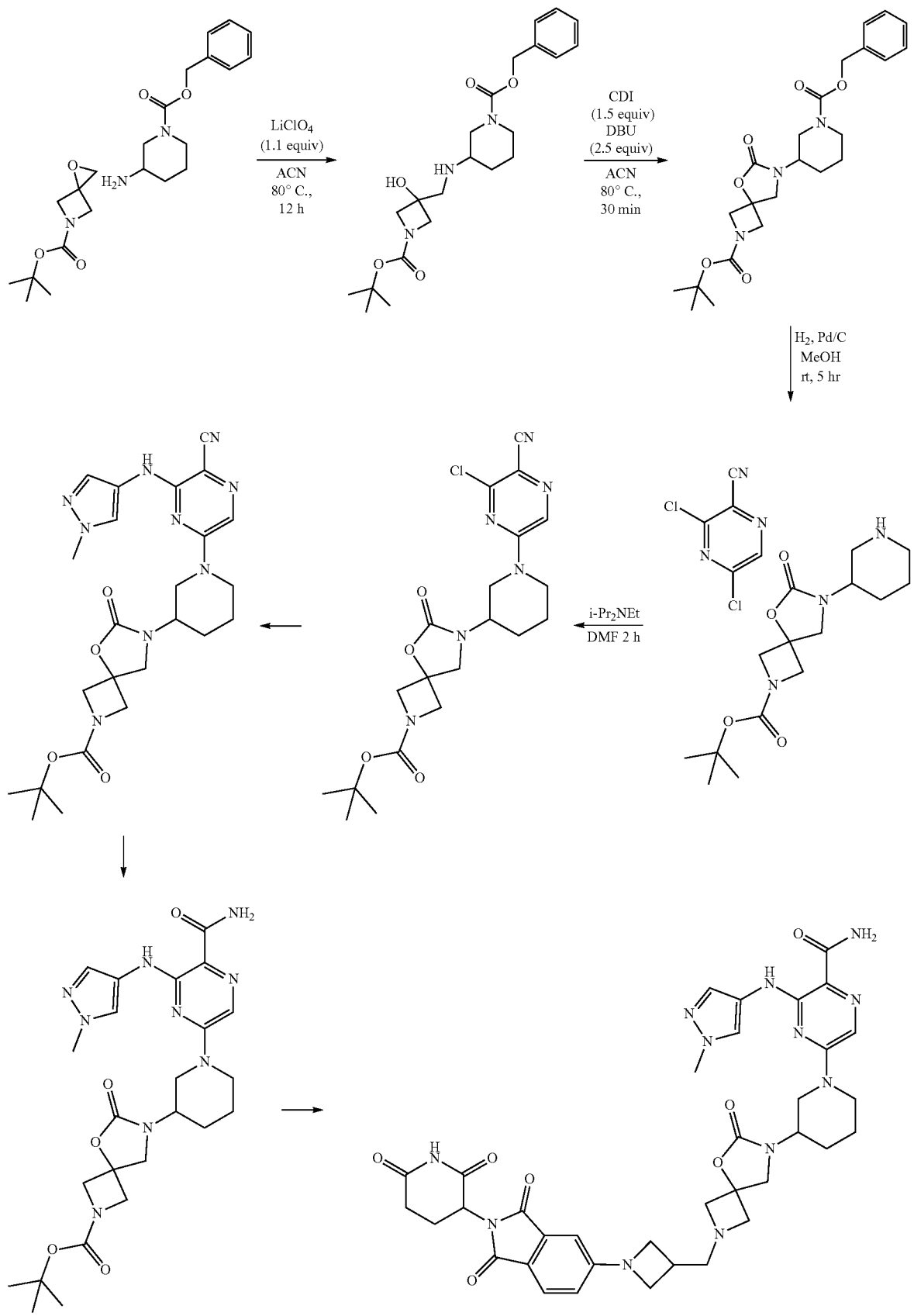

(R)-3-amino-1-N-Cbz-piperidine (253 mg, 1.08 mmol) and LiClO$_4$ (126 mg, 1.19 mmol) were added sequentially to a solution of tert-butyl 1-oxa-5-azaspiro[2.3]hexane-5-carboxylate (200 mg, 1.08 mmol) in ACN (10 mL). After stirring at 80° C. for 16 h the reaction mixture was concentrated under reduced pressure. Purification (SiO$_2$, 0-5% MeOH/CH$_2$Cl$_2$) afforded the desired product (441 mg, 97%). LCMS: C$_{22}$H$_{33}$N$_3$O$_5$ requires: 419, found: m/z=420 [M+H]$^+$.

CDI (255 mg, 1.57 mmol) and DBU (392 µL, 2.62 mmol) were added sequentially to a solution of benzyl (3R)-3-({[1-(tert-butoxycarbonyl)-3-hydroxyazetidin-3-yl]methyl}amino)piperidine-1-carboxylate (440 mg, 1.05 mmol) in ACN (2.6 mL). After stirring at 80° C. for 30 min, the reaction mixture was concentrated under reduced pressure. Purification (SiO$_2$, 0-5% MeOH/CH$_2$Cl$_2$) afforded the desired product (363 mg, 78%). LCMS: C$_{23}$H$_{31}$N$_3$O$_6$ requires: 445, found: m/z=446 [M+H]$^+$.

A solution of tert-butyl 7-[(3R)-1-[(benzyloxy)carbonyl]piperidin-3-yl]-6-oxo-5-oxa-2,7-diazaspiro[3.4]octane-2-carboxylate (363 mg, 0.81 mmol, 1 equiv) in MeOH (8.1 mL) was stirred with Pd/C (36.3 mg, 10 wt %) under a balloon of H$_2$. After stirring for 2 h, the reaction mixture was filtered through Celite and concentrated under reduced pressure to afford tert-butyl (R)-6-oxo-7-(piperidin-3-yl)-5-oxa-2,7-diazaspiro[3.4]octane-2-carboxylate. LCMS: C$_{15}$H$_{25}$N$_3$O$_4$ requires: 311, found: m/z=312 [M+H]$^+$.

Procedure A was followed to afford tert-butyl 7-[(3R)-1-(6-chloro-5-cyanopyrazin-2-yl)piperidin-3-yl]-6-oxo-5-oxa-2,7-diazaspiro[3.4]octane-2-carboxylate (364 mg, 95%, 2 steps). LCMS: C$_{20}$H$_{25}$ClN$_6$O$_4$ requires: 448, found: m/z=449 [M+H]$^+$.

Procedure B was followed to afford tert-butyl (R)-7-(1-(5-cyano-6-((1-methyl-1H-pyrazol-4-yl)amino)pyrazin-2-yl)piperidin-3-yl)-6-oxo-5-oxa-2,7-diazaspiro[3.4]octane-2-carboxylate (131 mg, 56%). LCMS: C$_{24}$H$_{31}$N$_9$O$_4$ requires: 509, found: m/z=510 [M+H]$^+$.

Procedure C was followed to afford tert-butyl (R)-7-(1-(5-carbamoyl-6-((1-methyl-1H-pyrazol-4-yl)amino)pyrazin-2-yl)piperidin-3-yl)-6-oxo-5-oxa-2,7-diazaspiro[3.4]octane-2-carboxylate (121 mg, 89%). LCMS: C$_{24}$H$_{33}$N$_9$O$_5$ requires: 527, found: m/z=528 [M+H]$^+$.

Compound 213: Procedure D was followed to afford a crude amine that was subjected to Procedure Q to afford 5-((3R)-3-(2-((1-(2-(2,6-dioxopiperidin-3-yl)-1,3-dioxoisoindolin-5-yl)azetidin-3-yl)methyl)-6-oxo-5-oxa-2,7-diazaspiro[3.4]octan-7-yl)piperidin-1-yl)-3-((1-methyl-1H-pyrazol-4-yl)amino)pyrazine-2-carboxamide (8.4 mg, 30%, 2 steps). $^1$H NMR (500 MHz, acetonitrile-d$_3$) δ 10.72 (s, 1H), 8.91-8.84 (m, 1H), 7.84 (s, 1H), 7.60 (d, J=8.3 Hz, 1H), 7.46 (d, J=17.7 Hz, 2H), 7.34 (s, 1H), 6.76 (s, 1H), 6.59 (d, J=8.5 Hz, 1H), 5.75 (s, 1H), 4.92 (dd, J=12.2, 5.3 Hz, 1H), 4.49 (dd, J=12.6, 4.2 Hz, 1H), 4.18 (d, J=13.7 Hz, 1H), 4.08 (t, J=7.7 Hz, 2H), 3.83-3.66 (m, 6H), 3.47-3.33 (m, 4H), 3.16-3.03 (m, 2H), 2.81-2.62 (m, 5H), 2.08 (d, J=17.1 Hz, 2H), 2.01-1.96 (m, 1H), 1.92-1.75 (m, 1H), 1.66 (qt, J=11.5, 4.0 Hz, 1H). LCMS: C$_{36}$H$_{40}$N$_{12}$O$_7$ requires: 752, found: m/z=753 [M+H]$^+$.

Example 36

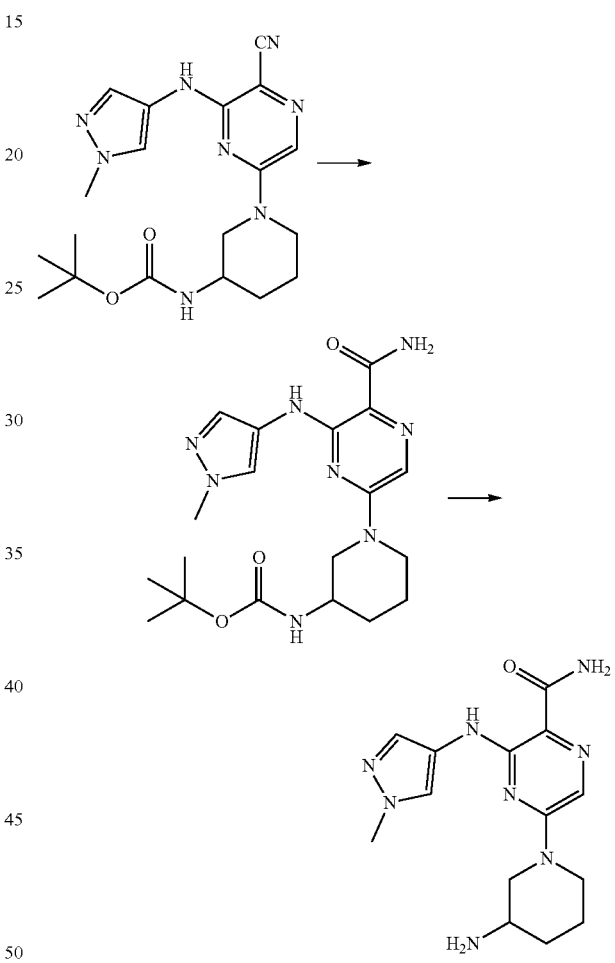

Procedure B was followed to afford tert-butyl (R)-(1-(5-cyano-6-((1-methyl-1H-pyrazol-4-yl)amino)pyrazin-2-yl)piperidin-3-yl)carbamate (941 mg, 80%). LCMS: C$_{19}$H$_{26}$N$_8$O$_2$ requires: 398, found: m/z=399 [M+H]$^+$.

Procedure C was followed to afford tert-butyl (R)-(1-(5-carbamoyl-6-((1-methyl-1H-pyrazol-4-yl)amino)pyrazin-2-yl)piperidin-3-yl)carbamate (297 mg, 95%). LCMS: C$_{19}$H$_{28}$N$_8$O$_3$ requires: 416, found: m/z=417 [M+H]$^+$.

Procedure D was followed to afford (R)-5-(3-aminopiperidin-1-yl)-3-((1-methyl-1H-pyrazol-4-yl)amino)pyrazine-2-carboxamide. LCMS: C$_{14}$H$_{20}$N$_8$O requires: 4=316, found: m/z=317 [M+H]$^+$.

Example 37

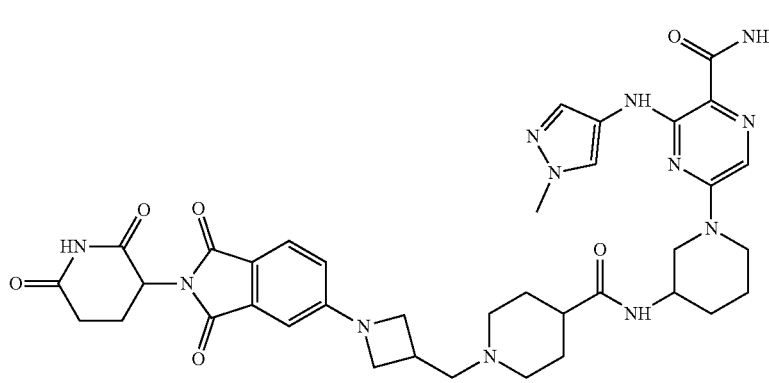

Compound 216

Procedure R was followed to afford (R)-3-((1-methyl-H-pyrazol-4-yl)amino)-5-(3-(piperidine-4-carboxamido)piperidin-1-yl)pyrazine-2-carboxamide (199 mg, 75%). LCMS: $C_{20}H_{29}N_9O_2$ requires: 427, found: m/z=428 [M+H]$^+$.

Procedure Q was followed to afford 5-[(3R)-3-[1-({1-[2-(2,6-dioxopiperidin-3-yl)-1,3-dioxoisoindol-5-yl]azetidin-3-yl}methyl)piperidine-4-amido]piperidin-1-yl]-3-[(1-methylpyrazol-4-yl)amino]pyrazine-2-carboxamide (8.4 mg, 10%). $^1$H NMR (500 MHz, acetonitrile-d$_3$) δ 10.74 (s, 1H), 8.87 (s, 1H), 7.92 (s, 1H), 7.59 (d, J=8.3 Hz, 1H), 7.45 (d, J=7.4 Hz, 2H), 7.38-7.22 (m, 1H), 6.76 (d, J=2.1 Hz, 1H), 6.59 (dd, J=8.3, 2.2 Hz, 1H), 6.34 (d, J=7.2 Hz, 1H), 5.72 (s, 1H), 4.92 (dd, J=12.3, 5.3 Hz, 1H), 4.24-4.16 (m, 1H), 4.11 (t, J=8.1 Hz, 2H), 3.87 (s, 3H), 3.85-3.78 (m, 2H), 3.68 (dd, J=8.2, 5.4 Hz, 2H), 3.45 (td, J=9.0, 8.5, 4.4 Hz, 1H), 3.35 (dd, J=13.1, 7.8 Hz, 1H), 3.28 (s, 1H), 2.97 (ddt, J=10.1, 7.8, 4.2 Hz, 1H), 2.90-2.79 (m, 2H), 2.70 (dddt, J=21.8, 13.4, 7.8, 4.3 Hz, 3H), 2.57 (d, J=7.4 Hz, 2H), 2.11-2.01 (m, 3H), 1.87-1.77 (m, 2H), 1.71-1.49 (m, 6H). LCMS: $C_{37}H_{44}N_{12}O_6$ requires: 752, found: m/z=753.

Example 38

General Procedure 1: Amide Coupling

A mixture of amine (0.03 mmol), acid (0.03 mmol), HATU (0.04 mmol), DIPEA (0.15 mmol), and DMF was allowed to stir at room temperature for 30 minutes. The mixture was purified by HPLC (H$_2$O/MeCN with 0.1% TFA) to afford the amide product.

General Procedure 2: Reductive Amination

A mixture of amine TFA salt (0.07 mmol), aldehyde (0.1 mmol), triethylamine (0.28 mmol), and DCE were allowed to stir at room temperature for 10 minutes. NaBH(OAc)$_3$ (0.14 mmol) was added and the mixture was allowed to stir at room temperature for 2 h. The mixture was filtered through celite, washed with CH$_2$Cl$_2$, concentrated, and purified by HPLC (H$_2$O/MeCN with 0.1% TFA) to afford the amine product.

General Procedure 3: Aryl Fluoride Displacement

A mixture of amine (0.22 mmol), aryl fluoride (0.22 mmol), DIPEA (0.88 mmol), and DMF (1 mL) was allowed to stir at 90° C. for 16 h. The mixture was purified by HPLC (H$_2$O/MeCN with 0.1% TFA) to afford the desired product.

Example 39

Prepared according to General Procedure 2

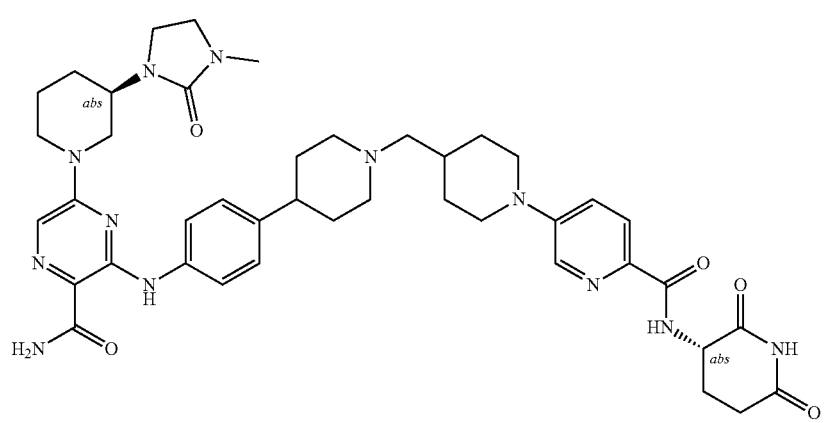

Compound 195

$^1$H NMR (500 MHz, DMSO-d$_6$) δ 11.19 (s, 1H), 10.85 (s, 1H), 8.71 (d, J=8.2 Hz, 1H), 8.32 (d, J=2.9 Hz, 1H), 7.85 (d, J=8.8 Hz, 1H), 7.76 (s, 1H), 7.67 (s, 1H), 7.51 (d, J=8.1 Hz, 2H), 7.42 (dd, J=8.9, 2.9 Hz, 1H), 7.34 (s, 1H), 7.18 (d, J=8.2 Hz, 2H), 4.75 (ddd, J=13.2, 8.2, 5.4 Hz, 1H), 4.34 (dd, J=39.7, 12.8 Hz, 2H), 3.96 (d, J=12.5 Hz, 2H), 3.62 (d, J=11.0 Hz, 1H), 3.28 (dd, J=14.4, 7.4 Hz, 5H), 3.11-2.76 (m, 8H), 2.73 (s, 3H), 2.19 (dd, J=10.7, 5.3 Hz, 3H), 2.08-1.93 (m, 3H), 1.89-1.71 (m, 8H), 1.59 (d, J=29.1 Hz, 4H), 1.23 (d, J=14.3 Hz, 5H). LCMS: C$_{42}$H$_{54}$N$_{12}$O$_5$ requires: 806, found: m/z=807 [M+H]$^+$.

Compound 194

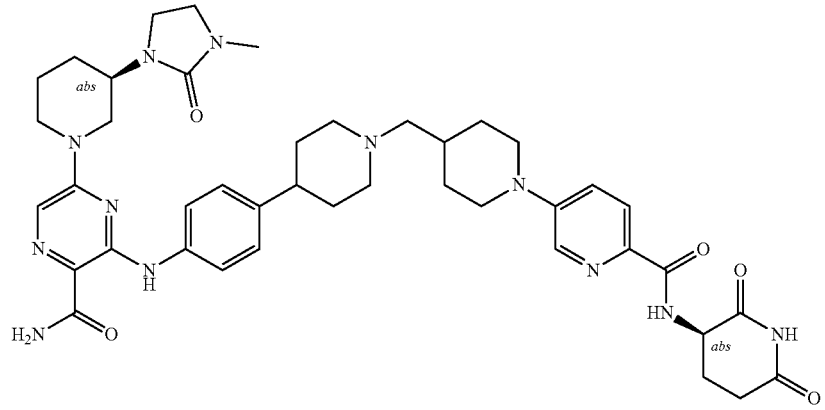

$^1$H NMR (500 MHz, DMSO-d$_6$) δ 11.30 (s, 1H), 10.86 (s, 1H), 8.71 (d, J=8.1 Hz, 1H), 8.36 (s, 1H), 7.88 (d, J=8.7 Hz, 1H), 7.79 (s, 1H), 7.69 (s, 1H), 7.58 (d, J=7.9 Hz, 2H), 7.46 (d, J=8.8 Hz, 1H), 7.36 (s, 1H), 7.19 (d, J=8.2 Hz, 2H), 4.75 (ddd, J=13.1, 8.2, 5.4 Hz, 1H), 4.42-4.25 (m, 2H), 4.01 (d, J=12.9 Hz, 2H), 3.65 (dd, J=13.8, 7.9 Hz, 3H), 3.27 (t, J=8.3 Hz, 3H), 3.17-2.87 (m, 6H), 2.86-2.70 (m, 5H), 2.27-2.10 (m, 2H), 2.11-1.69 (m, 12H), 1.68-1.47 (m, 2H), 1.30 (d, J=52.1 Hz, 3H). LCMS: C$_{42}$H$_{54}$N$_{12}$O$_5$ requires: 806, found: m/z=807 [M+H]$^+$.

Compound 201

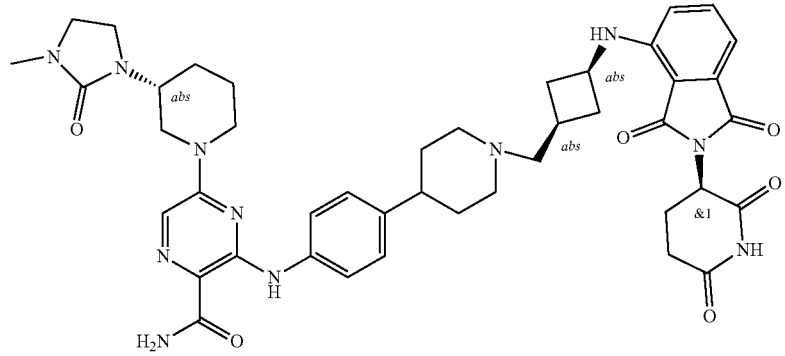

$^1$H NMR (500 MHz, acetonitrile-d$_3$) δ 11.13 (s, 1H), 8.92 (s, 1H), 7.67-7.55 (m, 5H), 7.43 (s, 1H), 7.21 (d, J=8.0 Hz, 2H), 7.11 (d, J=7.4 Hz, 1H), 6.99 (d, J=8.5 Hz, 1H), 6.37 (s, 1H), 5.81 (s, 1H), 5.01-4.92 (m, 1H), 4.43 (d, J=12.4 Hz, 1H), 4.31 (d, J=13.2 Hz, 1H), 4.11 (d, J=8.5 Hz, 1H), 3.71 (s, 1H), 3.63-3.54 (m, 2H), 3.45-3.23 (m, 5H), 3.19 (s, 2H), 3.14-2.92 (m, 4H), 2.76 (d, J=14.2 Hz, 9H), 1.93-1.63 (m, 5H). LCMS: C$_{43}$H$_{51}$N$_{11}$O$_6$ requires: 817, found: m/z=818 [M+H]$^+$.

Compound 202

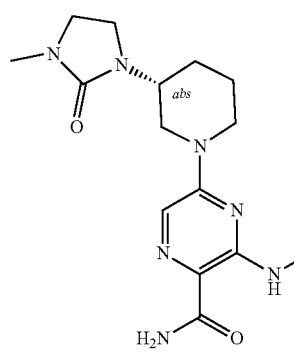 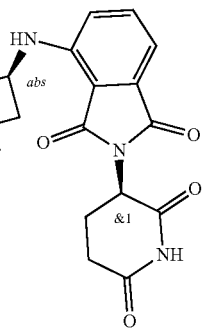

¹H NMR (500 MHz, acetonitrile-d₃) δ 11.13 (s, 1H), 8.93 (s, 1H), 8.65 (s, 1H), 7.60 (dd, J=17.5, 6.7 Hz, 5H), 7.43 (s, 1H), 7.21 (d, J=8.0 Hz, 2H), 7.12 (d, J=7.0 Hz, 1H), 6.89 (d, J=8.3 Hz, 1H), 6.46 (s, 1H), 5.83 (s, 1H), 4.98 (dd, J=12.5, 5.2 Hz, 1H), 4.51-4.16 (m, 4H), 3.72 (s, 1H), 3.60 (d, J=12.4 Hz, 2H), 3.46-3.26 (m, 7H), 3.03 (tt, J=30.3, 14.5 Hz, 6H), 2.89-2.63 (m, 8H), 2.42 (d, J=8.7 Hz, 2H), 2.31 (d, J=12.7 Hz, 2H), 2.05 (d, J=17.6 Hz, 3H), 1.94-1.59 (m, 4H). LCMS: $C_{43}H_{51}N_{11}O_6$ requires: 817, found: m/z=818 [M+H]⁺.

2H), 3.79-3.40 (m, 9H), 3.28-3.05 (m, 16H), 2.97-2.82 (m, 2H), 2.67 (s, 4H), 2.24-1.95 (m, 2H), 1.78 (q, J=5.6, 5.1 Hz, 5H), 1.52 (s, 2H), 1.25 (s, 4H). LCMS: $C_4H_{48}N_{14}O_6$ requires: 820, found: m/z=821 [M+H]⁺.

Compound 204

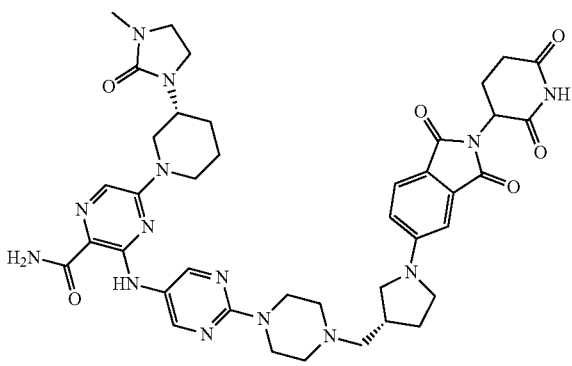

¹H NMR (500 MHz, DMSO-d₆) δ 11.07 (s, 1H), 10.72 (s, 1H), 8.57 (s, 2H), 7.75 (s, 1H), 7.66 (d, J=8.8 Hz, 2H), 7.34 (s, 1H), 6.92 (d, J=2.1 Hz, 1H), 6.84 (dd, J=8.4, 2.1 Hz, 1H), 5.06 (dd, J=12.9, 5.4 Hz, 1H), 4.22 (dd, J=37.3, 13.0 Hz,

Compound 207

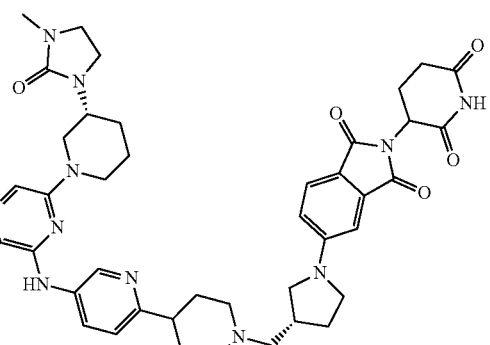

¹H NMR (500 MHz, DMSO-d₆) δ 11.27 (s, 1H), 11.07 (s, 1H), 8.55 (d, J=2.4 Hz, 1H), 8.13-8.05 (m, 1H), 7.84-7.78 (m, 1H), 7.73 (s, 1H), 7.65 (d, J=8.4 Hz, 1H), 7.40 (d, J=2.5 Hz, 1H), 7.22 (d, J=8.6 Hz, 1H), 6.92 (d, J=2.2 Hz, 1H), 6.83 (dd, J=8.7, 2.2 Hz, 1H), 5.06 (dd, J=12.9, 5.4 Hz, 1H), 4.31 (s, 2H), 3.67-3.38 (m, 4H), 3.30-2.81 (m, 8H), 2.72 (s, 3H), 2.69-2.55 (m, 1H), 2.43-2.33 (m, 2H), 2.23-1.46 (m, 11H), 1.25 (s, 3H). LCMS: $C_{42}H_{50}N_{12}O_6$ requires: 818, found: m/z=819 [M+H]⁺.

Compound 208

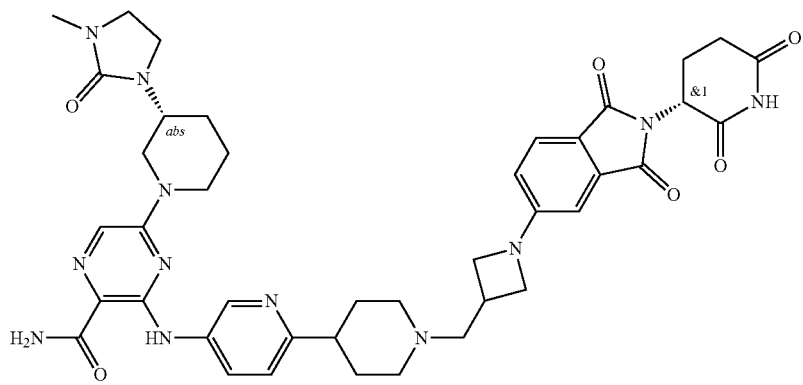

$^1$H NMR (500 MHz, DMSO-d$_6$) δ 11.28 (s, 1H), 11.08 (s, 1H), 8.55 (d, J=2.6 Hz, 1H), 8.10 (d, J=8.4 Hz, 1H), 7.81 (s, 1H), 7.73 (s, 1H), 7.65 (d, J=8.2 Hz, 1H), 7.40 (d, J=2.6 Hz, 1H), 7.21 (d, J=8.6 Hz, 1H), 6.79 (d, J=2.1 Hz, 1H), 6.66 (dd, J=8.4, 2.1 Hz, 1H), 5.06 (dd, J=12.8, 5.4 Hz, 1H), 4.31 (d, J=12.8 Hz, 2H), 4.16 (t, J=8.2 Hz, 2H), 3.77-3.55 (m, 4H), 3.27 (dd, J=11.3, 4.9 Hz, 2H), 3.16-2.81 (m, 6H), 2.74-2.55 (m, 7H), 2.16-1.97 (m, 3H), 1.91-1.42 (m, 9H), 1.25 (s, 5H). LCMS: C$_{41}$H$_{48}$N$_{12}$O$_6$ requires: 818, found: m/z=819 [M+H]$^+$.

Compound 209

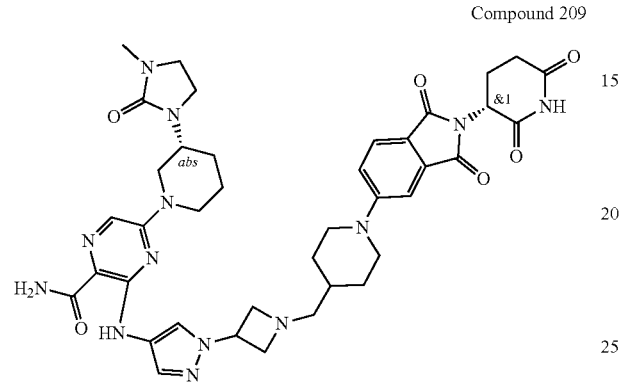

$^1$H NMR (500 MHz, DMSO-d$_6$) δ 11.08 (s, 1H), 10.89 (s, 1H), 8.10 (s, 1H), 7.71 (d, J=2.8 Hz, 1H), 7.66 (d, J=8.5 Hz, 1H), 7.61 (d, J=4.5 Hz, 2H), 7.31 (dd, J=7.8, 2.5 Hz, 2H), 7.24 (dd, J=8.8, 2.3 Hz, 1H), 5.12-4.94 (m, 2H), 4.43 (d, J=12.5 Hz, 1H), 4.30 (d, J=13.2 Hz, 1H), 4.05 (d, J=12.9 Hz, 2H), 3.75-3.56 (m, 3H), 3.28 (t, J=8.2 Hz, 2H), 3.10-2.83 (m, 5H), 2.73 (s, 3H), 2.67-2.53 (m, 2H), 2.40 (d, J=6.8 Hz, 2H), 2.02 (ddd, J=12.9, 5.7, 3.2 Hz, 1H), 1.90-1.69 (m, 6H), 1.68-1.48 (m, 2H), 1.20 (qd, J=14.1, 12.4, 4.3 Hz, 2H). LCMS: C$_{39}$H$_{47}$N$_{13}$O$_6$ requires: 793, found: m/z=794 [M+H]$^+$.

Compound 210

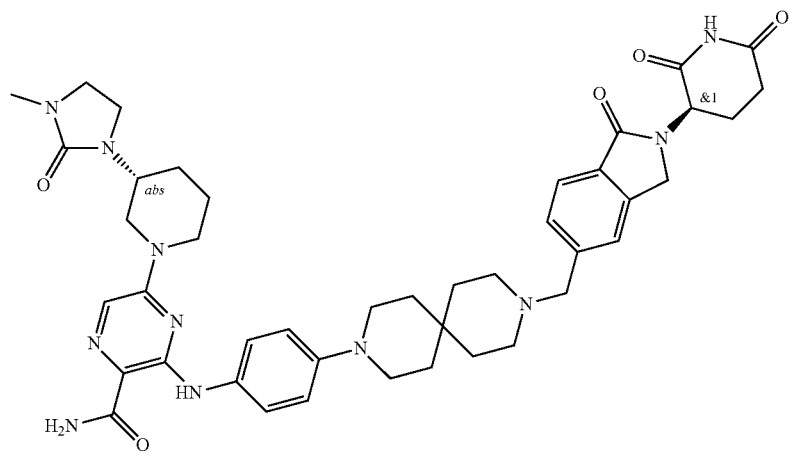

$^1$H NMR (500 MHz, DMSO-d$_6$) δ 11.15 (s, 2H), 11.03 (s, 1H), 9.46 (d, J=28.8 Hz, 1H), 7.87 (d, J=7.8 Hz, 1H), 7.75 (d, J=9.7 Hz, 2H), 7.65 (d, J=7.3 Hz, 2H), 7.53 (s, 2H), 7.33 (s, 1H), 7.09 (s, 2H), 5.16 (dd, J=13.2, 5.2 Hz, 1H), 4.41 (dtd, J=57.1, 31.0, 29.6, 15.4 Hz, 7H), 3.62 (tt, J=9.7, 4.2 Hz, 1H), 3.43-2.85 (m, 16H), 2.71 (s, 3H), 2.67-2.58 (m, 1H), 2.09-1.70 (m, 9H), 1.66-1.42 (m, 6H). LCMS: C$_{43}$H$_{53}$N$_{11}$O$_5$ requires: 793, found: m/z=794 [M+H]$^+$.

Compound 196

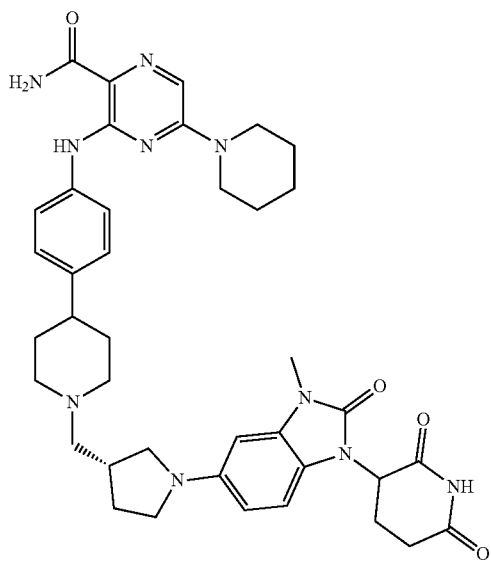

¹H NMR (500 MHz, acetonitrile-d₃) δ 11.17 (s, 1H), 8.91 (s, 1H), 7.65 (d, J=8.2 Hz, 2H), 7.58 (s, 1H), 7.41 (s, 1H), 7.24 (d, J=8.2 Hz, 2H), 6.84 (d, J=8.6 Hz, 1H), 6.41 (s, 1H), 6.33 (d, J=8.7 Hz, 1H), 5.79 (s, 1H), 5.14 (dd, J=12.9, 5.3 Hz, 1H), 3.81-3.65 (m, 5H), 3.61 (t, J=8.3 Hz, 1H), 3.49-3.39 (m, 2H), 3.38-3.31 (m, 4H), 3.27-3.20 (m, 2H), 3.20-3.12 (m, 1H), 3.10-2.96 (m, 2H), 2.95-2.80 (m, 3H), 2.80-2.67 (m, 2H), 2.54-2.01 (m, 6H), 1.92-1.80 (m, 1H), 1.78-1.70 (m, 2H), 1.70-1.65 (m, 4H). LCMS: $C_{39}H_{48}N_{10}O_4$ requires 720, found: m/z=721 [M+H]⁺.

Compound 197

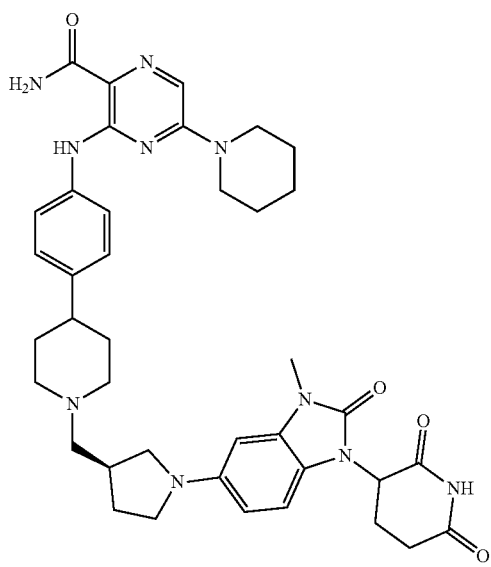

¹H NMR (500 MHz, acetonitrile-d₃) δ 11.18 (s, 1H), 9.77 (s, 1H), 8.91 (s, 1H), 7.65 (d, J=8.2 Hz, 2H), 7.58 (s, 1H), 7.41 (s, 1H), 7.24 (d, J=8.2 Hz, 2H), 6.85 (d, J=8.5 Hz, 1H), 6.41 (s, 1H), 6.33 (d, J=8.5 Hz, 1H), 5.80 (s, 1H), 5.15 (dd, J=12.8, 5.4 Hz, 1H), 3.78-3.70 (m, 5H), 3.61 (t, J=8.5 Hz, 1H), 3.49-3.39 (m, 2H), 3.38-3.31 (m, 4H), 3.28-3.20 (m, 2H), 3.20-3.13 (m, 1H), 3.12-2.96 (m, 2H), 2.92-2.84 (m, 3H), 2.80-2.71 (m, 2H), 2.57-2.03 (m, 6H), 1.92-1.79 (m, 1H), 1.80-1.71 (m, 2H), 1.71-1.65 (m, 4H). LCMS: $C_{39}H_{48}N_{10}O_4$ requires 720, found: m/z=721 [M+H]⁺.

Compound 198

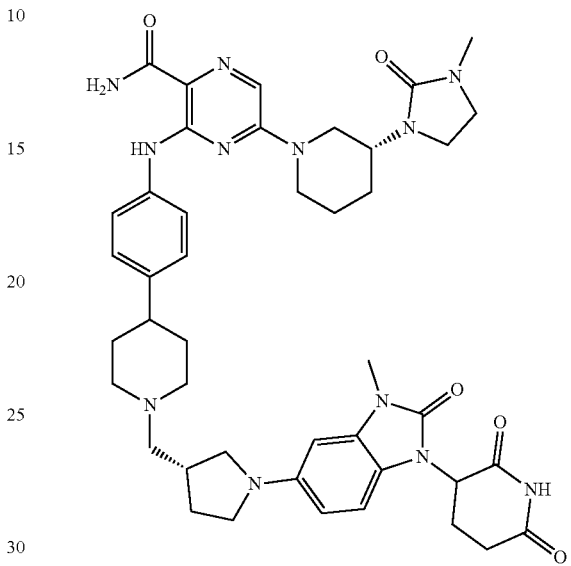

¹H NMR (500 MHz, acetonitrile-d₃) δ 11.14 (s, 1H), 8.99 (s, 1H), 8.93 (s, 1H), 7.66-7.56 (m, 3H), 7.43 (s, 1H), 7.23 (d, J=8.2 Hz, 2H), 6.86 (d, J=8.4 Hz, 1H), 6.45 (s, 1H), 6.37 (s, 1H), 5.84 (s, 1H), 5.15 (dd, J=12.8, 5.4 Hz, 1H), 4.42 (d, J=12.8 Hz, 1H), 4.31 (d, J=13.7 Hz, 1H), 3.77-3.67 (m, 3H), 3.63-3.59 (m, 1H), 3.50-3.13 (m, 10H), 3.13-2.96 (m, 4H), 2.95-2.41 (m, 7H), 2.36-2.32 (m, 1H), 2.17-2.08 (m, 6H), 1.94-1.77 (m, 6H), 1.68-1.64 (m, 1H). LCMS: $C_{43}H_{54}N_{12}O_5$ requires 818, found: m/z=819 [M+H]⁺.

Compound 199

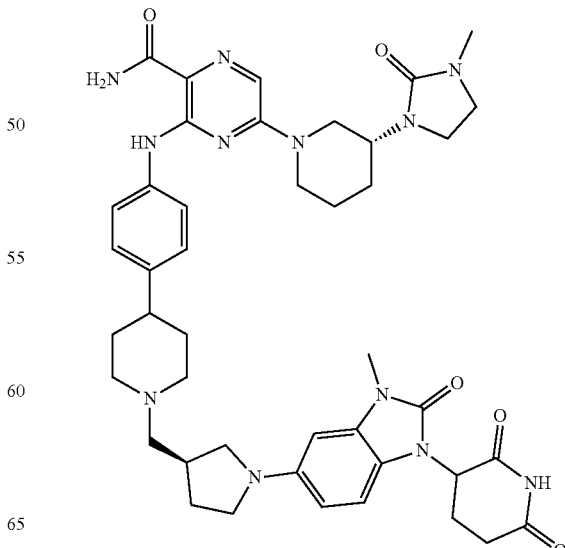

293

¹H NMR (500 MHz, acetonitrile-d₃) δ 11.14 (s, 1H), 9.07 (s, 1H), 8.92 (s, 1H), 7.66-7.56 (m, 3H), 7.43 (s, 1H), 7.23 (d, J=8.3 Hz, 2H), 6.85 (d, J=8.4 Hz, 1H), 6.44 (s, 1H), 6.36 (s, 1H), 5.83 (s, 1H), 5.15 (dd, J=12.8, 5.2 Hz, 1H), 4.42 (d, J=12.4 Hz, 1H), 4.31 (d, J=13.5 Hz, 1H), 3.77-3.67 (m, 3H), 3.62-3.56 (m, 1H), 3.50-3.12 (m, 8H), 3.13-2.96 (m, 4H), 2.95-2.68 (m, 6H), 2.69-2.19 (m, 6H), 2.18-2.09 (m, 5H), 1.97-1.85 (m, 5H), 1.70-1.64 (m, 1H). LCMS: $C_{43}H_{54}N_{12}O_5$ requires 818, found: m/z=819 [M+H]⁺.

Compound 200

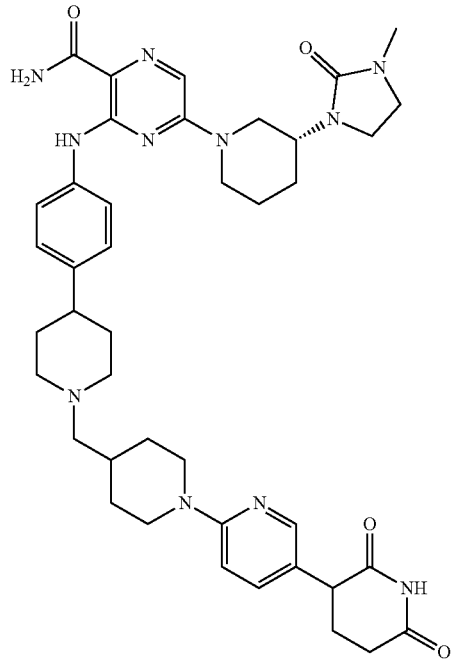

¹H NMR (500 MHz, DMSO-d₆) δ 11.30 (s, 1H), 10.82 (s, 1H), 7.97 (d, J=2.5 Hz, 1H), 7.79 (d, J=2.7 Hz, 1H), 7.69 (s, 1H), 7.57 (d, J=8.2 Hz, 2H), 7.43-7.34 (m, 2H), 7.22-7.14 (m, 2H), 6.86 (d, J=8.8 Hz, 1H), 4.31 (d, J=14.0 Hz, 4H), 3.75 (dd, J=12.2, 4.9 Hz, 1H), 3.65-3.56 (m, 3H), 3.40-3.21

294

(m, 3H), 3.13-2.94 (m, 6H), 2.90-2.62 (m, 6H), 2.27-2.10 (m, 3H), 2.10-1.94 (m, 5H), 1.88-1.76 (m, 6H), 1.61-1.55 (m, 1H), 1.35-1.14 (m, 3H). LCMS: $C_{41}H_{53}N_{11}O_4$ requires 763, found: m/z=764 [M+H]⁺.

Compound 206

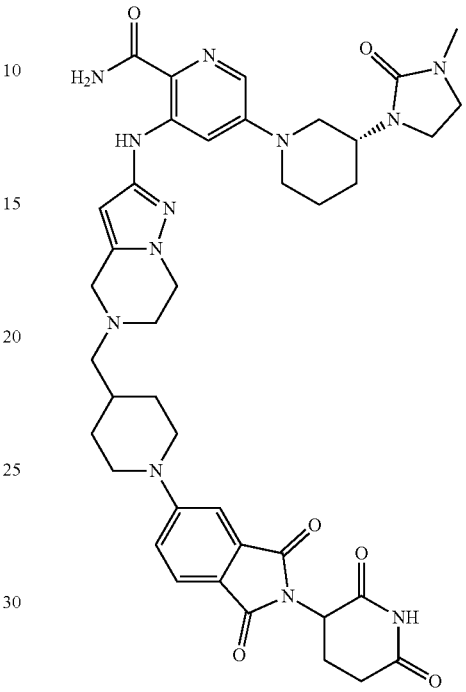

¹H NMR (500 MHz, DMSO-d₆) δ 11.08 (s, 1H), 10.93 (s, 1H), 7.89-7.84 (m, 2H), 7.75 (d, J=2.6 Hz, 1H), 7.66 (d, J=8.5 Hz, 1H), 7.35-7.18 (m, 3H), 5.83 (s, 1H), 5.77 (s, 1H), 5.06 (dd, J=13.0, 5.4 Hz, 1H), 4.12-3.95 (m, 5H), 3.83 (d, J=13.2 Hz, 1H), 3.74 (t, J=12.2 Hz, 1H), 3.70-3.55 (m, 3H), 3.28-3.21 (m, 2H), 3.04-2.95 (m, 3H), 2.93-2.82 (m, 4H), 2.67 (s, 3H), 2.62-2.35 (m, 3H), 2.05-1.98 (m, 1H), 1.94-1.90 (m, 1H), 1.87-1.76 (m, 5H), 1.75-1.66 (m, 1H), 1.63-1.53 (m, 1H), 1.26-1.15 (m, 3H). LCMS: $C_{40}H_{48}N_{12}O_6$ requires 792, found: m/z=793 [M+H]⁺.

Compound 214

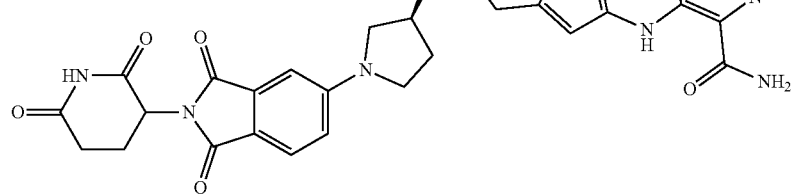

$^1$H NMR (500 MHz, DMSO-d$_6$) δ 11.07 (s, 1H), 10.93 (s, 1H), 7.89-7.82 (m, 2H), 7.75 (d, J=2.6 Hz, 1H), 7.64 (d, J=8.4 Hz, 1H), 7.32 (d, J=3.2 Hz, 1H), 6.93 (d, J=2.2 Hz, 1H), 6.84 (dd, J=8.7, 2.2 Hz, 1H), 5.83 (s, 1H), 5.05 (dd, J=13.3, 5.3 Hz, 1H), 4.02 (t, J=5.7 Hz, 2H), 3.83 (d, J=13.2 Hz, 1H), 3.78-3.58 (m, 4H), 3.56-3.38 (m, 2H), 3.27-3.16 (m, 3H), 3.05-2.82 (m, 4H), 2.71 (q, J=7.4 Hz, 1H), 2.66 (s, 3H), 2.62-2.40 (m, 6H), 2.22-2.14 (m, 1H), 2.02-1.98 (m, 1H), 1.86-1.66 (m, 4H), 1.62-1.53 (m, 1H), 1.36-1.08 (m, 2H). LCMS: C$_{39}$H$_{46}$N$_{12}$O$_6$ requires 778, found: m/z=779 [M+H]$^+$.

Compound 216

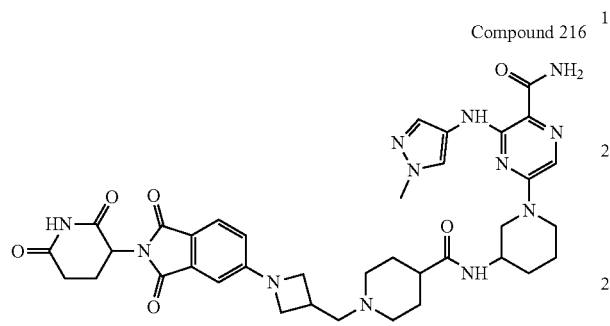

$^1$H NMR (500 MHz, acetonitrile-d$_3$) δ 10.74 (s, 1H), 8.87 (s, 1H), 7.92 (s, 1H), 7.59 (d, J=8.3 Hz, 1H), 7.45 (d, J=7.4 Hz, 2H), 7.38-7.22 (m, 1H), 6.76 (d, J=2.1 Hz, 1H), 6.59 (dd, J=8.3, 2.2 Hz, 1H), 6.34 (d, J=7.2 Hz, 1H), 5.72 (s, 1H), 4.92 (dd, J=12.3, 5.3 Hz, 1H), 4.24-4.16 (m, 1H), 4.11 (t, J=8.1 Hz, 2H), 3.87 (s, 3H), 3.85-3.78 (m, 2H), 3.68 (dd, J=8.2, 5.4 Hz, 2H), 3.45 (td, J=9.0, 8.5, 4.4 Hz, 1H), 3.35 (dd, J=13.1, 7.8 Hz, 1H), 3.28 (s, 1H), 2.97 (ddt, J=10.1, 7.8, 4.2 Hz, 1H), 2.90-2.79 (m, 2H), 2.70 (dddt, J=21.8, 13.4, 7.8, 4.3 Hz, 3H), 2.57 (d, J=7.4 Hz, 2H), 2.11-2.01 (m, 3H), 1.87-1.77 (m, 2H), 1.71-1.49 (m, 6H). LCMS: C$_{37}$H$_{44}$N$_{12}$O$_6$ requires: 753, found: m/z=754.

Compound 213

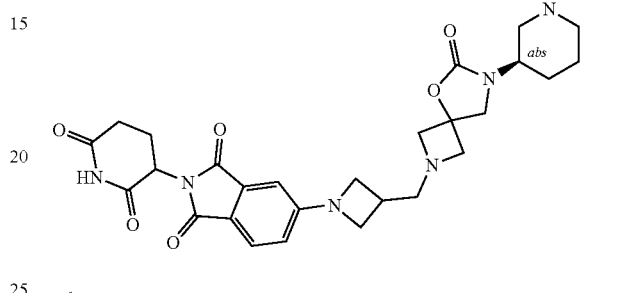

$^1$H NMR (500 MHz, acetonitrile-d$_3$) δ 10.75 (s, 1H), 8.90 (s, 1H), 7.87 (s, 1H), 7.63 (d, J=8.2 Hz, 1H), 7.50 (s, 1H), 7.47 (s, 1H), 7.37 (s, 1H), 6.79 (d, J=2.1 Hz, 1H), 6.62 (dd, J=8.3, 2.1 Hz, 1H), 5.78 (s, 1H), 4.95 (dd, J=12.3, 5.4 Hz, 1H), 4.52 (d, J=13.0 Hz, 1H), 4.21 (d, J=13.6 Hz, 1H), 4.11 (t, J=7.7 Hz, 2H), 3.85 (s, 3H), 3.80 (q, J=9.1 Hz, 2H), 3.73 (ddd, J=12.7, 8.2, 4.7 Hz, 3H), 3.48 (d, J=8.0 Hz, 1H), 3.45-3.35 (m, 3H), 3.20-3.05 (m, 2H), 2.86-2.63 (m, 6H), 2.05-1.99 (m, 1H), 1.93-1.78 (m, 2H), 1.76-1.59 (m, 1H), 0.97-0.81 (m, 1H). LCMS: C$_{36}$H$_{40}$N$_{12}$O$_7$ requires: 753, found: m/z=754.

Compound 205

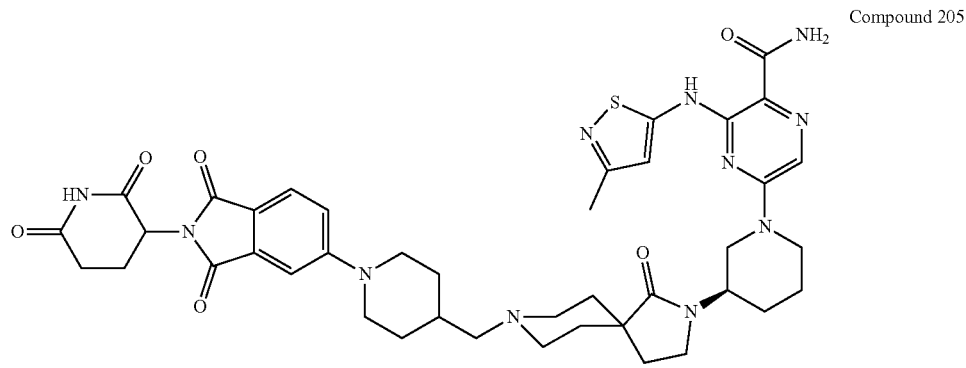 [SMILES: Cc1cc(Nc2nc(N3CCC[C@@H](N4CCC5(CCN(CC6CCN(c7ccc8c(c7)C(=O)N(C7CCC(=O)NC7=O)C8=O)CC6)CC5)C4=O)C3)cnc2C(N)=O)sn1]

$^1$H NMR (500 MHz, DMSO-d$_6$) δ 12.29 (s, 1H), 11.08 (s, 1H), 7.92 (s, 1H), 7.84 (s, 1H), 7.66 (d, J=8.5 Hz, 1H), 7.58 (s, 1H), 7.32 (d, J=2.3 Hz, 1H), 7.24 (dd, J=8.8, 2.3 Hz, 1H), 6.86 (s, 1H), 5.07 (dd, J=12.8, 5.4 Hz, 1H), 4.46 (s, 2H), 4.05 (d, J=13.0 Hz, 2H), 3.83 (d, J=10.9 Hz, 1H), 3.12 (t, J=12.6 Hz, 1H), 2.98 (t, J=12.4 Hz, 2H), 2.89 (t, J=12.9 Hz, 1H), 2.76 (d, J=9.1 Hz, 2H), 2.71-2.55 (m, 3H), 2.30 (s, 3H), 2.15 (d, J=6.9 Hz, 2H), 2.09-1.94 (m, 3H), 1.94-1.69 (m, 9H), 1.62 (d, J=13.1 Hz, 1H), 1.36 (dd, J=25.7, 12.6 Hz, 2H), 1.25 (s, 1H), 1.15 (d, J=12.5 Hz, 2H). LCMS: C$_{41}$H$_{49}$N$_{11}$O$_6$S requires: 823, found: m/z=824.

5.5 Hz, 3H). LCMS: $C_{38}H_{44}N_{12}O_7$ requires: 780, found: m/z=781.

Compound 211

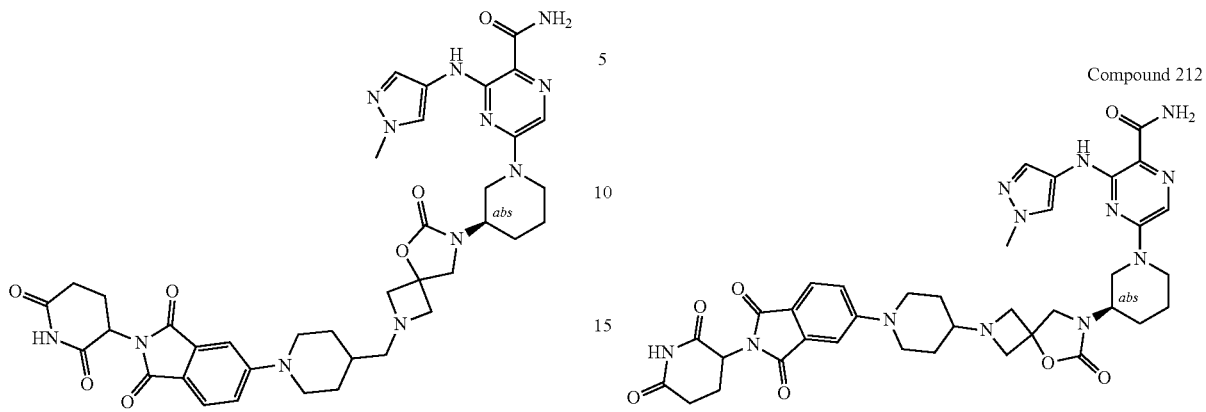

¹H NMR (500 MHz, acetonitrile-d₃) δ 10.74 (s, 1H), 8.94 (s, 1H), 7.87 (s, 1H), 7.65 (d, J=8.6 Hz, 1H), 7.50 (s, 1H), 7.47 (d, J=0.8 Hz, 1H), 7.37 (s, 1H), 7.31 (d, J=2.4 Hz, 1H), 7.17 (dd, J=8.7, 2.4 Hz, 1H), 5.79 (s, 1H), 5.07-4.88 (m, 1H), 4.50 (d, J=12.8 Hz, 1H), 4.19 (d, J=13.6 Hz, 1H), 4.00 (d, J=13.1 Hz, 2H), 3.84 (s, 3H), 3.78 (dd, J=19.2, 10.2 Hz, 2H), 3.45 (d, J=8.1 Hz, 1H), 3.39 (d, J=8.1 Hz, 1H), 3.34 (d, J=8.1 Hz, 1H), 3.31-3.25 (m, 1H), 3.17 (dd, J=12.9, 10.4 Hz, 1H), 3.14-3.07 (m, 1H), 2.97 (td, J=12.8, 2.7 Hz, 2H), 2.87-2.63 (m, 3H), 2.39 (d, J=6.9 Hz, 2H), 2.31-2.26 (m, 1H), 2.15-2.08 (m, 1H), 1.91 (dt, J=13.3, 3.5 Hz, 1H), 1.88-1.84 (m, 1H), 1.81 (dd, J=12.1, 3.6 Hz, 3H), 1.70 (tt, J=11.1, 3.9 Hz, 1H), 1.61 (dtd, J=11.6, 7.4, 4.0 Hz, 1H), 0.90 (dq, J=7.8, 6.0, ¹H NMR (500 MHz, acetonitrile-d₃) δ 10.71 (s, 1H), 8.90 (s, 1H), 7.84 (s, 1H), 7.63 (d, J=8.5 Hz, 1H), 7.47 (s, 1H), 7.44 (s, 1H), 7.34 (s, 1H), 7.28 (d, J=2.4 Hz, 1H), 7.15 (dd, J=8.6, 2.4 Hz, 1H), 5.75 (s, 1H), 4.93 (dd, J=12.3, 5.4 Hz, 1H), 4.50 (dd, J=13.1, 4.1 Hz, 1H), 4.18 (d, J=13.6 Hz, 1H), 3.81 (s, 3H), 3.81-3.66 (m, 3H), 3.44 (d, J=8.0 Hz, 1H), 3.40 (d, J=8.0 Hz, 1H), 3.34 (d, J=7.9 Hz, 1H), 3.31 (d, J=7.8 Hz, 1H), 3.17-3.00 (m, 4H), 2.83-2.60 (m, 3H), 2.36 (tt, J=8.3, 3.7 Hz, 1H), 2.12-2.05 (m, 2H), 1.96 (s, 1H), 1.87 (dq, J=13.4, 3.3 Hz, 1H), 1.79 (ddd, J=16.5, 10.2, 4.2 Hz, 3H), 1.70-1.59 (m, 1H), 1.33 (qd, J=9.6, 5.0 Hz, 1H), 0.87 (dt, J=11.1, 5.7 Hz, 2H). LCMS: $C_{37}H_{42}N_{12}O_7$ requires: 766, found: m/z=767.

Compound 215

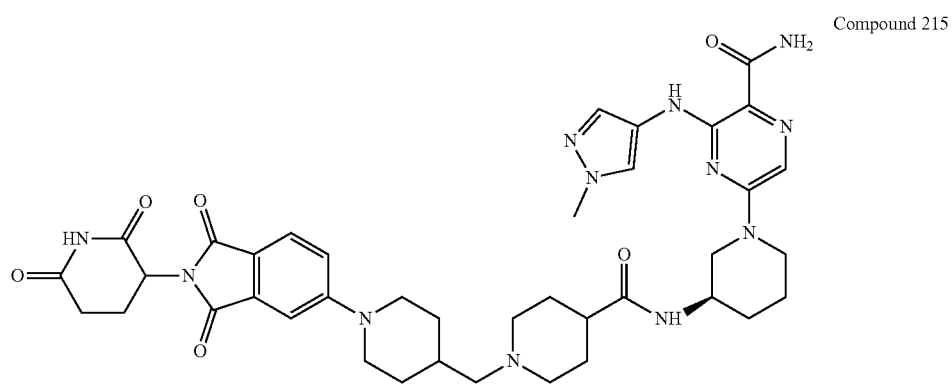 [SMILES: Cn1cc(Nc2nc(N3CCC[C@@H](NC(=O)C4CCN(CC5CCN(c6ccc7c(c6)C(=O)N(C6CCC(=O)NC6=O)C7=O)CC5)CC4)C3)cnc2C(N)=O)cn1]

¹H NMR (500 MHz, DMSO-d₆) δ 11.07 (s, 1H), 10.87 (s, 1H), 7.98 (s, 1H), 7.81 (d, J=6.9 Hz, 1H), 7.66 (s, 1H), 7.64 (d, J=8.5 Hz, 1H), 7.55 (s, 1H), 7.48 (s, 1H), 7.30 (d, J=2.1 Hz, 1H), 7.28-7.19 (m, 2H), 5.06 (dd, J=12.8, 5.4 Hz, 1H), 4.29 (s, 1H), 4.04 (d, J=13.0 Hz, 2H), 3.94 (d, J=13.0 Hz, 1H), 3.86 (s, 3H), 3.70 (s, 1H), 3.08 (t, J=10.9 Hz, 1H), 3.01-2.92 (m, 2H), 2.90-2.78 (m, 3H), 2.09 (h, J=6.3 Hz, 3H), 2.00 (dd, J=11.8, 6.0 Hz, 1H), 1.92-1.71 (m, 8H), 1.59 (d, J=24.4 Hz, 7H), 1.12 (d, J=12.5 Hz, 3H). LCMS: $C_{39}H_{48}N_{12}O_6$ requires: 780, found: m/z=781.

Compound 217
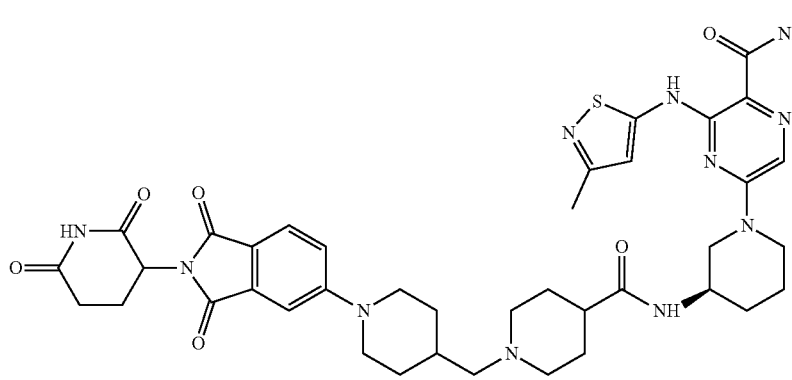
$^1$H NMR (500 MHz, DMSO-d$_6$) δ 12.27 (d, J=32.4 Hz, 1H), 11.06 (s, 1H), 8.01 (s, 1H), 7.84 (d, J=18.1 Hz, 1H), 7.63 (d, J=8.4 Hz, 1H), 7.58-7.43 (m, 2H), 7.28 (s, 1H), 7.20 (d, J=9.1 Hz, 1H), 6.85 (d, J=22.5 Hz, 1H), 5.05 (dd, J=12.9, 5.4 Hz, 1H), 4.17 (s, 1H), 4.00 (d, J=14.4 Hz, 2H), 3.74 (d, J=14.2 Hz, 1H), 3.57 (s, 1H), 3.48-3.35 (m, 3H), 3.09-2.77 (m, 3H), 2.72-2.54 (m, 2H), 2.28 (s, 3H), 2.22-2.05 (m, 2H), 2.05-1.90 (m, 3H), 1.80 (s, 3H), 1.70 (d, J=11.6 Hz, 3H), 1.64-1.28 (m, 5H), 1.23 (s, 1H), 1.20-0.96 (m, 3H). LCMS: C$_{38}$H$_{46}$N$_{12}$O$_6$S requires: 798, found: m/z=799.
Compound 218
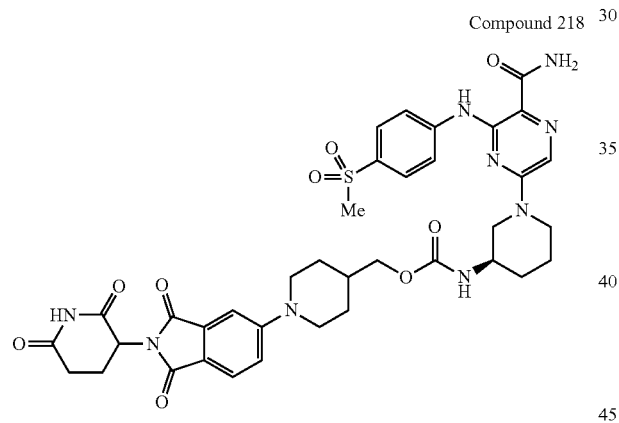
$^1$H NMR (500 MHz, chloroform-d) δ 11.60 (s, 1H), 7.99 (d, J=13.7 Hz, 1H), 7.94-7.75 (m, 4H), 7.55 (s, 1H), 5.30 (s, 2H), 4.96 (dd, J=12.2, 5.8 Hz, 1H), 4.39-3.12 (m, 13H), 2.89 (t, J=19.6 Hz, 1H), 2.84-2.65 (m, 1H), 2.20-2.10 (m, 1H), 2.10-1.98 (m, 1H), 1.59 (s, 15H). LCMS: C$_{37}$H$_{41}$N$_9$O$_9$S requires: 787, found: m/z=788.
Compound 203
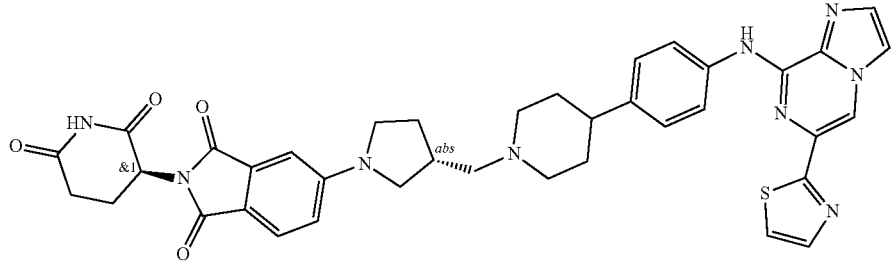
LCMS: C$_{38}$H$_{37}$N$_9$O$_4$S requires: 715, found: m/z=716.

Biological Example 1

Cell Culture

Ramos cells (CRL-1596) were obtained from American Type Culture Collection. TMD8 cells were obtained from Tokyo Medical and Dental University. Ramos cells were grown in RPMI-1640 media (ATCC, 30-2001) supplemented with 10% heat-inactivated FBS (Corning Premium Fetal Bovine Serum from Fisher, MT35015CV). TMD8 cells were grown in MEM alpha media (Fisher, 12571063) supplemented with 10% heat-inactivated FBS (Corning Premium Fetal Bovine Serum from Fisher, MT35015CV). All cells were cultured at 37° C. and 5% $CO_2$.

Human peripheral blood mononuclear cells (PBMC) were obtained either: 1) by using Ficoll-Paque™ (GE Healthcare) for separation of peripheral blood hematopoietic cells from buffy coats of healthy human donors; or 2) directly from LeukoPak donations. PBMCs were grown at 37° C. and 5% $CO_2$ in RPMI supplemented with 10% heat-inactivated FBS (Corning Premium Fetal Bovine Serum from Fisher, MT35015CV), 1× Penicillin/Streptomycin, and 2 mM Glutamine.

Generation of $BTK^{C481S}$ Knock-in Cell Lines

To generate cell lines expressing $BTK^{C481S}$, Cas9 RNP with a specific gRNA was introduced into cells by electroporation. Gene editing was assessed in polyclonal cell populations by sequencing. Monoclonal cell lines were made by diluting single cells into single wells, and mutation was confirmed by sequencing.

Western Blot Time-Course Assays

Determine the Kinetics of CTM-Induced BTK Degradation

Cells were plated in 6-well plates and treated with DMSO or CTM with a final DMSO concentration of >0.2%. At indicated timepoints after treatment, cells were harvested, washed once with PBS and lysed. Western blot analysis was performed using a BTK-specific antibody (Cell Signaling, 8547).

Biological Example 2

Cellular BTK Degradation Assay

In Vitro Cellular Screening to Determine Potency as Measured by $DC_{50}$ Values after Four Hour Incubation BTK CTMs were added to cells in round-bottom 96-well plates with a final DMSO concentration of >0.2% and were incubated at 37° C. and 5% $CO_2$ for four hours. BTK levels were determined using Cisbio Total-BTK HTRF (Homologous Time-Resolved Fluorescence) kit (63ADK064PEG) according to the manufacturer's protocol. Briefly, cells were incubated in 1× supplied lysis buffer for 30 minutes. In an opaque white low volume 96-well plate (Cisbio, 66PL96005), cell lysate was combined with two different specific BTK antibodies, one conjugated with $Eu^{3+}$-Cryptate FRET donor and one conjugated with d2 FRET acceptor. Assay controls include wells containing cell lysate with only the $Eu^{3+}$-Cryptate FRET donor antibody and wells containing both HTRF antibodies and lysis buffer without cells or control lysate provided by Cisbio. HTRF ratio was calculated as (acceptor signal at 665 nm/donor signal at 620 nm)×$10^4$. Background HTRF levels were determined from the control well containing the donor, but no acceptor, antibody. Background HTRF levels were subtracted from all samples. Readouts were reported as HTRF levels relative to HTRF levels of DMSO-treated cells. Four-parameter non-linear regressions were performed in GraphPad Prism 7.02 to obtain DC50 values.

Figure 2:
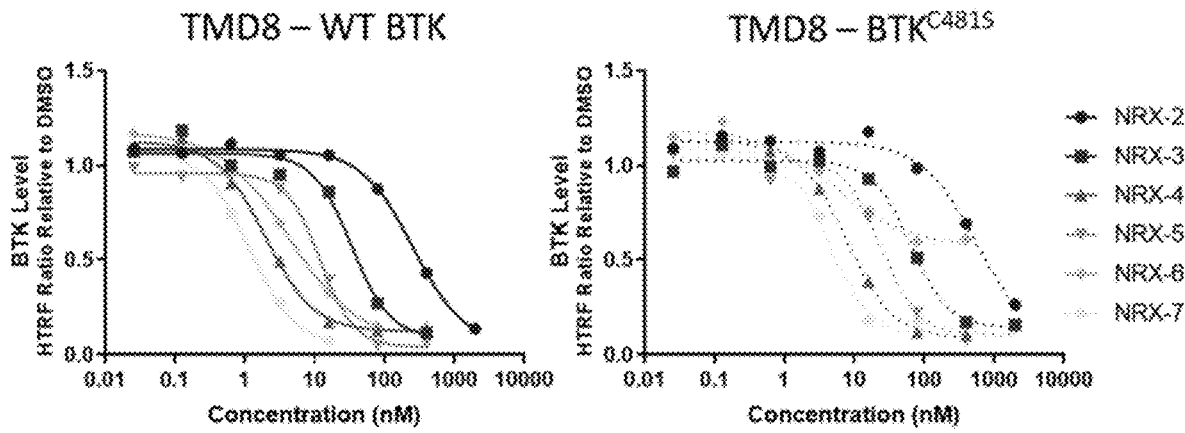
FIG. 2 provides degradation of wild-type BTK and ibrutinib-resistant C481S BTK by a compound herein.

As shown in FIG. 1, robust, time-dependent degradation of BTK was observed in multiple cell lines and primary human B cells in the presence of a compound provided herein. As shown in FIG. 2, several compounds provided herein induced degradation of BTK in Ramos cells expressing wild-type BTK or ibrutinib-resistant C481S mutant BTK.

Biological Example 3

Proteomics

Determine Global Effects of BTK CTM Treatment on the Proteome

TMD8 cells were treated with DMSO or 50 nM CTM in triplicate. After six hours, cells were harvested, washed twice with PBS, and stored as frozen cell pellets. Proteomic analysis, including sample preparation, tandem mass tag (TMT) labeling, fraction, mass spectrometry, and data processing, was performed by MS Bioworks.

Figure 3:
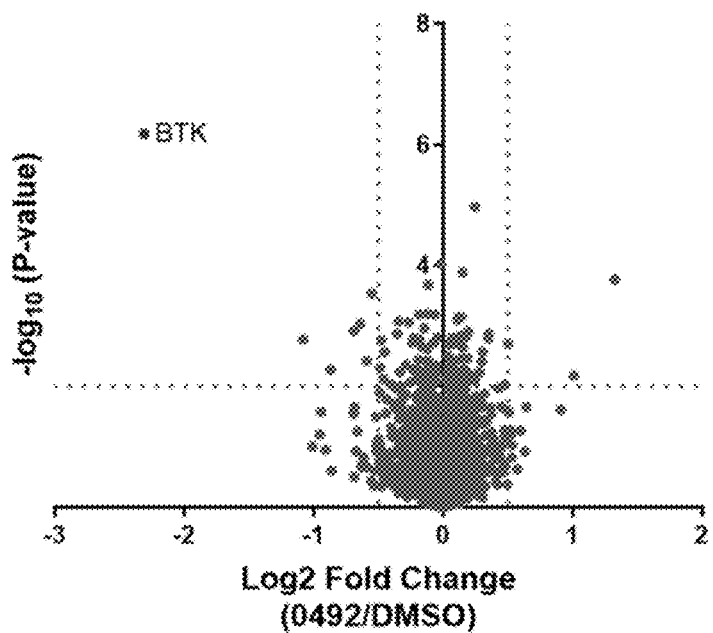
FIG. 3 demonstrates highly selective degradation of BTK by a compound herein.

As shown in FIG. 3, a compound provided herein selectively degraded BTK in TMD8 cells.

Biological Example 4

Cellular Viability Assay

Evaluate Effects of BTK Degradation in BTK-Dependent Cell Lines

Cell viability was determined using CellTiter-Glo 2.0 Luminescent Cell Viability Assay (Promega, G9242), which quantitates the amount of ATP present as a proxy for the number of viable cells in culture. Cells were plated with densities between 2000-4000 cells per well in 96-well plates. Serial dilutions of BTK CTMs or comparator compounds were added with a final DMSO concentration of >0.3% and were incubated at 37° C. and 5% $CO_2$ for seventy-two hours. CellTiter-Glo reagent was added to cells at a dilution of 1:20, and the plate was incubated ten minutes at room temperature prior to reading the luminescence signal using an EnVision plate reader. Controls included cells treated with DMSO and wells that contained no cells, only media. Background luminescence signal was determined by control wells containing no cells, only media, and was then subtracted from all sample wells. Luminescence values were then normalized to DMSO-treated wells and reported at proportion viable cells.

Figure 4:
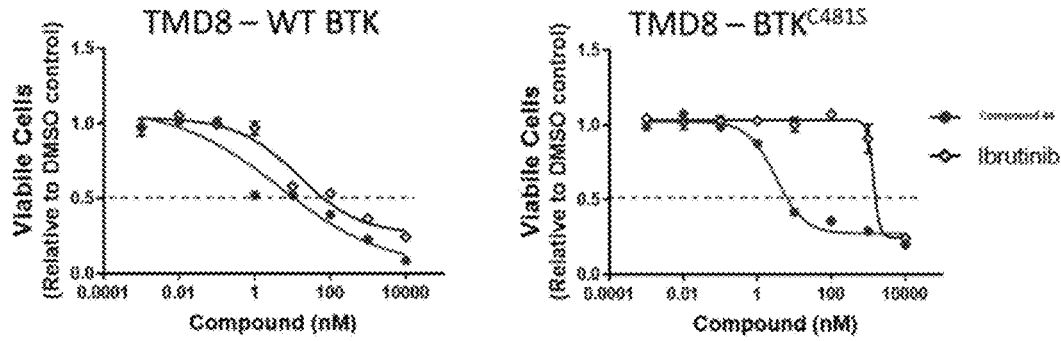
FIG. 4 demonstrates increased C481S BTK cell viability sensitivity to a compound herein relative to ibrutiniib.

As shown in FIG. 4, wild-type BTK cells were sensitive to a compound provided herein and to ibrutinib. Mutant C481S BTK cells retained sensitivity to the compound provided herein but were less sensitive to ibrutinib.

Biological Example 5

B Cell Activation Assay

Evaluate Effects of BTK Degradation on B Cell Receptor Signaling

Frozen human peripheral blood mononuclear cells (PBMCs) were thawed and treated with DMSO or compound for four hours and then stimulated for 18 hours with 10 μg/ml anti-IgM (Jackson Immunoresearch 109-006-129), and an additional DMSO-treated sample was left unstimulated. Compound was present throughout the stimulation. Cells were stained with Live/Dead dye (Fisher L34976) and then fluorophore-conjugated antibodies against CD20 (Biolegend 302330), CD3 (BD Pharmingen 557705), CD86 (Biolegend 305416) and CD69 (Biolegend 310906). Stained cells were fixed in PFA and run on an Attune NxT Acoustic Focusing Flow Cytometer (Thermo-Fisher A29004), and data was analyzed using FlowJo (v10.5.3) and GraphPad Prism (v7.00) software. Single live lymphocytes were gated for B cells (CD20+CD3−) and T cells (CD3+CD20−), and the geometric mean fluorescence intensity (MFI) of CD86 and CD69 was calculated for each population. The MFI of the unstimulated sample was used to quantify baseline activation.

Figure 5:
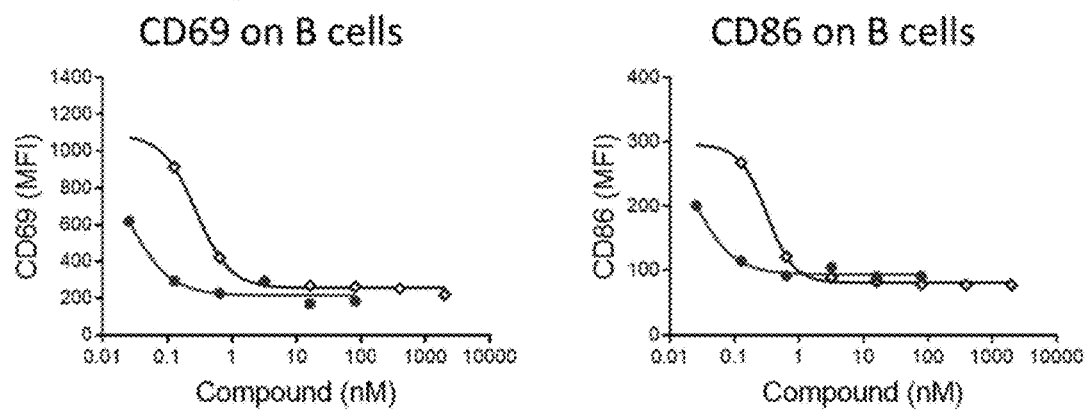
FIG. 5 demonstrates that a compound herein prevents B cell activiation.

As shown in FIG. 5, compound-mediated degradation of BTK prevented anti-IgM-induced upregulation of activation markers CD69 and CD86 on B cells.

Biological Example 6

Cellular Aiolos Degradation Assay
In Vitro Cellular Screening to Determine IMiD Activity
Frozen human peripheral blood mononuclear cells (PBMCs) were thawed and treated with DMSO or compound for twenty-four hours and then fixed and permeabilized using a Foxp3/Transcription Factor Fixation/Permeabilization Kit (eBioscience, 00-5523). Cells were stained with fluorophore-conjugated antibodies against CD20 (Biolegend 302330), CD3 (BD Pharmingen 552127), and Aiolos (Biolegend 371106). An additional set of DMSO-treated PBMCs was stained for CD20, CD3, and an AlexaFluor 647-conjugated mouse IgG1 isotype control antibody (Biolegend 400136). Stained cells were run on an Attune NxT Acoustic Focusing Flow Cytometer (Thermo-Fisher A29004), and data was analyzed using FlowJo (v10.5.3) and GraphPad Prism (v7.00) software. Single lymphocytes were gated for B cells (CD20+CD3−) and T cells (CD3+CD20−), and the geometric mean fluorescence intensity (MFI) of Aiolos was calculated for each population. The MFI of the isotype control was calculated for each population and used to quantify background staining. Percent Aiolos degradation was calculated for each compound-treated sample using the following equation:

$$\% \text{ Degradation} = 100 * (\text{Sample MFI} - \text{Isotype MFI}) / (\text{DMSO MFI} - \text{Isotype MFI}).$$

Figure 9:
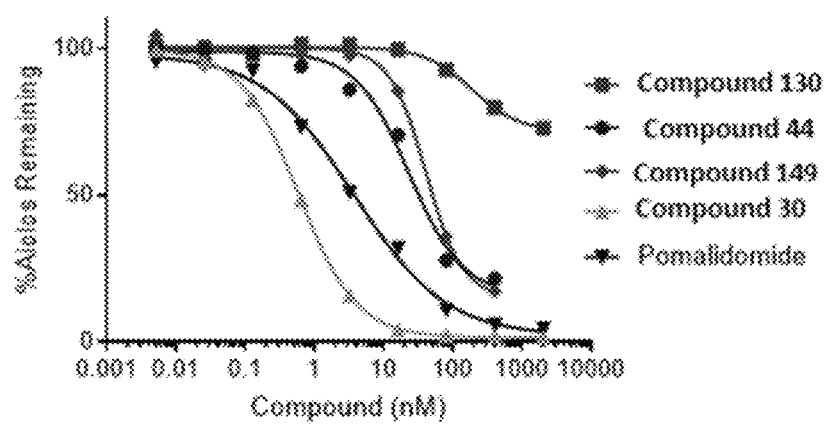
FIG. 9 demonstrates degradation of BTK neosubstrate Aiolos.

Exemplary results are shown in FIG. 9.

Biological Example 7

Mouse PD Assays
Determine Whether CTMs Catalyze BTK Degradation In Vivo

A method of determining the pharmacodynamic profile of BTK degraders was performed by dosing either CD-1 or BALB/c mice with CTM. The CTM was prepared in a suitable formulation and was administered via oral gavage (PO) at a suitable dose level and frequency as informed by prior pharmacokinetic and tolerability studies. Following administration of CTM, BTK levels in blood or splenocytes are measured using flow cytometry or HTRF. For assessment of BTK levels via flow cytometry, either whole blood or splenocytes were first treated with ACK RBC lysis buffer to facilitate lysing of red blood cells. Remaining cells were then stained with fluorophore-conjugated antibodies against CD45, TCR beta and CD45R (B220). Cell pellets were washed with 1×PBS, fixed, and permeabilized for twenty-four hours with Foxp3/Transcription Factor Fixation/Permeabilization Kit. Cells were then stained intracellularly with unconjugated BTK antibody and detected with a fluorophore-conjugated secondary antibody. Stained cells were run on an Attune NxT Acoustic Focusing Flow Cytometer (Thermo-Fisher A29004), and data was analyzed using FlowJo (v10.5.3) and GraphPad Prism (v7.00) software. Lymphocytes were gated for B cells defined as CD45+ TCR beta− B220+ and T cells as CD45+ TCR beta+ B220−. The BTK geometric mean fluorescence intensity (MFI) was calculated for B and T cells. Percent BTK degradation for each compound-treated sample was calculated using the equation described below:

$$\% \text{ Degradation} = 100 * (\text{Treated sample B cell BTK MFI} - \text{treated sample T cell BTK MFI}) / (\text{Vehicle B cell BTK MFI} - \text{Vehicle T cell BTK MFI})$$

Figure 6:
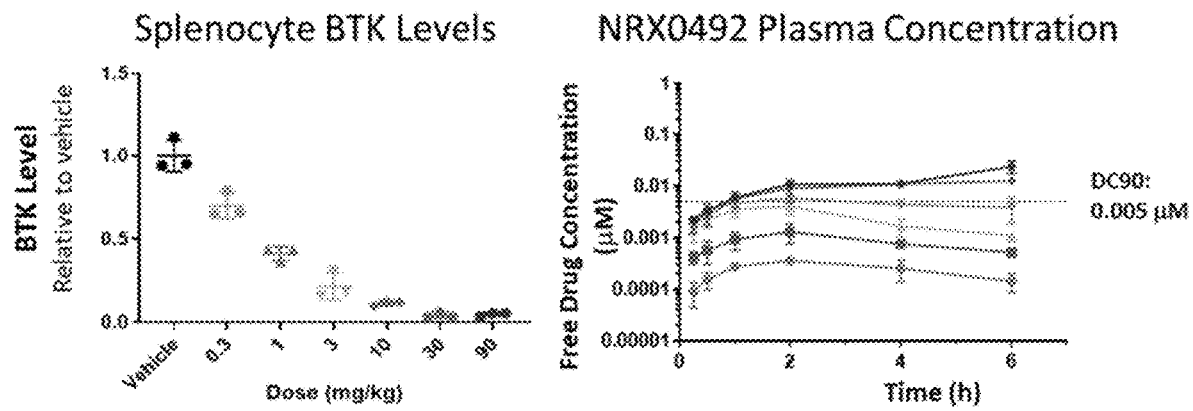
FIG. 6 demonstrates dose proportional degradation of BTK in splenocytes following oral administration of a compound herein to mice.
Figure 7:
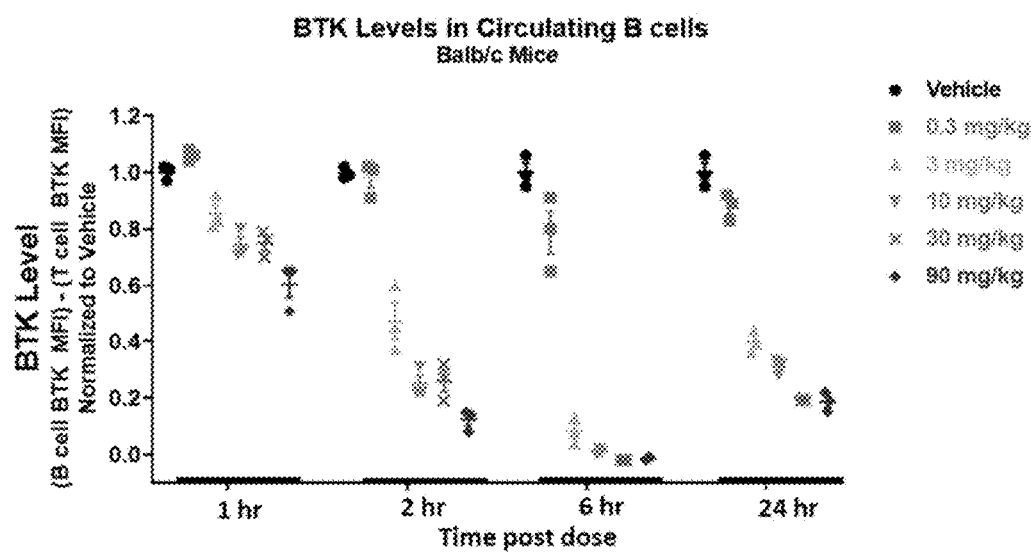
FIG. 7 demonstrates dose- and time-proportional reduction of BTK in circulating B cells following oral administration of a compound herein.

As shown in FIG. 6, a dose-proportional decrease in BTK levels was observed in splenocytes after six hours of treatment and was associated with compound exposure in plasma. As shown in FIG. 7, dose- and dimt-dependent reduction in BTK levels were observed in circulating murine B cells after a single oral dose.

Biological Example 8

TMD8 Xenograft Efficacy Studies
Evaluate Anti-Tumor Effects of BTK Degradation In Vivo
The anti-tumor activity of CTM and Ibrutinib was evaluated in CB.17 SCID female mice bearing either TMD8 or TMD8 BTK$^{C481S}$ tumor cells. Mice were inoculated subcutaneously with either TMD8 or TMD8 BTK$^{C481S}$ cells and were randomized when tumors reached the predetermined size into treatment groups, vehicle control, CTM (30 mg/kg) or ibrutinib (30 mg/kg). Tumor bearing mice received either once a day (QD) or twice daily (BID) oral dose of CTM or ibrutinib.

Tumor and body weights were measured three times per week over a duration of twenty-one days. Tumor growth inhibition (% TGI) were calculated on the final day of measurement using the equation $[1-(T-T_0/C-T_0)] \times 100$, where T and C represent the mean size of tumors in the treated (T) and control (C) groups, and $T_0$ refers to the tumor size at randomization.

Figure 8:
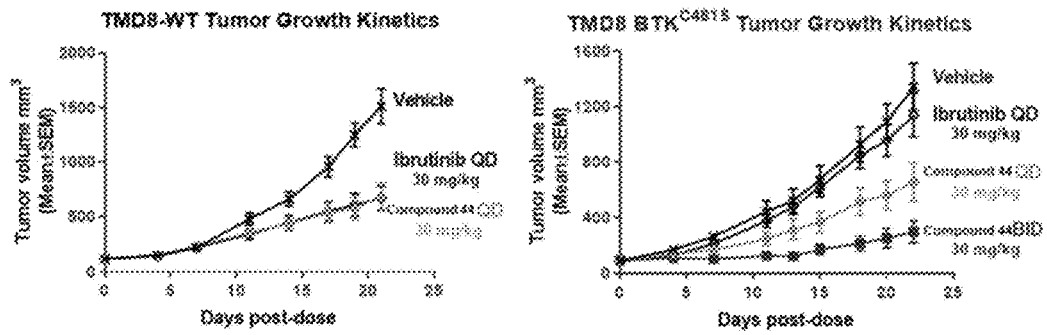
FIG. 8 demonstrates anti-tumor activity of a compound herein following oral administration of a compound herein to mice in a xenograft model of a tumor and an ibrutinib-resistant tumor.

As shown in FIG. 8, treatment with a compound herein caused tumor growth inhibition in a wild-type BTK xenograft model and in an ibrutinib-resistant C481S xenograft model.

Biological Example 9

Cellular BTK Degradation Assay
Cellular BTK degradation was measured as above for four hours in TMD8 cells for two diastereomers of compound 130. $DC_{50}$ and $EC_{50}$ values are the concentration at which the response is halfway between the top and bottom of the fitted non-linear regression curve.

| Compound | Treatment Time (h) | Cells | $DC_{50}$ (µM) |
|---|---|---|---|
| 195 | 4 | TMD8 | 0.00026 |
| 194 | 4 | TMD8 | 0.0043 |

Biological Example 10

BTK Degradation (Total BTK HTRF) at Twenty-Four Hours in TMD8 Cells
The present example evaluates whether potency of BTK CTMs shifts with longer timepoints. $DC_{50}$ values are typically calculated with a 4-hour timepoint. Most CTMs tested were slightly more potent at twenty-four hours compared to four hours.

| Compound ID | Treatment Time (h) | Cells | $DC_{50}$ (µM) |
|---|---|---|---|
| 44 | 24 | TMD8 | 0.00036 |
| 148 | 24 | TMD8 | 0.00068 |
| 149 | 24 | TMD8 | 0.0023 |
| 150 | 24 | TMD8 | 0.0047 |
| 72 | 24 | TMD8 | 0.00021 |
| 121 | 24 | TMD8 | 0.0010 |

Biological Example 11

BTK Degradation (Total BTK HTRF) at Four Hours in TMD8 cells Expressing BTK-C481S This example evaluates the potency of CTM in degrading BTK-C481S. The BTK binding moieties utilized in CTMs bind to the BTK active site. This example evaluates whether the active site mutation C481S affects CTM-induced degradation of BTK. The CTMs are potent towards Bruton's tyrosine kinase-C481S, but they are generally two- to three-fold more potent towards WT BTK compared to BTK-C48S.

| Compound ID | Treatment Time (h) | Cells | $DC_{50}$ (µM) |
|---|---|---|---|
| 55 | 4 | TMD8 BTK-C481S (clone2C3) | 0.0058 |
| 53 | 4 | TMD8 BTK-C481S (clone2C3) | 0.0080 |
| 44 | 4 | TMD8 BTK-C481S (clone2C3) | 0.0018 |
| 37 | 4 | TMD8 BTK-C481S (clone2C3) | 0.0027 |
| 101 | 4 | TMD8 BTK-C481S (clone2C3) | 0.0043 |
| 83 | 4 | TMD8 BTK-C481S (clone2C3) | 0.0027 |
| 121 | 4 | TMD8 BTK-C481S (clone2C3) | 0.0041 |
| 73 | 4 | TMD8 BTK-C481S (clone2C3) | 0.0012 |
| 72 | 4 | TMD8 BTK-C481S (clone2C3) | 0.0020 |
| 70 | 4 | TMD8 BTK-C481S (clone2C3) | 0.0031 |
| 69 | 4 | TMD8 BTK-C481S (clone2C3) | 0.0008 |
| 149 | 4 | TMD8 BTK-C481S (clone2C3) | 0.0144 |
| 148 | 4 | TMD8 BTK-C481S (clone2C3) | 0.0097 |
| 133 | 4 | TMD8 BTK-C481S (clone2C3) | 0.0083 |
| 130 | 4 | TMD8 BTK-C481S (clone2C3) | 0.0018 |
| 129 | 4 | TMD8 BTK-C481S (clone2C3) | 0.0053 |
| 126 | 4 | TMD8 BTK-C481S (clone2C3) | 0.0077 |
| 166 | 4 | TMD8 BTK-C481S (clone2C3) | 0.0081 |
| 182 | 4 | TMD8 BTK-C481S (clone2C3) | 0.0145 |
| 156 | 4 | TMD8 BTK-C481S (clone2C3) | 0.0004 |

Biological Example 12

BTK Degradation (Total BTK HTRF) at Four Hours in Mino Cells

This example evaluates the potency of CTMs in a model of Mantle Cell Lymphoma (MCL). To evaluate potential therapeutic indications, BTK CTMs were assayed in models of Mantle Cell Lymphoma as with the TMD8 cells (ABC-DLBCL) above. Tested CTMs had similar potencies for BTK degradation in the MCL cell lines (Mino and Rec-1) and TMD8 cells.

| Compound ID | Treatment Time (h) | Cells | $DC_{50}$ (µM) |
|---|---|---|---|
| 44 | 4 | Mino | 0.00056 |
| 149 | 4 | Mino | 0.0059 |
| 130 | 4 | Mino | 0.00058 |
| 44 | 4 | Rec-1 | 0.001 |
| 149 | 4 | Rec-1 | 0.004 |
| 130 | 4 | Rec-1 | 0.002 |

Biological Example 13

BTK Degradation in Human PBMCs (BTK Flow Cytometry)

This example evaluates the potency of CTMs in primary human B cells, rather than transformed or immortalized cancer cell lines. Primary cells are believed to be a physiologically relevant model. Thus, this example confirms the potency, kinetics, and level of BTK degradation in these cells in addition to the cell line models. Furthermore, this assay establishes that it is possible to monitor BTK degradation in primary human B cells, which can serve as a clinical biomarker.

| Compound ID | Treatment Time (h) | $DC_{50}$ (µM) |
|---|---|---|
| 44 | 4 | 0.00051 |
| 149 | 4 | 0.0019 |
| 130 | 4 | 0.00013 |
| 44 | 2 | 0.003 |
| 44 | 1 | 0.006 |

Biological Example 14

Ikaros and Aiolos Degradation in Mantle Cell Lymphoma Lines (Ikaros and Aiolos Flow Cytometry)

This example evaluates the IMiD activity of CTMs in cellular models of Mantle Cell Lymphoma (MCL). Currently approved treatments for MCL include ibrutinib and lenalidomide, suggesting that targeting BTK and engaging CRBN are both viable therapeutic approaches in this indication. These assays are to determine potency of CTMs for degrading IMiD neo-substrates in cellular models of MCL and to generate data to inform efficacy studies in MCL xenografts. These data demonstrate IMiD activity for some compounds (e.g., compound 149) and not others (e.g., compound 130) and shows that IMiD neo-substrates are more potently degraded in Rec-1 cells compared to Mino cells, supporting us of Rec-1 cells in subsequent in vitro and in vivo studies.

| Compound ID | Treatment Time (h) | Cells | Aiolos $DC_{50}$ (µM) | Ikaros $DC_{50}$ (µM) |
|---|---|---|---|---|
| 44 | 24 | Mino | 0.1 | 1.4 |
| 44 | 24 | Rec-1 | 0.07 | 0.072 |
| 149 | 24 | Mino | 0.087 | 0.13 |

-continued

| Compound ID | Treatment Time (h) | Cells | Aiolos DC$_{50}$ (μM) | Ikaros DC$_{50}$ (μM) |
|---|---|---|---|---|
| 149 | 24 | Rec-1 | 0.081 | 0.061 |
| 130 | 24 | Mino | >2 | >2 |
| 130 | 24 | Rec-1 | >2 | >2 |
| 30 | 24 | Mino | 0.01 | 1.1 |
| 30 | 24 | Rec-1 | 0.034 | 1.0 |
| 25 | 24 | Mino | 0.01 | 0.029 |
| 25 | 24 | Rec-1 | 0.031 | 0.063 |
| Lenalidomide | 24 | Rec-1 | 0.394 | 1.904 |
| Pomalidomide | 24 | Rec-1 | 0.033 | 0.056 |
| Lenalidomide | 24 | Mino | 0.91 | >2 |
| Pomalidomide | 24 | Mino | 0.049 | 0.244 |

Figure 10A:
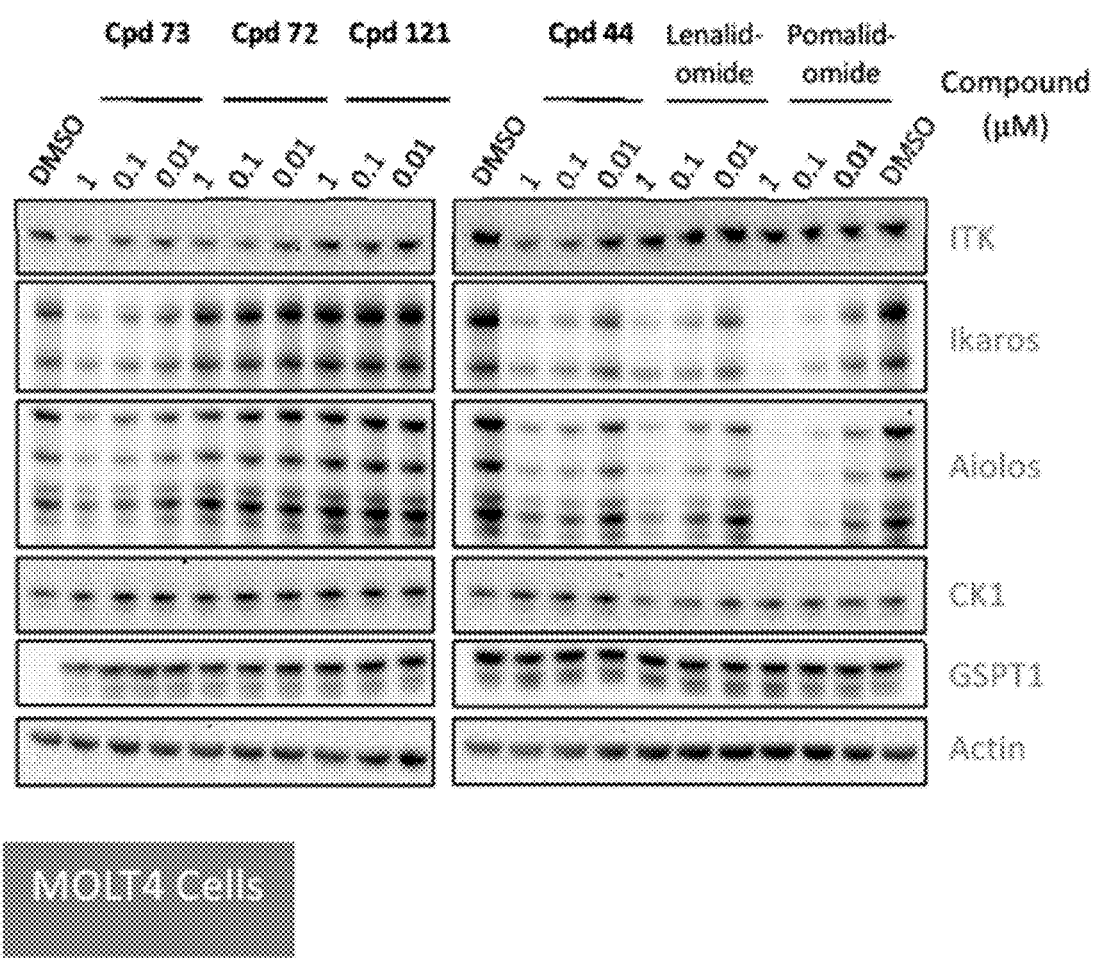
FIGS. 10A and 10B provide effects of compounds 73, 72, 121, and 44, and control compounds, on neo-substrate and ITK or BTK levels after twenty-four hours in MOLT4 cells (FIG. 10A) and TMD8 cells (FIG. 10B).
Figure 10B:
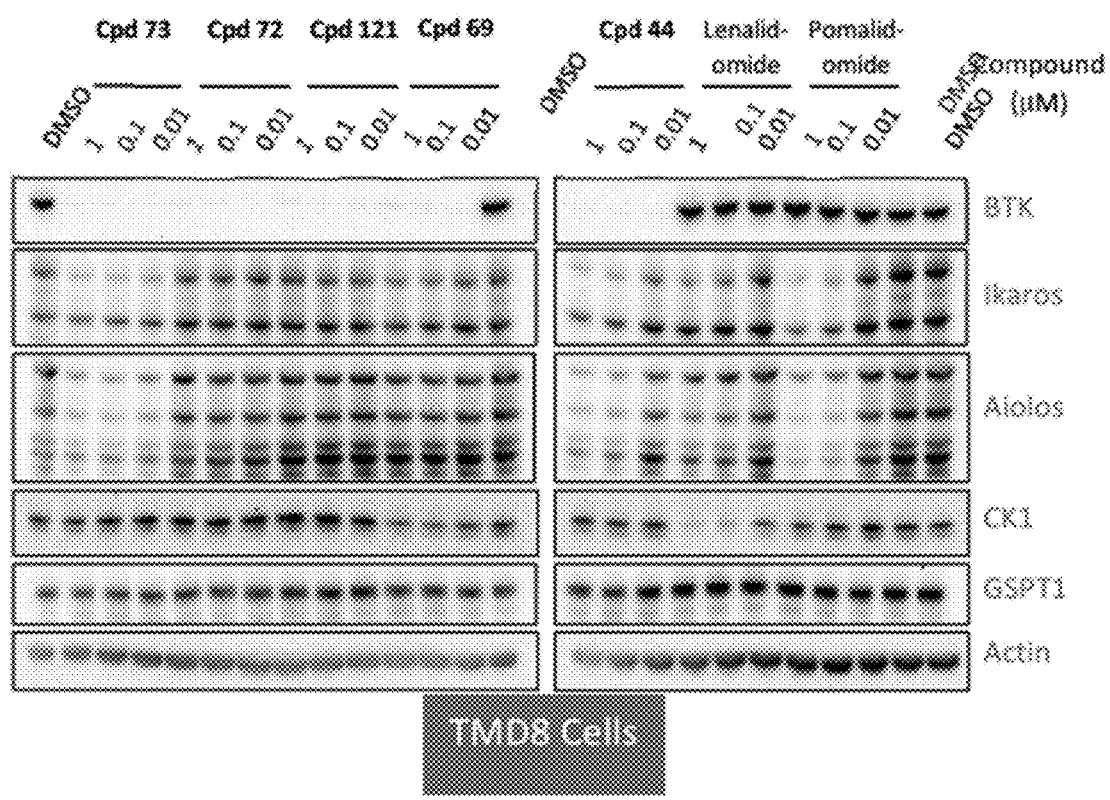

As shown in FIGS. 10A and 10B, compound 44 has some effects on neo-substrate and ITK levels after twenty-four hours in TMD8 and/or MOLT4 cells.

As shown in FIGS. 10A and 10B, compound 72 does not effect CRBN neo-substrates but does affect ITK levels at twenty-four hours.

As shown in FIGS. 10A and 10B, compound 121 has minimal effects on CRBN neo-substrates and ITK at twenty-four hours.

Figure 11A:
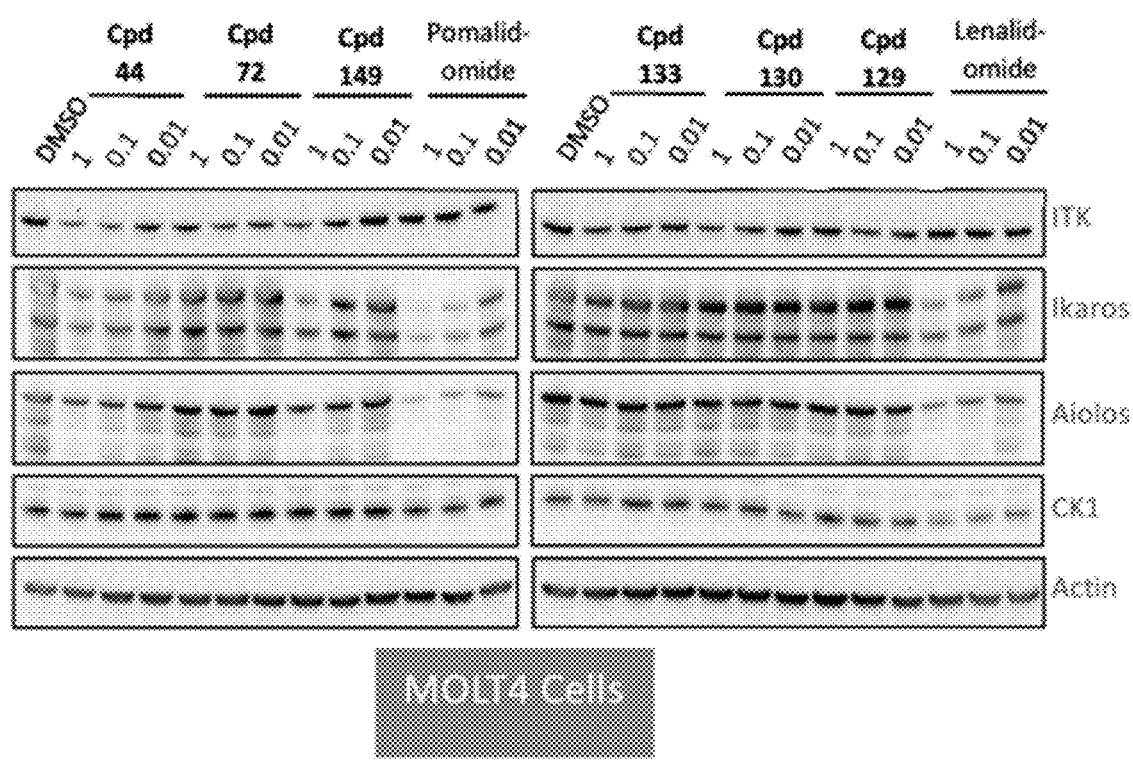
FIGS. 11A and 11B provide effects of compounds 44, 72, and 149, and control compounds, on CRBN neo-substrate and ITK levels in MOLT4 cells (FIG. 1A) and TMD8 cells (FIG. 11B).
Figure 11B:
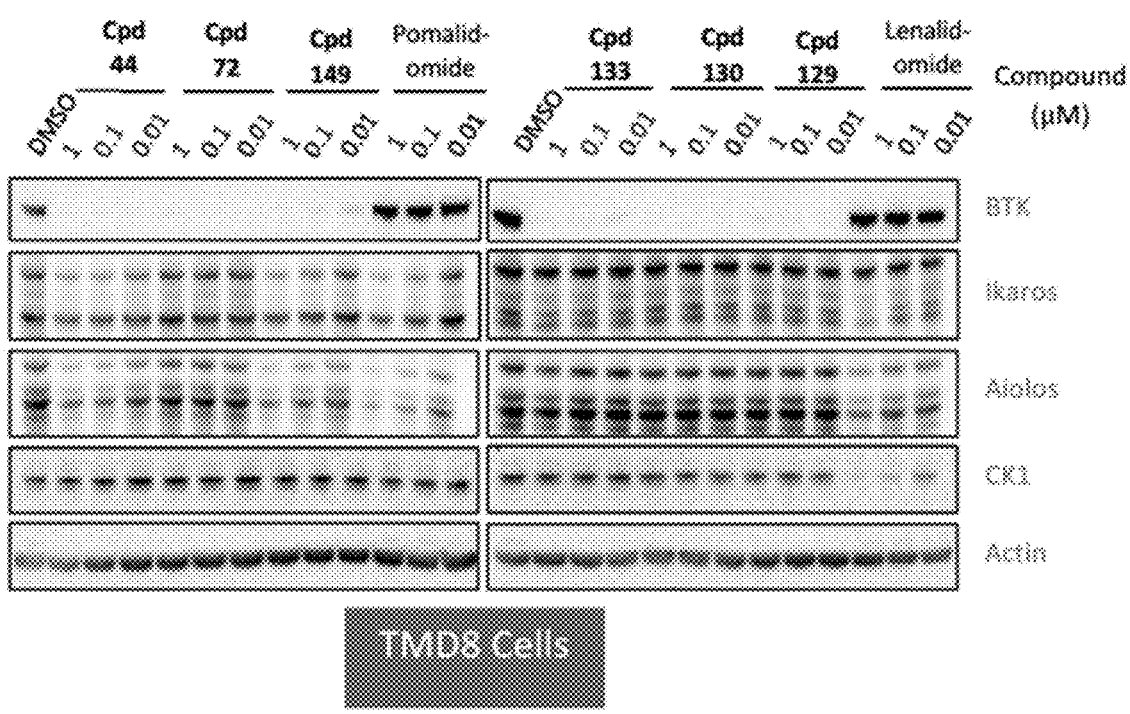

As shown in FIGS. 11A and 11B, compounds 44 and 149 have some effect on CRBN neo-substrate and ITK levels in cells.

Figure 12:
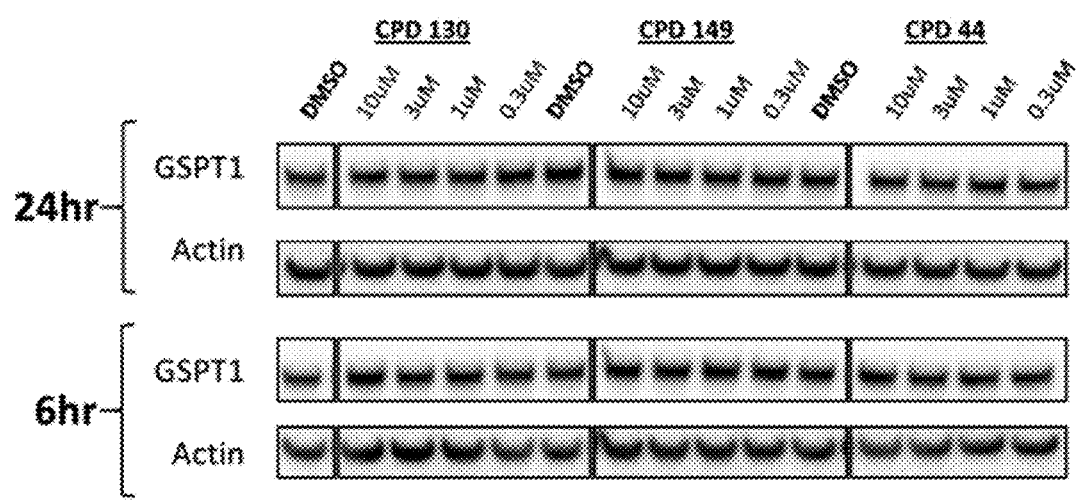
FIG. 12 provides effects of compounds 130, 149, and 44 on ITK levels and IMiD activity.
Figure 13A:
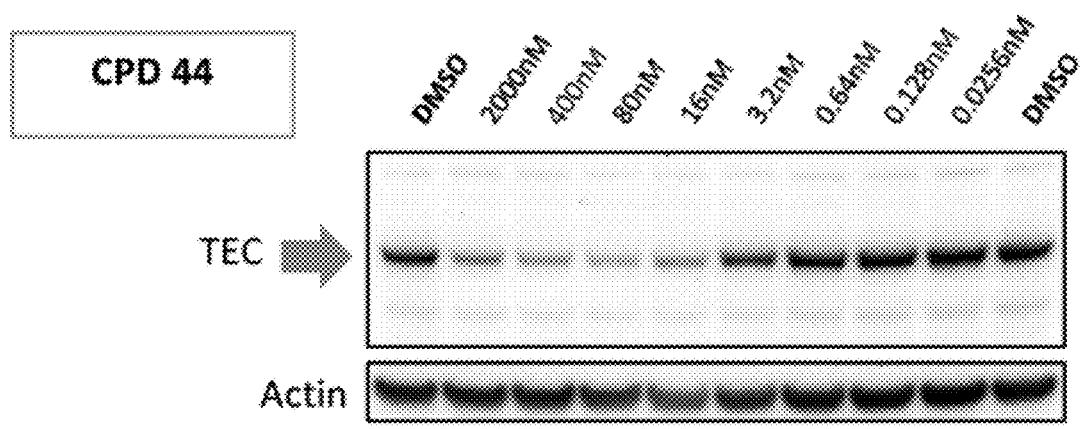
FIGS. 13A-D provide TEC degradation by chimeric targeting molecules (CTMs) in K562 cells.
Figure 13B:
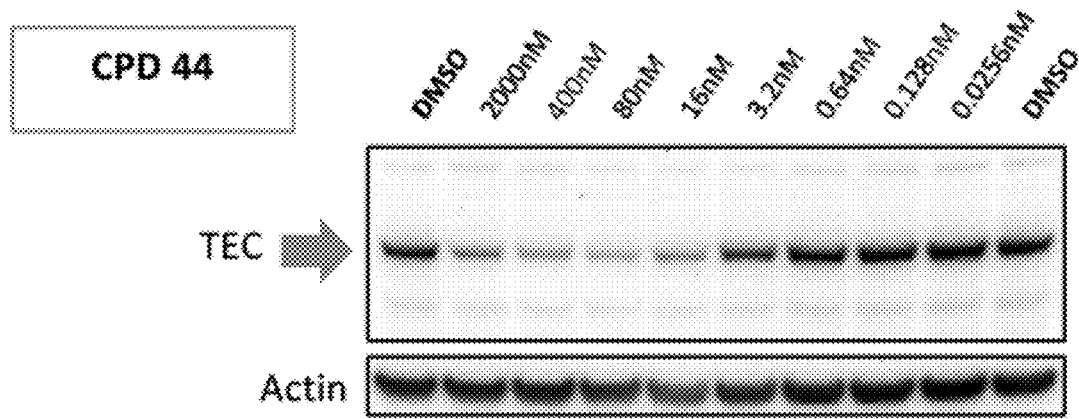
Figure 13C:
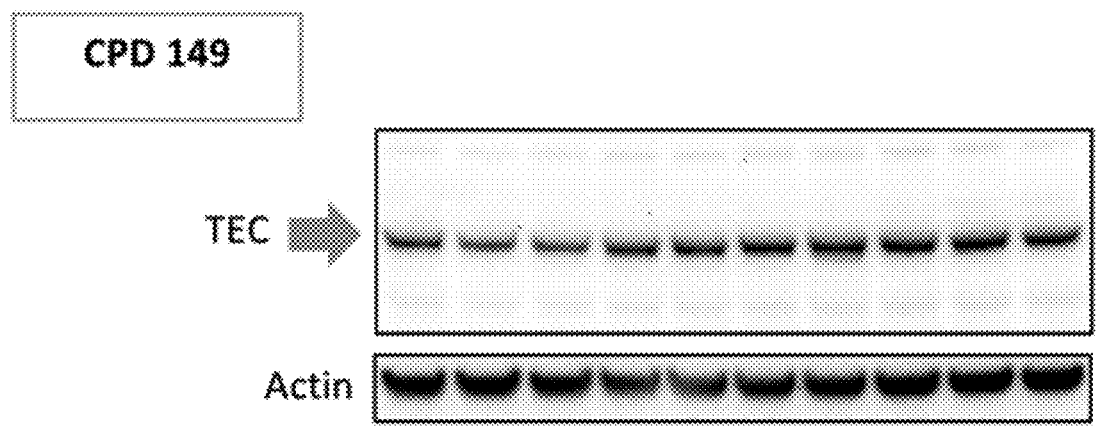
Figure 13D:
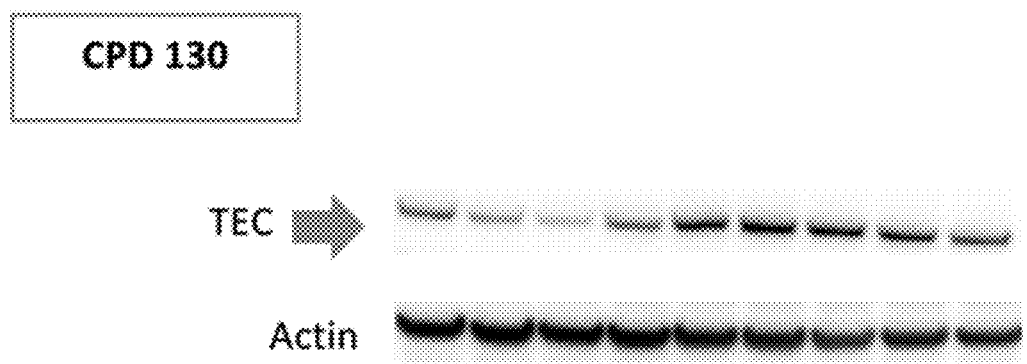

As shown in FIG. 12, other CTMs tested had slight effects on ITK levels but did not have IMiD activity, including compounds 72 and 130.

Biological Example 15

TEC Kinase Degradation

This example assesses whether CTM treatment affects levels of off-target protein TEC kinase.

BTK and TEC kinase are two members of the TEC kinase family, and BTK inhibitors, such as ibrutinib, have been shown to affect TEC activity. This off-target effect of ibrutinib on TEC kinase has been implicated in the bleeding effects observed clinically with ibrutinib treatment. To determine effects of BTK CTMs on TEC levels in cells, K562 cells were treated for four hours with CTMs at concentrations between 0.026-2000 nM. TEC levels in cell lysate was assessed by western blot.

Tested CTMs have mild to moderate effects on TEC kinase levels in K562 cells but exhibit more potent degradation of BTK than TEC as shown in FIGS. 13A-13D. The CTMs include compounds 44, 72, 149, and 130.

Biological Example 16

B Cell Activation Assay (Flow Cytometry)

This example evaluates whether CTM treatment affects B cell receptor (BCR) signaling. BTK is activated downstream of the B cell receptor and leads to upregulation of activation markers CD86 and CD69 on the surface of B cells. These data illustrate that degradation of BTK can block this signaling pathway similar to inhibition of BTK with ibrutinib.

| Compound ID | Treatment Time (h) | IgM Stimulation Time (h) | Cells | CD86 EC$_{50}$ (μM) | CD69 EC$_{50}$ (μM) |
|---|---|---|---|---|---|
| 44 | 4 | 18 | Mouse B cells | 0.0004 | 0.0002 |
| 37 | 4 | 18 | Mouse B cells | 0.0002 | 0.0001 |
| 83 | 4 | 18 | Mouse B cells | 0.0001 | 0.00008 |
| 69 | 4 | 18 | Mouse B cells | 0.0003 | 0.0001 |
| 121 | 4 | 18 | Mouse B cells | 0.0009 | 0.0005 |
| 72 | 4 | 18 | Mouse B cells | 0.0002 | 0.00007 |
| 73 | 4 | 18 | Mouse B cells | 0.0002 | ~0.0002 |
| 71 | 4 | 18 | Mouse B cells | 0.002 | 0.001 |
| Ibrutinib | 4 | 18 | Mouse B cells | 0.001 | 0.0007 |
| Acalabrutinib | 4 | 18 | Mouse B cells | 0.003 | 0.001 |
| ARQ531 | 4 | 18 | Mouse B cells | 0.07 | 0.05 |
| 44 | 4 | 18 | Human B cells | 0.0005 | 0.0005 |
| 149 | 4 | 18 | Human B cells | 0.005 | 0.004 |
| 130 | 4 | 18 | Human B cells | 0.0005 | 0.0004 |
| Ibrutinib | 4 | 18 | Human B cells | 0.0002 | 0.0002 |
| Acalabrutinib | 4 | 18 | Human B cells | 0.003 | 0.002 |

Biological Example 17

T Cell Activation Assay (ELISA and Flow Cytometry)

This example evaluates whether CTMs with IMiD activity affect T cell activation.

Activation of T cells is thought to be one way in which IMiDs, such as Lenalidomide and Pomalidomide can modulate the immune system. These assays were performed to assess whether BTK CTMs with and without IMiD activity affected activation of primary human T cells after stimulation of the T cell receptor with anti-CD3/anti-CD28 stimulation. T cell activation was measured by IL-2 secretion (ELISA assay) and upregulation of activation markers CD25 and CD69 on the surface of T cells (flow cytometry). Data are presented as the fold-change of response relative to baseline (stimulation with anti-CD3/anti-CD28 stimulation in the absence of compound).

Lenalidomide and Pomalidomide induce IL-2 secretion and increase expression of CD25 and CD69 above the baseline level (anti-CD3/anti-CD28 stimulation alone).

Ibrutinib treatment results in decreases in IL-2 secretion and expression of CD25 and CD69 compared to baseline. As BTK is not present in T cells, this could be due to ibrutinib's off-target effects on other kinases such as ITK.

CTMs with IMiD activity (such as compounds 44, 149, 30, and 25) increased IL-2 secretion but not to the level observed with IMiDs. Treatment with these CTMs resulted in unchanged or decreased levels of CD25 and CD69, potentially due to non-IMiD effects of the CTM, like affecting ITK.

These data suggest there is a correlation between IMiD neo-substrate degradation activity of certain CTMs and their phenotypic effects on T cell activation in terms of IL-2 secretion.

| Compound ID | IL-2 Secretion Anti-CD3/Anti-CD28 Stimulation | | | CD25 Staining Anti-CD3/Anti-CD28 Stimulation | | | CD69 Staining Anti-CD3/Anti-CD28 Stimulation | | |
|---|---|---|---|---|---|---|---|---|---|
| | 333 nM | 37 nM | 1.4 nM | 333 nM | 37 nM | 1.4 nM | 333 nM | 37 nM | 1.4 nM |
| Ibrutinib | 0.34 | 0.85 | 0.84 | 0.22 | 0.74 | 0.92 | 0.22 | 0.74 | 0.89 |
| Lenalidomide | 8.67 | 4.48 | 1.63 | 1.93 | 1.73 | 1.26 | 1.81 | 1.49 | 1.20 |
| Pomalidomide | 5.50 | 4.80 | 1.31 | 1.63 | 1.39 | 1.03 | 1.77 | 1.33 | 1.01 |
| 25 | 3.86 | 3.35 | 2.42 | 1.39 | 1.30 | 1.25 | 1.39 | 1.33 | 1.18 |
| 17 | 2.92 | 3.14 | 1.59 | 1.11 | 1.34 | 1.06 | 1.12 | 1.23 | 1.05 |
| 64 | 1.48 | 1.80 | 1.28 | 0.34 | 1.04 | 1.17 | 0.64 | 1.14 | 1.14 |
| 53 | 2.53 | 2.08 | 1.22 | 0.84 | 1.14 | 1.09 | 0.83 | 1.07 | 1.06 |
| 51 | 2.12 | 1.99 | 1.19 | 0.38 | 0.62 | 0.86 | 0.39 | 0.62 | 0.91 |
| 44 | 3.75 | 3.49 | 1.43 | 0.52 | 0.86 | 1.25 | 0.60 | 0.85 | 1.21 |
| 38 | 1.81 | 1.58 | 1.21 | 0.86 | 1.02 | 1.05 | 0.90 | 0.99 | 1.02 |
| 37 | 1.64 | 2.06 | 1.16 | 0.43 | 0.79 | 1.11 | 0.45 | 0.77 | 1.08 |
| 34 | 1.58 | 1.66 | 1.48 | 1.25 | 1.31 | 1.21 | 1.23 | 1.21 | 1.14 |
| 31 | 3.59 | 2.45 | 1.23 | 1.32 | 1.34 | 1.15 | 1.26 | 1.24 | 1.12 |
| 30 | 3.95 | 3.82 | 1.59 | 1.17 | 1.14 | 1.01 1 | 1.16 | 1.10 | 1.01 |
| 92 | 1.63 | 2.19 | 1.53 | 1.06 | 1.21 | 1.14 | 1.35 | 1.29 | 1.09 |
| 78 | 1.20 | 1.17 | 1.00 | 0.44 | 0.73 | 0.99 | 0.43 | 0.66 | 1.00 |
| 149 | 4.24 | 3.63 | 1.86 | 0.61 | 1.02 | 1.31 | 0.63 | 0.93 | 1.22 |
| 130 | 2.02 | 1.42 | 1.19 | 0.55 | 0.98 | 1.02 | 0.55 | 0.96 | 1.00 |
| 155 | 3.11 | 3.13 | 1.62 | 1.21 | 1.46 | 1.31 | 1.20 | 1.34 | 1.25 |
| 154 | 3.45 | 3.38 | 1.77 | 1.13 | 1.36 | 1.23 | 1.16 | 1.29 | 1.18 |

Biological Example 18

Cell Viability Assay (CellTiter-Glo)

This example evaluates effects of CTM-mediated degradation on cell viability. Certain B cell malignancies have been shown to be dependent on BCR signaling and thus BTK for survival. Here, the ability of CTMs to affect viability in BTK-dependent cell lines was assessed. Mino and Rec-1 are models of Mantle Cell Lymphoma, which is sensitive to IMiD. In these MCL cell lines, BTK CTMs affected degradation, and CTMs with IMiD activity (compounds 44 and 149) were more potent than a CTM with minimal IMiD activity (compound 130).

| Compound ID | Treatment Time (h) | Cells | $EC_{50}$ (μM) | $E_{MAX}$ (% viable cells) |
|---|---|---|---|---|
| 44 | 72 | Mino | 11.7 | 61 |
| 149 | 72 | Mino | 3.4 | 50 |
| 130 | 72 | Mino | 176 | 78 |
| Ibrutinib | 72 | Mino | 498 | 79 |
| Acalabrutinib | 72 | Mino | 1.241 | 84 |
| Ibnitinib | 72 | Rec-1 | 268 | 68 |
| Acalabrutinib | 72 | Rec-1 | 582 | 76 |
| 44 | 72 | Rec-1 | 0.82 | 37 |
| 149 | 72 | Rec-1 | 0.17 | 24 |
| 130 | 72 | Rec-1 | 155 | 63 |

Biological Example 19

This example evaluates the effects of CTM-mediated degradation on cell viability. Certain B cell malignancies have been shown to be dependent on BCR signaling and thus BTK for survival. Here, the ability of CTMs to affect viability in BTK-dependent cell lines was assessed. The ABC-DLBCL cell line TMD8 was very sensitive to BTK degradation or inhibition, while the TMD8 cell line expressing the ibrutinib-resistant mutant BTK-C481S retained sensitivity to BTK degradation (~2-5 fold less sensitive than WT) but were not sensitive to BTK inhibition.

| Compound ID | Treatment Time (h) | Cells | $EC_{50}$ (μM) | $E_{MAX}$ (% viable cells) |
|---|---|---|---|---|
| 21 | 72 | TMD8 | 0.001600 | 19 |
| 17 | 72 | TMD8 | 0.000600 | 7 |
| 60 | 72 | TMD8 | 0.000970 | 20 |
| 59 | 72 | TMD8 | 0.000150 | 31 |
| 55 | 72 | TMD8 | 0.002405 | 15 |
| 54 | 72 | TMD8 | 0.000610 | 13 |
| 53 | 72 | TMD8 | 0.002240 | 16 |
| 51 | 72 | TMD8 | 0.000320 | 20 |
| 49 | 72 | TMD8 | 0.000610 | 28 |
| 47 | 72 | TMD8 | 0.003831 | 39 |
| 44 | 72 | TMD8 | 0.003728 | 15 |
| 42 | 72 | TMD8 | 0.000217 | 40 |
| 37 | 72 | TMD8 | 0.021090 | 10 |
| 31 | 72 | TMD8 | 0.015884 | 27 |
| 101 | 72 | TMD8 | 0.093380 | 27 |
| 86 | 72 | TMD8 | 0.000670 | 27 |
| 83 | 72 | TMD8 | 0.001660 | 38 |
| 80 | 72 | TMD8 | 0.045160 | 45 |
| 78 | 72 | TMD8 | 0.009040 | 41 |
| 212 | 72 | TMD8 | 0.015080 | 42 |
| 211 | 72 | TMD8 | 0.011700 | 30 |
| 121 | 72 | TMD8 | 0.001542 | 28 |
| 210 | 72 | TMD8 | 0.005610 | 32 |
| 209 | 72 | TMD8 | 0.007410 | 49 |
| 208 | 72 | TMD8 | 0.000007 | 24 |
| 206 | 72 | TMD8 | 0.000005 | 43 |
| 73 | 72 | TMD8 | 0.000004 | 25 |
| 72 | 72 | TMD8 | 0.000429 | 26 |
| 149 | 72 | TMD8 | 0.009615 | 7 |
| 148 | 72 | TMD8 | 0.003265 | 2 |
| 115 | 72 | TMD8 | 0.002743 | 13 |
| 133 | 72 | TMD8 | 0.006981 | 15 |
| 130 | 72 | TMD8 | 0.001496 | 27 |
| 129 | 72 | TMD8 | 0.003174 | 16 |
| Acalabrutinib | 72 | TMD8 | 0.012 | 35 |
| ARQ531 | 72 | TMD8 | 0.10 | 16 |
| Ibrutinib | 72 | TMD8 | 0.003 | 16 |
| Vecabrutinib | 72 | TMD8 | 0.256 | 38 |
| 17 | 72 | TMD8 C481S | 0.003710 | 15 |
| 60 | 72 | TMD8 C481S | 0.008370 | 26 |
| 59 | 72 | TMD8 C481S | 0.002030 | 52 |
| 55 | 72 | TMD8 C481S | 0.016840 | 19 |
| 54 | 72 | TMD8 C481S | 0.007110 | 6 |
| 53 | 72 | TMD8 C481S | 0.016060 | 24 |
| 51 | 72 | TMD8 C481S | 0.001950 | 49 |
| 49 | 72 | TMD8 C481S | 0.003860 | 23 |

-continued

| Compound ID | Treatment Time (h) | Cells | EC$_{50}$ (µM) | E$_{MAX}$ (% viable cells) |
|---|---|---|---|---|
| 47 | 72 | TMD8 C481S | 0.043520 | 61 |
| 44 | 72 | TMD8 C481S | 0.008104 | 25 |
| 42 | 72 | TMD8 C481S | 0.001960 | 57 |
| 37 | 72 | TMD8 C481S | 0.051657 | 16 |
| 31 | 72 | TMD8 C481S | 0.059425 | 33 |
| 101 | 72 | TMD8 C481S | 0.431100 | 27 |
| 86 | 72 | TMD8 C481S | 0.004780 | 30 |
| 83 | 72 | TMD8 C481S | 0.004315 | 52 |
| 80 | 72 | TMD8 C481S | 0.124800 | 78 |
| 78 | 72 | TMD8 C481S | 0.007190 | 37 |
| 212 | 72 | TMD8 C481S | 0.062955 | 44 |
| 211 | 72 | TMD8 C481S | 0.112690 | 28 |
| 121 | 72 | TMD8 C481S | 0.004943 | 31 |
| 210 | 72 | TMD8 C481S | 0.005290 | 40 |
| 209 | 72 | TMD8 C481S | 0.055200 | 44 |
| 208 | 72 | TMD8 C481S | 0.000038 | 16 |
| 207 | 72 | TMD8 C481S | 0.000009 | 54 |
| 206 | 72 | TMD8 C481S | 0.000102 | 46 |
| 73 | 72 | TMD8 C481S | 0.000054 | 19 |
| 72 | 72 | TMD8 C481S | 0.001158 | 21 |
| 149 | 72 | TMD8 C481S | 0.037184 | 18 |
| 148 | 72 | TMD8 C481S | 0.009176 | 4 |
| 115 | 72 | TMD8 C481S | 0.001931 | 16 |
| 133 | 72 | TMD8 C481S | 0.006829 | 9 |
| 130 | 72 | TMD8 C481S | 0.004829 | 33 |
| 129 | 72 | TMD8 C481S | 0.004356 | 14 |
| Acalabrutinib | 72 | TMD8 C481S | >2 | 96 |
| ARQ531 | 72 | TMD8 C481S | 0.10 | 17 |
| Ibrutinib | 72 | TMD8 C481S | 1.044 | 46 |
| Vecabrutinib | 72 | TMD8 C481S | 0.530 | 51 |

Biological Example 20

In Vivo Degradation of BTK in Mouse PD Experiments with Oral Dosing

This example evaluates in vivo activity of BTK CTMs via a direct mouse PD measurement following oral dosing Various BTK CTMs demonstrate robust BTK degradation activity in vivo; activity varies from inactive compounds to compounds with sustained BTK degradation even twenty-four hours after single oral dose; this data helped understand BTK degradation/resynthesis rates in vivo. Screens were completed at 90 mg/kg for six hours, and then changed to lower doses/longer time points after seeing strong BTK degradation activity with an initial set of compounds. This assay was useful in selecting compounds for in vivo efficacy experiments. The assay showed a good correlation between mouse PD results and in vivo efficacy in mouse tumor models.

| Compound ID | Oral Dose (mg/kg) | Time (h) | Tissue | % BTK Remaining | Analysis Method |
|---|---|---|---|---|---|
| 60 | 90 | 6 | Splenocytes | 3% | HTRF |
| 59 | 90 | 6 | Splenocytes | 7% | HTRF |
| 54 | 90 | 6 | Splenocytes | 1% | HTRF |
| 58 | 90 | 6 | Splenocytes | 89% | HTRF |
| 47 | 90 | 6 | Splenocytes | 80% | HTRF |
| 44 | 90 | 6 | Splenocytes | 4% | HTRF |
| 44 | 1 | 6 | Splenocytes | 58% | HTRF |
| 44 | 3 | 6 | Splenocytes | 32% | HTRF |
| 44 | 10 | 6 | Splenocytes | 11% | HTRF |
| 44 | 30 | 6 | Splenocytes | 4% | HTRF |
| 44 | 10 | 24 | Splenocytes | 34% | HTRF |
| 44 | 30 | 24 | Splenocytes | 23% | HTRF |
| 44 | 1 (IV) | 24 | Splenocytes | 58% | HTRF |
| 45 | 90 | 6 | Splenocytes | 8% | HTRF |
| 46 | 90 | 6 | Splenocytes | 14% | HTRF |
| 48 | 90 | 6 | Splenocytes | 7% | HTRF |
| 49 | 90 | 6 | Splenocytes | <1% | HTRF |
| 50 | 90 | 6 | Splenocytes | 9% | HTRF |
| 51 | 90 | 6 | Splenocytes | 2% | HTRF |
| 52 | 90 | 6 | Splenocytes | 2% | HTRF |
| 43 | 90 | 6 | Splenocytes | 4% | HTRF |
| 42 | 90 | 6 | Splenocytes | 5% | HTRF |
| 41 | 90 | 6 | Splenocytes | 15% | HTRF |
| 40 | 1 | 6 | Splenocytes | 82% | HTRF |
| 39 | 1 | 6 | Splenocytes | 79% | HTRF |
| 38 | 1 | 6 | Splenocytes | 68% | HTRF |
| 38 | 1 | 6 | Splenocytes | 76% | HTRF |
| 38 | 3 | 6 | Splenocytes | 38% | HTRF |
| 32 | 1 | 6 | Splenocytes | 93% | HTRF |
| 34 | 1 | 6 | Splenocytes | 75% | HTRF |
| 35 | 1 | 6 | Splenocytes | 74% | HTRF |
| 55 | 1 | 6 | Splenocytes | 80% | HTRF |
| 55 | 1 | 6 | Splenocytes | 66% | HTRF |
| 55 | 3 | 6 | Splenocytes | 18% | HTRF |
| 55 | 0.3 | 24 | Blood | 83% | Flow cytometry |
| 55 | 3 | 24 | Blood | 55% | Flow cytometry |
| 55 | 10 | 24 | Blood | 47% | Flow cytometry |
| 55 | 30 | 24 | Blood | 39% | Flow cytometry |
| 55 | 90 | 24 | Blood | 23% | Flow cytometry |
| 55 | 0.3 | 24 | Splenocytes | 114% | Flow cytometry |
| 55 | 3 | 24 | Splenocytes | 72% | Flow cytometry |
| 55 | 10 | 24 | Splenocytes | 45% | Flow cytometry |
| 55 | 30 | 24 | Splenocytes | 36% | Flow cytometry |
| 55 | 90 | 24 | Splenocytes | 48% | Flow cytometry |
| 108 | 1 | 6 | Splenocytes | 116% | HTRF |
| 113 | 1 | 6 | Splenocytes | 70% | HTRF |
| 113 | 30 | 24 | blood | 59% | |
| 113 | 30 | 24 | splenocytes | 52% | HTRF |
| 76 | 1 | 6 | Splenocytes | 100% | HTRF |
| 79 | 1 | 6 | Splenocytes | 102% | HTRF |
| 105 | 1 | 6 | Splenocytes | 85% | HTRF |
| 101 | 1 | 6 | Splenocytes | 18% | HTRF |
| 101 | 1 | 6 | Splenocytes | 55% | HTRF |
| 218 | 1 | 6 | Splenocytes | 97% | HTRF |
| 86 | 3 | 6 | blood | 56% | Flow cytometry |
| 86 | 3 | 24 | blood | 70% | Flow cytometry |
| 83 | 3 | 6 | blood | 48% | Flow cytometry |
| 83 | 3 | 24 | blood | 63% | Flow cytometry |
| 217 | 3 | 6 | blood | 97% | Flow cytometry |
| 217 | 3 | 24 | blood | 97% | Flow cytometry |
| 37 | 3 | 6 | blood | 26% | Flow cytometry |
| 37 | 3 | 24 | blood | 51% | Flow cytometry |
| 53 | 3 | 6 | blood | 35% | Flow cytometry |
| 53 | 3 | 24 | blood | 56% | Flow cytometry |
| 31 | 3 | 6 | blood | 67% | Flow cytometry |
| 31 | 3 | 24 | blood | 69% | Flow cytometry |
| 216 | 3 | 6 | blood | 100% | Flow cytometry |
| 215 | 3 | 6 | blood | 88% | Flow cytometry |
| 214 | 3 | 6 | blood | 100% | Flow cytometry |
| 80 | 3 | 6 | blood | 96% | Flow cytometry |
| 80 | 0.3 | 24 | blood | 88% | Flow cytometry |
| 80 | 3 | 24 | blood | 77% | Flow cytometry |
| 80 | 10 | 24 | blood | 59% | Flow cytometry |
| 80 | 30 | 24 | blood | 52% | Flow cytometry |
| 80 | 90 | 24 | blood | 48% | Flow cytometry |
| 80 | 0.3 | 24 | Splenocytes | 115% | Flow cytometry |
| 80 | 3 | 24 | Splenocytes | 111% | Flow cytometry |
| 80 | 10 | 24 | Splenocytes | 74% | Flow cytometry |
| 80 | 30 | 24 | Splenocytes | 69% | Flow cytometry |
| 80 | 90 | 24 | Splenocytes | 65% | Flow cytometry |
| 213 | 3 | 6 | blood | 97% | Flow cytometry |
| 78 | 3 | 6 | blood | 74% | Flow cytometry |
| 212 | 3 | 6 | blood | 78% | Flow cytometry |
| 211 | 3 | 6 | blood | 74% | Flow cytometry |
| 71 | 30 | 24 | splenocytes | 27% | HTRF |
| 73 | 30 | 24 | splenocytes | 26% | HTRF |
| 206 | 30 | 24 | splenocytes | 59% | HTRF |
| 207 | 30 | 24 | splenocytes | 46% | HTRF |
| 72 | 30 | 24 | splenocytes | 20% | HTRF |

-continued

| Compound ID | Oral Dose (mg/kg) | Time (h) | Tissue | % BTK Remaining | Analysis Method |
|---|---|---|---|---|---|
| 121 | 30 | 24 | splenocytes | 33% | HTRF |
| 121 | 0.3 | 24 | blood | 102% | Flow cytometry |
| 121 | 3 | 24 | blood | 68% | Flow cytometry |
| 121 | 30 | 24 | blood | 28% | Flow cytometry |
| 120 | 30 | 24 | splenocytes | 59% | HTRF |
| 70 | 30 | 24 | splenocytes | 42% | HTRF |
| 204 | 30 | 24 | splenocytes | 87% | HTRF |
| 119 | 30 | 24 | splenocytes | 77% | HTRF |
| 69 | 30 | 24 | splenocytes | 33% | HTRF |
| 69 | 0.3 | 24 | blood | 112% | Flow cytometry |
| 69 | 3 | 24 | blood | 43% | Flow cytometry |
| 69 | 30 | 24 | blood | 30% | Flow cytometry |
| 118 | 30 | 24 | splenocytes | 85% | HTRF |
| 205 | 30 | 24 | splenocytes | 66% | HTRF |
| 153 | 30 | 24 | blood | 33% | Flow cytometry |
| 117 | 30 | 24 | blood | 49% | Flow cytometry |
| 146 | 30 | 24 | blood | 37% | Flow cytometry |
| 144 | 30 | 24 | blood | 29% | Flow cytometry |
| 143 | 30 | 24 | blood | 37% | Flow cytometry |
| 116 | 30 | 24 | blood | 39% | Flow cytometry |
| 142 | 30 | 24 | blood | 43% | Flow cytometry |
| 148 | 30 | 24 | blood | 24% | Flow cytometry |
| 149 | 10 | 24 | blood | 27% | Flow cytometry |
| 149 | 30 | 24 | blood | 11% | Flow cytometry |
| 149 | 90 | 24 | blood | 1% | Flow cytometry |
| 149 | 10 | 24 | splenocytes | 21% | HTRF |
| 149 | 30 | 24 | splenocytes | 8% | HTRF |
| 149 | 90 | 24 | splenocytes | 1% | HTRF |
| 145 | 30 | 24 | blood | 100% | Flow cytometry |
| 150 | 30 | 24 | blood | 25% | Flow cytometry |
| 203 | 30 | 24 | blood | 95% | Flow cytometry |
| 115 | 30 | 24 | blood | 30% | Flow cytometry |
| 133 | 30 | 24 | blood | 10% | Flow cytometry |
| 130 | 30 | 24 | blood | 5% | Flow cytometry |
| 129 | 30 | 24 | blood | 16% | Flow cytometry |
| 126 | 30 | 24 | blood | 33% | Flow cytometry |
| 176 | 30 | 24 | splenocytes | 48% | HTRF |
| 175 | 30 | 24 | splenocytes | 62% | HTRF |
| 168 | 30 | 24 | splenocytes | 84% | HTRF |
| 166 | 30 | 24 | splenocytes | 19% | HTRF |
| 164 | 30 | 24 | splenocytes | 29% | HTRF |
| 165 | 30 | 24 | splenocytes | 29% | HTRF |
| 182 | 30 | 24 | splenocytes | 12% | HTRF |
| 196 | 30 | 24 | blood | 33% | Flow cytometry |
| 197 | 30 | 24 | blood | 13% | Flow cytometry |
| 198 | 30 | 24 | blood | 25% | Flow cytometry |
| 199 | 30 | 24 | blood | 20% | Flow cytometry |
| 200 | 30 | 24 | blood | 23% | Flow cytometry |
| 202 | 30 | 24 | blood | 79% | Flow cytometry |
| 201 | 30 | 24 | blood | 71% | Flow cytometry |
| 195 | 3 | 24 | Blood | 40% | Flow cytometry |
| 194 | 3 | 24 | blood | 90% | Flow cytometry |
| 195 | 10 | 24 | Blood | 25% | Flow cytometry |
| 194 | 10 | 24 | blood | 63% | Flow cytometry |
| 195 | 3 | 24 | splenocytes | 39% | Flow cytometry |
| 194 | 3 | 24 | splenocytes | 95% | Flow cytometry |
| 195 | 10 | 24 | splenocytes | 23% | Flow cytometry |
| 194 | 10 | 24 | splenocytes | 57% | Flow cytometry |

Biological Example 21

PD Data from Rat, Dog and Cyno

In this example, compounds were profiled for activity in non-mouse species. These data were used to assess likelihood of BTK degradation activity in humans and to estimate an efficacious human dose Multiple BTK CTMs demonstrated potent BTK degradation activity across rat, dog, and cyno species. Human dose projections based upon this data suggest an efficacious human dose of <500 mg/day.

| Compound ID | Dose (mg/kg) | Route of Administration | Time (h) | Species | Tissue | % BTK Remaining |
|---|---|---|---|---|---|---|
| 44 | 10 | PO | 2 | cyno | blood | 82% |
| 44 | 10 | PO | 4 | cyno | blood | 42% |
| 44 | 10 | PO | 8 | cyno | blood | 27% |
| 44 | 10 | PO | 24 | cyno | blood | 29% |
| 44 | 30 | PO | 2 | cyno | blood | 83% |
| 44 | 30 | PO | 4 | cyno | blood | 47% |
| 44 | 30 | PO | 8 | cyno | blood | 22% |
| 44 | 30 | PO | 24 | cyno | blood | 17% |
| 44 | 1 | IV | 2 | cyno | blood | 6% |
| 44 | 1 | IV | 4 | cyno | blood | 6% |
| 44 | 1 | IV | 8 | cyno | blood | 7% |
| 44 | 1 | IV | 24 | cyno | blood | 9% |
| 44 | 10 | PO | 2 | dog | blood | 88% |
| 44 | 10 | PO | 4 | dog | blood | 56% |
| 44 | 10 | PO | 8 | dog | blood | 35% |
| 44 | 10 | PO | 24 | dog | blood | 19% |
| 44 | 30 | PO | 2 | dog | blood | 87% |
| 44 | 30 | PO | 4 | dog | blood | 58% |
| 44 | 30 | PO | 8 | dog | blood | 28% |
| 44 | 30 | PO | 24 | dog | blood | 14% |
| 44 | 1 | PO | 2 | cyno | blood | 85% |
| 44 | 1 | PO | 4 | cyno | blood | 65% |
| 44 | 1 | PO | 8 | cyno | blood | 52% |
| 44 | 1 | PO | 24 | cyno | blood | 40% |
| 44 | 10 | PO | 2 | cyno | blood | 59% |
| 44 | 10 | PO | 4 | cyno | blood | 35% |
| 44 | 10 | PO | 8 | cyno | blood | 22% |
| 44 | 10 | PO | 24 | cyno | blood | 15% |
| 44 | 100 | PO | 2 | cyno | blood | 48% |
| 44 | 100 | PO | 4 | cyno | blood | 27% |
| 44 | 100 | PO | 8 | cyno | blood | 12% |
| 44 | 100 | PO | 24 | cyno | blood | 8% |
| 130 | 10 | PO | 4 | rat | blood | <1% |
| 130 | 30 | PO | 4 | rat | blood | <1% |
| 130 | 10 | PO | 24 | rat | blood | <1% |
| 130 | 30 | PO | 24 | rat | blood | <1% |
| 130 | 1 | IV | 4 | rat | blood | <1% |
| 130 | 1 | IV | 24 | rat | blood | <1% |
| 130 | 1 | IV | 2 | Cyno | blood | 8 |
| 130 | 1 | IV | 4 | cyno | blood | 6 |
| 130 | 1 | IV | 8 | Cyno | blood | 5 |
| 130 | 1 | IV | 24 | cyno | blood | 13 |
| 130 | 10 | PO | 2 | Cyno | blood | 4 |
| 130 | 10 | PO | 4 | cyno | blood | <1 |
| 130 | 10 | PO | 8 | Cyno | blood | <3 |
| 130 | 10 | PO | 24 | cyno | blood | <1 |
| 130 | 30 | PO | 2 | Cyno | blood | 6 |
| 130 | 30 | PO | 4 | cyno | blood | <1 |
| 130 | 30 | PO | 8 | Cyno | blood | <1 |
| 130 | 30 | PO | 24 | cyno | blood | 1 |
| 149 | 1 | IV | 2 | Cyno | blood | 24 |
| 149 | 1 | IV | 4 | cyno | blood | 9 |
| 149 | 1 | IV | 8 | Cyno | blood | 4 |
| 149 | 1 | IV | 24 | cyno | blood | 7 |
| 149 | 10 | PO | 2 | Cyno | blood | 81 |
| 149 | 10 | PO | 4 | cyno | blood | 39 |
| 149 | 10 | PO | 8 | Cyno | blood | 17 |
| 149 | 10 | PO | 24 | cyno | blood | 12 |
| 149 | 30 | PO | 2 | Cyno | blood | 89 |
| 149 | 30 | PO | 4 | cyno | blood | 51 |
| 149 | 30 | PO | 8 | Cyno | blood | 26 |
| 149 | 30 | PO | 24 | cyno | blood | 19 |
| 149 | 100 | PO | 2 | Cyno | blood | 97 |
| 149 | 100 | PO | 4 | cyno | blood | 56 |
| 149 | 100 | PO | 8 | Cyno | blood | 20 |
| 149 | 100 | PO | 24 | cyno | blood | 12 |
| 149 | 1 | IV | 2 | dog | blood | 43 |
| 149 | 1 | IV | 4 | dog | blood | 22 |
| 149 | 1 | IV | 8 | dog | blood | 10 |
| 149 | 1 | IV | 24 | dog | blood | 11 |
| 149 | 10 | PO | 2 | dog | blood | 61 |
| 149 | 10 | PO | 4 | dog | blood | 47 |
| 149 | 10 | PO | 8 | dog | blood | 29 |
| 149 | 10 | PO | 24 | dog | blood | 17 |

Biological Example 22

Non-Human Primate (Cyno) DRF PD Data

This example evaluates potency and tolerability of BTK CTMs following multiple, consecutive days of dosing and examines potency of compounds for BTK and Aiolos degradation. Compounds were generally well tolerated, even at high doses. All compounds demonstrated potent BTK degradation. Compound 149 demonstrated Aiolos degradation after fourteen days of dosing, whereas the other CTMs tested did not demonstrate Aiolos degradation.

The data in the table below is from a study in which animals were dosed daily with the designated oral dose. Analysis for BTK and Aiolos levels was performed twenty-four hours following the previous dose.

| Compound ID | Dose (mg/kg) | Route of Administration | Days of Dosing | Species | Tissue | % BTK Remaining in B cells | % Aiolos Remaining in T cells |
|---|---|---|---|---|---|---|---|
| 44 | 10 | PO | 1 | cyno | blood | 35 | 96 |
| 44 | 30 | PO | 1 | cyno | blood | 31 | 99 |
| 44 | 100 | PO | 1 | cyno | blood | 14 | 96 |
| 44 | 10 | PO | 14 | cyno | blood | 16 | 71 |
| 44 | 30 | PO | 14 | cyno | blood | 10 | 69 |
| 44 | 100 | PO | 14 | cyno | blood | 6 | 63 |
| 149 | 10 | PO | 1 | cyno | blood | 9 | 79 |
| 149 | 30 | PO | 1 | cyno | blood | 4 | 74 |
| 149 | 100 | PO | 1 | cyno | blood | 3 | 77 |
| 149 | 10 | PO | 14 | cyno | blood | 7 | 76 |
| 149 | 30 | PO | 14 | cyno | blood | 6 | 55 |
| 149 | 100 | PO | 14 | cyno | blood | 6 | 43 |
| 130 | 10 | PO | 1 | cyno | blood | 6 | 102 |
| 130 | 30 | PO | 1 | cyno | blood | 3 | 98 |
| 130 | 100 | PO | 1 | cyno | blood | 4 | 106 |
| 130 | 10 | PO | 14 | cyno | blood | 5 | 96 |
| 130 | 30 | PO | 14 | cyno | blood | 5 | 108 |
| 130 | 100 | PO | 14 | cyno | blood | 4 | 99 |

Biological Example 23

Mouse DRF PD Data

This example evaluates potency and tolerability of BTK CTMs following multiple, consecutive days of dosing and evaluates potency of compounds for BTK degradation.

Compounds were generally well tolerated, even at high doses. All compounds tested demonstrated potent BTK degradation.

The data in the table below is from a study in which animals were dosed daily with the designated oral dose. Analysis for BTK levels was performed twenty-four hours following the previous dose.

| Compound ID | Dose (mg/kg) | Route of Administration | Days of Dosing | Species | Tissue | % BTK Remaining in B cells |
|---|---|---|---|---|---|---|
| 44 | 30 | PO | 1 | mouse | blood | 16 |
| 44 | 100 | PO | 1 | mouse | blood | 10 |
| 44 | 300 | PO | 1 | mouse | blood | 8 |
| 44 | 30 | PO | 14 | mouse | blood | 16 |
| 44 | 100 | PO | 14 | mouse | blood | 11 |
| 44 | 300 | PO | 14 | mouse | blood | 10 |
| 149 | 30 | PO | 1 | mouse | blood | 11 |
| 149 | 100 | PO | 1 | mouse | blood | 10 |
| 149 | 300 | PO | 1 | mouse | blood | 6 |
| 149 | 30 | PO | 14 | mouse | blood | 8 |
| 149 | 100 | PO | 14 | mouse | blood | 5 |
| 149 | 300 | PO | 14 | mouse | blood | 2 |
| 130 | 30 | PO | 1 | mouse | blood | 11 |
| 130 | 100 | PO | 1 | mouse | blood | 3 |
| 130 | 300 | PO | 1 | mouse | blood | 2 |
| 130 | 30 | PO | 14 | mouse | blood | 6 |
| 130 | 100 | PO | 14 | mouse | blood | 2 |
| 130 | 300 | PO | 14 | mouse | blood | <1 |

Biological Example 24

Compound Plasma Exposure in Cyno DRF Study

This example evaluates compound plasma concentration which results in in vivo BTK and/or Aiolos degradation in cyno.

Plasma concentrations were determined and this data indicates dose and efficacious compound concentrations inhuman.

The data in the table below is from a study in which animals were dosed daily with the designated oral dose. Analysis for compound concentration in plasma was performed twenty-four hours following the previous dose.

| Compd | Species | Strain | Dose (mg/kg) | Route of Administration | Days of Dosing | $C_{max}$ (µM) | AUC (hr * µM) |
|---|---|---|---|---|---|---|---|
| 44 | Monkey | Cynomolgus | 10 | PO | 1 | 0.0106 | 0.1477 |
| 44 | Monkey | Cynomolgus | 30 | PO | 1 | 0.0180 | 0.2683 |
| 44 | Monkey | Cynomolgus | 100 | PO | 1 | 0.0226 | 0.2939 |
| 44 | Monkey | Cynomolgus | 10 | PO | 14 | 0.0340 | 0.4672 |
| 44 | Monkey | Cynomolgus | 30 | PO | 14 | 0.0555 | 0.7940 |
| 44 | Monkey | Cynomolgus | 100 | PO | 14 | 0.0942 | 1.5197 |
| 44 | Mouse | CD-1 | 30 | PO | 1 | 0.23 | 2.32 |
| 44 | Mouse | CD-1 | 100 | PO | 1 | 0.40 | 4.15 |
| 44 | Mouse | CD-1 | 300 | PO | 1 | 0.74 | 9.53 |
| 44 | Mouse | CD-1 | 30 | PO | 14 | 0.25 | 2.22 |
| 44 | Mouse | CD-1 | 100 | PO | 14 | 0.59 | 8.07 |
| 44 | Mouse | CD-1 | 300 | PO | 14 | 0.94 | 12.84 |
| 149 | Monkey | Cynomolgus | 10 | PO | 1 | 0.042 | 0.386 |
| 149 | Monkey | Cynomolgus | 30 | PO | 1 | 0.051 | 0.720 |
| 149 | Monkey | Cynomolgus | 100 | PO | 1 | 0.076 | 0.714 |
| 149 | Monkey | Cynomolgus | 10 | PO | 14 | 0.049 | 0.763 |
| 149 | Monkey | Cynomolgus | 30 | PO | 14 | 0.088 | 1.481 |
| 149 | Monkey | Cynomolgus | 100 | PO | 14 | 0.159 | 2.664 |
| 149 | Mouse | CD-1 | 30 | PO | 1 | 0.94 | 12.24 |
| 149 | Mouse | CD-1 | 100 | PO | 1 | 2.05 | 27.69 |
| 149 | Mouse | CD-1 | 300 | PO | 1 | 2.61 | 38.65 |
| 149 | Mouse | CD-1 | 30 | PO | 14 | 1.64 | 22.81 |
| 149 | Mouse | CD-1 | 100 | PO | 14 | 2.41 | 33.40 |
| 149 | Mouse | CD-1 | 300 | PO | 14 | 4.10 | 64.24 |
| 130 | Monkey | Cynomolgus | 10 | PO | 1 | 0.020 | 0.172 |
| 130 | Monkey | Cynomolgus | 30 | PO | 1 | 0.055 | 0.582 |
| 130 | Monkey | Cynomolgus | 100 | PO | 1 | 0.096 | 1.404 |
| 130 | Monkey | Cynomolgus | 10 | PO | 14 | 0.028 | 0.387 |
| 130 | Monkey | Cynomolgus | 30 | PO | 14 | 0.054 | 0.844 |
| 130 | Monkey | Cynomolgus | 100 | PO | 14 | 0.177 | 3.839 |
| 130 | Mouse | CD-1 | 30 | PO | 1 | 2.2 | 23.2 |
| 130 | Mouse | CD-1 | 100 | PO | 1 | 3.8 | 51.3 |
| 130 | Mouse | CD-1 | 300 | PO | 1 | 5.1 | 67.0 |
| 130 | Mouse | CD-1 | 30 | PO | 14 | 1.7 | 21.1 |
| 130 | Mouse | CD-1 | 100 | PO | 14 | 3.4 | 49.8 |
| 130 | Mouse | CD-1 | 300 | PO | 14 | 5.2 | 72.2 |

Biological Example 25

Efficacy in Mouse Xenograft Models

This example examines the activity of various BTK CTMs in relevant disease models, including the WT and C481S TMD8 model, which models B cell malignancies with/without inhibitor-driven BTK mutations at C481.

BTK CTMs demonstrate significant efficacy in both WT and C481S tumor models.

| Compd | Model | Route of Admin. | Dose (mg/kg) | Dosing Frequency | Days of Dosing | Tumor Growth Inhibition (relative to vehicle) | BTK Remaining (% relative to vehicle) |
|---|---|---|---|---|---|---|---|
| 17 | TMD8 WT | IP | 10 | QD | 14 | 14% | 20 |
| 17 | TMD8 WT | IP | 30 | QD | 14 | 66% | 15 |
| 44 | TMD8 WT | PO | 30 | QD | 23 | 83% | Not determined |
| 44 | TMD8 WT | PO | 90 | QD | 23 | 93% | Not determined |
| 44 | TMD8 WT | PO | 30 | BID | 23 | 99% | Not determined |
| 44 | TMD8 WT | PO | 90 | BID | 23 | 100% | Not determined |
| Ibrutinib | TMD8 WT | PO | 30 | QD | 23 | 80% | Not determined |
| Ibrutinib | TMD8 WT | PO | 90 | QD | 23 | 99% | Not determined |
| Ibrutinib | TMD8 WT | PO | 30 | BID | 2. | 100% | Not determined |
| Ibrutinib | TMD8 WT | PO | 90 | BID | 23 | 100% | Not determined |
| 17 | TMD8 WT | IP | 30 | QD | 21 | 81% | 7 |
| 44 | TMD8 WT | PO | 30 | QD | 21 | 49% | 32 |
| Ibrutinib | TMD8 WT | PO | 25 | QD | 21 | 43% | 109 |
| 55 | TMD8 WT | PO | 30 | QD | 21 | 17% | 27 |
| 53 | TMD8 WT | PO | 30 | QD | 21 | 27% | 19 |
| 37 | TMD8 WT | PO | 30 | QD | 21 | 41% | 16 |
| 83 | TMD8 WT | PO | 30 | QD | 21 | 39% | 22 |
| 44 | TMD8 WT | PO | 30 | QD | 21 | 54% | 20 |
| 44 | TMD8 WT | PO (water bottle) | 15 | QD (water bottle) | 21 | 29% | 7 |
| Ibrutinib | TMD8 WT | PO | 30 | QD | 21 | 56% | 42 |
| 44 | TMD8 C481S | PO | 30 | QD | 23 | 48% | 1 |
| 44 | TMD8 C481S | PO | 30 | BID | 23 | 70% | 39 |
| Ibrutinib | TMD8 C481S | PO | 30 | QD | 23 | 26% | 69 |
| Ibrutinib | TMD8 C481S | PO | 30 | BID | 23 | 10% | 102 |
| 44 | TMD8 C481S | PO | 5 | BID | 23 | 65% | 44 |
| 44 | TMD8 C481S | PO | 10 | QD | 23 | 48% | 38 |

-continued

| Compd | Model | Route of Admin. | Dose (mg/kg) | Dosing Frequency | Days of Dosing | Tumor Growth Inhibition (relative to vehicle) | BTK Remaining (% relative to vehicle) |
|---|---|---|---|---|---|---|---|
| 44 | TMD8 C481S | PO | 15 | BID | 23 | 62% | 25 |
| 44 | TMD8 C481S | PO | 30 | QD | 23 | 51% | 42 |
| 44 | TMD8 C481S | PO | 30 | BID | | 78% | 35 |
| 44 | TMD8 C481S | PO | 60 | QD | 23 | 70% | 36 |
| 44 | TMD8 WT | PO (water bottle) | 35 | QD (water bottle) | 23 | 89% | 18 |
| Ibrutinib | TMD8 C481S | PO | 30 | QD | 23 | 15% | 73 |
| 44 | 1:1 TMD8 WT:TMD8 C481S | PO | 30 | BID | 2 | 54% | Not determined |
| 44/ibrutinib | 1:1 TMD8 WT:TMD8 C481S | PO | 30/30 | QD/QD | 21 | 55% | Not determined |
| 44/ibrutinib | 1:1 TMD8 WT:TMD8 C481S | PO | 15/30 | QD/QD | 21 | 47% | Not determined |
| 44/ibrutinib | 1:1 TMD8 WT:TMD8 C481S | PO | 7.5/30 | QD/QD | 2 | 41% | Not determined |
| Ibrutinib | 1:1 TMD8 WT:TMD8 C481S | PO | 30 | QD | 21 | −8% | Not determined |
| ibrutinib | 1:1 TMD8 WT:TMD8 C481S | PO | 30 | BID | 2 | 21% | Not determined |
| 149 | TMD8 C481S | PO | 10 | QD | 23 | 27% | Not determined |
| 149 | TMD8 C481S | PO | 30 | QD | 23 | 29% | Not determined |
| 130 | TMD8 C481S | PO | | QD | 23 | 58% | Not determined |
| 130 | TMD8 C481S | PO | 30 | QD | 23 | 79% | Not determined |
| 44 | TMD8 C481S | PO | 10 | QD | 23 | 23% | Not determined |
| 44 | TMD8 C481S | PO | 30 | QD | 23 | 36% | Not determined |
| ibrutinib | TMD8 C481S | PO | 30 | QD | 23 | 0% | Not determined |
| 149 | TMD8 C481S | PO | 10 | QD | 24 | 17% | Not determined |
| 149 | TMD8 C481S | PO | 30 | QD | 24 | 43% | Not determined |
| 149 | TMD8 C481S | PO | 90 | QD | 24 | 59% | Not determined |
| 130 | TMD8 C481S | PO | 10 | QD | 24 | 90% | Not determined |
| 130 | TMD8 C481S | PO | 30 | QD | 24 | 100% | Not determined |
| 130 | TMD8 C481S | PO | 90 | QD | 24 | 100% | Not determined |
| Ibrutinib | TMD8 C481S | PO | 30 | QD | 24 | 8% | Not determined |
| 44 | TMD8 WT | PO | 7.5 | BID | 2 | 100 | Not determined |
| 44 | TMD8 WT | PO | 15 | BID | 2 | 100 | Not determined |
| 44 | TMD8 WT | PO | 30 | QD | 21 | 100 | Not determined |
| 44/ibrutinib | TMD8 WT | PO | 7.5/7.5 | QD/QD | 21 | 97 | Not determined |
| 44/ibrutinib | TMD8 WT | PO | 15/15 | QD/QD | 21 | 71 | Not determined |
| Ibrutinib | TMD8 WT | PO | 7.5 | BID | 21 | 68 | Not determined |
| ibrutinib | TMD8 WT | PO | 15 | BID | 21 | 100 | Not determined |
| ibrutinib | TMD8 WT | PO | 30 | QD | 21 | 90 | Not determined |

% TGI is defined as (1 − (mean volume of treated tumors)/(mean volume of control tumors)) × 100%.

Biological Example 26

PK data for BTK CTMs

The present example evaluates in vivo plasma concentrations of BTK CTMs to develop PK-PD-efficacy relationship and predict human exposure.

In vivo PK properties of BTK CTMs varied among the various compounds tested. Molecules with moderate-to-low in vivo clearance were identified. Suitable exposure to enable potent BTK degradation was demonstrated with multiple compounds and enabled prediction of human dose and human PK.

| Compd | Species | Strain | Dose (mg/kg) | Route of Admin. | Cl (mL/min/kg) | Volume of Distribution (L/kg) | AUC (hr * μM) | % F |
|---|---|---|---|---|---|---|---|---|
| 55 | Mouse | Balb/c | 1 | IV | 2.4 | 0.48 | 8.64 | |
| 55 | Mouse | Balb/c | 30 | PO | | | 74.3 | 29 |
| 53 | Mouse | Balb/c | 1 | IV | 7.5 | 0.88 | 2.75 | |
| 53 | Mouse | Balb/c | 30 | PO | | | 96 | 113 |
| 53 | Rat | Sprague-Dawley | 1 | IV | 75 | 5.9 | 0.31 | |
| 53 | Rat | Sprague-Dawley | 10 | PO | | | 2.3 | 97 |
| 44 | Mouse | Balb/c | 1 | IV | 5.1 | 0.69 | 4.07 | |
| 44 | Mouse | Balb/c | 10 | PO | | | 4.0 | 10 |
| 37 | Mouse | Balb/c | 1 | IV | 12.0 | 1.2 | 1.77 | |
| 37 | Mouse | Balb/c | 30 | PO | | | 1.79 | 5 |
| 37 | Rat | Sprague-Dawley | 1 | IV | 36.3 | 4.6 | 0.59 | |

-continued

| Compd | Species | Strain | Dose (mg/kg) | Route of Admin. | Cl (mL/min/kg) | Volume of Distribution (L/kg) | AUC (hr * μM) | % F |
|---|---|---|---|---|---|---|---|---|
| 37 | Rat | Sprague-Dawley | 10 | PO | | | 0.027 | 1 |
| 86 | Mouse | Balb/c | 1 | IV | 35.0 | 7.7 | 0.50 | |
| 86 | Mouse | Balb/c | 30 | PO | | | 0.34 | 2 |
| 83 | Mouse | Balb/c | 1 | IV | 68.3 | 4.0 | 0.29 | |
| 83 | Mouse | Balb/c | 30 | PO | | | 0.81 | 9 |
| 121 | Mouse | Balb/c | 1 | IV | 6.6 | 0.77 | 2.87 | |
| 121 | Mouse | Balb/c | 30 | PO | | | 2.22 | 11 |
| 121 | Rat | Sprague-Dawley | 1 | IV | 20 | 3.12 | 0.919 | |
| 121 | Rat | Sprague-Dawley | 10 | PO | | | 0.083 | 1 |
| 121 | Rat | Sprague-Dawley | 30 | PO | | | 0.73 | |
| 73 | Mouse | Balb/c | 1 | IV | 33.8 | 3.4 | 0.6 | |
| 73 | Mouse | Balb/c | 10 | PO | | | 2.9 | 47 |
| 72 | Mouse | Balb/c | 1 | IV | 5.1 | 0.68 | 3.96 | |
| 72 | Mouse | Balb/c | 10 | PO | | | 2.9 | 7 |
| 69 | Mouse | Balb/c | 1 | IV | 31.4 | 2.2 | 0.68 | |
| 69 | Mouse | Balb/c | 10 | PO | | | 0.078 | 1 |
| 149 | Mouse | Balb/c | 1 | IV | 5.2 | 1.0 | 4.5 | |
| 149 | Mouse | Balb/c | 10 | PO | | | 16 | 35 |
| 149 | Mouse | Balb/c | 30 | PO | | | 27.7 | 1 |
| 149 | Mouse | Balb/c | 90 | PO | | | 37.5 | 1 |
| 149 | Mouse | CD-1 | 1 | IV | 12.6 | 1.5 | 1.8 | |
| 149 | Mouse | CD-1 | 10 | PO | | | 11.5 | 64 |
| 149 | Rat | Sprague-Dawley | 1 | IV | 19 | 2.8 | 1.2 | |
| 149 | Rat | Sprague-Dawley | 10 | PO | | | 0.88 | 7 |
| 149 | Dog | Beagle | 1 | IV | 18.4 | 7.0 | 1.2 | |
| 149 | Dog | Beagle | 10 | PO | | | 0.11 | 0.9 |
| 149 | Monkey | cynomolgus | 1 | IV | 22.2 | 7.5 | 1.0 | |
| 149 | Monkey | cynomolgus | 10 | PO | | | 0.09 | 0.8 |
| 149 | Monkey | cynomolgus | 30 | PO | | | 0.08 | |
| 130 | Mouse | Balb/c | 1 | IV | 6.0 | 0.72 | 3.4 | |
| 130 | Mouse | Balb/c | | PO | | | 5.81 | 17 |
| 130 | Mouse | Balb/c | 30 | PO | | | 2.3 | |
| 130 | Mouse | CD-1 | 1 | IV | 11.6 | 1.4 | 1.7 | |
| 130 | Mouse | CD-1 | 10 | PO | | | 5.2 | 33 |
| 130 | Rat | Sprague-Dawley | 1 | IV | 99.5 | 32 | 0.18 | |
| 130 | Rat | Sprague-Dawley | 10 | PO | | | 0.69 | 32 |
| 130 | Rat | Sprague-Dawley | 30 | PO | | | 1.62 | 7 |
| 130 | Dog | Beagle | 1 | IV | 118 | 56 | 0.16 | |
| 130 | Dog | Beagle | 10 | PO | | | 0.17 | 10 |
| 130 | Dog | Beagle | 30 | PO | | | 0.23 | |
| 130 | Monkey | cynomolgus | 0.75 | IV | 90.9 | 16 | 0.17 | |
| 130 | Monkey | cynomolgus | 10 | PO | | | 0.028 | 1 |
| 130 | Monkey | cynomolgus | 30 | PO | | | 0.45 | |

% F = (AUCinf PO * IV dose)/(AUCinf IV * PO dose) * 100

OTHER EMBODIMENTS

It is to be understood that the foregoing description is intended to illustrate and not limit the scope of this disclosure, which is defined by the scope of the appended claims. Other aspects, advantages, and modifications are within the scope of the following claims.

What is claimed is:

1. A method of treating an autoimmune disease or cancer in a subject in need thereof, comprising the step of orally administering to the subject an amount of a bifunctional compound, wherein said bifunctional compound is capable of inducing proteolytic degradation of Bruton's tyrosine kinase, and wherein said amount is effective to treat the autoimmune disease or the cancer, wherein:

the bifunctional compound is a compound of Formula (A):

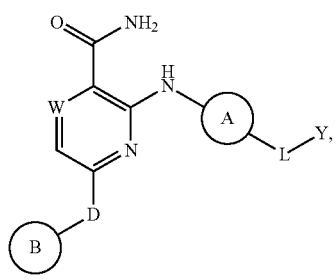

or a pharmaceutically acceptable salt thereof, wherein:

W is CH or N;

D is a bond or —NH—;

Ring A is phenyl, a 9-10 membered bicyclic aryl, a 5-6 membered partially or fully unsaturated monocyclic heterocycle, or a 9-10 membered bicyclic heteroaryl, wherein the monocyclic heterocycle and bicyclic heteroaryl of Ring A each possess one to three heteroatoms independently selected from N, O, or S, wherein Ring A is optionally and independently substituted with up to three substituents selected from halo, —CN, —COOH, NH$_2$, and optionally substituted C$_{1-6}$ alkyl;

Ring B is a phenyl, a 5-6 membered heteroaryl, a 4-6 membered heterocycloalkyl, or a 8-10 membered spiro bicyclic heterocycle, wherein Ring B is optionally substituted with R$^{10}$, and wherein the heteroaryl and heterocycloalkyl of Ring B has one to three heteroatoms independently selected from N, O, or S;

L is —X$^1$-X$^2$-X$^3$-X$^4$-X$^5$;

X$^1$ is a bond, —C(O)—N(R)—, —N(R)—C(O)—, —(O—CH$_2$—CH$_2$)$_m$—, —O(C$_6$H$_4$)—, —(O—CH$_2$—CH$_2$—CH$_2$)$_m$—, —C$_{1-5}$ alkyl-, 7-12 membered spiro or fused bicyclic heterocycloalkyl having one to three heteroatoms independently selected from N, O, or S, or 4-6 membered monocyclic heterocycloalkyl having one to two heteroatoms independently selected from N, O, or S, wherein each of the monocyclic and bicyclic heterocycloalkyl of X$^1$ is optionally substituted with —CH$_3$;

X$^2$ is a bond, —(O—CH$_2$—CH$_2$)$_n$—, —(CH$_2$—CH$_2$—O)$_n$—, —N(R)—C(O)—, —N(R)—, —C(O)—, —C$_{1-5}$ alkyl-, 4-6 membered monocyclic cycloalkyl, or 4-6 membered monocyclic heterocycloalkyl having one to two heteroatoms independently selected from N, O, or S;

X$^3$ is a bond, —C$_{1-8}$ alkyl-, —C≡C—, 4-6 membered cycloalkyl, —N(R)—, —N(R)—C(O)—, —(O—CH$_2$—CH$_2$)$_p$—, —(CH$_2$—CH$_2$—O)$_p$—, 4-6 membered heterocycloalkyl having one to two heteroatoms independently selected from N, O, or S, wherein the heterocycloalkyl is optionally substituted with —CH$_3$;

X$^4$ is a bond, —CH$_2$—CH$_2$—N(R)—, —N(R)—, —C$_{1-4}$ alkyl-, —(O—CH$_2$—CH$_2$—CH$_2$)$_m$—, a 5-6 membered saturated, partially unsaturated, or fully unsaturated carbocycle, or a 5-6 membered saturated, partially unsaturated, or fully unsaturated heterocycle having one to three heteroatoms independently selected from N, O, or S;

X$^5$ is a bond, —C$_{1-4}$ alkyl-, —N(R)—, —O—, —C(O)—, or —C(O)—N(R)—;

each R is independently hydrogen or —C$_{1-3}$ alkyl;

each of m, n, and p is independently an integer from one to three; and

Y

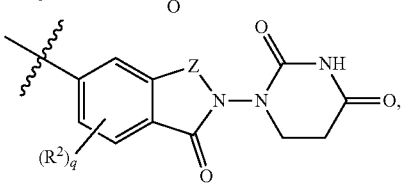

is

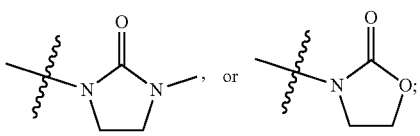

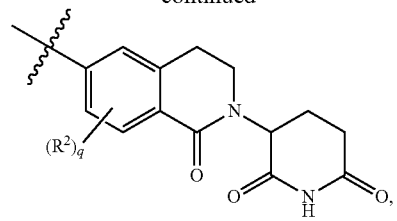

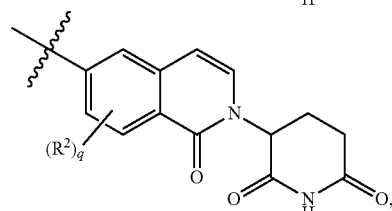

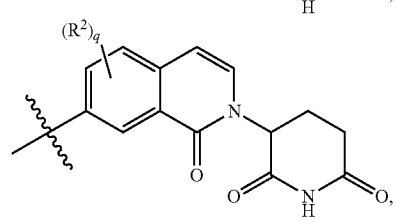

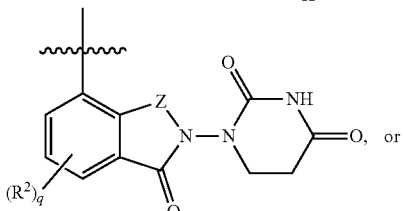

or wherein:
each R$^2$ is independently halo, —CN, or C$_{1-4}$ alkyl, wherein each C$_{1-4}$ alkyl is optionally and independently substituted with up to three instances of halo, —CN, —COOH, —COONH$_2$, —NH$_2$, or —CF$_3$;

R$^{10}$ is halo, —H, —C$_{1-5}$ alkyl, 3-6 membered cycloalkyl, 5-6 membered heterocycloalkyl, —CN, —OH, —CF$_3$, —CH$_2$OH, —CH$_2$CH$_2$OH, —C(O)OH,

[structures]

, or

;

each Z is —C(R$^A$)$_2$— or —C(O)—;
each R$^A$ is independently hydrogen or —C$_{1-4}$ alkyl; and
q is zero, one, or two;
wherein the cancer is selected from the group consisting of:
a B cell malignancy, diffuse large B-cell lymphoma (DLBCL), non-Hodgkin lymphoma, mantle cell lymphoma (MCL), and acute lymphoblastic leukemia;

wherein the autoimmune disease is selected from the group consisting of graft-versus-host disease (GVHD), acute graft-versus-host disease, and immune thrombocytopenic purpura (ITP).

2. The method of claim 1, wherein the subject has a C481 mutant Bruton's tyrosine kinase.

3. The method of claim 1, wherein the cancer is ibrutinib-resistant.

4. The method of claim 2, wherein the subject has a C481 mutant Bruton's tyrosine kinase and the cancer is chronic lymphocytic leukemia (CLL).

5. The method of claim 1, wherein the bifunctional compound is administered to the subject at a dose of 0.1-500 mg/kg.

6. The method of claim 1, wherein the bifunctional compound is administered to the subject at a dose selected from the group consisting of 100 mg/kg, 200 mg/kg, 300 mg/kg, 450 mg/kg, 600 mg/kg, 800 mg/kg, and 1000 mg/kg.

7. The method of claim 1, wherein the bifunctional compound is administered one, two, three, or four times per day.

8. The method of claim 1, wherein the bifunctional compound is administered daily for one, two, three, four, five, six, seven, eight, nine, ten, eleven, twelve, thirteen, or fourteen days.

9. The method of claim 1, wherein the bifunctional compound is administered cyclically.

10. The method of claim 1, wherein Ring B is

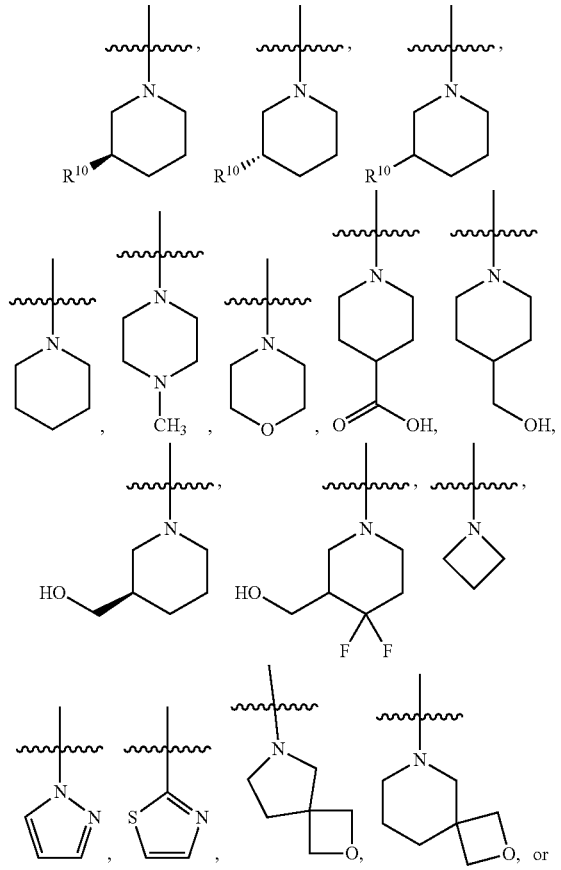

-continued

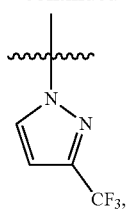

wherein $R^{10}$ is

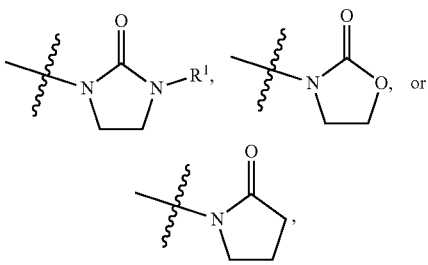

and wherein $R^1$ is a $C_{1-4}$ alkyl group.

11. The method of claim 10, wherein Ring B is

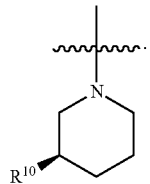

12. The method of claim 10, wherein $R^{10}$ is

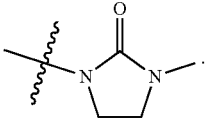 [SMILES: *N1CCN(C)C1=O]

13. The method of claim 1, wherein Ring A is

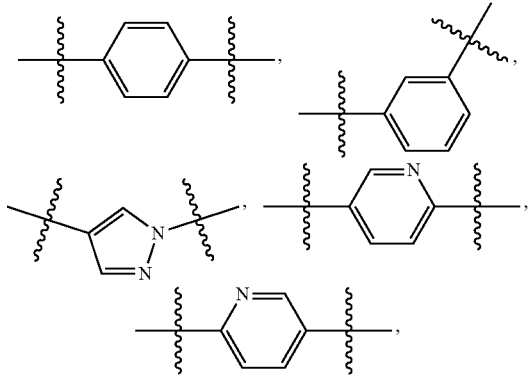

327

-continued

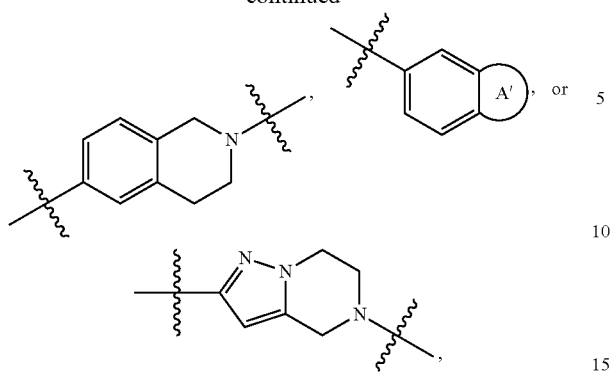

wherein Ring A' together with the phenyl ring to which Ring A' is fused forms a 9-10 membered bicyclic aryl or a 9-10 membered bicyclic heteroaryl wherein the bicyclic heteroaryl has one to three heteroatoms independently selected from N, O, or S.

14. The method of claim 1, or a pharmaceutically acceptable salt thereof, wherein at least one of $X^1$, $X^2$, and $X^5$ is —N(R)—, —C(O)—N(R)—, or —CH$_2$—.

15. The method of claim 1, wherein $X^1$ is —CH$_2$—, —C(O)—,

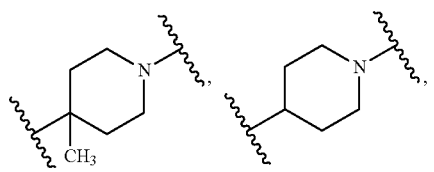

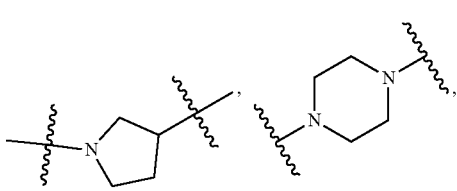

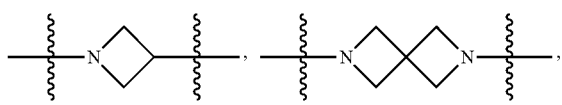

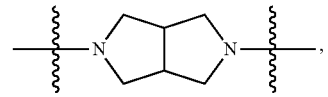

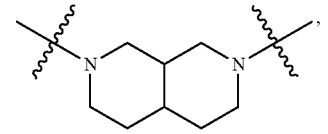

328

-continued

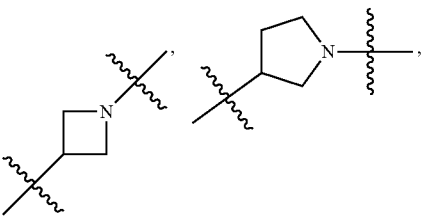

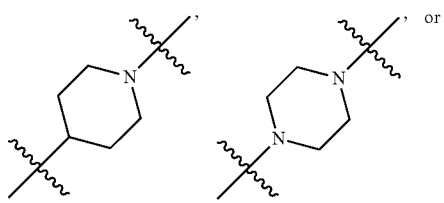

16. The method of claim 1, wherein $X^2$ is a bond, —C(O)—, —C$_{1-5}$ alkyl-,

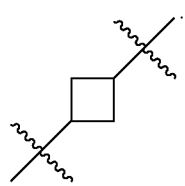

17. The method of claim 1, wherein $X^3$ is a bond, —C$_{1-4}$ alkyl-, —NH—,

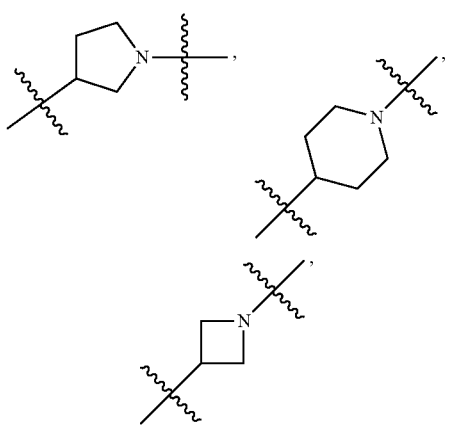
or —C≡C—.
18. The method of claim 1, wherein $X^4$ is a bond,
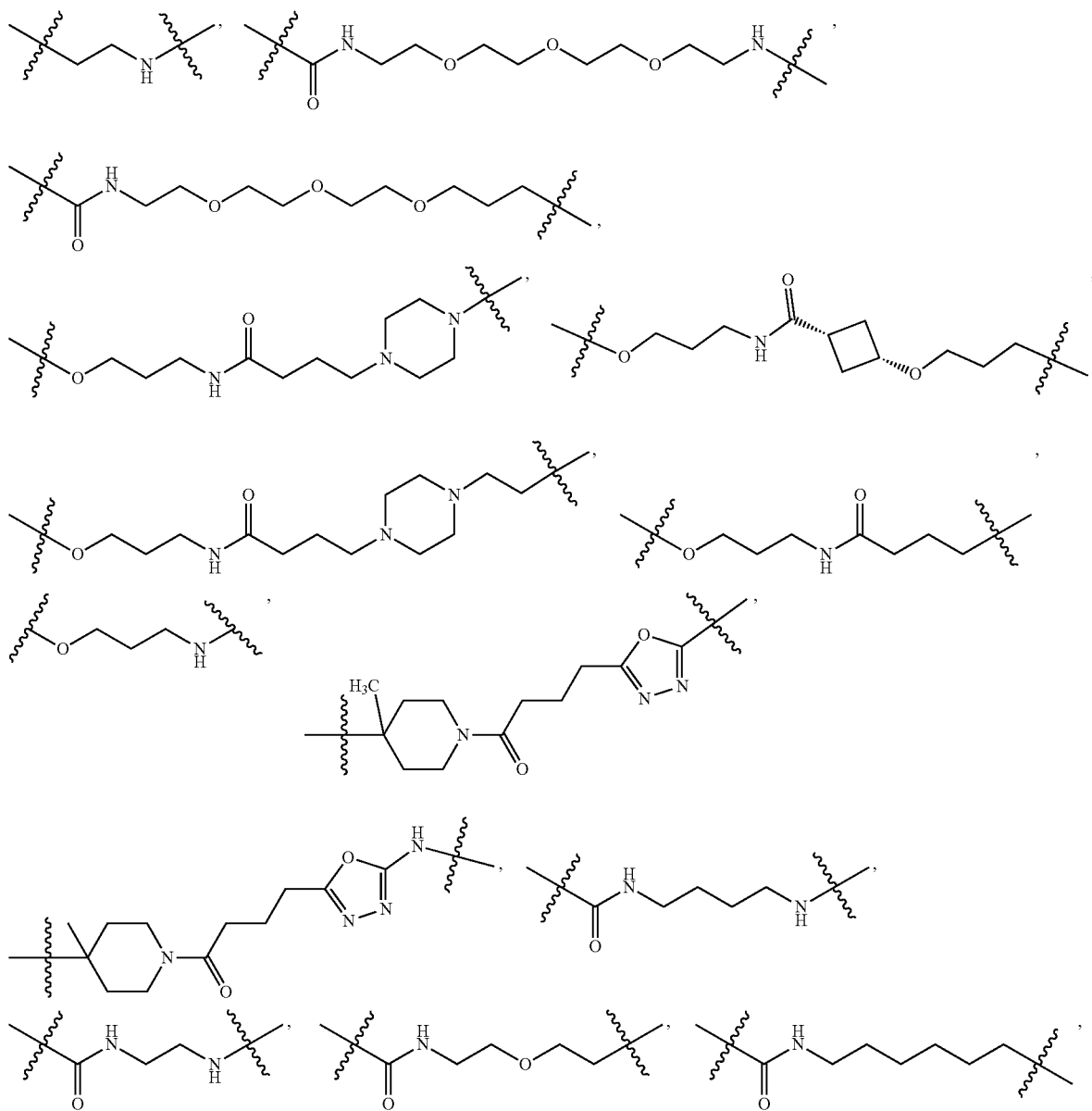
—$C_{1-4}$ alkyl-, —$CH_2$—$CH_2$—N(R)—, or —N(R)—.
19. The method of claim 1, wherein $X^5$ is a bond, —$C_{1-4}$ alkyl-, —N(R)—, or —C(O)—N(R)—.
20. The method of claim 1, wherein L is 331
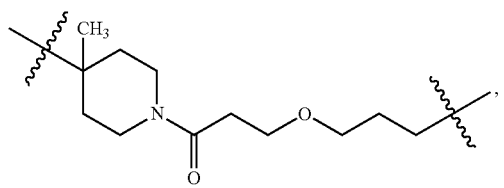
-continued
332
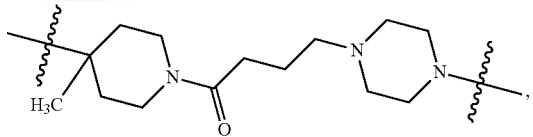
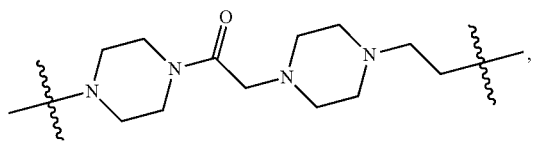
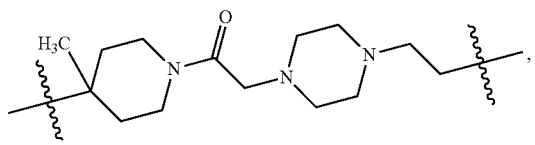
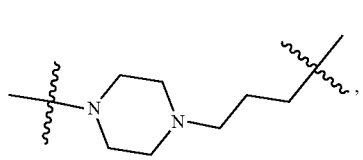
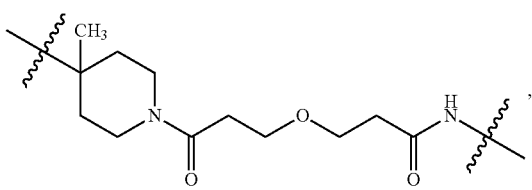
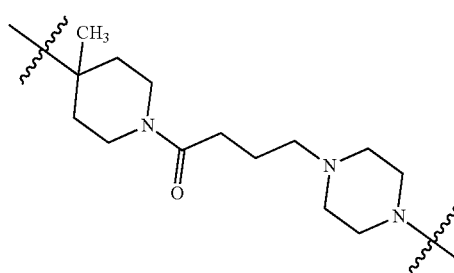
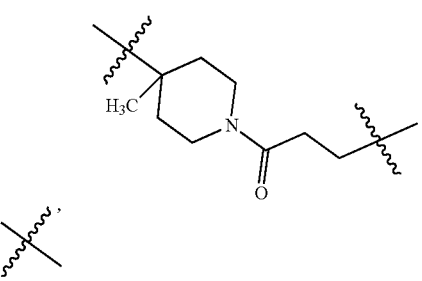
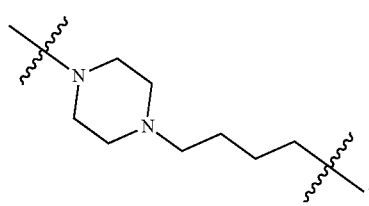
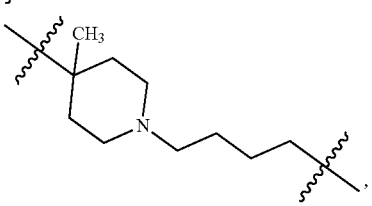
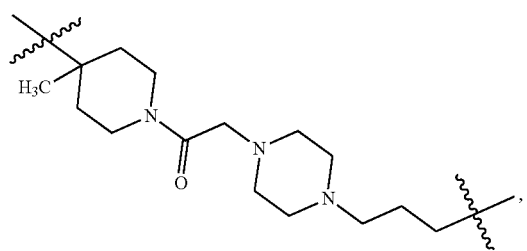
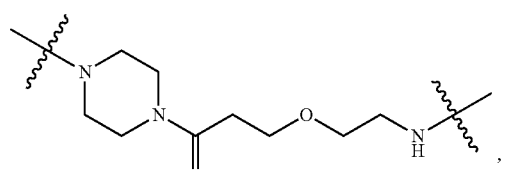
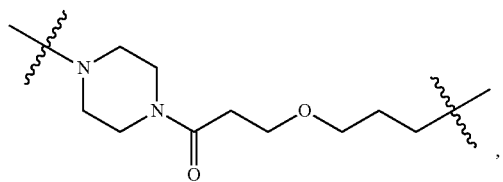
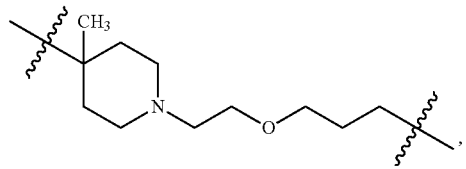
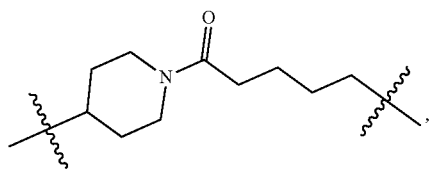
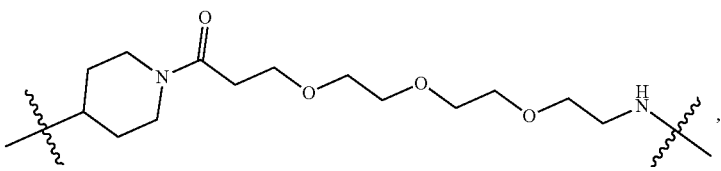

-continued
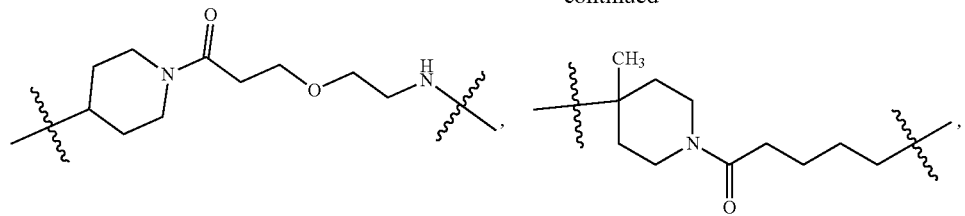
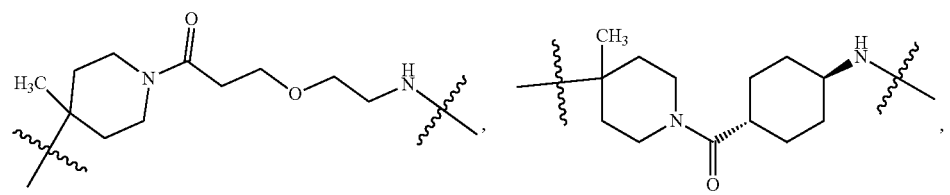
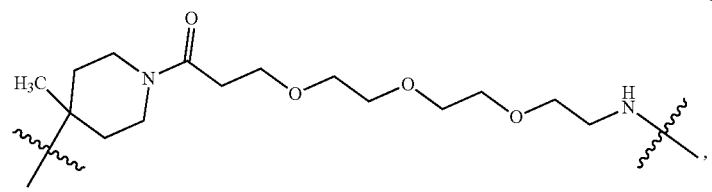
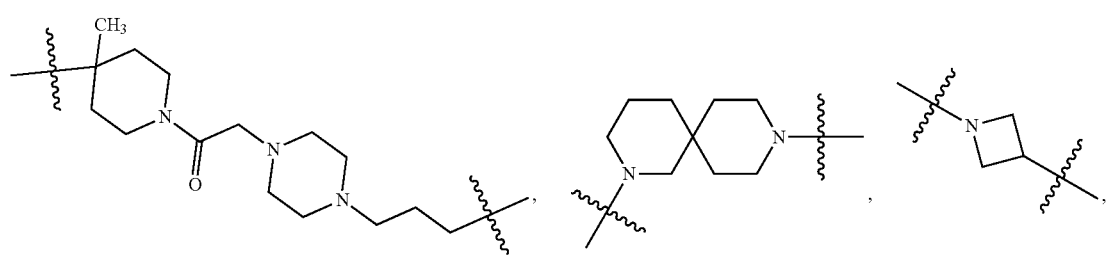
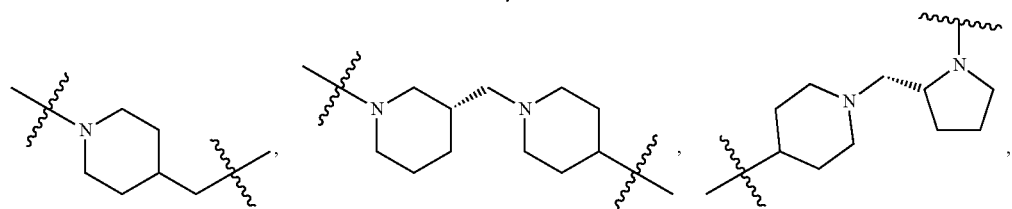
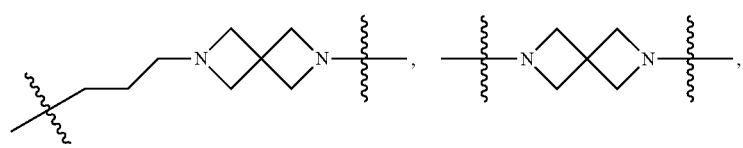
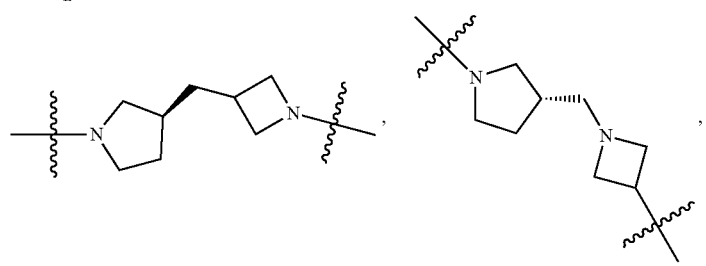
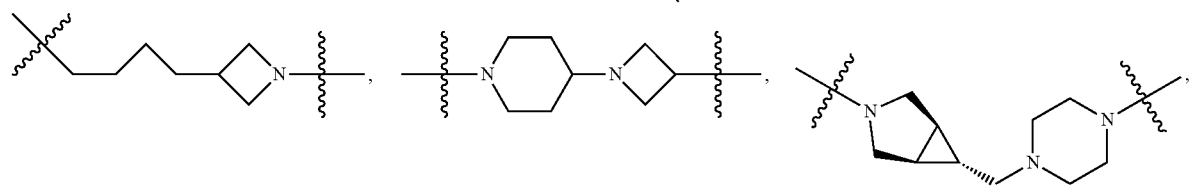

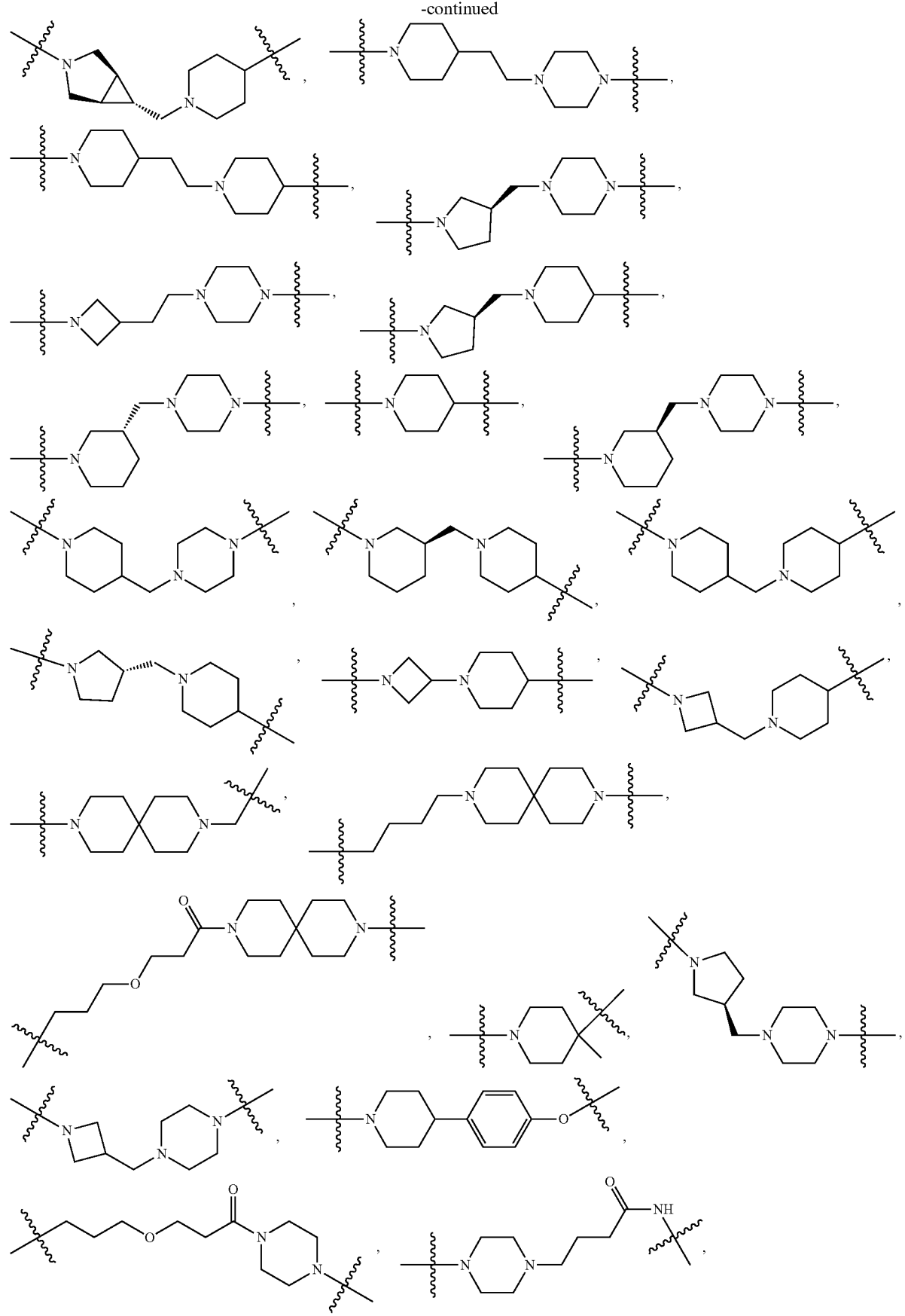

-continued
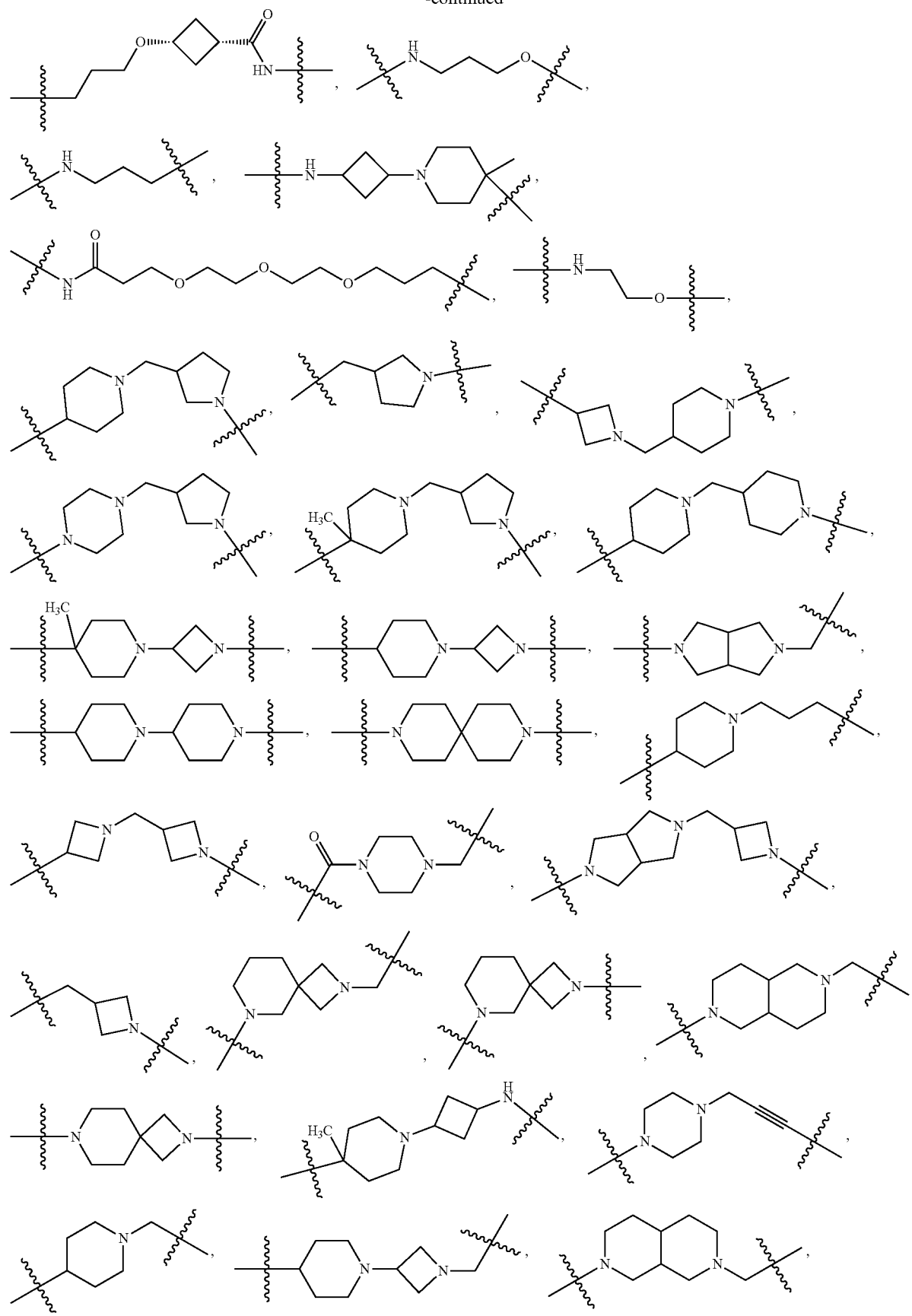

-continued
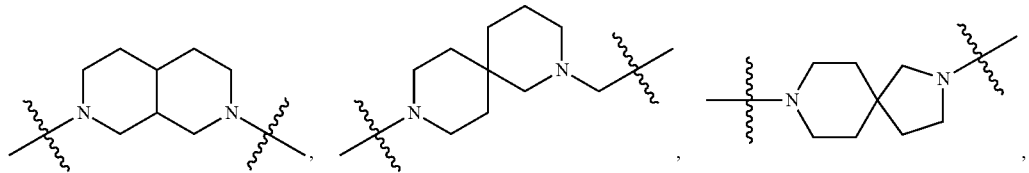
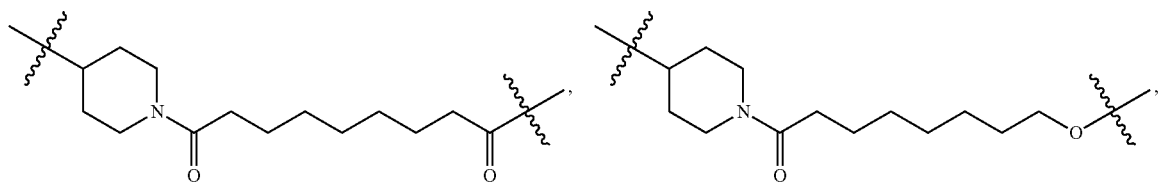
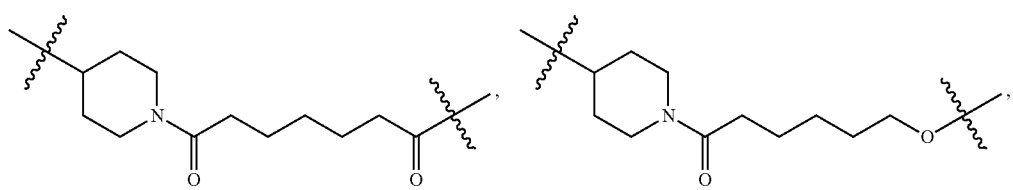
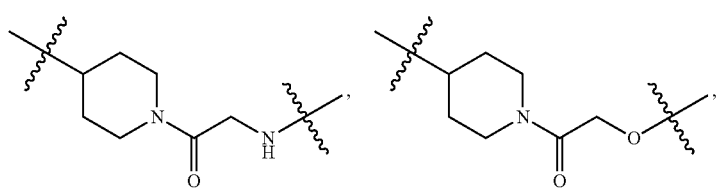
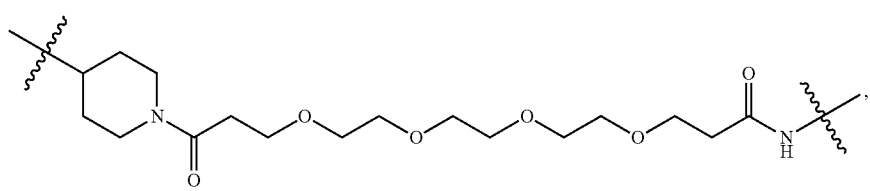
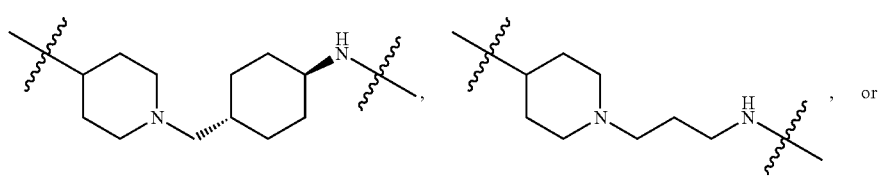
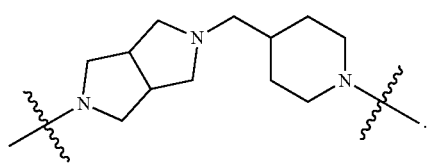

21. The method of claim 1, wherein Y is

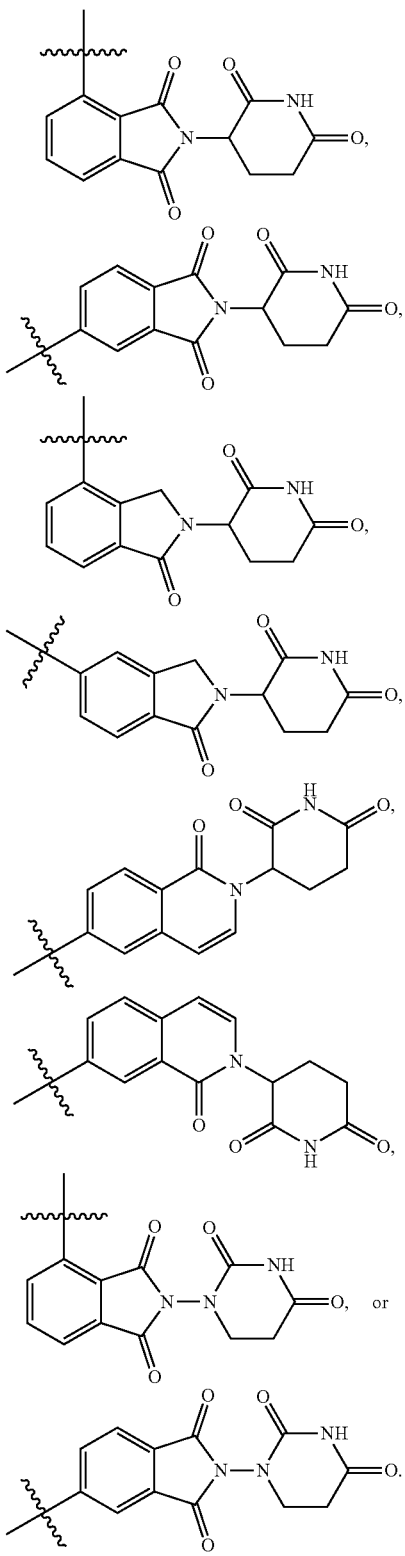

22. The method of claim 1, wherein W is N.
23. The method of claim 1, wherein D is a bond.
24. The method of claim 1, wherein the compound of Formula (A) is a compound of Formula (G):

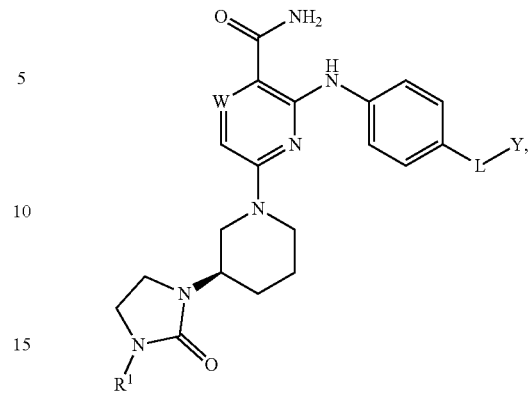

or a pharmaceutically acceptable salt thereof.

25. The method of claim 1, wherein the compound of Formula (A) is a compound of Formula (M):

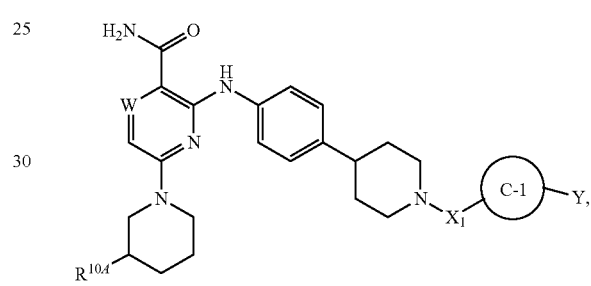

or a pharmaceutically acceptable salt thereof, wherein:
$R^{10A}$ is hydrogen,

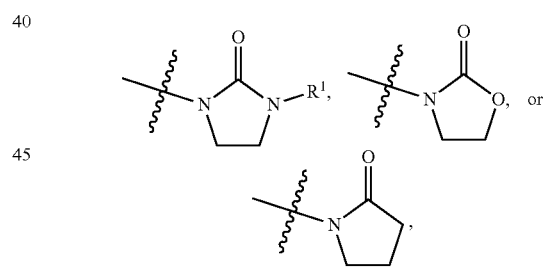

wherein $R^1$ is $C_{1-4}$ alkyl;
$X^1$ is —$C_{1-5}$ alkyl-;
Ring C-1 is a 5-6 membered heterocycloalkyl having one nitrogen atom; and
Y is

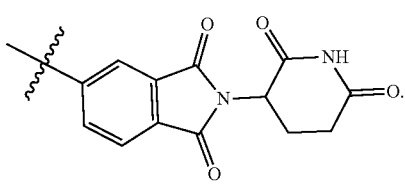 [SMILES: *c1ccc2c(c1)C(=O)N(C1CCC(=O)NC1=O)C2=O]

26. The method of claim 1, wherein the compound is selected from:

(Compound Number 1)
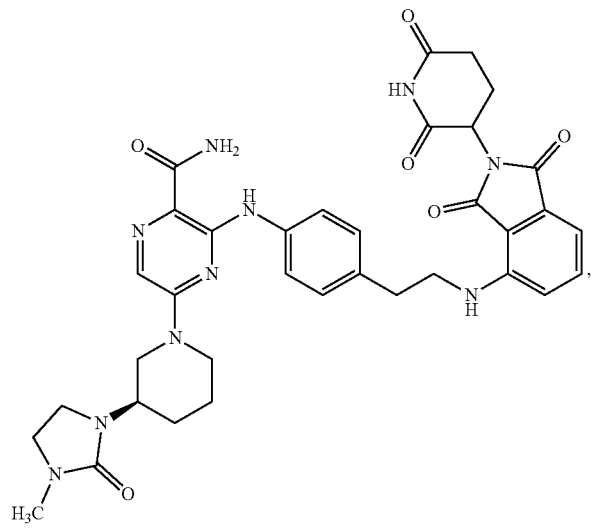
(Compound Number 2)
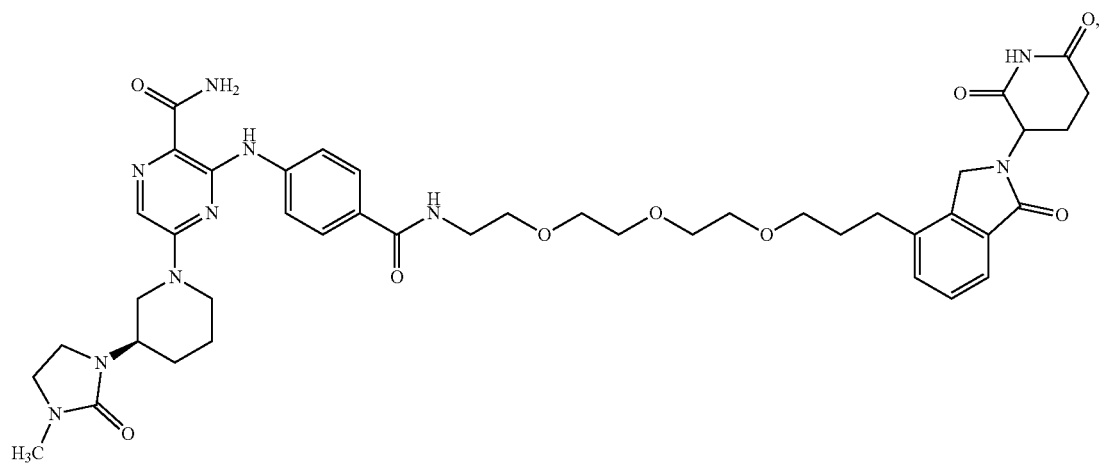
(Compound Number 3)
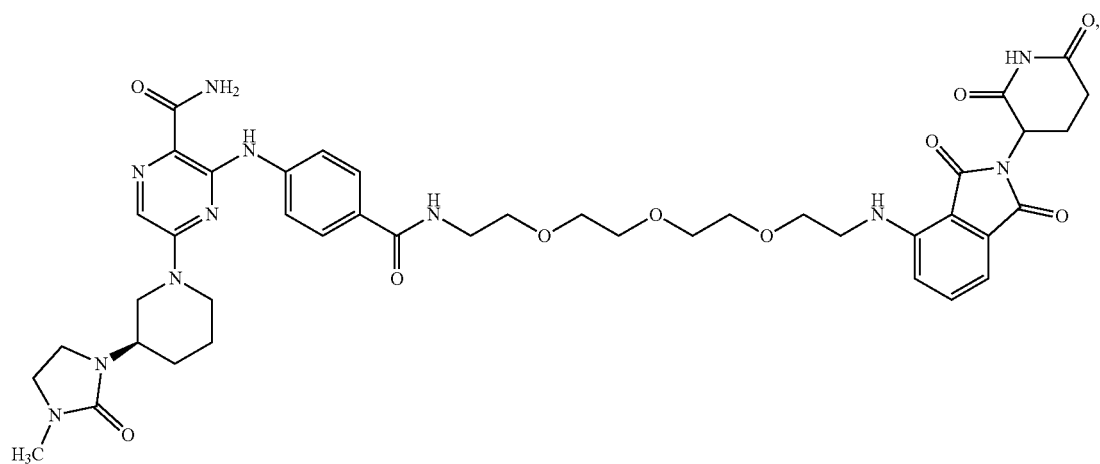

-continued
(Compound Number 4)
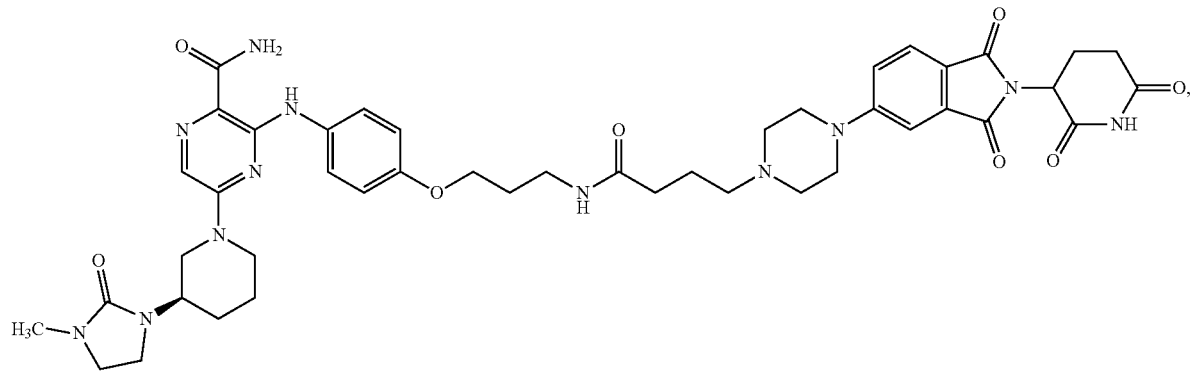
(Compound Number 5)
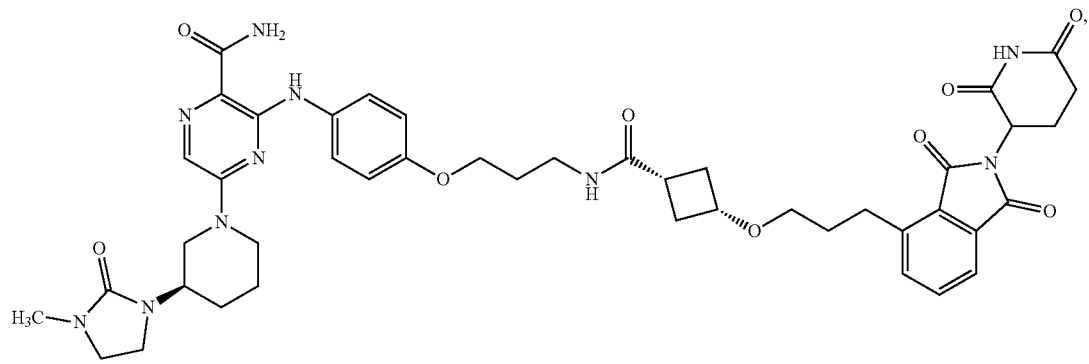
(Compound Number 6)
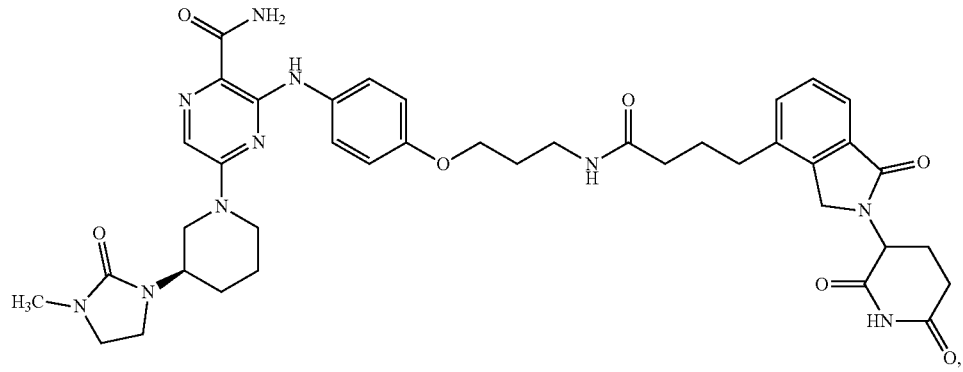
(Compound Number 7)
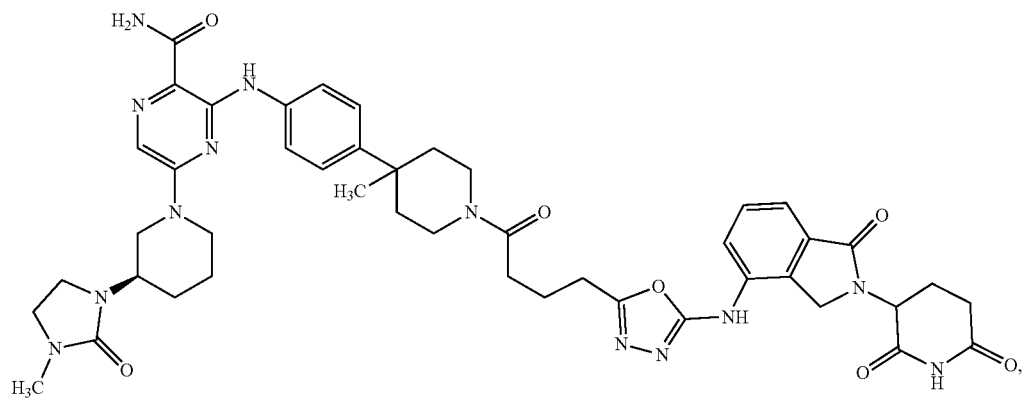

(Compound Number 8)
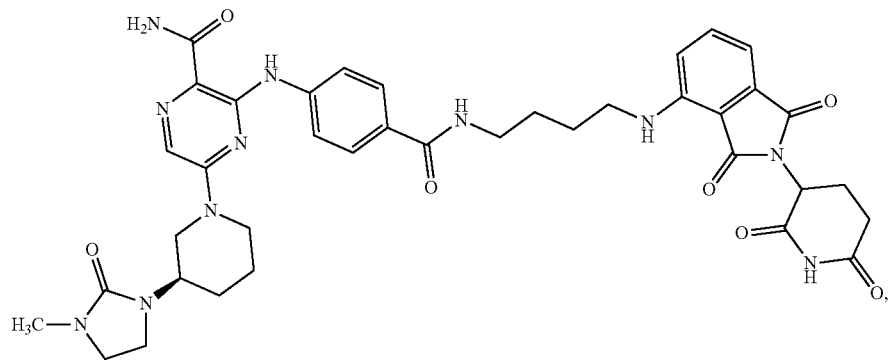
(Compound Number 9)
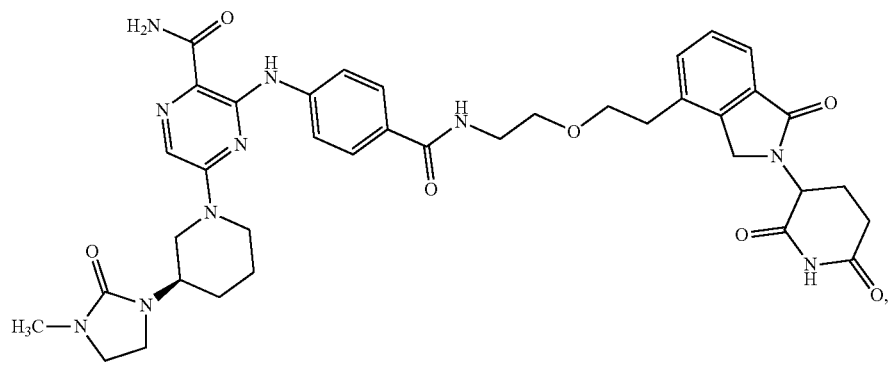
(Compound Number 10)
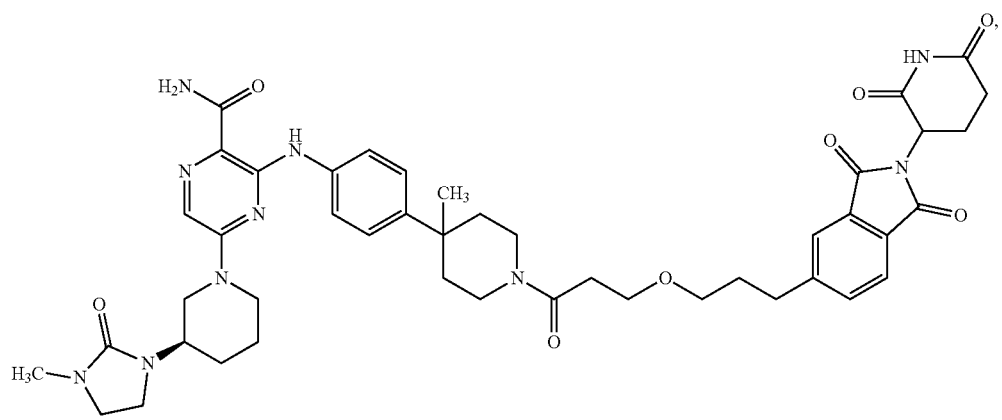
(Compound Number 11)
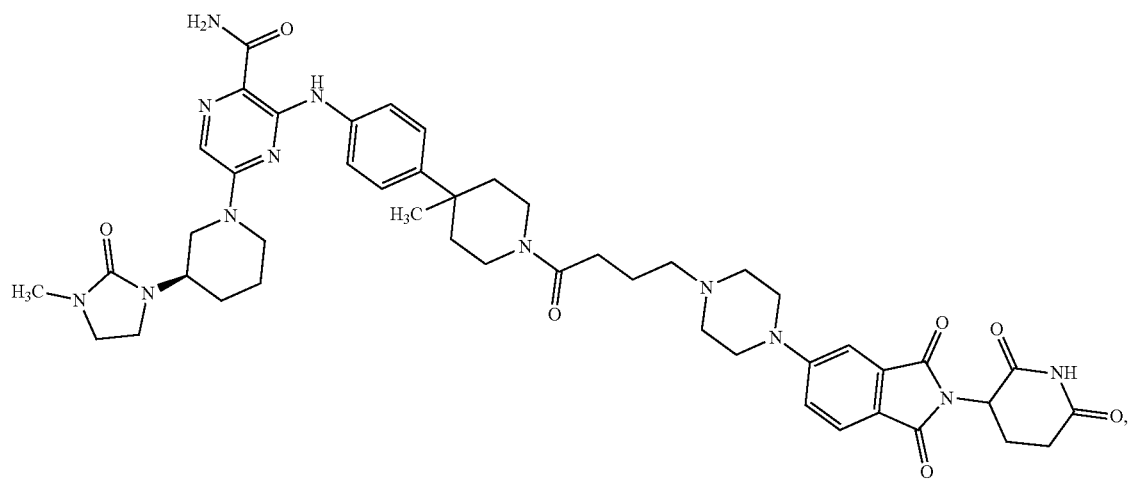

(Compound Number 12)
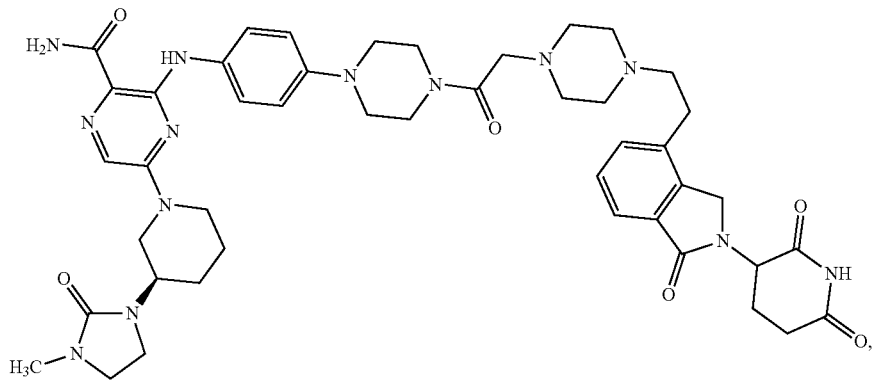
(Compound Number 13)
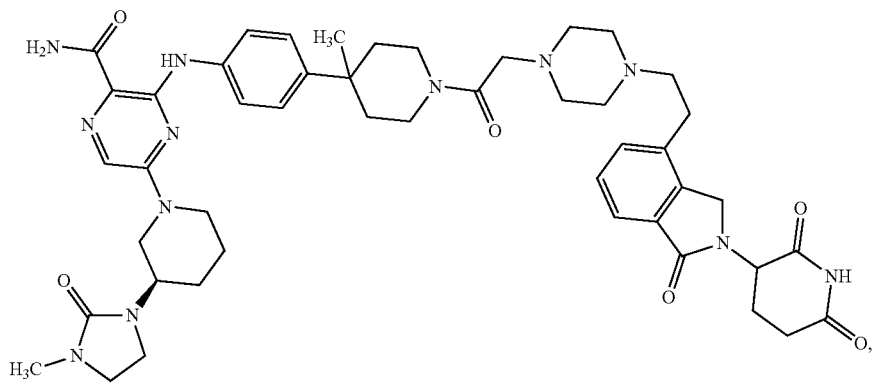
(Compound Number 14)
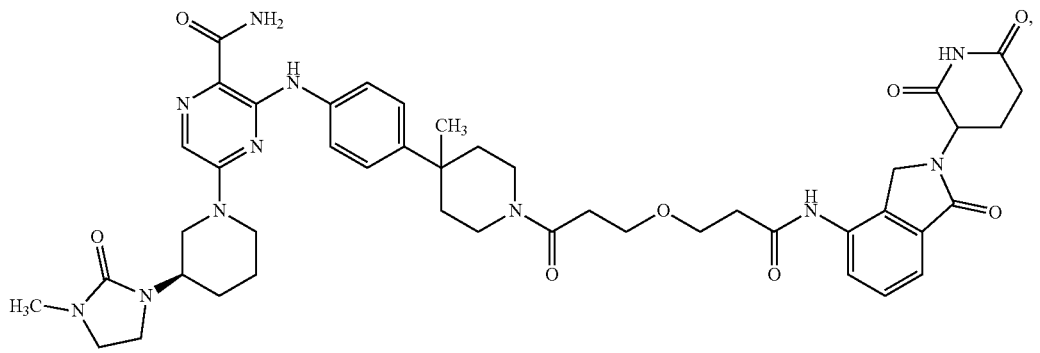
(Compound Number 15)         (Compound Number 16)
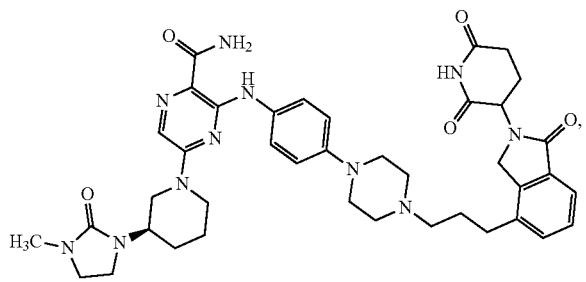

(Compound Number 17)
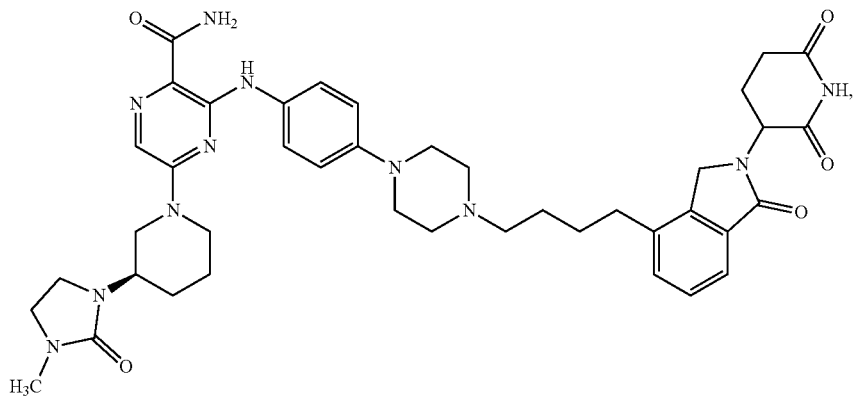
(Compound Number 18)
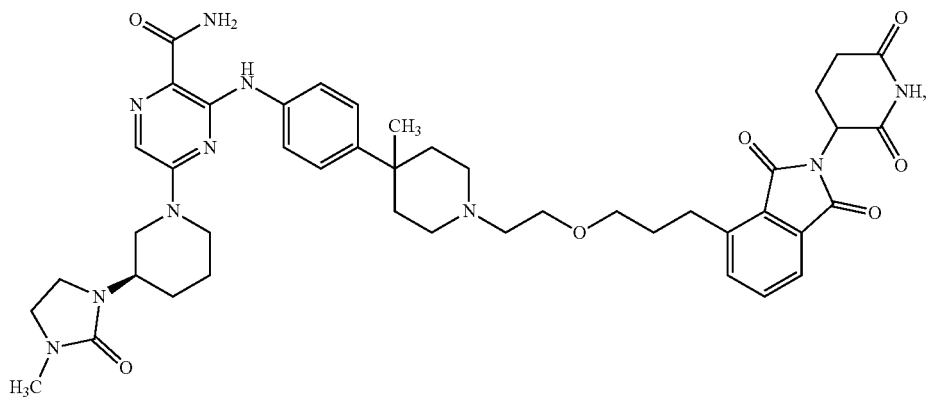
(Compound Number 19)
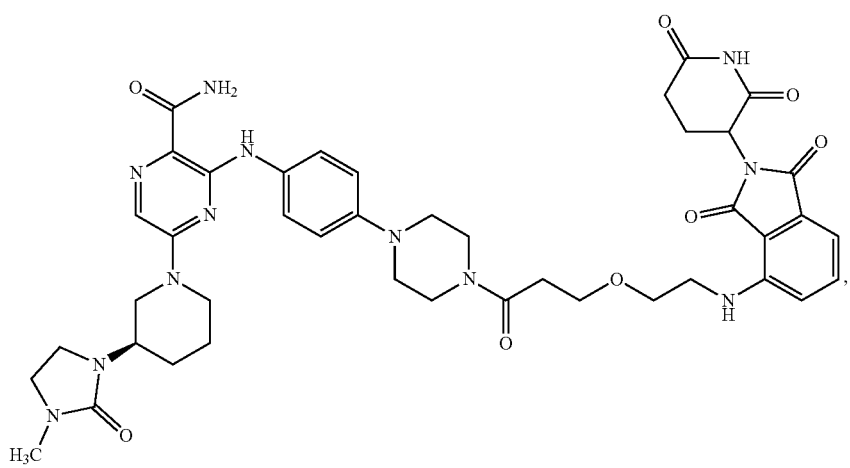
(Compound Number 20)
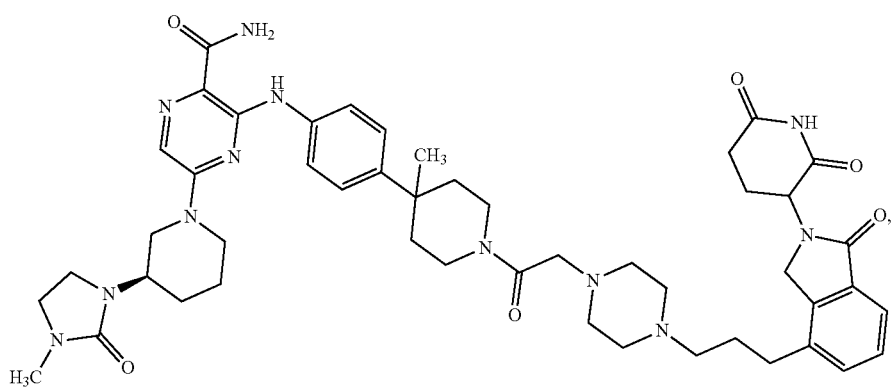

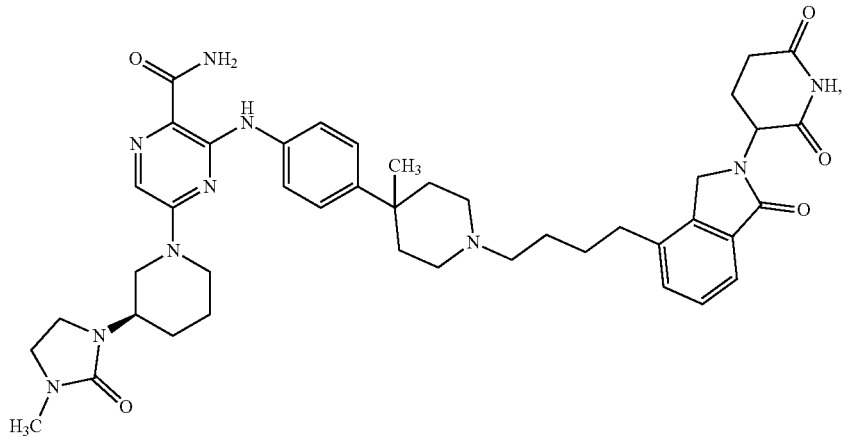
(Compound Number 21)
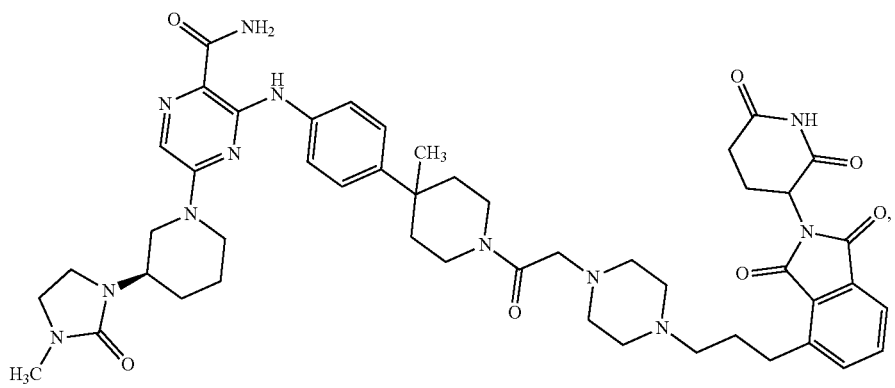
(Compound Number 22)
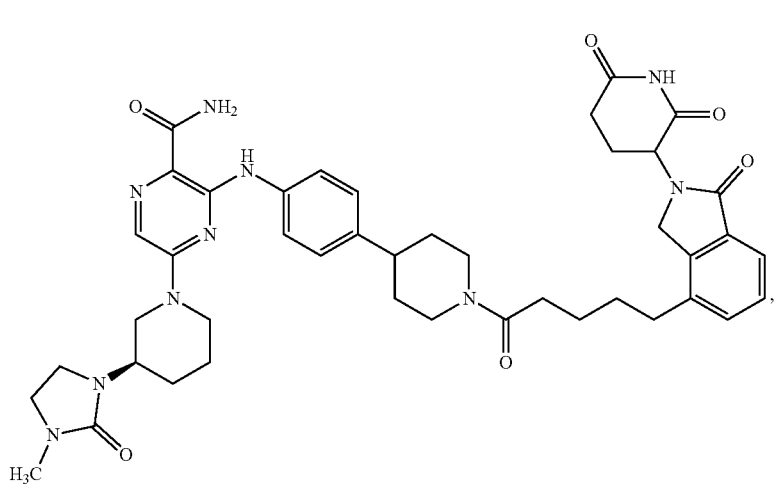
(Compound Number 23)

(Compound Number 24)
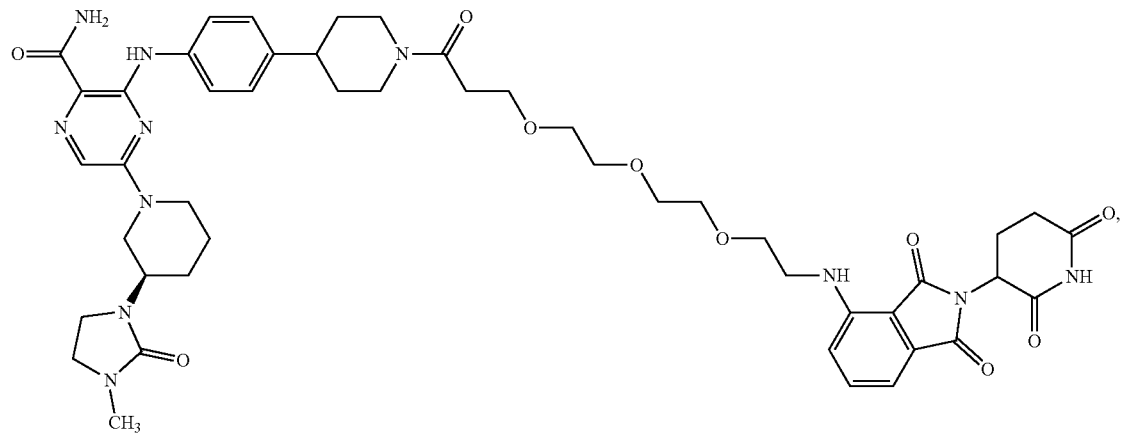
(Compound Number 25)
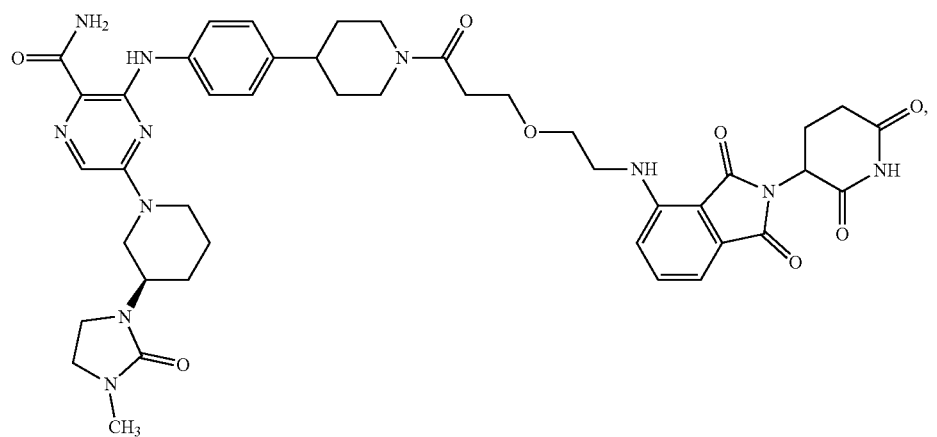
(Compound Number 26)
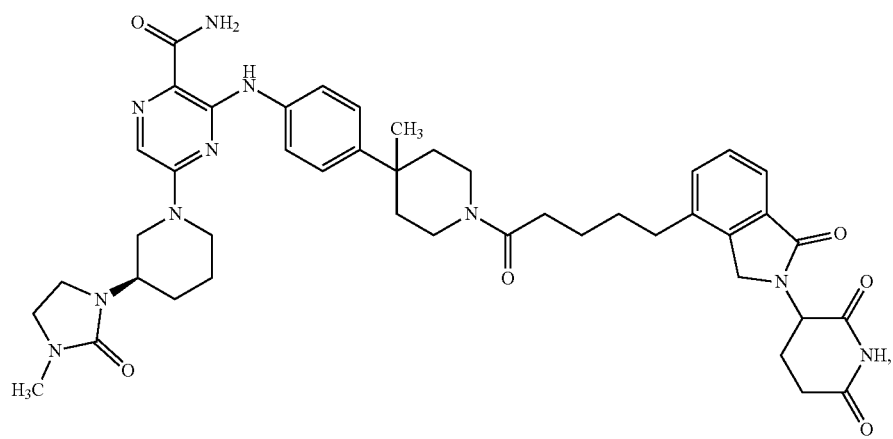

(Compound Number 27)
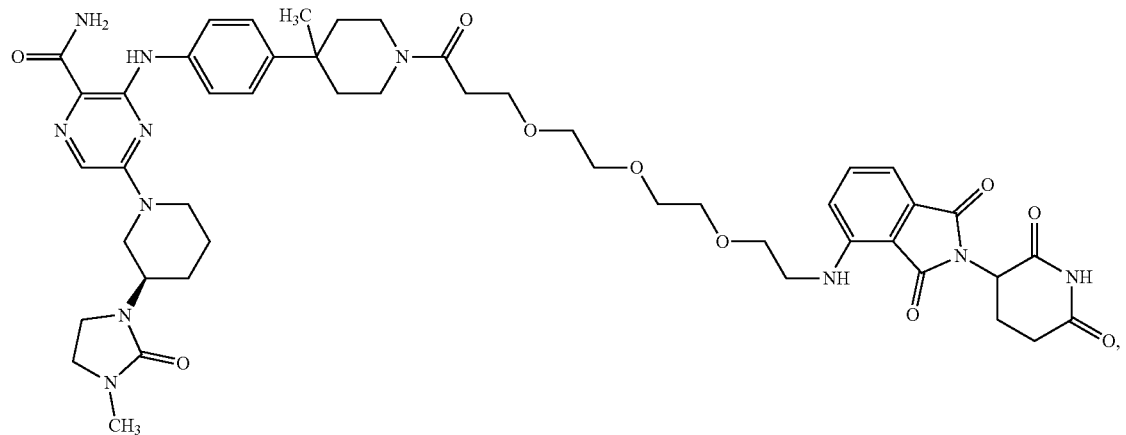
(Compound Number 28)
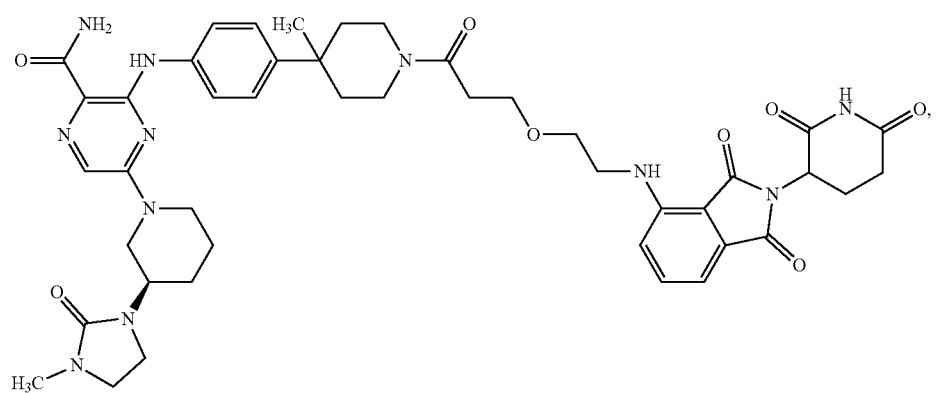
(Compound Number 29)
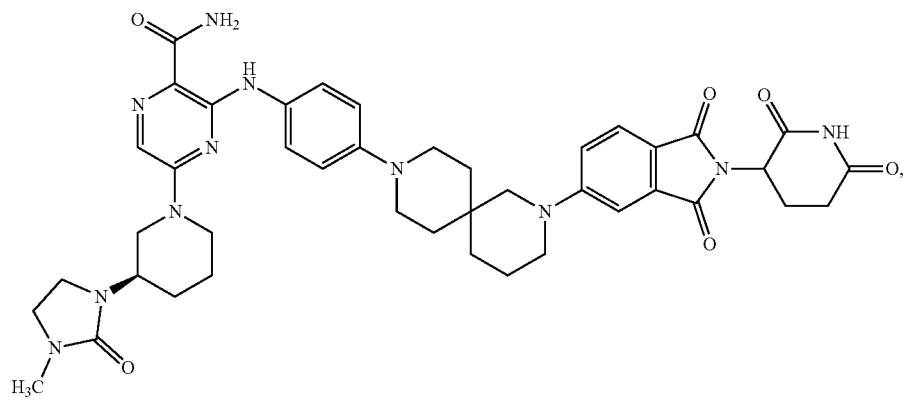

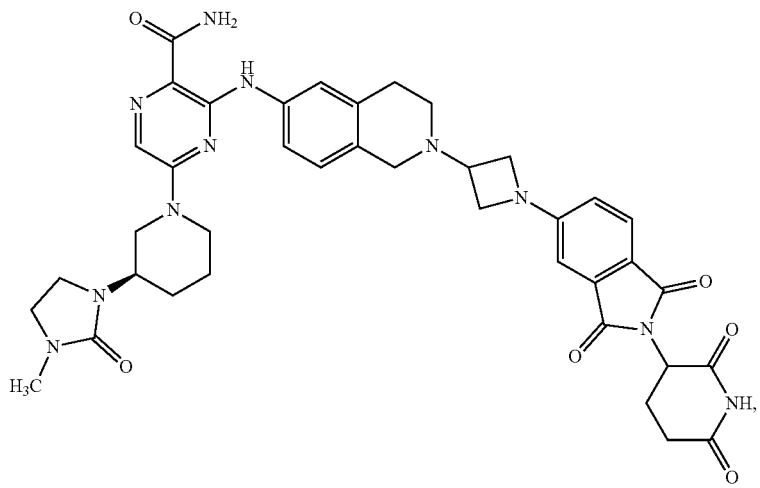
(Compound Number 30)
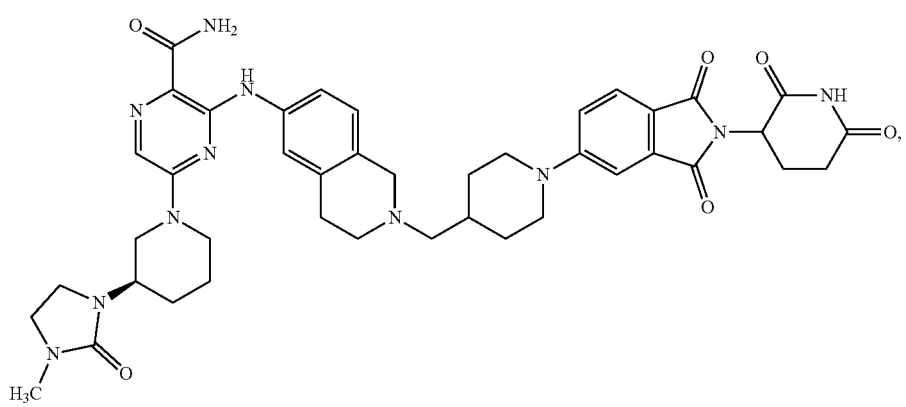
(Compound Number 31)
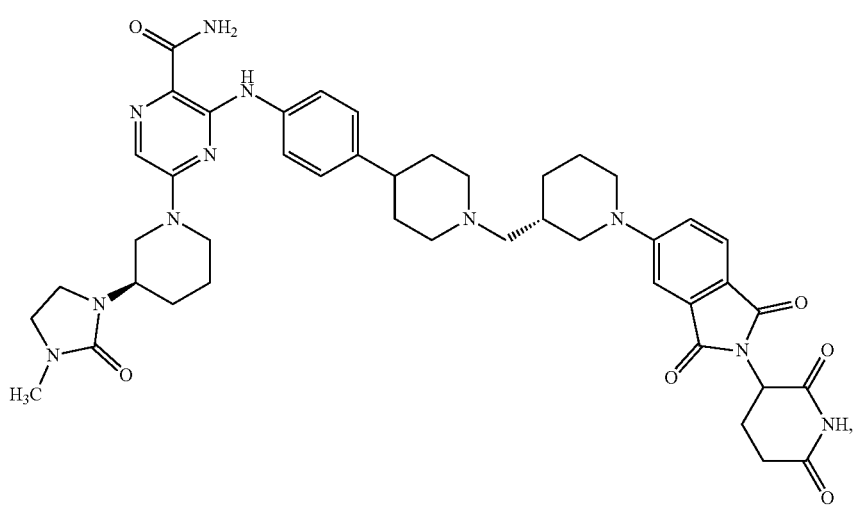
(Compound Number 32)

-continued
(Compound Number 33)
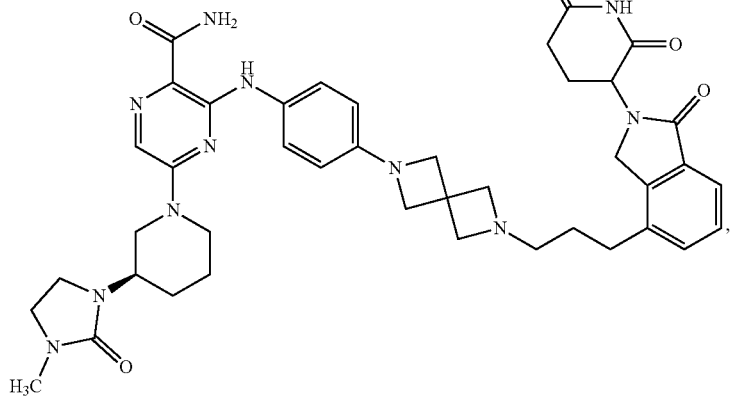
(Compound Number 34)
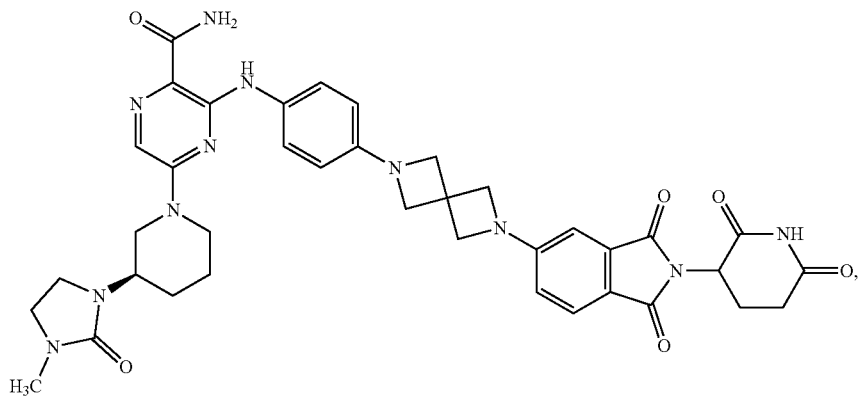
(Compound Number 35)
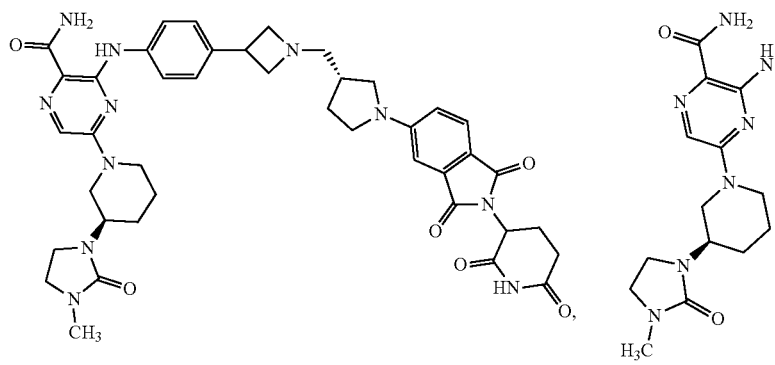
(Compound Number 36)
(Compound Number 37)
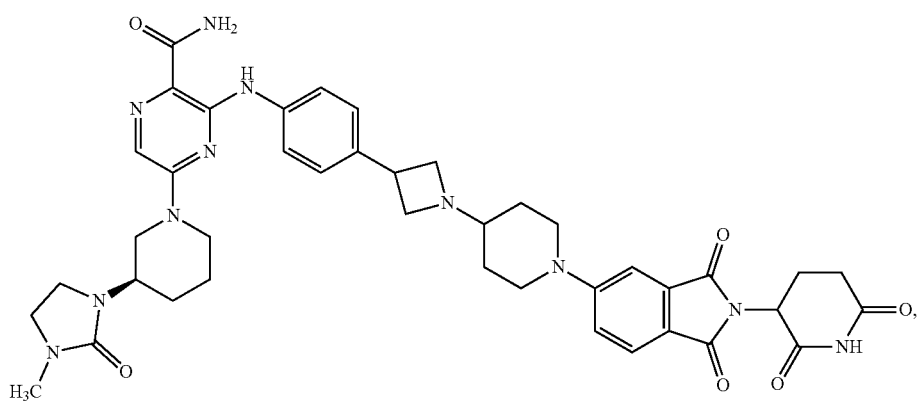

-continued
(Compound Number 38)
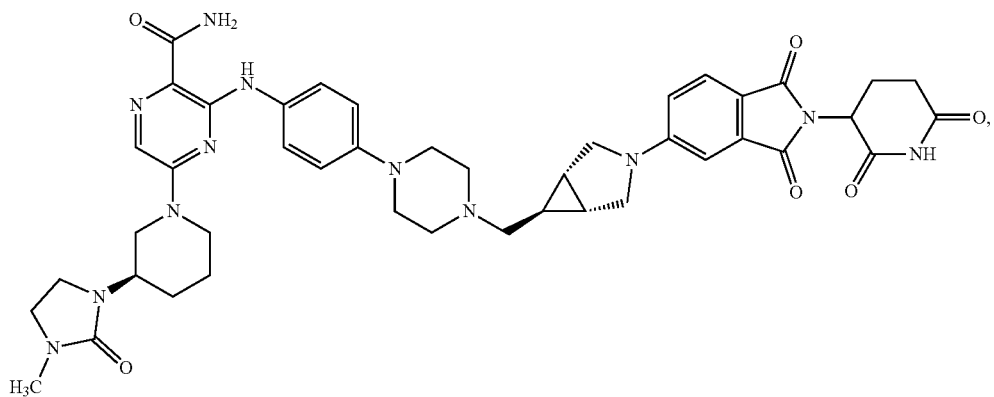
(Compound Number 39)
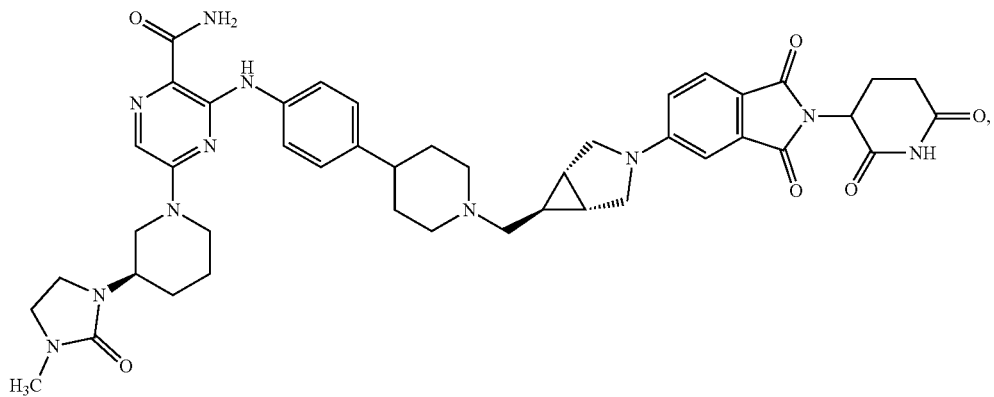
(Compound Number 40)
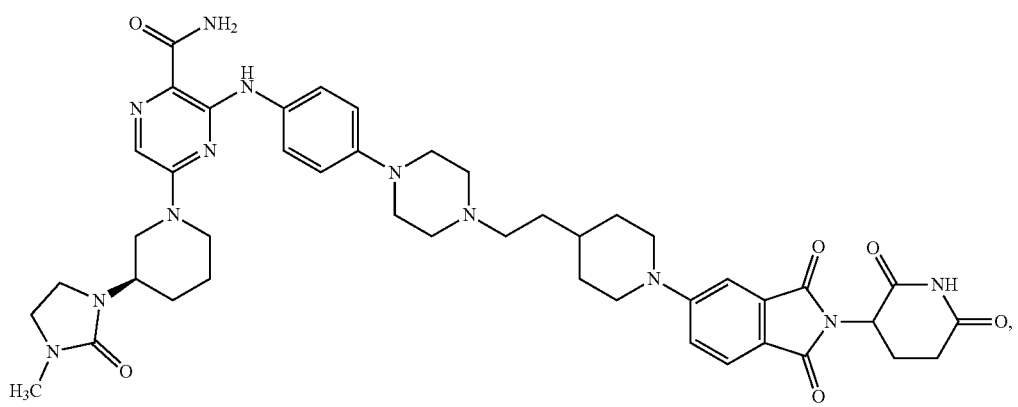
(Compound Number 41)
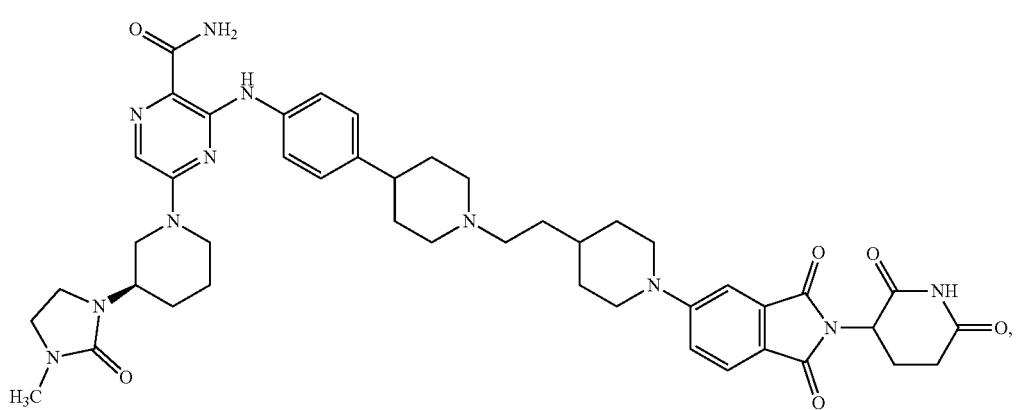

(Compound Number 42)
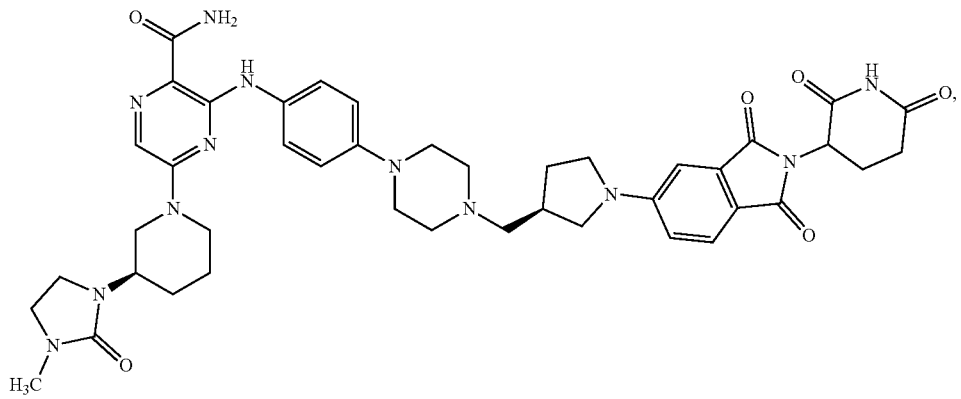
(Compound Number 43)
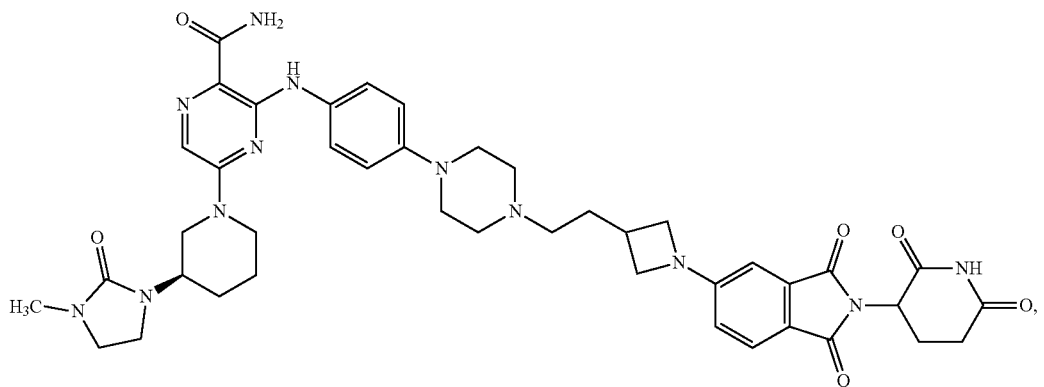
(Compound Number 44)
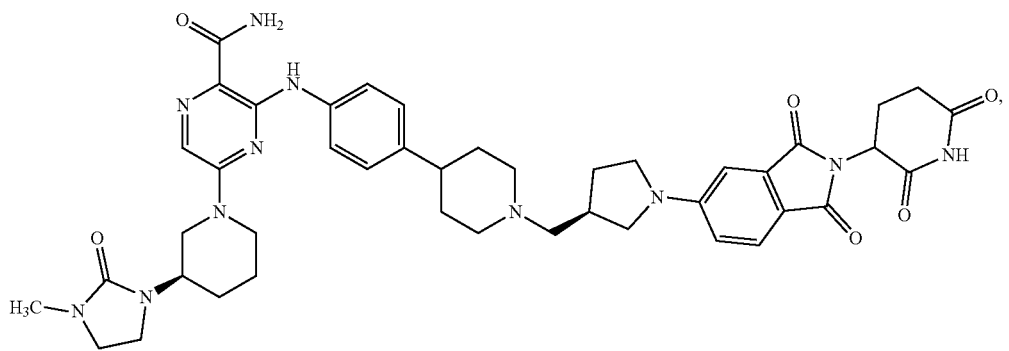
(Compound Number 45)
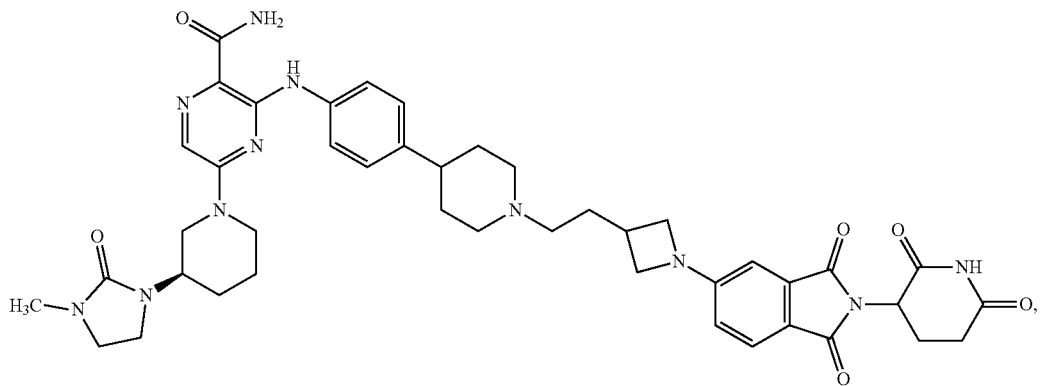

-continued
(Compound Number 46)
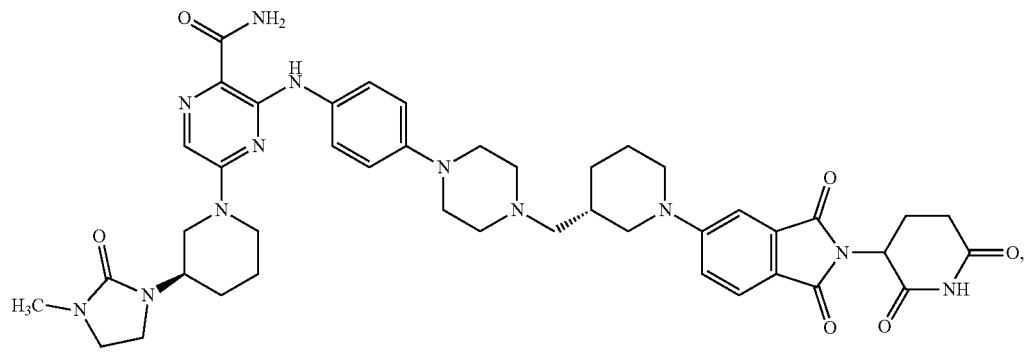
(Compound Number 47)
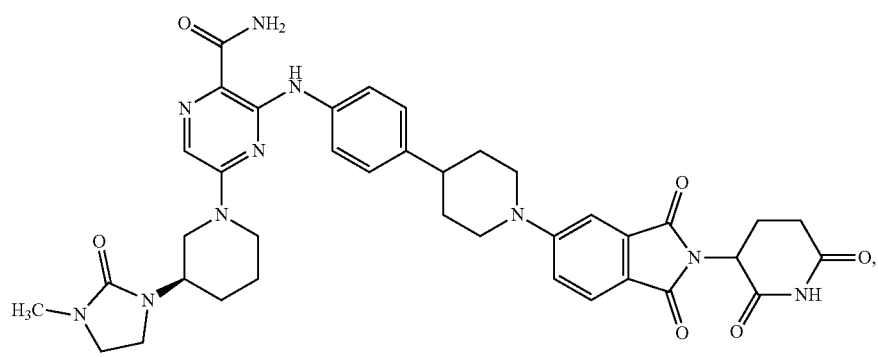
(Compound Number 48)
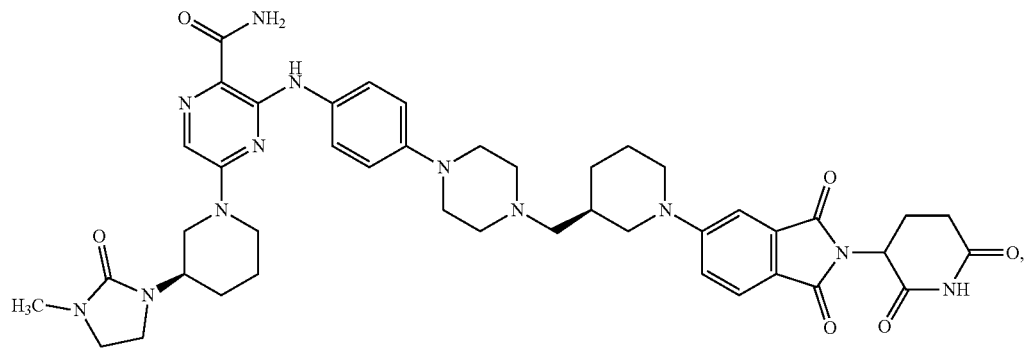
(Compound Number 49)
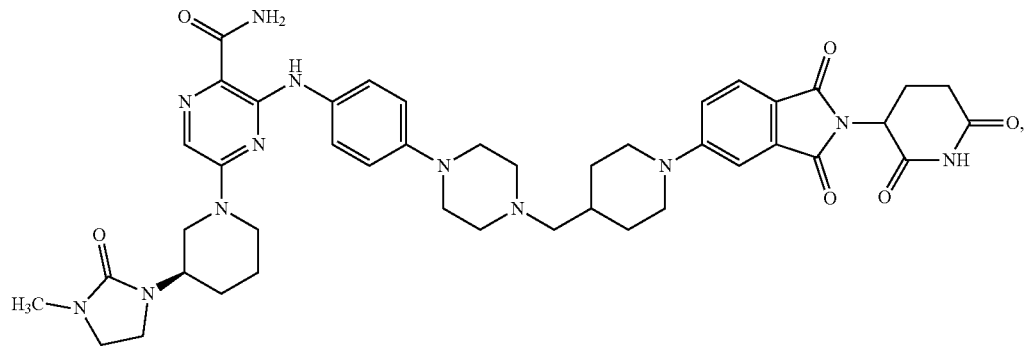

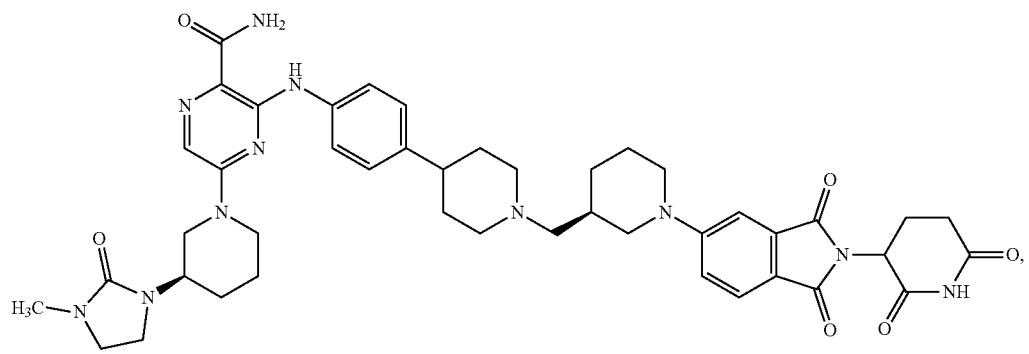
(Compound Number 50)
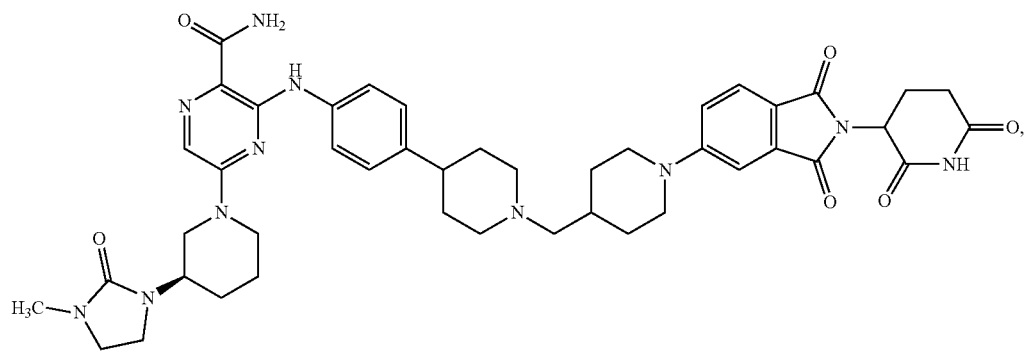
(Compound Number 51)
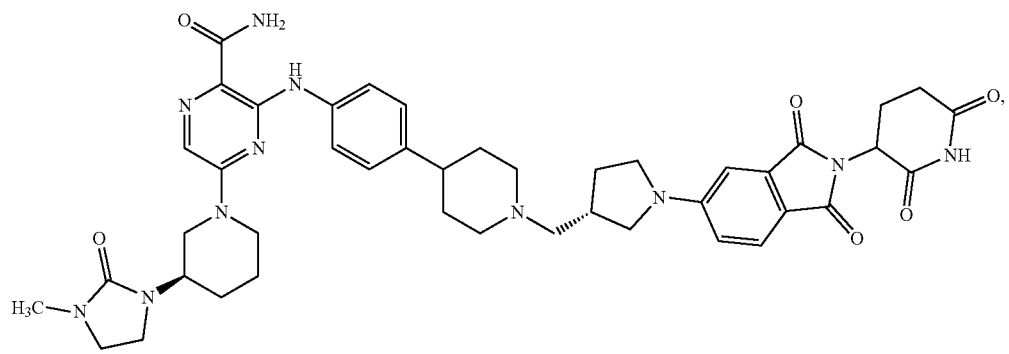
(Compound Number 52)
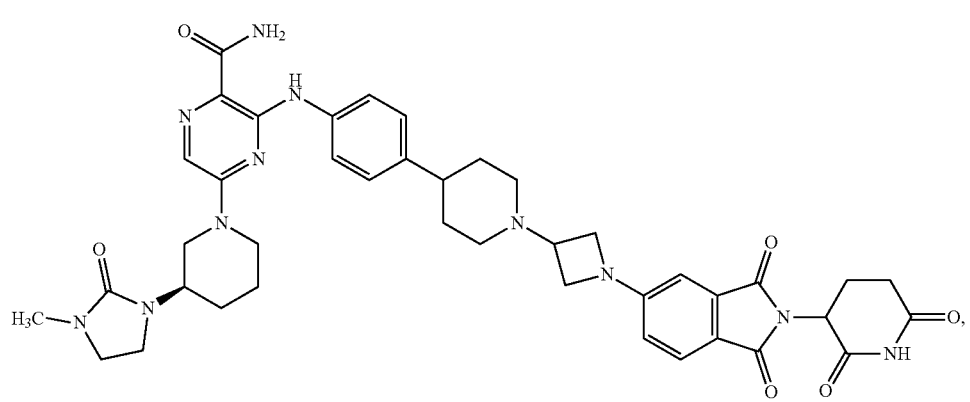
(Compound Number 53)

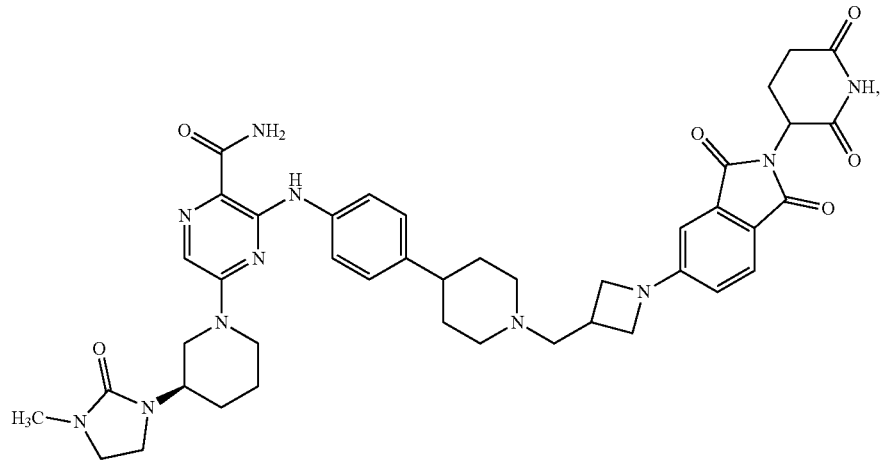
(Compound Number 54)
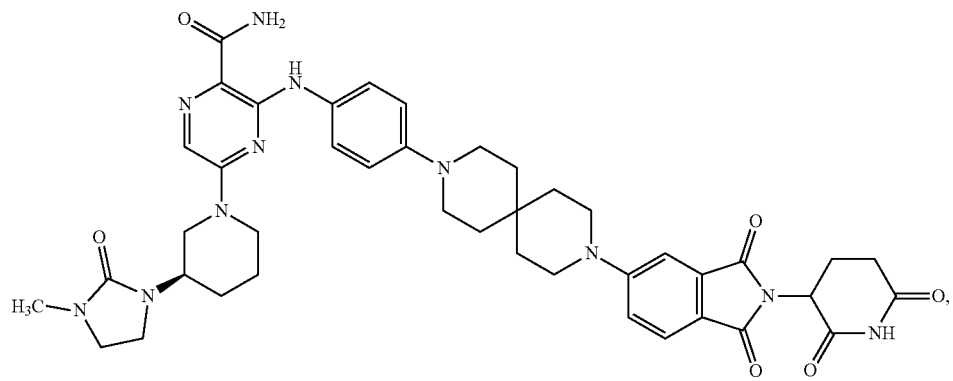
(Compound Number 55)
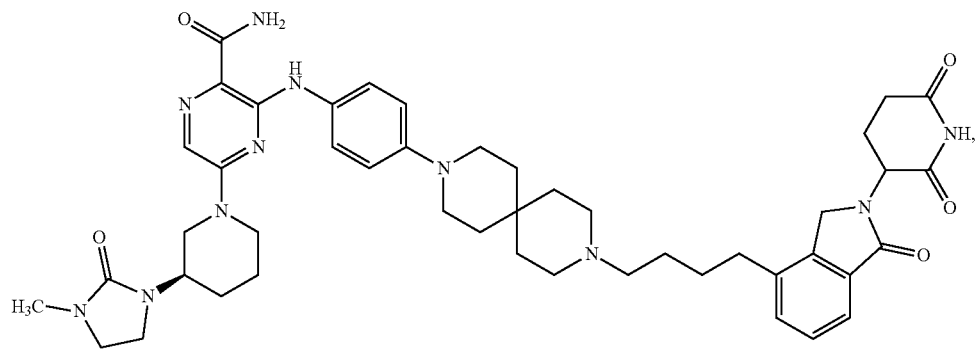
(Compound Number 56)
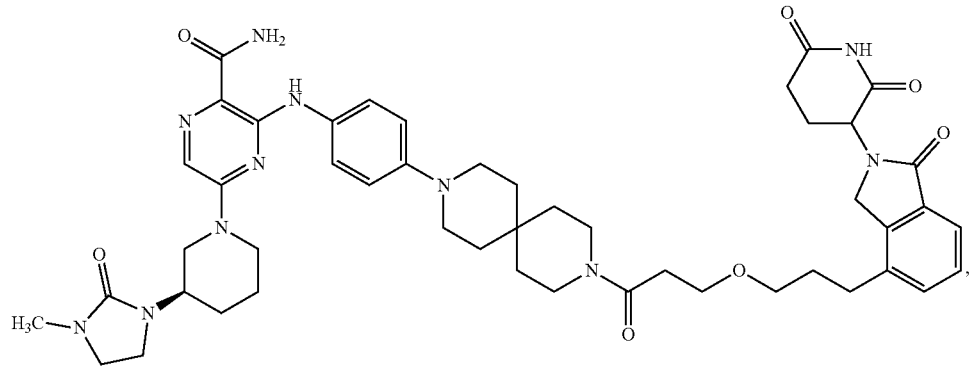
(Compound Number 57)

(Compound Number 58)
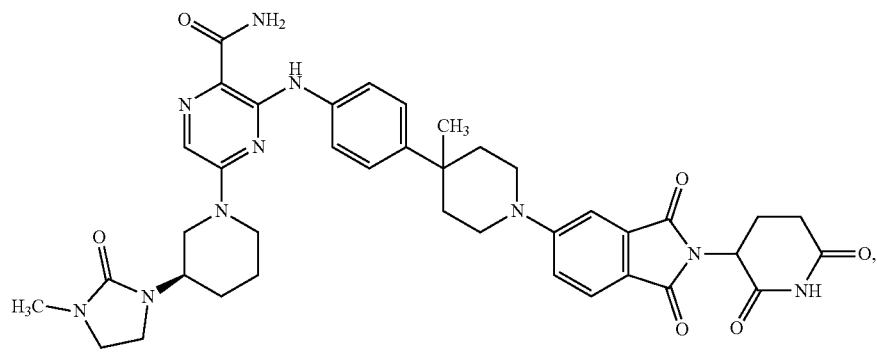
(Compound Number 59)
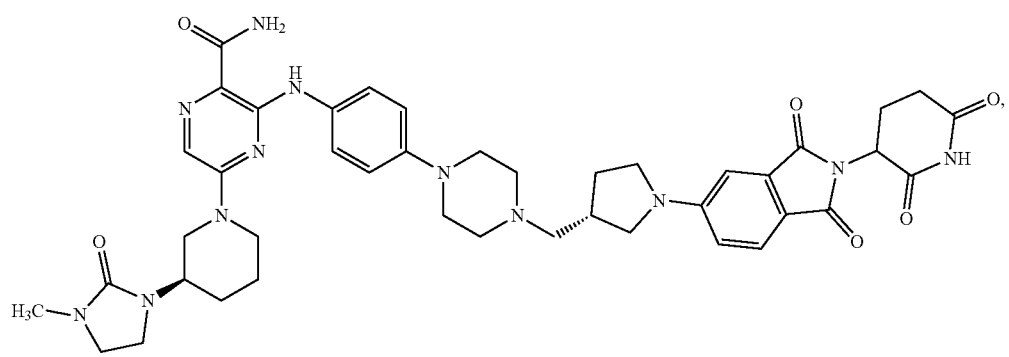
(Compound Number 60)
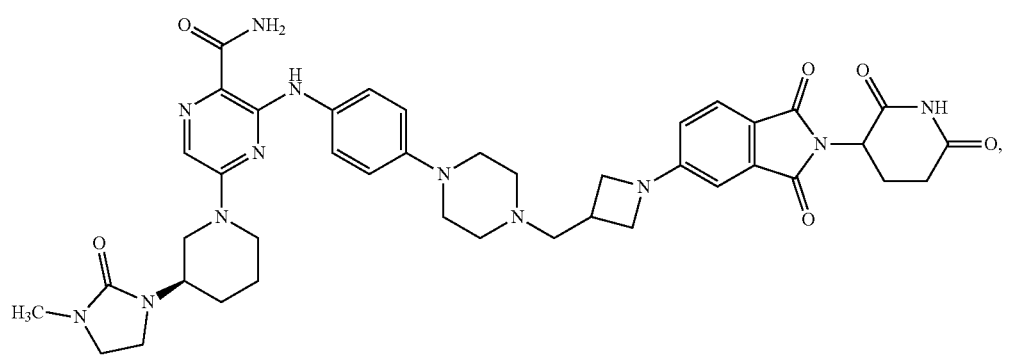
(Compound Number 61)
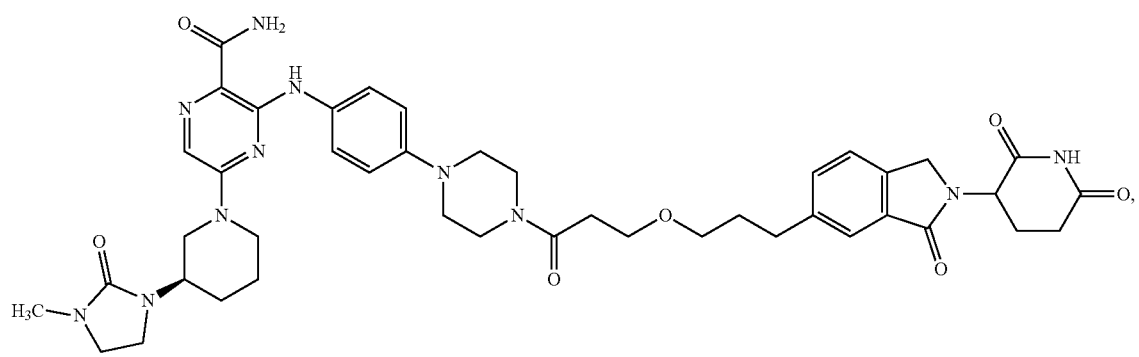

(Compound Number 62)
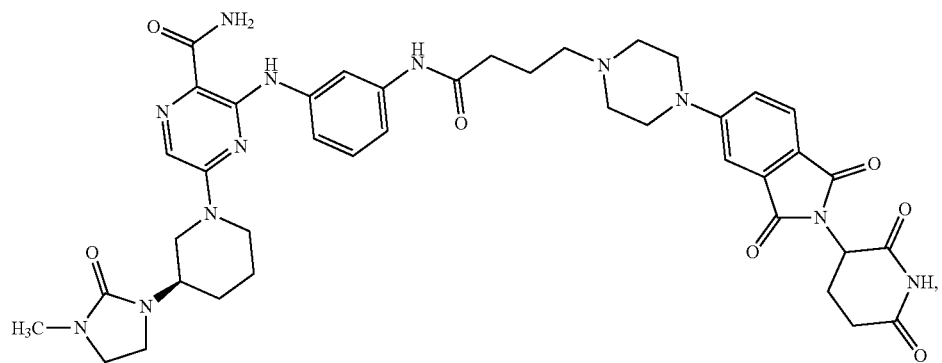
(Compound Number 63)
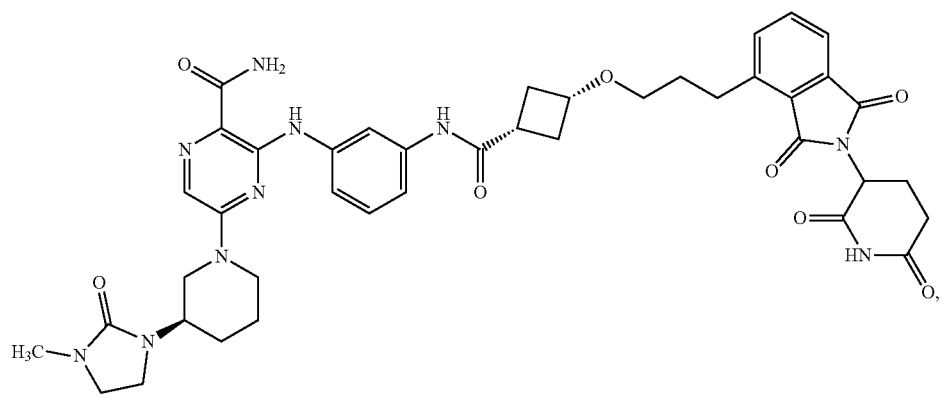
(Compound Number 64)
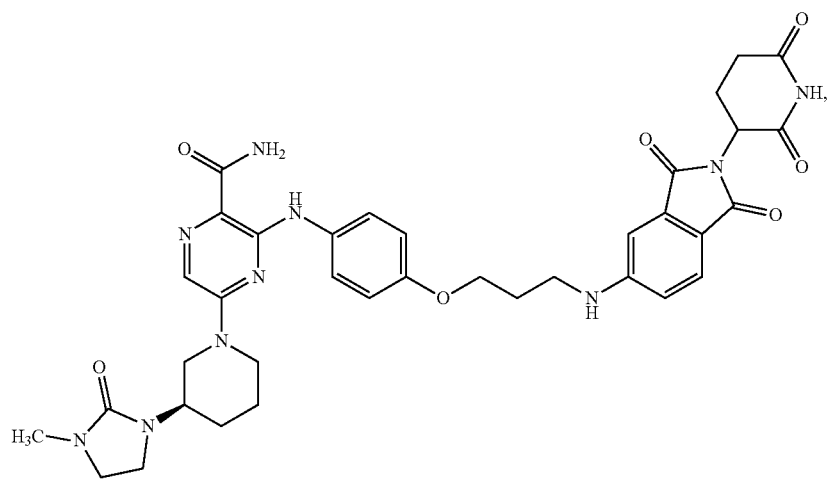
(Compound Number 65)
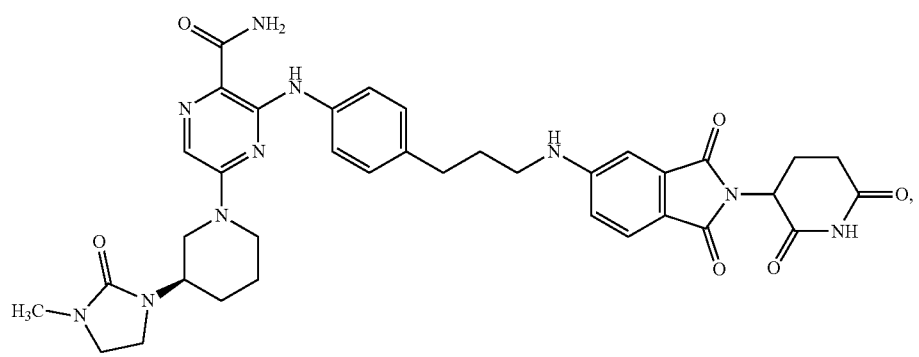

-continued
(Compound Number 66)
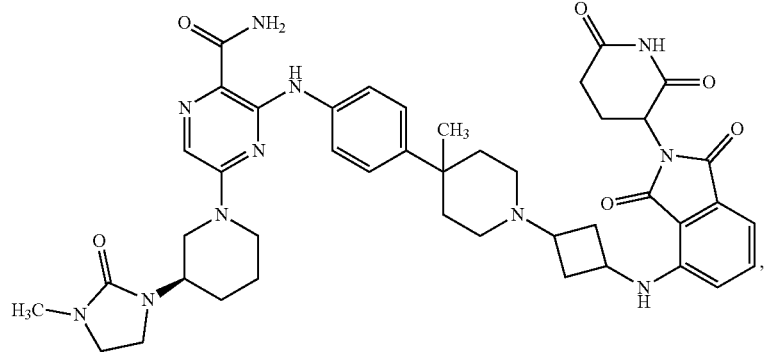
(Compound Number 67)
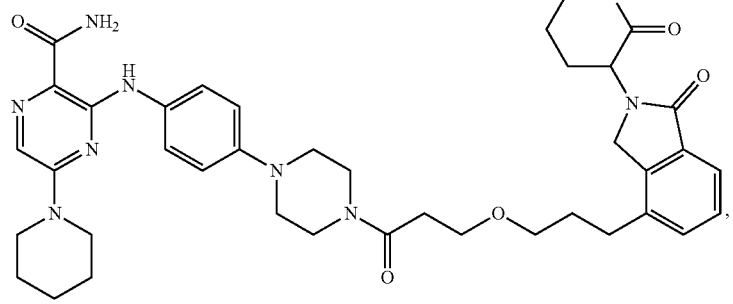
(Compound Number 68)
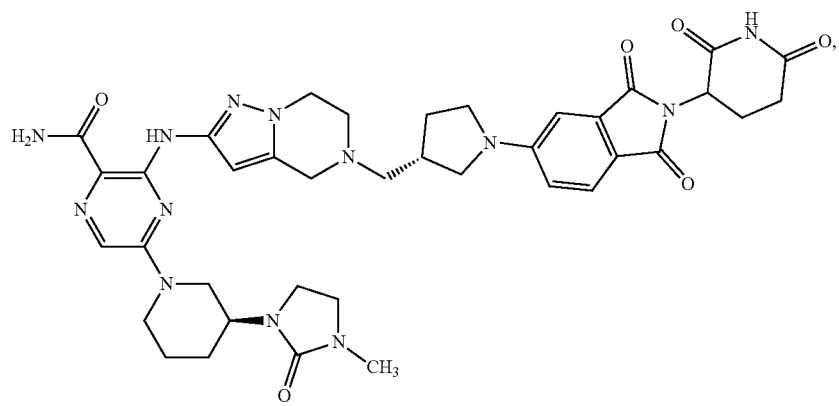
(Compound Number 69)
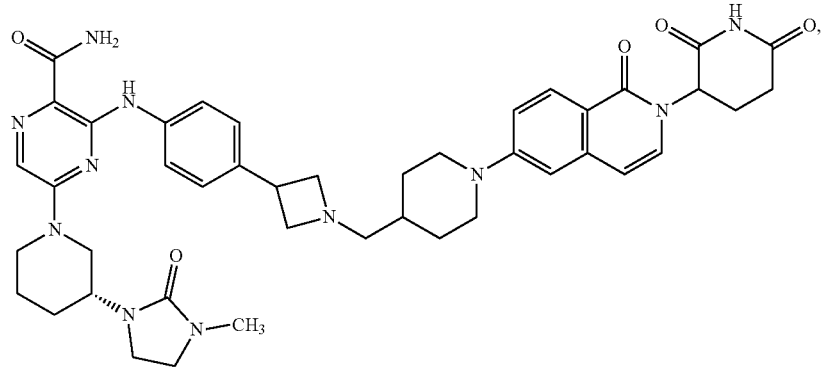

(Compound Number 70)
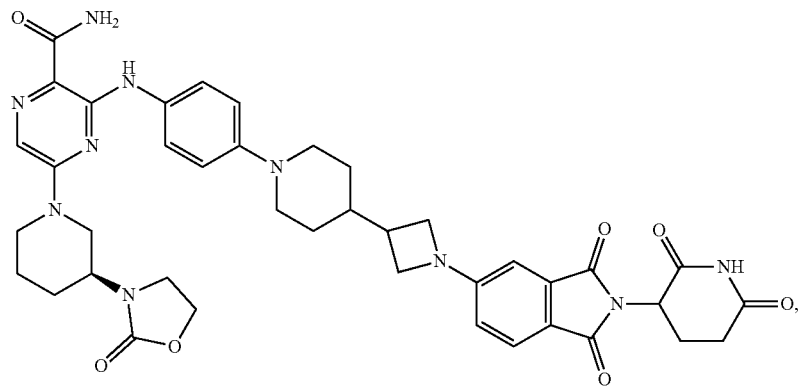
(Compound Number 71)
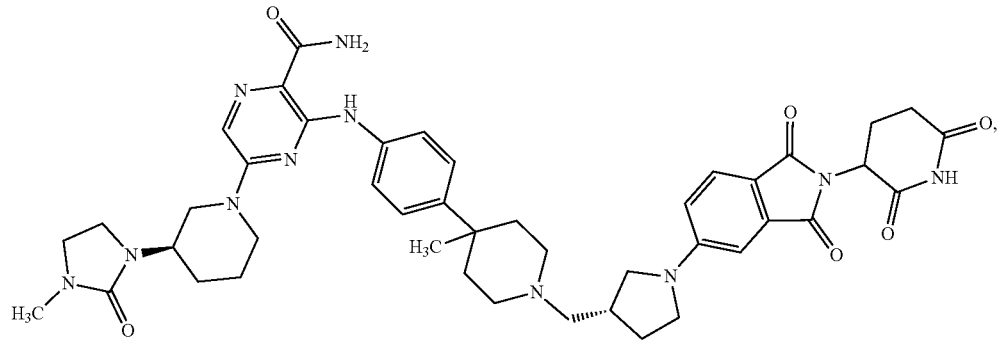
(Compound Number 72)
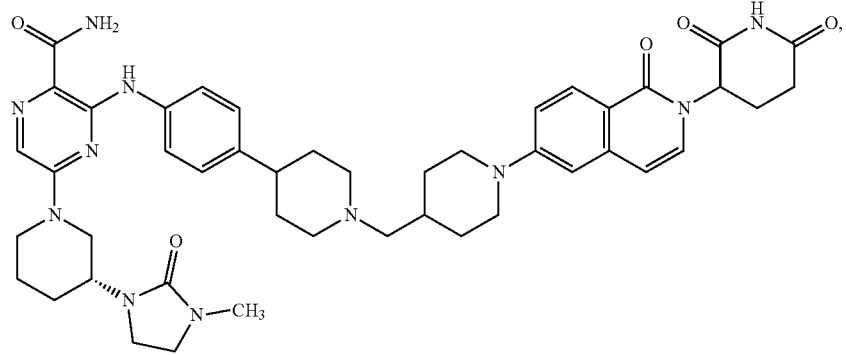
(Compound Number 73)
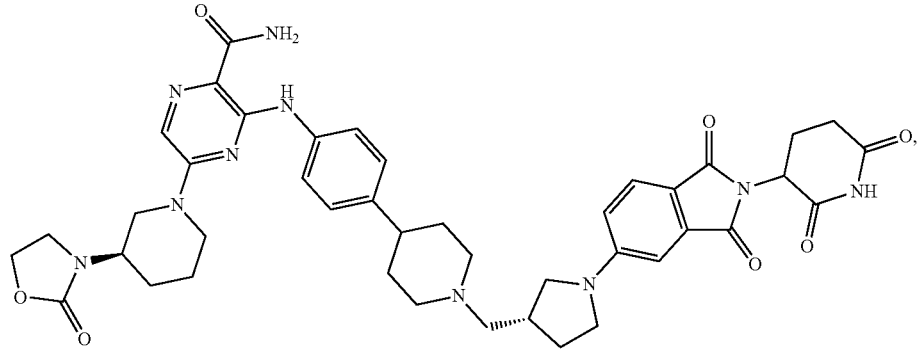

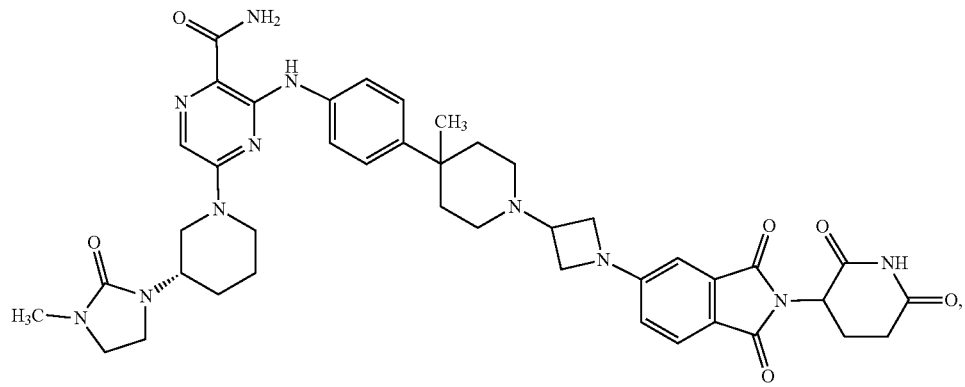
(Compound Number 74)
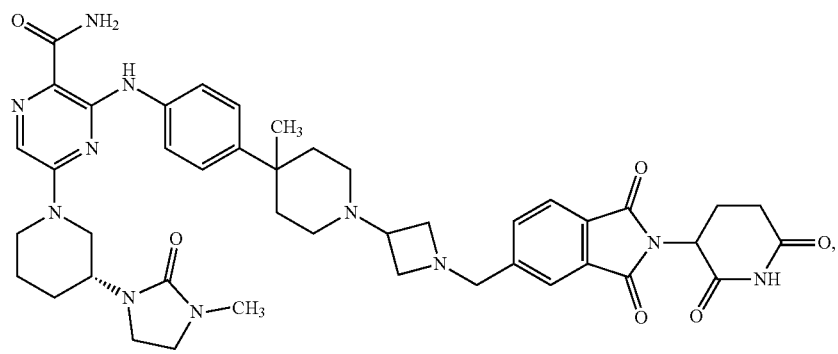
(Compound Number 75)
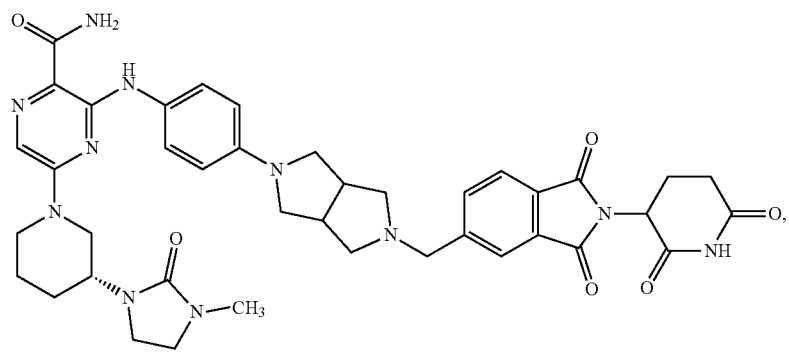
(Compound Number 76)
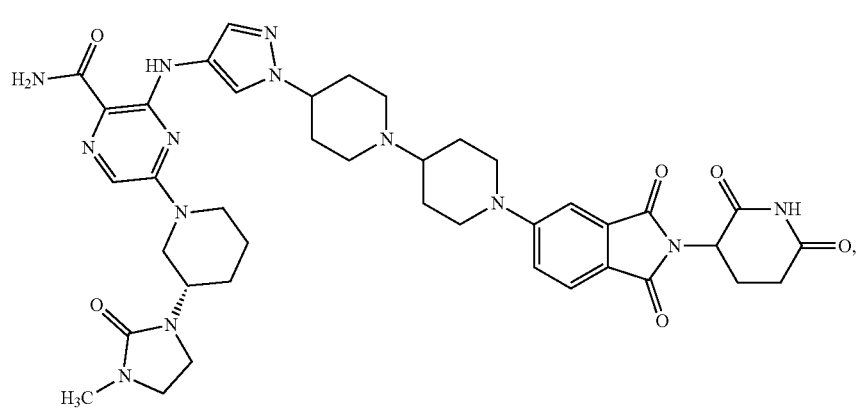
(Compound Number 77)

-continued
(Compound Number 78)
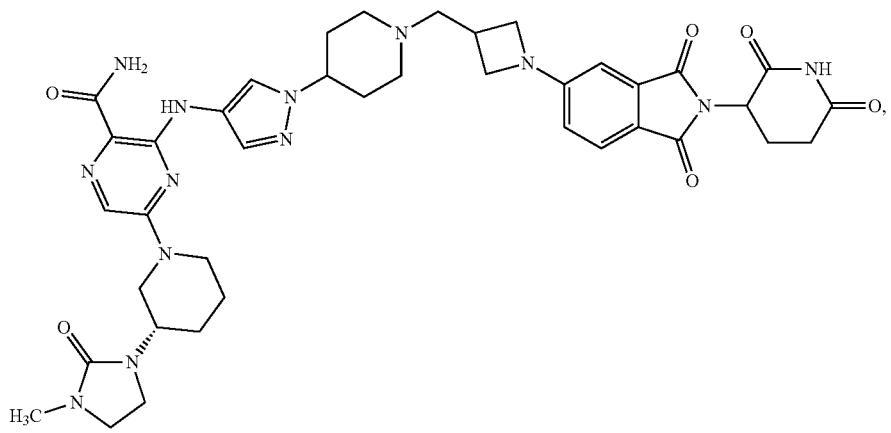
(Compound Number 79)
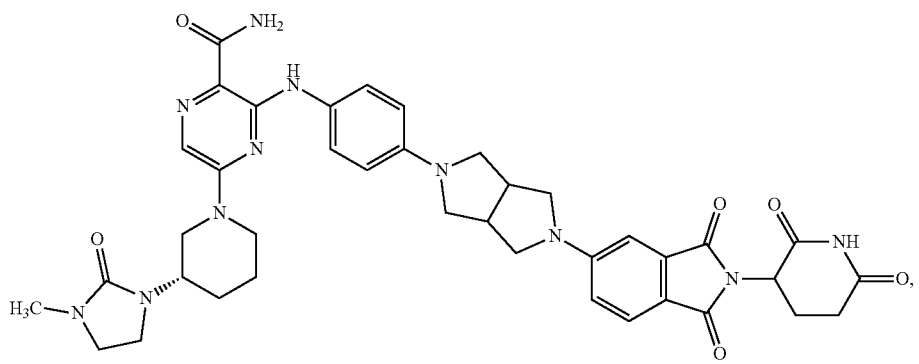
(Compound Number 80)
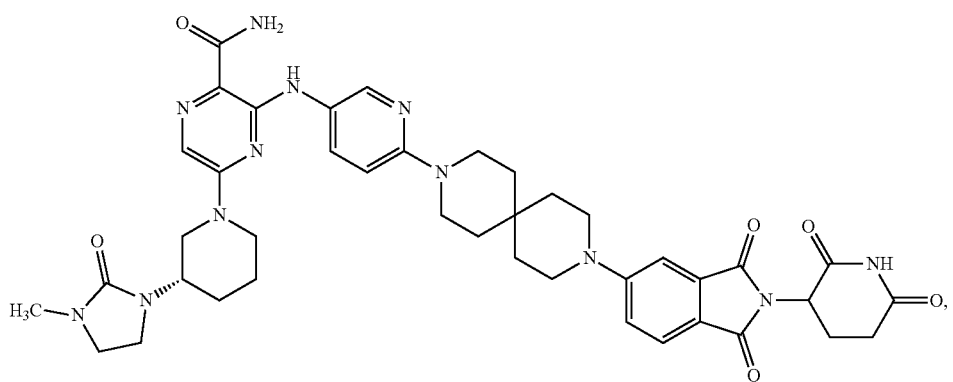
(Compound Number 81)
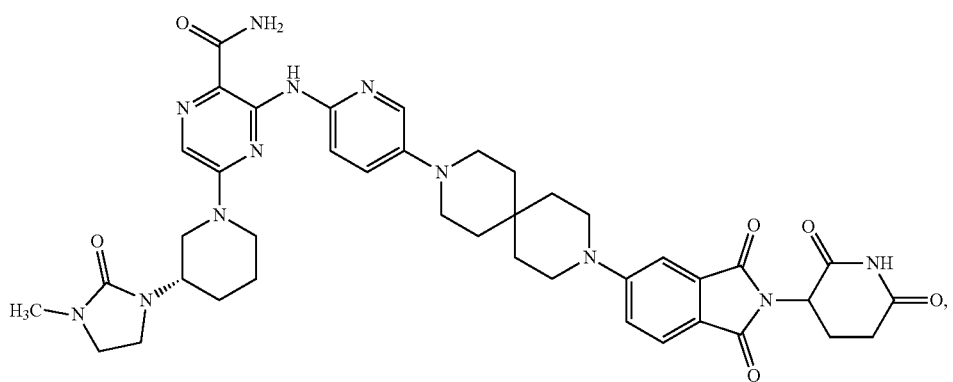

(Compound Number 82)
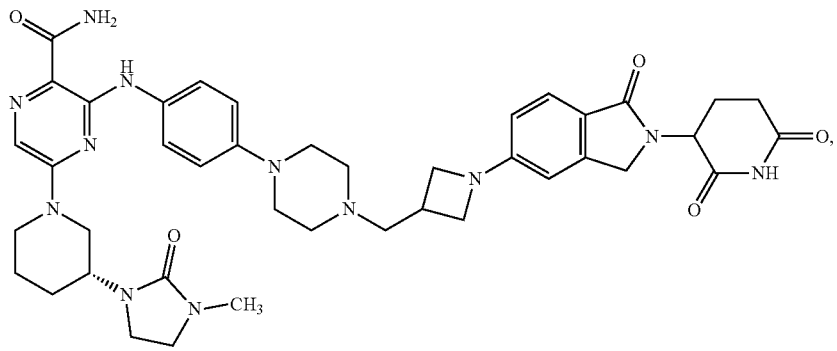
(Compound Number 83)
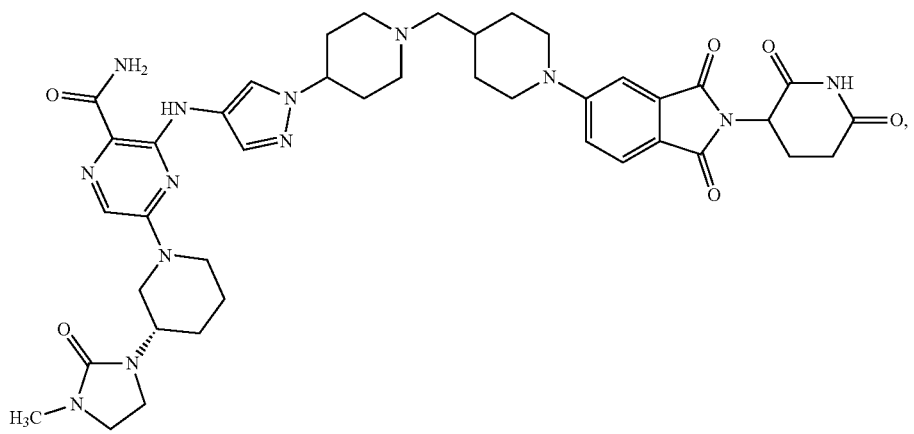
(Compound Number 84)
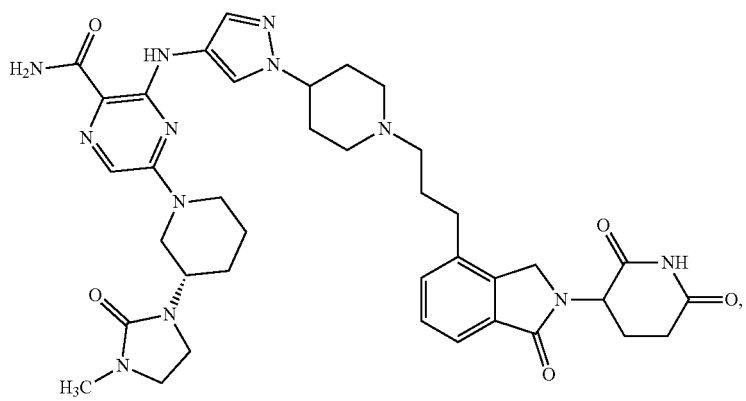
(Compound Number 85)
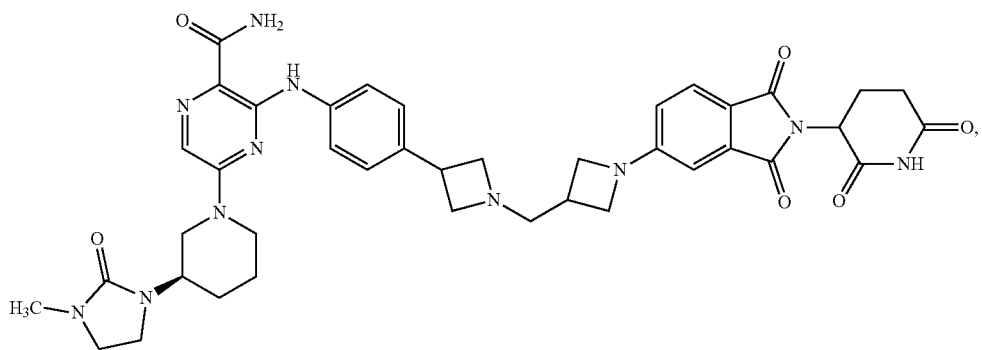

-continued
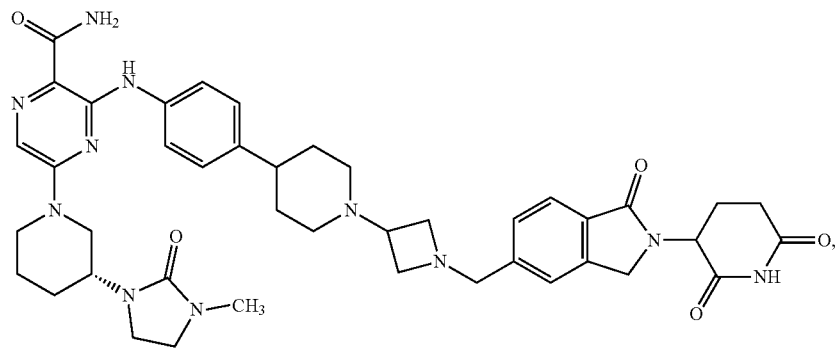
(Compound Number 86)
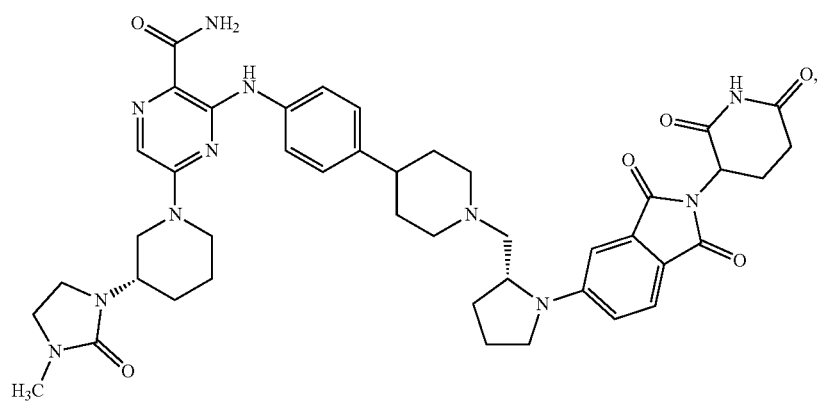
(Compound Number 87)
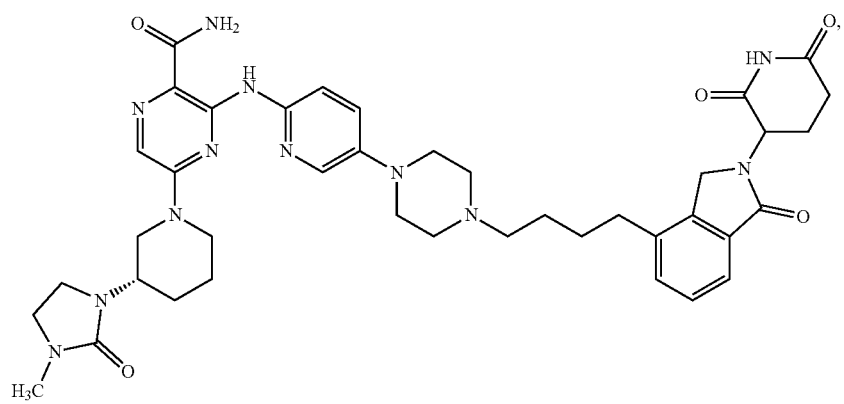
(Compound Number 88)
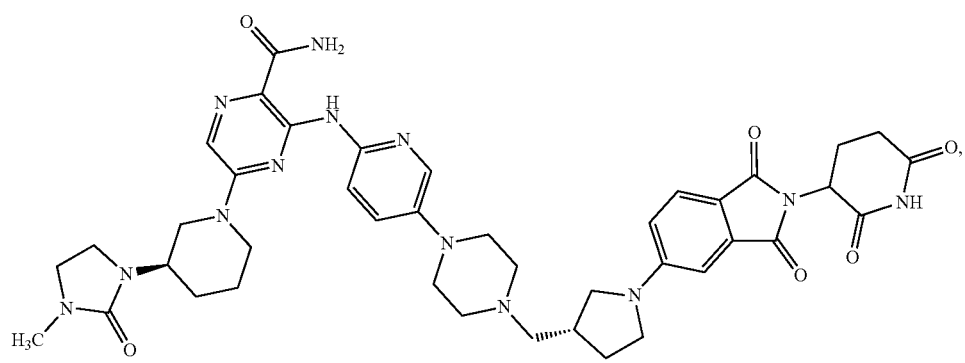
(Compound Number 89)

-continued
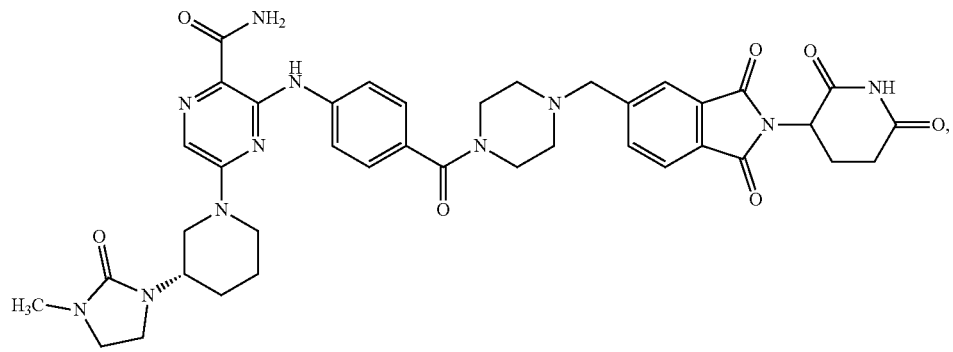
(Compound Number 90)
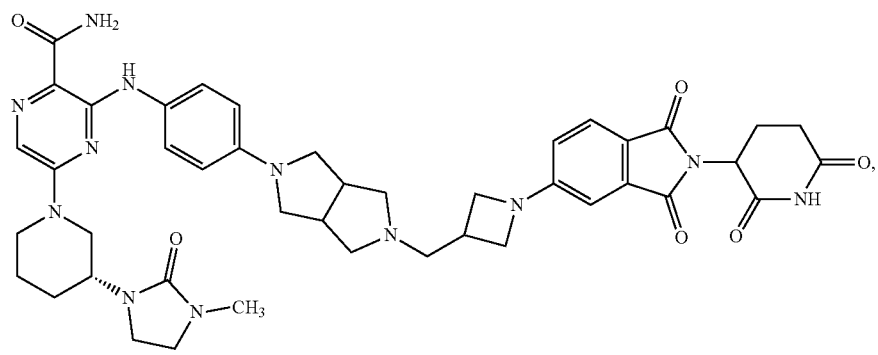
(Compound Number 91)
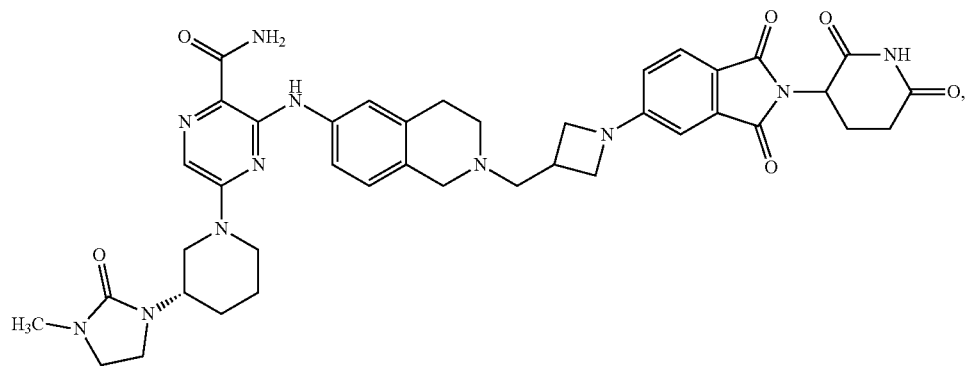
(Compound Number 92)
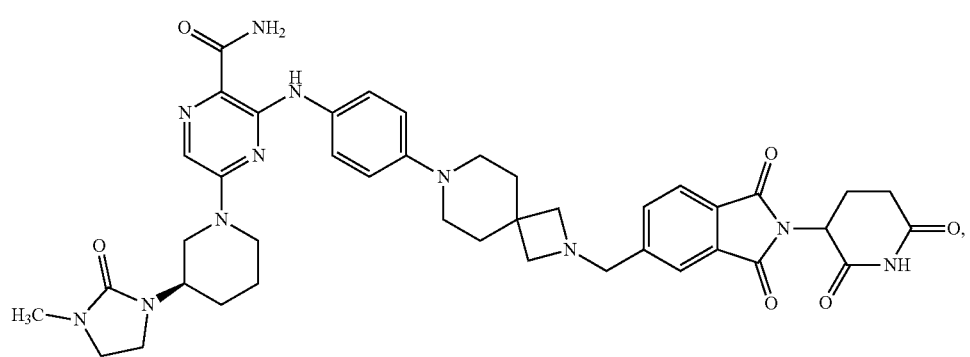
(Compound Number 93)

(Compound Number 94)
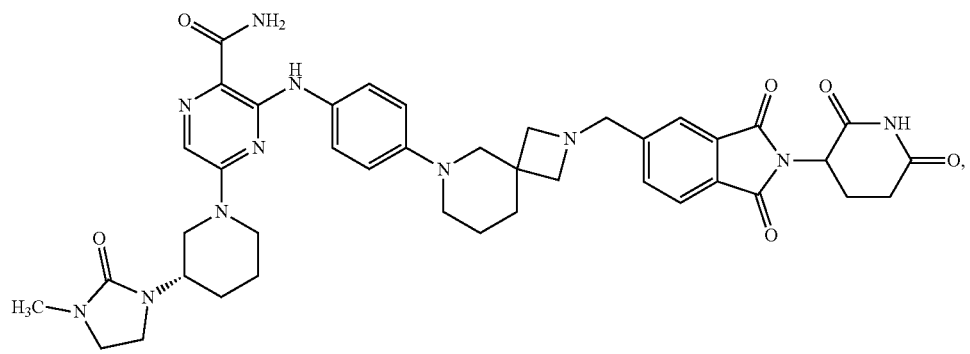
(Compound Number 95)
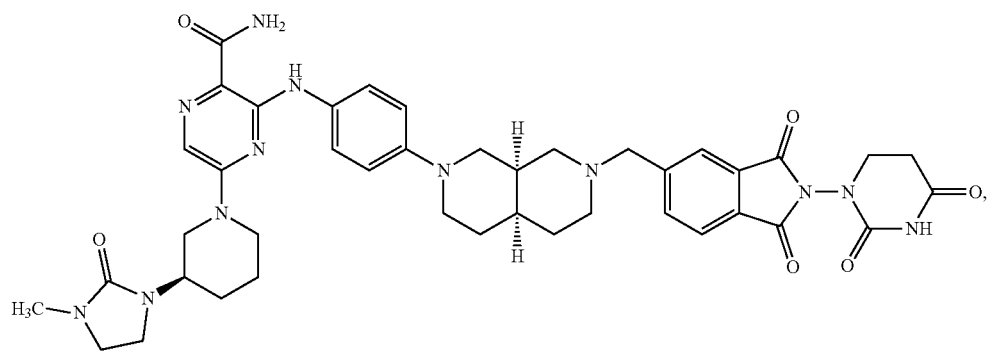
(Compound Number 96)
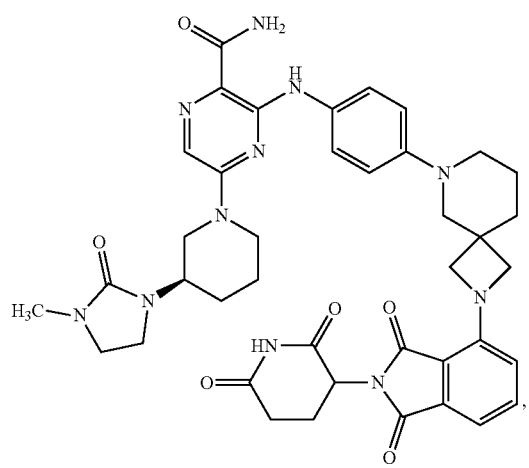
(Compound Number 97)
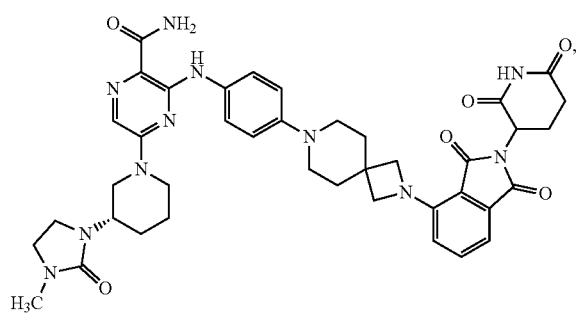
(Compound Number 99)
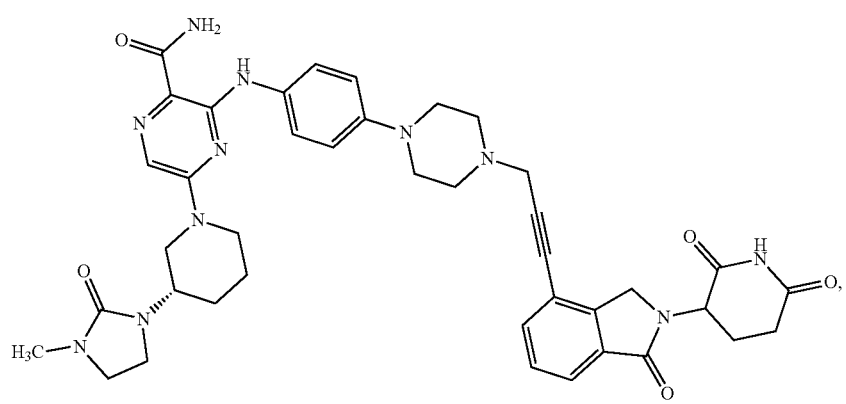

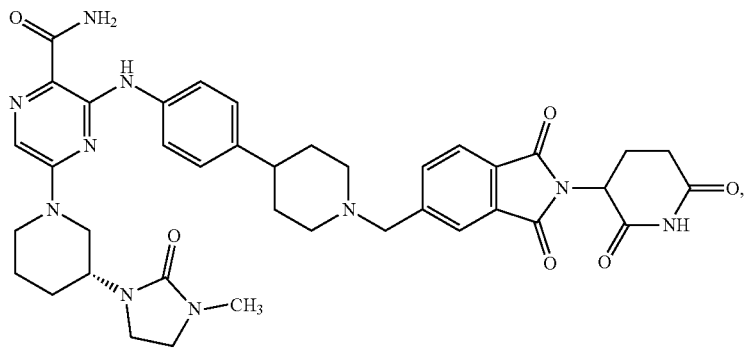
(Compound Number 100)
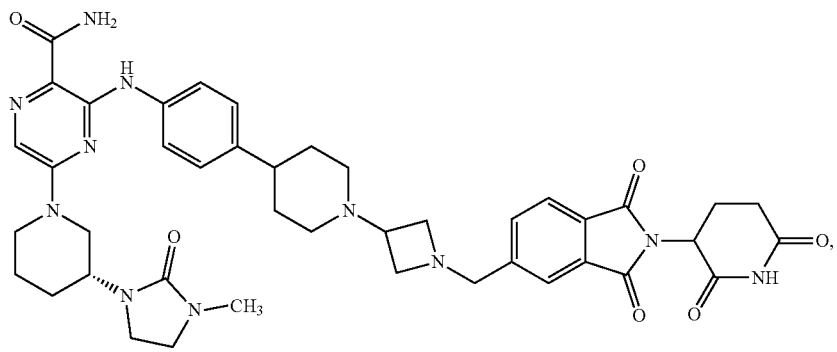
(Compound Number 101)
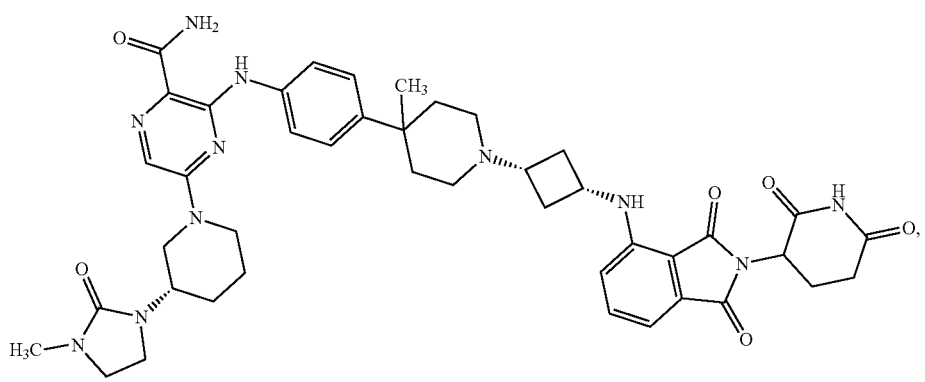
(Compound Number 102)
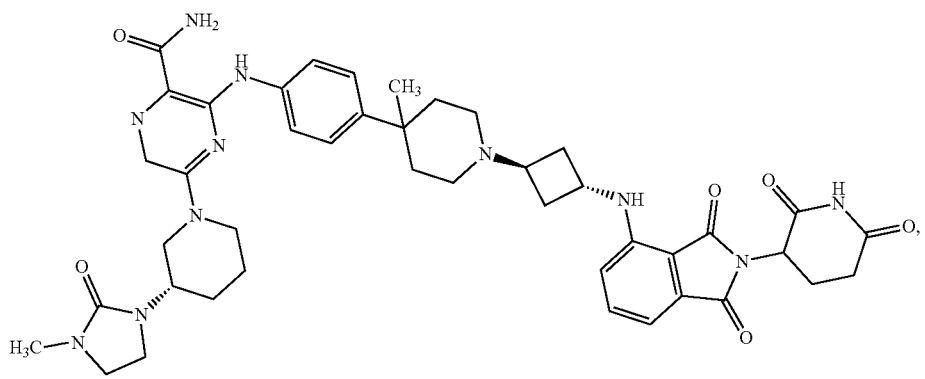
(Compound Number 103)

-continued
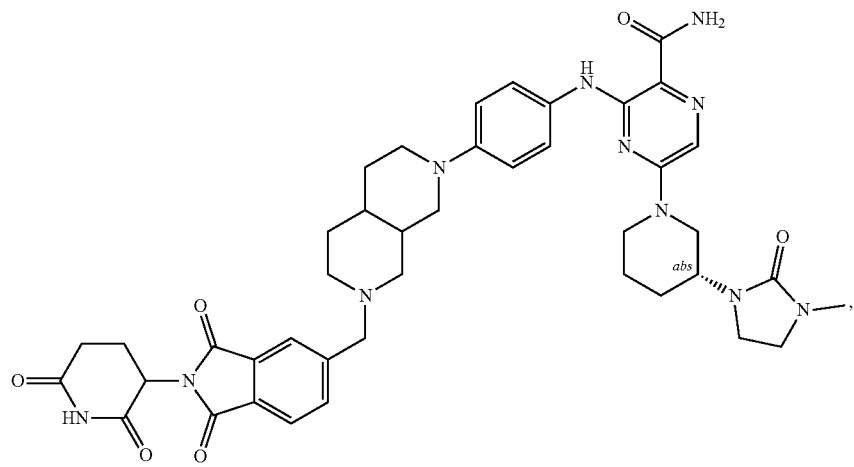
(Compound Number 104)
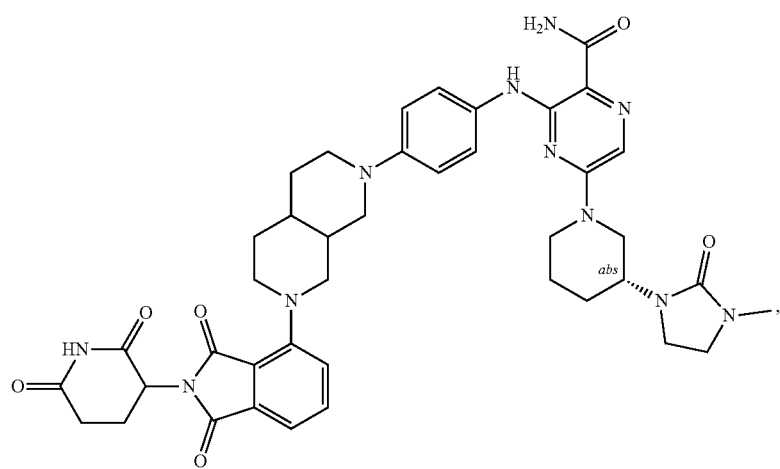
(Compound Number 105)
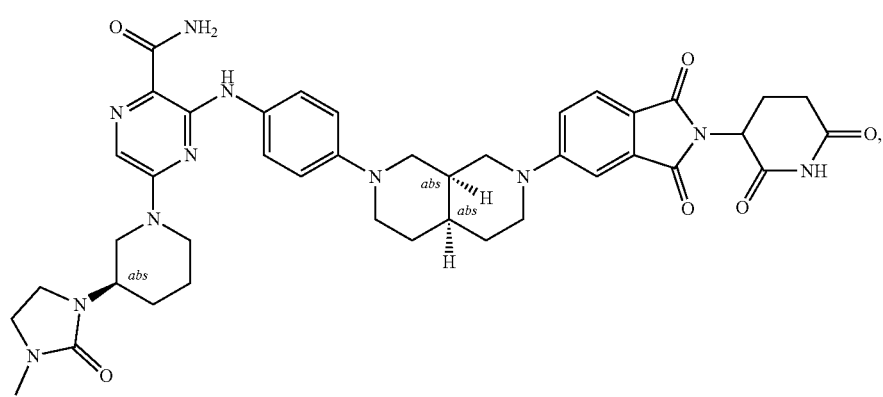
(Compound Number 106)

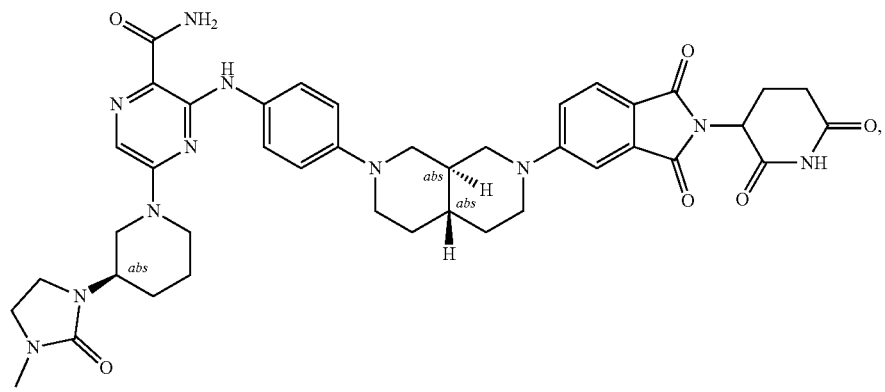
(Compound Number 107)
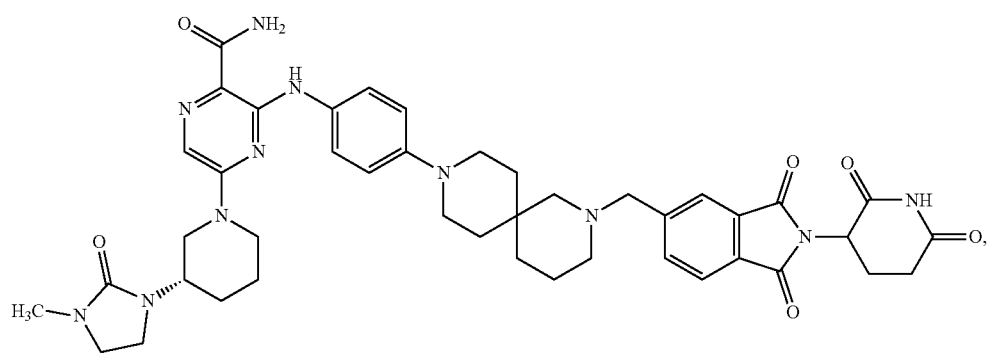
(Compound Number 108)
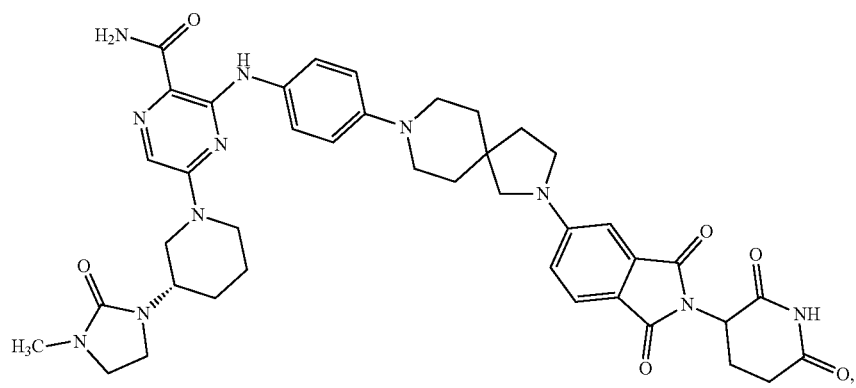
(Compound Number 109)
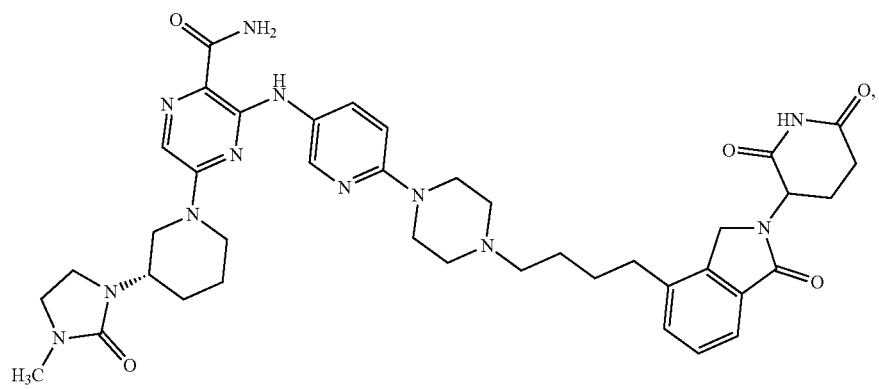
(Compound Number 110)

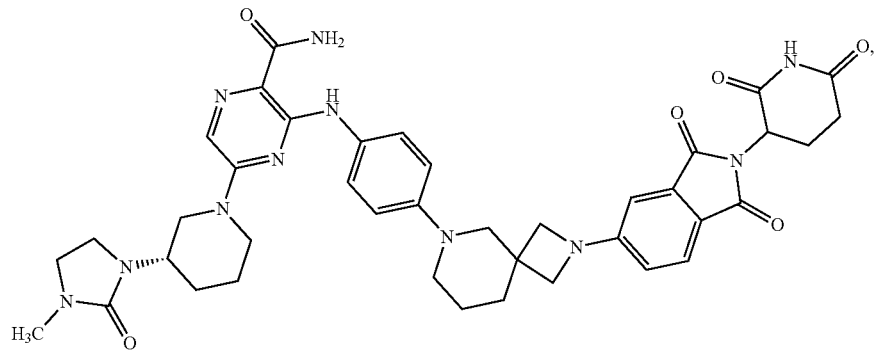
(Compound Number 111)
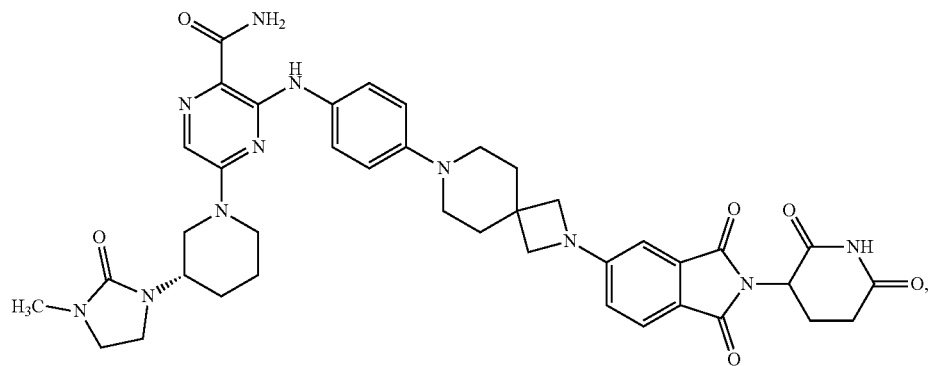
(Compound Number 112)
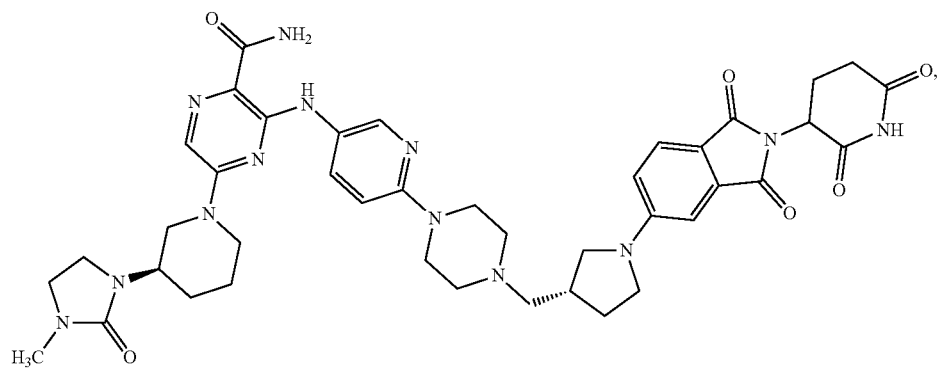
(Compound Number 113)
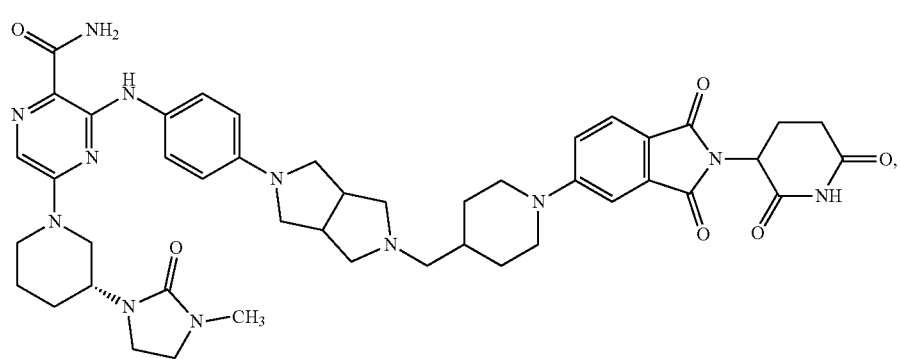
(Compound Number 114)

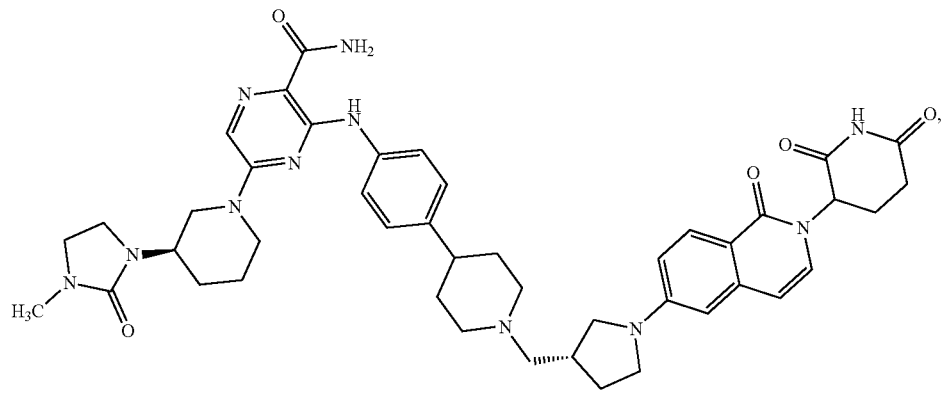
(Compound Number 115)
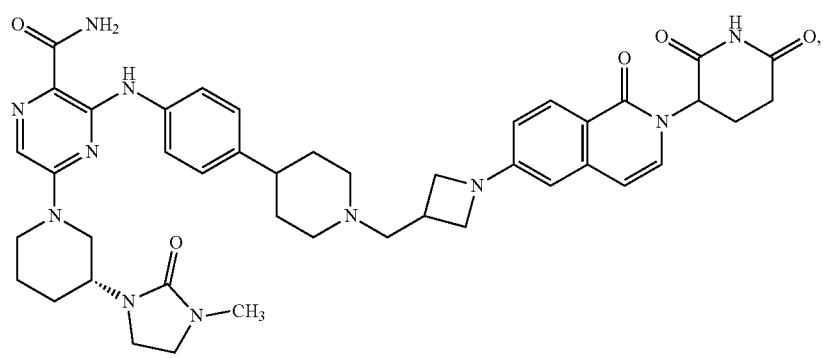
(Compound Number 116)
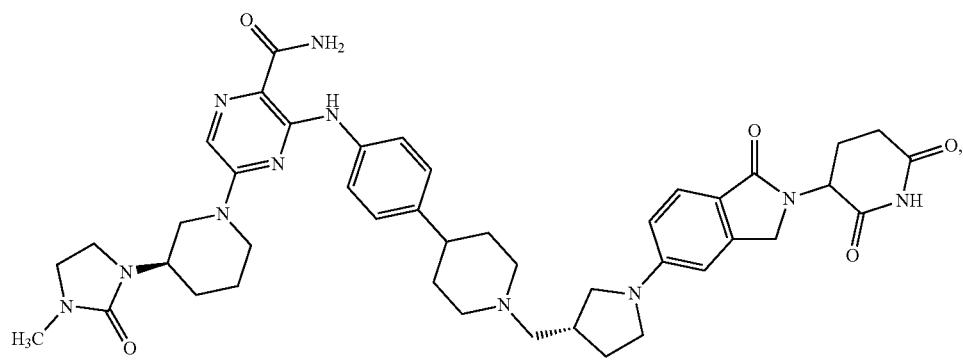
(Compound Number 117)
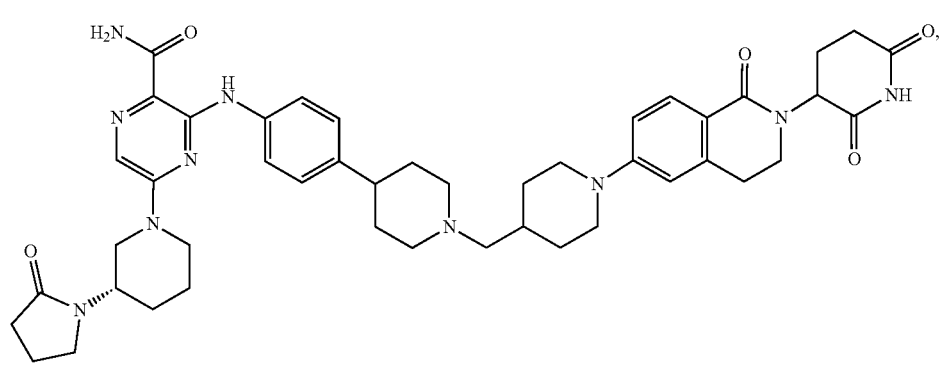
(Compound Number 122)

-continued
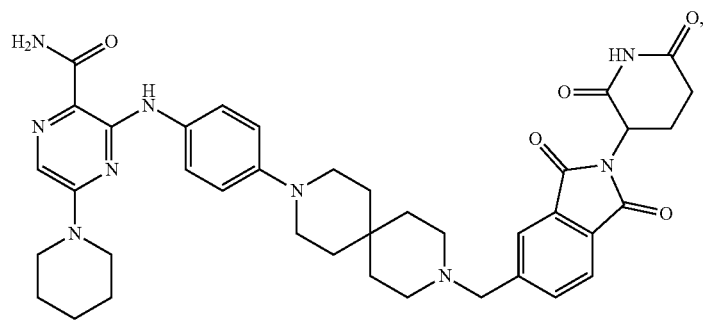
(Compound Number 123)
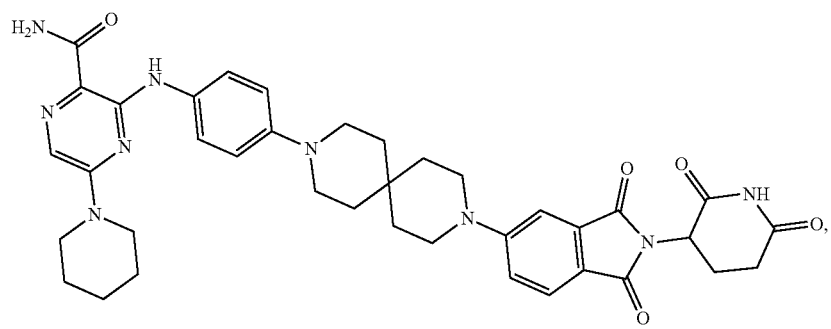
(Compound Number 124)
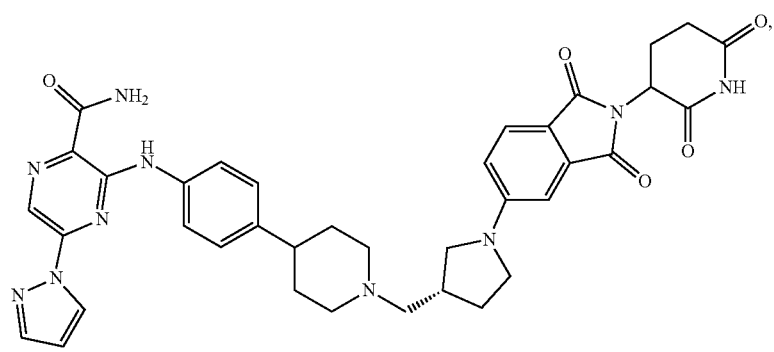
(Compound Number 125)
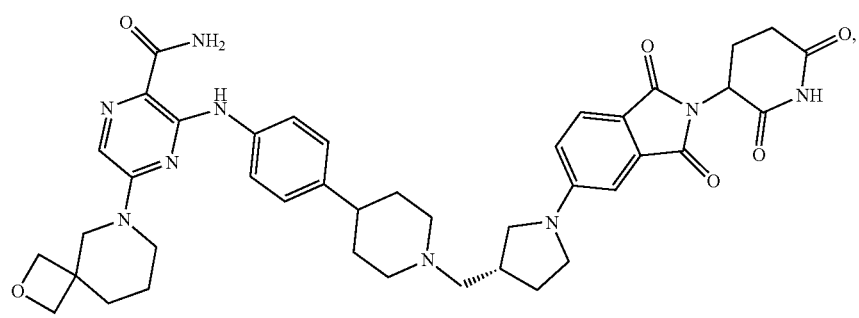
(Compound Number 126)
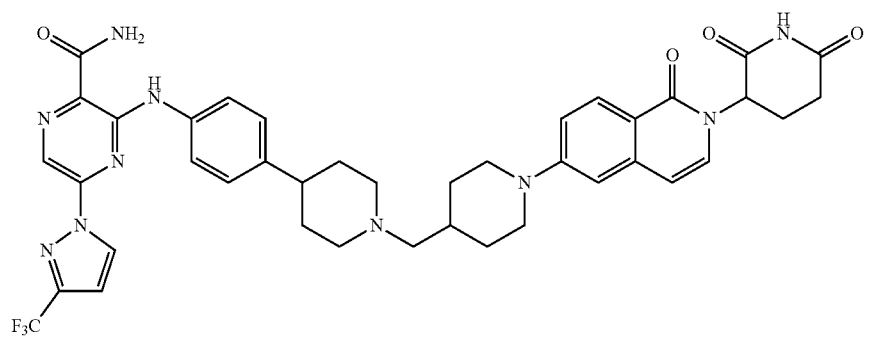
(Compound Number 127)

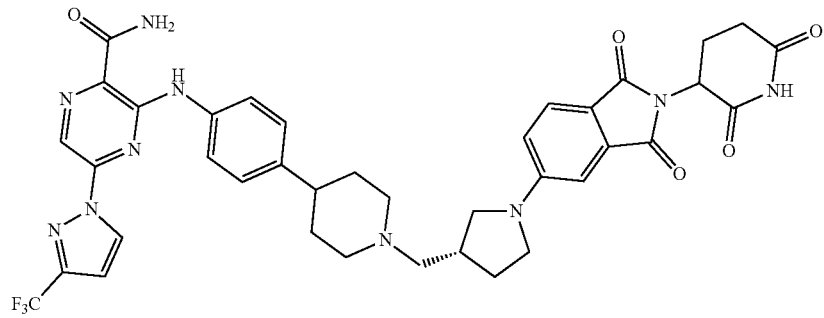
(Compound Number 128)
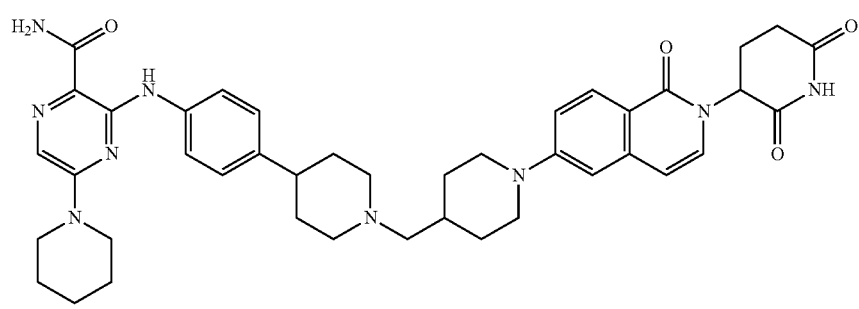
(Compound Number 133)
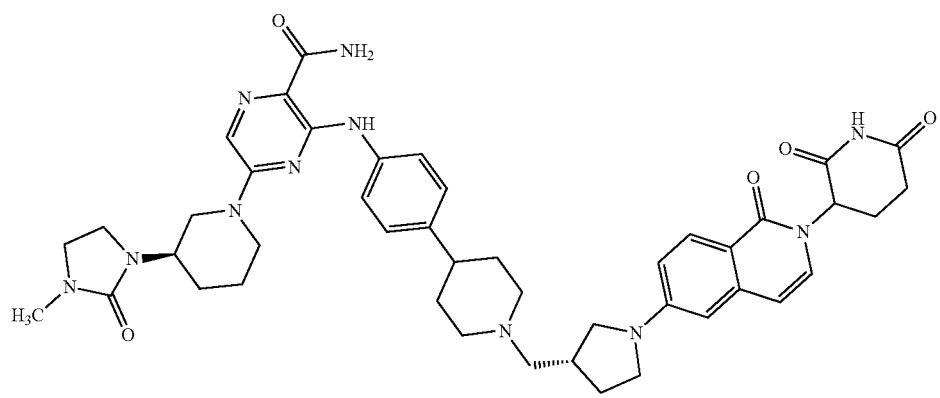
(Compound Number 134)
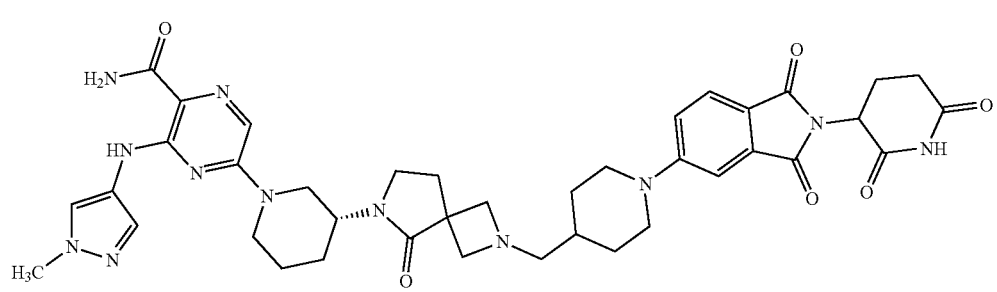
(Compound Number 137)
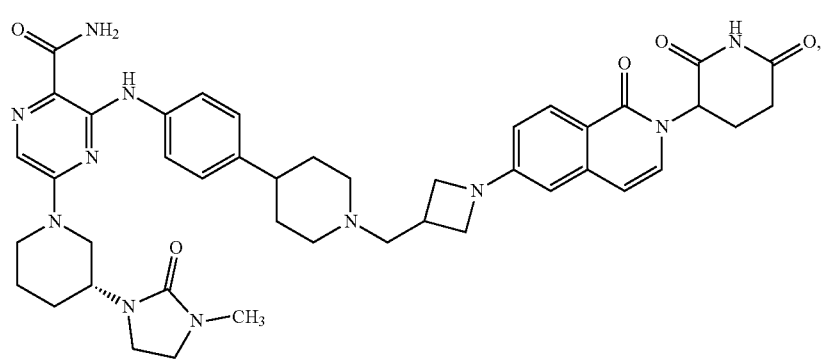
(Compound Number 138)

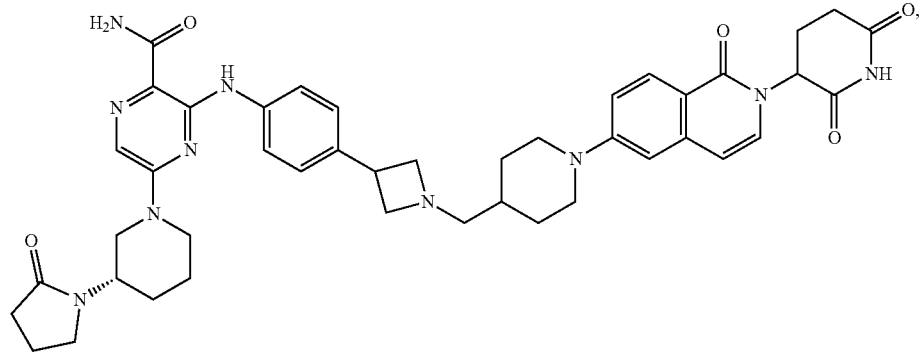
(Compound Number 139)
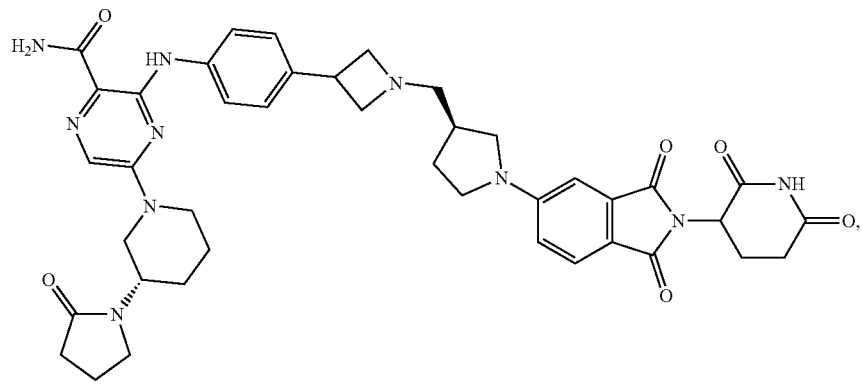
(Compound Number 140)
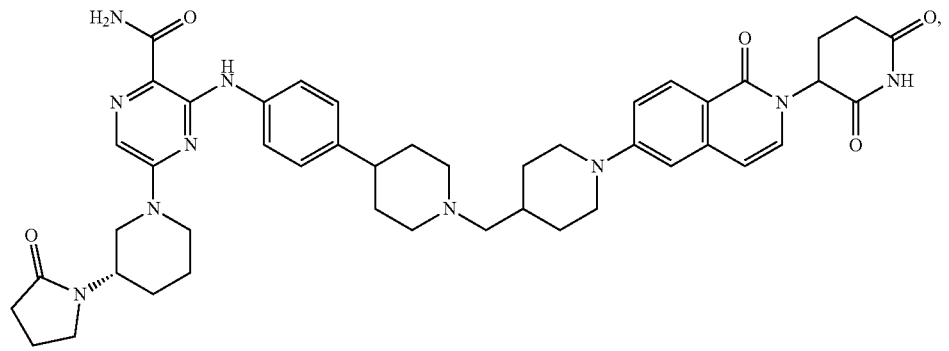
(Compound Number 144)
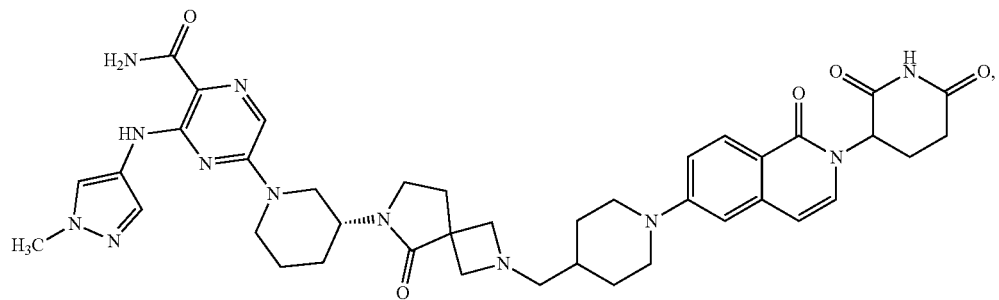
(Compound Number 145)

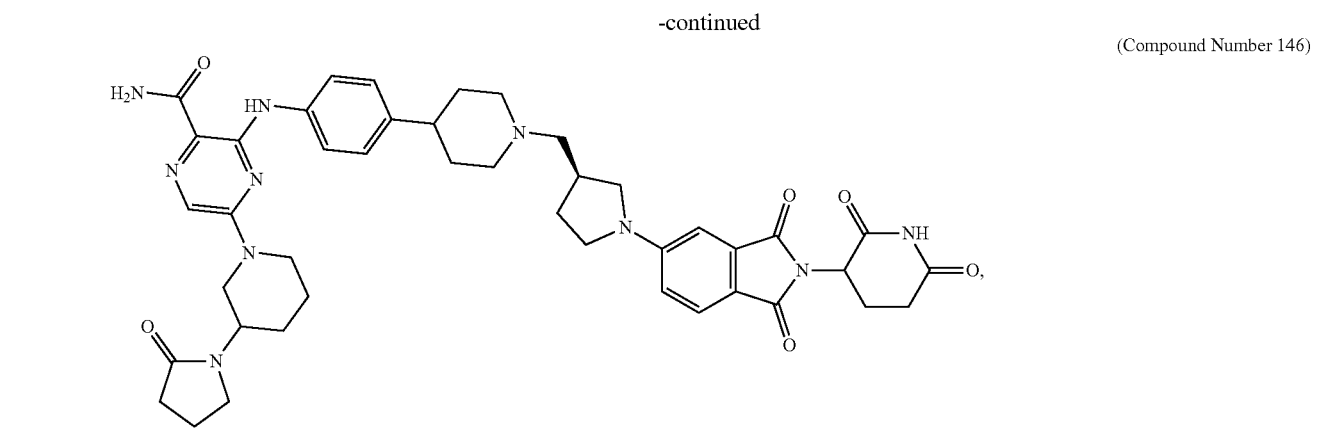
(Compound Number 146)
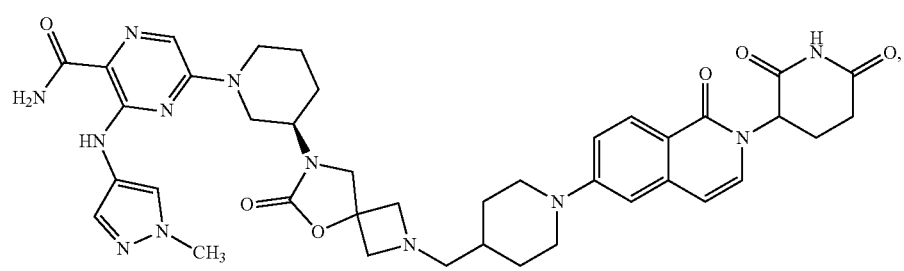
(Compound Number 147)
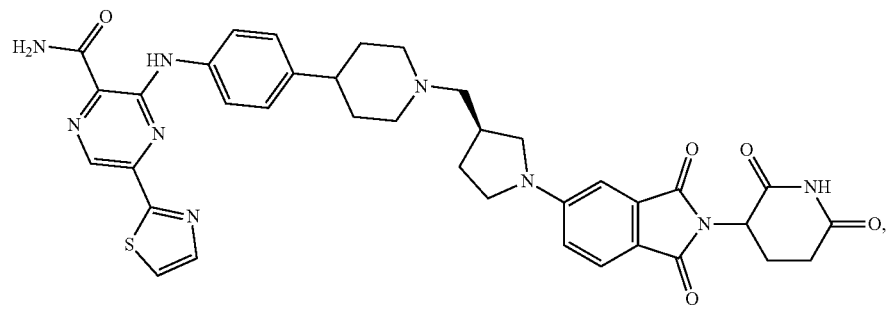
(Compound Number 148)
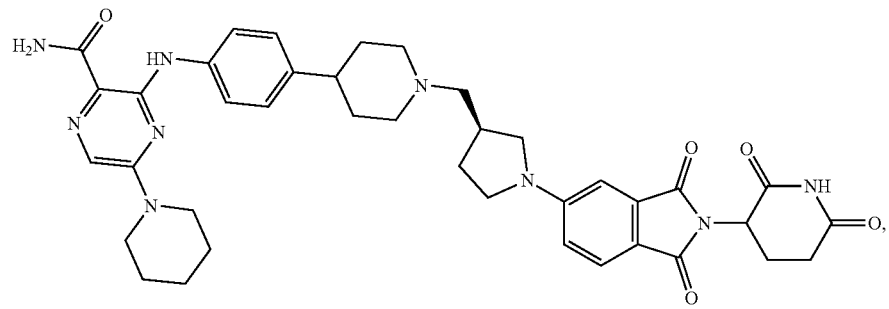
(Compound Number 149)
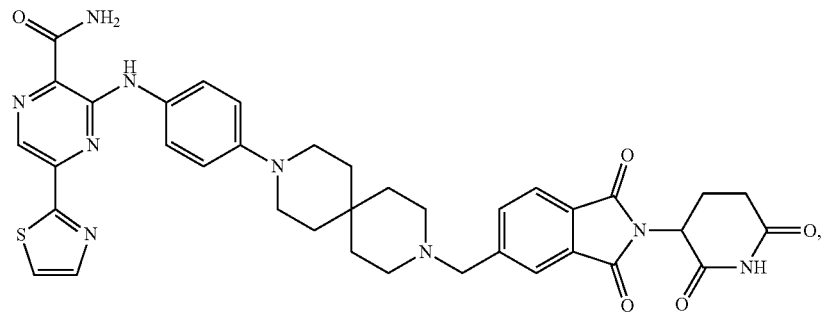
(Compound Number 150)

(Compound Number 151)
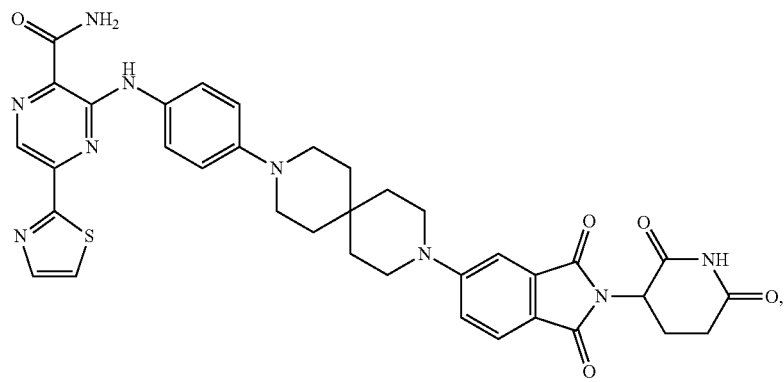
(Compound Number 152)
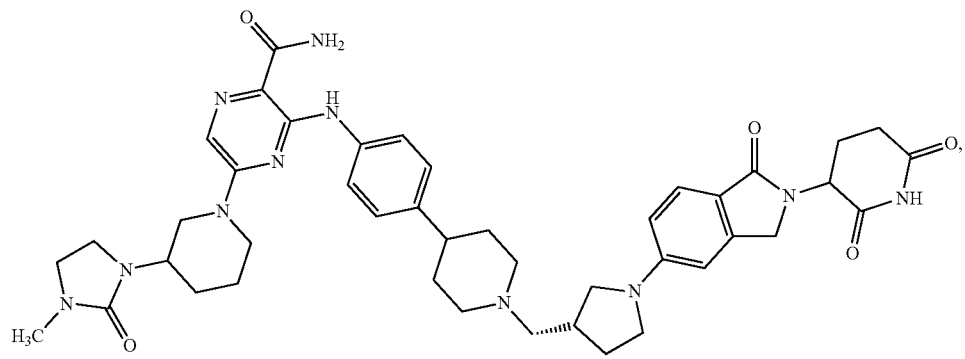
(Compound Number 153)
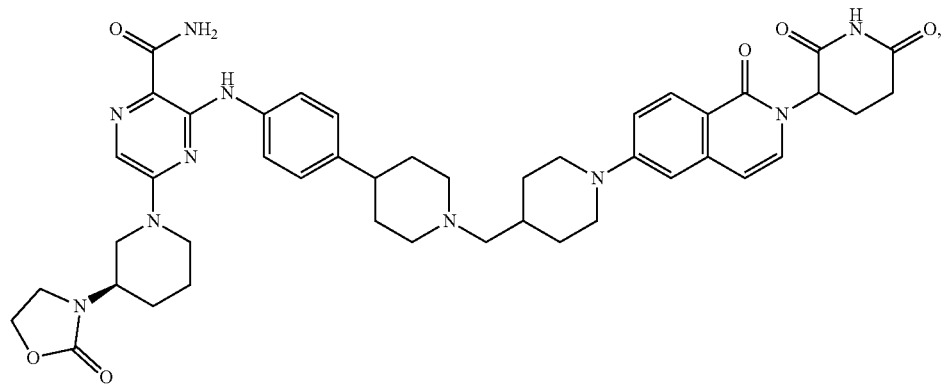
(Compound Number 154)
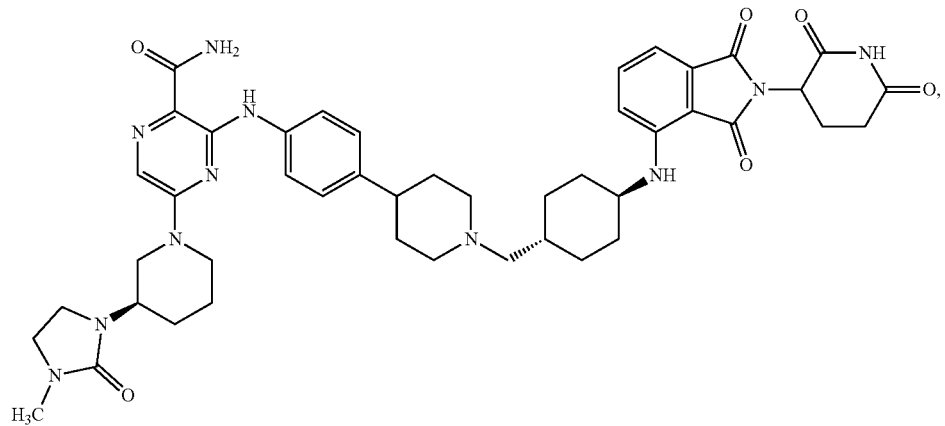

-continued
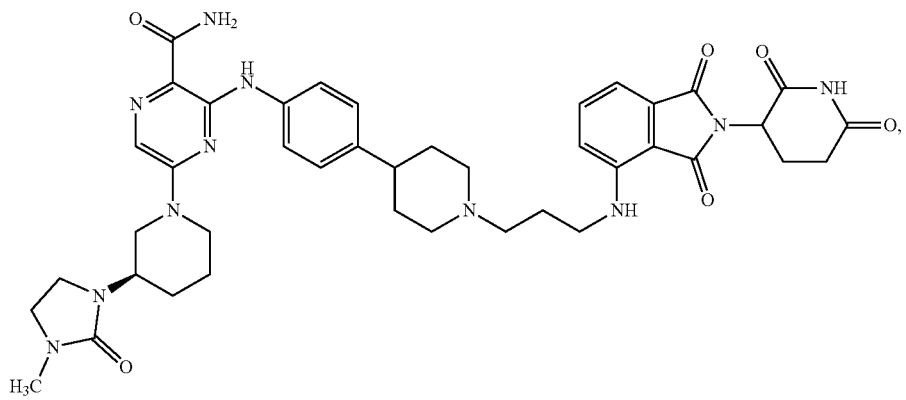
(Compound Number 155)
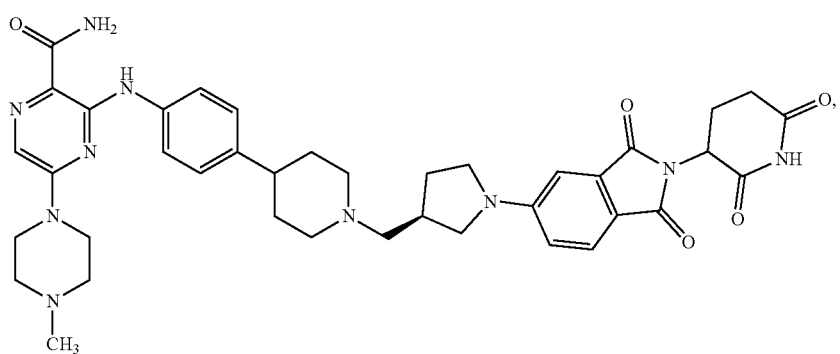
(Compound Number 157)
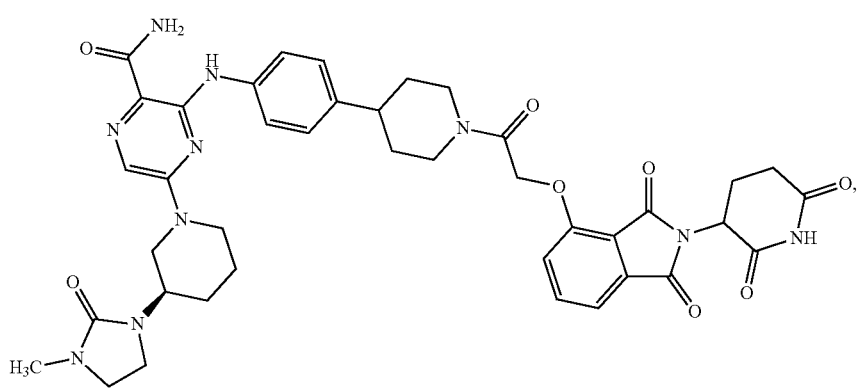
(Compound Number 158)
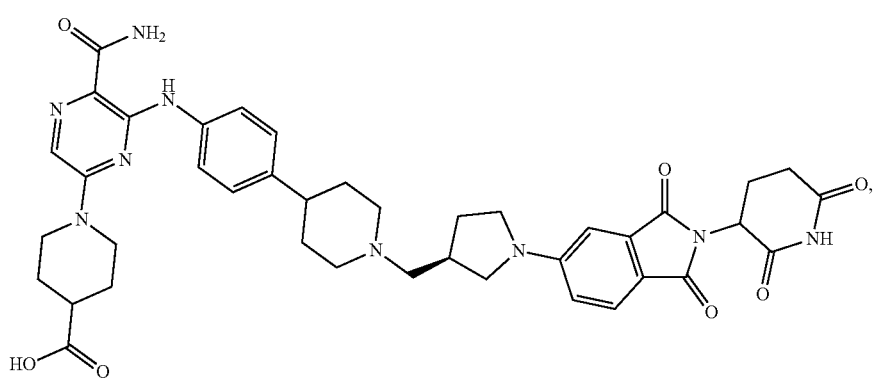
(Compound Number 159)

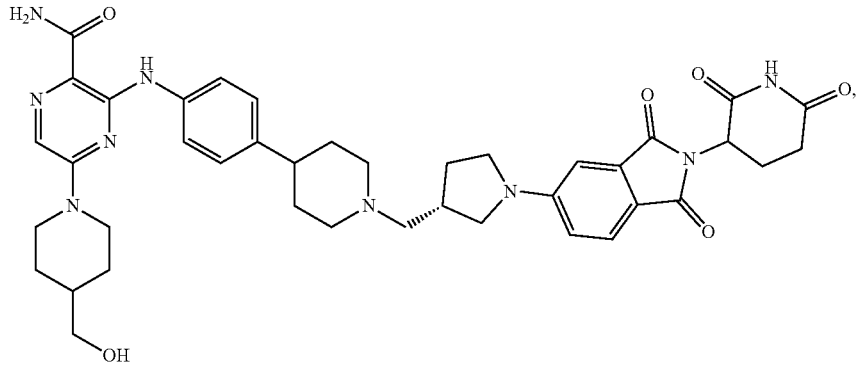
(Compound Number 160)
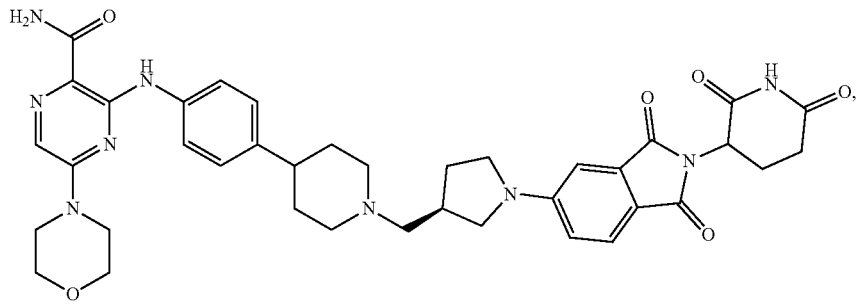
(Compound Number 161)
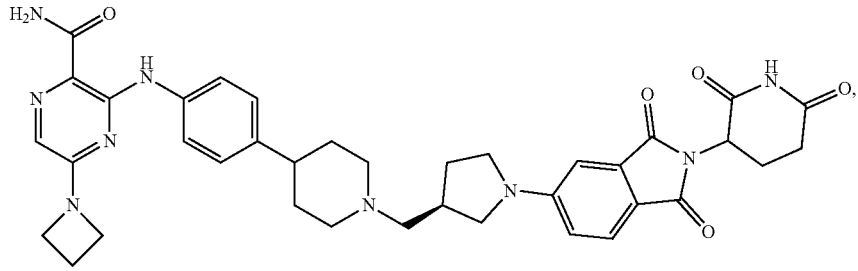
(Compound Number 162)
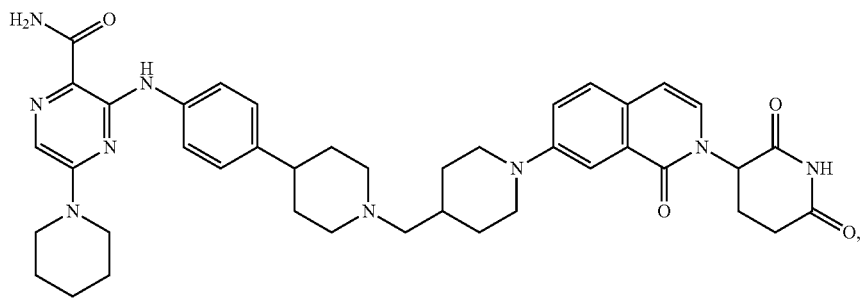
(Compound Number 163)
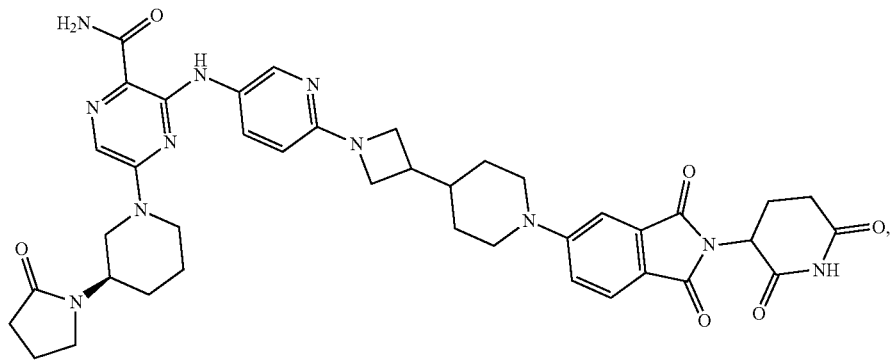
(Compound Number 168)

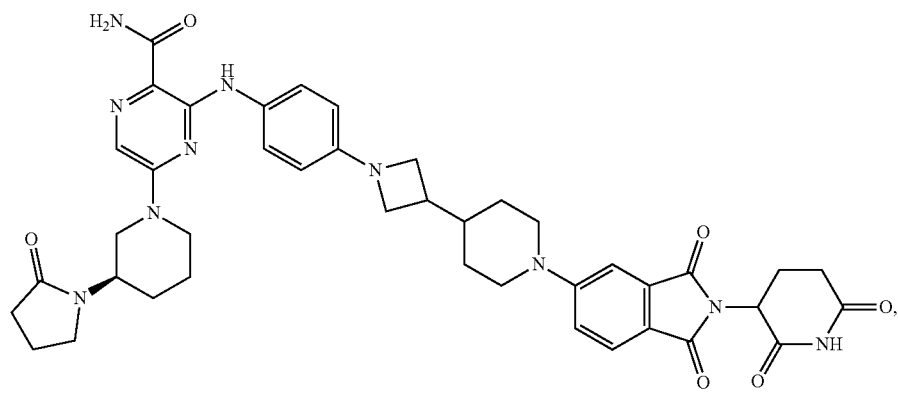
(Compound Number 169)
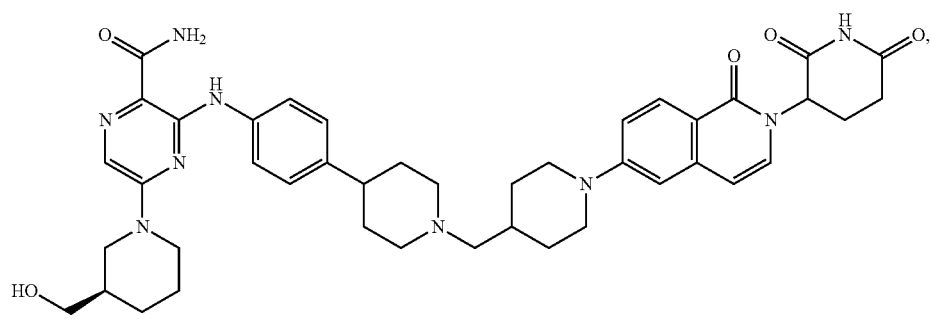
(Compound Number 172)
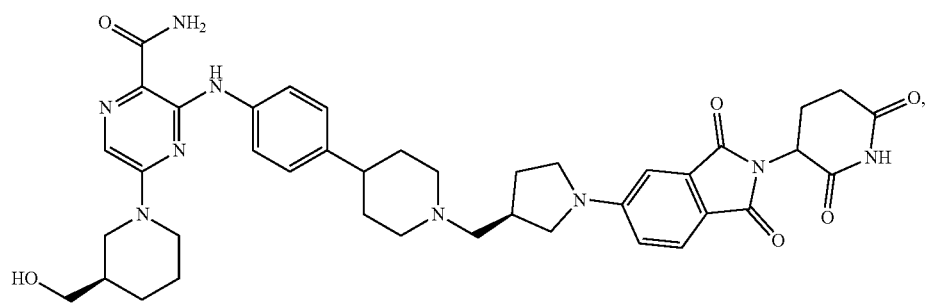
(Compound Number 174)
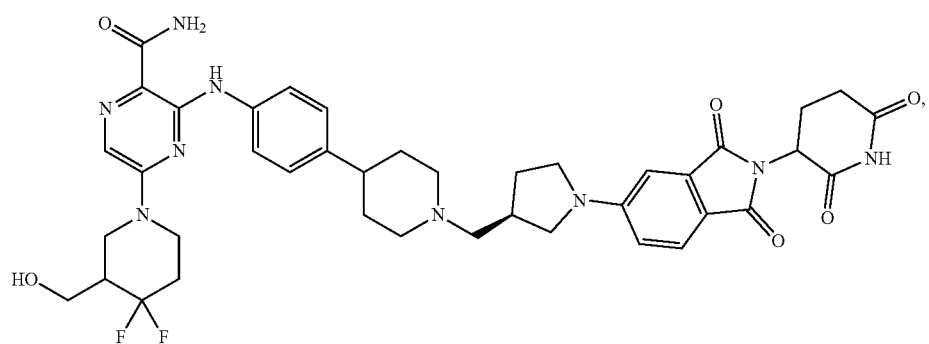
(Compound Number 175)

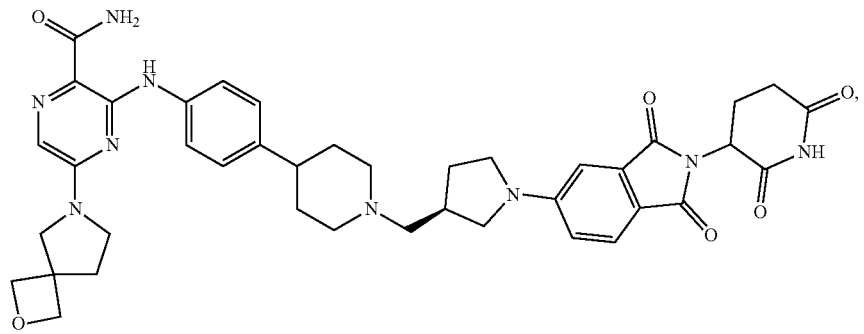
(Compound Number 176)
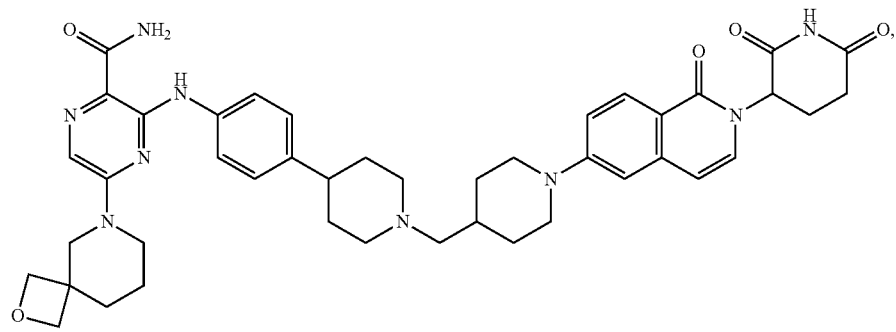
(Compound Number 177)
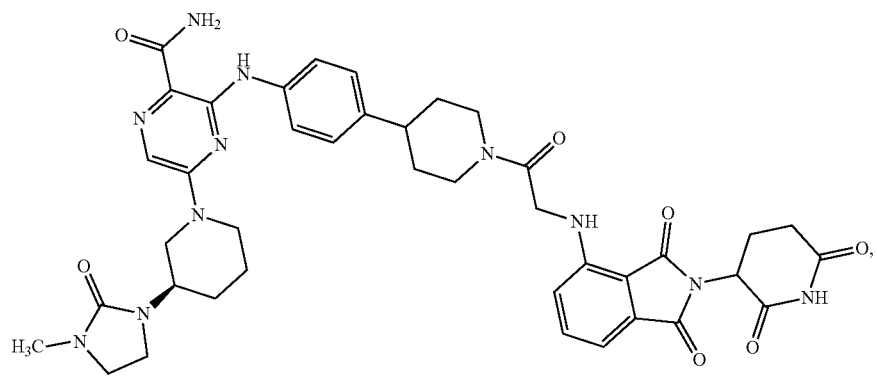
(Compound Number 184)
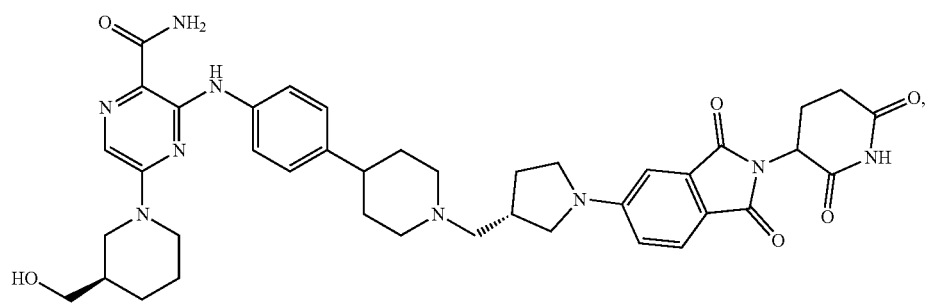
(Compound Number 193)

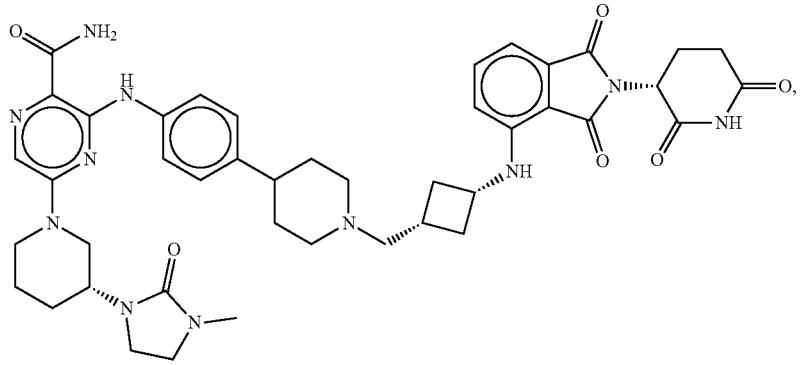
(Compound Number 201)
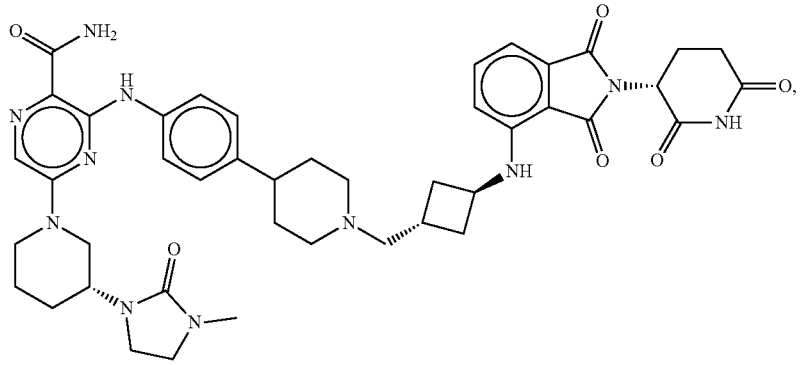
(Compound Number 202)
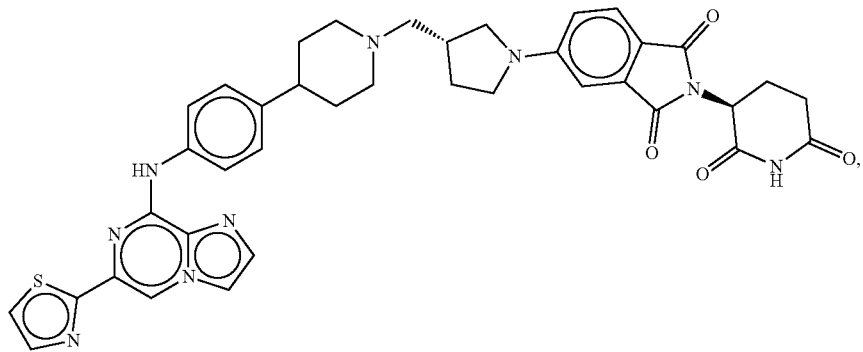
(Compound Number 203)
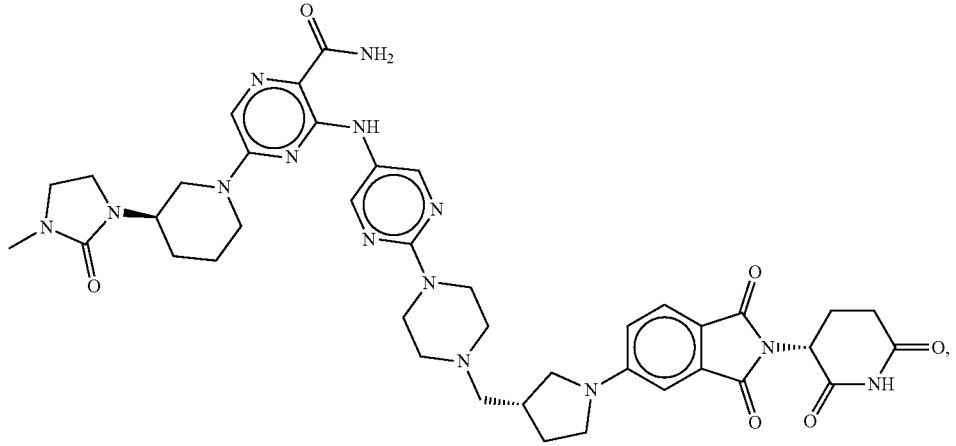
(Compound Number 204)

(Compound Number 205)
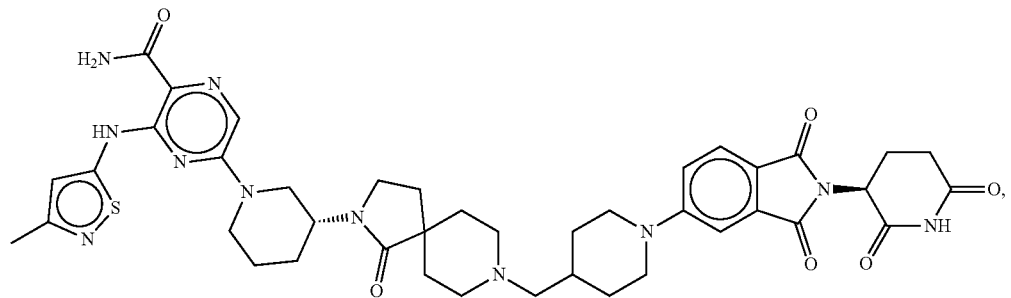
(Compound Number 206)
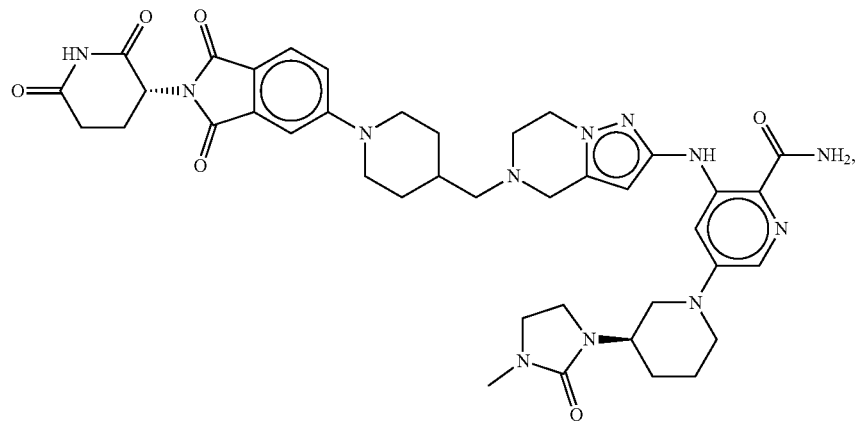
(Compound Number 207)
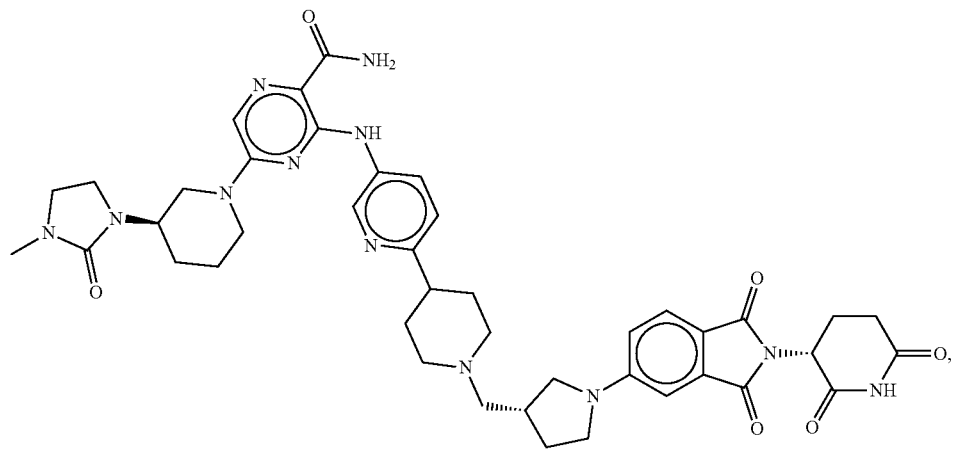
(Compound Number 208)
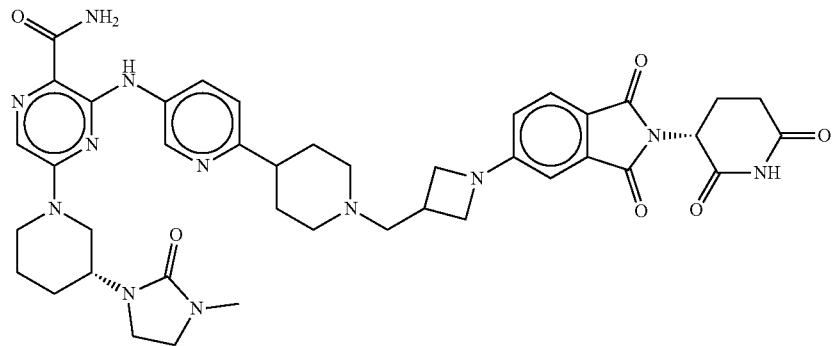

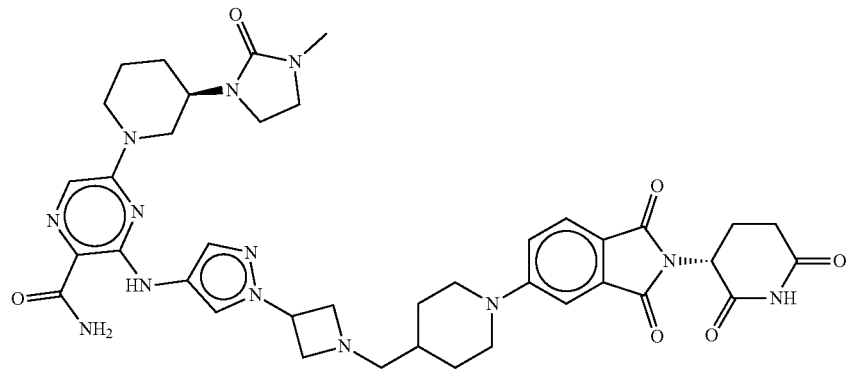
(Compound Number 209)
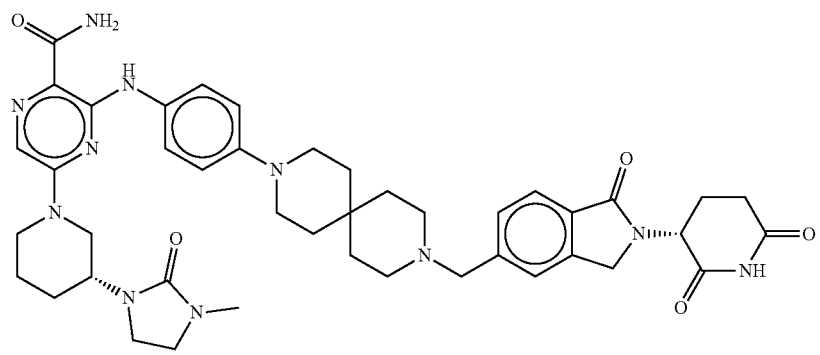
(Compound Number 210)
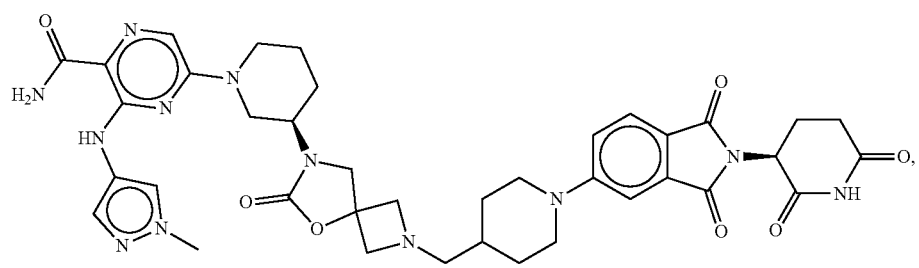
(Compound Number 211)
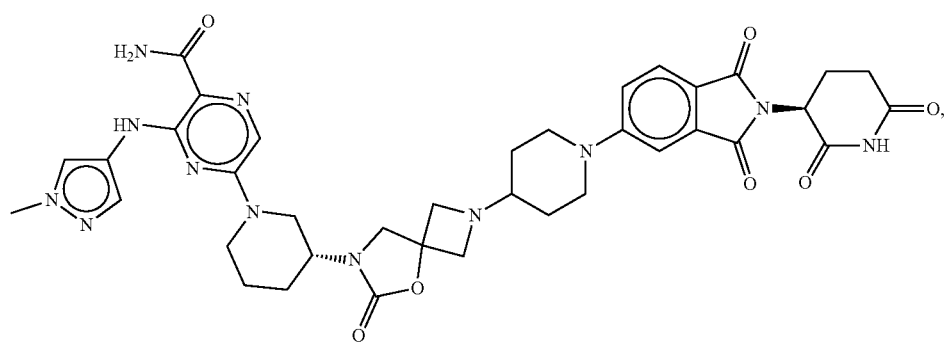
(Compound Number 212)
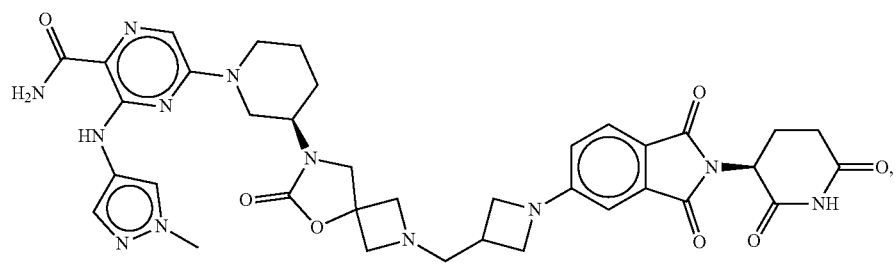
(Compound Number 213)

(Compound Number 214)
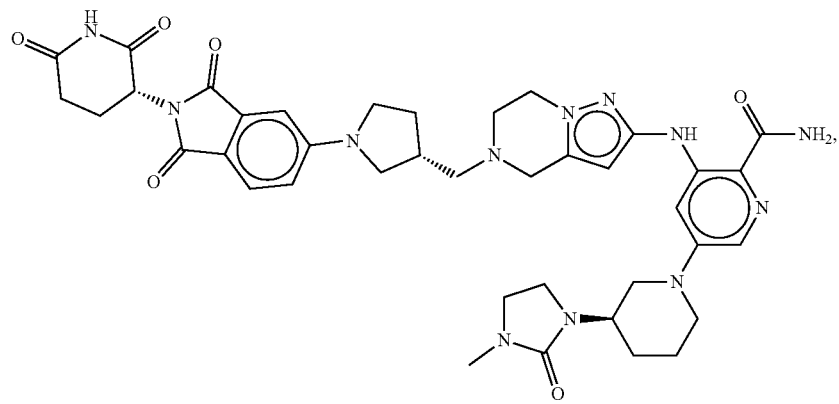
(Compound Number 215)
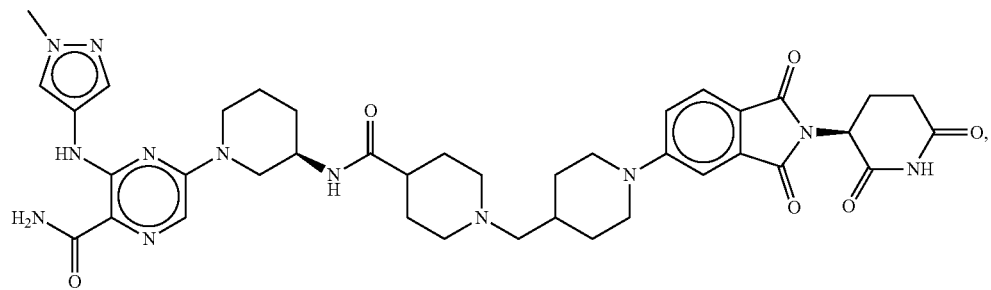
(Compound Number 216)
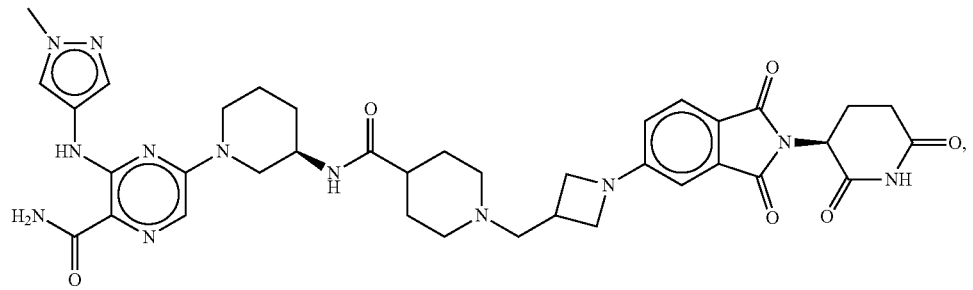
(Compound Number 217)
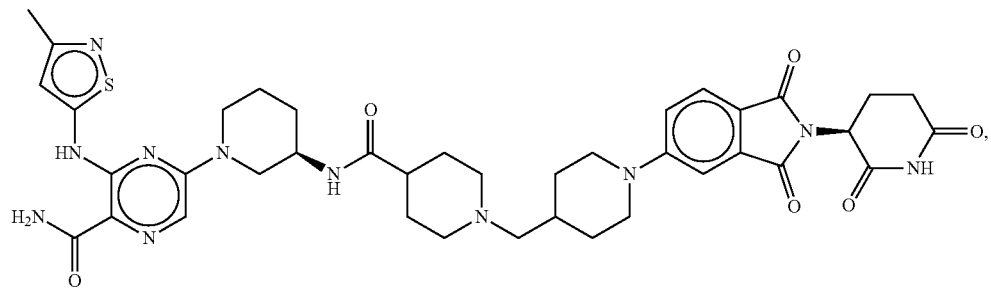

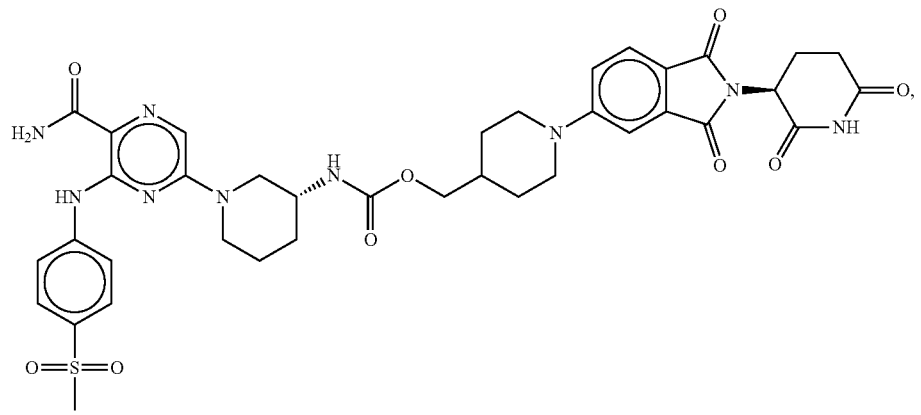

(Compound Number 218)

or a pharmaceutically acceptable salt thereof.

27. The method of claim 1, wherein the compound is administered in the form of a pharmaceutical composition comprising the compound or pharmaceutically acceptable salt thereof and a pharmaceutically acceptable carrier, vehicle, or adjuvant.

28. The method of claim 1, wherein the compound is selected from:

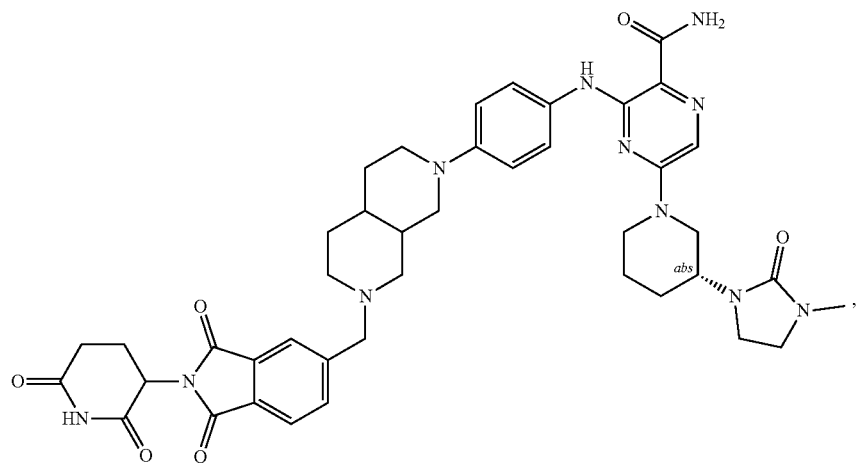

(Compound Number 104)

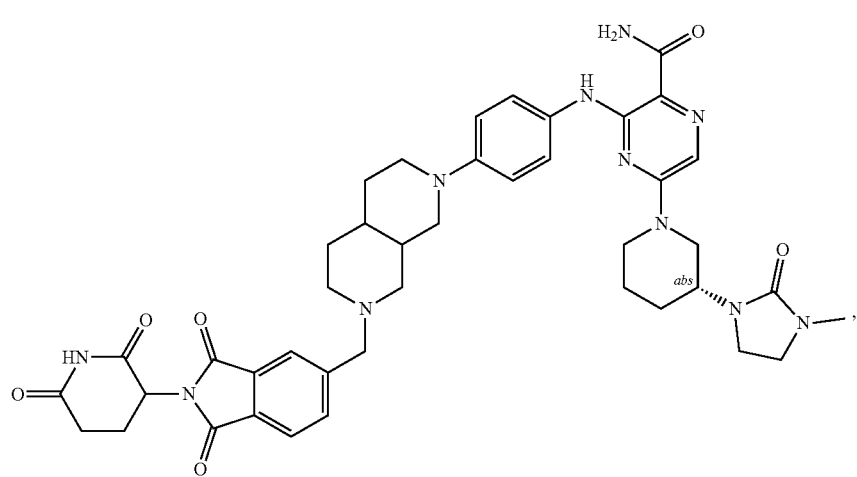

(Compound Number 105)

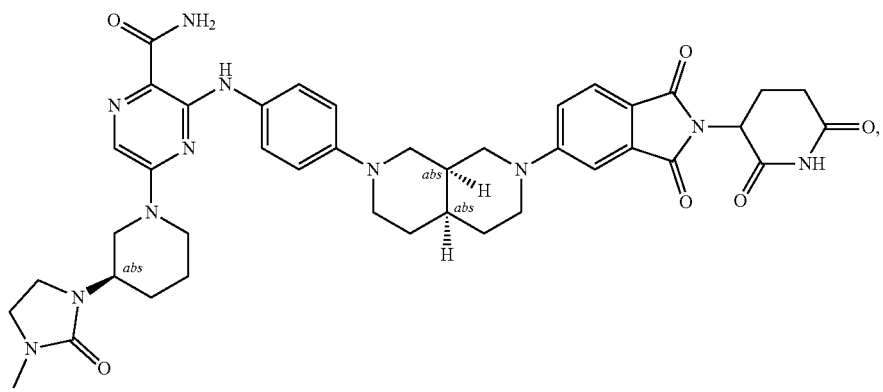
(Compound Number 106)
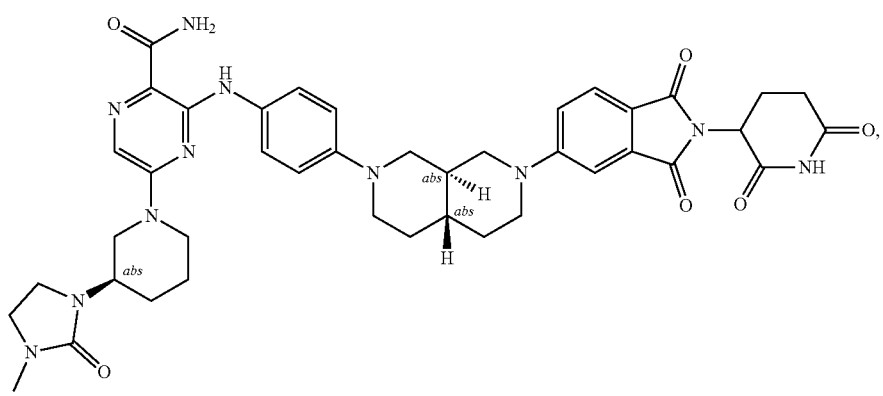
(Compound Number 107)
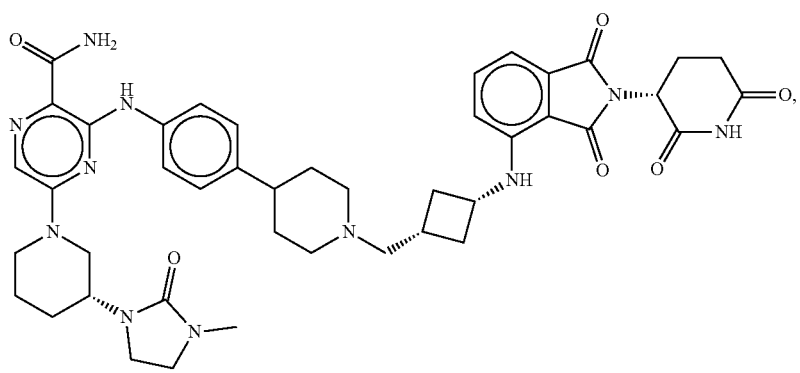
(Compound Number 201)
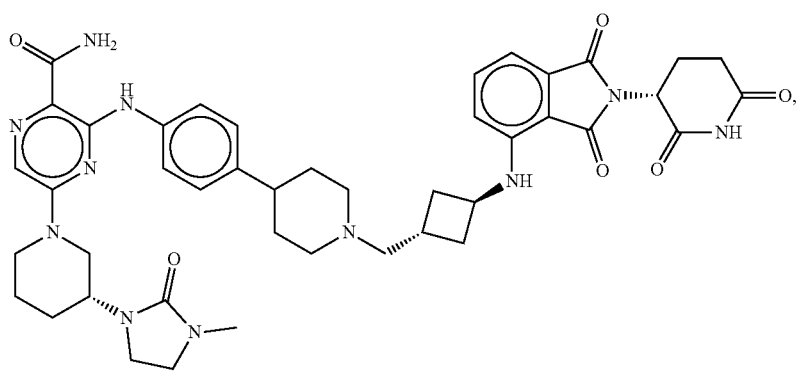
(Compound Number 202)

-continued
(Compound Number 203)
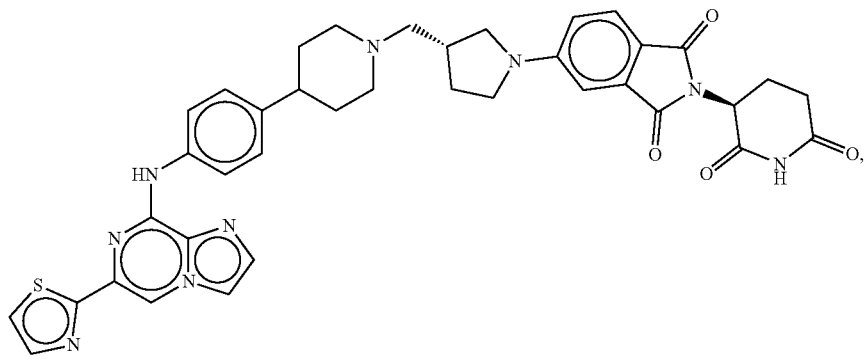
(Compound Number 204)
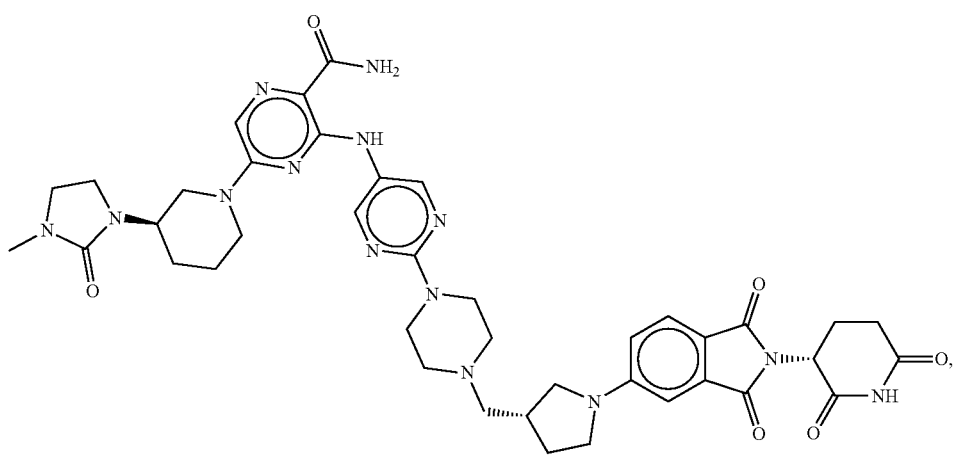
(Compound Number 205)
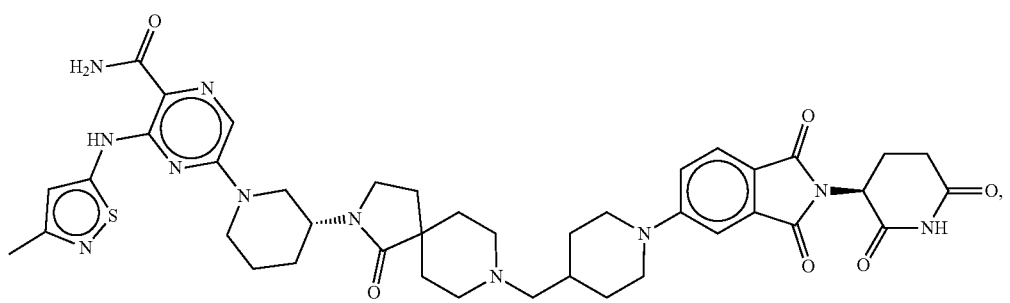
(Compound Number 206)
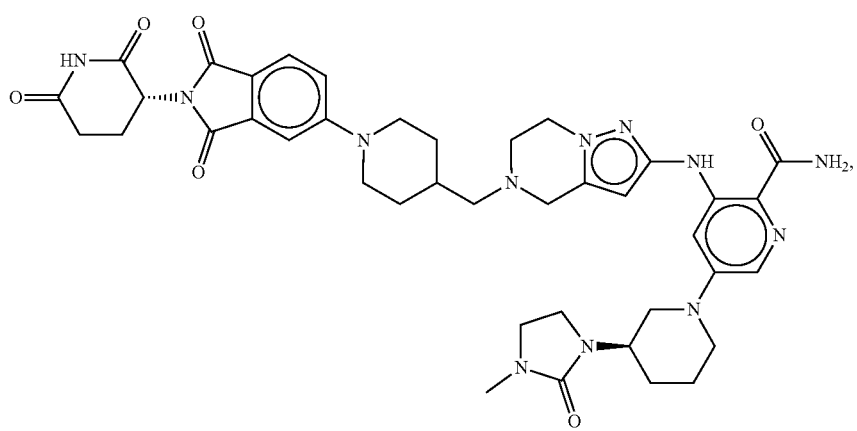

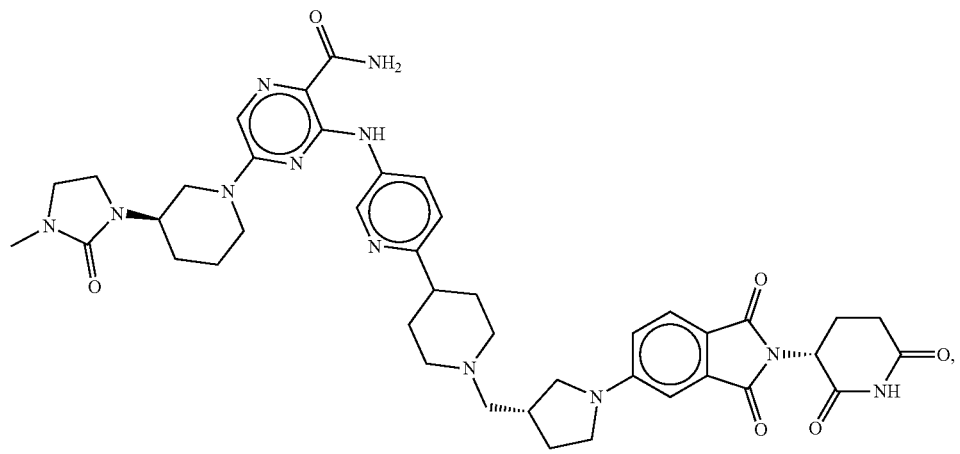
(Compound Number 207)
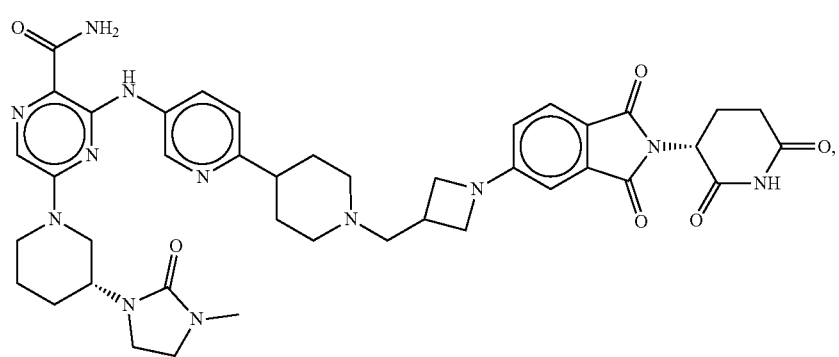
(Compound Number 208)
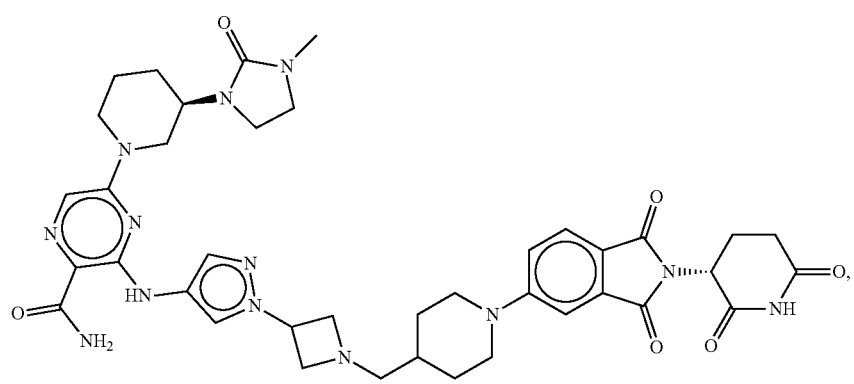
(Compound Number 209)
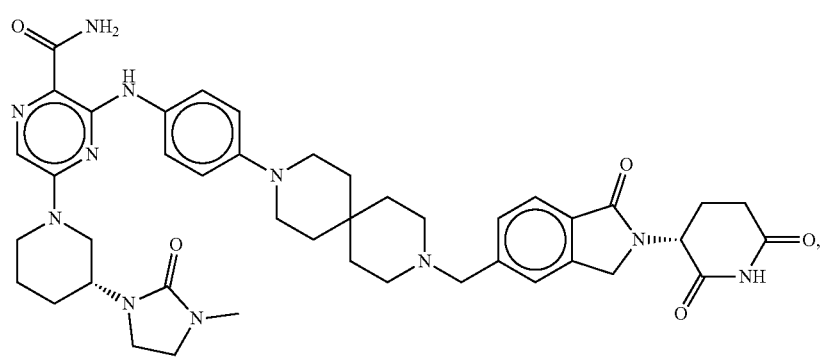
(Compound Number 210)

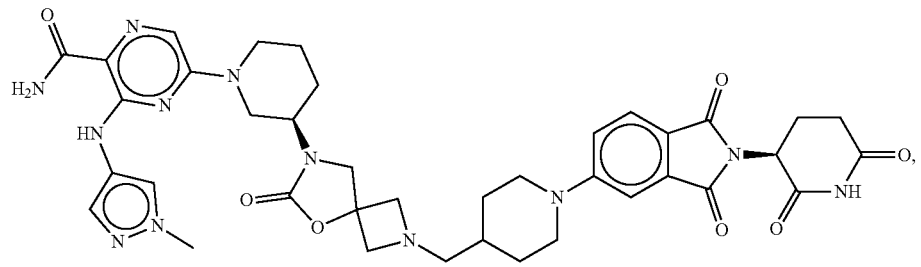
(Compound Number 211)
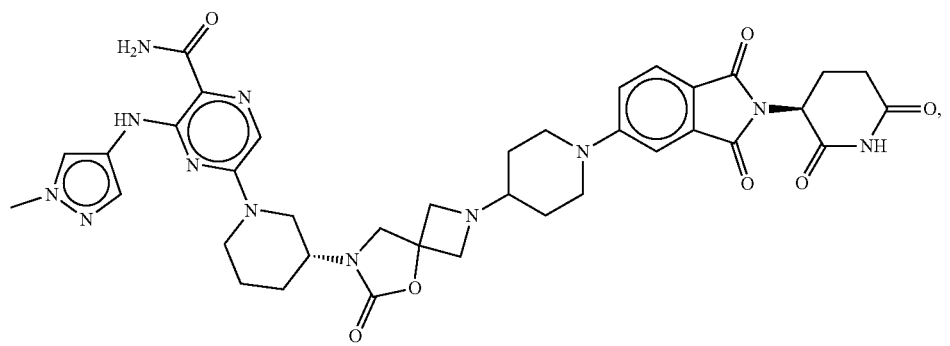
(Compound Number 212)
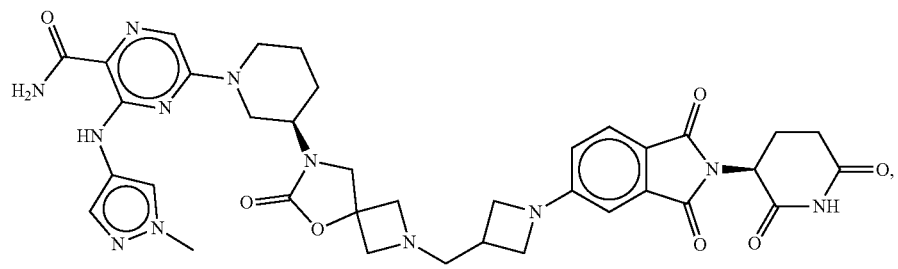
(Compound Number 213)
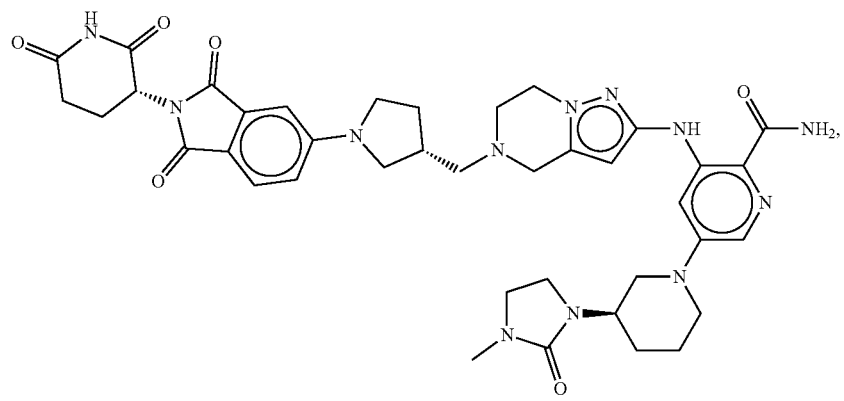
(Compound Number 214)

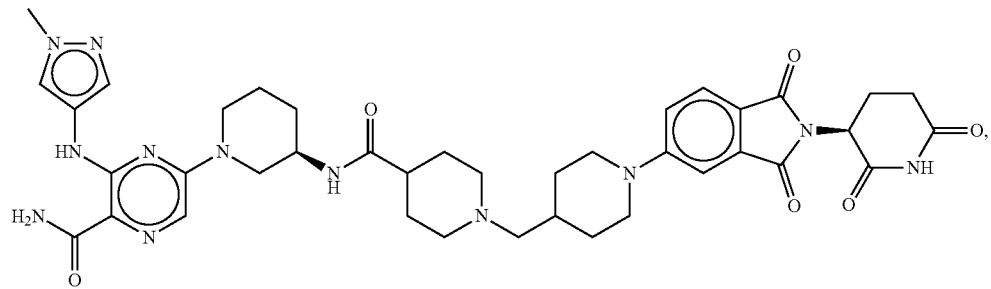
(Compound Number 215)
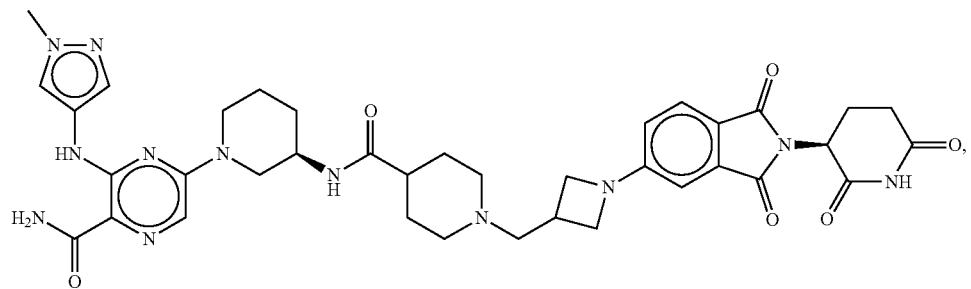
(Compound Number 216)
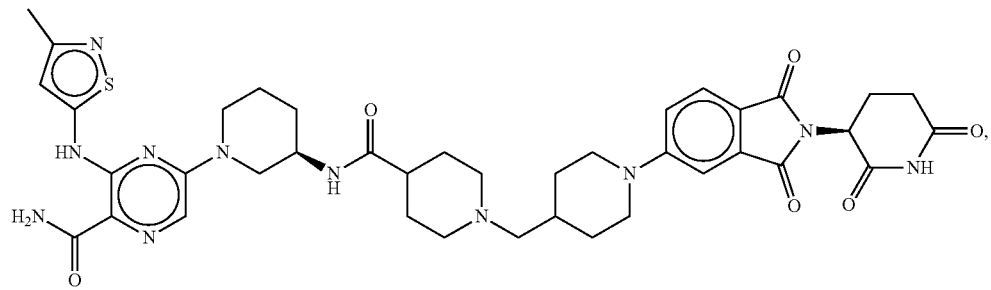
(Compound Number 217)
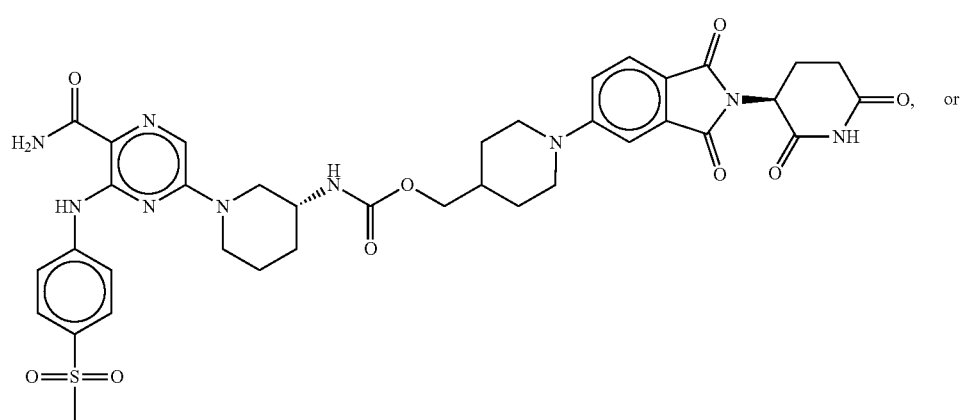
(Compound Number 218) or
a pharmaceutically acceptable salt thereof.

29. A compound selected from the following, or a pharmaceutically acceptable salt thereof:
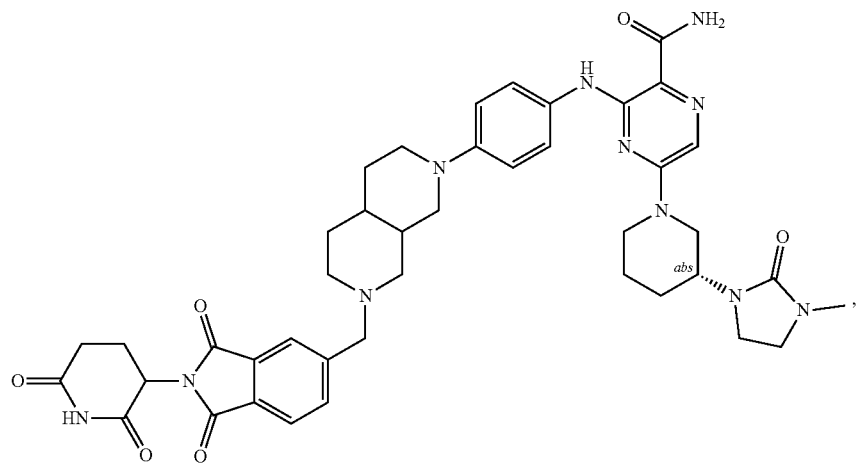
(Compound Number 104)
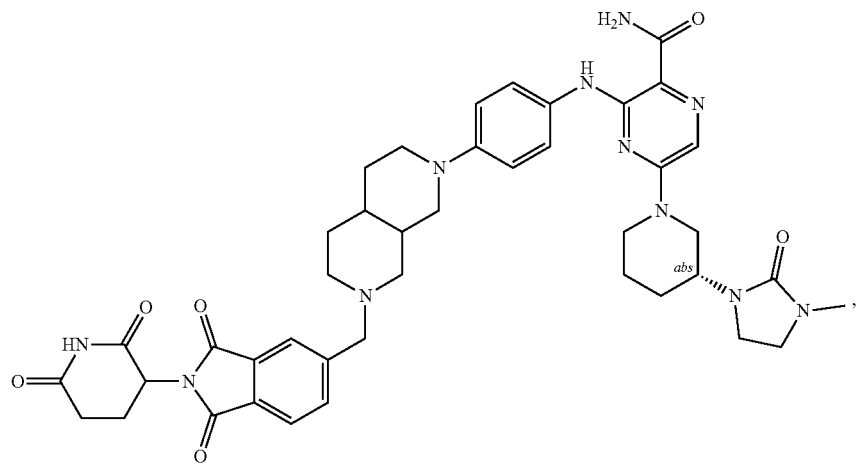
(Compound Number 105)
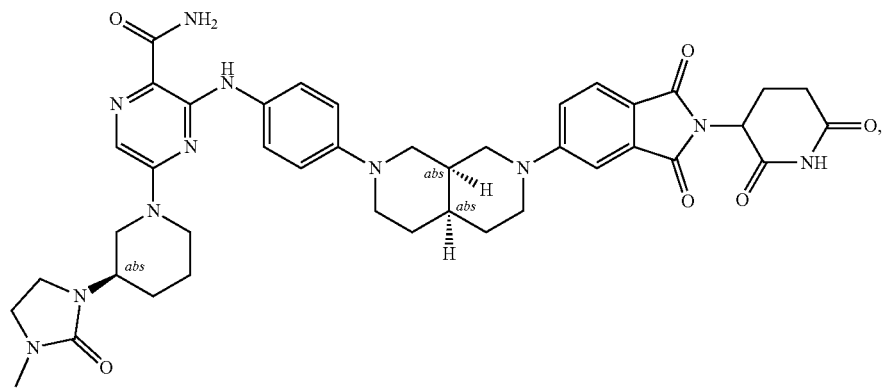
(Compound Number 106)

-continued
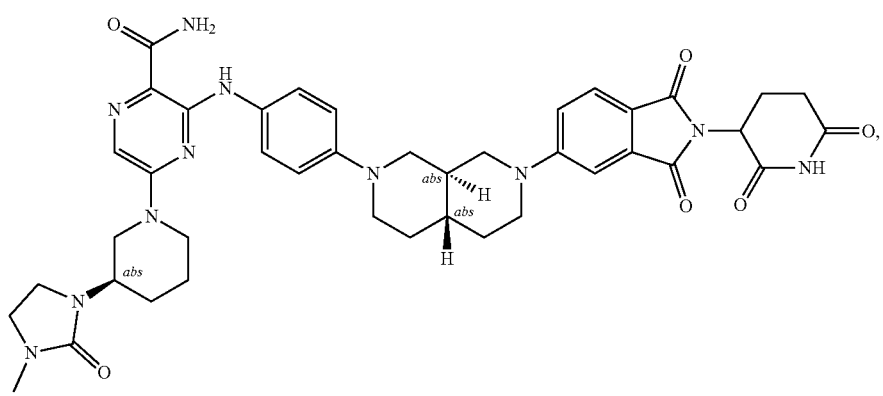
(Compound Number 107)
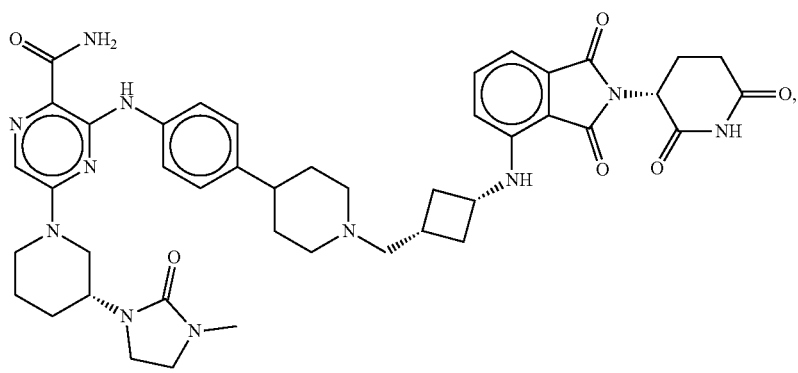
(Compound Number 201)
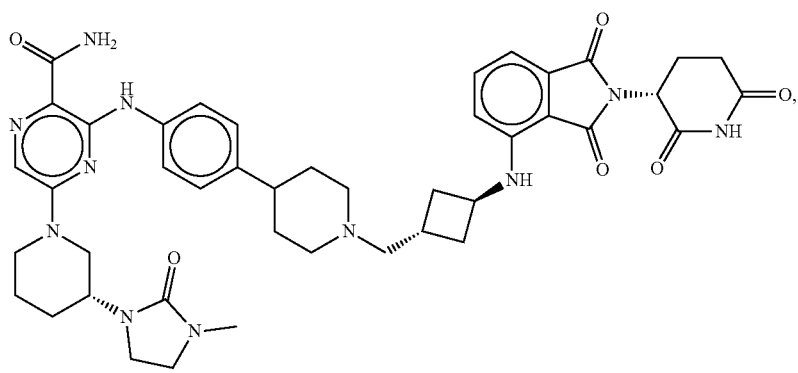
(Compound Number 202)
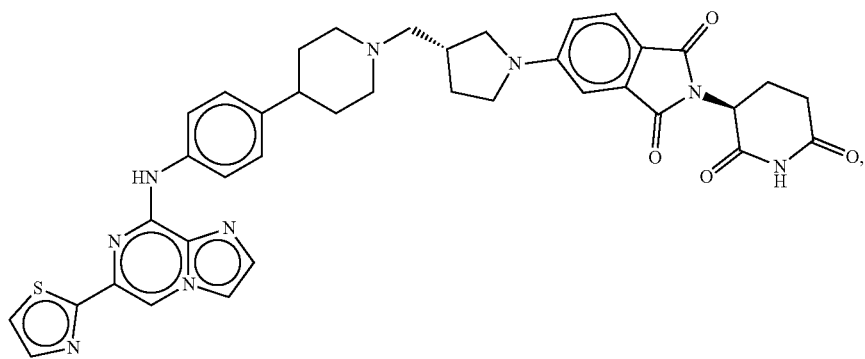
(Compound Number 203)

(Compound Number 204)
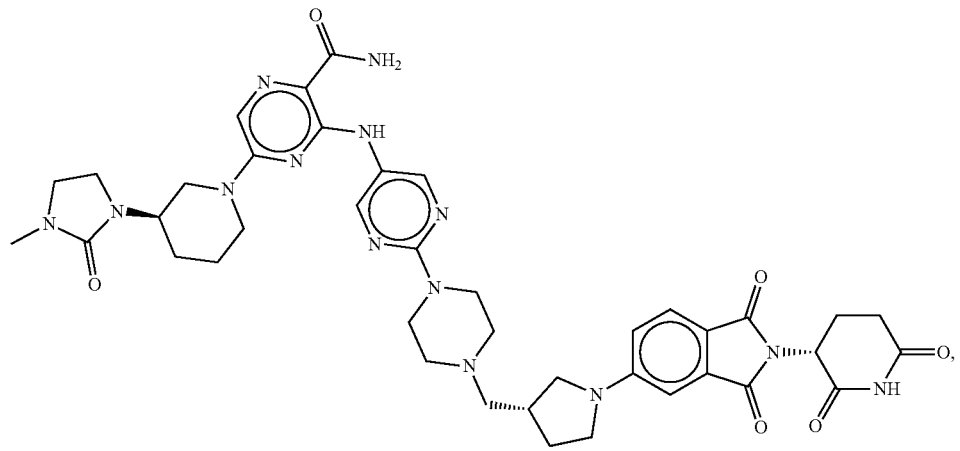
(Compound Number 205)
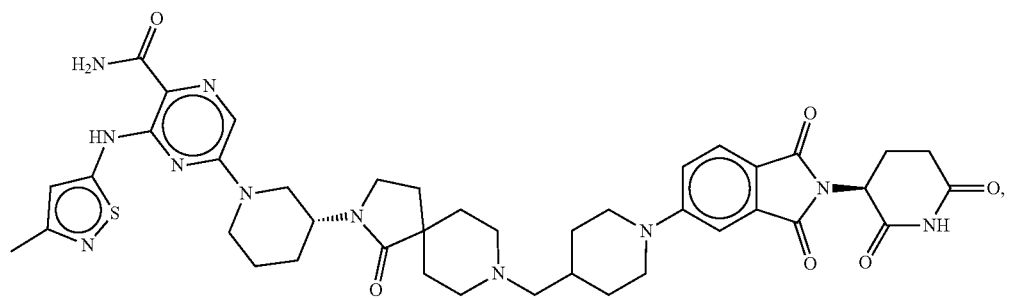
(Compound Number 206)
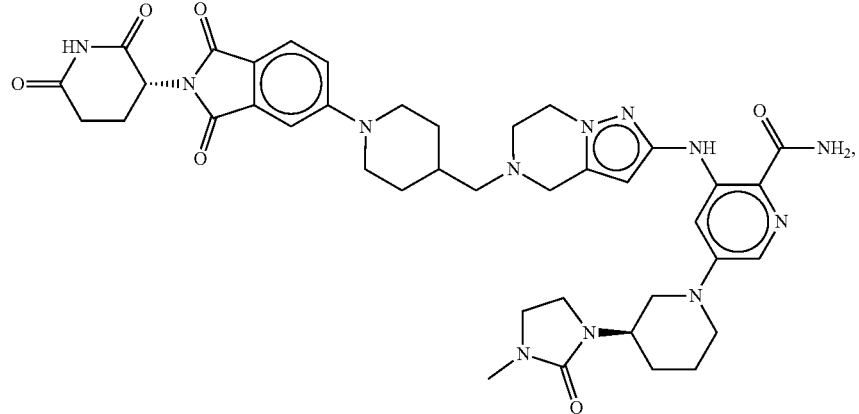
(Compound Number 207)
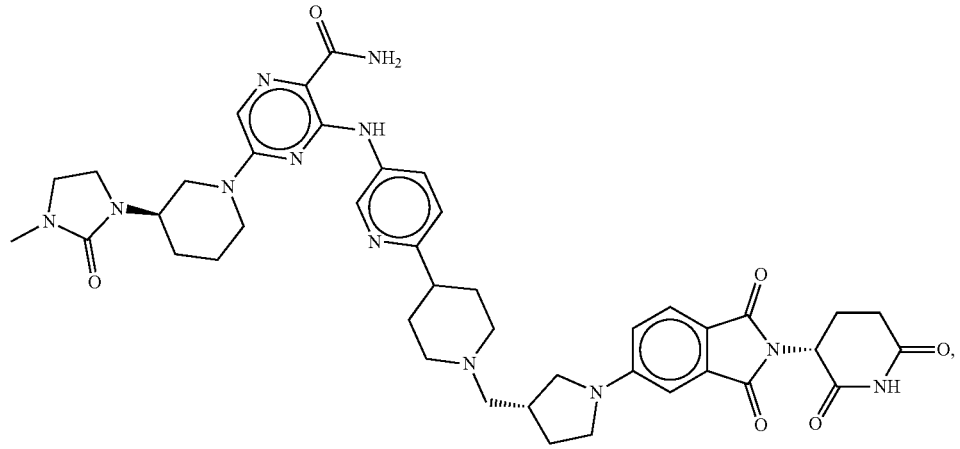

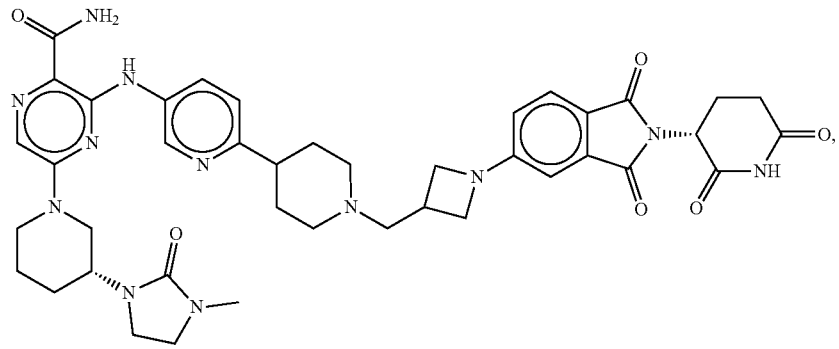
(Compound Number 208)
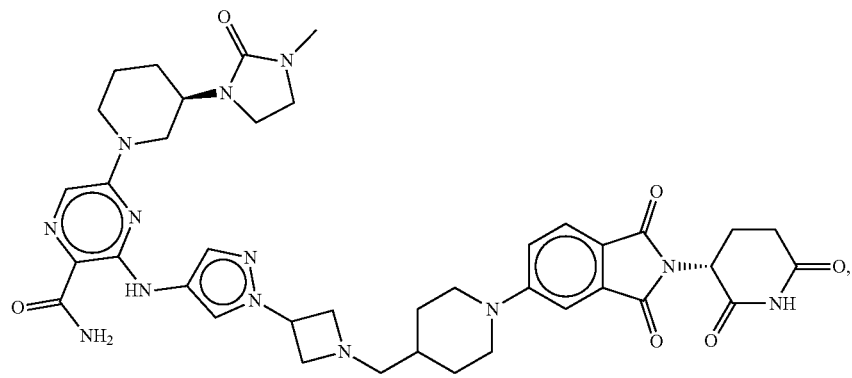
(Compound Number 209)
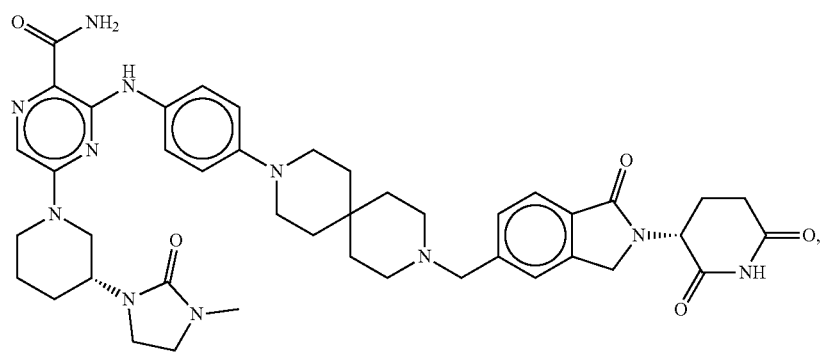
(Compound Number 210)
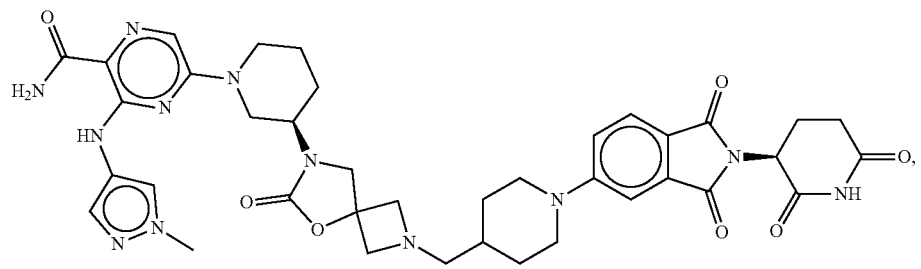
(Compound Number 211)

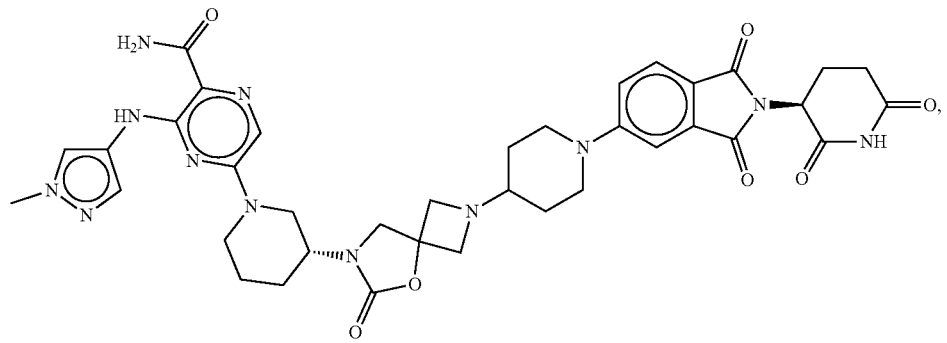
(Compound Number 212)
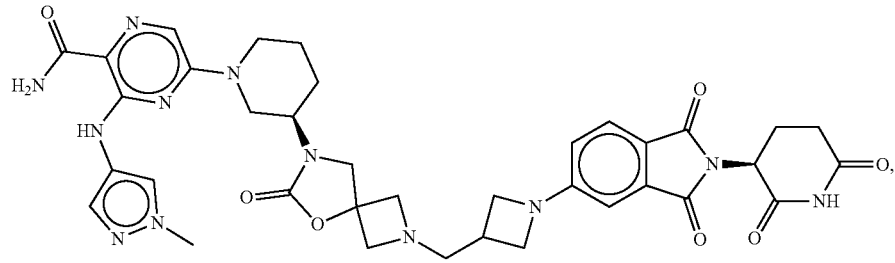
(Compound Number 213)
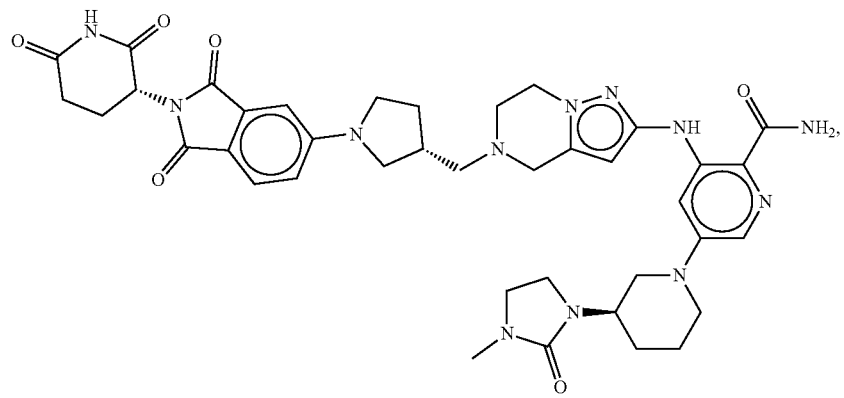
(Compound Number 214)
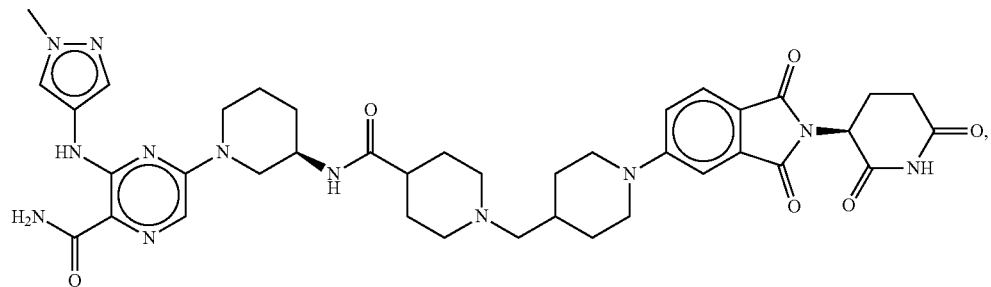
(Compound Number 215)
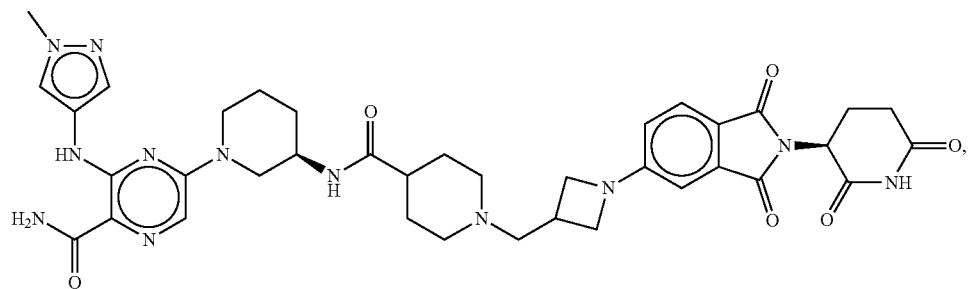
(Compound Number 216)

(Compound Number 217)

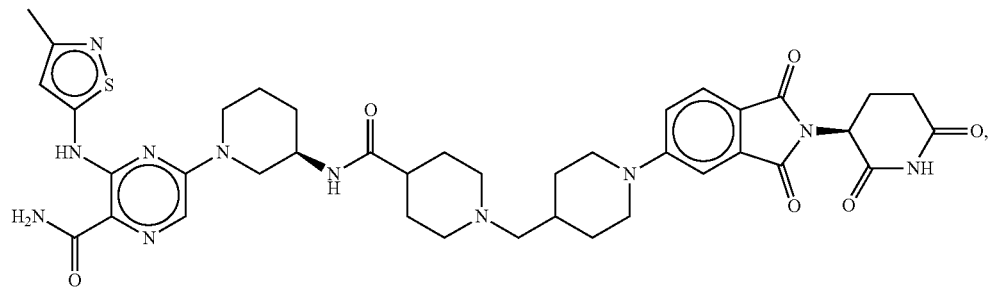

(Compound Number 218)

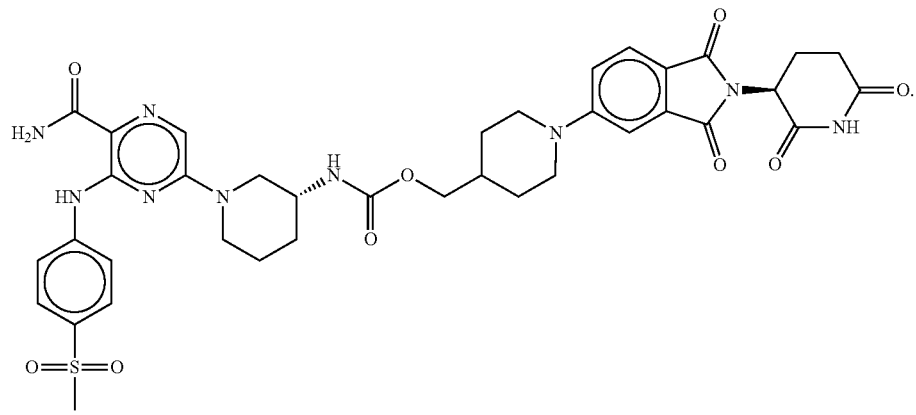

30. The method of claim 1, wherein the cancer is a B cell malignancy.
31. The method of claim 30, wherein the B cell malignancy is chronic lymphocytic leukemia (CLL).
32. The method of claim 31, wherein the compound is (compound 149)

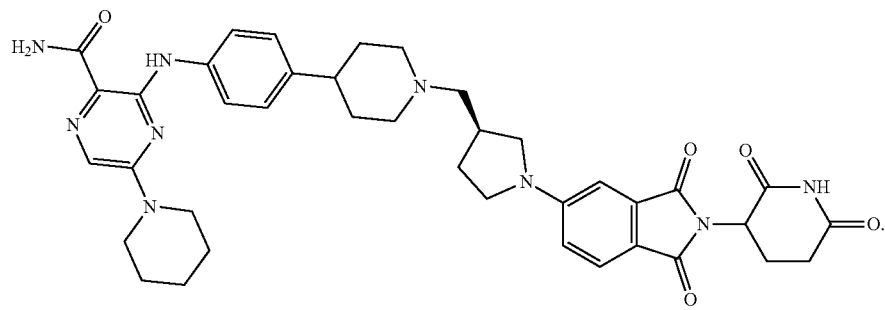

33. The method of claim 1, wherein the cancer is diffuse large B-cell lymphoma (DLBCL).
34. The method of claim 33, wherein the compound is (compound 149)

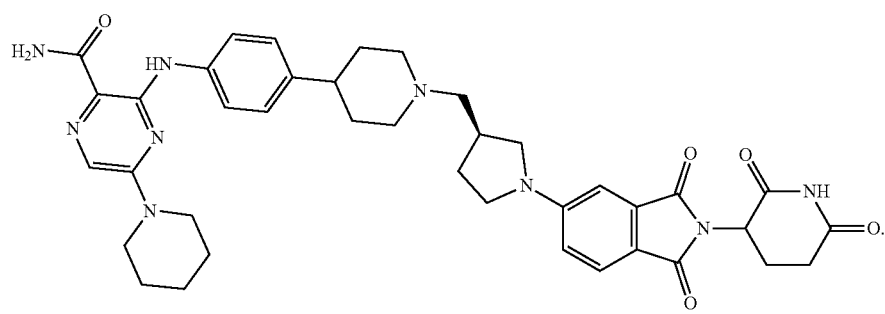

* * * * *